(12) United States Patent
Skaaksrud

(10) Patent No.: US 10,755,552 B2
(45) Date of Patent: Aug. 25, 2020

(54) SYSTEMS FOR COORDINATED MEDIATION ACTION IN RESPONSE TO AN IDENTIFIED ENVIRONMENTAL ANOMALY ON A SHIPPING CONTAINER

(71) Applicant: FEDEX CORPORATE SERVICES, INC., Collierville, TN (US)

(72) Inventor: Ole-Petter Skaaksrud, Germantown, TN (US)

(73) Assignee: FEDEX CORPORATE SERVICES, INC., Collierville, TN (US)

( * ) Notice: Subject to any disclaimer, the term of this patent is extended or adjusted under 35 U.S.C. 154(b) by 0 days.

(21) Appl. No.: 16/546,427

(22) Filed: Aug. 21, 2019

(65) Prior Publication Data

US 2020/0143664 A1 May 7, 2020

Related U.S. Application Data

(60) Provisional application No. 62/735,075, filed on Sep. 22, 2018.

(51) Int. Cl.
| | | |
|---|---|---|
| G08B 25/10 | (2006.01) |
| A62C 3/08 | (2006.01) |
| A62C 3/10 | (2006.01) |
| A62C 31/22 | (2006.01) |
| G01J 5/02 | (2006.01) |
| G08B 17/06 | (2006.01) |

(Continued)

(52) U.S. Cl.
CPC ............. *G08B 25/10* (2013.01); *A62C 3/08* (2013.01); *A62C 3/10* (2013.01); *A62C 31/22* (2013.01); *G01J 5/0014* (2013.01); *G01J 5/025* (2013.01); *G08B 17/06* (2013.01); *A62C 37/44* (2013.01)

(58) Field of Classification Search
CPC combination set(s) only.
See application file for complete search history.

(56) References Cited

U.S. PATENT DOCUMENTS

| | | |
|---|---|---|
| 7,142,110 B2 | 11/2006 | Schmidtberg et al. |
| 7,834,754 B2 | 11/2010 | Kulesz et al. |

(Continued)

OTHER PUBLICATIONS

PCT Application No. PCT/US2019/050528 International Search Report and Written Opinion, dated Nov. 29, 2019.

*Primary Examiner* — Travis R Hunnings
(74) *Attorney, Agent, or Firm* — Withers & Keys, LLC

(57) ABSTRACT

An improved system on a transit vehicle is described for coordinated mediation action in response to an identified environmental anomaly on a shipping container transported by the vehicle. The system has wirelessly broadcasting ID nodes at different locations within the container, and a fire suppression system on the vehicle having a wireless transceiver-based controller operating as a master node that can cause the suppression system to deliver fire suppressant material to the container using a delivery nozzle and pump. The controller, as master node, is configured to operate as a primary monitor for the anomaly by being operative to monitor ID node signals; identify the anomaly based on the signals; generate a layered alert notification related to the anomaly (identifying a targeted mediation action and establishes a mediation response priority); and initiate a mediation response by the suppression system related to the targeted mediation action and the mediation response priority.

74 Claims, 107 Drawing Sheets

(51) Int. Cl.
  *G01J 5/00*      (2006.01)
  *A62C 37/44*     (2006.01)

(56)        References Cited

U.S. PATENT DOCUMENTS

| | | |
|---|---|---|
| 8,220,051 B2 | 7/2012 | Norton et al. |
| 8,224,576 B2 | 7/2012 | Jensen et al. |
| 8,836,503 B2 | 9/2014 | Gelvin et al. |
| 8,905,633 B2 | 12/2014 | Popp et al. |
| 9,062,537 B1 | 6/2015 | Holt et al. |
| 10,639,509 B2 | 5/2020 | Skaaksrud |
| 2008/0084295 A1 | 4/2008 | Libby |
| 2010/0278222 A1 | 11/2010 | De Lind Van Wijngaarden et al. |
| 2011/0247958 A1 | 10/2011 | Lucas et al. |
| 2012/0168184 A1* | 7/2012 | Enk, Sr. ............ A62C 3/08 169/14 |
| 2013/0316680 A1 | 11/2013 | Norton et al. |
| 2014/0313061 A1 | 10/2014 | Gatsonides et al. |
| 2016/0300183 A1 | 10/2016 | Berger et al. |
| 2017/0013547 A1* | 1/2017 | Skaaksrud ......... H04B 17/318 |
| 2018/0154199 A1 | 6/2018 | Popp et al. |
| 2020/0098240 A1* | 3/2020 | Skaaksrud ......... B65D 25/02 |
| 2020/0100077 A1* | 3/2020 | Skaaksrud ......... B65D 25/02 |

\* cited by examiner

- Locations of Master Nodes M1, M2, and M3 are known
- Location of ID Nodes A and B are determined through triangulation across Master Nodes M1, M2 and M3

• Location of ID Node C determined through triangulation across ID Node B and Master Nodes M1 and M2

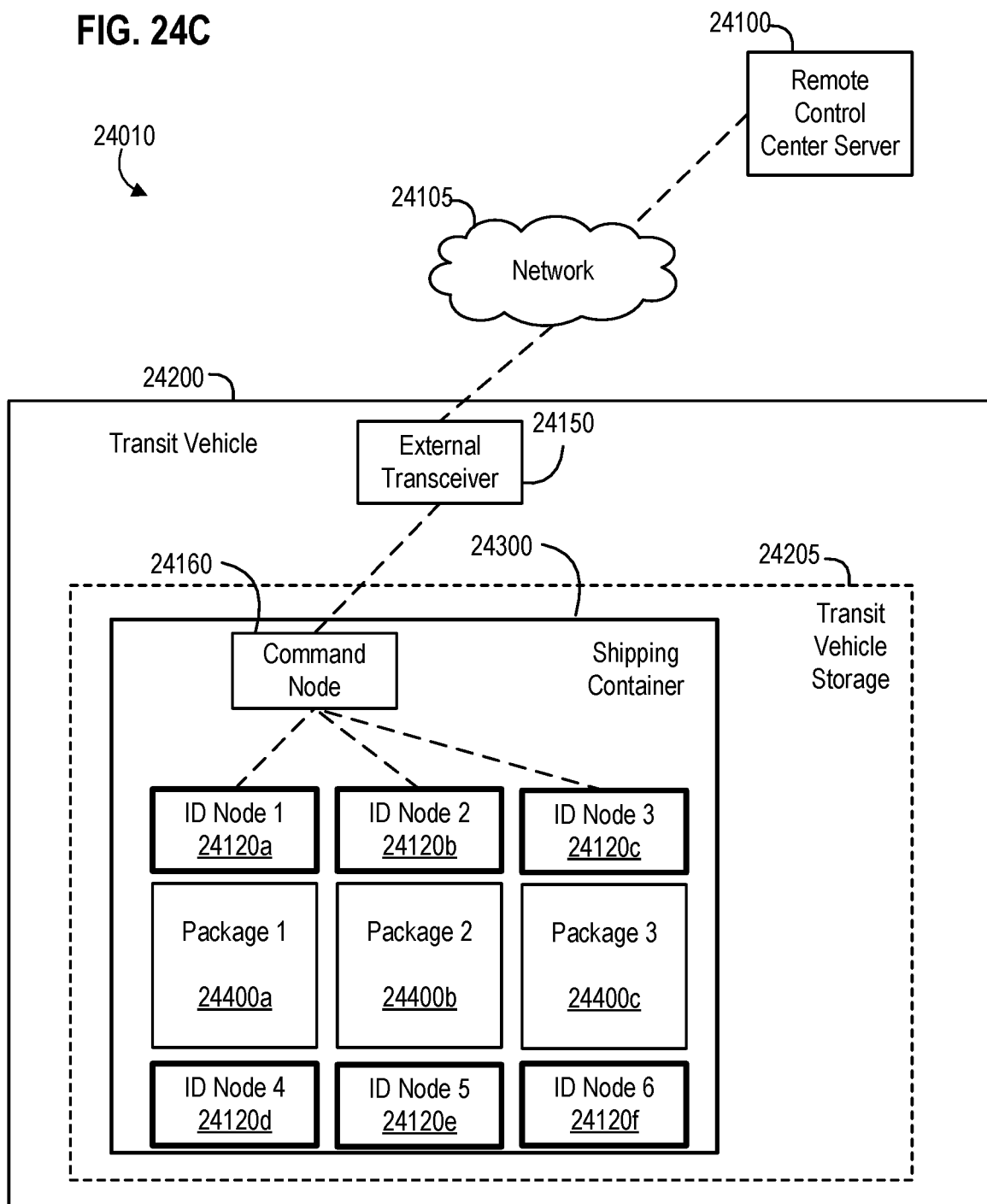

33000

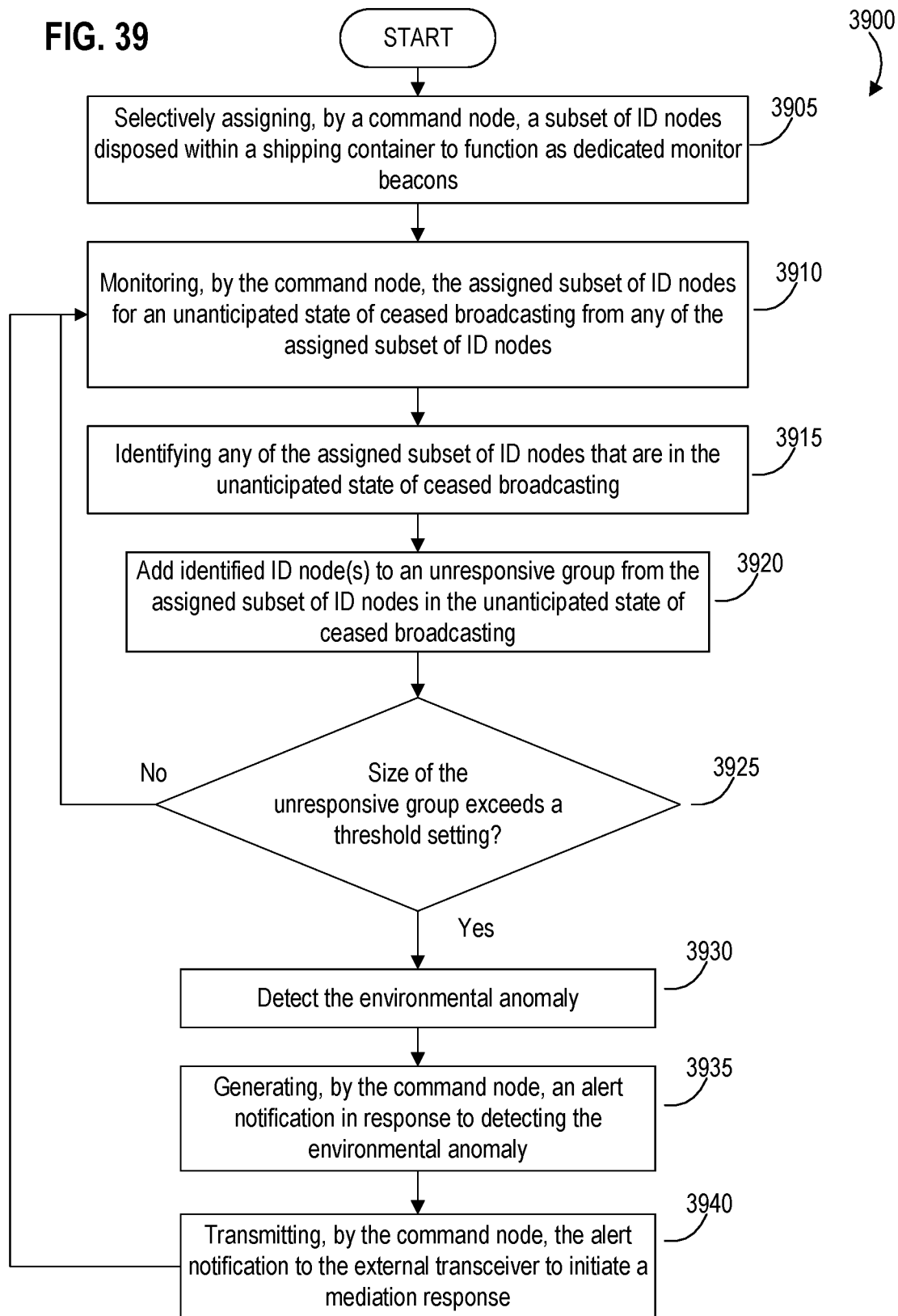

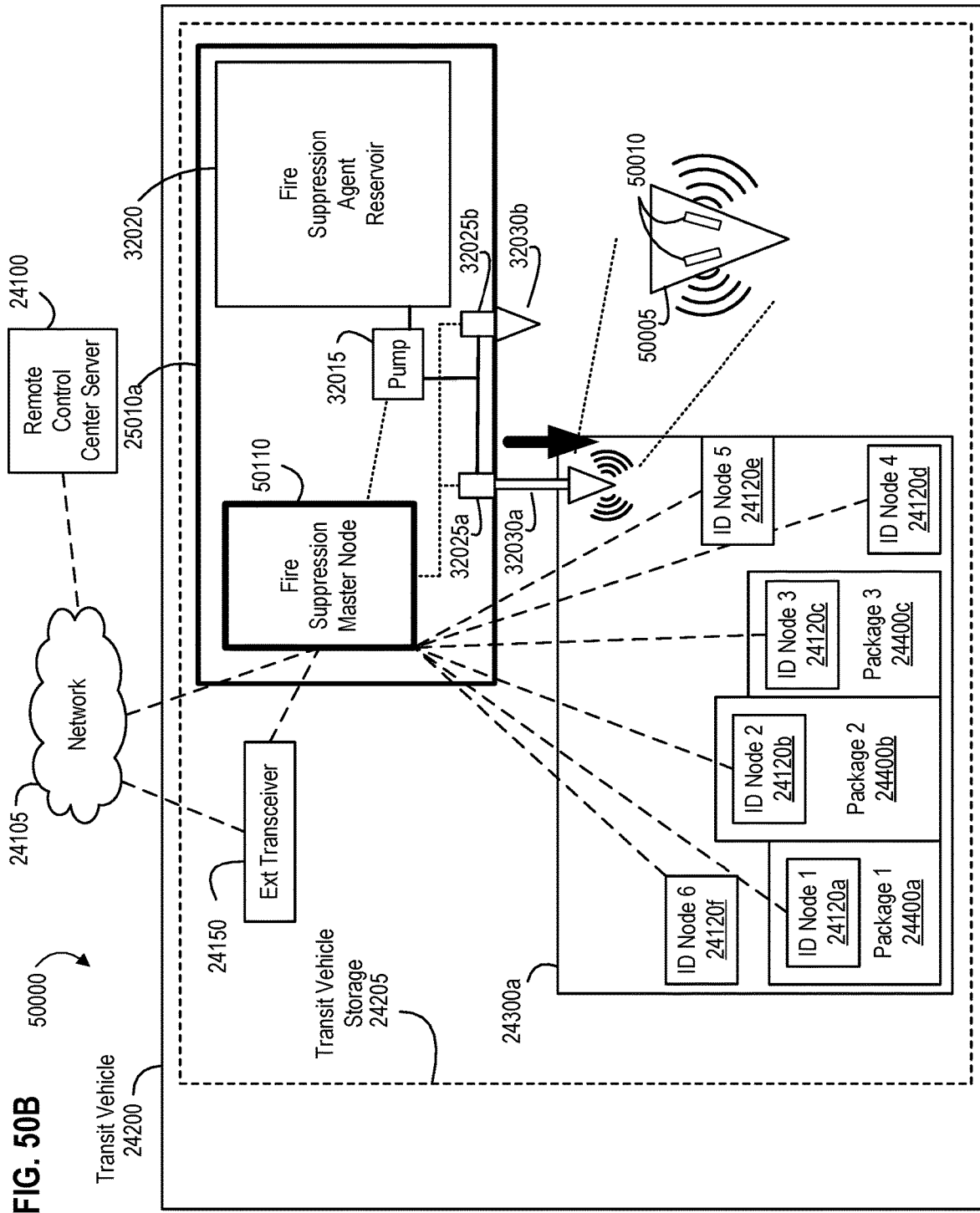

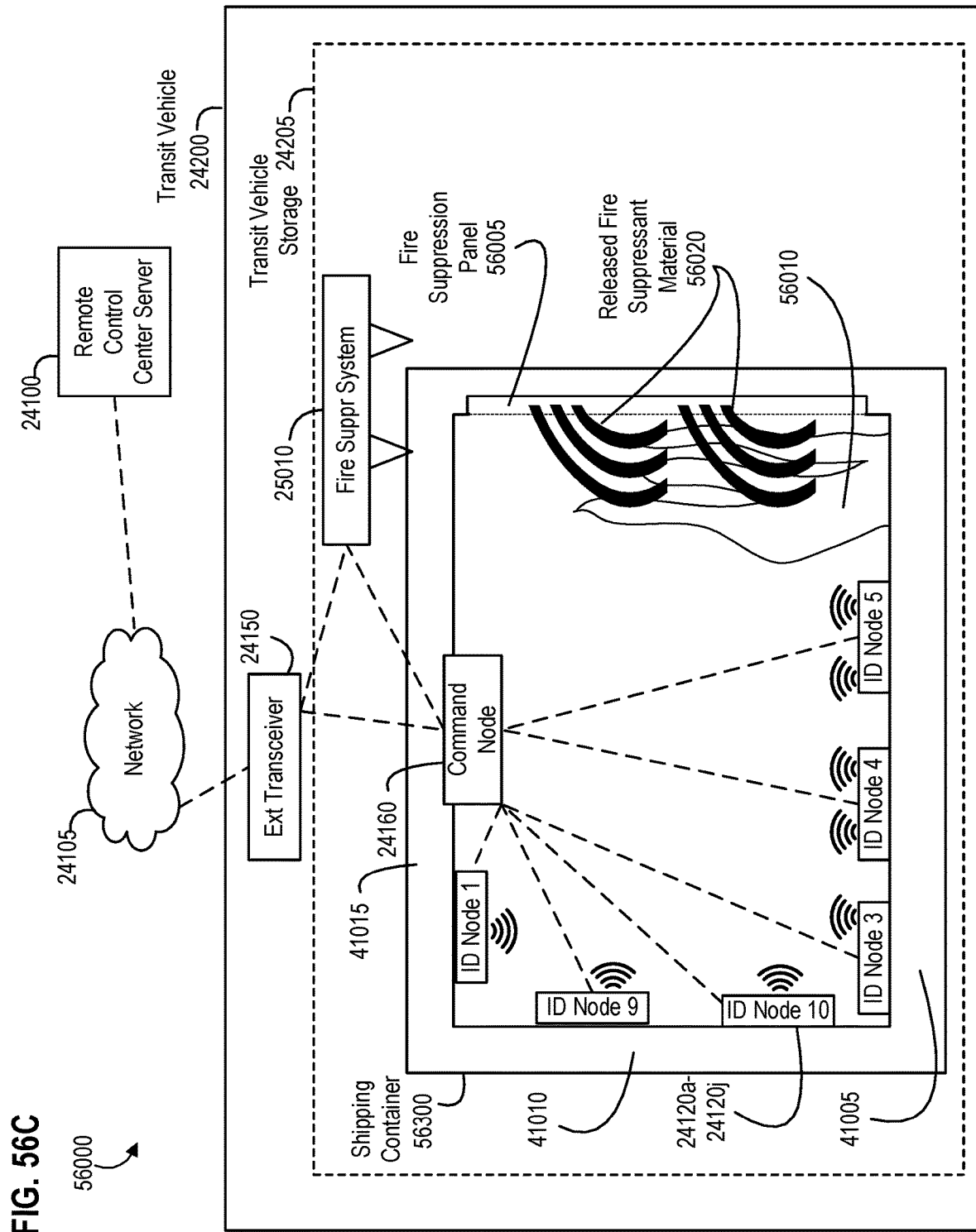

Node-Enhanced
Multi-Battery
Package
(NEMBP)

Node-Enhanced
Multi-Battery
Package
(NEMBP)

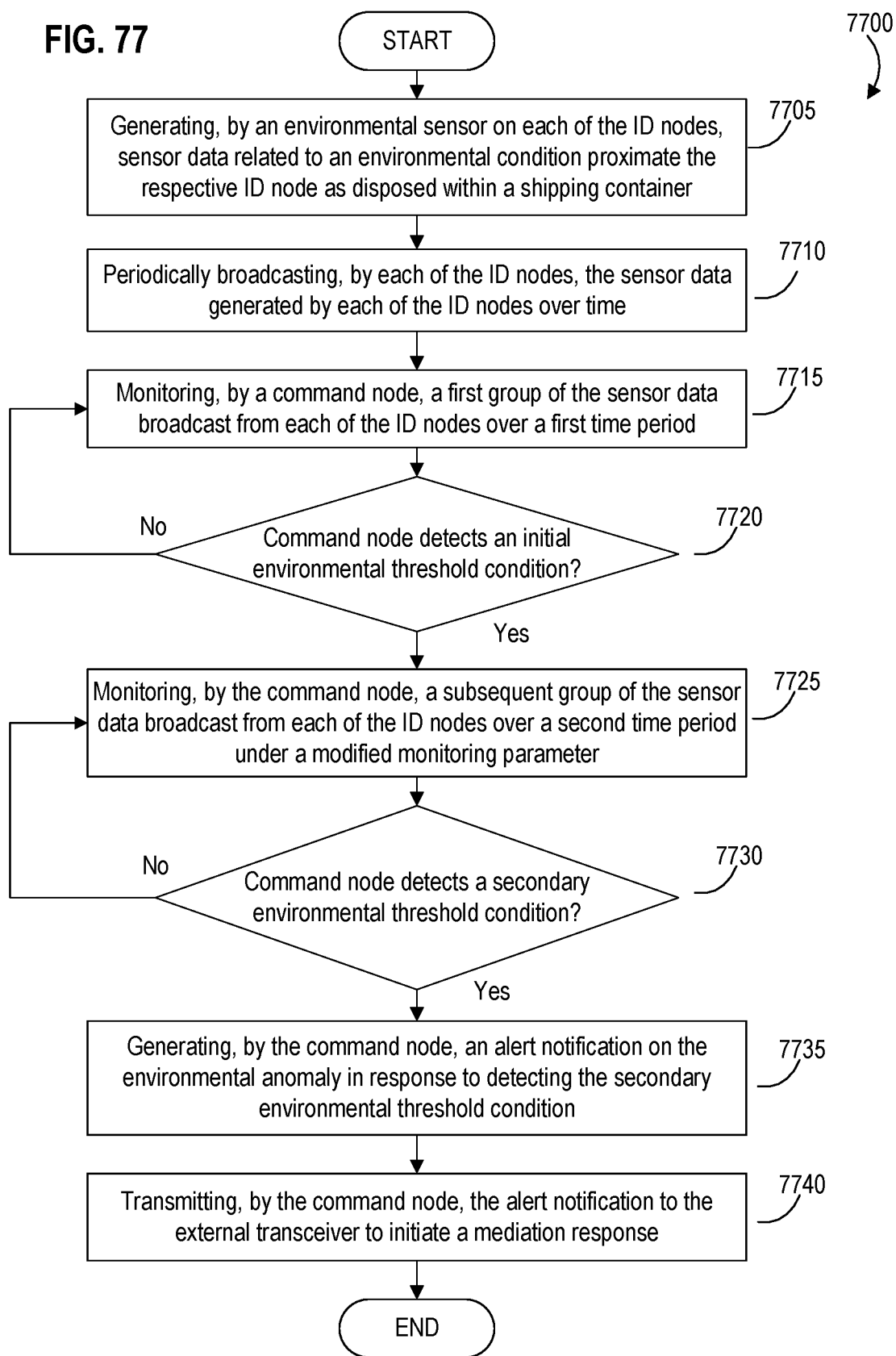

SYSTEMS FOR COORDINATED MEDIATION ACTION IN RESPONSE TO AN IDENTIFIED ENVIRONMENTAL ANOMALY ON A SHIPPING CONTAINER

PRIORITY AND RELATED APPLICATIONS

The present application hereby claims the benefit of priority to related U.S. Provisional Patent Application No. 62/735,075 and entitled "Improved Systems, Apparatus, and Methods for Detecting an Environmental Anomaly and Initiating an Enhanced Automatic Response Using Elements of a Wireless Node Network."

The present non-provisional application is also related in subject matter to the following U.S. non-provisional patent applications where each also claims the benefit of priority to the same above-referenced provisional patent application: (1) Non-Provisional Patent application Ser. No. 16/456,596, entitled "Improved Systems, Apparatus, and Methods for Detecting an Environmental Anomaly and Initiating an Enhanced Automatic Response Using Elements of a Wireless Node Network and Using Sensor Data from ID Nodes Associated with Packages and Environmental Threshold Conditions Per Package"; (2) Non-Provisional Patent application Ser. No. 16/456,671, entitled "Improved Systems, Apparatus, and Methods for Detecting an Environmental Anomaly and Initiating an Enhanced Automatic Response Using Elements of a Wireless Node Network Using ID Nodes and Environmental Threshold Conditions Per ID Node"; (3) Non-Provisional patent application Ser. No. 16/456,725, entitled "Improved Systems, Apparatus, and Methods for Detecting an Environmental Anomaly and Initiating an Enhanced Automatic Response Using Elements of a Wireless Node Network Including a Command Node Having a Command Node Environmental Sensor"; (4) Non-Provisional Patent application Ser. No. 16/456,800, entitled "Methods and Systems for Unresponsive ID Node Monitoring for an Environmental Anomaly"; (5) Non-Provisional patent application Ser. No. 16/508,591, entitled "Systems and Methods for Internal and External Monitoring for an Environmental Anomaly Within a Shipping Container and Reporting to an External Transceiver to Initiate a Mediation Response"; (6) Non-Provisional Patent application Ser. No. 16/508,647, entitled "Systems and Methods for Internal and External Monitoring for an Environmental Anomaly Within a Shipping Container with Responsive Reporting to an External Transceiver and Initiating a Mediation Response Directly with an Onboard Fire Suppression System"; (7) Non-Provisional Patent application Ser. No. 16/508,709 entitled "Methods, Systems, and Enhanced Shipping Container Apparatus Assembly for Monitoring for an Environmental Anomaly Using a Selectively Assigned Group of ID Nodes in a Wireless Node Network"; (8) Non-Provisional Patent application Ser. No. 16/508,763, entitled "Systems and Methods for Adaptively Monitoring for an Environmental Anomaly Using a Designated Bridging ID Node for a Remote Monitor Beacon"; (9) Non-Provisional Patent application Ser. No. 16/546,359, entitled "Enhanced Shipping Container Apparatus for Sensor-based Self-Monitoring, Detecting, and Reporting on an Environmental Anomaly"; (10) Non-Provisional patent application Ser. No. 16/546,376, entitled "Systems and Methods for Adaptive Monitoring for an Environmental Anomaly in a Shipping Container Using Elements of a Wireless Node Network"; (11) Non-Provisional Patent application Ser. No. 16/546,392, entitled "Dynamically Transitioning System for Monitoring a Shipping Container for an Environmental Anomaly Related to the Shipping Container"; (12) Non-Provisional Patent application Ser. No. 16/546,438, entitled "Enhanced Shipping Container Apparatus having Integrated Fire Suppression and Systems Using the Same for Detecting and Responding to an Environmental Anomaly within the Container"; (13) Non-Provisional Patent application Ser. No. 16/546,451, entitled "Node-enabled Battery Apparatus and Packaging Systems with Integrated Environmental Detection and Reporting, and Improved Systems for Coordinated Mediation Action in Response to an Environmental Anomaly Using the Same"; (14) Non-Provisional Patent application Ser. No. 16/546,483, entitled "Systems for Layered Initiation of a Mediation Response to a Battery-Related Environmental Anomaly within a Shipping Container;" (15) Non-Provisional Patent application Ser. No. 16/546,497, entitled "Systems, Apparatus, and Methods for Detecting and Verifying an Environmental Anomaly Using Multiple Command Nodes"; (16) Non-Provisional patent application Ser. No. 16/566,971, entitled "Systems and Methods for Securely Monitoring a Shipping Container for an Environmental Anomaly"; (17) Non-Provisional Patent application Ser. No. 16/566,999, entitled "Systems and Apparatus for Enhanced Detection of an Environmental Anomaly Related to a Shipping Container Using a Node-Enhanced Detection Blanket"; (18) Non-Provisional patent application Ser. No. 16/567,046, entitled "Systems and Methods for Adaptive Monitoring of a Shipping Container for an Environmental Anomaly"; and (19) Non-Provisional Patent application Ser. No. 16/567,096, entitled "Apparatus and Systems for Detecting an Environmental Anomaly Related to a Shipping Container Using a Package Command Node."

FIELD OF THE DISCLOSURE

The present disclosure generally relates to systems, apparatus and methods in the field of detecting an environmental anomaly onboard a container and responsively initiating an improved mediation response. In particular, the present disclosure relates to various aspects involving systems, apparatus and methods for improved environmental anomaly detection, related enhanced layered alerting as part of a mediated response, and initiating layered types of mediation responses to such an environmental anomaly using one or more elements of an adaptive, context-aware wireless node network.

BACKGROUND

Transporting items, objects, or materials (collectively and generally referred to herein as "packages" whether the items, objects, or materials are wrapped in packaging material or the items, objects, or materials are being shipped without packaging material) is an important part of commerce. In some instances, the type of item being transported may involve an item, object, or material that may be caustic, flammable, incendiary (e.g., easy to catch fire), or have a composition that inherently may pose some danger when transporting the item, object or material. For example, the transportation and shipment for certain types of batteries (e.g., lithium-based or lithium-ion batteries) may incur the risk of creating an environmental anomaly (such as a fire, explosion, chemical leak, or radiation leak).

Common monitoring techniques for monitoring the condition of what is being shipped within a shipping container may involve sensors remote from the shipping container. Such monitoring techniques and may be located too far away, which may cause a lag or undesirable delay in detecting any type of environmental anomaly associated with what is being shipped or just maintained within the shipping container (e.g., a unit load device (ULD) type of container, an intermodal shipping container, a palletized containment for shipping one or more packages, a storage facility that may temporarily maintain packages as a non-mobile type of shipping container, and the like). Such an environmental anomaly may involve extremely hot and caustic conditions that may rapidly spread. As a result, any delay in detecting such an environmental anomaly is inherently risky and adverse environmental conditions may rapidly intensify and spread so as to cause damage to the package, container, other packages in the container, other nearby containers, the transit vehicle transporting the container, and possible injury and loss of life to those operating the transit vehicle or manipulating the shipping container. Furthermore, any delay in assessing the risk from such an environmental anomaly as well as putting a mediation plan into action to address the environmental anomaly also increases the undesired severity of any environmental anomaly and its ability to rapidly intensify, spread so as to cause rapid damage to the package, container, other packages in the container, other nearby containers, the transit vehicle transporting the container, and possible injury and loss of life to those operating the transit vehicle or manipulating the shipping container Accordingly, those skilled in the art will appreciate that when transporting certain types of items, objects, and materials, the ability to quickly detect any environmental anomaly is important as time is of the essence. This is even more true when transporting packages (e.g., items, objects, materials) on aircraft where the existence of any environmental anomaly may be catastrophic in the damage it causes and loss of property and life due to any delay in detecting such an environmental anomaly, as well as any resulting delay in causing or initiating a response or mediation action to address the detected anomaly.

To address these requirements, a variety of systems, apparatus, and methods are needed that may improve and enhance environmental anomaly detection—especially, onboard a shipping container with one or more packages—and improve how to respond to such a detected environmental anomaly. Thus, there remains a need for improved systems, apparatus, and methods that may provide more extensive and robust detection of an environmental anomaly and automated generation of layered alerts and adaptive initiation of one or more mediation responses in a more timely and integrated manner than previously thought possible.

SUMMARY

In the following description, certain aspects and embodiments will become evident. It should be understood that the aspects and embodiments, in their broadest sense, could be practiced without having one or more features of these aspects and embodiments. It should be understood that these aspects and embodiments are merely exemplary.

One aspect of the disclosure relates to an improved system on a transit vehicle for coordinated mediation action in response to an identified environmental anomaly on a shipping container being transported by the transit vehicle (which has an external transceiver). The system includes multiple wireless ID nodes disposed at different locations within the shipping container. Each of the ID nodes is at a low level of a hierarchical wireless node network and respectively configured and operative to broadcast signals over a first wireless communication path. The system also includes a fire suppression system disposed on the transit vehicle transporting the shipping container. The system's fire suppression system has at least a fire suppressant material reservoir, a fire suppressant material pump, an articulating delivery nozzle, and a wireless transceiver-based controller. The fire suppressant material reservoir temporarily maintains a fire suppressant material. The fire suppressant material pump is connected to the fire suppressant material reservoir and responsive to a pump control input to activate pumping the fire suppressant material from the fire suppressant material reservoir. The articulating delivery nozzle is connected to the fire suppressant material pump, and receives the pumped fire suppressant material so that it can deploy such materials to deliver the fire suppressant material to the shipping container. The wireless transceiver-based controller operates as a master node at a middle level of the hierarchical wireless node network. As the master node, the controller is operative to generate the pump control input and cause the articulating delivery nozzle to deploy and deliver the fire suppressant material to the shipping container. As the master node, the controller is further configured to operate as a primary monitor for the environmental anomaly by being operative to: (a) wirelessly monitor the signals being broadcast from the ID nodes; (b) responsively identify the environmental anomaly based upon the monitored signals broadcast from the ID nodes; (c) generate a layered alert notification related to the environmental anomaly for the shipping container in response to identifying the environmental anomaly for the shipping container (where the layered alert notification identifies a targeted mediation action and establishes a mediation response priority); and (d) initiate a mediation response by the fire suppression system related to the targeted mediation action and the mediation response priority.

In another aspect of the disclosure, an improved system on a transit vehicle having an external transceiver is described for coordinated mediation action in response to an identified environmental anomaly on a shipping container being transported by the transit vehicle. The system in this aspect includes multiple wireless ID nodes and a fire suppression system. The wireless ID nodes are disposed at different locations within the shipping container, where each of the ID nodes is at a low level of a hierarchical wireless node network and each of the ID nodes is respectively configured and operative to broadcast signals over a first wireless communication path. The system's fire suppression system is disposed on the transit vehicle transporting the shipping container, and has a pressurized fire suppressant material container, a release nozzle, and a wireless transceiver-based controller. The pressurized fire suppressant material container temporarily maintains a fire suppressant material. The release nozzle is coupled to the pressurized fire suppressant material container where it receives the pressurized fire suppressant material and selectively opens to allow the fire suppressant material to flow from the pressurized fire suppressant material container, in response to an activation input signal, to deliver the fire suppressant material to the shipping container. The wireless transceiver-based controller in the fire suppression system operates as a master node at a middle level of the hierarchical wireless node network, and is operative to generate the activation input signal and cause the release nozzle to open and deliver the fire suppressant material to the shipping container. The wireless transceiver-based controller in the fire suppression system operating as the master node is further configured to operate as a primary monitor for the environmental anomaly by being operative to: (a) wirelessly monitor the signals being broadcast from the ID nodes; (b) responsively identify the environmental anomaly based upon the monitored signals broadcast from the ID nodes; (c) generate a layered alert notification related to the environmental anomaly for the shipping container in response to identifying the environmental anomaly for the shipping container (where the layered alert notification identifies a targeted mediation action and establishes a mediation response priority); and (d) initiate a mediation response by the fire suppression system related to the targeted mediation action and the mediation response priority.

Each of these aspects respectively effect improvements to the technology of monitoring for and detecting environmental anomalies and how to more robustly and quickly respond to any such detected environmental anomalies. Additional advantages of this and other aspects of the disclosed embodiments and examples will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments according to one or more principles of the invention and together with the description, serve to explain one or more principles of the invention. In the drawings.

FIG. 24C is a diagram of another exemplary wireless node network used for detecting environmental anomalies using a command node and ID nodes geographically dispersed within a shipping container in accordance with an embodiment of the invention;

FIG. 39 is a flow diagram illustrating an exemplary method for monitoring a shipping container for an environmental anomaly using a command node mounted to the shipping container and selective ones of a plurality of ID nodes disposed at different locations within the shipping container in accordance with an embodiment of the invention;

FIGS. 50A-50C are a series of diagrams of another exemplary onboard fire suppression system having an integrated master node and be activated and deployed on a transit vehicle for monitoring for an environmental anomaly and initiating a mediation action in response to a detected environmental anomaly related to a shipping container being transported on the transit vehicle in accordance with an embodiment of the invention;

FIGS. 56A-56D are a series of diagrams illustrating details of and operations involving an enhanced shipping container having at least one fire suppression panel and as used in an improved system for coordinated mediation action in response to an identified environmental anomaly related to the shipping container in accordance with an embodiment of the invention;

FIG. 77 is a flow diagram illustrating an exemplary adaptive method for monitoring a shipping container for an environmental anomaly using a wireless node network as a command node refines monitoring when detecting the environmental anomaly in accordance with an embodiment of the invention;

DESCRIPTION OF THE EMBODIMENTS

Figure 1:
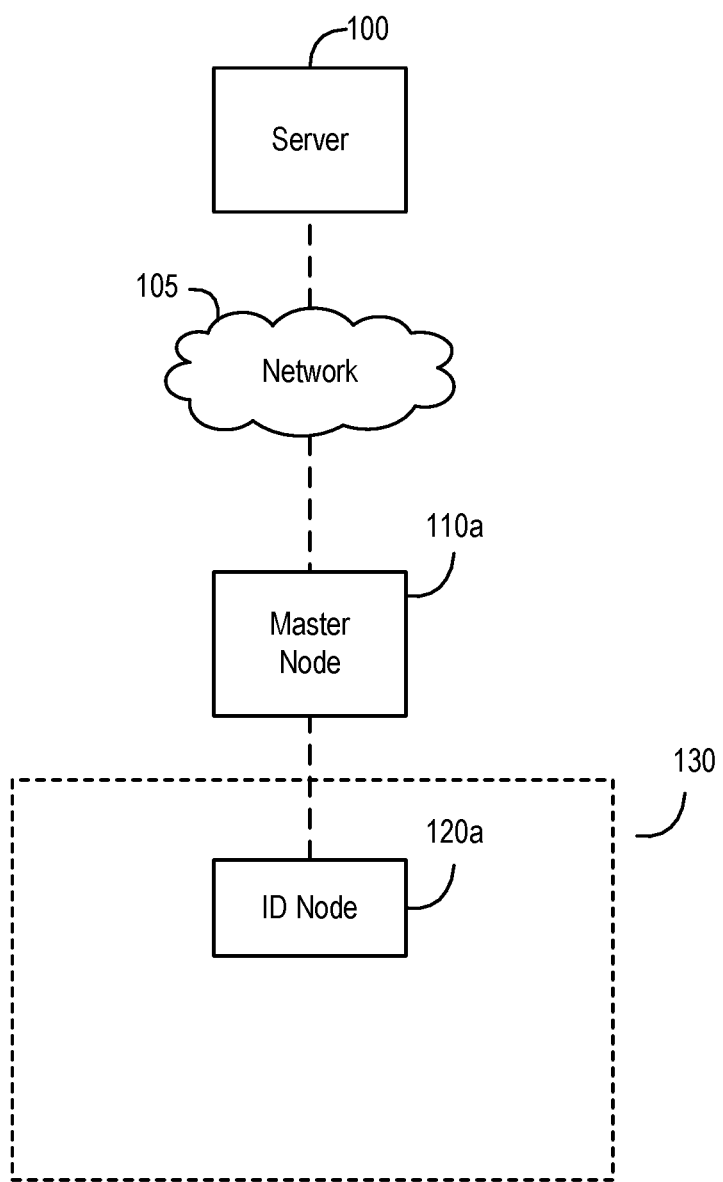
FIG. 1 is a diagram of an exemplary wireless node network in accordance with an embodiment of the invention.

Reference will now be made in detail to exemplary embodiments. Wherever possible, the same reference numbers are used in the drawings and the description to refer to the same or like parts.

In general, the following describes various embodiments of a contextually aware hierarchical wireless node network that may be managed, operated, and applied by principles as set forth herein as part of exemplary systems, apparatus, and methods involved with detecting environmental anomalies. In general, exemplary embodiments of the wireless node network may include various interconnected devices. For example, there may be one or more lower level devices or nodes (e.g., an ID node not having a sensor or a sensor-based ID node) that rely on shorter-range communication with a mid-level device or node (e.g., a master node capable of self-locating or a command node that may not have self-location circuitry onboard), which is operative to communicate with a higher level device (e.g., a transceiver that is part of a transit vehicle but disposed external to shipping containers on the vehicle) over a different communication path while the lower and mid-level node is unable to communicate directly with the higher level device. In some embodiments of the network, a further higher level device (e.g., a remote control center or remote server) may be in communication with one or more of the higher level devices (e.g., the external transceiver on the transit vehicle) below it in the network.

Those skilled in the art will appreciate that such a hierarchy of different functional communicating network components (generally referred to as network devices) may be characterized as a network of nodes. Those skilled in the art will appreciate that in some embodiments, the wireless node network may include the external transceiver and/or remote server as well as different wireless nodes despite the fact that the external transceiver and/or remote server may not be a dedicated wireless component. In other embodiments, the network may include similar types of wireless nodes or different types of wireless nodes.

Further, those skilled in the art will appreciate that each embodiment described herein effects improvements to particular technologies, such as enhancing and improving how to quickly and automatically detect an environmental anomaly as well as providing an enhanced method of initiating an automatic mediation response to the detected environmental anomaly that helps avoid damage to property being shipped, vehicles transporting such property, and helping to avoid loss of life due to such an environmental anomaly using an adaptive, context-aware wireless node network of node elements. Each embodiment describes a specific technological application of one or more nodes that operate in such a wireless node network where the specific technological application improves or otherwise enhances such technical fields as explained and supported by the disclosure that follows.

Those skilled in the art will understand through the following detailed description that the nodes may be associated with items, objects, or materials (collectively and generally referred to herein as "packages") or be disposed near such packages and may be used to identify and locate the packages, detect a surrounding environmental condition near the node and/or package while being dynamically programmed during operation of the network and while the packages may be loaded, unloaded, and during transport alone or within a shipping container (such as a ULD type of container). The following further describes various embodiments of a wireless node network, exemplary ways to monitor and manage components of a wireless node network, exemplary ways to better determine the location of components of a wireless node network, and applications of a wireless node network to enhance logistics operations that rely upon a wireless node network that can improve the detection of an environmental anomaly, provide enhanced layered alerting as part of a mediated response to the detected anomaly, cause or initiate layered types of mediation responses to such an environmental anomaly, and conduct such mediation responses in a targeted, selective, and rapid manner so as to improve the safety of transporting any such packages.

Wireless Node Networks

FIG. 1 illustrates a basic diagram of an exemplary wireless node network in accordance with an embodiment of the invention. The exemplary network shown in FIG. 1 comprises a server 100 connected to a network 105, which is also operatively connected to different network components, such as a master node 110a and indirectly to an ID node 120a through master node 110a. Master node 110a is typically connected to an ID node 120a via short-range wireless communications (e.g., Bluetooth® formatted communications). Master node 110a is typically connected to server 100 through network 105 via longer-range wireless communication (e.g., cellular) and/or medium range wireless communication (e.g., wireless local area data networks or Wi-Fi). ID node 120a is typically a low cost device that may be easily placed into a package, be integrated as part of packaging, or otherwise associated with an item to be tracked and located, such as package 130, a person, or object (e.g., vehicle, etc.). As shown in FIG. 1, an ID node is generally capable of communicating directly with a master node but incapable of communicating directly with the server, while a master node is capable of communicating directly with the server and separately and directly communicating with other nodes (such as an ID node or another master node). Additional exemplary wireless node networks may include additional nodes (such as type of master node referred to as a command node, and a further network element referred to as an external transceiver associated with a transit vehicle). The ability to deploy a hierarchy of nodes within an exemplary wireless node network to distribute tasks and functions at the different levels in an efficient and economical manner helps to facilitate a wide variety of adaptive locating, tracking, managing, monitoring, detecting, reporting, and mediation responsive applications using such a network of nodes as discussed in more detail below.

In general, the lower cost, lower complexity ID node 120a is managed by the higher complexity master node 110a and server 100 as part of keeping track of the location of ID node 120a (and the associated item), thereby providing intelligent, robust, and broad visibility about the location and status of ID node 120a. In a typical embodiment, ID node 120a is first associated with an item (e.g., package 130, a person, or object). As ID node 120a moves with the item, the ID node 120a becomes associated with the master node 110a, and the server 100 is updated with such information. Further movement of the ID node 120a and item may cause the ID node 120a to disassociate with master node 110a and be handed off to become associated another master node (not shown), after which the server 100 is again updated. As such, the server 100 generally operates to coordinate and manage information related to the ID node 120a as the item physically moves from one location to another. Further details of the architecture and functionality of an embodiment of an exemplary ID node and master node as described below in more detail with respect to FIGS. 3 and 4, while exemplary server 100 is described below in more detail with respect to FIG. 5.

While server 100 is shown connecting through network 105, those skilled in the art will appreciate that server 100 may have a more direct or dedicated connections to other components illustrated in FIG. 1, such as master node 110a, depending upon implementation details and desired communication paths. Furthermore, those skilled in the art will appreciate that an exemplary server may contain a collection of information in a database (not shown in FIG. 1), while multiple databases maintained on multiple server platforms or network storage servers may be used in other embodiments to maintain such a collection of information. Furthermore, those skilled in the art will appreciate that a database may be implemented with cloud technology that essentially provides networked storage of collections of information that may be directly accessible to devices, such as master node 110a.

Network 105 may be a general data communication network involving a variety of communication networks or paths. Those skilled in the art will appreciate that such exemplary networks or paths may be implemented with hard wired structures (e.g., LAN, WAN, telecommunication lines, telecommunication support structures and telecommunication processing equipment, etc.), wireless structures (e.g., antennas, receivers, modems, routers, repeaters, etc.) and/or a combination of both depending upon the desired implementation of a network that interconnects server 100 and other components shown in FIG. 1 in an embodiment of the present invention.

Master node 110a and ID node 120a are types of nodes. A node is generally an apparatus or device used to perform one or more tasks as part of a network of components. An embodiment of a node may have a unique identifier, such as a Media Access Control (MAC) address or an address assigned to a hardware radio like an Internet Protocol 6 (IPv6) identifier. In some embodiments, the node's unique identifier may be correlated to a shipment identifier (e.g., a shipment tracking number in one example), or may itself be a shipment's tracking reference.

An ID node, such as ID node 120a, is generally a low cost active wireless device. In one embodiment, an exemplary ID node is a transceiver-based processing or logic unit having a short-range radio with variable RF characteristics (e.g., programmable RF output power range, programmable receiver sensitivity), memory accessible by the processing unit, a timer operatively coupled to the processing unit, and a power source (e.g., a battery) that provides power for the circuitry of the ID node. For example, the physical implementation of an exemplary ID node may be small, and, thus, amenable to integration into a package, label, container, or other type of object. In some implementations of an ID node, the node is rechargeable while other implementations do not permit recharging the power source for the ID node. In other implementations, the ID node is environmentally self-contained or sealed so as to enable robust and reliable operations in a variety of environmentally harsh conditions.

A master node, such as master node 110a, generally serves as an intelligent bridge between the ID node 120a and the server 100. Accordingly, a master node is generally more sophisticated than an ID node. In one example embodiment, an exemplary master node is a device having a processing or logic unit, a short-range radio (with may have variable RF characteristics) used for communicating with other nodes (ID nodes and other master nodes), a medium and/or long-range radio for communication with the server 100, memory accessible by the processing unit, a timer operatively coupled to the processing unit, and a power source (e.g., a battery or a wired power supply connection) that provides power for the circuitry of the master node. The exemplary master node, such as master node 110a, may be positioned in a known fixed location or, alternatively, be a mobile unit having dedicated location positioning circuitry (e.g., GPS circuitry) to allow the master node to determine its location by itself.

While the embodiment illustrated in FIG. 1 shows only a single master node and a single ID node, those skilled in the art will appreciate that a wireless network consistent with an embodiment of the invention may include a wide array of similar or different master nodes that each communicate with the server 100 and/or other master nodes, and a wide variety of similar or different ID nodes. Thus, the exemplary network shown in FIG. 1 is a basic embodiment, while the exemplary network shown in FIG. 2 is a more detailed exemplary wireless node network in accordance with another embodiment of the invention.

Figure 2:
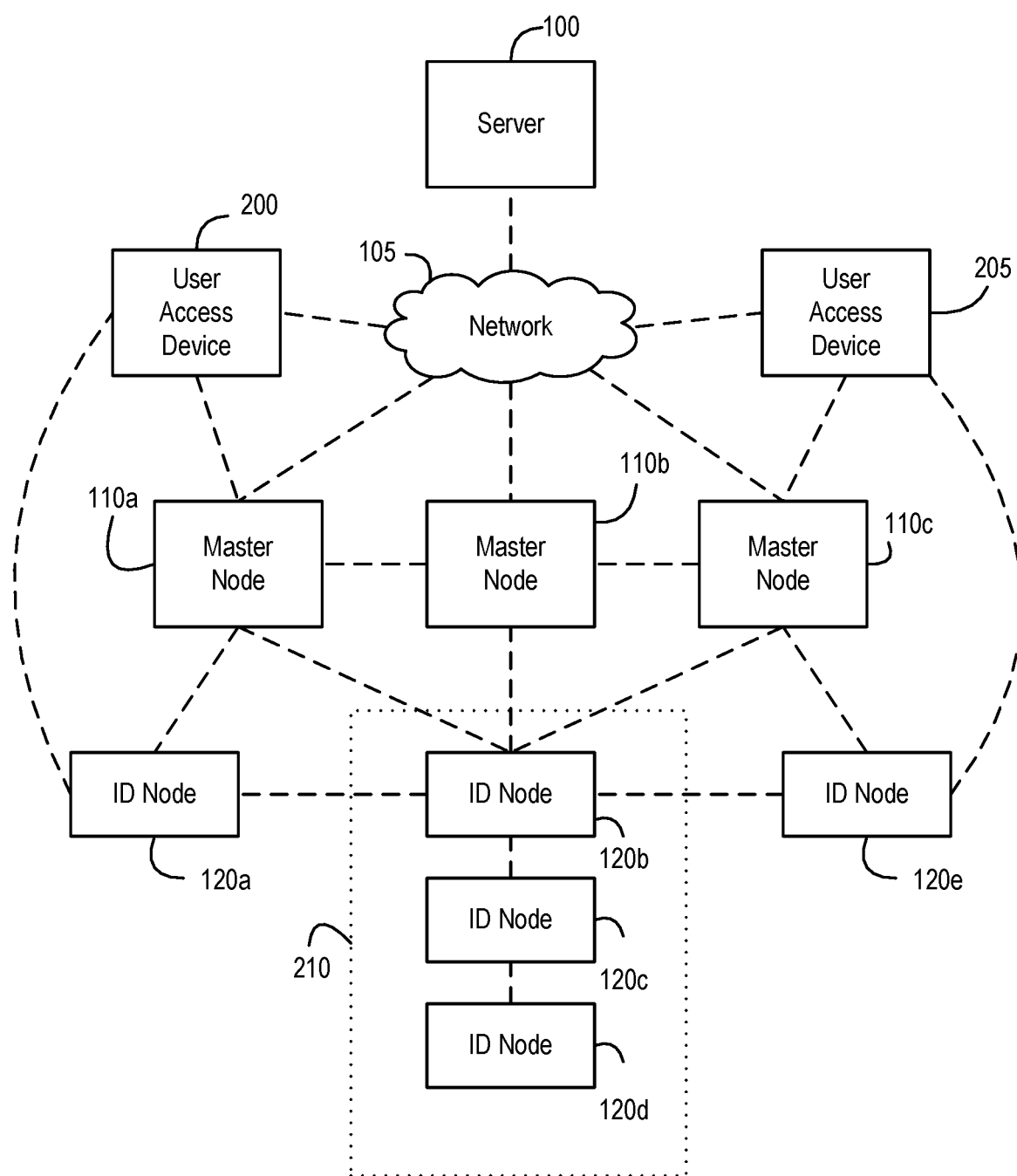
FIG. 2 is a more detailed diagram of an exemplary wireless node network in accordance with an embodiment of the invention.

Referring now to FIG. 2, another exemplary wireless node network is shown including server 100 and network 105. Here, master nodes 110a, 110b, 110c are deployed and connected to network 105 (and by virtue of those respective connections, to server 100) as well as to each other. ID nodes 120a, 120b, 120e are shown as connectable or operative to communicate via different paths to various master nodes. However, ID nodes 120c and 120d are shown in FIG. 2 connected to ID node 120b but not to any of the master nodes. This may be the case if, for example, ID nodes 120b, 120c, 120d are associated with different items (e.g., packages) within a larger container 210 (or grouped together on a pallet). In such an example, only ID node 120b may remain within the wireless communication range of any master node. This may, for example, be because of the positions of the different ID nodes within the container relative to the closest master node, adverse RF shielding caused by the container, adverse RF shielding caused by packaging of the item, or adverse RF shielding caused by other proximate material that interferes with radio transmissions (e.g., several packages of metal items between the ID node and any master node outside the container). Thus, in the illustrated configuration of the exemplary network shown in FIG. 2, ID nodes 120c and 120d may be out of range from the master nodes, yet still have an operative communication path to a master node through ID node 120b.

Indeed, in one example, prior to placement within container 210, ID node 120b may actually be a master node but the changed RF environment when placing it in container 210 may interfere with the master node's ability to locate itself via location signals (e.g., GPS signals) and cause the master node to temporarily operate as an ID node while still providing communications and data sharing with other ID nodes in container 210.

User access devices 200, 205 are also illustrated in FIG. 2 as being able to connect to network 105, master nodes, and ID nodes. Generally, user access devices 200 and 205 allow a user to interact with one or more components of the exemplary wireless node network. In various embodiments, user access devices 200, 205, may be implemented using a desktop computer, a laptop computer, a tablet (such as an Apple iPad® touchscreen tablet), a personal area network device (such as a Bluetooth® device), a smartphone (such as an Apple iPhone®), a smart wearable device (such as a Samsung Galaxy Gear™ smartwatch device, or a Google Glass™ wearable smart optics) or other such devices capable of communicating over network 105 with server 100, over a wired or wireless communication path to master node and ID nodes. Thus, an exemplary user access device may be a mobile type of device intended to be easily moved (such as a tablet or smartphone), and may be a non-mobile type of device intended to be operated from a fixed location (such as a desktop computer).

As shown in FIG. 2, user access devices 200, 205 are coupled and in communication with network 105, but each of them may also be in communication with each other or other network components in a more direct manner (e.g., via near field communication (NFC), over a Bluetooth® wireless connection, over a Wi-Fi network, dedicated wired connection, or other communication path).

In one example, a user access device, such as device 200 or 205, may facilitate associating an ID node (such as ID node 120a) with the tracking number of a package at the start of a shipment process, coordinating with the server 100 to check on the status and/or location of the package and associated ID node during transit, and possibly retrieving data from a master node or ID node related to the shipped package. Thus, those skilled in the art will appreciate that a user access device, such as devices 200, 205, are essentially interactive communication platforms by which a user may initiate shipment of an item, track an item, determine the status and location of an item, and retrieve information about an item.

An exemplary user access device, such as device 200 or 205, may include sufficient hardware and code (e.g., an app or other program code section or sections) to operate as a master node or an ID node in various embodiments as discussed in more detail below. For example, device 200 may be implemented as a mobile smartphone and functionally may operate as an exemplary ID node that broadcasts advertising packet messages to other ID nodes or master nodes for association and sharing data with such nodes. In another example, device 200 is implemented as a mobile smartphone and may operate as an exemplary master node that communicates and associates with ID nodes and other master nodes, as described herein, and communicates with the server 100. Thus, those skilled in the art will appreciate an exemplary ID node in FIG. 3 and an exemplary master node in FIG. 4, and their respective parts, code and program modules, may be implemented with an appropriately programmed user access device, such as device 200 or 205. Thus, the following description of an exemplary ID node in FIG. 3 and an exemplary master node in FIG. 4 will be applicable to a user access device operating as an ID node or a master node, respectively.

ID Node

Figure 3:
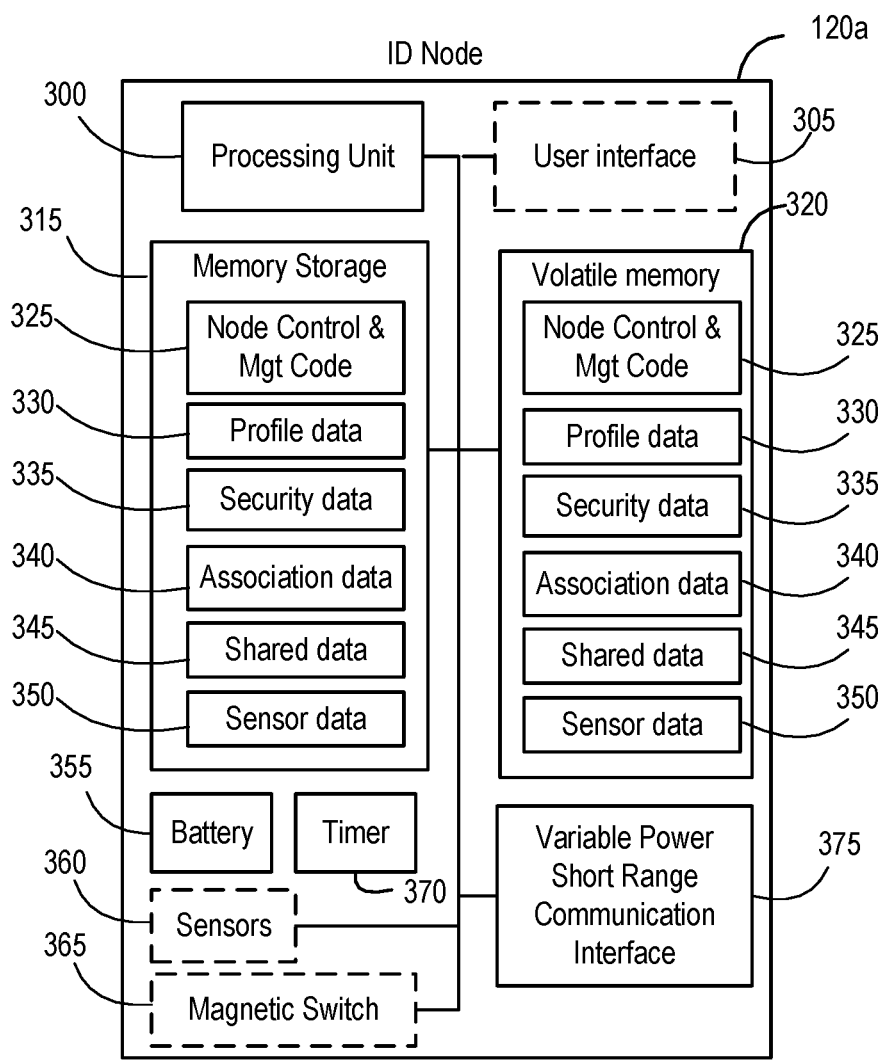
FIG. 3 is a more detailed diagram of an exemplary ID node device in accordance with an embodiment of the invention.

FIG. 3 is a more detailed diagram of an exemplary ID node device in accordance with an embodiment of the invention where components of the ID node device are shown as disposed within an ID node enclosure for housing such a device. In general, the node enclosure is used to house the components of the ID node and may be made from an environmentally resistant material so as to survive harsh environments resulting from, for example, temperature, pressure, chemical leaks, and/or radiation leaks. However, in some embodiments, the ID node enclosure may be a purposefully selected environmentally sensitive material that breaks down when exposed to a particular harsh environmental condition (e.g., breaking down when exposed to a predetermined threshold temperature corresponding to a threshold condition indicative of an environmental anomaly). For example, the ID node enclosure may be made from temperature sensitive materials that may expose one or more of the ID node's main components (e.g., its processor, battery, memory, wireless transceiver) when the ID node is deployed in a very high temperature environment. Further, the ID node enclosure may use a temperature sensitive material with a higher melting point so that failure of the ID node with that type of enclosure may be indicative of a secondary environmental condition at a predetermined threshold temperature above a temperature corresponding to a threshold condition for the environmental anomaly. Thus, the type of material used for a particular ID node's enclosure may be selectively chosen as part of apparatus and systems that monitor, detect, and respond to environmental anomalies.

As previously described, one embodiment of an ID node includes a transceiver-based processing or logic unit (processor) having a short-range radio with variable RF characteristics (e.g., programmable RF output power range, programmable receiver sensitivity), memory accessible by the processing unit, a timer operatively coupled to the processing unit, and a power source (e.g., a battery) that provides power for the circuitry of the ID node. Referring now to the more detailed embodiment of FIG. 3, exemplary ID node 120a is shown to comprise a processing or logic unit 300 coupled to a variable power short-range communication interface 375, memory storage 315, volatile memory 320, timer 370, and battery 355. Those skilled in the art will appreciate that processing unit 300 is logic, such as a low power consumption microcontroller, that generally performs computations on data and executes operational and application program code and other program modules or sections thereof within the ID node 120a. As such, exemplary processing unit 300 operates as a transceiver-based processing core of ID node 120a.

Those skilled in the art will also appreciate that exemplary ID node 120a is a hardware-based component that may be implemented with a single processor or logic unit, such as unit 300. In one embodiment, processing unit 300 may be implemented with an Intel® 8051 CPU Core and associated peripheral circuitry as dictated by the needs of the particular application. Less complex microcontrollers or discrete circuitry may be used to implement processing unit 300 as well as more complex and sophisticated microprocessors. Additionally, exemplary processing unit 300 may be integrated into a single chip transceiver used as a core of ID node 120a.

The variable power short-range communication interface 375 of ID node 120a is generally a programmable radio and an omni-directional antenna coupled to the processing unit 300. In other embodiments, interface 375 may use an antenna with a different antenna profile when directionality may be desired. Those skilled in the art will appreciate that short-range communication interface 375 may be implemented with hardware, implemented with a combination of hardware and software, as well as implemented as a software-defined radio (SDR). Examples of variable power short-range communication interface 375 may include other interfacing hardware or software elements (not shown) for operatively coupling the device to a specific short-range communication path (e.g., a Bluetooth® Low Energy (BLE) connection path communicating at 2.4 GHz).

In one embodiment, various RF characteristics of the radio's transceiver, such as the RF output power and/or the RF receiver sensitivity may be dynamically and programmatically varied under control of processing unit 300. In other embodiments, further RF characteristics of the radio's transceiver may be programmatically varied, such as frequency, duty cycle, timing, modulation schemes, spread spectrum frequency hopping aspects, etc., as needed to flexibly adjust the RF output signal depending upon a desired implementation and anticipated use of ID node 120a. As will be explained in more detail below, some embodiments may use Broadcast Profile having parameters that may be programmatically altered or adjusted. In other words, embodiments of ID node 120a (or any other ID node) may have programmatically adjustable RF characteristics (such as an adjustable RF output signal power, an adjustable RF receiver sensitivity, the ability to switch to a different frequency or frequency band, etc.).

In any of the embodiments described herein, communication interface 375 may be implemented as a wireless transceiver-based communication interface with both short-range and longer range communication capabilities (i.e., may function as both a first and second communication interface as described in the various embodiments herein). This type of wider range communication interface 375 may be implemented using LPWAN (Low Power Wide Area Network) connectivity, such as LTE 5G, LTE-M, and NB-IOT (NarrowBand IoT). LPWAN, also commonly referred to low-power wide-area (LPWA) network or just low-power network (LPN), is a type of wide-area network wireless communication format that allows for extended range, low-bandwidth communications for power sensitive application, such as with devices that are battery powered devices (e.g., ID nodes, mobile master nodes, container nodes, command nodes, and the like). Exemplary types of LPWAN may include ultra-narrowband (UNB) technology from Sigfox, random phase multiple access (RPMA) technology from Ingenu, and other long-range WAN protocol (LoRaWAN) technology as promoted by the LoRa Alliance of companies (e.g., IBM, MicroChip, Cisco, Semtech, Singtel, KPN, Bouygues Telecom). LTE-M is a communication technology that allows a node-based device (such as a sensor-based ID node or command node) to directly connect to a Long Term Evolution (4G) cellular network without a gateway and on batteries. NB-IOT is a low-power communication technology that applies a narrowband approach to cellular IoT (Internet of Things) communications allowing for usage of parts of the GSM spectrum bandwidth in unused 200 kHz bands.

The battery 355 for ID node 120a is a type of power source that generally powers the circuitry implementing ID node 120a. In one embodiment, battery 355 may be a rechargeable power source. In other embodiments, battery 355 may be a non-rechargeable power source intended to be disposed of after use. In some embodiments of an ID node, the power source may involve alternative energy generation, such as a solar cell.

The timer 370 for ID node 120a generally provides one or more timing circuits used in, for example, time delay, pulse generation, and oscillator applications. In an embodiment where ID node 120a conserves power by entering a sleep or dormant state for a predetermined time period as part of overall power conservation techniques, timer 370 assists processing unit 300 in managing timing operations. Additionally, an embodiment may allow an ID node to share data to synchronize different nodes with respect to timer 370 and a common timing reference between nodes and the server.

An embodiment may implement ID node 120a to optionally include a basic user interface (UI) 305 indicating status and allowing basic interaction like start/stop. In one embodiment, the UI 305 may be implemented with status lights, such as multi-mode LEDs. Different colors of the lights may indicate a different status or mode for the ID node 120*a* (e.g., an advertising mode (broadcasting), a scanning mode (listening), a current power status, a battery level status, an association status, an error, as sensed condition (e.g., exceeding a temperature threshold, exceeding a moisture threshold, and the like)). Other embodiments of an ID node may implement UI 305 in a more sophisticated manner with a graphics display or the like where such status or mode information may be displayed as well as one or more prompts.

In a further embodiment, an exemplary status light used as part of the UI 305 of an ID node may also indicate a shipment state. In more detail, an exemplary shipment state may include a status of the shipped item or a status of the item's current shipment journey from an origin to a destination.

An embodiment may also implement ID node 120*a* to optionally include one or more sensors 360. In some embodiments, an ID node implemented with one or more sensors 360 may be referred to as a sensor node or sensor-based ID node. Examples of sensor 360 may include one or more environmental sensors (e.g., pressure, movement, light, temperature, humidity, chemical, radiation, magnetic field, altitude, attitude, orientation, acceleration, etc.) and dedicated location sensors (e.g., GPS sensor, IR sensor, proximity sensor, etc.). Those skilled in the art will understand that additional types of sensors that measure other characteristics are contemplated for use as sensor 360. Additionally, those skilled in the art will understand that a sensor node or sensor-based ID node may include additional program features to manage the detection, collection, storage, sharing, and publication of the captured sensor data.

An embodiment may further implement ID node 120*a* to optionally include one or more magnetic switches 365. A magnetic switch 365, such as a reed switch, generally operates to close or open an electrical path or connection in response to an applied magnetic field. In other words, magnetic switch 365 is actuated by the presence of a magnetic field or the removal of a magnetic field. Various applications, as discussed in embodiments described in more detail below, may involve the operation of ID node 120*a* having magnetic switch 365.

Consistent with the embodiment shown in FIG. 3, exemplary ID node 120*a* may be implemented based upon a Texas Instruments CC2540 Bluetooth® Low Energy (BLE) System-on-Chip, which includes various peripherals (e.g., timer circuitry, USB, USART, general-purpose I/O pins, IR interface circuitry, DMA circuitry) to operate as an ID node and, if necessary, to interface with different possible sensors and other circuitry (e.g., additional logic chips, relays, magnetic switches) that make up the ID node.

In additional embodiments, one skilled in the art will appreciate that similar functionality in an ID node may be implemented in other types of hardware. For example, ID node 110*a* may be implemented with specially optimized hardware (e.g., a particular application specific integrated circuit (ASIC) having the same operational control and functionality as node control and management code, as described below, discrete logic, or a combination of hardware and firmware depending upon requirements of the ID node, such as power, processing speed, level of adjustability for the RF characteristics, number of memory storage units coupled to the processor(s), cost, space, etc.

As noted above, ID node 120*a* includes memory accessible by the processing unit 300. Memory storage 315 and volatile memory 320 are each operatively coupled to processing unit 300. Both memory components provide programming and data elements used by processing unit 300. In the embodiment shown in FIG. 3, memory storage 315 maintains a variety of program code (e.g., node control and management code 325) and other data elements (e.g., profile data 330, security data 335, association data 340, shared data 345, sensor data 350, and the like). Memory storage 315 is a tangible, non-transient computer readable medium on which information (e.g., executable code/modules, node data, sensor measurements, etc.) may be kept in a non-volatile and non-transitory manner. Examples of such memory storage 315 may include a hard disk drive, ROM, flash memory, or other media structure that allows long term, non-volatile storage of information. In contrast, volatile memory 320 is typically a random access memory (RAM) structure used by processing unit 300 during operation of the ID node 120*a*. Upon power up of ID node 120*a*, volatile memory 320 may be populated with an operational program (such as node control and management code 325) or specific program modules that help facilitate particular operations of ID node 120*a*. And during operation of ID node 120*a*, volatile memory 320 may also include certain data (e.g., profile data 330, security data 335, association data 340, shared data 345, sensor data 350, and the like) generated as the ID node 120*a* executes instructions as programmed or loaded from memory storage 315. However, those skilled in the art will appreciate that not all data elements illustrated in FIG. 3 must appear in memory storage 315 and volatile memory 320 at the same time.

Node Control & Management Code

Generally, an embodiment of node control and management code 325 is a collection of software features implemented as programmatic functions or program modules that generally control the behavior of a node, such as ID node 120*a*. In an embodiment, the functionality of code 325 may be generally similar as implemented in different types of nodes, such as a master node, an ID node, and a sensor node. However, those skilled in the art will appreciate that while some principles of operation are similar between such nodes, other embodiments may implement the functionality with some degree of specialization or in a different manner depending on the desired application and use of the node. In other words, node control and management code 325 may also include further program code specific for ID node functionality described in the embodiments described in more detail below that use an ID node. As such, the collective code executing on an ID node, such as ID node 120*a* (or any of the other implementations of ID nodes as described herein), acts to programmatically configure the ID node beyond that of a generic processing device in order to be specially adapted, via such program code, to be operative to function unconventionally—whether alone with the specific functionality described herein or as part of a system.

In a general embodiment, exemplary node control and management code 325 may generally comprise several programmatic functions or program modules including (1) a node advertise and query (scan) logic manager (also referred to herein as a node communications manager), which manages how and when a node communicates; (2) an information control and exchange manager, which manages whether and how information may be exchanged between nodes; (3) a node power manager, which manages power consumption and aspects of RF output signal power and/or receiver sensitivity for variable short-range communications; and (4) an association manager focusing on how the node associates with other nodes. What follows is description of various embodiments of these basic program modules used by nodes.

Node Communications Manager—Advertising & Scanning

In an exemplary embodiment, the node advertise and query (scan) logic manager governs how and when a node should advertise (transmit) its address or query (scan) for the address of neighboring nodes. Advertising is generally done with a message, which may have different information in various parts (e.g., headers, fields, flags, etc.). The message may be a single or multiple packets.

In the exemplary embodiment, the "advertise" mode (as opposed to "query" or "scan" mode) is a default mode for an ID Node and has the node broadcasting or transmitting a message with its address and related metadata regarding the node. For example, in one embodiment, exemplary metadata may include information such as the RF output power level, a reference number, a status flag, a battery level, and a manufacturer name for the node.

Figure 6:
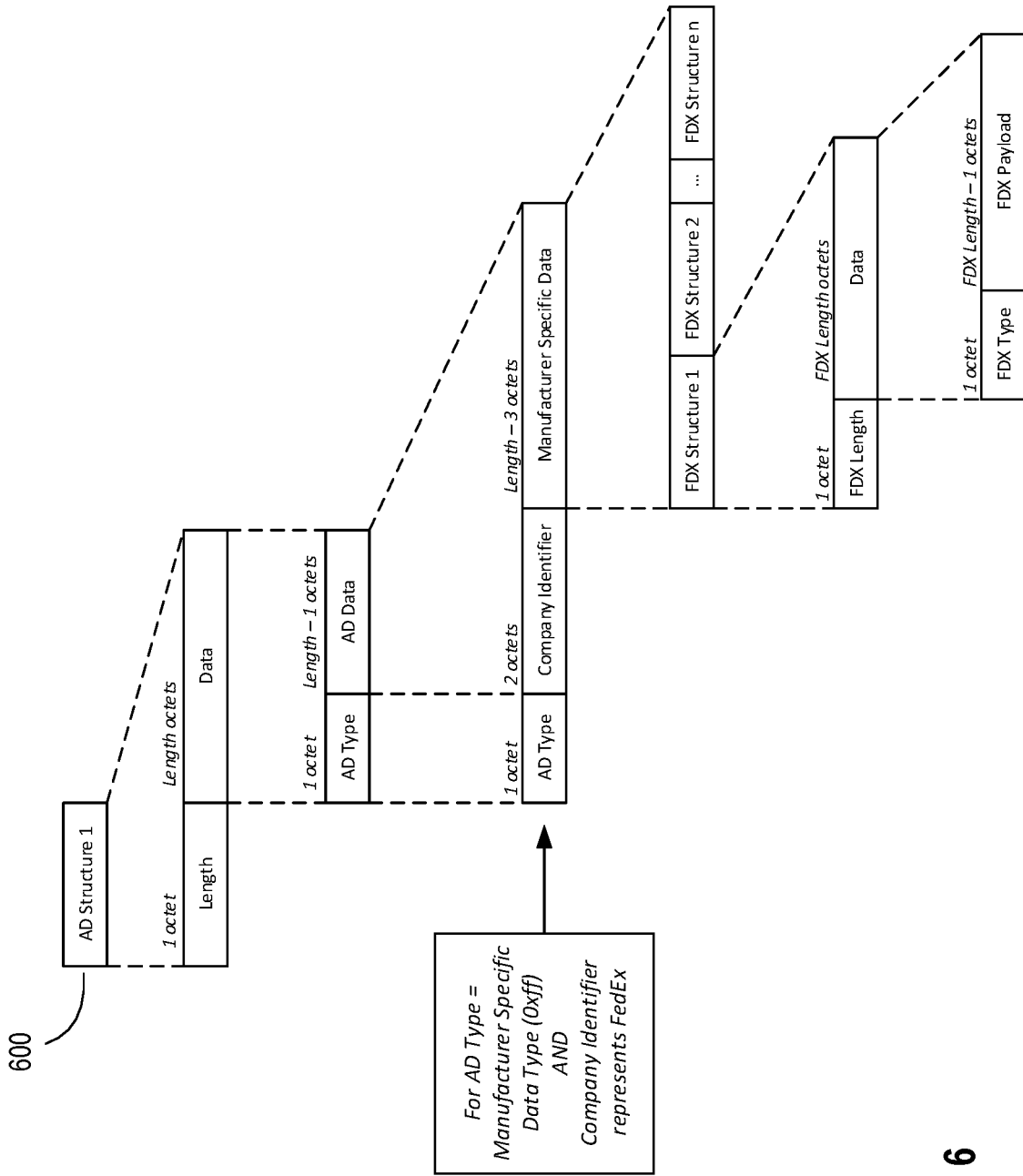
FIG. 6 is a diagram illustrating the structure or format of an exemplary advertisement data packet in accordance with an embodiment of the invention.

FIG. 6 is a diagram illustrating the structure or format of an exemplary advertisement data packet in accordance with a general embodiment of the invention. Referring now to FIG. 6, the structure of an exemplary advertisement data packet 600 broadcast as a signal or message from an ID node, such as ID node 120a, is shown. Packet 600 appears with an increasing level of detail showing exemplary metadata and a format that separately maintains distinct types of metadata in different parts of the packet. Different embodiments may include different types of metadata depending on the deployed application of the ID node.

Figure 7:
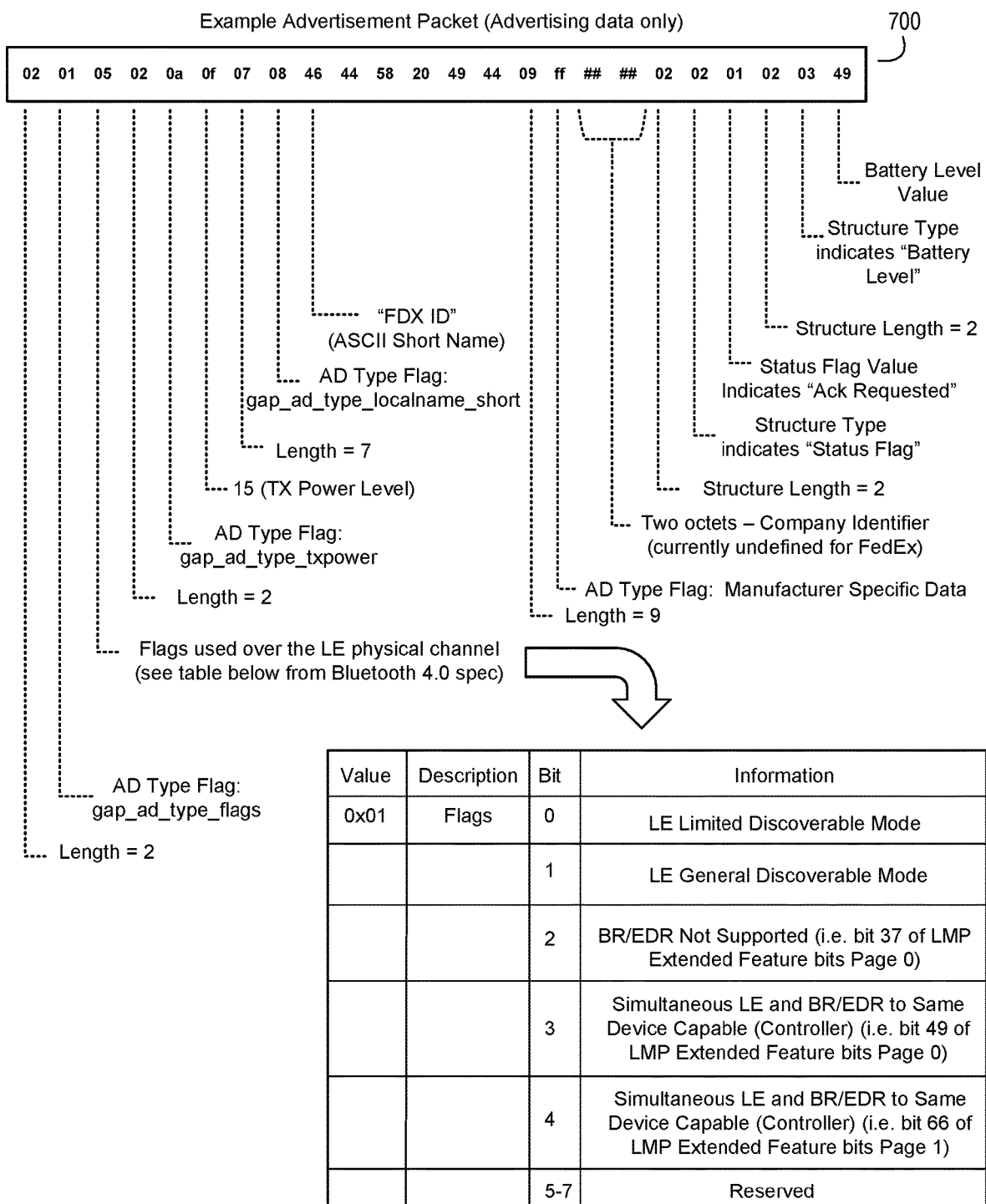
FIG. 7 is a diagram illustrating sample content for an exemplary advertisement data packet in accordance with an embodiment of the invention.

FIG. 7 is a diagram illustrating sample content for an exemplary advertisement data packet in accordance with an embodiment of the invention. Referring now to FIG. 7, an exemplary advertisement data packet 700 is illustrated with exemplary metadata including showing sample information such as the RF Output Power level (e.g., "TX Power Level"), a reference number (e.g., "'FDX ID' (ASCII Short Name)", a status flag (e.g., "Status Flag Value (indicates 'Ack Requested')"), a battery level (e.g., "Battery Level Value (Indicates 73% charge)", and a manufacturer name for the node (e.g., "Company Identifier (currently undefined for FedEx)"). In one embodiment, those skilled in the art will appreciate that the reference number may be omitted or obfuscated for security purposes.

In one embodiment, an exemplary advertising data packet may include the RF Output power level, as noted above in FIG. 7, to enable one way to help identify the type of node doing the broadcasting and the location of the broadcasting node. However, if the broadcast RF output power level is fixed and known by the node type, only the node type need be identifiable from an exemplary advertising data packet, such as packet 700.

Regarding how a node communicates, an exemplary node may be in one of several different communication modes. A node in an advertising (or transmit or broadcast) mode is visible to any other node set in a query (or scan or listen) mode. In an embodiment, the frequency and length of advertising may be application and power dependent. For example, in normal operations, an exemplary node will generally advertise in a periodic manner and expect to make an active connection to another node at certain intervals without the need for polling or responsive prompting from another node, which may be dictated by conditions set by server 100. In an embodiment, such conditions may be set individually for a node by the server or a higher level node in the network.

If an exemplary node has not received acknowledgement for an advertising packet within a particular period, it may enter one or more alert stages. For example, if an exemplary node has not received acknowledgement from another node for an advertising packet broadcast by the exemplary node within a particular time period (also generally referred to as an Alert Interval), the exemplary node will enter an Alert Stage 1 status. This prompts the exemplary node to issue a follow-up advertising packet having one or more parts of it altered to indicate the Alert Stage 1 status. In more detail, this exemplary follow-up advertising packet may have a different advertising alert header instructing nearby nodes to send a SCAN_REQ message upon receiving an advertisement packet.

If an exemplary node has not received acknowledgement from a master node for an advertising packet broadcast by the exemplary node within another time period (e.g., a request from the master node to actively connect and a success connection made), it will enter another alert stage, such as an Alert Stage 2 status. This prompts the exemplary node to issue a follow-up advertising packet having one or more parts of it altered to indicate the Alert Stage 2 status. In more detail, this exemplary follow-up advertising packet may have a different advertising alert header instructing nearby master nodes to send a SCAN_REQ message upon receiving an advertisement packet.

If an exemplary node has data to upload to the backend, it may also enter another type of alert stage. In one embodiment, for example, if an exemplary node has sensor data collected by the exemplary node (or received from one or more other nodes that have communicated with the exemplary node), and the data needs to be uploaded to server 100, the exemplary node may enter an update alert stage, such as an Alert Stage 3. This prompts the exemplary node to issue a follow-up advertising packet having one or more parts of it altered to indicate the Alert Stage 3 status. In more detail, this exemplary follow-up advertising packet may have a different advertising alert header instructing nearby master nodes to make a connection with the exemplary node so that the data (e.g., sensor data 350) may be transmitted from the exemplary node (e.g., ID node 120a) to a nearby master node (e.g., master node 110a). The transmitted data may then be stored by the nearby master node as sensor data 450 in either or both of the master node's volatile memory 420 and memory storage 415. Subsequent to that storage operation, the nearby master node will transfer the data (e.g., sensor data 450) to server 100.

As illustrated in FIG. 7 and explained in the above description of alert level stages, a status flag in a header of an exemplary advertising data packet is a field used in the association logic in one or more embodiments. For example, in one embodiment, the existence of a status flag in the advertising data packet allows a first node to communicate its status to a second node, and for the second node to report that status to the backend server, such as server 100, without an active direct connection from the first node to the server. In other words, the status flag helps facilitate passive interactions between nodes (such as passive associations).

In a more detailed embodiment, several exemplary status types are established with respect to communications with other nodes. For example, the exemplary status types may comprise the following:

Alert Level 0—no issue, operating normal;
Alert Level 1—The advertising node is requesting that any available node acknowledge the receipt of its advertisement packet;

Alert Level 2—The advertising node is requesting that any available master node acknowledge the receipt of its advertisement packet;

Alert Level 3—Data for Upload—node has captured data available for upload through a master node; and Synchronize—The advertising node requests to connect with a device or sensor that can synchronize data (such as timer or location information).

By broadcasting the status via, for example, a portion of a header in an advertising data packet, one or more nodes within range of the broadcasting node can determine the node's status and initiate active connections if requested in the status message.

A request for more information from the advertising node may, in some embodiments, come in the form of a SCAN_REQ message. In general, an exemplary SCAN_REQ is a message sent from a scanning (listening) master node to an advertising node requesting additional information from the advertising node. In this example, the alert status bit may indicate to the scanning master node, for example, at an application layer, whether the advertising node is in a mode that will or will not accept a SCAN_REQ. In one embodiment, the non-connectable and discoverable modes of node advertising are in compliance with Bluetooth® Low Energy (BLE) standards.

In another embodiment, a node may have further different modes of operation while scanning or listening for other nodes. For example, a node's query or scanning mode may be active or passive. When a node is scanning while passive, the node will receive advertising data packets, but will not acknowledge and send SCAN_REQ. However, when a node is scanning while active, the node will receive advertising data packets, and will acknowledge receipt by sending a SCAN_REQ. A more detailed embodiment may provide the passive and active modes of scanning or inquiry in compliance with Bluetooth® Low Energy (BLE) standards.

In an embodiment, an exemplary node is scanning as it listens for other wireless nodes broadcasting on the short-range radio. Such scanning may be in the form of monitoring for an unprompted signal broadcast from other wireless nodes. An exemplary scanning node may capture, for example, a MAC address of the advertising node, a signal strength of the RF output signal transmitted from the advertising node, and any other metadata published by the advertising node (e.g., other information in the advertising data packet). Those skilled in the art will appreciate that the scope of "listening" when a node is scanning may vary. For example, the query may be limited. In other words, the scope of what a node is particularly interested in and for which it is listening may be focused or otherwise limited. In such a case, for example, the information collected may be limited to particular information from a targeted population of short-range wireless nodes advertising; but the information collection may be considered "open" where information from any advertising device is collected.

When nodes are advertising or scanning, an embodiment may make further use of status flags and additional modes when advertising or scanning as part of how nodes communicate and may be managed. In one example, when a scanning (listening) node receives an advertising data packet with the status flag indicating an Alert Level 1 or 2 status, and the scanning node is in "Passive" scanning mode, the node will switch to "Active" scanning mode for some interval. However, when the scanning node in this situation is already in an "Active" scanning mode, the node will send the SCAN_REQ message and receive a SCAN_RSP from the advertising node (e.g., a message providing the additional information requested from the advertising node). The scanning node will then switch back to a "Passive" scanning mode.

In another example, when an advertising (broadcasting) node receives a SCAN_REQ from a scanning node, the advertising node will consider that its advertising data packet has been acknowledged. Further, the advertising node will reset its "Alert" status flag back to an Alert Level 0 status. This allows the advertising node to effectively receive an acknowledgement to its advertisement without ever making a connection to the scanning node, which advantageously and significantly saves on power consumption.

In yet another example, when a scanning node receives an advertising data packet with an Alert Level 3 status flag set, the scanning node will attempt to make a connection with the advertising device. Once the connection is made, the advertising device will attempt to upload its data to the connected device Thus, an embodiment of the node advertise and query (scan) logic manager of code 325 may rely upon one or more status flags, advertising modes, scanning modes, as nodes communicate with each other in various advantageous manners.

Node Information Control & Exchange Manager

In an exemplary embodiment, the information control and exchange manager part of node control and management code 325 determines whether and how information may be exchanged between nodes. In the exemplary embodiment, the information control and exchange manager establishes different node operational states where information may be changed according to a desired paradigm for the state. In more detail, an embodiment of information control and exchange manager may establish different levels of information exchange between nodes with a "non-connectable advertising" state or mode of operation, a "discoverable advertising" state or mode, and a "general advertising" state or mode operation. When a node is in the "non-connectable advertising" mode, the node information exchange is limited. For example, the advertising node may broadcast information that is captured by one or more querying (scanning) nodes, but no two-way exchange of information happens.

When a node is in the "discoverable advertising" mode and a scanning node is in "Active" mode, the node information exchange in enabled both ways. For example, the advertising node sends the advertising packet, and in response the scanning node sends the SCAN_REQ packet. After the advertising node receives the SCAN_REQ requesting additional information, the advertising node sends the SCAN_RSP with the requested information. Thus, in the "discoverable advertising" mode there is a two-way exchange of information, but no active connection is made between the two nodes exchanging information.

Finally, for advanced two-way information exchange, an active connection may be used between nodes and information may be exchanged both ways to and from different nodes. In a more detailed embodiment, at this level of two-way information exchange, nodes are first identified and then authenticated as part of establishing the active connection. Once authenticated and thereafter actively connected to each other, the nodes may securely share information back and forth. In one example, a sensor node uploading previously captured environmental information to a master node may be in this mode or state. In another example, an ID node uploading the stored results of a node scanning operation to a master node may be in this mode or state. In yet another example, a master node sharing a timer and/or location information with corresponding nodes may be in this mode or state.

Node Power Manager

In an exemplary embodiment, the node power manager part of node control and management code 325 focuses on managing power consumption and the advantageous use of power (e.g., an adjustable level of RF output signal power) in a node. In general, nodes are either powered by a battery (such as battery 355 in an ID node), or by an interface (such as battery/power interface 470 in a master node) to an external power source. Examples of an external power source may include, in some embodiments, power supplied from an outlet or power connection within a facility, or power generated onboard a conveyance (e.g., automobile, truck, train, aircraft, ship, etc.). Those skilled in the art will appreciate that an interface to an external power source will be generally referred to as a "wired" power connection, and that node power manager may be informed whether a node is wired or powered off a battery, such as battery 355. Further embodiments may implement an interface to an external power source with wireless power transmission, such as via inductive coils.

In one embodiment, a node may manage power used when performing tasks. For example, a node may manage power when determining which node should perform a particular task. In more detail, the collective power consumption of a group of devices may be managed by electing to employ wired nodes, when feasible or desired, to accomplish a particular task, and saving the battery-powered nodes for other less energy burdensome or taxing tasks. In another embodiment, historic data may inform the system of the power needed to accomplish a particular task, and the system may make a determination of which node should accomplish the particular task based upon such historic data. In other embodiments, profile data may also be used to inform the system of the power needed to accomplish a particular task (e.g., a sensor profile that describes power requirements for operation of a sensor node that gathers sensor data over a certain period of time and under certain conditions). The system may also make a determination of which node should accomplish the particular task based upon such profile data.

In another example, the exemplary node power manager may manage power when determining how to best to use and adjust power to more accurately accomplish a particular task. In one embodiment, an RF signal output from a node (such as a short-range RF output signal from an ID node) may periodically move through a range of output power or simply switch between two or more settings that differ in a detectable manner. As disclosed in more detail below, the variability and dynamic adjustment of RF output signal power may allow other nodes (such as one or more master nodes) to see each node at the upper range of the RF output signal power, and only see nodes physically close to the advertising node at the lower range of signal power.

In another example, the exemplary node power manager may cause a change to a characteristic of its RF output signal power when the node has been associated to a physical place or another node by virtue of context data (such as context data 560 and association logic that utilizes that type of information). In one embodiment, the node may be instructed to change how often the node communicates and/or a characteristic of its RF output power to preserve power.

In yet another example, all advertising nodes may have their respective node power managers periodically cause each respective node to broadcast at a maximum RF output signal power level to ensure they still are within range of a scanning ID Node or Master Node. Doing so may increase the chance of being in communication range and allows the individual nodes to be properly located and managed within the network. The broadcast duration may be set or dynamically changed to allow pairing to occur if needed.

Rather than adjust the RF output signal power level, the exemplary node power manager may, in some embodiments, adjust the RF receiver sensitivity of a node. This allows for an adjustable range of reception (as opposed to merely an adjustable range of broadcast), which may similarly be used to manage power and enhance location determinations as discussed herein.

In yet another embodiment, a combination approach may be used in which the node power manager may concurrently and independently adjust more than one RF characteristic of a node. For example, an exemplary node power manager may adjust an RF output signal power level and also adjust the RF receiver sensitivity of a node as the node is located and associated with other nodes. Those skilled in the art will realize that this may be especially useful in an area with an unusually dense concentration of nodes, and a combination of changing RF output signal power levels An embodiment of the exemplary node manager may refer to a power profile (e.g., an exemplary type of profile data 330, 430) when adjusting a node's power characteristics (e.g., consumption of power, use of power, output signal frequency, duty cycle of the output put signal, timing, power levels, etc.).

Node Association Manager

In an exemplary embodiment, the node association manager part of node control and management code 325 focuses on how the nodes associate with other nodes in conjunction and consistent with the server-side association manager in code 525, as discussed in more detail below. Thus, exemplary node association manager, when executing in a node, directs how the node associates (e.g., enters an active connection mode or generates association data reflecting a temporary logical connection) with one or more other nodes with input from the server.

The exemplary node association manager for a node may indicate through a Status Flag if the node requires an acknowledgement or connection, or if it has information available for upload to the backend. Thus, while a node may not be associated or actively connected yet to another node, a status of the node may be inferred from, for example, the status information in the node's broadcast header.

Regarding connections between nodes, there are generally secure connections and unsecure connections. While an embodiment may allow unsecure connections between one or more sets of nodes, other embodiments rely upon secure connections or authenticate pairings of nodes. In one embodiment, for a node to pair with another node, the exemplary node association manager first identifies the nodes to be associated and transmits an association request to the server. The request may include a specific request to pair the nodes and ask for the corresponding pairing credentials from the server, such as server 100. Such a pairing may be considered a logical pairing of the node, which may be tracked by the server 100 (or other nodes in the network, such as a master node, command node, external transceiver, or remote control center located outside of the transit vehicle). The server 100 may have staged pairing credentials on particular nodes based on information indicating the nodes would be within wireless proximity and future pairing may occur. Visibility to the node relationship may have been determined through scan-advertising, or 3$^{rd}$ party data such as barcode scan information indicating the nodes to be within proximity currently or at a future state.

As described in more detail below, associating nodes may involve local generation of association data (e.g., association data 340, 440, and the like) that reflects the logical pairing between the associating nodes. As such, the association data may operate as temporal data indicating the logical connection between the nodes whether the nodes are actually communicating with each other or not.

When connecting or not connecting to exchange information under the exemplary node information exchange modes described above, nodes generally operate in a number of states, which make up an exemplary advertise cycle for an exemplary ID node. Such an exemplary advertise cycle for a node is further explained below with reference to FIG. 8 and in conjunction and consistent with the server-side association manager in code 525, as discussed in more detail below.

Airborne Mode Program Module

In one embodiment, node control and management code 325 may also include an airborne mode program module (not shown). In another embodiment, the airborne mode program module may be implemented as a part of the node power manager program module of code 325. An exemplary airborne mode program module generally operates to manage the output power of the ID node's variable power short-range communication interface 375 when the ID node is operating in an aircraft. Operating a wireless device within an aircraft may, in some circumstances, have an unintentional impact on other electronic systems on the aircraft. In more detail, an embodiment of the airborne mode program module may operate to transition the ID node from different states or modes depending upon particular operations and/or operational conditions of the aircraft. For example, an exemplary airborne mode program module may operate to transition the ID node from one state or mode (e.g., a normal mode prior to takeoff, a disabled mode during takeoff, an airborne mode while aloft, a disabled mode during descent, and a normal mode after landing) based upon detected environmental conditions (e.g., pressure, altitude) and/or flight detail information associated with the aircraft. In this way, an ID node may be allowed to normally operate when onboard an aircraft, be disabled from operating at all in some circumstances, and be able to operate in an aircraft mode that allows sensing and sensor data capture, but that may limit transmission of an RF output signal to avoid interference with the aircraft's onboard electronics. Further information related to a method of managing a wireless device (such as an ID node) in an aircraft is disclosed in greater detail in U.S. patent application Ser. No. 12/761,963 entitled "System and Method for Management of Wireless Devices Aboard an Aircraft," which is hereby incorporated by reference.

Node Data

As previously noted, volatile memory 320 may also include certain data (e.g., profile data 330, security data 335, association data 340, shared data 345, sensor data, and the like) generated as the ID node 120a executes instructions as programmed or loaded from memory storage 315. In general, data used on a node, such as an ID node, may be received from other nodes or generated by the node during operations.

In one embodiment, profile data 330 is a type of data that defines a general type of behavior for an ID node, such as a Broadcast Profile (discussed in more detail below). In another embodiment where ID node 120a is a BLE device, profile data 330 may include a Bluetooth® compatible profile related to battery service (exposing the state of a battery within a device), proximity between BLE devices, or messaging between BLE devices. Thus, exemplary profile data 330 may exist in volatile memory 320 and/or memory storage 315 as a type of data that defines parameters of node behavior.

In one embodiment, it may be desired to allow secured pairings of nodes. As will be explained in more detail below, as part of secure pairing of nodes, a request for pairing credentials is generated and sent to server 100. Thus, exemplary security data 335 (e.g., PIN data, security certificates, keys, etc.) may exist in volatile memory 320 and/or memory storage 315 as a type of data associated with providing secured relationships between nodes, such as the requested security credentials.

Association data, such as association data 340, generally identifies a connected relationship between nodes. Such a connection may be an interactive exchange type of connection, but other embodiments may reflect a mere logical connection between the nodes. For example, ID node 120a may become associated with the master node 110a as the ID node 120a moves within range of the master node 110a and after the server directs the two nodes to associate (with authorization). As a result, information identifying the relationship between ID node 120a and master node 110a may be provided to server 100 and may be provided, as some point, to each of ID node 120a and master node 110a. Thus, exemplary association data 340 may exist in volatile memory 320 and/or memory storage 315 as a type of data identifying associations between nodes. In another example, ID node 120a may detect advertising signals broadcast from master node 110a without prompting master node 110a to broadcast such signals (e.g., unprompted broadcasts or non-polling related signals from master node 110a). In this situation, ID node 120a may passively associate with master node 110a and generate association data 340 on ID node 120a reflecting the logical relationship or connection between ID node 120a and master node 110a despite a lack of response from the master node 110a, and such association data may be passed along to server 100 so that the server may track what nodes are logically associated with ID node 120a.

Shared data 345 may exist in volatile memory 320 and/or memory storage 315 as a type of data exchanged between nodes. For example, context data (such as environmental data) may be a type of shared data 345.

Sensor data 350 may also exist in volatile memory 320 and/or memory storage 315 as a type of data recorded and collected from an onboard sensor or from another node. For example, sensor data 350 may include temperature readings from a temperature sensor onboard an ID node and/or humidity readings from a humidity sensor in another ID node (e.g., from another of the ID nodes within container 210 as shown in FIG. 2).

Thus, an ID node (such as node 120a shown in FIG. 3) is a lower cost wireless node that communicates with other ID nodes and master nodes via a short-range radio with variable RF characteristics, can be associated with other nodes, can broadcast to and scan for other nodes, associated with other nodes, and store/exchange information with other nodes.

Master Node

Figure 4:
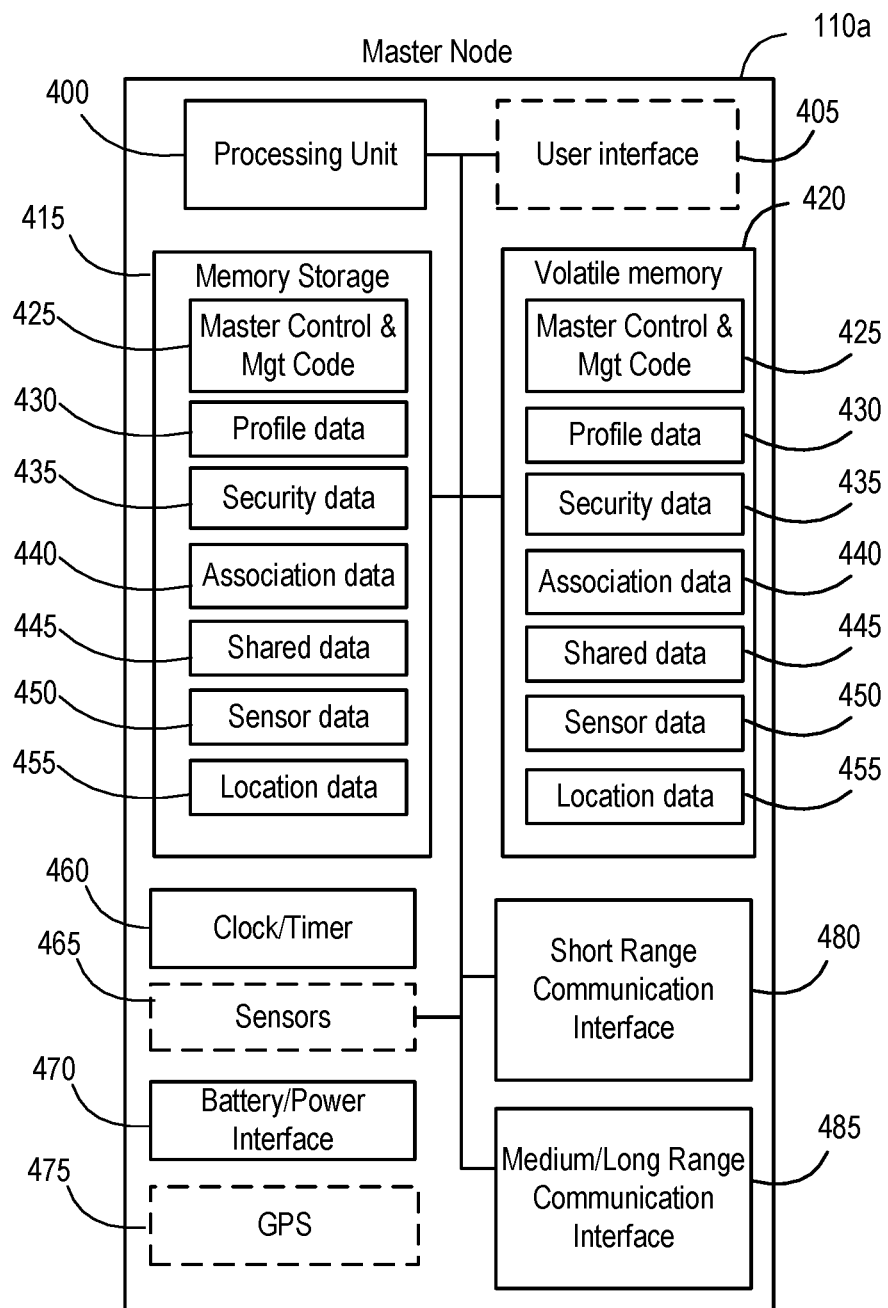
FIG. 4 is a more detailed diagram of an exemplary master node device in accordance with an embodiment of the invention.

A master node, such as master node 110a shown in more detail in FIG. 4, shares many ID node features but generally expands upon them in order to function as a bridge to a higher level network element, such as the server 100. In general, while an ID node is a type of lower level node in an exemplary wireless node network, a master node is a type of higher level node (also referred to as a mid-level network device). An exemplary master node may be in a fixed location or otherwise stationary, while other example master nodes may be implemented as movable and mobile devices. As will be explained further below, one type of master node may include a command node that may be disposed as part of or attached to a shipping container (such as a ULD container).

Referring now to FIG. 4, exemplary master node 110a comprises a processing or logic unit 400 coupled to a short-range communication interface 480, memory storage 415, volatile memory 420, clock/timer 460, and battery/power interface 470. In some embodiments, the short-range communication interface 480 may have variable power characteristics, such as receiver sensitivity and RF output power level. Those skilled in the art will appreciate that processing unit 400 is logic, such as a microprocessor or microcontroller, which generally performs computations on data and executes operational and application program code and other program modules within the master node 110a.

In general, those skilled in the art will appreciate that the description of hardware with respect to ID node 110a in FIG. 4 applies to the similar hardware and software features appearing in each type of node, including a master node. Those skilled in the art will appreciate that exemplary master node 110a is a hardware-based component that may implement processor 400 with a single processor or logic unit, a more powerful multi-core processor, or multiple processors depending upon the desired implementation. In one embodiment, processing unit 400 may be implemented with a low power microprocessor and associated peripheral circuitry. Less complex microcontrollers or discrete circuitry may be used to implement processing unit 400 as well as more complex and sophisticated general purpose or dedicated purpose processors.

In yet another embodiment, exemplary processing unit 400 may be implemented by a low power ARM1176JZ-F application processor used as part of a single-board computer, such as the Raspberry Pi Computer Model B-Rev-2. The ARM application processor is embedded within a Broadcom® BCM2835 system-on-chip (SoC) deployed in the Raspberry Pi Computer. In this embodiment, the Raspberry Pi Computer device operates as a core of exemplary master node 110a and includes a Secure Digital memory card slot and flash memory card operating as memory storage 415, a 512 Mbyte RAM memory storage operating as volatile memory 420, an operating system (such as Linux) stored on memory storage 415 and running in volatile memory 420, and peripherals that implement clock/timer 460, and a power supply operating as a power interface 470.

Like short-range interface 375 in ID node 120a, exemplary master node 110a includes a short-range communication interface 480 as a programmable radio and an omni-directional antenna coupled to the processing unit 400. In some embodiments, the short-range communication interface 480 may have variable RF power characteristics, such as receiver sensitivity and/or RF output signal power level. In some embodiments, interface 480 may use an antenna with a different antenna profile when directionality may be desired. Those skilled in the art will appreciate that short-range communication interface 480 (like that described above regarding interface 375) may be implemented with hardware, implemented with a combination of hardware and software, as well as implemented as a software-defined radio (SDR). Examples of short-range communication interface 480 may include other hardware (not shown) for operatively coupling the device to a specific short-range communication path (e.g., a Bluetooth® Low Energy (BLE) connection path communicating at 2.4 GHz). While BLE is used in one embodiment to enable a short-range communication protocol, variable power short-range interface 480 may be implemented with other low power, short-range communication protocols, such as ultra-low power communication protocols used with ultra-wideband impulse radio communications, ZigBee protocols, IEEE 802.15.4 standard communication protocols, and the like.

In one embodiment, various RF characteristics of the radio's transceiver, such as the RF output power and the RF receiver sensitivity may be dynamically and programmatically varied under control of processing unit 400. In other embodiments, further RF characteristics of the radio's transceiver may be programmatically varied, such as frequency, duty cycle, timing, modulation schemes, spread spectrum frequency hopping aspects, etc., as needed to flexibly adjust the RF output signal as needed depending upon a desired implementation and anticipated use of exemplary master node 110a. In other words, embodiments of master node 110a (or any other master node) may have programmatically adjustable RF characteristics (such as an adjustable RF output signal power, an adjustable RF receiver sensitivity, the ability to switch to a different frequency or frequency band, etc.).

In addition to the short-range communication interface 480, exemplary master node 110a includes a medium and/or long-range communication interface 485 to provide a communication path to server 100 via network 105. Those skilled in the art will appreciate that in some embodiments, an exemplary communication interface deployed may be considered to embody a short-range communication interface (such as interface 480) or a medium/long range communication interface (such as interface 485). However, in more general embodiments, reference to a communication interface may include an interface that collectively implements a plurality of different exemplary data communication interfaces while still being generally referenced as "a communication interface" or "wireless communication interface." Furthermore, those skilled in the art will appreciate that communication interface 485 may be implemented with hardware, implemented with a combination of hardware and software, as well as implemented as a software-defined radio (SDR).

In more detail, an exemplary embodiment of communication interface 485 may be implemented with a medium range radio in the form of an IEEE 802.11g compliant Wi-Fi transceiver. In another embodiment, communication interface 485 may be implemented with a longer range radio in the form of a cellular radio. In yet another embodiment, both a Wi-Fi transceiver and a cellular radio may be used when best available or according to a priority (e.g., first attempt to use the Wi-Fi transceiver if available due to possible lower costs; and if not, then rely on the cellular radio). In other words, an embodiment may rely upon the longer range cellular radio part of interface 485 as an alternative to the medium range Wi-Fi transceiver radio, or when the medium range radio is out of reach from a connecting infrastructure radio within network 105. In a further embodiment, interface 485 may be implemented as a module providing general purpose signal processing at its core as part of a software-defined radio, which provides flexibility in transmission techniques, software-defined antennas, and adaptive radio protocols that may be dynamically changed to implement different medium and longer range interfaces. Thus, in these embodiments, medium and/or long-range communication interface 485 may be used to communicate captured node information (e.g., profile data 430, association data 440, shared data 445, sensor data 450, and location data 455) to server 100.

In any of the embodiments described herein, communication interfaces 480 and 485 may be implemented as a single wireless transceiver-based communication interface with both short-range and longer range communication capabilities (i.e., may function as both a first and second communication interface as described in the various embodiments herein). This type of wider range communication interface may be implemented using LPWAN (Low Power Wide Area Network) connectivity, such as LTE 5G, LTE-M, and NB-IOT (NarrowBand IoT). LPWAN, also commonly referred to low-power wide-area (LPWA) network or just low-power network (LPN), is a type of wide-area network wireless communication format that allows for extended range, low-bandwidth communications for power sensitive application, such as with devices that are battery powered devices (e.g., ID nodes, mobile master nodes, container nodes, command nodes, and the like). Exemplary types of LPWAN may include ultra-narrowband (UNB) technology from Sigfox, random phase multiple access (RPMA) technology from Ingenu, and other long-range WAN protocol (LoRaWAN) technology as promoted by the LoRa Alliance of companies (e.g., IBM, MicroChip, Cisco, Semtech, Singtel, KPN, Bouygues Telecom). LTE-M is a communication technology that allows a node-based device (such as a sensor-based ID node or command node) to directly connect to a Long Term Evolution (4G) cellular network without a gateway and on batteries. NB-IOT is a low-power communication technology that applies a narrowband approach to cellular IoT (Internet of Things) communications allowing for usage of parts of the GSM spectrum bandwidth in unused 200 kHz bands.

The battery/power interface 470 for master node 110*a* generally powers the circuitry implementing master node 110*a*. In one embodiment, battery/power interface 470 may be a rechargeable power source. For example, a master node may have a rechargeable power source along with a solar panel that charges the power source in order to help facilitate deployment of the master in a remote location. In another embodiment, battery/power interface 470 may be a non-rechargeable power source intended to be disposed of after use. In yet another embodiment, battery/power interface 470 may be a power interface connector (such as a power cord and internal power supply on master node 110*a*). Thus, when an exemplary master node is in a fixed or stationary configuration, it may be powered by a power cord connected to an electrical outlet, which is coupled to an external power source. However, other mobile master nodes may use an internal power source, such as a battery.

The clock/timer 460 for master node 110*a* generally provides one or more timing circuits used in, for example, time delay, pulse generation, and oscillator applications. In an embodiment where master node 110*a* conserves power by entering a sleep or dormant state for a predetermined time period as part of overall power conservation techniques, clock/timer 460 assists processing unit 400 in managing timing operations.

Optionally, an embodiment may also implement master node 110*a* as including one or more sensors 465 (similar to sensors deployed on ID node based Sensor nodes and described above with respect to FIG. 3). Additionally, an embodiment of master node 110*a* may also provide a user interface 405 to indicate status and allow basic interaction for review of captured node data and interaction with nodes and server 100. In one embodiment, user interface 405 may provide a display, interactive buttons or soft keys, and a pointing device to facilitate interaction with the display. In a further embodiment, a data entry device may also be used as part of the user interface 405. In other embodiments, user interface 405 may take the form of one or more lights (e.g., status lights), audible input and output devices (e.g., a microphone and speaker), or touchscreen.

As previously noted, an exemplary master node, such as master node 110*a*, may be positioned in a known fixed location or, alternatively, includes dedicated location positioning circuitry 475 (e.g., GPS circuitry) to allow the master node self-determine its location or to determine its location by itself. In other embodiments, alternative circuitry and techniques may be relied upon for location circuitry 475 (rather than GPS), such as location circuitry compatible with other satellite-based systems (e.g., the European Galileo system, the Russian GLONASS system, the Chinese Compass system), terrestrial radio-based positioning systems (e.g., cell phone tower-based or Wi-Fi-based systems), infrared positioning systems, visible light based positioning systems, and ultrasound-based positioning systems).

Regarding memory storage 415 and volatile memory 420, both are operatively coupled to processing unit 400 in exemplary master node 110*a*. Both memory components provide program elements used by processing unit 400 and maintain and store data elements accessible to processing unit 400 (similar to the possible data elements stored in memory storage 315 and volatile memory 320 for exemplary ID node 120*a*).

In the embodiment shown in FIG. 4, memory storage 415 maintains a variety of executable program code (e.g., master control and management code 425), data similar to that kept in an ID node's memory storage 315 (e.g., profile data 430, security data 435, association data 440, shared data 445, sensor data 450, and the like) as well as other data more specific to the operation of master node 110*a* (e.g., location data 455 that is related to the location of a particular node). Like memory storage 315, memory storage 415 is a tangible, non-transient computer readable medium on which information (e.g., executable code/modules, node data, sensor measurements, etc.) may be kept in a non-volatile and non-transitory manner.

Like volatile memory 320 in ID node 120*a*, volatile memory 420 is typically a random access memory (RAM) structure used by processing unit 400 during operation of the master node 110*a*. Upon power up of master node 110*a*, volatile memory 120 may be populated with an operational program (such as master control and management code 425) or specific program modules that help facilitate particular operations of master node 110*a*. And during operation of master 110*a*, volatile memory 420 may also include certain data (e.g., profile data 430, security data 435, association data 440, shared data 445, sensor data 450, and the like) generated as the master node 110*a* executes instructions as programmed or loaded from memory storage 415.

Master Control & Management Code

Generally, an embodiment of master control and management code 425 is a collection of software features implemented as programmatic functions or program modules that generally control the behavior of a master node, such as master node 110*a*. In other words, master control and management code 425 may also include further program code specific for master node functionality described in the embodiments described in more detail below that use a master node (e.g., a command node 26000 or command node 24160 implemented with a master node). As such, the collective code executing on a master node, such as master node 110a (or any of the other implementations of a master node or command node as described herein), acts to programmatically configure the master or command node beyond that of a generic processing device in order to be specially adapted, via such program code, to be operative to function unconventionally—whether alone with the specific functionality described herein or as part of a system.

In one embodiment, master control and management code 425 generally comprises several programmatic functions or program modules including (1) a node advertise and query (scan) logic manager, which manages how and when a node communicates; (2) an information control and exchange manager, which manages whether and how information may be exchanged between nodes; (3) a node power manager, which manages power consumption and aspects of RF output signal power and/or receiver sensitivity for variable short-range communications; (4) an association manager focusing on how the node associates with other nodes; and (5) a location aware/capture module to determine node location.

Master Node Program Modules and ID Node Modules

In an exemplary embodiment, program modules (1)-(4) of master node control and management code 425 generally align with the functionality of similarly named program modules (1)-(4) of node control and management code 325 as described above with respect to FIG. 3. Additionally, as node control and management code 325 may also comprise an airborne mode program module, those skilled in the art will appreciate and understand that master node control and management code 425 may also comprise a similar functionality airborne mode program module in order to allow advantageous operations of a master node while airborne. However, and consistent with examples set forth below, such modules may have some differences when in a master node compared with those controlling an ID node.

Location Aware/Capture Module

In addition to exemplary program modules (1)-(4) of code 425, an exemplary embodiment of master node control and management code 425 will further comprise an exemplary location aware/capture module related to node location (more generally referred to as a location manager module for a master node). In general, the exemplary location aware/capture module deployed in an exemplary master node may determine its own location and, in some embodiments, the location of a connected node. Embodiments of the exemplary location aware/capture module may work in conjunction with location manager program code residing and operating in a server (e.g., as part of server control and management code 525) when determining node locations of other nodes, as discussed in more detail herein.

In one embodiment, a master node may be positioned in a known, fixed location. In such an embodiment, the exemplary location aware/capture module may be aware that the master node location is a known, fixed location, which may be defined in a fixed, preset, or preprogrammed part of memory storage 415 (e.g., information in the location data 455 maintained in memory storage 415). Examples of such location information may include conventional location coordinates or other descriptive specifics that identify the location of the master node. In another embodiment where the master node may not be inherently known or a fixed location at all times (e.g., for a mobile master node), the exemplary location aware/capture module may communicate with location circuitry, such as GPS circuitry 475 on a master node, to determine the current location of the master node.

In an embodiment, the location of the master node may be communicated to the server, which may use this location information as part of managing and tracking nodes in the wireless node network. For example, if an exemplary master node is mobile and has determined a new current location using location circuitry 475, the master node may provide that new current location for the master node to the server. Additionally, when the master node's exemplary location aware/capture module determines the location of a node associated with the master node, the master node may also provide the location of that node associated with the master node to the server.

Server

Figure 5:
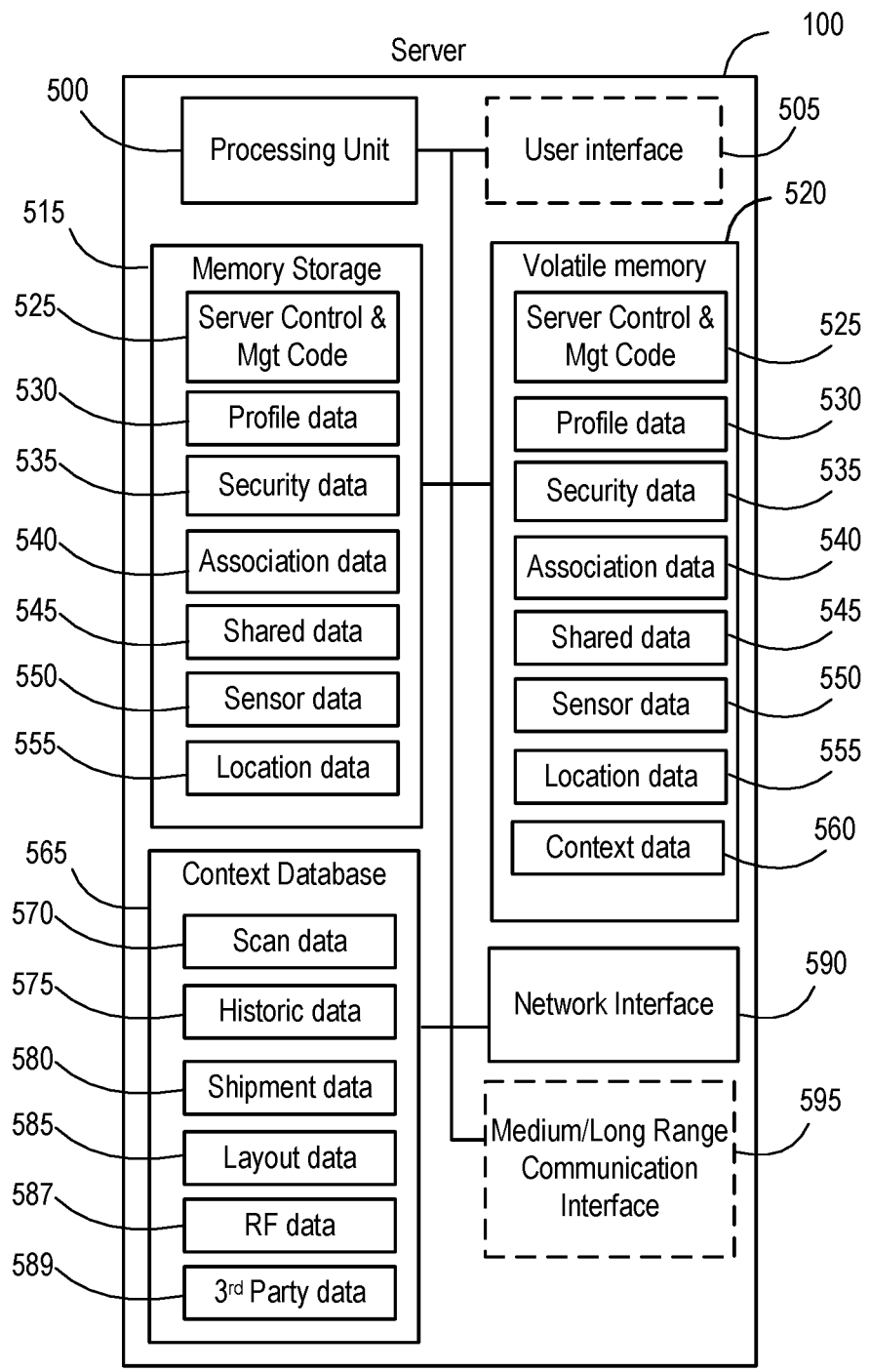
FIG. 5 is a more detailed diagram of an exemplary server in accordance with an embodiment of the invention.

While FIGS. 3 and 4 illustrate details of hardware and software aspects of an exemplary ID node and exemplary master node, respectively, FIG. 5 provides a more detailed diagram of an exemplary server that may operate as part of an exemplary wireless node network in accordance with an embodiment of the invention. In an exemplary embodiment, server 100 may be referred to as an Association and Data Management Server (ADMS) that manages the nodes, collects information from the nodes, stores the collected information from the nodes, maintains or has access to context data related to the environment in which the nodes are operating, and may provide information about the nodes (e.g., status, sensor information, etc.) to requesting entities. Further details on various embodiments that take advantage of this functionality are explained below. Those skilled in the art will appreciate that node density, geographic installation characterization, and network connectively are all types of examples of factors that may impact a final architecture desired for an embodiment of a wireless node network.

Referring now to FIG. 5, exemplary server 100 is shown as a networked computing platform capable of connecting to and interacting with at least the wireless master nodes. In other embodiments, exemplary server 100 is also capable of connecting to and interacting with one or more user access devices. Those skilled in the art will appreciate that exemplary server 100 is a hardware-based component that may be implemented in a wide variety of ways. For example, server 100 may use a single processor or may be implemented as one or more part of a multi-processor component that communicates with devices (such as user access devices 200, 205) and wireless nodes (such as master node 110a).

In general, those skilled in the art will further appreciate that server 100 may be implemented as a single computing system, a distributed server (e.g., separate servers for separate server related tasks), a hierarchical server (e.g., a server implemented with multiple levels where information may be maintained at different levels and tasks performed at different levels depending on implementation), or a server farm that logically allows multiple distinct components to function as one server computing platform device from the perspective of a client device (e.g., devices 200, 205 or master node 110a). In some regional deployments, an exemplary server may include servers dedicated for specific geographic regions as information collected within different regions may include and be subject to different regulatory controls and requirements implemented on respective regional servers.

Likewise, while the embodiment shown in FIG. 5 illustrates a single memory storage 515, exemplary server 100 may deploy more than one memory storage media. And memory storage media may be in differing non-transitory forms (e.g., conventional hard disk drives, solid state memory such as flash memory, optical drives, RAID systems, cloud storage configured memory, network storage appliances, etc.).

At its core, exemplary server 100 shown in FIG. 5 comprises a processing or logic unit 500 coupled to a network interface 590, which facilitates and enables operative connections and communications through network 105 with one or more master nodes as well as, in some embodiments, user access devices, such as devices 200, 205. In one embodiment, server 100 may include a medium and/or long-range communication interface 595 with which to more directly communicate with one or more master nodes. Using these communication paths as well as program code or program modules (such as server control and management code 525), the server 100 generally operates to coordinate and manage information related to an ID node as an item associated with the ID node physically moves from one location to another.

As a computing platform, the processing unit 500 of exemplary server 100 is operatively coupled to memory storage 515 and volatile memory 520, which collectively store and provide a variety of executable program code (e.g., server control and management code 525), data similar to that kept in a master or ID node's respective memory storage (e.g., profile data 530, security data 535, association data 540, shared data 545, sensor data 550, location data 555) and context data 560 related to the environment in which the nodes are operating (e.g., information generated from within the wireless node network and information created external to the wireless node network).

Like memory storage 315 and storage 415, memory storage 515 is a tangible, non-transient computer readable medium on which information (e.g., executable code/modules (e.g., server control and management code 525), node-related data (e.g., profile data 530, security data 535, association data 540, location data 555, etc.), measurement information (e.g., a type of shared data 545, sensor data 550, etc.), and information on the contextual environment for the nodes (e.g., context data 560) may be kept in a non-volatile and non-transitory manner.

Those skilled in the art will appreciate that the above identification of particular program code and data are not exhaustive and that embodiments may include further executable program code or modules as well as other data relevant to operations of a processing-based device, such as an ID node, a master node, and a server.

Context Data

As noted above, server 100 may access context data 560 as part of managing nodes in the wireless node network. The exemplary server 100 may contain a collection of such context data 560 in a context database 565 according to an embodiment. As illustrated in FIG. 5, exemplary context database 565 is a single database accessible by processing unit 500 internal to server 100. Those skilled in the art will readily understand that other configurations that provide an accessible collection of context data 560 are possible and contemplated within the scope and principles of embodiments of the invention. For example, context database 565 may be an externally accessible database (or multiple databases), such as an accessible storage maintained outside the server 100 via a dedicated interface or a network storage device (or network attached storage (NAS) unit). In yet another embodiment, the context database may be separately maintained by an external database server (not shown) that is distinct from server 100, but accessible through a communication path from server 100 to a separate database server (e.g., via network 105). Furthermore, those skilled in the art will appreciate that context database 565 may be implemented with cloud technology that essentially provides a distributed networked storage of collections of information (such as context data 560, sensor data 550, shared data 545, etc.) accessible to server 100.

Within context database 565, an exemplary embodiment of the collection of context data 560 may be maintained that generally relates to an environment in which the nodes are operating or anticipated to be operating. In more detail, the context data 560 may generally relate to what a similar node has experienced in a similar environment to what a given node is presently experiencing or is anticipated to experience as the given node moves.

In a general example, an environment in which a node may be actually or anticipated to be operating may include different types of environments—for example, an electronic communication environment (e.g., an RF environment that may be cluttered with signals or include materials or structure that may impede or otherwise shield RF communications), a physical environment of an anticipated path along with the identified node moves (e.g., temperature, humidity, security, and other physical characteristics), a conveyance environment related to how a node may move or be anticipated to be moving (e.g., speed and other parameters of a truck, aircraft, conveyor system), and a density environment related to the density of nodes within an area near a particular node (e.g., how many nodes are anticipated to occupy a corridor, such as structure 2200 shown in FIG. 22A, or a storage facility through which a particular ID node is anticipated to transit on its shipping path).

In light of these different aspects of a node's operating environment, exemplary context data 560 may provide information related to different structures and conditions related to movement of an item (e.g., a particular type of courier device, vehicle, facility, transportation container, etc.). Such information may be generated by an entity operating the wireless node network, such as a shipping company. Additionally, exemplary context data 560 may include third party data generated external to the wireless node network. Thus, context data, such as data 560, may include a wide variety of data that generally relates to the environment in which the nodes are operating and may be used to advantageously provide enhanced node management capabilities in accordance with embodiments of the present invention.

In general, FIG. 5 illustrates exemplary types of context data 560 being maintained in database 565 and in volatile memory 520. Those skilled in the art will appreciate that context data 560 may also be maintained in other data structures, in addition to or instead of maintaining such information in a database. As illustrated in FIG. 5, exemplary types of context data 560 may include but are not limited to scan data 570, historic data 575, shipment data 580, layout data 585, RF data 587, and $3^{rd}$ party data.

Scan data 570 is generally data collected for a particular item related to an event. For example, when an item is placed in a package (such as package 130), a label may be generated and placed on the exterior of the package. The label may include a visual identifier that, when scanned by an appropriate scanning device capable of capturing, identifies the package. The information generated in response to scanning the identifier (a type of event), may be considered a type of scan data. Other scan data 570 may include, for example, general inventory data generated upon manual entry of information related to the package; captured package custodial control data; and bar code scan data.

Historic data 575 is generally data previously collected and/or analyzed related to a common characteristic. Historic data 575 embodies operational knowledge and know-how for a particular characteristic relevant to operations of the wireless node network. For example, the common characteristic may be a particular event (e.g., movement of an item from an open air environment to within a particular closed environment, such as a building), a type of item (e.g., a type of package, a type of content being shipped, a location, a shipment path, etc.), a success rate with a particular item (e.g., successful shipment), and the like. Another example of historic data 575 may include processing information associated with how an item has been historically processed as it is moved from one location to another (e.g., when moving within a particular facility, processing information may indicate the item is on a particular conveyor and may include information about the conveyor (such as speed and how long it is anticipated the item will be on the conveyor)).

Shipment data 580 is generally data related to an item being moved from one location to another location. In one embodiment, shipment data 580 may comprise a tracking number, content information for an item being shipped, address information related to an origin and destination locations, and other characteristics of the item being moved.

Layout data 585 is generally data related to the physical area of one or more parts of an anticipated path. For example, an embodiment of layout data 585 may include building schematics and physical dimensions of portions of a building in which a node may be transiting. An embodiment may further include density information associated with physical areas to be transited and anticipated numbers of potential nodes in those areas as types of layout data. In another example, an embodiment of layout data may include a configuration of how a group of packages may be assembled on a pallet, placed into a shipping container (e.g., a unit load device (ULD)) that helps move a collection of items on various forms with single mode or intermodal transport.

RF data 587 is generally signal degradation information about a signal path environment for a particular type of node and may relate to particular adverse RF conditions that may cause signal fluctuations, interference, or other degradation from the otherwise optimal signal path environment for that type of node. For example, RF data may include shielding effects when using a particular packaging or location, shielding effects when the package is within a particular type of container or assembled as part of a palletized shipment, shielding effects when particular content is shipped, and other physical and electronic interference factors.

Third party data 589 is an additional type of context data 560 that generally includes data generated outside the network. For example, third party data may include weather information associated with particular areas to be transited as the item is moved along an anticipated path from one location to another. Those skilled in the art will appreciate other types of third party data that relate to physical and environmental conditions to be faced by an item being moved from one location to another may also be considered context data 560.

The use of context data, such as context data 560 described above, advantageously helps server 100 better manage movement of items, provide better location determination, enhance intelligent operation and management of different levels of the wireless node network, and provide enhanced visibility to the current location and status of the item during operation of the wireless node network. In one embodiment, server control and management code 525 may provide such functionality that enables the wireless node network to be contextually aware and responsive.

Server Control & Management Code

Generally, server control and management code 525 controls operations of exemplary server 100. In an embodiment, server control and management code 525 is a collection of software features implemented as programmatic functions in code or separate program modules that generally control the behavior of server 100. Thus, exemplary server control and management code 525 may be implemented with several programmatic functions or program modules including, but not limited to, (1) a server-side association manager, which provides a framework for more robust and intelligent management of nodes in the wireless node network; (2) a context-based node manager, which enhances management of nodes in the wireless node network based upon context data; (3) a security manager, which manages secure pairing aspects of node management; (4) a node update manager, which provides updated or different programming for a particular node and shares information with nodes; (5) a location manager for determining and tracking the location of nodes in the network; and (6) an information update manager, which services requests for information related to the current status of a node or generally providing information about a node or collected from a node.

Server-Side Association Manager

The server-side association manager (also referred to as a server-side association management function) is generally a program module in exemplary code 525 that is responsible for intelligently managing the nodes in the wireless node network using a secure information framework. In an embodiment, this framework may be implemented to be a context-driven, learning sensor platform. The framework may also enable a way for information (such as RF scan, location, date/time, and sensor data) to be securely shared across nodes, a way to change the behavior of a node, and for a node to know it is considered "missing." The framework established during operation of the server-side association manager allows the network of nodes to be managed as a system with enhanced and optimized accuracy of determining the physical location of each ID Node. Further information regarding particular embodiments of such an association management framework and methods are explained below in more detail.

Context-Based Association Manager

The context-based node manager is generally a program module in exemplary code 525 that is responsible for incorporating context data as part of management operations to provide an enhanced data foundation upon which visibility of the nodes may be provided. In some embodiments, the context-based node manager may be implemented as part of the server-side association manager while other embodiments may implement the context-based node manager as a separate program module.

In one embodiment, the enhanced data foundation relies upon context data, such as context data 560 (e.g., scan data 570, historic data 575, shipment data 580, layout data 585, and other third party contextual data providing information regarding the conditions and environment surrounding an item and ID node moving from one location to another. Such context data (e.g., the network know-how, building layouts, and operational knowledge of nodes and shipping paths used with the wireless node network) may provide the enhanced building blocks that allow the server 100 to manage tracking and locating of nodes in a robustly enriched contextual environment. In an embodiment, context-based management provides visibility to the system through data analysis for when and how associations should be expected as the nodes travel through the wireless node network. In other embodiments, it may provide the foundation for better understanding RF signal degradation, which can be caused by the operating environment, packaging, package content, and/or other packages related to an item and its ID node.

Security Manager

The security manager module, which may be implemented separately or as part of the association manager module in exemplary server control and management code 525, helps with associating two nodes in the wireless node network by managing aspects of secure pairing of the nodes. In one embodiment, security manager module provides the appropriate pairing credentials to allow a node to securely connect to another node. Thus, when a node desires to connect to another node, an embodiment requires appropriate pairing credentials be generated by the server, provided to the nodes, and observed within the nodes to allow for a successful connection or association of nodes.

In operation, a node (such as master node 110a) identifies the address of the node (such as ID node 120a) to whom it desires to connect. With this address, the node prepares a pairing request and sends the request to the server 110. The server 100 operates under the control of the security manager module of the association manager, and determines whether the requesting node should be connected or otherwise associated with the other node. If not, the server does not issue the requested security credentials. If so and in accordance with the desired association management paradigm set by the association manager of code 525, server provides the requested credentials necessary for a successful wireless pairing and the establishment of secure communications between the associated nodes.

Node Update Manager

The exemplary server control and management code 525 may include a node update manager module that provides updated programming information to nodes within the wireless node network and collects information from such nodes (e.g., shared data 545, sensor data 550). The node update module may be implemented separately or as part of the association manager module in exemplary server control and management code 525.

Providing an update to a node's programming may facilitate and enable distribution of node functions to save power and better manage the nodes as a system. For example, one embodiment may alter the functional responsibility of different nodes depending on the context or association situation by temporarily offloading responsibility for a particular function from one node to another node. Typically, the server directs other nodes to change functional responsibility. However, in some embodiments, a master node may direct other nodes to alter functional responsibility.

Sharing information between nodes and with server (e.g., via an exemplary node update manager) facilitates collecting information from a node and sharing information with other nodes as part of an association management function of server 100. For example, one embodiment may collect and share RF scan data (a type of shared data 545), information about a node's location (a type of location data 555), system information about date/time (another type of shared data 545), and sensor measurements collected from sensor nodes (a type of sensor data 550).

Location Manager

The exemplary server control and management code 525 may include a location manager module that helps determine and track node locations. In a general embodiment, the location of a node may be determined by the node itself (e.g., a master node's ability to determine its own location via location circuitry 475), by a node associated with that node (e.g., where a master node may determine the location of an ID node), by the server itself (e.g., using location information determined by one or more techniques implemented as part of code 525), and by a combined effort of a master node and the server.

In general, an exemplary ID node may be directly or indirectly dependent on a master node to determine its actual physical location. Embodiments may use one or more methodologies to determine node location. For example and as more specifically described below, possible methods for determining node location may relate to controlling an RF characteristic of a node (e.g., an RF output signal level and/or RF receiver sensitivity level), determining relative proximity, considering association information, considering location adjustments for context information and an RF environment, chaining triangulation, as well as hierarchical and adaptive methods that combine various location methodologies. Further information and examples of how an exemplary location manager module may determine a node's location in accordance with such exemplary techniques are provided in more detail below.

Additionally, those skilled in the art will appreciate that it may also be possible to determine what constitutes an actionable location versus actual location based upon contextual information about the item being tracked. For example, a larger item may require relatively less location accuracy than a small item such that operational decisions and status updates may be easier implemented with knowledge of context. If the size of the item is known, the location accuracy can be tuned accordingly. Thus, if a larger item is to be tracked, or if the system's contextual awareness of it is such that lower location accuracy can be used, a stronger signal and thus wider area of scanning may be employed, which may help in situations where RF interference or shielding is an issue.

Information Update Manager

The exemplary server control and management code 525 may include an information update manager module that provides information related to operations of the wireless node network and status of nodes. Such information may be provided in response to a request from a device outside the wireless node network (such as user access device 200). For example, someone shipping an item may inquire about the current status of the item via their laptop or smartphone (types of user access devices), which would connect to server 100 and request such information. In response, the information update manager module may service such a request by determining which node is associated with the item, gathering status information related to the item (e.g., location data, etc.), and provide the requested information in a form that is targeted, timely, and useful to the inquiring entity.

In another example, a user access device may connect to server 100 and request particular sensor data from a particular node. In response, information update manager may coordinate with node update manager, and provide the gathered sensor data 545 as requested to the user access device.

Node Filtering Manager

An embodiment of exemplary server control and management code 525 may optionally comprise a node filtering manager, which helps manage the traffic of nodes with a multi-level filtering mechanism. The filtering essentially sets up rules that limit potential associations and communications. An example of such a node filtering management may define different levels or modes of filtering for a master node (e.g., which ID nodes can be managed by a master node as a way of limiting the communication and management burdens on a master node).

In one example, a "local" mode may be defined where the ID node only communicates and is managed by the assigned master node at the location where the last wireless node contact back to server 100 and/or where third party data indicates the assigned master node and ID node are in physical and wireless proximity. Thus, for the "local" mode of traffic filtering, only the assigned master node communicates and processes information from a proximately close and assigned ID node.

Moving up to a less restrictive filtering mode, a "regional" mode of filtering may be defined where the ID node may communicate and be managed by any master node at the location last reported back to server 100 and/or where third party data indicates the ID node is located. Thus, for the "regional" mode of traffic filtering, any master node near the ID node may communicate and process information from that ID node. This may be useful, for example, when desiring to implement a limit on associations and pairings to within a particular facility.

At the least restrictive filtering mode, a "global" mode of filtering may be defined as essentially system-wide communication where the ID node may be allowed to communicate and be managed by any master node. In other words, the "global" mode of traffic filtering allows any ID node within the wireless node network to communicate information through a particular master node near the ID node may communicate and process information from that ID node.

Thus, with such exemplary filtering modes, an ID node in a certain condition (e.g., distress, adverse environmental conditions, adverse conditions of the node, etc.) may signal the need to bypass any filtering mechanism in place that helps manage communications and association by using the "Alert" Status Flag. In such an example, this would operate to override any filtering rules set at the Master Node level in order to allow an ID node to be "found" and connect to another node.

Thus, exemplary server 100 is operative, when executing code 525 and having access to the types of data described above, to manage the nodes, collect information from the nodes, store the collected information from the nodes, maintain or have access to context data related to the environment in which the nodes are operating, and provide information about the nodes (e.g., status, sensor information, etc.) to a requesting entity.

Node Communication & Association Examples

To better illustrate how exemplary management and communication principles may be implemented within an exemplary wireless node network, FIGS. 8-12 provide several examples of how exemplary components of the wireless node network may generally communicate (advertising & scanning), associate, and exchange information during different types of operations in various embodiments. FIGS. 22A-C also provide a more detailed application of such exemplary association and communication activities when an exemplary ID node moves along a transit path (e.g., through a corridor) and is tracked and managed by different master nodes and a server in an embodiment.

Node Advertising Cycle Example

As generally explained above, a node may have several different types of advertising states in which the node may be connectable with other nodes and may communicate with other nodes. And as a node moves within a wireless node network, the node's state of advertising and connection may change as the node disassociates with a previously connected node, associates with a new node, or finds itself not associated with other nodes. In some situations, a node may be fine and in normal operation not be connected or associated with another node. However, in other situations, a node may raise an issue with potentially being lost if it has not connected with any other node in a very long period of time. As such, a node may go through different types of advertising states in these different operational situations.

Generally, a node may be in a state where it is not connectable with other nodes for a certain period of time (also referred to as a non-connectable interval). But later, in another state, the node may want to be connected and advertises as such for a defined connectable period (also referred to as a connectable interval). As the node advertises to be connected, the node may expect to be connected at some point. In other words, there may be a selectable time period within which a node expects to be connected to another node. However, if the node is not connected to another node within that period of time (referred to as an Alert Interval), the node may need to take specific or urgent action depending upon the circumstances. For example, if a node has not been connected to another node for 30 minutes (e.g., an example alert interval), the node may change operation internally to look "harder" for other nodes with which to connect. More specifically, the node may change its status flag from an Alert Level 0 (no issue, operating normal) to Alert Level 2 in order to request that any available master node acknowledge receipt of the advertisement packet broadcasted by the node seeking a connection.

Figure 8:
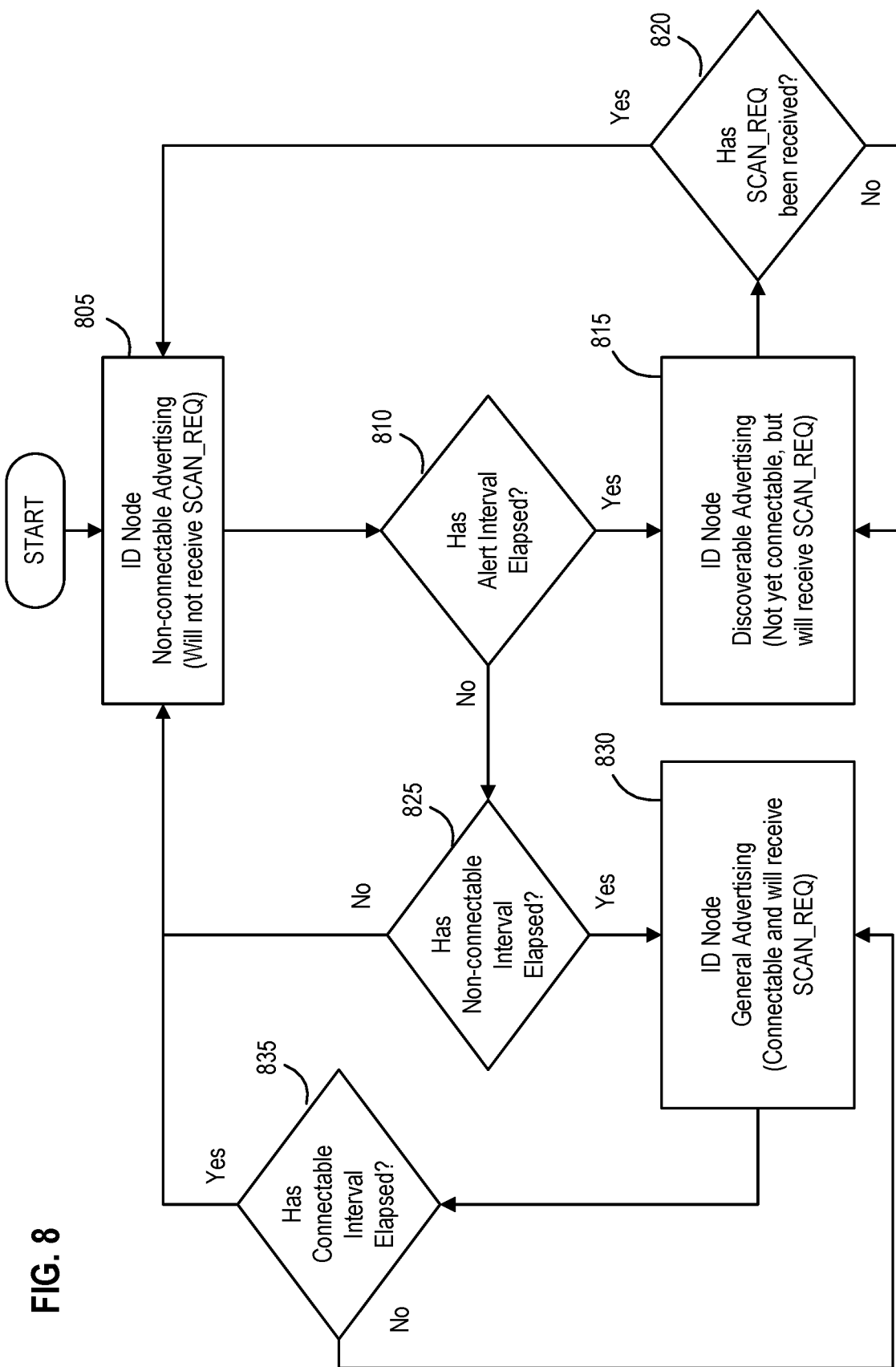
FIG. 8 is a state diagram illustrating exemplary states and transitions between the states as part of operations by an exemplary node in a wireless node network in accordance with an embodiment of the invention.

FIG. 8 is a diagram illustrating exemplary advertising states (or information exchange and node connectability states) and factors involved in transitions between the states by an exemplary ID node in a wireless node network in accordance with an embodiment of the invention. Referring now to FIG. 8, three exemplary states for a node are illustrated as part of an exemplary advertising cycle for the node—namely, an ID Node Non-Connectable Advertising state 805, an ID Node Discoverable Advertising state 815, and an ID Node General Advertising state 830. Transitions between these states will depend on factors related to expirations of the types of intervals described above. In an embodiment, the duration of each of these intervals will depend upon the system implementation and the contextual environment within which the ID node is operating. Such time intervals may, for example, be set by server 100 as part of data (e.g., profile data, association data, context data) provided to the node when updating the node and managing operations of the node.

Referring to the example illustrated in FIG. 8, an exemplary ID node may have an alert interval set at, for example, 30 minutes, and be in ID Node Non-Connectable Advertising state 805 with a non-connectable interval set at 5 minutes. In state 805, the ID node may broadcast or advertise, but is not connectable and will not receive a SCAN_REQ message (a type of request for more information sent to the advertising node from another node). Thus, the ID node in state 805 in this example may advertise in a non-connectable manner for at least 5 minutes but expects to be connected within 30 minutes.

If the alert interval has not yet elapsed (factor 810) and the non-connectable interval is still running (factor 825), the ID node simply stays in state 805. However, if the alert interval has not elapsed (factor 810) and the non-connectable interval elapses (factor 825), the ID node will enter a mode where it wants to try to connect to another node for a period of time (e.g., a 1 minute connectable interval) and will move to the ID Node General Advertising state 830 in the exemplary advertising cycle of FIG. 8. In state 830, as long as the connectable interval is running, the ID node will stay in this state where it is connectable to another node and will receive SCAN_REQ types of requests from other nodes in response to the advertising packets the ID node is broadcasting. However, when the connectable interval (e.g., the 1 min period) elapses or expires (factor 835), the ID node returns back to the Non-connectable Advertising state 805 for either the next time the non-connectable interval elapses (and the ID node again tries to connect in state 830) or the alert interval finally elapses (and the ID node finds itself in a situation where it has not connected to another node despite its efforts to connect in state 830).

When the alert interval finally elapses (factor 810), the ID node moves to the ID Node Discoverable Advertising state 815. Here, the ID node is not yet connectable but will receive a SCAN_REQ type of request from other nodes in response to advertising packets the ID node is broadcasting. In this state 815, the exemplary ID node may alter its status flag to indicate and reflect that its alert interval has expired and that the node is now no longer in normal operation. In other words, the ID node may change the status flag to a type of alert status being broadcasted to indicate the ID node urgently needs to connect with another node. For example, the status flag of the advertising packet broadcast by the ID node may be changed to one of the higher Alert Levels depending on whether the node needs to upload data (e.g., Alert Level 3 status) or synchronize timer or other data with another node (e.g., Synchronize status). With this change in status flag, and the ID node in state 815 broadcasting, the ID node awaits to receive a request from another node that has received the broadcast and requested more information via a SCAN_REQ message (factor 820) sent to the ID node from that other node. Once a SCAN_REQ message has been received by the ID node (factor 820), the ID node that went into the alert mode because it had not connected with another node within the alert interval can connect with that other node, upload or share data as needed, and then shift back to state 805 and restart the alert interval and non-connectable intervals.

Master Node to ID Node Association Example

Advertising (broadcasting) and scanning (listening) are ways nodes may communicate during association operations. FIGS. 9-12 provide examples of how network elements of a wireless node network (e.g., ID nodes, master nodes, and a server) may communicate and operate when connecting and associating as part of several exemplary wireless node network operations.

Figure 9:
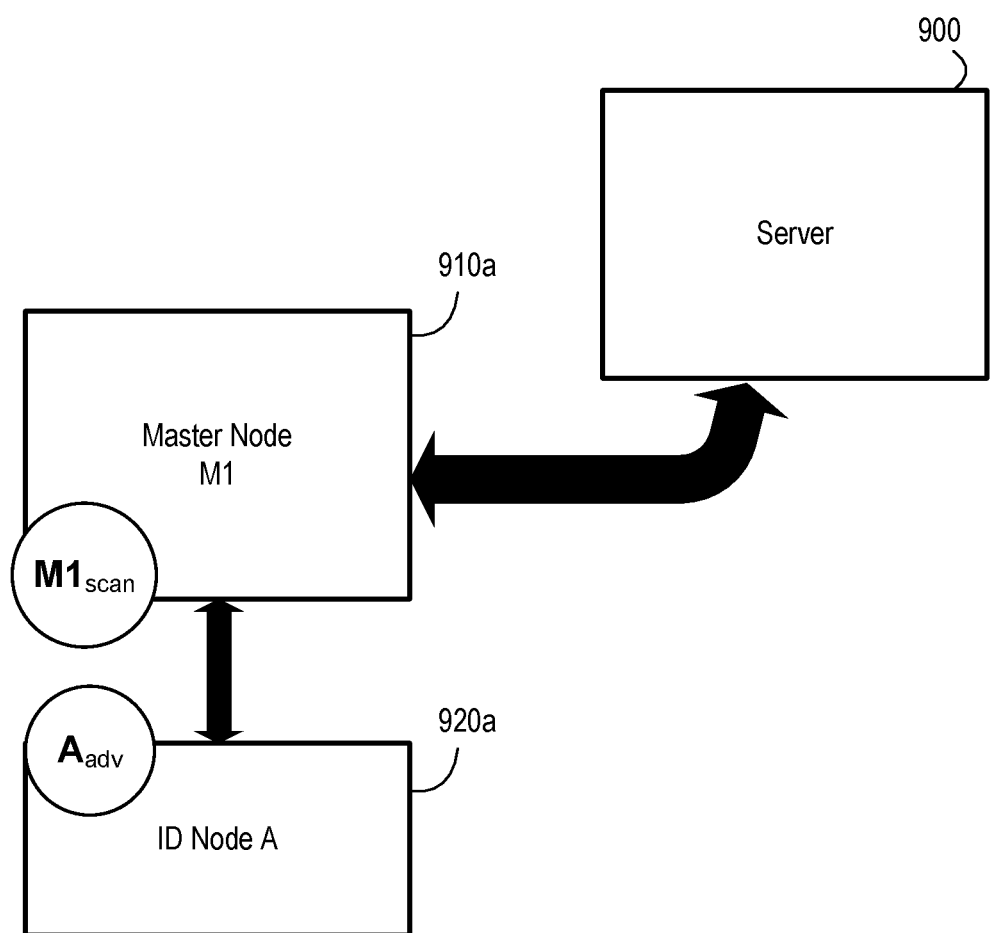
FIG. 9 is a diagram illustrating exemplary components of a wireless node network during an exemplary master-to-ID node association in accordance with an embodiment of the invention.

FIG. 9 is a diagram illustrating exemplary components of a wireless node network during an exemplary master-to-ID node association in accordance with an embodiment. Referring now to FIG. 9, exemplary master node M1 910*a* is illustrated within communication range of exemplary ID node A 920*a*. Master node M1 910*a* also has a communication path back to server 900. As shown, master node M1 910*a* is in a scanning or listening mode (e.g., indicated by the "M1$_{scan}$" label) while ID node A 920*a* is in an advertising or broadcasting mode (e.g., indicated by the "A$_{adv}$" label). In this example, M1 master node 910*a* has captured the address of ID node A 920*a* through A's advertising of at least one advertising data packet, and has reported it to the server 900. In this manner, the capturing and reporting operations effectively create a "passive" association between the nodes and proximity-based custodial control. Such an association may be recorded in the server, such as server 900, as part of association data, such as association data 540.

In another embodiment, passive association between a master node and ID node may be extended to an "active" association or connection. For example, with reference to the embodiment shown in FIG. 9, server 900 may instruct master node M1 910*a* to associate, connect, or otherwise pair with ID node A 920*a*, and forwards the required security information (e.g., PIN credentials, security certificates, keys) to master node M1 910*a*. Depending on the advertising state of ID node A 920*a*, ID node A 910*a* may only be visible (discoverable) but not connectable. In such a situation, the master node M1 910*a* must wait until ID node A 920*a* is in a connectable state (e.g., the ID Node General Advertising state) and can be paired. As discussed above with reference to FIG. 8, each ID node has a certain time window during each time period where it can be paired or connected.

In this example, when the ID node A 920*a* is successfully paired with master node M1 910*a*, ID node A 920*a* may no longer advertise its address. By default, only an unassociated device will advertise its address. A paired or associated node will only advertise its address if instructed to do so.

ID Node to ID Node Association Example

Figure 10:
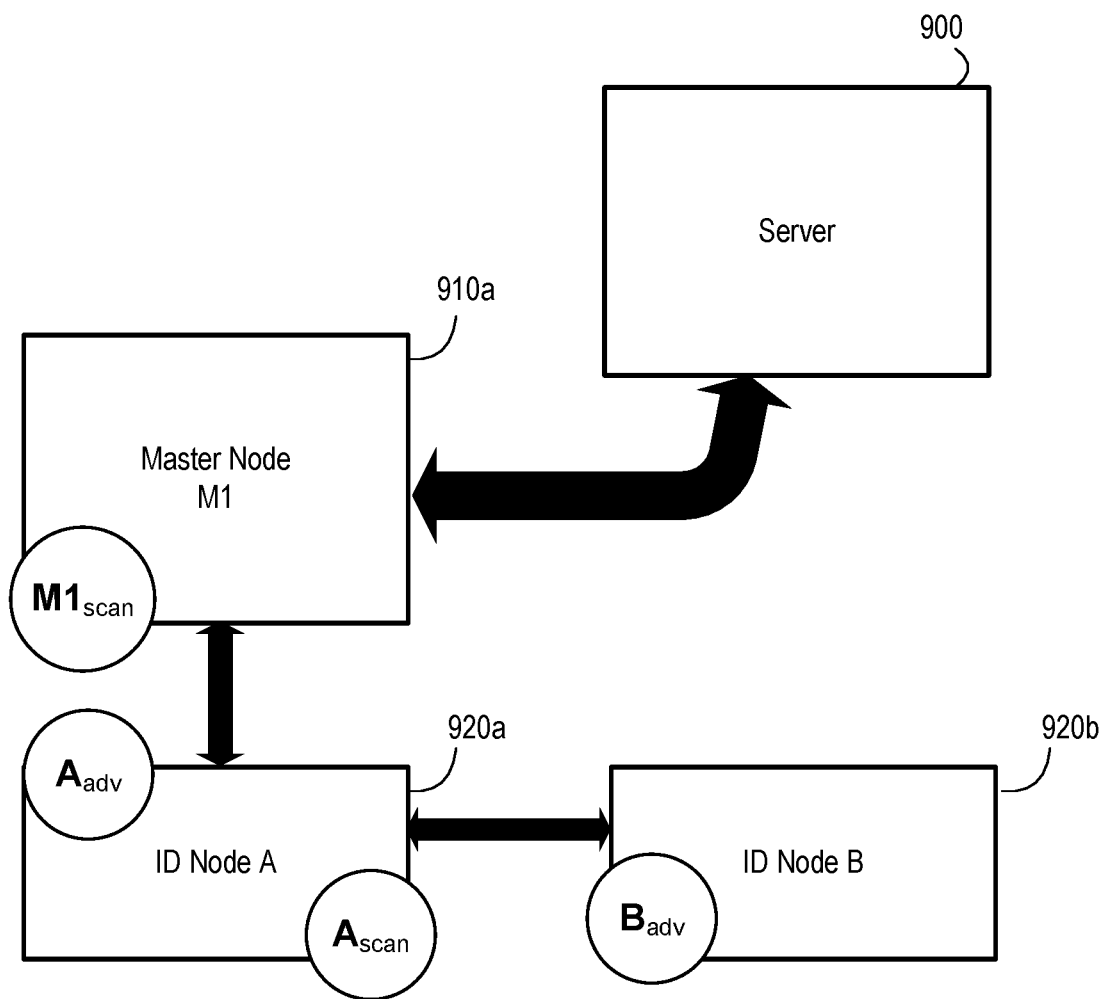
FIG. 10 is a diagram illustrating exemplary components of a wireless node network during an exemplary ID-to-ID node association in accordance with an embodiment of the invention.

In various embodiments, an ID node may associate with or connect to other ID nodes. FIG. 10 is a diagram illustrating exemplary components of a wireless node network during an exemplary ID-to-ID node association in accordance with an embodiment of the invention. Referring now to FIG. 10, exemplary master node M1 910*a*, ID node A 920*a*, and server 900 are similarly disposed as shown in FIG. 9, but with the addition of ID node B 920*b*, which is within communication range of ID node A 920*a*. In this example, ID node A 920*a* is running in query (scan) mode (e.g., A$_{scan}$) listening for ID node B 920*b*. When ID node A 910*a* detects ID node B 920*b* advertising (e.g., B$_{adv}$) with one or more advertising data packets as part of an advertised message from ID node B 920*b*, ID node A 920*a* identifies a status flag from the message indicating ID node B 920*b* has, for example, data (e.g., sensor data 350) for upload. As a result, ID node A 920*a* logs the scan result (e.g., as a type of association data 340) and, when next connected to master node M1 910*a*, ID node A 920*a* uploads the captured scan log information to the server 900. In this manner, the ID node scanning, capturing, and reporting operations effectively create a "passive" association between the different ID nodes. Such a passive association may be recorded in the server 900 as part of association data 540.

In another embodiment, passive association between two ID nodes may be extended to an "active" association or connection. For example, with reference to the embodiment shown in FIG. 10, based upon the captured status flag and uploaded information about ID node B 920*b* under that mode, the server 900 may issue a request to ID node A 920*a* through master node M1 910*a* to actively connect or pair with ID node B 920*b* for the purpose of downloading information from ID node B 920*b*. In one example, security credentials that authorize the active connection between ID node A 920*a* and ID node B 920*b* are downloaded to ID node A 920*a* from master node M1 910*a*, which received them from server 900. In another example, the requisite security credentials may have been pre-staged at ID node A 920*a*. And rather than rely upon an ID node to ID node connection, master node M1 may have connected directly with ID node B 920*b* if M1 was within communication range of ID node B 920*b*.

Information Query ID Node to Master Node Example

Figure 11:
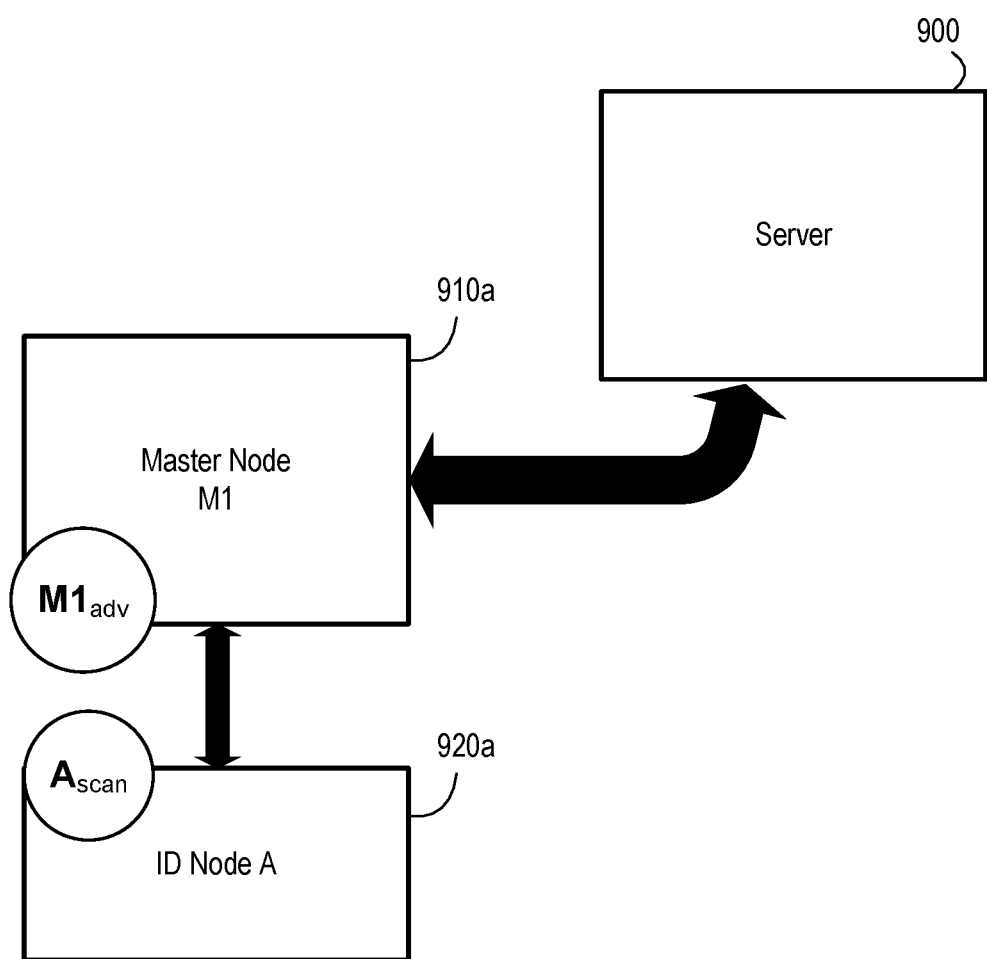
FIG. 11 is a diagram illustrating exemplary components of a wireless node network during an exemplary ID-to-master node query in accordance with an embodiment of the invention.

An exemplary ID Node may also issue queries to other nodes, both master nodes and ID nodes. FIG. 11 is a diagram illustrating exemplary components of a wireless node network during an exemplary ID-to-master node query in accordance with an embodiment of the invention. Referring now to FIG. 11, a similar group of nodes as shown in FIG. 9 appears, except that exemplary master node M1 910a is in an advertising or broadcasting mode (e.g., M1$_{adv}$) while ID node A 920a is in a scanning mode (e.g., A$_{scan}$). In this configuration, ID node A 920a may query master node M1 910a for information. In one embodiment, the query may be initiated through the ID node setting its status flag. The requested information may be information to be shared, such as a current time, location, or environmental information held by the master node M1 910a.

In a passive association example, ID node A 920a in A$_{scan}$ mode may have captured the address of master node M1 910a. However, since an ID node cannot directly connect to the server 900 to request pairing security credentials (e.g., security pin information that authorizes an active connection between ID node A 920a and master node M1 910a), a passive association and corresponding pairing will have been initiated from the master node. In another example, it may be possible for ID node A 920a to have the pairing credentials stored as security data 335 from a previous connection. This would allow ID node A 920a then to initiate the active association with master node M1 910a after a passive association.

Alert Level Advertising Example

Figure 12:
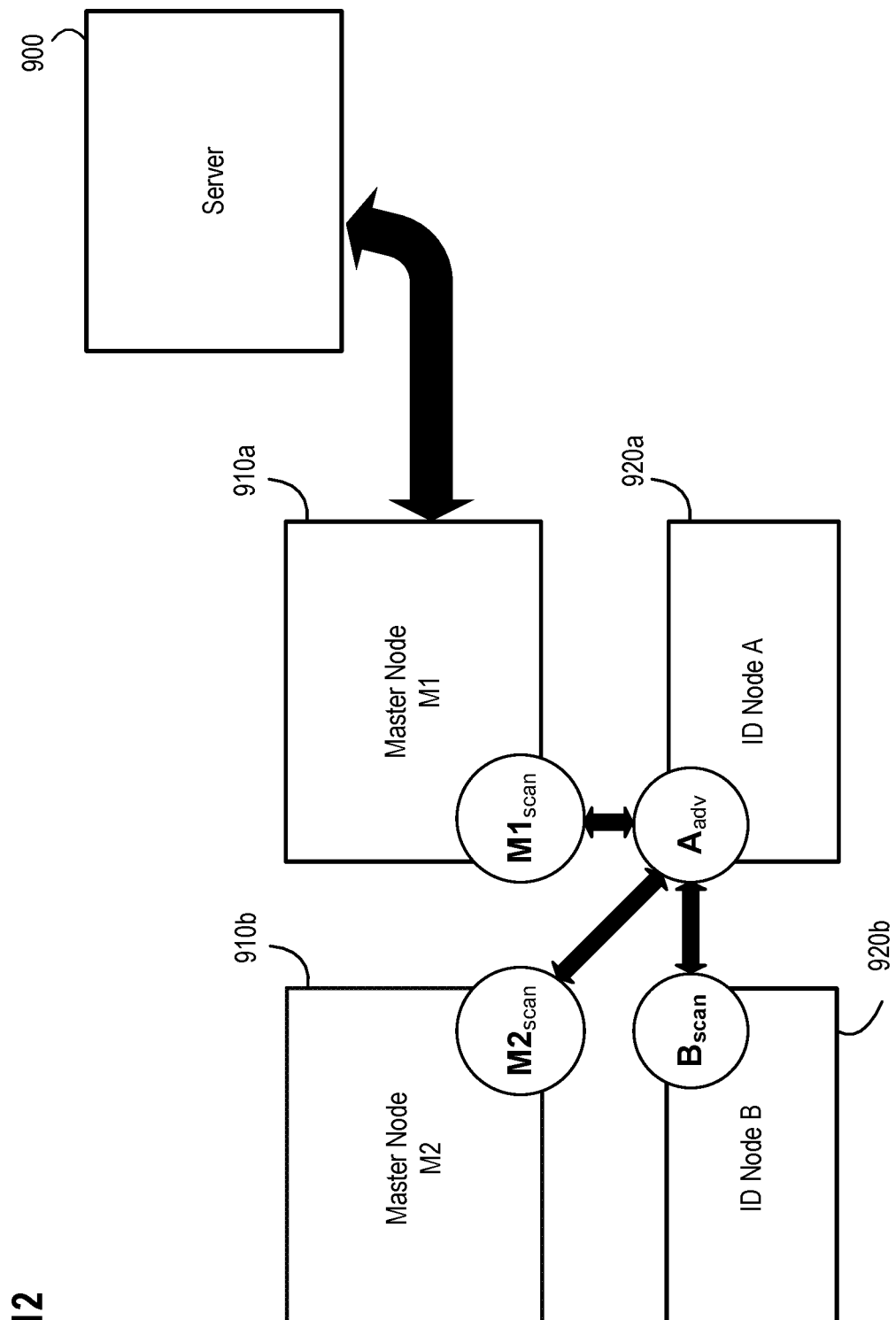
FIG. 12 is a diagram illustrating exemplary components of a wireless node network during an exemplary alert advertising mode in accordance with an embodiment of the invention.

As previously noted, a node may enter an alert stage or level in one or more embodiments. For example, if a node has not received an acknowledgement from a master node for an advertising packet within a set period (e.g., an Alert Interval as described in some embodiments), the node will enter a particular alert stage for more specialized advertising so that it may be "found" or pass along information. FIG. 12 is a diagram illustrating exemplary components of a wireless node network during an exemplary alert advertising mode in accordance with an embodiment of the invention. Referring now to FIG. 12, a similar group of nodes as shown in FIG. 9 appears, with the addition of another master node (master node M2 910b) and another ID node (ID node B 920b). Exemplary ID node A 920a is in an advertising or broadcasting mode (e.g., A$_{adv}$) while nodes M1, M2, and B are each in scanning mode (e.g., M1$_{scan}$, M2$_{scan}$, and B$_{scan}$). In this example and configuration as shown in FIG. 12, the status flag in an advertising message from ID node A 920a has been set to a particular alert level (e.g., Alert Level 2) in the header of the message, requesting any nearby master node to acknowledge it. In one example, this mode may be entered if ID node A 920a has not connected with another node for a set period or time. In another example, ID node A 920a may enter this specialized advertising mode upon received instructions (e.g., from server 900 or another nearby node) or a triggered condition (other than time), such as when a sensor input (such as light) is detected or otherwise registered and the node issues continuous updates of its address as a security feature. The ID node A 920a set at this alert level and in this specialized advertising mode is thus set in an active pairing mode, waiting for pairing credentials.

From a passive association perspective, any node in scanning mode can passively associate with such an advertising node (e.g., ID node A 920a in this alert mode). Thus, in an embodiment, the Alert Level 2 status flag in the advertising header broadcast by ID node A 920a indicates that urgent and active intervention is requested, rather than merely passively associate without an active connection.

From an active association perspective, any node that uploads the special advertising header of ID node A 920a may be forwarded the security credentials from the server 900. This would allow for the node receiving such credentials to actively associate or pair with ID node A 920a.

While FIG. 8 provides examples of how a node may advertise, and FIGS. 9-12 provide examples of how different exemplary devices (e.g., ID nodes, master nodes, and a server) may advertise and associate in different ways, FIGS. 22A-C provide a progressive set of illustrations that expand upon how associating and disassociating may be applied within an exemplary wireless node network. More specifically, FIGS. 22A-C show how associations and disassociations may occur when an exemplary ID node is tracked and managed by a server and different master nodes as the ID node moves through an exemplary transit path in accordance with an exemplary embodiment of the invention.

Referring now to FIG. 22A, a structure 2200 is shown having an entry and exit point. In one example, the structure 2200 may be a corridor or another part of a building or facility. In another example, structure 2200 may be a conveyor system that transports an item and its ID node from the entry point to the exit point. Master node M1 2210a is located near the entry point of structure 2200 while master node M2 2210b is located near the exit point. Those skilled in the art will appreciate that other master nodes may be disposed at additional points in structure 2200, but are not shown for sake of convenience and to simplify the association hand-off explanation that follows. Server 100 is operatively connected to each of master node M1 2210a and master node M2 2210b via network 105.

In one embodiment, server 100 has access to context data 560 related to the structure 2200, such as layout data 585 on dimensions and materials making up structure 2200. Context data 560 may include historic data 575 on how an ID node has operated and successfully been tracked as it traverses structure 2200 from the entry point to the exist point. For example, server 100 may have context data indicating structure 2200 is a conveyor that can transport an item and its ID node from the entry point to the exit point over a distance of 800 feet. The context data may further indicate typical items are moved at a certain speed on the conveyor of structure 2200 and a nominal time from the entry point to the exit point may be about 5 minutes. Thus, the server 100 has access to context data about the environment within with an ID node is operating and may leverage this to better and more accurately manage the ID node.

In FIG. 22A, ID node A 2220a is shown entering the structure 2200 at the entry point. Here, ID node A 2220a may be advertising in hopes of connecting with a master node as it enters structure 2200 with, for example, a non-connectable interval of 10 seconds with a connectable interval of 5 seconds. In this example, the server 100 knows that ID node A 2220a is located near the entry point and anticipates that ID node A 2220a should be coming near to master node M1 2210a at the entry point. Thus, server 100 may set the connectable and non-connectable intervals accordingly so as to provide a sufficient opportunity for ID node A 2220a to connect to the next master node along the predicted path of the ID node and in accordance with the speed of travel.

Additionally, server 100 may set the alert interval to 1 minute in this context. Here, if ID node A 2220a is not connected to another node within 1 minute, ID node A 2220a may broadcast or advertise with a message having a changed status flag that indicates an alert status so that ID node A 2220a can connect to a broader range of other nodes that see it is urgent for ID node A 2220a to connect and, essentially, be found. Depending on the context (e.g., the type of conveyor, the speed of the conveyor, the density of nodes near the entry point, etc.), those skilled in the art will appreciate that the server 100 can adjust the advertising cycle intervals to better accommodate the ID node's current environment.

When master node M1 2210a is scanning (listening), it may initially detect an advertising packet from ID node A 2220a during node A's non-connectable interval. But when ID node A 2220a changes advertising states and broadcasts as a connectable node in the general advertising state (i.e., during the connectable interval), master node M1 2210a may respond with a SCAN_REQ that acknowledge receipt of the broadcasted message and asks for further information from ID node A 2220a. Master node M1 2210a receives the requested information from ID node A 2220a, and then communicates with the server 100 to notify the server of its passive association with ID node A 2220a. Server 100 determines if active association is desired, and may authorize the active association between master node M1 2210a and ID node A 2220a by sending security credentials to master node M1 2210a, which allow the nodes to securely connect and share information. And master node M1 2210a may determine the location of ID node A 2220a (or server 100 may do so by directing master node M1 and/or ID node A), and provide the location of ID node A 2220a to server 100. Thus, server 100 is able to manage and track the location of ID node A 2220a as it enters structure 2220 via at least association.

In FIG. 22B, ID node A 2220a has traversed down part of the transit path through structure 2200 while remaining associated with master node M1 2210a. However, at some point master node M1 2210a and ID node A 2220a are disassociated at the direction of server 100 (or when they can no longer communicate). In one example where ID node A 2220a is on the conveyor within structure 2200, server 100 may instruct ID node A 2220a to go to a low power mode for a particular period of time in order to, for example, conserve ID node power. In another example, the low power mode may also provide better location accuracy. As the server 100 has access to the context data, the server 100 may know that ID node A 2220a was associated with master node M1 2210a near the entry point at a given time, and determine that ID node A 2220a will not be near the exit point until the end of the particular period of time. With the ID node A 2220a programmed this way, once the particular period elapses, the ID node A 2220a should be near the exit point and may again be placed into a normal operation mode so that it can seek to connect with master node M2 2210b.

Similar to the association process discussed with respect to ID node A and master node M1, ID node A 2220a and master node M2 2210b may be associated as ID node A 2220a approaches master node M2 2210b near the exit point. Once connected, the node locations and association data are updated on the server 100. And as ID node A 2220a continues to move through structure 2200, ID node A 2200a may arrive at the exit point as shown in FIG. 22C, where the node locations and association data are updated once again on the server 100.

Those skilled in the art will appreciate how such principles may be applied to further movements of an ID node as it is handed off (e.g., via active/passive associations and disassociations) between other master nodes and keeping track of these associations and node locations on the server 100. Additionally, as server 100 tracks and monitors associations, disassociations, and contextual environmental operations, server 100 essentially learns how to better use context information better track nodes, manage power used by ID nodes, and enhance accuracy for locations.

Those skilled in the art will also appreciate the general tradeoff with a level of RF power level and accuracy of location. If a node's RF power level is set high, it may advertise and connect with other nodes a longer distance away. But at such a high power level setting, the ability for the system to discriminate between and locate different nodes may be a challenge.

Association Management within a Wireless Node Network

As explained above in general, management of nodes may rely upon associations created and tracked between nodes and as indicated by association data generated on one or more of the nodes to reflect such logical associations. In some embodiments, the association relied upon may be an active association where the server expressly authorizes an active connection between nodes. In other embodiments, the association relied upon may be a passive association where the master node or command node (a type of managing node) is associated with the other node, but not actively connected to the other node. By virtue of the passive association, the server may be able to keep track of and manage the other node without requiring an active association. Thus, those skilled in the art will appreciate that in still other embodiments, associations relied upon for managing a wireless node network may include both active and passive associations and may be generally authenticated or, more specially, authorize a secure connection that has a degree of protection for the connection and communications using that connection.

Context Management within a Wireless Node Network

As explained above in general, management of nodes may rely upon the contextual environment of the nodes. As shown in FIG. 5, server 100 has access to a wide variety of different context data 560. Context data, such as data 560, may include a wide variety of data that generally relates to the environment in which the nodes are operating and may be used to advantageously provide enhanced node management capabilities in accordance with embodiments of the present invention. As such, the use of such context data provides a data foundation in an embodiment so that the server may better and more efficiently implement management tasks related to nodes in the network, and adjust such tasks to account for relevant context data as nodes move within the network (e.g., as an ID node moves with an item being shipped along an anticipated or predicted transit path from an origin to a destination). For example, the server take advantage of its ability to rely upon relevant context data to advantageously alter how it instructs a node operate, how it associates a node with the another node, how it can better locate a node, and how it can more efficiently track and respond to requests to report the location of the node.

Node Location Determination Methodologies

As part of managing and operating a wireless node network in accordance with one or more embodiments of the invention, determining a node's location may be performed. As explained above, an exemplary ID node may be directly or indirectly dependent on a master node to determine its location. In the embodiments discussed and described herein, a location of a node may generally encompass a current or past location. For example, an embodiment that determines a node's location may be a current location if the node is not moving, but may necessarily determine the location as a past location should the node be in a state of motion.

Likewise, the term location alone may include a position with varying degrees of precision. For example, a location may encompass an actual position with defined coordinates in three-dimensional space, but use of the term location may also include merely a relative position. Thus, the term location is intended to have a general meaning unless otherwise expressly limited to a more specific type of location.

Determining node location may done by a master node alone, the server alone, or the master node working together with the server. And on such devices, embodiments may use one or more methodologies to determine a node's location and further refine the location. Such example methodologies may include, but are not limited to, determining node location may relate to controlling an RF characteristic of a node (e.g., an RF output signal level and/or RF receiver sensitivity level), determining relative proximity, considering association information, considering location adjustments for context information and an RF environment, chaining triangulation, as well as hierarchical and adaptive methods that combine various location methodologies. A more detailed description of these exemplary node location determination techniques is provided below.

Location Through Proximity

In one embodiment, a signal strength measurement between two or more nodes may be used to determine the proximity of the nodes. If neither node's actual location is known, one embodiment may infer a location relationship of the two nodes through proximity.

Proximity when Varying Power Characteristics

For example, an exemplary method of determining a node's location in a wireless node network of nodes may involve varying a node's power characteristic, such as the output power of one of the nodes. Generally and as explained with reference to FIG. 13, the power characteristic may be varied to identify closer ones of the nodes to the node broadcasting. The node broadcasting may transmit one or a series of signals while other nodes may report receiving one or more of the signals. Those other nodes that receive at least one signal broadcast from the transmitting node may be deemed part of a close group of nodes. And as the power characteristic is varied (increased or decreased or both), a closest group of nodes (or single node) may be identified as the smallest group of nodes of those that receive at least one signal from the broadcasting node. Accordingly, while not absolute, a type of location for the broadcasting node may be determined based on the closest one or group of nodes. This may be repeated for neighboring nodes to yield a set of closest node information for each of the nodes. In more detail, an exemplary set of closest node information for each of the nodes may include which nodes are closest (via the lowest power characteristic) and more robustly supplement this information with which other nodes are incrementally further away (via increasingly larger power characteristics). Thus, the set of closest node information provides the basis for a determination of how close the nodes in the network are to each other, which provides a type of location determination for each node.

Additionally, context data may be referenced in certain embodiments to further enhance determining how close the nodes are to each other. For example, combining the set of closest node information with context data, such as scan information that registers when an item changes custodial control in a delivery system, may further refine how to determine the location of the nodes. Scan and other context information will help determine if one or more of the nodes, for example, are known to be in the same container, vehicle or moving on a belt together.

Thus, this type of context data may be integrated into a further step of refining how close the nodes are to each other based upon the context data.

In general, a location of a node based upon proximity may be determined when a power characteristic of nodes is changed or varied in a wireless node network. An exemplary method for location determination by varying a power characteristic of nodes in a wireless node network in accordance with an embodiment of the invention begins by instructing a first of the nodes to vary the power characteristic for one or more signals broadcast by the first node. In a more detailed embodiment, such an instruction may cause the first node, for example, to incrementally decrease or incrementally increase the power characteristic (such as an output power level) between values.

This method continues by identifying a first group of other nodes in the wireless node network that are near the first node based upon those of the other nodes that received at least one of the signals broadcast by the first node as the first node varies the power characteristic. In a further embodiment, this identifying step may incrementally identifying which of the first group of other nodes are receiving at least one of the broadcast signals as the first node incrementally varies the output power level of the signals broadcast. The incrementally identified nodes may be deemed a set of increasingly close nodes to the first node.

The method continues by identifying a closest one or more of the other nodes as a smallest group of the other nodes that received at least one of the one or more signals broadcast by the first node as the first node varies the power characteristic.

The method concludes by determining a location of the first node based upon the closest one or more of the other nodes. Thus, as the power characteristic is varied, the group of nodes that have received at least one of the signals broadcast by the first node may change and the smallest such group being a closest group of nodes (even if just one node) to the first node. In a more detailed embodiment, this determining step may comprise determining the location of the first node based upon the closest one or more of the other nodes and the set of increasingly close nodes to the first node as the set of increasingly close nodes provides more detailed proximity information for a refined location determination.

Figure 14:
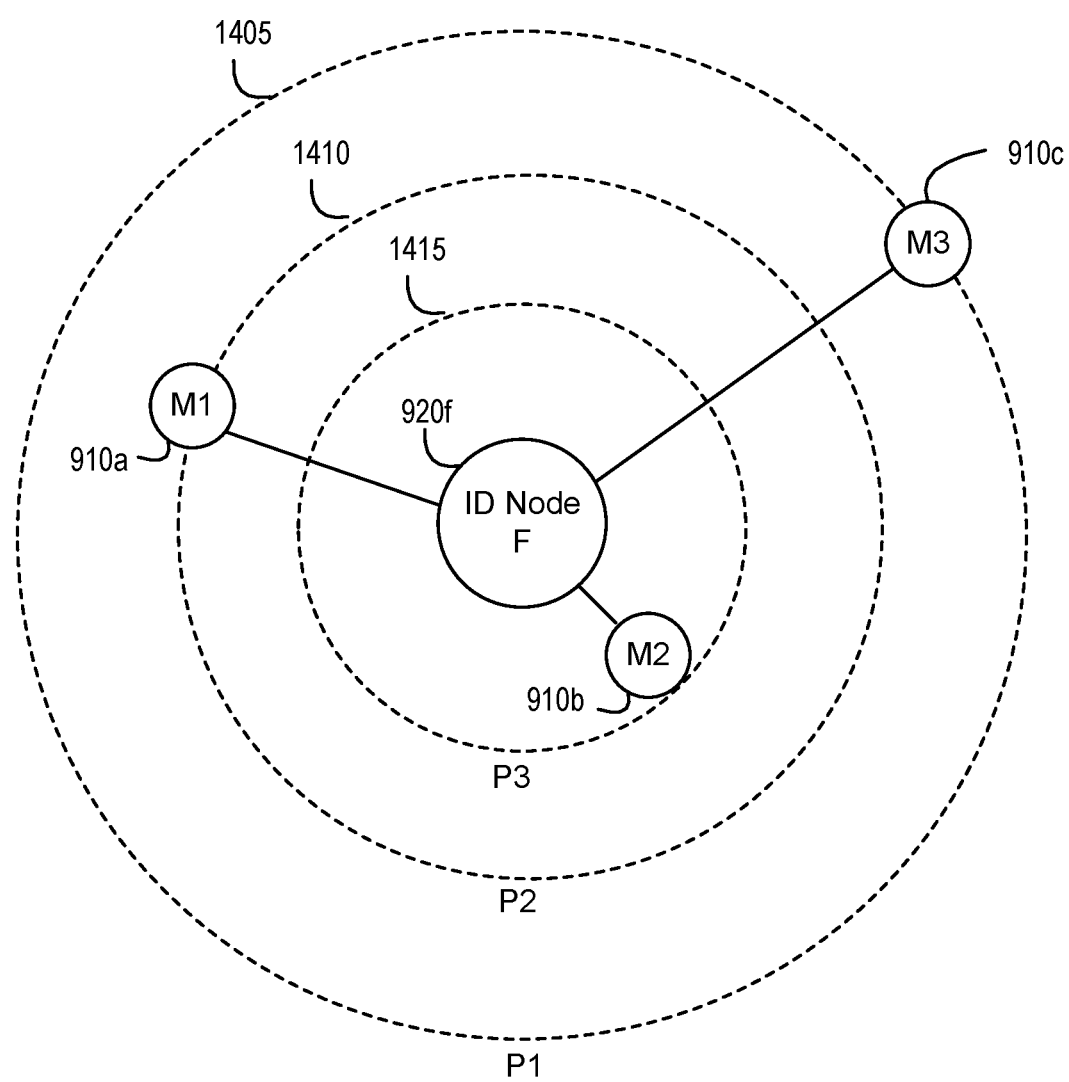
FIG. 14 is a diagram illustrating an exemplary location determination using ID node advertise in accordance with an embodiment of the invention.

For example, referring to FIG. 14, the set of increasingly close nodes to the ID node F 920*f* may include node M3 as being farthest away and M1 being closer than M3. When the power characteristic of ID node F incrementally decreases, and its output power level changes from P1 to P2, M3 can no longer receive the signal, but M1 and M2 still do. And as the power characteristic of ID node F continues to incrementally decrease, and its output power level is changed from P2 to P3, M1 can no longer receive the signal, but only M2 does as the last of the nodes closest to ID node F. Thus, in this example, determining the location of ID node F may be based upon the fact that M2 is the closest node and the set of increasingly close nodes include M1 and M3 with M1 being closer than M3.

In another embodiment, one or more further refinements to the first nodes location may be performed. In one example, the steps of the above described locating by proximity technique may be repeated where a second of the nodes is instructed to vary the power characteristic for one or more signals broadcast by the second node, and then the method may further refine the location of the first node based upon a location of the second node. In a more detailed example, the steps may be repeated where a second of the nodes is instructed to vary the power characteristic for one or more signals broadcast by the second node, and then this method may further the location of the first node based upon a location of the second node and a set of increasingly close nodes to the second node. With this increasingly cross-related information on what nodes are closer to other nodes and to what degree, which may be further repeated for additional nodes, embodiments may further refine the location of the first node within the network.

This method may further include determining context data related to the first node, and refining the location of the first node based upon the context data. In an embodiment where the power characteristic is output power level, the incremental changes in the output power level of the broadcast signal may be set according to the context data.

This method may also determine the context data to be related to the closest node to the first node, and refine the location of the first node based upon the context data. In still another example, this method may determine the context data to be related to the incrementally identified nodes in the set of increasingly close nodes to the first node, and refining the location of the first node based upon the context data. For example, the closest node and the set of increasingly close nodes may have scan data that indicate they are within the same container. This exemplary context data may be used to further refine the location of the node being located, which may help efficiently determine that node is near the container. As such, those skilled in the will appreciate that context data for the node being located as well as nodes identified to be close to that node may provide relevant input to advantageously help further refine the location of the node.

Those skilled in the art will appreciate that this proximity locating method as disclosed and explained above in various embodiments may be implemented on a server apparatus, such as server 100 illustrated in FIG. 5, running one or more parts of server control and management code 525 (e.g., the location manager). Such code may be stored on a non-transitory computer-readable medium such as memory storage 515 on server 100. Thus, when executing code 525, the server's processing unit 500 may be operative to perform operations or steps from the exemplary methods disclosed above, including this method and variations of that method.

An embodiment of such a server apparatus may include a server (such as server 100) operative to communicate with a plurality of nodes in the wireless node network. As explained with respect to FIG. 5, the server generally includes a server processing unit, a server volatile memory, a server memory storage, and at least one communication interface. In this embodiment, the volatile memory, memory storage, and communication interface are each coupled to the processing unit. The memory storage maintains at least a program code section and location data related to a location of one or more of the nodes. The communication interface provides a communication path operatively coupling the server with the nodes.

The server processing unit, as mentioned above, is operative when running the program code section, to perform the steps and operations as described above relative to the above described method for locating by proximity via varying power and variations of that method described above.

Proximity when Observing Signal Patterns and Strengths Over a Time Period

In another embodiment, an improved method for determining a node's location through proximity may include analyzing the signal patterns and strengths between an advertising node and a listening node. In one embodiment, a threshold may be set for association based on an observed message count and/or recorded signal strength within a specific time period may improve the ability to locate a node (e.g., an ID node) to that of another node (e.g., a master node). In some embodiments, the observed message count may be implemented as an averaged count over a repeated time periods. Further still, other embodiments may filter outlying observations in the observation data set to help improve the quality of data relied upon for setting a threshold for association and, as a result, determine a node's location.

In a more detailed example, an improved method for determining a node's location through proximity may show captured advertising message counts as a component for a node's location and determining a node's direction of travel. In this example, two exemplary master nodes (e.g., master node M1 910a and M2 910b) may capture advertising messages from one ID node (e.g., ID node A 920a). Master node M1 may observe and capture (e.g., record information related to the observation) 60 messages from ID node A within a 2 minute period, while master node M2 only observes and captures 7 advertising messages from ID node A within that same period. Based upon the difference in how often messages are observed from ID node A by master node M1 compared to those observed by master node M2, the system is able to determine that ID node A would more proximate to master node M1, and it's known location.

In a further embodiment, comparing the average time stamp of the captured records may allow the system can make a more accurate determination of location. For example, if the average captured message found on master node M2 is increasingly growing larger (e.g., taking longer for messages to go from ID node A to master node M2), this indicates ID node A is moving away from master node M2. If the average captured message found on master node M2 is growing increasingly larger while the average captured message found on master node M1 is increasingly growing smaller, this indicates ID node A is moving away from master node M2 and toward master node M1. Thus, over a number of observed time periods, the change in message timing (transmission to reception) may also be relied upon to enhance or refine a node's location.

In yet another embodiment, the observed signal strength may be a component in location determination and estimating direction of travel and may allow the system can make a more accurate determination of location. For example, two master nodes (M1 910a and M2 920b) may be capturing advertising messages from a node (ID node A 920a). M1 captures 60 messages from ID node A within 2 minutes, while M2 captures only 7 messages. The average signal strength observed for signals from ID node A by master node M1 is higher compared to the average signal strength observed by master node M2. Based upon this observed signal strength information, the system would determine that ID node A to be at M1, but a predicted path may indicate ID node A is heading towards M2. As the master nodes M1 and M2 continue to capture records, the system (e.g., management code 524 operating on server 900, which is in communication with M1 and M2) processes the continued feed of capture records from M1 and M2. With this observed signal strength information, the server 900 would expect that the count and average signal strength of messages from ID node A over the time period observed (2 minutes) to increase for observations at M2 and to decrease for observations at M1 when ID node A is physically moving closer to M2 and away from M1. Thus, the change in observed powers levels and in how often messages are observed may indicate actual node movement in an embodiment.

Basing node proximity location and node directional determinations on observed signal patterns and characteristic strengths over a period of time has the advantage of reducing the likelihood of unwanted and spurious signal anomalies causing an ID node's location to be incorrectly determined. And the above exemplary methods for determining movement characteristics of a node (e.g., moving closer to one node, moving closer to one but away from another, etc.) as part of refining the node location may be applied in combination with the various embodiments for determining node location described herein.

Figure 17:
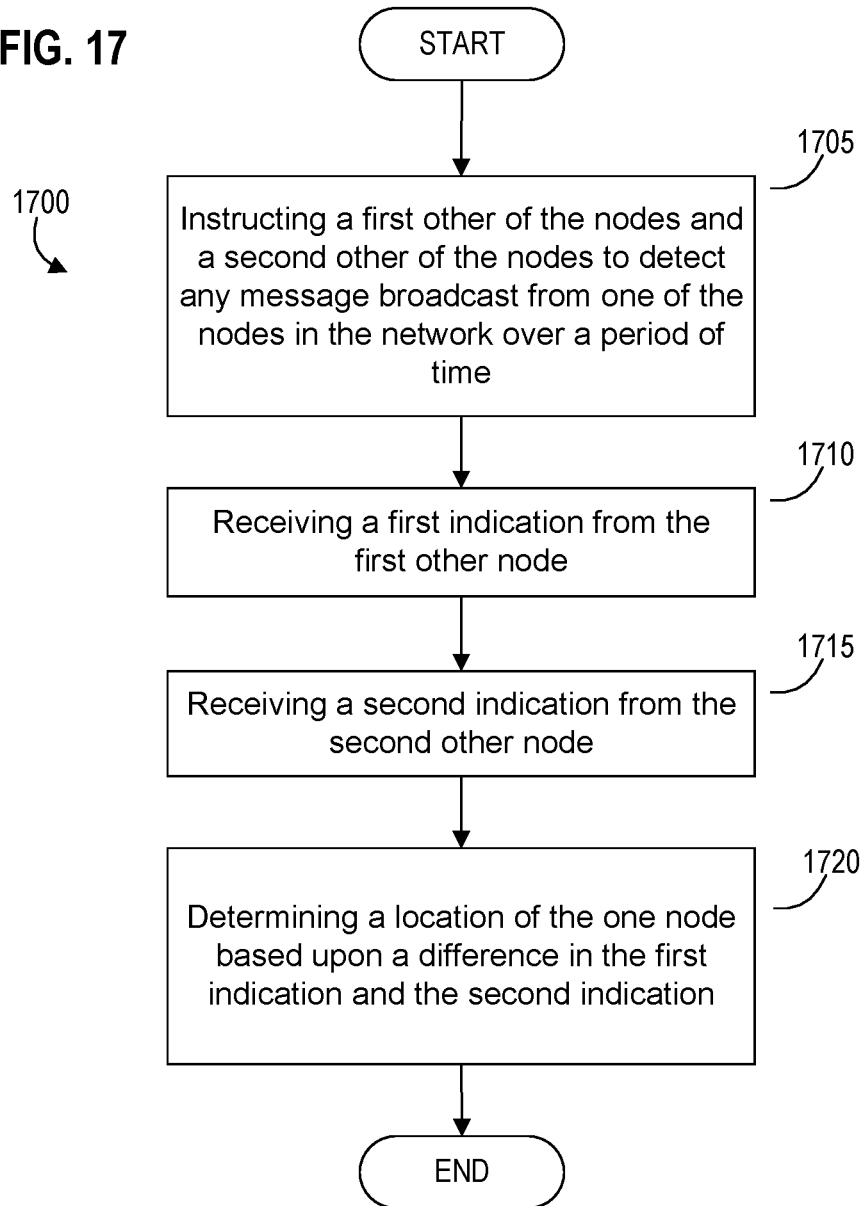
FIG. 17 is a flow diagram illustrating an exemplary method for locating a node in a wireless node network based upon observed signal patterns and characteristic indications over a period of time in accordance with an embodiment of the invention.
Figure 18:
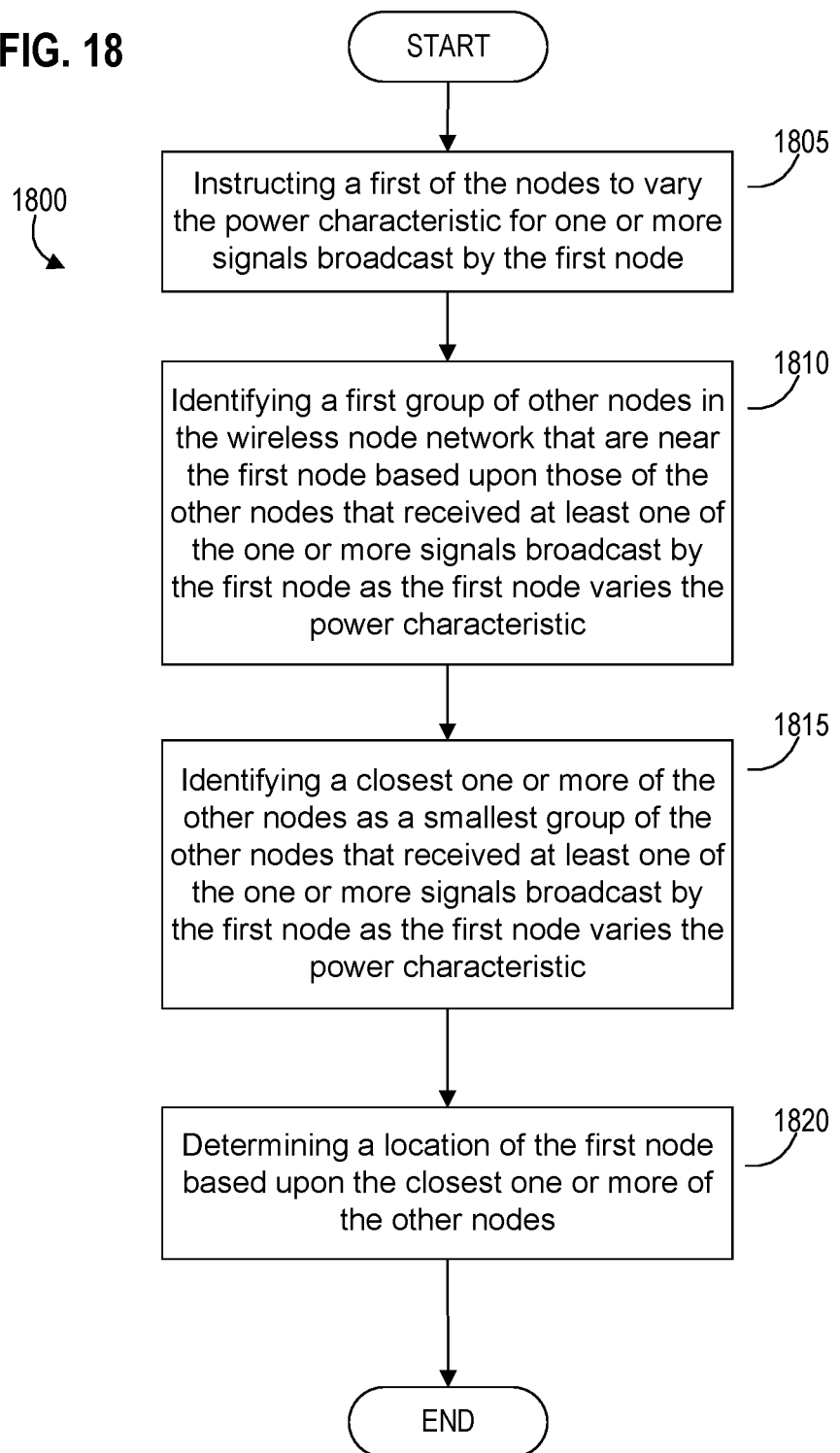
FIG. 18 is a flow diagram illustrating an exemplary method for location determination by varying a power characteristic of nodes in a wireless node network in accordance with an embodiment of the invention.

FIG. 17 is a flow diagram illustrating an exemplary method for proximity locating a node in a wireless node network based upon observed signal patterns and characteristic indications over a period of time in accordance with an embodiment of the invention. Referring now to FIG. 17, method 1700 begins at step 1705 by instructing a first and a second other nodes to detect any message broadcast from the one node over a period of time. The period of time may be set based upon a variety of factors, such as context data. In more detail, the period of time may be dynamically changed based upon context data as the one node moves into different contextual environments.

Method 1700 has the server receiving a first indication from the first other node at step 1710 and receiving a second indication from the second other node at step 1715. Finally, the method 1700 determines a location of the one node based upon a difference in the first indication and the second indication at step 1720.

The first indication is related to a characteristic of messages broadcast from the one node that are detected by the first other node during the period of time. Likewise, the second indication is related to the characteristic of messages broadcast from the one node that are detected by the second other node during the period of time. These indications may include, for example, a count of messages received by the respective other nodes, a transit time factor (e.g., an average transit time for a message to be detected after broadcast), and an average signal strength.

In one embodiment, the first indication may be a first count of messages broadcast from the one node that are detected by the first other node during the period of time, and the second indication may be a second count of messages broadcast from the one node that are detected by the second other node during the period of time. As such, determining the location of the one node may be the location that is closer to the first other node than the second other node when the first count is greater than the second count. Additionally, the method 1700 may further include determining an actual node movement direction for the one node based upon comparing the first count and the second count over a plurality of time periods. For example, the method 1700 may repeat observations over several of these time periods and track the first count and second count over time to determine which is increasing, which is decreasing, and determine movement of the one node based upon these measurements over time.

In another detailed embodiment, the first indication may be a first time factor of messages broadcast from the one node that are detected by the first other node during the predetermined time period, and the second indication may be a second time factor of messages broadcast from the one node that are detected by the second other node during the period of time. And an actual node movement direction for the one node may be based upon comparing the first time factor and the second time factor. In a more detailed embodiment, the first time factor may be an average transit time for a message detected at the first other node to go from the one node to the first other node, and the second time factor is an average transit time for a message detected at the second other node to go from the one node to the second other node. As such, determining the location of the one node may be that the location is closer to the first other node than the second other node when the first time factor is less than the second time factor.

In yet another embodiment, the first indication may be a first average signal strength of messages broadcast from the one node that are detected by the first other node during the period of time, and the second indication may be a second average signal strength of messages broadcast from the one node that are detected by the second other node during the period of time. As such, determining the location of the one node may be that the location is closer to the first other node than the second other node when the first average signal strength is greater than the second average signal strength.

The method 1700 may also include, in an embodiment, observing a degree of change in the first average signal strength and a degree of change in the second average signal strength over repeated time periods, and determining an actual node movement direction for the one node based upon comparing the degree of change in the first average signal strength and the degree of change in the second average signal strength.

In another embodiment, the method 1700 may also refine the determined location of the one node. In this embodiment, the method 1700 may further comprise refining the location of the one node based upon at least one of a first updated location received from the first other node and a second updated location received from the second other node. For example, when first other node is a mobile master node and it is the closer of the two nodes to the one node being located, the embodiment can take advantage of the location signaling onboard the first other node that provides the current location of the first other node. That current location data may be transmitted by the first other node to the server to update the server in its calculation of the location for the one node.

In still another embodiment, the method 1700 may layer context data with the determined location to refine the location of the node. Context data related to the one node may be determined by the server, and so the location of the one node may be refined based upon that context data. In another example, context data related to the closer of the first other node and the second other node when compared to the location of the one node. For example, the server may be aware that a particular master node is closer to the one node compared to a second master node, and that the particular master node is within a container. With this additional context data related to the particular master node, the server may refine the location of the one node based upon the context data. Other exemplary types of relevant context data may be relied upon when refining the location of the one node, such as context data of a particular shielding associated with the environment near the particular master node (e.g., a particular type of ULD having known RF shielding characteristics, etc.)

Additionally, the method 1700 may involve looking to see if the one node is behaving as expected. More specifically, a further embodiment of the method 1700 may further compare the location of the one node to a predicted path of the one node to determine if the one node is located outside the predicted path. This may allow the server to use learned, historic data when creating a predicted path, and keep track of the one node relative to being within an acceptable range associated with this predicted path. The method may also generate a notification if the one node is outside the predicted path. In this manner, actionable tasks can then be taken to locate the one node—e.g., changing filter mode options for nodes in that general area, etc.

Those skilled in the art will appreciate that method 1700 as disclosed and explained above in various embodiments may be implemented on a server, such as server 100 illustrated in FIG. 5, running one or more parts of server control and management code 525 (e.g., the location manager). Such code may be stored on a non-transitory computer-readable medium such as memory storage 515 on server 100. Thus, when executing code 525, the server's processing unit 500 may be operative to perform operations or steps from the exemplary methods disclosed above, including method 1700 and variations of that method.

Association Driven Locating with Variable RF Characteristics

As noted above, a signal strength measurement between two or more nodes may be used to determine relative distance between nodes. If one of the nodes has a known location (such as master node M1 910*a*), a relative location of one or more nodes within a range of the known location node is generally a function of how accurate the system may determine a distance between the node with known location and associated nodes. In other words, an embodiment may identify a relative location of an item and its related node by relying upon association-driven variable low-power RF output signals to determine a distance the node is from a known location.

Location Determination Through Master Node Advertise

Figure 13:
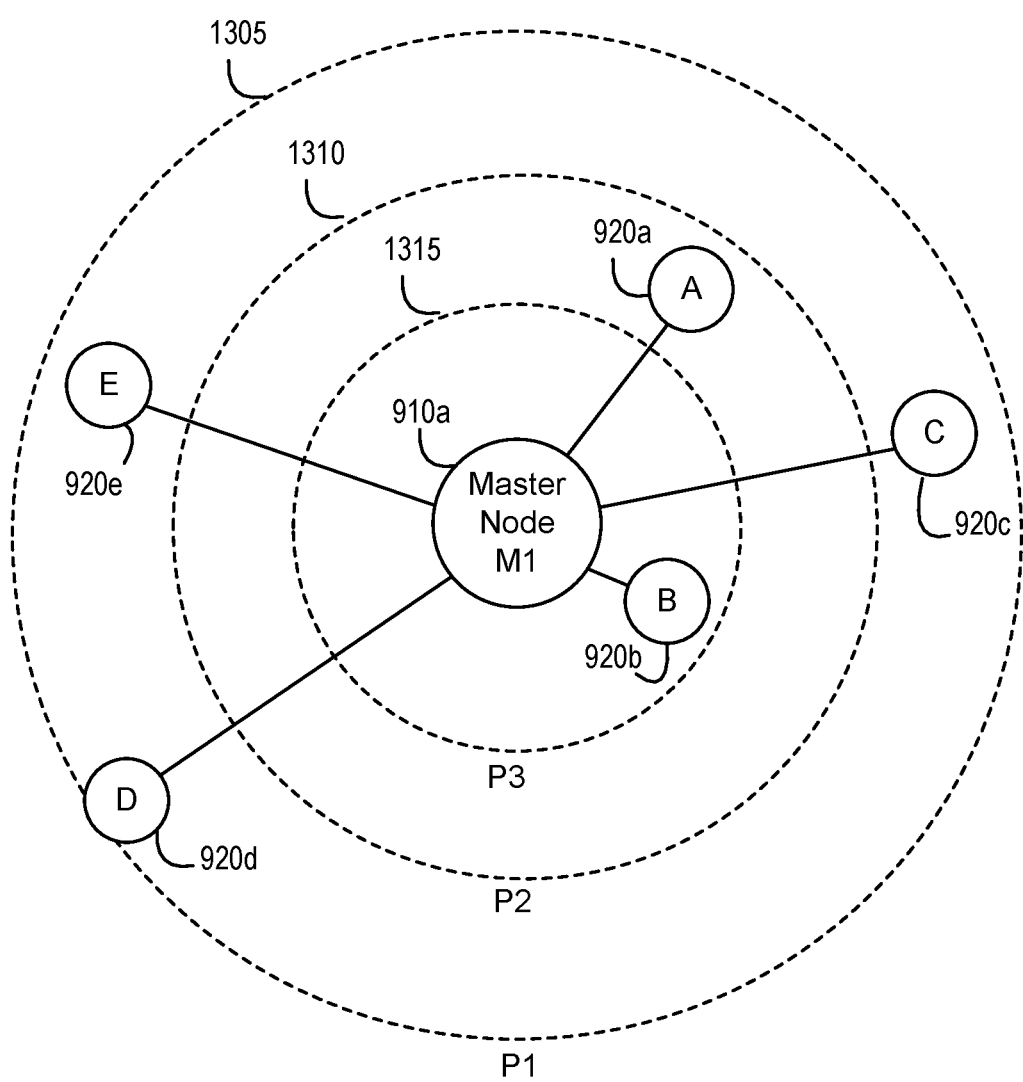
FIG. 13 is a diagram illustrating an exemplary location determination using master node advertise in accordance with an embodiment of the invention.

As generally mentioned above, determining node location may relate to controlling an RF characteristic of a node (e.g., an RF output signal level and/or RF receiver sensitivity level) and, more specifically, may involve aspects of controlling master node advertising. FIG. 13 is a diagram illustrating an exemplary location determination using master node advertise in accordance with an embodiment of the invention. In the illustrated embodiment shown in FIG. 13, a master node, such as master node M1 910*a*, with a known location is broadcasting an advertising message at varying RF output power levels. FIG. 13 illustrates the exemplary different RF output power levels as concentric ranges 1305-1315 about master node M1 910*a*. Thus, master node M1 910*a* may broadcast at a maximum power P1, related to range 1305, but may control the RF output power level and dynamically change the RF output power level to P2 and broadcast at a smaller range 1310, or to P3 and broadcast to an even smaller range 1315.

In the illustrated embodiment, receiving ID nodes A-E 920*a*-920*e* are in query (scan) mode and can each use the received signal at different levels to determine how far away from the transmitting M1 they are located. Those skilled in the art will appreciate that while the illustrated embodiment shown in FIG. 13 has the receiving nodes all as ID nodes, other embodiments may have receiving nodes be either master or ID nodes or a mixture.

In the exemplary embodiment of FIG. 13, the location for nodes A-E may be determined based upon the known location of master node M1 910*a*. That location, plus a range measurement when each of respective receiving nodes A-E last receives a signal from node M1, and factoring in a confidence factor of the range measurement, provides a location determination for the nodes according to variable RF signal power. Depending on a quality of the range measurement, the individual receiving nodes may or may not have an individually calculated location. In yet another embodiment, if third party or context data, such as scan information, is available, a refined location may be determined using such data as an additional confidence factor. As the communication range of M1 is limited from P1 to P3, the accuracy of location by association goes up.

In the illustrated example of FIG. 13, an exemplary method of determining a node's location may be described that uses master node advertising. First, when the master node M1's variable power short range communication interface 480 is set to P1, its maximum output, master node M1 910*a* is seen by each of ID nodes A-E 920*a*-920*e*. Based upon analytics or historic measurements, the open air performance (optimal range) of the radio in M1's variable power short range communication interface 480 at P1 power level may have been previously been found to be approximately 30 feet. Thus, without the need to examine RSSI levels from the individual ID nodes A-E 920*a*-920*e* and without the need for active calibration phases, the system may know that ID nodes A-E are within 30 feet of master node M1 910*a*.

Next, when the master node M1's variable power short range communication interface 480 is set to P2, a medium output level in this example, master node M1 is seen by nodes A and B. From previous analytics or historic measurements, it was determined the open air performance (optimal range) of the master node M1's variable power short range communication interface 480 running at P2 power level is approximately 15 feet. Thus, without the need to examine RSSI levels from the individual nodes, we know ID nodes A 920*a* and B 920*b* are within 15 feet of master node M1. Furthermore, we know the ID nodes no longer receiving the broadcasted RF signal from master node M1 910*a* (e.g., ID nodes C 920*c*, D 920*d*, and E 920*e*) are somewhere within 30 feet of master node M1 910*a*, but probably more than 15 feet away from M1.

And when the master node M1's variable power short range communication interface 480 is set to P3, its minimum output level in this example, it is seen by ID node B 920*b*. From previous analytics or historic measurements, it was determined the open air performance (optimal range) of the master node M1's variable power short range communication interface 480 running at P3 power level is approximately 5 feet. Thus, without the need to examine RSSI levels from the individual ID nodes, we know the location of ID node B 920*b* is within 5 feet of the known location of master node M1 910*a*.

The ranging steps, as discussed in the example above, may then be repeated for any of the identified nodes in order to build a more accurate picture of the relative location of each node. The granularity of RF characteristic settings (e.g., the RF output signal power level setting) will provide more granularity of location differentiation when performing the ranging steps. In one embodiment, the ranging steps may be performed over a set of gross RF characteristics settings (e.g., few settings over a wide range), and similar steps may then be performed over more select ranges for the RF characteristics settings.

Figure 19:
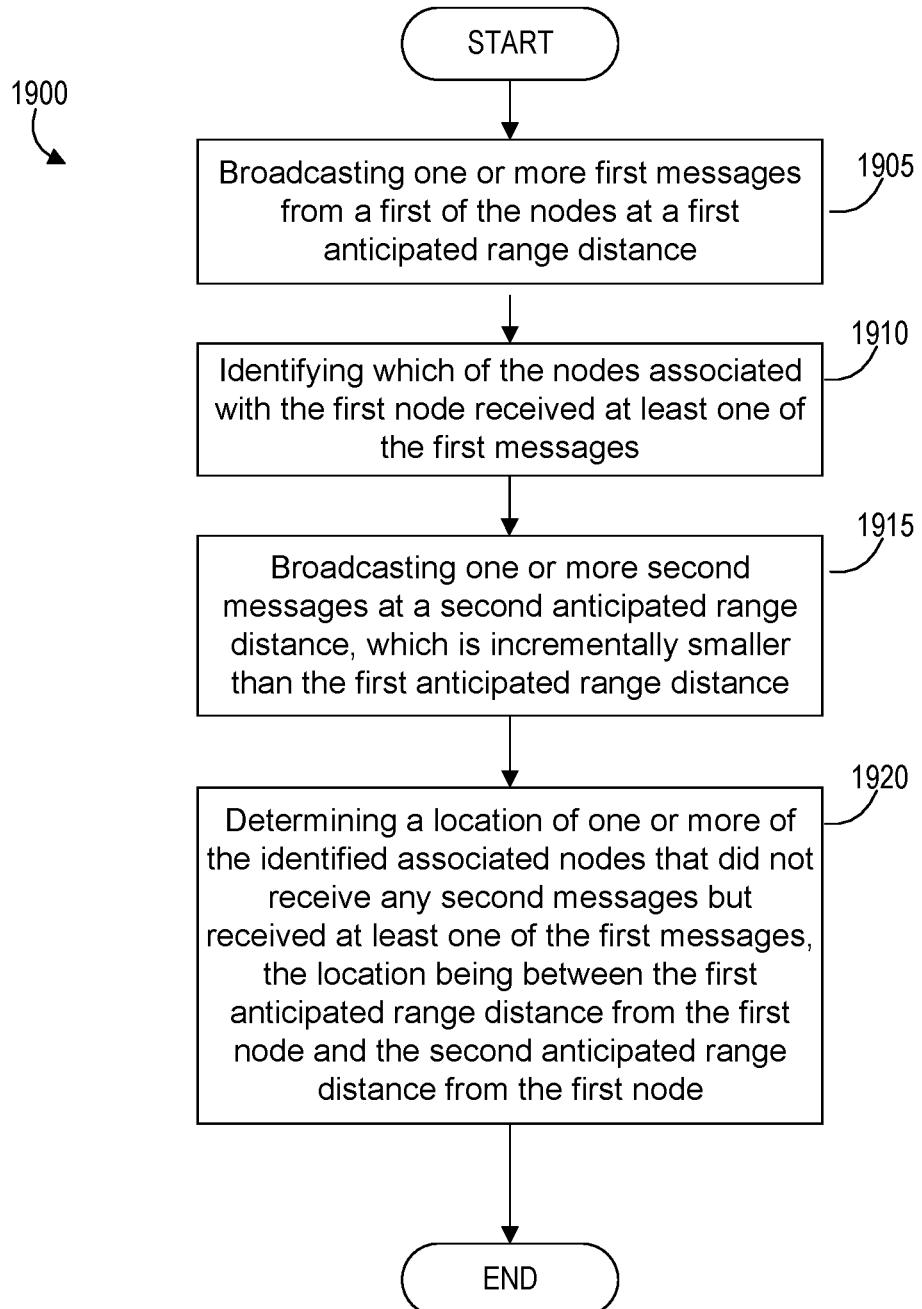
FIG. 19 is a flow diagram illustrating an exemplary method for location determination using one or more associations of nodes in a wireless node network in accordance with an embodiment of the invention.

FIG. 19 is a flow diagram illustrating an exemplary method for location determination using one or more associations of nodes in a wireless node network in accordance with an embodiment of the invention. Referring now to FIG. 19, method 1900 begins at step 1905 where a first of the nodes broadcasts one or more first messages at a first anticipated or predicted range distance. In one embodiment, the first anticipated range distance is an optimal range for the first node. For example, the first node's radio in its communication interface may have a maximum setting to allow the node to broadcast at maximized range assuming a clear environment. Such a setting provides a known anticipated range distance. In the example of FIG. 13, master node M1 910a may be broadcasting at a maximum power level P1 that reaches a first range distance from node M1. However, if node M1 is known to be within an adverse RF shielding environment, the first anticipated range distance may be a distance adjusted to account for the contextual environment of such shielding (e.g., a type of context data). Anticipated range distances may be adjusted depending upon one or more types of relevant context (e.g., one or more types of context data related to how an RF output signal from the node may be impeded).

At step 1910, method 1900 identifies which of the nodes associated with the first node received at least one of the first messages. In one embodiment, the first node may be able to access and review association data in its onboard memory storage as part of identifying which are the nodes associated with it. In one example, the associations with the first node may be passive associations (e.g., not actively paired and securely connected) or active associations (e.g., actively paired and able to securely connect and share data), or a combination of both types of associations.

Next, at step 1915, the first node broadcasts one or more second messages at a second anticipated range distance, which is incrementally smaller than the first anticipated range distance. In the example of FIG. 13, master node M1 910a may be the first node and now is broadcasting at a medium power level P2 that reaches a second anticipated range distance from node M1. By incrementally changing the RF power level in this manner, master node M1 910a now no longer can reach nodes C-E as shown in FIG. 13.

At step 1920, method 1900 concludes by determining a location of one or more of the identified associated nodes that did not receive any of the second messages but received at least one of the first messages, where the location is between the first and second anticipated range distances from the first node. Again, in the example of FIG. 13, master node M1 910a may determine the location of nodes C-E (given they did not receive the message sent out the second anticipated range distance at RF power level P2) to between the first anticipated range distance (when master node M1 was broadcasting at power level P1) and the second anticipated range distance (when master node M1 was broadcasting at power level P2) from the known location of master node M1.

In one embodiment, the method 1900 may also have the first node broadcasting one or more third messages at a third anticipated range distance (incrementally smaller range than the second anticipated range distance), and determining a location of one or more of the identified associated nodes that did not receive any of the third messages but received at least one of the second messages, where the location is approximately near the second anticipated range distance from the first node. Again, in the example of FIG. 13, by incrementally changing the power level down to P1 and broadcasting a third message at an anticipated range distance for that P1 level, the master node M1 can determine the location of node A (as node A received the second message but did not receive the third message) to be approximately near the anticipated range distance for P2 from the location of master node M1.

Additional embodiments of method 1900 may also refine such determined locations by updating the location of the first node. In one embodiment, the first node may be a mobile node. As such, refining may involve determining a current mobile location of the first node, and refining the location of the one or more of the identified associated nodes that did not receive any of the second messages but received at least one of the first messages based upon the current mobile location of the first node. Thus, as the first node moves and updates its own location (e.g., via GPS signals received by location circuitry 475 on a master node), the first node is able to leverage its own updated location and advantageously refine the location of nodes associated with it.

And, in some embodiments, the refined location of associated nodes may be transmitted to a server. This provides an update to the server, and aids in tracking and managing the location of nodes in the network. Again, referring back to the example of FIG. 13, master node M1 910a may take advantage of such a method for locating associated nodes, such as the locations of ID nodes A-E 920a-920e, and update server 100 with this new location data related to the current location of node M1 and any of the nodes associated with node M1.

Those skilled in the art will appreciate that method 1900 as disclosed and explained above in various embodiments may be implemented on a node (e.g., master node 110a in FIG. 4, or master node M1 910a in FIG. 13) running one or more parts of master control and management code 425 (e.g., the location aware/capture module). Such code may be stored on a non-transitory computer-readable medium, such as memory storage 415 on master node 110a. Thus, when executing code 425, the master node's processing unit 400 may be operative to perform operations or steps from the exemplary methods disclosed above, including method 1900 and variations of that method.

In another embodiment, a node apparatus is described in a wireless node network that uses location determination by association as described with reference to the steps related to method 1900. As mentioned above, such as node apparatus may be implemented with a master node having a node processing unit, a node volatile memory, a node memory storage, and a first and second communication interface. Each of the memories and communication interfaces are coupled to the node processing unit. Further, the node memory storage maintains at least a program code section, association data, and location data and, at times, shipping information. The first communication interface provides a first communication path operatively coupling the node with a plurality of other nodes in the network, while the second communication interface provides a second communication path operatively and separately coupling the node with a server in the network.

In this embodiment, the node processing unit is operative to transmit one or more first messages via the first communication interface at a first anticipated range distance, and identify which of the others nodes that are associated with the first node received at least one of the first messages. In one embodiment, the node processing unit may be operative to access the association data in the node memory storage when identifying which of the nodes associated (e.g., passive, active, or both types of associations) with the first node received at least one of the first messages.

The first anticipated range distance may be an optimal transmission range for the first communication interface and, in a more detailed example, may be adjusted based upon context data (e.g., RF shielding inherent from the surrounding environment of the node). In yet another embodiment, the first anticipated range distance and the second anticipated range distance may be adjusted based upon one or more types of context data related to how an RF output signal transmit from the first communication interface may be impeded by an environment of the node.

The node processing unit is also operative to transmit one or more second messages via the first communication interface at a second anticipate range distance (incrementally smaller than the first anticipated range distance) and determine a location of one or more of the identified associated nodes that did not receive any of the second messages but received at least one of the first messages. That location is between the first anticipate range distance from a known location of the node and the second anticipated range distance from the known location of the node. In a further example, the node processing unit may be operative to store the determined location in the node memory storage as part of the location data.

The node processing unit may also be operative to transmit one or more third messages via the first communication interface at a third anticipated range distance (incrementally smaller range than the second anticipated range distance) and determine a location of one or more of the identified associated nodes that did not receive any of the third messages but received at least one of the second messages, where the location is between the second anticipated range distance from the known location of the node and the third anticipated range distance from the known location of the node.

In another embodiment, the node may be mobile and the node processing unit may be further operative to refine the location of the one or more of the identified associated nodes that did not receive the second message but received the first message by updating a location of the first node. In more detail, the node processing unit may be operative to determine a current mobile location of the first node (e.g., check with location circuitry onboard the node for valid GPS signals and a location lock based on such signals), and refine the location of the one or more of the identified associated nodes that did not receive any of the second messages but received at least one of the first messages based upon the current mobile location of the first node. The node processing unit may also be operative to transmit the refined location to the server over the second communication interface.

Location Determination through ID Node Advertise

While FIG. 13 provides an example of location determination through master node advertising, FIG. 14 focuses on location determination through ID node advertising. In particular, FIG. 14 is a diagram illustrating an exemplary location determination using ID node advertise in accordance with an embodiment of the invention. In the illustrated embodiment shown in FIG. 14, exemplary ID node F 920*f* is in an advertising mode but is without a known location. As with FIG. 13, FIG. 14 illustrates the exemplary different RF output power levels from ID node F 920*f* as concentric ranges 1405-1415 about ID node F 920*f*. Thus, ID node F 920*f* may broadcast at a maximum power P1, related to range 1405, but may control the RF output power level and dynamically change the RF output power level to P2 and broadcast at a smaller range 1410, or to P3 and broadcast to an even smaller range 1415. Master nodes M1-M3 910*a*-910*c* are disposed in various known locations relatively near ID node F 920*f*, which has an unknown location. As such, ID node F 920*f* may take advantage of the ability to adjust an RF characteristic, such as RF output signal power level, of its own short-range communication interface as part of how the system may determine location of ID node F through ID node advertising.

In the illustrated embodiment, an RF output signal power level of ID node F 920*f* may be varied or dynamically adjusted via programmable settings (such as profile settings or parameters) related to operations of variable power short range communication interface 375. Additionally, while an actual communication range may vary with the surrounding environment, a maximum anticipated communication range of the ID node's transmitter at each power level is known assuming an optimal operating environment or no substantial RF shielding or interference. Thus, a particular power level setting for a broadcasting node is inherently associated with a corresponding anticipated range distance.

In an exemplary method of determining a nodes location using ID node advertising, the RF output signal power level may be varied across multiple power levels to improve location through master node association. In more detail, when the ID node F's variable power short range communication interface 375 is set to P1, its maximum output, ID node F 920*f* is seen by each of master nodes M1-3 910*a*-910*c*. The anticipated open air performance or range distance (optimal range, or range based upon analytics or historic measurements) of the radio in ID node F's variable power short range communication interface 375 at P1 power level may have been previously been found to be approximately 30 feet. Thus, without any examination of RSSI levels from the individual master nodes, the system knows ID Node F is within 30 feet of master nodes M1-M3.

Next, when the ID node F's variable power short range communication interface 375 is set to P2, a medium output level in this example, ID node F 920*f* is seen by master nodes M1 910*a* and M2 910*b*. The anticipated open air performance or range distance (optimal range, or range based upon analytics or historic measurements) of the radio in ID node F's variable power short range communication interface 375 at running at P2 power level is approximately 15 feet. Thus, without any examination of RSSI levels from the individual nodes, we know master nodes M1 910*a* and M2 910*b* are within 15 feet of ID node F 920*f* in this example. Furthermore, we know the master node no longer receiving the broadcasted RF signal from ID node F 920*f* (e.g., master node M3 910*c*) is somewhere within 30 feet of ID node F 920*f*, but probably more than 15 feet away from node F in this example.

And when ID node F's variable power short range communication interface 375 is set to P3, its minimum output level in this example, ID node F 920*f* is seen by only master node M2 910*b*. The anticipated open air performance or range distance (optimal range, or range based upon analytics or historic measurements) of the radio in ID node F's variable power short range communication interface 375 at P3 power level is approximately 5 feet. Thus, without any examination of RSSI levels from the master nodes, we know the location of ID node F 920*f* is within 5 feet of the known location of master node M2 910*b* in this example.

The ranging steps with respect to the changed RF characteristics of an advertising ID node, as discussed in the example above, may then be repeated for any of the identified nodes in order to building a more complete picture of the relative location of each node.

Furthermore, the timing between such ranging steps may vary dynamically depending upon whether the node is moving. Those skilled in the art will appreciate that when moving, a quicker flow through such ranging steps will help to provide better accuracy given the movement of nodes.

Thus, the time interval between instructing a node to broadcast one or more messages at a particular power level and then instructing that node to broadcast one or more messages at a different power level may be desired to be shorter when the node is moving, which can be determined based upon context data. For example, the context data may indicate the node is within a node package an on a moving conveyor system. As such, the node is moving relative to fixed master nodes that may be positioned along the conveyor system. Thus, server may have the first node perform the ranging steps where power is varied in relative quick succession compared to a situation where the context data indicates the node is not moving or is substantially stationary.

Figure 20:
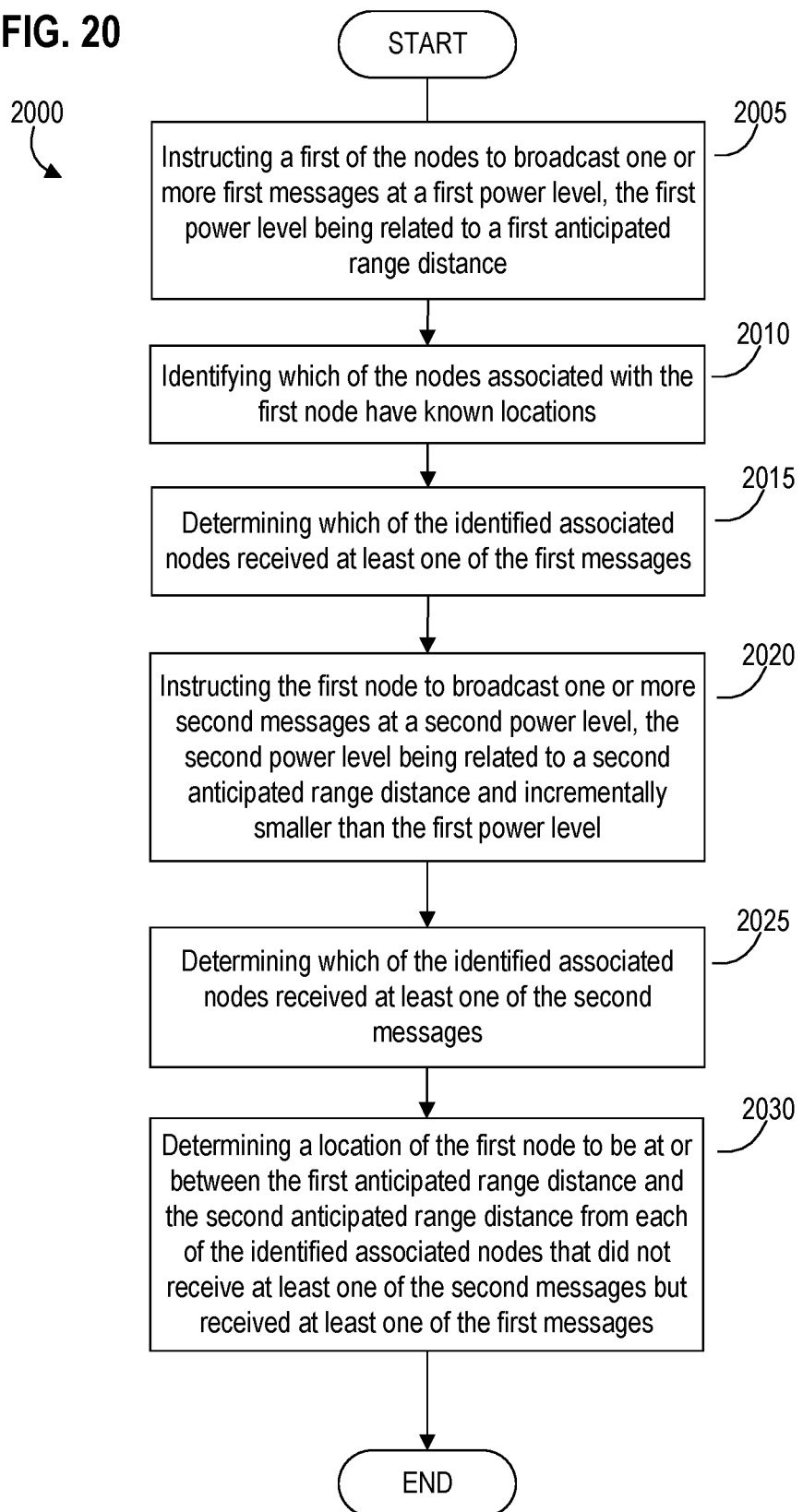
FIG. 20 is a flow diagram illustrating another exemplary method for location determination using one or more associations of nodes in a wireless node network in accordance with an embodiment of the invention.

FIG. 20 is a flow diagram illustrating another exemplary method for location determination using one or more associations of nodes in a wireless node network in accordance with an embodiment of the invention. Referring to FIG. 20 and how it explains a particular way to locate a node using associations and master node one or more master node advertising techniques, method 2000 begins at step 2005 by instructing a first of the nodes to broadcast one or more first messages at a first power level, the first power level being related to a first anticipated range distance. In one example, the first anticipated range distance may be an optimal range for the first of the nodes (e.g., a transmission range that assumes there are no obstructions and a clear signal path between nodes). In another example, the first anticipated range distance may be an optimal range for the first node adjusted based upon context data (e.g., data related to the surrounding RF environment of the first node).

At step 2010, the method 2000 identifies which of the nodes associated with the first node have known locations at step 2010. For example, this type of identification may be accomplished by reviewing association data that indicates which of the nodes are associated with the first node (e.g., via passive association, via active association, or via a combination of both), determining which of the nodes are associated with the first node based upon the reviewed association data, and identifying which of those associated nodes have known locations.

The method 2000 continues at step 2015 by determining which of the identified associated nodes received at least one of the first messages. Next, the method 2000 instructs the first node at step 2020 to broadcast one or more second messages at a second power level, where the second power level is related to a second anticipated range distance and the second power level incrementally smaller than the first power level. In a further example, the first anticipated range distance and the second anticipated range distance may be adjusted based upon one or more types of context data related to how an RF output signal from the first node may be impeded.

At step 2025, method 2000 determines which of the identified associated nodes received at least one of the second messages. Method 2000 concludes at step 2030 where the method determines a location of the first node to be at or between the first anticipated range distance and the second anticipated range distance from each of the identified associated nodes that did not receive at least one of the second messages but received at least one of the first messages.

As mentioned above, determining the node's location may be improved when accounting for movement. As such, an embodiment of method 2000 may instruct the first node to broadcast the one or more second messages within a time interval after instructing the first node to broadcast the one or more first messages. The time interval may be predetermined in some implementations, but also may be a dynamically set parameter in other implementations based upon context data related to the first node. In more detail, the time interval may be reduced from a prior value when the context data related to the first node indicates the first node is moving, but may be increased from a prior value when the context data related to the first node indicates the first node is substantially stationary.

In another embodiment, method 2000 may further include instructing the first node to broadcast one or more third messages at a third power level. Such a third power level is related to a third anticipated range distance and incrementally smaller range than the second anticipated range distance. Thereafter, the method may determining the location of the first node to be at or between the second anticipated range distance and the third anticipated range distance from each of the identified associated nodes that did not receive any of the third messages but received at least one of the second messages.

In another embodiment, method 2000 may comprise refining the location of the first node with an updated location of one or more of the identified associated nodes that did not receive at least one of the second messages but received at least one of the first messages. For example, if the first node is associated with a mobile master node, the location of the first node may be refined with an updated location of the mobile master node (which may be closer to the first node than previously determined).

In a further embodiment, the first node in the operation of method 2000 may not be self-aware of its own location. In another embodiment, the first node in the operation of method 2000 may have been previously self-aware of the location of the first node but may no longer be self-aware of the location of the first node prior to broadcasting the one or more first messages. In more detail, the first node may no longer be self-aware of the location of the first node prior to broadcasting the first message because of a change in the environment surrounding the first node. Such a change in the environment may be, for example, when the first node has moved inside a structure (e.g., building, vehicle, aircraft, container, etc.) that blocks location signals from being received by the first node.

Those skilled in the art will appreciate that method 2000 as disclosed and explained above in various embodiments may be implemented on a node (e.g., master node 110a in FIG. 4) running one or more parts of master control and management code 425 (e.g., the location aware/capture module) to control operations of an ID node (such as ID node F in FIG. 14) as part of location determination via ID node advertising. Such code may be stored on a non-transitory computer-readable medium, such as memory storage 415 on master node 110a. Thus, when executing code 425, the master node's processing unit 400 may be operative to perform operations or steps from the exemplary methods disclosed above, including method 2000 and variations of that method.

From an apparatus perspective, an exemplary node apparatus in a wireless node network that uses location determination by association may comprises a node processing unit, node memory coupled to and used by the node processing unit (e.g., a node volatile memory and a node memory storage). The node memory storage maintains at least a program code section, association data, and location data. The node apparatus further includes a first communication interface that provides a first communication path coupled to the node processing unit and operatively coupling the node with a plurality of other nodes in the network. For example, the master node 110 illustrated in FIG. 4 includes such types of operational structure.

The node processing unit (e.g., processing unit 400 of master node 110*a*), when executing at least the program code section resident in the node volatile memory, is operative to perform specific functions or steps. In particular, the node processing unit is operative to communicate an instruction to a first of the other nodes (e.g., an ID node or master node temporarily operating as an ID node) via the first communication interface to cause the first other node to broadcast one or more first messages at a first power level, where the first power level is related to a first anticipated range distance.

The first anticipated range distance may be an optimal range for the first of the nodes and, in more detail, an optimal range for the first of the nodes adjusted based upon context data. In even more detail, the first anticipated range distance and the second anticipated range distance may be adjusted based upon one or more types of context data related to how an RF output signal broadcast from the first node may be impeded.

The node processing unit is also operative to identify which of the nodes associated with the first node have known locations. To do this, the node processing unit may access and review association data stored on the node memory storage (e.g., data indicating what nodes are passively or actively associated with the first other node), may determine which of the remaining other nodes are associated with the first other node based upon the reviewed association data, and may identify which of the remaining other nodes determined to be associated with the first other node have known locations.

The node processing unit is also operative to determine which of the identified associated nodes received at least one of the first messages, and to communicate another instruction via the first communication interface to the first node to cause the first node to broadcast one or more second messages at a second power level, where the second power level being is to a second anticipated range distance and incrementally smaller than the first power level.

Finally, the node processing unit is operative to determine which of the identified associated nodes received at least one of the second messages, and then determine a location of the first node to be at or between the first anticipated range distance and the second anticipated range distance from each of the identified associated nodes that did not receive at least one of the second messages but received at least one of the first messages.

In a further embodiment, the node processing unit may be operative to communicate a third instruction via the first communication interface to the first node to cause the first node to broadcast one or more third messages at a third power level. The third power level is related to a third anticipated range distance and incrementally smaller range than the second anticipated range distance. Additionally, the node processing unit may then be operative to determine the location of the first node to be at or between the second anticipated range distance and the third anticipated range distance from each of the identified associated nodes that did not receive any of the third messages but received at least one of the second messages.

In still another embodiment, the node processing unit is able to account for movement of the first node with a time interval between instructions sent to the first node. In particular, the node processing unit may be further operative to communicate another instruction via the first communication interface to the first node to broadcast the second messages within a time interval after instructing the first node to broadcast the first messages. In a more detailed example, the time interval may be dynamically set based upon context data related to the first node. In even more detail, the time interval may be programmatically reduced from a prior value when the context data related to the first node indicates the first node is moving (e.g., the first node is on a moving conveyor system) and/or the time value of the interval may be increased from a prior value when the context data related to the first node indicates the first node is substantially stationary (e.g., the node is within a node package recently placed in a storage area).

The node processing unit, in a further embodiment, may be operative to refine the location of the first other node with an updated location of one or more of the identified associated nodes that did not receive at least one of the second messages but received at least one of the first messages, and cause a second communication interface (e.g., medium/long range communication interface 485 coupled to processing unit 400) to transmit the refined location to the server.

Figure 21:
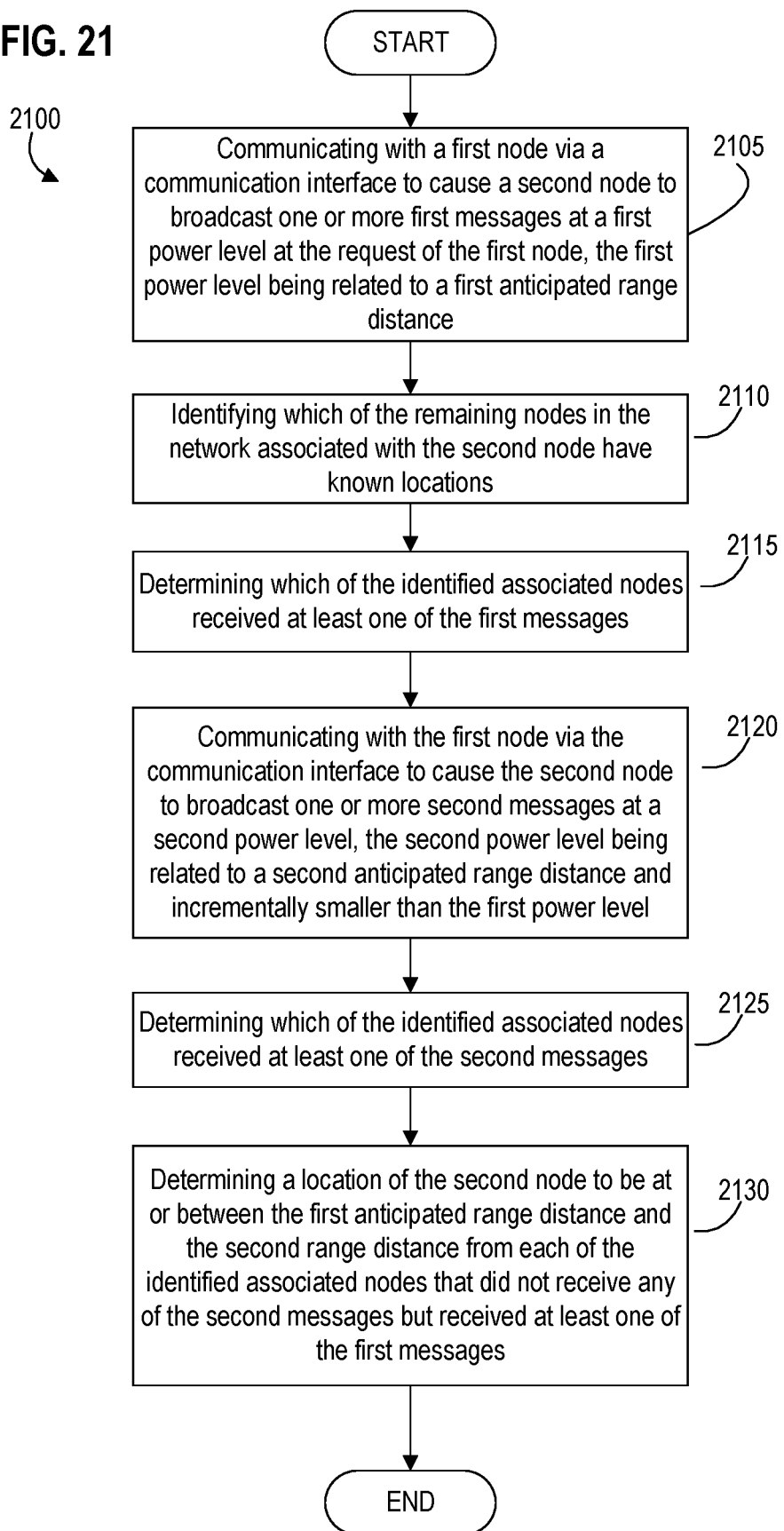
FIG. 21 is a flow diagram illustrating yet another exemplary method for location determination using one or more associations of nodes in a wireless node network in accordance with an embodiment of the invention.

From a server perspective, FIG. 21 is a flow diagram (similar to FIG. 20) illustrating yet another exemplary method for location determination using one or more associations of nodes in a wireless node network in accordance with an embodiment of the invention. Those skilled in the art will appreciate that while a server may operate to implement the steps as laid out in method 2000 and discussed above, FIG. 21 provides more details as to how a server processing unit (such as processing unit 500 running server code 525) may implement such a method at that level of the network via method 2100. In this more detailed embodiment, the server is communicating directly with a master node (e.g., a first node) to direct and control how the master node interacts with and causes operations to be undertaken on the ID node (e.g., a second node). Thus, step 2105 is similar to step 2005 but more precisely calls for communicating with a first node via a communication interface to cause a second node in the network to broadcast one or more first messages at a first power level at the request of the first node, where the first power level is related to and corresponds with a first anticipated range distance. Likewise, step 2120 is similar to step 2020 but more precisely calls for communicating with the first node via the communication interface to cause the second node to broadcast one or more second messages at a second power level at the request of the first node, the second power level being related to a second anticipated range distance and incrementally smaller than the first power level. The other steps of method 2100 are similar to those illustrated and explained above relative to method 2000, and that the similar principles will apply to method 2100.

Those skilled in the art will appreciate that method 2100 as disclosed and explained above in various embodiments may be implemented on a server (e.g., server 100 in FIG. 5) running one or more parts of server control and management code 525 to direct a master node to control operations of an ID node (such as ID node F in FIG. 14) as part of location determination via ID node advertising. Such code may be stored on a non-transitory computer-readable medium, such as memory storage 515 on server 100. Thus, when executing code 525, the server's processing unit 500 may be operative to perform operations or steps from the exemplary methods disclosed above, including method 2100 and variations of that method.

And similar to the node apparatus described above, one embodiment includes an exemplary server apparatus in a wireless node network that uses location determination by association. The exemplary server apparatus generally comprises a server processing unit, server memory coupled to and used by the server processing unit (e.g., a server volatile memory and a server memory storage). The server memory storage maintains at least a program code section, association data, and location data. The server apparatus further includes a communication interface coupled to the server processing unit and that provides access to a communication path operatively coupling the server with at least a first node in the network.

The exemplary server processing unit, when executing at least the program code section resident in the server volatile memory, is operative to perform specific functions or steps. In particular, the server processing unit is operative to communicate with the first node via the communication interface to cause a second node in the network to broadcast one or more first messages at a first power level at the request of the first node, where the first power level is related to a first anticipated range distance; identify which of the remaining nodes in the network associated with the second node have known locations; determine which of the identified associated nodes received at least one of the first messages; communicate with the first node via the communication interface to cause the second node to broadcast one or more second messages at a second power level at the request of the first node, where the second power level is related to a second anticipated range distance and incrementally smaller than the first power level; determine which of the identified associated nodes received at least one of the second messages; and determine a location of the second node to be at or between the first anticipated range distance and the second anticipated range distance from each of the identified associated nodes that did not receive any of the second messages but received at least one of the first messages. And in a further embodiment, the server apparatus' processing unit may be further operative to store the determined location in the server memory storage as part of the location data.

In another embodiment, the server apparatus' processing unit may be operative to communicate with the first node via the communication interface to cause the second node to broadcast the one or more second messages within a time interval after communicating with the first node to cause the second node to broadcast the one or more first messages. As previously mentioned, this type of time interval may dynamically set based upon context data related to the second node. Context data may also be used as set forth above with respect to the node apparatus but applied here to the second node—such was where the first anticipated range distance is the optimal range for the second node adjusted based upon context data.

Master Node Location Determination through Advertise

In another embodiment, a master node may no longer know its location. For example, such a situation may occur when a master node determines it's current location via GPS location circuitry 475, but the master node finds itself without access to an adequate number of GPS signals (e.g., it cannot determine a location due to the lack of a sufficient number of GPS signals from diverse GPS satellites). Such a situation may happen when the master node moves indoors is proximate to a structure that interferes with the location signals.

In an exemplary embodiment where a master node attempts to determine its own location via advertising techniques, the master node may detect a loss of location confidence (e.g., upon a loss of detected GPS signals; upon detecting a separate signal to processing unit 400 indicating the master node's location is unknown; when processing unit 400 senses movement (e.g., via accelerometers (not shown) or the like) but cannot confirm that the location circuitry 475 is providing updated location information for the node, etc.). In other words, the master node becomes aware that it no longer has a known location.

Next, the master node responds by beginning to broadcast one or more advertising messages in a similar way as ID node F 920*f* is described as doing with respect to FIG. 14. This is done so that the master node having an unknown location can advantageously leverage off the known locations of nearby other nodes. As such, an embodiment may allow a type of leveraged chaining effect whereby known locations of particular types of nodes may be used to extend location information to other nodes that do not know their locations (e.g., ID nodes) or nodes that have detected a loss of location confidence (e.g., master nodes). Thus, such an embodiment may be used to determine an indoor location of a master node (including equipment equipped with master node functionality) in cases where signals for the conventional onboard location circuitry 475 are not available.

Referring back to the exemplary method 2000 and FIG. 20, method 2000 may be such that the first node is not self-aware of the location of the first node. This may happen when the first node (e.g., an ID node) is actually a master node that was previously self-aware of its own location (e.g., via received GPS signals) but is no longer self-aware of its location (e.g., when the GPS signals can no longer be received), which has the master node changing operation to operate as an ID node prior to broadcasting the first message. In other words, the master node may no longer be self-aware of its location and begin operating as an ID node for purposes of location determination prior to broadcasting the first message because of a change in the environment surrounding the master node, such as when the master node has moved inside a structure that blocks location signals from being received by the master node. Thus, an embodiment may advantageously allow a node to adaptively alter operations when moving from a clear outdoor environment to an indoor environment. And a server may interact with such a master node while that master node is operating, for location purposes, as an ID node, temporarily.

Location with Improved RSSI Measurements

In another embodiment, a signal strength measurement between two or more nodes may be used to determine the proximity of the nodes by using one or more improvements to conventional RSSI measurements. In conventional RSSI measurements, such as with Bluetooth 4.0, those skilled in the art will appreciate that adaptive frequency hopping as part of spread spectrum techniques may cause undesirably cause the signal strength to fluctuate. In other words, the advantage of using frequency hopping and spread spectrum for security and avoidance of interference may have a negative impact on using such signals for stable proximity-based location determinations. Thus, it may be desired to emphasize stability of a signal and limits to fluctuation for purposes of location determination.

In one embodiment, a type of improvement for RSSI measurements may include reducing the number of channels and/or a corresponding frequency range in use during advertising from nodes. For example, a node may have processing unit 300/400 adaptively control variable power short range communication interface 375/480 to reduce the number of channels and/or the frequency range used during node advertising. Such a dynamic change may be implemented, in some embodiments, by altering the content of a particular type of profile data 330/430, such as an RF profile data that effectively defines RF characteristics of a node (e.g., frequency, power level, duty cycle, channel numbers, channel spacing, alternative fluctuation modes, etc.). In one further embodiment, a first fluctuation mode may be defined that provides a default or more standard communication protocol, such as the conventional frequency hopping, spread spectrum, and channel allocations for Bluetooth® communications. Other alternative modes (one or more) may be defined that alter one or more RF characteristics to provide increasingly more stable and less fluctuations of the RF output signal from a node. Thus, a node may be dynamically placed into one or more modes regarding such RF characteristics that increasingly emphasize stability of the node's RF output signal and limits fluctuation for purposes of enhanced location determination using RSSI measurements.

In another embodiment, a type of improvement for RSSI measurements may include ensuring visibility to and advantageously managing automatic gain control (AGC) circuitry (not shown) that may cause the RF output signal to vary for a node. For example, a node may include a type of AGC circuitry as part of variable power short range communication interface 375/480. This type of AGC circuitry may allow node processing unit 300/400 or other logic circuitry that is part of variable power short range communication interface 375/480 to limit fluctuations under certain conditions (e.g., when attempting to use RSSI location determination techniques). In this example, different AGC circuitry settings may be defined in exemplary RF profile data that effectively defines RF characteristics of a node (e.g., frequency, power level, duty cycle, channel numbers, channel spacing, alternative fluctuation modes, etc.). This is yet another example of how a node may be dynamically placed into one or more modes regarding such RF characteristics (including AGC circuitry settings) that increasingly emphasize stability of the node's RF output signal and limits fluctuation for purposes of enhanced location determination using RSSI measurements.

Location with Adjustments for Environmental Factors in RF Signal Quality

In general, those skilled in the art will appreciate that environmental factors may cause a communication signal, such as an RF signal, to fluctuate or be transmitted and received in a manner that undesirably varies depending upon a signal path environment. Passive physical interference factors (e.g., forms of electronic signal shielding) may be substantially close and cause drops in signal strength across the output ranges of the nodes. Additionally, active radio interference factors may vary across the RF output ranges of the nodes depending upon other active devices in the reception vicinity. Thus, the proximate environment of a node may have a multitude of adverse factors that impact communications and, as a result, the ability to locate the node.

In one embodiment, making location determinations may be enhanced by a data analytics type of approach that may adjust and account for different RF environmental factors for a similar type of node in a similar type of situation. For example, the quality of the RF output signal of a particular type of node and the corresponding physical range of that signal to a receiver of known sensitivity may be determined for a given environment. In this example, the system defines a maximum range of that signal based on a predetermined condition, such as open-air connectivity. This may assume an environment with no signal degradation due to interference or physical shielding. However, both interference and physical shielding may diminish the range of the RF output signal of a node. In a dynamically adaptive and learning manner, the system may collect information on how a particular type of node may operate in a particular environment under certain settings (e.g., reported signal strengths and corresponding settings for RF output signal power levels). This analysis of a similar environment may be repeated. In other words, through such data analytics of an anticipated environment to be faced by a similar node, signal loss information can be generated and applied as a type of context data (i.e., RF data) for a node in a similar environment to refine location determination. Thus, an exemplary embodiment may refine location determinations with adaptive signal loss characteristics based on a contextual appreciation of an anticipated environment (e.g., physical shielding such as packaging, package contents, proximate package, proximate package contents, and physical infrastructure causing signal variance) without requiring a calibration phase.

And advantageously combining those data points with $3^{rd}$ party data describing the physical environment, in which the node was located in at that time, may refine location even further. Such information may be used as RF data (a type of context data) in future efforts to manage and locate a similar type of node anticipated to be in a similar environment.

In more detail, in an embodiment that refines a location determination based upon context and data analytics to adjust for known RF impediments, the maximum physical range of a node's RF output signal relative to a receiver of known RF sensitivity is determined. In one example, this first range value may be referred to as a theoretical or nominal open-air range of a similar type transmitter-receiver node pair in a similar environment but with substantially no physical shielding or signal interference negatively impacting the signal range. A second range value, which may be considered an actual RF range value, may be the observed range of the signal in a similar environment but where there are contextual factors reducing the communication range, including physical shielding due to factors like packaging, package contents, proximate package, proximate package contents, physical infrastructure, interference from other radio sources, or shipper specific information such as vehicle or facility layout information. Through access to prior data analysis of the differing range values and with knowledge of the operational environment of the transmitting node was in (e.g., a similar environment to the proximate environment of the node), a refined location may be determined using an approximation of an actual RF output range that intelligently adjusts what may be anticipated to be the RF environment of the node. In other words, by knowing the appropriate contextual environment related to a node (such as signal degradation information on how a similar node operates in a similar environment), an improved location determination may be made to make intelligent yet efficient adjustments (such as communication distance adjustments) that provide a refined location of the node.

In one example, such as the example shown in FIG. 2, master node 110*b* is outside of a container (such as a Uniform Load Device (ULD) container 210 known to be used for transporting groups of items on aircraft) that has an ID node inside the container. A first or theoretical range value between master node 110*b* and ID node 120*b* may be determined to be 10 feet at a specific RF output power level when the package (and related ID node) may be known to be less than 10 feet away from the scanning node (e.g., master node 110*b*). A second range value at similar distances with similar types of nodes, but with incident RF signal loss as a result of communicating through the wall of the container 210, may be between 4 and 5 feet. If context data, such as $3^{rd}$ party information or scan data, indicates the transmitting node is within the ULD container 210, the system would expect the transmission range to be limited according to the data analytics associated with this known RF impediment (e.g., characteristics for transmitting through ULD container 210), thus reducing the possible scanning nodes that may see the broadcasting node within the ULD container, or require the transmitting node to increase its RF output power to be heard.

Figure 22:
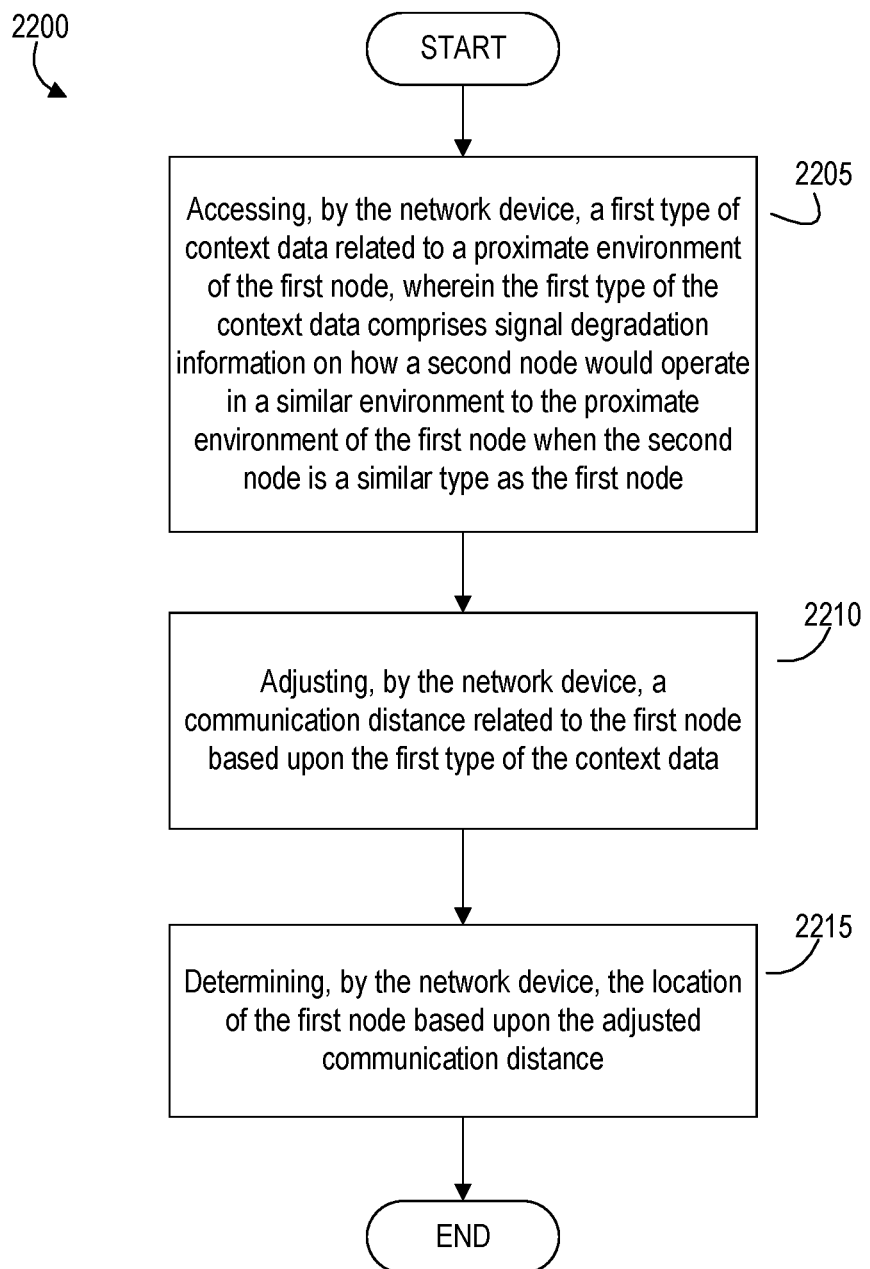
FIG. 22 is a flow diagram illustrating an exemplary method for location determination of a first node in a wireless node network based on context data in accordance with an embodiment of the invention.

FIG. 22 is a flow diagram illustrating an exemplary method for location determination of a first node in a wireless node network based on context data in accordance with an embodiment of the invention. Referring now to FIG. 22, method 2200 begins at step 2205 with a network device (such as a master node or server) accessing a first type of the context data related to a proximate environment of the first node.

The first type of context data comprises signal degradation information on how a second node would operate in a similar environment to the proximate environment of the first node when the second node is a similar type as the first node. Thus, rather than calibrating with an actual measurement relative to the current proximate environment of the first node, the signal degradation information provides compensation information on what may be generally anticipated in a more general proximate environment based on how a similar type of node may operate in a similar environment. As the similar environment of the similar node is generally an approximation for what is anticipated to be the proximate environment of the first node, this advantageously avoids the need for an actual calibration of the proximate environment. In one embodiment, the signal degradation information may be based upon a difference in how the second node communicates when exposed to an adverse communication environment (such as a similar environment to the proximate environment of the first node) compared to how the second node would communicates when exposed to a nominal communication environment (such as an environment that is unencumbered by shielding and interference factors). Those skilled in the art will appreciate that a nominal communication environment need not be perfectly clear of all influences that shield or interfere with communications.

The types and aspects of signal degradation information may vary depending on a wide variety of factors. In one embodiment, the signal degradation information may be related to at least one of shielding and interference. Thus, signal degradation information may include both passive and active factors that impact the communication environment.

In another embodiment, the signal degradation environment may be based upon a degraded operation of the second node when the similar environment is an adverse communication environment. In more detail, the signal degradation information may be based upon a difference in how the second node communicates when exposed to the adverse communication environment compared to how the second node communicates when exposed to a substantially normal communication environment, such as an open air environment.

In still another embodiment, signal degradation information may relate to at least shipment data for one or more items being shipped (e.g., currently shipped or shipped in the past) and located in the proximate environment of the first node. For instance, a package near the first node may include metallic materials that may impede or block RF signals and the signal degradation information may relate to such information about close packages being shipped near the first node. In another example, the signal degradation information may relate to at least layout data for one or more physical structures in the proximate environment of the first node. In more detail, the layout data may be for one or more physical structures (e.g., walls, machinery, enclosures, and conveyances) in the proximate environment of the node near a predicted path for the first node. In yet another example, the signal degradation information relates to at least historic data on one or more analyzed prior operations of the second node.

At step 2210, the network device, such as a master node or server, may adjust an anticipated communication distance related to the first node based upon on the first type of the context data. In one example, the anticipated communication distance may be a theoretical broadcast distance based upon parameters of the device's radio. Such an anticipated communication distance is known as it is an estimate of the radio's range. In one example, the adjusted communication distance comprises an anticipated reduced range distance for a transmission from the first node. In another example, the adjusted communication distance comprises an anticipated reduced receiver sensitivity distance for the first node.

In yet another example, adjusting the communication distance may be accomplished by adaptively adjusting, by the network device, the communication distance based upon the signal degradation information and a second type of the context data. In other words, the communication distance may be adjusted based upon signal degradation information considered along with other types of context data, such as how the first node is being moved (such as an anticipated movement of the first node along a predicted transit path for the first node) or a density of other nodes near the first node.

At step 2215, the network device determines the location of the first node based upon the adjusted communication distance. In a further embodiment, the method may also update the adjusted communication distance by the network device based upon movement of the first node, and may refine the location of the first node with an updated adjusted communication distance. This may happen with the first node is a mobile master node capable of self-determining its own location.

Those skilled in the art will appreciate that method 2200 as disclosed and explained above in various embodiments may be implemented on a network device (e.g., exemplary master node 110*a* in FIG. 4 or server 100 in FIG. 5) running one or more parts of their respective control and management code to perform steps of method 2200 as described above. Such code may be stored on a non-transitory computer-readable medium, such as memory storage 415 on master node 110*a* or memory storage 515 on server 100. Thus, when executing such code, the respective network device's processing unit may be operative to perform operations or steps from the exemplary methods disclosed above, including method 2200 and variations of that method.

In more detail, an exemplary network device apparatus for determining a location of a first node in a wireless node network based on context data, the exemplary network device may include a processing unit, a volatile memory coupled to the processing unit, and a memory storage coupled to the processing unit. The exemplary network device further includes a communication interface coupled to the processing unit and that provides a communication path operatively coupling the network device with the first node in the network.

The memory storage for the device maintains at least a program code section and context data having at least signal degradation information. Such signal degradation information, as a type of context data, is information on how a second node would operate in a similar environment to a proximate environment of the first node when the second node is a similar type as the first node. Examples of signal degradation information may include those discussed above relative to step 2205 of method 2200.

When executing at least the program code section when resident in the volatile memory, the processing unit of the network device is operative to perform the steps noted and described above with respect to method 2200. In more detail, the processing unit is operative to at least connect with the memory storage to access the signal degradation information, adjust a communication distance (if needed) related to the first node based upon on the signal degradation information, determine the location of the first node based upon the adjusted communication distance, and store the determined location of the first node as location data on the memory storage.

Adjusting the communication distance by the processing unit may be accomplished as described above with regard to step 2210 of method 2200. And as mentioned above, the processing unit may be further operative to adaptively adjust the communication distance where other types of context data are also considered, such as movement and anticipated node movement as detailed out above.

In a further embodiment, the network device may be a mobile master node that includes location circuitry (such as GPS circuitry 475 of exemplary master node 110*a* shown in FIG. 4). In this embodiment, the processing of the network device may be further operative to determine a location of the network device based upon an output signal from the location circuitry received by the processing unit, and determine the location of the first node based upon the adjusted communication distance and the location of the network device. As such, the first type of the context data related to the proximate environment of the first node is based upon the determined location of the first node.

Those skilled in the art will also appreciate that in some operational environments, the signal degradation information may not require any adjustment to the communication distance in an embodiment. However, in other environments (e.g., adverse RF environments), the signal degradation information may provide a basis for adjusting the communication distance in the embodiment, even if not performed every time. Thus, an adjustment to the communication distance may not be needed in all proximate environments of the first node but may be performed, if needed, based on the proximate environment of the first node. It is the ability of an embodiment to adjust this communication distance when needed and if needed that advantageously allows for locating the first node with more accuracy.

Location Through Triangulation

Figure 15:
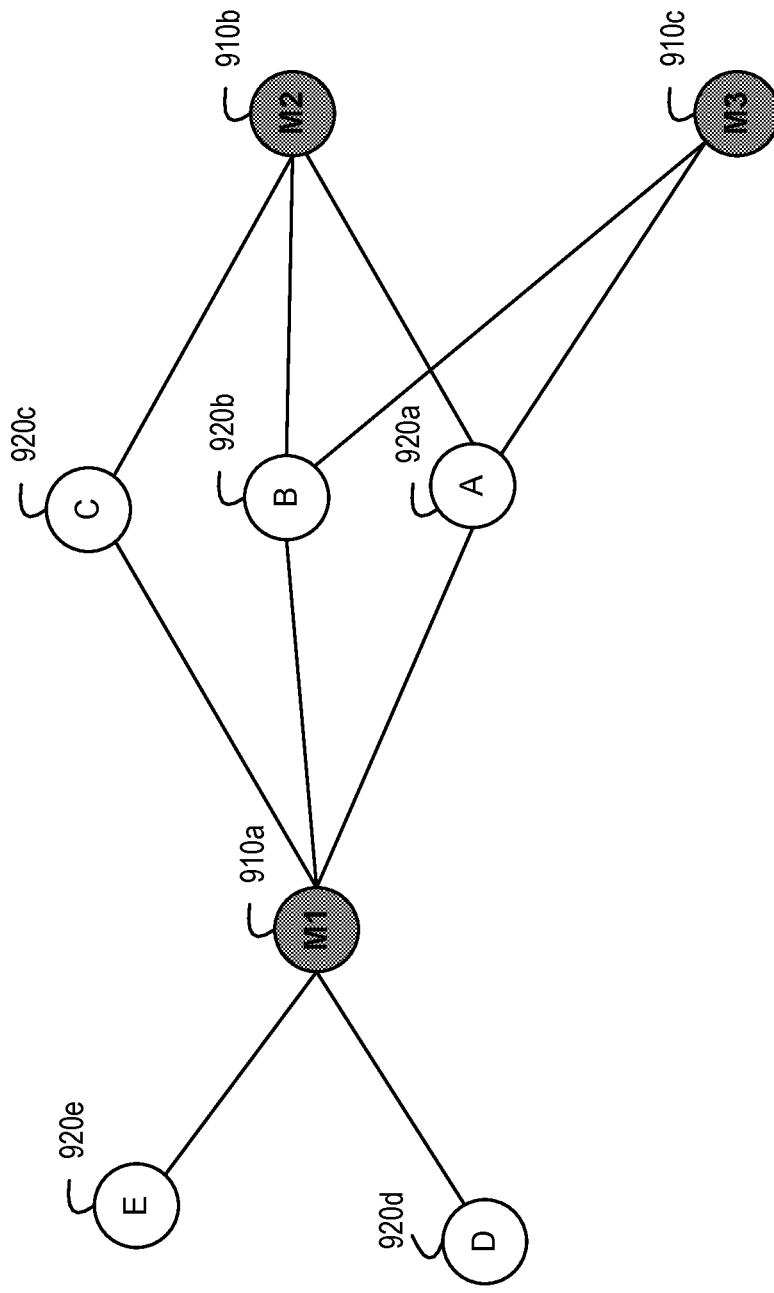
FIG. 15 is a diagram illustrating an exemplary location determination through triangulation in accordance with an embodiment of the invention.

In some embodiments, various methods for determining a node's location may rely upon, at least in part, triangulation techniques. In other words, as the wireless node network collects data on receiver-transmitter pairs, other methods for determining location of the individual nodes that utilize triangulation, at least in part, may become possible. FIG. 15 is a diagram illustrating an exemplary location determination through triangulation within a wireless node network in accordance with an embodiment of the invention. Referring now to the illustrated embodiment of FIG. 15, three exemplary master nodes M1-M3 910*a*-910*c* are shown with each master node having a known location. Exemplary ID nodes A-E 920*a*-920*e* are also shown where they are at least in communication range of one or more of exemplary master nodes MA-M3 910*a*-910*c*.

In this illustrated example, the master nodes M1-M3 may detect and collect advertising messages from ID nodes A-E at varying and known power levels. The captured information is forwarded by the master nodes M1-M3 to the backend server 100, where location determinations may be made. For example, factors like RSSI and visibility of each node at each power level may be used to determine, with a higher degree of accuracy, the location of nodes where sufficient information is available.

For an exemplary system to triangulate a node, three nodes with known locations must have seen the broadcasting node. In this example, two advertising ID nodes, A 920*a* and B 920*b*, were seen by the three nodes having known locations (master nodes M1-M3 910*a*-910*c*). Based upon the captured information, the locations of ID node A 920*a* and ID node B 920*b* are calculated.

Chaining Triangulation

Figure 16:
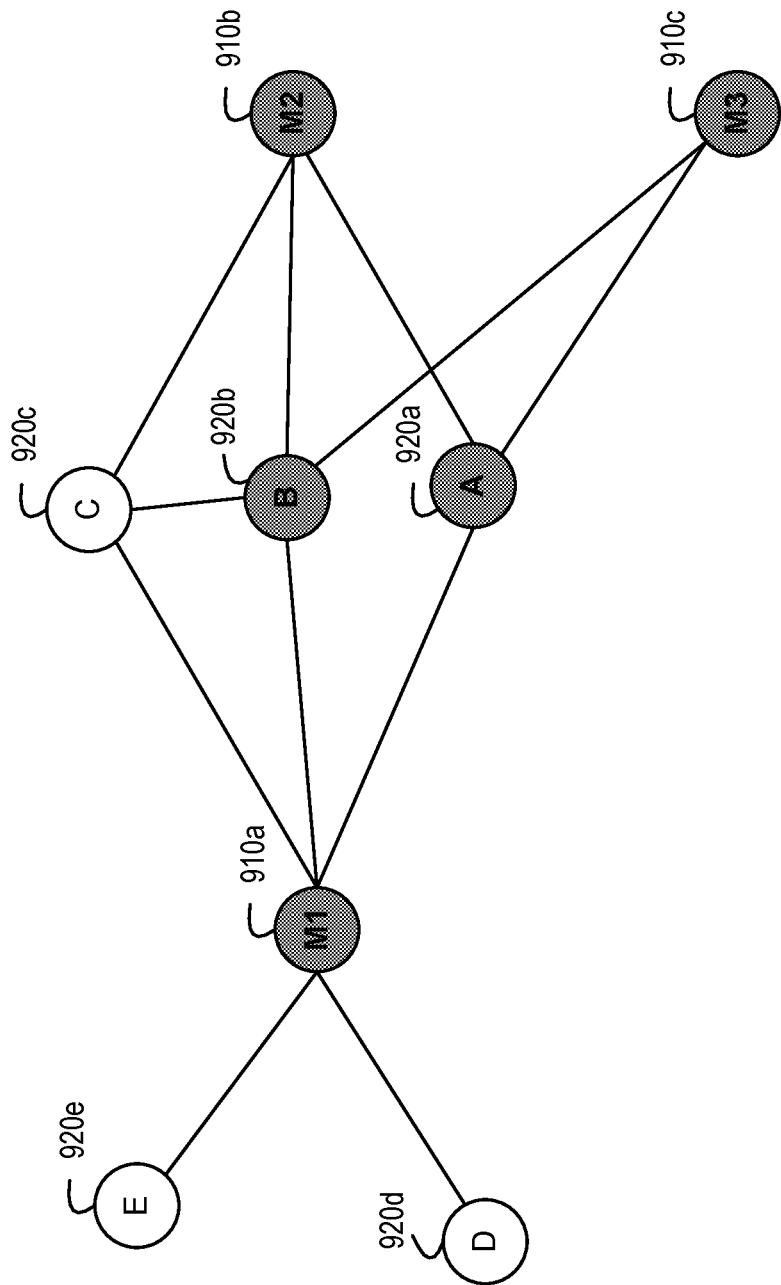
FIG. 16 is a diagram illustrating an exemplary location determination through chaining triangulation in accordance with an embodiment of the invention.

In another embodiment, a node with an inferred location may be used with triangulation techniques to determine a location of another node in a wireless node network. FIG. 16 is a diagram illustrating an exemplary location determination through chaining triangulation in accordance with an embodiment of the invention. The locations of ID nodes A 920*a* and B 920*c* have been determined by triangulating across master nodes M1-M3, as illustrated in the exemplary embodiment shown in FIG. 15. However, as illustrated in FIG. 16, the location of ID node C 920*c* may also be determined according to an embodiment.

For example, an exemplary method of determining a node's location through chaining triangulation begins with determining the calculated location of ID node B 920*b* (as explained with reference to FIG. 15). Next, a node closer to ID node B 920*b* may be used to get the missing third signal point needed for triangulation. This may be accomplished by placing ID node B 920*b* in a query (scan) mode such that it listens for a message from ID node C 902*c*. ID node C is instructed to advertise, thus providing a signal that may be captured by ID node B. After capturing the signal profile of C, ID node B may communicate or share the captured information and forward it along to the backend server 100 through either of the master nodes M1 or M2. The resulting location determination of ID node C 920*c* may have a higher level of position error due to it being partially based on a calculated reference (e.g., the location of ID node B), but the leveraged location determination of ID node C 920*c* may be sufficiently accurate (or be an actionable location) that useful information may be gleaned about ID node C 920*c*. For example, a leveraged or chained location determination of ID node C may indicate, with the help of context data, that nodes M1, M2, and ID node B are all close enough to ID node C that ID node C is determined to be within the same command nodes M1, M2, and ID node B.

Location Through Proximity to Triangulation (LP2T)

In an embodiment where chaining triangulation may determine location through proximity to triangulation (LP2T), a starting point may be determining the relative location of an ID node to a master node based on the proximity method, as explained above. However, when the relative location of the ID node has been determined, a more accurate or refined location of the ID node may be determined based upon the location of all master nodes that can capture the RF output signal broadcast from the ID node, and then triangulating based on observed signal strength of the ID node. In this example, the proximity-based location is used as an input in the triangulation calculation to estimate likely signal deterioration historically observed between a node at the proximity-determined location and scanning master nodes. In a further embodiment, by taking into account historic data on patterns of signal deterioration, a more accurate triangulation may be possible, leading to a more accurate location determination.

Figure 23:
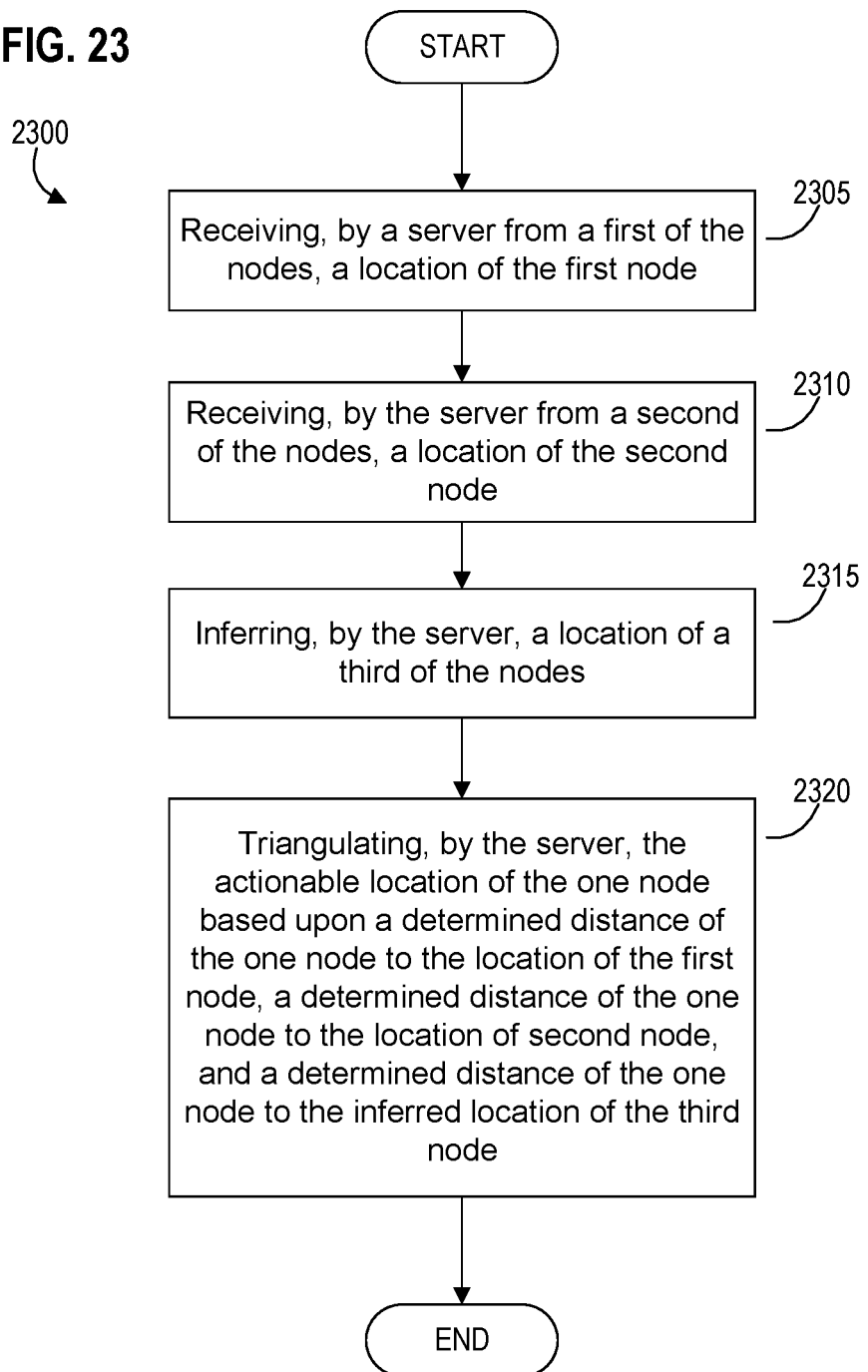
FIG. 23 is a flow diagram illustrating an exemplary method for determining a location using chaining triangulation for one of a plurality of nodes in a wireless node network having a server in accordance with an embodiment of the invention.

FIG. 23 is a flow diagram illustrating an exemplary method for determining a node location using chaining triangulation for one of a plurality of nodes in a wireless node network having a server in accordance with an embodiment of the invention. Such an exemplary node location need not be precise or exacting, but can be sufficiently accurate without absolutes.

Referring now to FIG. 23, method 2300 begins at step 2305 with the server receiving a location of a first of the nodes from the first node. Next, at step 2310, the server receives a location of a second of the nodes from the second node. For example, with reference to the example shown in FIG. 16, master nodes M1 910a and M2 910b may transmit their respective location coordinates from their respective onboard location circuitry to the server so that the server has the current locations of these two master nodes.

At step 2315, the server infers a location of a third of the nodes. For instance, in the example illustrated in FIG. 16, the server may infer the location of ID node B 920b. In one embodiment, inferring may comprise having the server determine a proximate-based location of the third node relative to another of the nodes having a known location, such that the proximate-based location operates as the inferred location of the third node.

In another embodiment, inferring the location of the third node may comprise having the server determine a relative location of the third node to the first node (as the node having a known location) or to the second node (as another node having a known location). Method 3300 may also, in another embodiment, include having the server adjust the inferred location of the third node to determine a refined location of the third node based upon third node context data related to the inferred location of the third node At step 2320, method 2300 concludes with the server triangulating the location of the one node based upon determined distances to each of the first and second nodes, and a determined distance of the one node to the inferred location of the third nodes.

In a more detailed embodiment, method 2300 may triangulate the location of the one node by accessing first node context data related to a contextual environment near the first node and second node context data related a contextual environment near the second node. Such contextual environments may include an environment of being on a conveyor system, or within a particular facility, or next to materials that may degrade or shield signals being received by the one node. Next, the more detailed triangulating may have the server adjust the determined distance of the one node to the location of the first node based upon the first node context data to provide a refined distance of the one node to the location of the of the first node. Then, the server may triangulate the location of the one node based upon the adjusted determined distance of the one node to the location of the first node, the adjusted determined distance of the one node to the location of second node, and a determined distance of the one node to the refined location of the third node.

In a further embodiment, method 2300 may also have the server transmitting an instruction so as to cause the server to transmit an instruction to cause the one node to broadcast a plurality of advertising signals over a period of time. In such an embodiment, the determined distance of the one node to the location of the first node may be based upon captured signals from the one node by the first node over the period of time and reported to the server by the first node. In another embodiment, the determined distance of the one node to the location of the second node may be based upon captured signals from the one node by the second node and reported to the server by the second node.

In still another embodiment, the server may transmit an instruction to cause the one node to broadcast a plurality of advertising signals at different power levels. In such an embodiment, the determined distance of the one node to the location of the first node may be based upon captured signals from the one node by the first node and reported to the server by the first node. In another embodiment, the determined distance of the one node to the location of the second node may be based upon captured signals from the one node by the second node and reported to the server by the second node.

In yet another embodiment, method 2300 may also have the server transmitting the location information out to a requesting entity (e.g., another node, a user access device, etc.) upon receipt of a request for a location of the one node from that entity.

Those skilled in the art will appreciate that method 2300 as disclosed and explained above in various embodiments may be implemented on a server (such as exemplary server 100 as illustrated in FIG. 5) running one or more parts of a control and management code (such as an code 525) to implement any of the above described functionality. Such code may be stored on a non-transitory computer-readable medium (such as memory storage 515 in an exemplary server). Thus, when executing such code, a processing unit of the server (such as unit 500) may be operative to perform operations or steps from the exemplary methods disclosed above, including method 2300 and variations of that method.

A server apparatus is also described in an embodiment for determining a location using chaining triangulation for one of a plurality of nodes in a wireless node network. The server apparatus generally comprises a server processing unit, a server volatile memory, a server memory storage, and a communication interface. The server volatile memory, server memory storage, and communication interface are each configured in the apparatus as coupled to the server processing unit. The server memory storage maintains at least a program code section and location data related to nodes in the network. In some embodiments, the server memory storage may also maintain context data, such as first node context data and second node context data. The communication interface provides a communication path operatively coupling the server with nodes in the network, such as a first and second node.

The server processing unit, when executing at least the program code section resident in the server volatile memory, is operative to perform various functions, such as the functions described in the steps above related to method 2300. In particular, the server processing unit is operative to receive a request over the communication interface for the location of the one node. Based on the request, the server processing unit is then operative to receive the respective locations of the first and second nodes, and store the locations as part of the location data kept on the server memory storage. The server processing unit is further operative to infer a location of a third of the nodes, and store the inferred location of the third node as part of the location data kept on the server memory storage. The server processing unit then is operative to triangulate the location of the one node based upon a determined distance of the one node to the location of the first node, a determined distance of the one node to the location of second node, and a determined distance of the one node to the inferred location of the third node. And finally, the server processing unit is operative to transmit the location information to the requesting entity over the communication interface in response to the request.

In one embodiment, the server processing unit may be further operative to infer the location of the third of the nodes by being operative to determine a proximate-based location of the third node relative to another of the nodes having a known location, where the proximate-based location operates as the inferred location of the third node.

In another embodiment, the server processing unit may be further operative to transmit an instruction over the communication interface to cause the one node to broadcast a plurality of advertising signals over a period of time. In this embodiment, the determined distance of the one node to the location of the first node may be based upon captured signals from the one node by the first node over the period of time and reported to the server by the first node. Alternatively, the determined distance of the one node to the location of the second node may be based upon captured signals from the one node by the second node and reported to the server by the second node.

In another embodiment, the server processing unit may be further operative to transmit an instruction over the communication interface to cause the one node to broadcast a plurality of advertising signals at different power levels. In such an embodiment, the determined distance of the one node to the location of the first node may be based upon captured signals from the one node by the first node and reported to the server by the first node. Alternatively, the determined distance of the one node to the location of the second node may be based upon captured signals from the one node by the second node and reported to the server by the second node.

In yet another embodiment, the server processing unit may be further operative to infer the location of the third node by being operative to determine a relative location of the third node to the first node or, alternatively, to the second node.

In still another embodiment, context data may be relied upon to refine locations. More specifically, the server processing unit may be further operative to adjust the inferred location of the third node to determine a refined location of the third node based upon third node context data related to the inferred location of the third node.

In a more detailed embodiment, the server memory storage may further maintains context data, and the server processing unit may be further operative to triangulate by being operative to access first node context data as part of the context data maintained on the server memory storage, where the first node context data is related to a contextual environment near the first node. Likewise, the server processing unit may be further operative to access second node context data as part of the context data maintained on the server memory storage, where the second node context data is related a contextual environment near the second node. The server processing unit may then be operative to adjust the determined distance of the one node to the location of the first node based upon the first node context data to provide a refined distance of the one node to the location of the of the first node. As such, the server processing unit may be operative to triangulate the location of the one node based upon the adjusted determined distance of the one node to the location of the first node, the adjusted determined distance of the one node to the location of second node, and a determined distance of the one node to the refined location of the third node.

Combined Methods for Determining Node Location

In light of the examples explained above for locating a node, one skilled in the art will appreciate that a further embodiment expressly contemplates using more than one of the above-described location determination techniques when determining a refined location of a node in a wireless node network. For example, such combination embodiments may apply an ordered or prioritized approach whereby a first location technique is applied to generate first location information regarding the location of a node in the wireless network. Thereafter, a second location technique may be selected from a hierarchy or prioritized set of techniques (some of which may work better in certain circumstances and be chosen or dynamically prioritized based upon the contextual environment), and applied to generate second location information regarding the location of the node or refining the location of the node. Other embodiments may apply additional location techniques to generate further refined location information.

In an embodiment, the information in the exemplary hierarchy generally identifies which technique may be preferred to be used initially as well as a ranked grouping or listing of when to apply other location techniques. Such information in the exemplary hierarchy may be fixed (based upon successful historic data and experience) or be dynamically altered over time as nodes may move relative to each other and, for example, based upon context data that provides more information relative to the a current or anticipated contextual environment.

Environmental Anomaly Detection & Responsive Mediation Actions

Leveraging these types of hierarchical node elements and their ability to associate, locate, and communicate as part of a further exemplary wireless node network, a variety of additional embodiments involve node-based technical solutions that enhance and improve how to detect and automatically react to dangerous conditions due to an environmental anomaly, such as a fire, explosion, chemical leak, radiation leak, or a combination of such environmental conditions indicative of a multi-faceted environmental anomaly. Detecting such an environmental anomaly and automatically generating an alert that selectively initiates different types of mediation responses may be performed in the context of packages being transported in a shipping container on a transit vehicle (such as an aircraft). As such, those skilled in the art will appreciate that the above described basics of a wireless node network may be used and extended as parts of embodiments of systems, apparatus, and methods described below for improved environmental anomaly detection, related enhanced layered alerting of particularly targeted mediation recipients, and initiating different types of mediation responses to such an environmental anomaly using one or more elements of an adaptive, context-aware wireless node network.

Figure 24A:
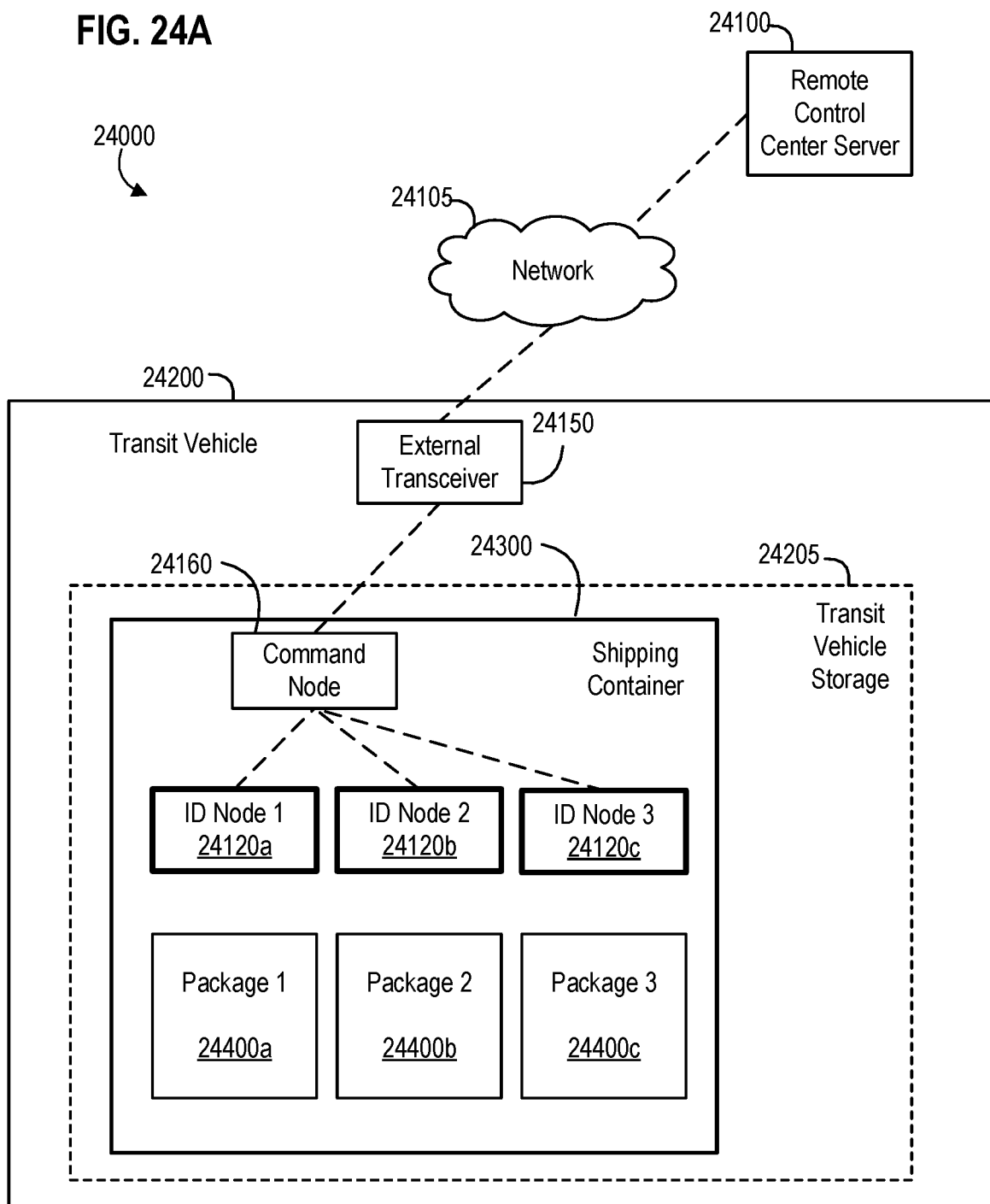
FIG. 24A is a diagram of an exemplary wireless node network used for detecting environmental anomalies using a command node and ID nodes disposed within a shipping container in accordance with an embodiment of the invention.
Figure 24B:
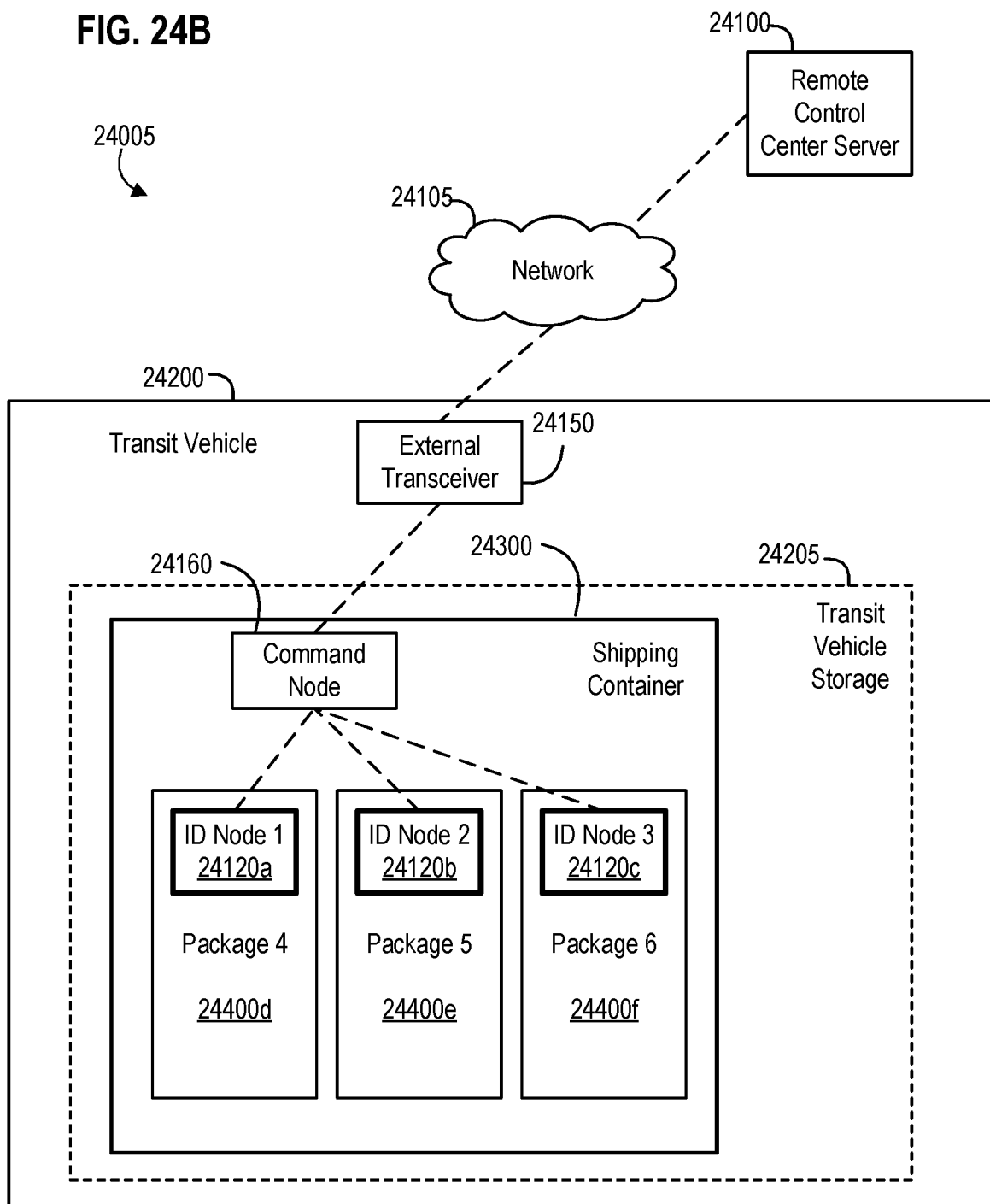
FIG. 24B is a diagram of another exemplary wireless node network used for detecting environmental anomalies using a command node and ID nodes associated with packages disposed within a shipping container in accordance with an embodiment of the invention.

In general, FIGS. 24A-24C illustrated various general examples of systems using an exemplary wireless node network of elements for detecting environmental anomalies. In more detail, FIG. 24A is a diagram of an exemplary wireless node network used for detecting environmental anomalies using a command node and multiple ID nodes disposed within a shipping container in accordance with an embodiment of the invention. Referring now to FIG. 24A, an exemplary system 24000 is illustrated for monitoring a shipping container 24300 being transported by a transit vehicle 24200 within transit vehicle storage 24205 of the vehicle. The shipping container 24300 is shown as maintaining packages 24400a-24400c and is being monitored by system 24000 for an environmental anomaly using a wireless node network. Such a system 24000 has multiple ID nodes 24120a-24120c disposed within the shipping container 24300 along with a command node 24160 mounted to and associated with the shipping container 24300. In some embodiments, each of the ID nodes 24120a-24120c may be implemented with at least one environmental sensor (e.g., sensors 360). However, in other embodiments, ID nodes 24120a-24120c need not include sensors as the command node may be monitoring the function of particular ID nodes (rather than sensor data generated by the ID node) as part of detecting an environmental anomaly.

In some embodiments, each of the ID nodes 24120a-24120c may be specifically associated with one of the packages 24400a-24400c maintained within the shipping container 24300 (e.g., travel with one of the packages, be affixed to the outside or inside of one of the packages, or be integrated as part of one of the packages). However, in other embodiments, ID nodes 24120a-24120c need not be specifically part of or associated with a particular one of packages 24400a-24400c and, instead, be disposed at different locations within shipping container 24300.

The command node 24160 is a type of master node that may be implemented without self-location circuitry (e.g., GPS location circuitry 475), but some embodiments of command node 24160 may be implemented as a master node 110a capable of self-locating as described above. As such and in embodiments involving detecting an environmental anomaly, command node 24160 is operative to communicate with each of the ID nodes 24120a-24120c within container 24300 as well as an external transceiver 24150 disposed within and associated with transit vehicle 24200.

In some embodiments, external transceiver 24150 may be implemented without being associated specifically with transit vehicle 24200. For example, an example of external transceiver 24150 may be implemented by a handheld wireless communication device (e.g., exemplary user access devices 200, 205 as explained above that may be implemented by a computer, a laptop computer, a tablet (such as an Apple iPad® touchscreen tablet), a personal area network device (such as a Bluetooth® device), a smartphone (such as an Apple iPhone®), a smart wearable device (such as a Samsung Galaxy Gear™ smartwatch device, or a Google Glass™ wearable smart optics) or other such devices capable of communicating over network 24105 with remote server 24100, over a wired or wireless communication path to command nodes and ID nodes described herein). Further, exemplary external transceiver 24150 may be a mobile type of device intended to be easily moved (such as a tablet or smartphone), and may be a non-mobile type of device intended to be operated from a fixed location (such as a desktop computer disposed on transit vehicle 24200).

As explained in more detail below, embodiments of the external transceiver 24150 may receive alert notifications from the command node 24160, and automatically respond to such alerts by initiating a mediation response related to a particular mediation action based upon the particular environmental anomaly detected. Some responses may have the external transceiver 24150 triggering a fire suppression system on transit vehicle 24200 and/or communicating with an operator or logistics crew aboard transit vehicle 24200 using a display interface on the transceiver (e.g., an LCD display for the operator or crew, a touch screen display, status lights, speaker) and user input interface on the transceiver (e.g., a touchscreen interface, buttons, keys, switches, microphone, or other feedback input devices). Further, external transceiver 24150 may communicate with remote control center server 24100 over network 24105 to report the detected environmental anomaly and any mediation response initiated as well as to receive information about the packages 24400a-24400c, environmental threshold conditions related to such packages, and other updated data to be used for detecting environmental anomalies and initiating responsive mediation actions. As such, prompted messages and user input about any environmental anomaly may take the form of visual, audible, or electronic form (e.g., a prompted message on a visual screen on external transceiver 24150, a sound alert message as the prompt, or an electronic message about the anomaly and/or responsive mediation actions being initiated).

In further embodiments, command node 24160 may be able to send the alert notification directly to onboard systems (such as a display in a cockpit or logistics support area of a transit vehicle 24200, or an onboard fire suppression system on the transit vehicle 24200) without needing to involve an intermediary separate external transceiver that receives the alert notification and responds by initiating a mediation action by communicating with such onboard systems. In this manner, some embodiments may deploy an exemplary onboard system involved with the mediation action where that system may be considered to have a built-in communication interface that may operate as a type of external transceiver with which to communicate with the command node 24160 of a particular shipping container 24300. Additional embodiments may also deploy transceiver 24150 as being internal to the shipping container or may have the command node and internal transceiver that initiates the mediation responsive action being the same node-based transceiver device.

As noted above, each of the ID nodes 24120a-24120c may be specifically associated with a package or may be disposed at different locations within shipping container 24300. In more detail, while FIG. 24A illustrates system 24000 using a command node 24160 and ID nodes 24120a-24120c disposed within shipping container 24300 in accordance with different embodiments of the invention, FIG. 24B is a diagram of exemplary system 24005 for detecting environmental anomalies using command node 24160 and ID nodes 24120a-24120c as disposed on or within packages 24400d-24400f being transported within shipping container 24300 in storage 24205 of transit vehicle 24200. In this manner, the sensor data generated by each of ID nodes 24120a-24120c as deployed in system 24005 may be sensor data specifically about the interior environmental condition relative to particular packages (i.e., packages 24400d-24400f) where the sensor data generated by each of ID nodes 24120a-24120c as deployed in system 24000 may be sensor data more targeting the environmental conditions next to or outside of particular packages (i.e., packages 24400d-24400f).

Further still, FIG. 24C is a diagram of still another exemplary wireless node network implementing an exemplary system 24010 for detecting environmental anomalies using command node 24160 and ID nodes 24120a-24120f that are less focused on particular packages and more geographically dispersed within a shipping container in accordance with an embodiment of the invention. In this manner, the embodiment shown in FIG. 24C deploys the ID nodes 24120a-24120f so as to have different ID nodes in different parts of the shipping container 24300 so that each ID node may monitor different spatial regions of the shipping container 24300.

Figure 25A:
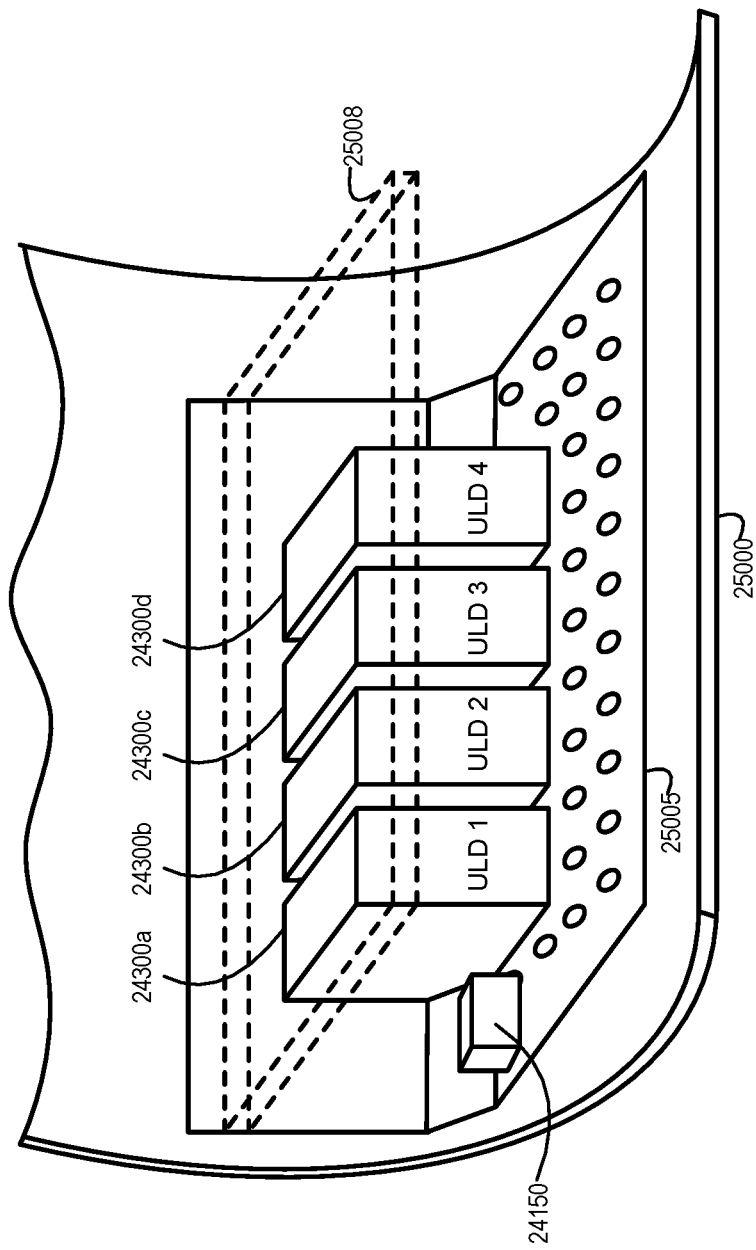
FIG. 25A is a diagram illustrating multiple shipping containers in the form of exemplary ULD containers, as loaded into a cargo storage of an aircraft in accordance with an embodiment of the invention.

While FIGS. 24A-24C generally illustrate exemplary transit vehicle 24200, those skilled in the art will appreciate that embodiments may implement exemplary transit vehicle 24200 as an aircraft, automotive vehicle, a railway conveyance, a maritime vessel, or other roadway conveyance (e.g., tractor trailer, etc.) that are capable of transporting containers maintaining packages being shipped. Shipping of containerized groups of packages (e.g., ULD types of containers made to optimize airborne logistics handling of packages) is an example of where a mobile storage unit (such as a movable ULD container) may be deployed when shipping node packages in an airborne environment. For example, FIG. 25A is a diagram illustrating multiple shipping containers in the form of exemplary ULD containers 24300a-24300d, as loaded into a cargo storage of an aircraft in accordance with an embodiment of the invention. Referring now to FIG. 25, a cut-away perspective view of an exemplary aircraft fuselage 25000 is illustrated. In particular, an exemplary floor 25005 of a cargo storage area (a type of transit vehicle storage 24205) within fuselage 25000 is shown having multiple roller elements that help facilitate movement of cargo within the cargo area. Additionally, while not shown in FIG. 25A, the cargo storage area and floor 25005 typically include structure and fastening points to help hold any cargo loaded within fuselage 25000. The cargo storage area within exemplary fuselage 25000 may be split into an upper area and a lower area by an additional floor 25008.

The cut-away perspective example illustrated in FIG. 25A shows a lower cargo area where various ULD containers 24300a-24300d are shown along with an exemplary airborne external transceiver 24150 on the aircraft. Exemplary external transceiver 24150 may be implemented with a master node or other wireless transceiver external to the ULD containers 24300a-24300d and be operative to communicate with command nodes within each of the respective ULD containers 24300a-24300d as part of embodiments that detect environmental anomalies within such containers. While exemplary external transceiver 24150 is shown disposed within the cargo storage area of the aircraft, those skilled in the art will appreciate that other embodiments may have the external transceiver 24150 disposed in another part of the aircraft (such as in a cockpit area or a logistics support area) so long as it is deployed and configured to communicate with command nodes within each of the respective ULD containers 24300a-24300d. Similar to that shown in FIGS. 24A-24C, the external transceiver 24150 illustrated in FIG. 25A may communicate with a remote server (such as remote control center server 24100) located outside the aircraft in order, for example, to report on any detected environmental anomalies and receive updated information about shipments or relevant logistics transit information that may be used to help assess potential mediation response actions to be taken onboard the aircraft.

Figure 25B:
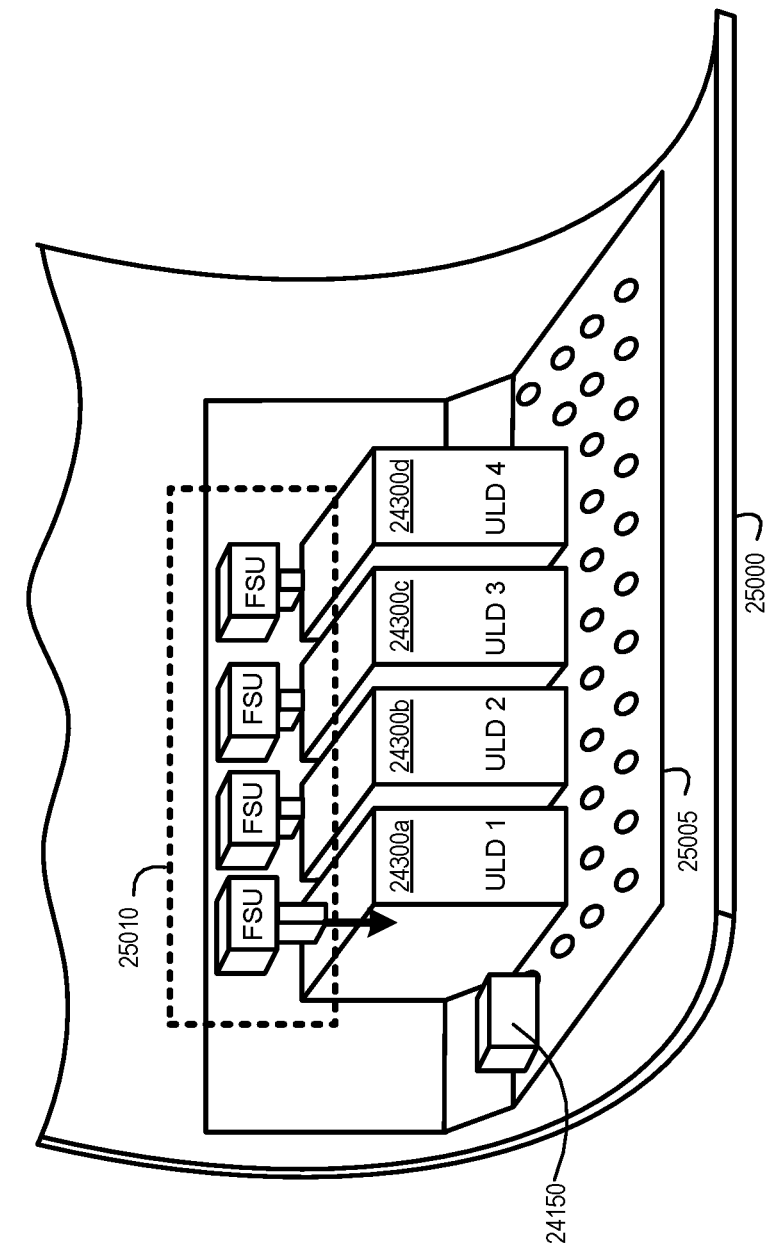
FIG. 25B is a diagram illustrating multiple exemplary shipping containers in a cargo storage of an aircraft having an exemplary fire suppression system onboard that selectively and responsively deploys as part of a mediation response to a detected environmental anomaly in accordance with an embodiment of the invention.

Further embodiments may have exemplary external transceiver 24150 in operative communication with other systems onboard the aircraft, such as a fire suppression system that may be automatically triggered for deployment by the external transceiver 24150 in response to an alert notification from one or more of the command nodes within ULD containers 24300a-24300d on the transit vehicle (e.g., the aircraft). FIG. 25B is a diagram illustrating multiple exemplary shipping containers in a cargo storage area of an aircraft having an exemplary fire suppression system onboard that selectively and responsively deploys as part of a possible targeted mediation response to a detected environmental anomaly in one or more of the shipping containers in accordance with an embodiment of the invention. Referring now to FIG. 25B, exemplary fire suppression system 25010 is illustrated as having respective deployable fire suppression modules respective to each of ULD containers 24300a-24300d. Each of the modules of exemplary fire suppression system 25010 may be selectively activated with a signal to a controller that initiates pressurized expulsion of a fire suppression agent from fire suppression agent reservoir chamber into its respective ULD container. This may occur using an articulating puncture that forcibly creates an opening in a surface of the respective ULD container and through which the fire suppression agent may flow into the ULD container so as to address a detected environmental anomaly within that ULD container. A more detailed embodiment of such an exemplary fire suppression system 25010 is described in U.S. Pat. No. 9,901,764 assigned to FedEx Corporation, which is hereby incorporated by reference.

Figure 25C:
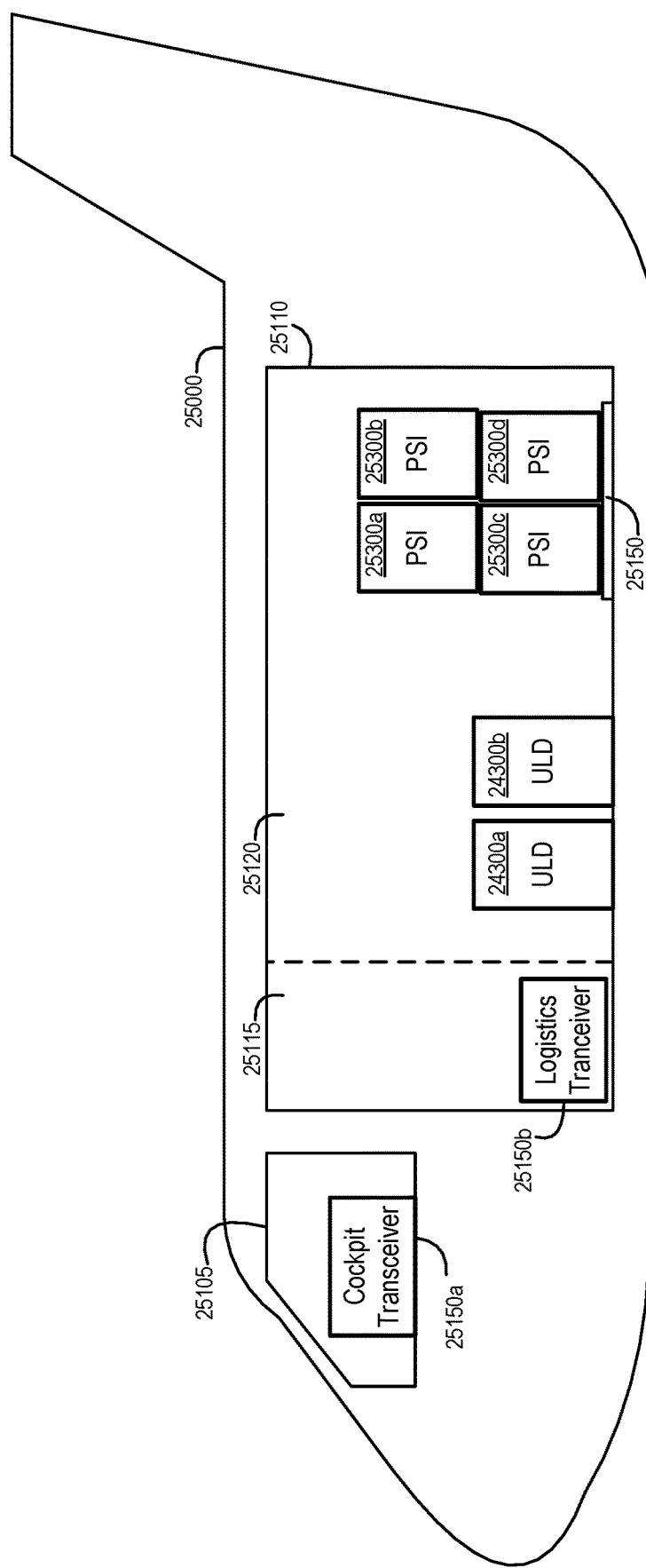
FIG. 25C is a diagram illustrating further exemplary external transceivers disposed in various control compartments of an exemplary aircraft transit vehicle in accordance with an embodiment of the invention.

In further embodiments, the exemplary external transceiver may be disposed in other parts of the aircraft manned by aircraft personnel (e.g., as a pilot operator or logistics support crew personnel) and may have one or more displays (e.g., a screen, status light, touchscreen for prompted messages) and user input interfaces (e.g., buttons, switches, keys, and the like for receiving feedback input). FIG. 25C is a diagram illustrating further exemplary external transceivers disposed in various control compartments of an exemplary aircraft transit vehicle in accordance with an embodiment of the invention. Referring now to FIG. 25C, exemplary aircraft 25100 is generally shown having a cockpit compartment 25105 in the front of aircraft 25100 and a cargo storage compartment 25110 within the fuselage of aircraft 25100. In the illustrated embodiment, cargo storage compartment 25100 includes an interior shipment storage area 25120 (similar to that shown in cutaway view in FIG. 25A) where items/packages to be shipped or transported may be loaded for transport and where such items are temporarily maintained during transport. For example, ULD containers 24300a, 24300b are shown secured within interior shipment storage area 25120. Additionally, palletized packaged shipping items (PSI) 25300a-25300d are secured to pallet 25150 as another type of shipping container maintained within interior shipment storage area 25120. In the illustrated embodiment, cargo storage compartment 25110 also includes a logistics support area 25115 where logistics support personnel may be located and from where such personnel may be prompted to inspect one or more of the containers within area 25120 in response to detecting an environmental anomaly.

Within the cockpit compartment 25105, an embodiment may have a cockpit transceiver 25150a as a type of external transceiver operative to communicate with command nodes in shipping containers on the aircraft (such as ULD containers 24300a, 24300b or a command node associated with palletized PSI 25300a-25300d secured to pallet 25150). As such, the command node of a particular shipping container may generate a layered alert notification to the cockpit transceiver 25150a that identifies the pilot operator working in cockpit compartment 25105 as a targeted mediation recipient to be notified about a particular detected environmental anomaly with a shipping container. Similarly, an embodiment may alternatively or also have a logistics transceiver 25150b as a type of external transceiver operative to communicate with command nodes in shipping containers on the aircraft (such as ULD containers 24300a, 24300b or a command node associated with palletized PSI 25300a-25300d secured to pallet 25150). As such, the command node of a particular shipping container may generate a layered alert notification to the logistics transceiver 25150a that identifies the logistics crew working in logistics support area 25115 as a targeted mediation recipient to be notified about a particular detected environmental anomaly with a shipping container. These type of alert notifications sent by the command node to the cockpit/logistics transceiver initiate a mediation response to what the command node identifies to be a targeted mediation action as will be explained in more detail below. Such mediation response may, for example, generate a prompt that requests for a change in course for the aircraft and/or a request to investigate a particular shipping container.

Figure 26:
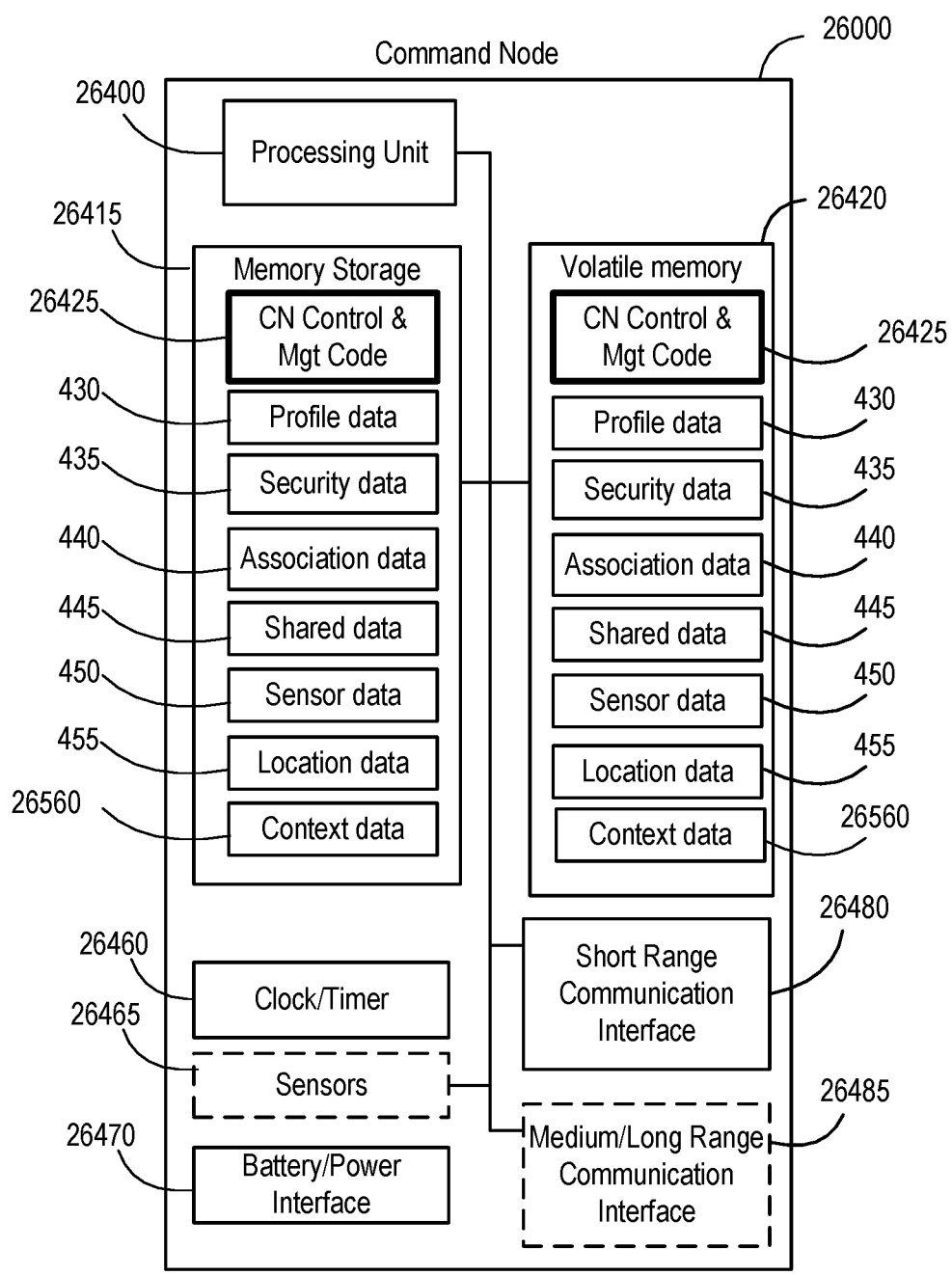
FIG. 26 is a more detailed diagram of an exemplary command node device in accordance with an embodiment of the invention.

As noted above with respect to FIGS. 24A-24C, an exemplary command node, such as command node 24160 mounted to and associated with shipping container 24300, may be implemented as a type of master node. FIG. 26 is a more detailed diagram of an exemplary command node device in accordance with an embodiment of the invention where components of the command node device are shown as disposed within a command node enclosure for housing such a device. Referring now to FIG. 26, those skilled in the art will appreciate that one embodiment of exemplary command node 26000 includes many of the same hardware, code, and data components as shown for exemplary master node 110a of FIG. 4 (including context data maintained within memory 26415 and 26420), but simplified so as not to include location circuitry. As such, similar functionality exists for what is numbered the same and described above regarding exemplary master node 110a of FIG. 4. Thus, while master node 110a shown in FIG. 4 includes processing unit 400, memory storage 415, volatile memory 420, clock/timer 460, sensors 465, battery/power interface 470, short range communication interface 475, and medium/long range communication interface 480, exemplary command node 26000 may use similar hardware components as shown in FIG. 26 including processing unit 26400, memory storage 26415, volatile memory 26420, clock/timer 26460, sensors 26465, battery/power interface 26470, short range communication interface 26475, and medium/long range communication interface 26480. Additionally, an alternative embodiment of command node 26000 may include location circuitry to enable the command node to self-locate using circuitry similar to that described with location circuitry 475 on master node 110a and shown in FIG. 4. Also, another embodiment of command node 26000 may be implemented as a master node separately from the shipping container but being mounted to the shipping container.

Notably, an embodiment of exemplary command node 26000 illustrated in FIG. 26 deploys command node (CN) control and management code 26425 (as stored in memory storage 26415 and loaded for execution by processing unit 26400 in volatile memory 26420), which is similar in functionality to master node control and management code 425 described above in more detail. Essentially, CN control and management code 26425 operates similar to that as described above for master node control and management code 425 but may also include program code for improved monitoring for an environmental anomaly as described in more detail below. Thus, in the illustrated embodiment, such further program code is implemented as an integrated part of CN control and management code 26425, such as one or more programmatic functions or additional program modules within code 26425. But in other embodiments, the further program code used to implement the methods and functionality as described for a command node below may be implemented separately from code 26425. As such, the collective code executing on a command node, such as exemplary command node 26000 (or any of the other implementations of a command node as described herein), acts to programmatically configure the command node beyond that of a generic processing device in order to be specially adapted, via such program code, to be operative to function unconventionally—whether alone with the specific functionality described herein or as part of a system.

Command node 26000 (and embodiments based upon such an exemplary command node) may receive updates to is CN control and management code 26425 (including any program code related to the functionality as set forth in the embodiments described herein that improves or enhances monitoring for, detecting, and responding to a detected environmental anomaly). For example, an exemplary command node (such as command node 26000 or command node 24160) may receive updates of such code (or other data used on the command node) from external transceiver 24150, which may have received the updated code for the command node from remote control center server 24100. Such updates may be sent to the exemplary command node or, alternatively, the command node may download the updates periodically.

An embodiment of the exemplary CN control and management code 26425 that provides for improved monitoring for an environmental anomaly as described in more detail below may also include rules for managing which of its two different communication interfaces to use when communicating with the facility master node. In some embodiments, command node 26000 may have node processing unit communicating with external transceiver 24150 over the medium/long range communication interface 26485 because the distance between the external transceiver 24150 and command node 26000 (e.g., command node 24160 as shown in FIGS. 24A-24C) may be too far for effective communications using the short range communication interface 26480. As such, the effective communication range between the nodes may be a factor considered by the processing unit 26400 within command node 26000 when determining how to accomplish communicating with the facility master node 37110a.

However, when the range between the command node 26000 and external transceiver 24150 is close enough to where the command node 26000 may use either interface to established communications with the external transceiver 24150, other factors may be considered when determining which interface on the command node to use, such as relative congestion of data communications on the short range modes of communication versus the longer range mode of communication.

In another embodiment, command node 26000 may depend upon the medium/long range communication interface 26480 when node-to-node communications may not be possible with the short range communication interface 26485. For example, a ULD having a command node may be loaded on an aircraft where the external transceiver may not have an operating short range communication interface. As such, command node 26000 is operative to determine which of the communication interfaces to use, and broadcast messages to and received messages from the external transceiver using an appropriate one of the two communication interfaces onboard the command node 26000.

As described above, exemplary command node 26000 may use data and software components as shown in FIG. 26 similar to that used by a master node, including context data as a type of shared data. For example and as shown in FIG. 26, exemplary command node 26000 may locally maintain context data 26560 within memory storage 26415 and volatile memory 26450. Those skilled in the art will appreciate that context data 26560 as used on a command node may be stored and maintained as a separate data structure, as shown in FIG. 26, but may also be part of shared data 445 (as context data may be considered a type of shared data for local use and storage on a particular node).

As explained in more detail below, such context data 26560 used with a command node may be related to packages (e.g., environmental threshold conditions related to a particular package, group of packages, or a shipment container generally) and may be updated by other network devices (such as an external transceiver or remote control center server) or manually updated by interactions with such network devices by logistics personnel or transit vehicle operators or pilots. Additional embodiments described below may have context data 26560 used with a command node as being container status data related to a particular shipping container, vehicle status data, geolocation data (also a type of location data 455), or facility status data on a storage facility for the shipping container. Furthermore, an embodiment may have context data 26560 as being relative location data (another type of location data 455) indicating a relative location of a package in the container based on when in the container load cycle that package was processed.

Additionally, exemplary command node 2600 may use one or more of its own sensor or sensors 25465, which may be monitored in addition to what is monitored from the ID nodes within or near the command node's shipping container when attempting to detect potential environmental anomalies. Thus, while some embodiments may have the command node rely on what is (or is not) broadcast from particular ID nodes when identifying and detecting an environmental anomaly related to the command node's shipping container, further embodiments may deploy the command node's own onboard sensor as part of this monitoring, identification, and detection scheme.

In summary, such an exemplary command node 26000 may function in a particularly programmed and collectively unconventional manner to add a further management layer within an exemplary wireless node network used to monitoring a shipping container for an environmental anomaly and responsively help initiate an automate and layered response that more quickly addresses any detected environmental anomaly.

Multi-Sensor Monitoring for an Environmental Anomaly & Layered Alert Generation

In light of the description above related to different wireless node network elements, their operation, interconnections and interoperability as part of systems, and the above general description of embodiments that may deploy of such network elements when detecting an environmental anomaly related to a shipping container (whether during transport, loading for transport, unloading after transport, or during other logistics operations involving such a shipping container), additional detailed information about several embodiments described below focus on use of signals and sensor data gathered from multiple sensor-based ID nodes within a container as part of monitoring a shipping container for an environmental anomaly. In general, the ID nodes may be traveling within packages, but some embodiments may the ID nodes affixed to the outside of the packages, integrated within the packing materials of the packages, or may deploy the ID nodes within the container but not specifically associated with any particular one of the packages in the container. In these embodiments, the ID nodes may provide their respective sensor data to the command node, which has the monitoring responsibility beyond just a single sensor data threshold. Depending on the particular embodiment, the command node for the container may also have its own sensor or sensors to use as part of identifying and detecting a possible environmental anomaly related to the shipping container. As explained below, such exemplary sensor data may include temperature, radiation, chemical detection, barometric pressure, and the like as part of determining if an environmental anomaly exists and to rapidly and automatically respond. For example, a sudden change in barometric pressure may indicate fire or an explosive event. As detailed below in the different embodiments, the resulting improved alert generation can focus on a type of response needed depending on context data regarding what is loaded in the shipping container as well as to whom to send the alert (e.g., a fire suppression system for automatic response; a pilot or transit vehicle operator for a quick decisive change in transit for the vehicle; or a crew operator for investigative response within the vehicle).

In a one system embodiment, the sensor data may be from particular ID nodes that are respectively associated with particular packages in a shipping container. The embodiment more specifically focuses on an improved monitoring system for detecting an environmental anomaly in a shipping container that maintains a multiple packages and for reporting a layered alert notification related to the environmental anomaly to an external transceiver unit associated with a transit vehicle (e.g., an aircraft) transporting the shipping container. The system includes at least a command node and a plurality of ID nodes disposed within the shipping container. Each of the ID nodes are associated with a respective one of the packages maintained within the shipping container (such as that shown in FIG. 24B where each ID node 24120a-24120c) are associated with packages 24400d-2440f). Each of the ID nodes has an ID node processing unit (also commonly referred to as an ID node processor,), an ID node memory coupled to the ID node processing unit (and maintain at least an ID node monitoring program as part of its node control and management code), and at least one environmental sensor configured to generate sensor data related to an environmental condition of the respective package associated with each of the ID nodes. Each ID node further includes a wireless radio transceiver (such as communication interface 375) coupled to the ID node processing unit, where the wireless radio transceiver is configured to access the sensor data generated by the environmental sensor and broadcast the sensor data in response to a report command from the ID node processing unit when the ID node processing unit executes the ID node monitoring program code as part of its control and management code (e.g., code 325).

The system's command node is mounted to the shipping container. For example, in the embodiment shown in FIG. 24B, command node 24160 may be considered mounted to the inside or outside of shipping container 24300. Outside of the shipping container exemplary command node 24160 may be permanently mounted or temporarily mounted (e.g., loaded into a shipment pouch that may be temporarily attached to the container having the command node and other items for the container, such as shipment paperwork). When mounted inside the container, the command node 24160 may be permanently mounted, temporarily mounted, or integrated as part of shipping container 24300. The system's command node includes at least a command node processing unit (also commonly referred to as a command node processor (e.g., processor 26400 or processor 400 as described above)), a command node memory coupled to the command node processing unit, and two communication interfaces. The command node memory maintains at least a command node container management program code (such as CN control and management code 26425) and context data related to each of the ID nodes (such as context data 26560), where the context data includes environmental threshold conditions respectively corresponding to each of the packages. For example, a certain temperature threshold may be uses as an environmental threshold condition for a package of lithium-ion batteries.

The communication interfaces on the system's command node include a first communication interface coupled to the command node processing unit (such as short range communication interface 26480), where the first communication interface is configured to communicate with each of the ID nodes using a first wireless communication format compatible with the wireless radio transceiver on each of the ID nodes. A second communication interface on the command node (such as medium/long range communication interface 26485) is coupled to the command node processing unit and configured to communicate with the external transceiver unit associated with a transit vehicle using a second wireless communications format.

During operation of this system embodiment, the command node processing unit of the command node is programmatically configured, when executing the command node container management program code, to be operative to detect the sensor data broadcasted from the ID nodes using the first communication interface. For example, the sensor data broadcast by each of ID nodes 24120a-24120c shown in FIG. 24B are detected by command node 24160, which then compares the detected sensor data from each of the ID nodes and the context data related to each of the ID nodes. The command node then is operative to detect the environmental anomaly for the shipping container 24300 when the comparison of the detected sensor data and the context data indicates an environmental condition for at least one of the packages 24400d-24400f exceeds its respective environmental threshold condition. The command node is then operative to generate a layered alert notification related to the environmental anomaly for the shipping container in response to detecting the environmental anomaly, where the layered alert notification identifies a targeted mediation recipient, identifies a targeted mediation action, and establishes a mediation response priority based upon the comparison of the received sensor data and the context data; and cause the second communication interface to transmit the layered alert notification to the transceiver unit to initiate a mediation response related to the targeted mediation action.

Such a system embodiment may have the command node detecting the environmental anomaly based upon relative changes in the environmental sensor data. For example, in a more detailed embodiment, the command node processing unit in command node 24160 may be further programmatically configured to detect the environmental anomaly for the shipping container 24300 when the comparison of the detected sensor data and the context data indicates a relative change in the environmental condition for the at least one of the packages 24400d-24400f exceeds its respective environmental threshold condition.

In another more detailed embodiment, the command node processing unit in command node 24160 may be further programmatically configured to compare the detected sensor data and the context data by comparing a relative change in the detected sensor data from at least one of the ID nodes 24120a-24120c and the context data locally maintained in the command node memory of command node 24160 for that one of the ID nodes 24120a-24120c. Here, the environmental threshold condition for the particular package with that one of the ID nodes 24120a-24120c comprising a threshold relative environmental change condition that when exceeded is indicative of the environmental anomaly for the shipping container 24300. As such, the command node processing unit is further programmatically configured to detect the environmental anomaly for the shipping container when the comparison of the detected sensor data and the context data indicates the environmental condition for that package (or set of packages associated with those of the ID nodes) exceeds the threshold relative environmental change condition.

In more detail, the system described above may have each of the ID nodes being further operative to incrementally generate the sensor data over a time period using the environmental sensor on each of the respective ID nodes. As such, the command node processing unit of the system's command node 24160 may be further programmatically configured to monitor the generated sensor data from each of the ID nodes 24120a-24120c over the time period to identify relative changes in the generated sensor data over the time period; compare the identified relative changes in the generated sensor data and the context data 26560 locally maintained on the command node memory related to those of the ID nodes 24120a-24120c that are related to the relative changes in the generated sensor data (where the context data 26560 in the command node memory includes at least relative environmental threshold conditions respectively corresponding to each of the packages 24400d-24400f); and detect the environmental anomaly for the shipping container when the comparison of identified relative changes in the generated sensor data and the context data related to those of the ID nodes 24120a-24120c that correspond to the identified relative changes in the generated sensor data indicates a changed environmental condition for at least one of packages 24400d-24400f that exceeds its respective relative environmental threshold condition. In this more detailed embodiment of the system, the mediation response priority is based upon the comparison of the identified relative changes in the generated sensor data and the part of context data 26560 related to those of the ID nodes 24120a-24120c that correspond to the relative changes in the generated sensor data.

In more detail, the environmental sensor for a first of the ID nodes 24120a may be implemented with a temperature sensor and the environmental sensor for a second of the ID nodes 24120b may be implemented with a barometric pressure sensor. With these types of sensors deployed on ID nodes 24120a and 24120b, the command node processing unit of command node 24160 may be further programmatically configured to detect the environmental anomaly when: (a) the sensor data detected from the first ID node 24120a comprises a temperature value; (b) the sensor data detected from the second ID node 24120b comprises a barometric pressure value; (c) the temperature value indicates the environmental condition of the first package 24400d associated with the first ID node 24120a exceeds the environmental threshold condition for the first package 24400d according to the context data 26560 for the first package 24400d; and (d) the barometric pressure value indicates the environmental condition of a second package 24400e associated with the second of the ID nodes 24120b exceeds the environmental threshold condition for the second package 24400e according to the context data 26560 for the second package 24400e.

In another embodiment, the system may have the environmental sensor for a first of the ID nodes 24120a being a temperature sensor and the environmental sensor for a second of the ID nodes 24120b being one from a group consisting of a barometric pressure sensor, a radiation sensor, and a chemical sensor. In such an embodiment, the command node processing unit for the system's command node 24160 may be further programmatically configured to detect the environmental anomaly when: (a) the sensor data detected from the first of the ID nodes 24120a comprises a temperature value; (b) the sensor data detected from the second of the ID nodes 24120b comprises an environmental condition value of one of a sensed barometric pressure level by the barometric sensor, a detected radiation level by the radiation sensor, or a detected chemical by the chemical sensor; (c) the temperature value indicates the environmental condition of a first package 24400d associated with the first of the ID nodes 24120a exceeds the environmental threshold condition for the first package 24400d according to the context data 26560 for the first package 24400d; and (d) the environmental condition value indicates the environmental condition of a second package 24400e associated with the second of the ID nodes 24120b exceeds the environmental threshold condition for the second package 24400e according to the context data 26560 for the second package 24400e. In such an embodiment, the detected chemical may be indicative of an explosive, fire, or one of either CO or $CO_2$.

In still another system embodiment, the environmental sensor for one the ID nodes 24120a-24120c may have multiple sensor elements, where such sensor elements include at least a temperature sensor element and a barometric pressure sensor element.

In a system embodiment where the environmental sensors include a temperature and pressure sensor, various types of environmental anomalies may be identified based on the environmental sensor data as well as context data for the particular packages (e.g., particular thresholds related to such environmental type of conditions). For example, the command node 24160 may be operative to detect the environmental anomaly for shipping container 24300 as a fire within the shipping container 24300 when the temperature value exceeds a temperature threshold maintained by the command node 24160 in the command node memory as part of the context data 26560 for the first package 24400d and when the barometric pressure value exceeds a pressure threshold maintained by the command node 24160 in the command node memory as part of the context data 26560 for the second package 24400e. In another example, the command node 24160 may be operative to detect the environmental anomaly for shipping container 24300 as an explosion within the shipping container 24300 when the temperature value exceeds a temperature threshold maintained by the command node 24160 in the command node memory as part of the context data 26560 for the first package 24400d and when the barometric pressure value is below a pressure threshold maintained by the command node 24160 in the command node memory as part of the context data 26560 for the second package 24400e. In yet another example, the command node 24160 may be operative to detect the environmental anomaly for shipping container 24300 as an explosion within the shipping container 24300 when the temperature value exceeds a temperature threshold maintained by the command node 24160 in the command node memory as part of the context data 26560 for the first package 24400d and when the barometric pressure value drops faster than a pressure drop threshold maintained by the command node 24160 in the command node memory as part of the context data 26560 for the second package 24400e.

Further still, in an additional system embodiment where the environmental sensors include temperature and chemical detectors, the command node 24160 may be operative to detect the environmental anomaly for shipping container 24300 as a detected chemical related fire within the shipping container 24300 when the temperature value exceeds a temperature threshold maintained by the command node 24160 in the command node memory is part of the context data 26560 for the first package 24400d and when the detected chemical matches a predetermined chemical profile maintained by the command node 24160 in the command node memory as part of the context data 26560 for the second package 24400e.

Additionally, in a further system embodiment where the environmental sensors include temperature and radiation detectors, the command node 24160 may be operative to detect the environmental anomaly for shipping container 24300 as a radiation leak within the shipping container 24300 when the temperature value exceeds a temperature threshold maintained by the command node 24160 as part of the context data 26560 for the first package 24400d and when the detected radiation matches a predetermined radiation profile maintained by the command node 24160 as part of the context data 26560 for the second package 24400e.

A further feature in such a system embodiment may include the ability to selectively set and adjust rates for obtaining sensor data from ID nodes. This can help with following up on potentially spreading or worsening environmental anomalies. For example, in a further system embodiment, each of the ID nodes may broadcast their respectively generated sensor data by transmitting such sensor data according to a broadcast profile maintained by each of the ID nodes. Such a broadcast profile (e.g., part of profile data 330 for a particular ID node, such as any of ID nodes 24120a-24120c) defines a first messaging rate used to regulate how often the generated sensor data is transmitted to the command node 24160, where the first messaging rate is higher than a default messaging rate. The command node 24160 may then instruct each of the ID nodes 24120a-24120c to broadcast future generated sensor data at a rate different from the default messaging rate after transmitting the layered alert notification to the transceiver unit—e.g., changing from the default messaging rate to the higher first messaging rate, or changing to a second messaging rate that exceeds the first messaging rate. Such a first messaging rates may be an initial value correlated to an environmental risk associated with at least one of the packages within the shipping container. Likewise, the second messaging rate may be a predetermined messaging rate based upon a type of material existing within at least one of the packages within the shipping container (e.g., a rate that is higher than other rates due to the character of what is being transported in package 24400a, such as lithium-ion batteries or other materials having transport risks associated with them).

In the system embodiment, the layered alert notification generated and broadcast by the command node identifies a targeted mediation recipient for such an alert. In more detail, the command node may be further programmatically configured to automatically select the targeted mediation recipient based upon an excess condition on how much the detected sensor data and the context data indicates the environmental condition for the at least one of the packages exceeds the environmental threshold condition for the at least one of the packages. For example, the targeted mediation recipient identified by the command node 24160 in the layered alert notification may be a triggered fire suppression system on the transit vehicle (e.g., exemplary fires suppression system 25010 within an aircraft as shown and explained in FIG. 25B) that is operative to automatically respond to the detected environmental anomaly based upon receipt of the layered alert notification. Such a triggered response may involve deploying fire suppression material within the shipping container 24300 having the command node 24160 sending the layered alert notification. In another example, the targeted mediation recipient identified by the command node 24160 in the layered alert notification may be an operator of the transit vehicle (e.g., pilot of the aircraft) that can alter movement of the transit vehicle. In still another example, the targeted mediation recipient identified by the command node 24160 in the layered alert notification may be a logistics crew member of the transit vehicle that can inspect the shipping container 24300. In like manner, the targeted mediation response in the layered alert notification may be an automatic response to be performed by a triggered fire suppression system on the transit vehicle, a request to change course of the transit vehicle from an existing travel path of the transit vehicle (displayed on a screen of, for example, cockpit transceiver 25150a to a pilot/operator), and/or a request to investigate the shipping container (displayed on a screen of, for example, logistics transceiver 25150b to logistics crew member).

In the system embodiment, the layered alert notification generated and broadcast by the command node also identifies a targeted mediation action as part such an alert. In more detail, the targeted mediation action may be automatically selected by the command node 24160 based upon an excess condition on how much the detected sensor data from the ID nodes 24120a-24120c and the context data 26560 indicates the environmental condition for at least one of the packages 24400d-24400f exceeds the environmental threshold condition for that one of the packages. In another example, the targeted mediation action identified by the command node 24160 in the layered alert notification depends upon what is loaded within the shipping container 24300 as indicated by shipping information maintained on the command node 24160 (e.g., shipment data (similar to shipment data 580) maintained as part of context data 26560 in memory of command node 24160). In still another example, the targeted mediation action identified by the command node 24160 in the layered alert notification depends upon an excess condition on how many of the packages 24400d-24400f have their detected sensor data and their context data indicating that their environmental condition exceed the environmental threshold condition for the packages 24400d-24400f. Thus, as more packages have exceeded their respective environmental threshold conditions, the command node 24160 may shift what the appropriate targeted mediation action is identified to be as part of the layered alert notification.

In some embodiments, the targeted mediation action may depend upon further types of context information or data. As described above, exemplary context data 26560 may include container status data related to a particular shipping container, vehicle status data, geolocation data (also a type of location data 455), or facility status data on a storage facility for the shipping container. As such, a further system embodiment may have the command node processing unit of the system's command node (e.g., command node 24160) further programmatically configured to receive vehicle status data from the external transceiver unit 24150 of the transit vehicle 24200 using the second communication interface and maintain the vehicle status data in the command node memory as part of context data 26560, and where the targeted mediation action identified in the layered alert notification depends upon a state of the transit vehicle 24200 as indicated by the vehicle status data. The state or status of the vehicle indicated by the vehicle status data may, for example, be a takeoff vehicular status, a cruising vehicular status, a landing vehicular status, and an on-the-ground vehicular status. In another example, the command node memory may maintain container status data as part of context data 26560, where such container status data container information corresponding to the state of a shipping container (such as ULD container 24300). As such, the targeted mediation action in the layered alert notification sent by command node 24160 can depend upon a state of the shipping container as indicated in the container status data.

As noted with respect to exemplary command node 2600, an embodiment of such a command node may include location circuitry (similar to that shown as location circuitry 475 with master node 110a) that is coupled to the command node's processor 26400. Such location circuitry is operative to detect geolocation data related to a current location of the shipping container within the transit vehicle, such that a further embodiment may have the targeted mediation action identified in the layered alert notification depending upon the current location of the shipping container as indicated in the geolocation data.

In a further system embodiment, the command node may maintain loading plan data indicating the relative location of the command node's shipping container within the transit vehicle. For example, command node 24160 may having loading plan data as part of its context data 26560 and such loading plan data may indicate the relative location of ULD container 24300 within the storage 24205 of transit vehicle 24200. As such, a further system embodiment may have the targeted mediation action identified by command node 24160 in the layered alert notification broadcast by command node 24160 depending upon the relative location of ULD container 24300 within the transit vehicle 24200 as indicated in the loading plan data within context data 26560 on command node 24160.

In still a further system embodiment, the command node may maintain facility status data associated with a storage facility for the shipping container (such as facility status data associated with an aircraft hangar used by an aircraft, a logistics depot used by a delivery vehicle or other storage facility that may temporarily be used by the shipping container). For example, command node 24160 may having facility status data as part of its context data 26560 and the targeted mediation action identified by command node 24160 in the layered alert notification broadcast by command node 24160 depending upon the state of the storage facility as indicated in the facility status data.

The layered alert notification generated by the system's command node also identifies a mediation response priority based upon the comparison of the received sensor data and the context data. In a more detailed embodiment, the mediation response priority may be automatically selected by the command node processing unit when generating the layered alert notification based upon an excess condition on how much the detected sensor data and the context data indicates the environmental condition for the at least one of the packages exceeds the environmental threshold condition for the at least one of the packages. Thus, for example, when the sensor data indicated an environmental condition for at least one of the packages in the container far exceeds the respective environmental threshold condition for that package (which may indicate a fire or explosive event), the mediation response priority established by the command node as part of the layered alert notification may be a high priority level indicating further travel by the transit vehicle is to be at least minimized when responding to the detected environmental anomaly. In another example, the mediation response priority established by the command node as part of the layered alert notification may be an intermediate priority level indicating further travel by the transit vehicle is permissible when responding to the detected environmental anomaly.

A further embodiment of this system may selectively use particular ID nodes when monitoring for the environmental anomaly. In such a further embodiment, the command node processing unit of the system's command node may be further programmatically configured to select each of the ID nodes from a larger group of network elements being loaded into the shipping container. For example, command node 24160 may select only ID nodes 24120*a* and 24120*c* within shipping container 24300 as shown in FIG. 25B. The ID nodes selected provide the gathered sensor data for use in detecting the environmental anomaly for the shipping container 24300 as described above. In more detail, the command node processing unit may be further programmatically configured to identify each of the ID nodes selected based upon package content information and/or loading plan data maintained within the command node memory (e.g., package content information and loading plan data being part of exemplary context data 26560 maintained on command node 24160).

Another further embodiment of this system may remotely alter threshold limits as part of improving the responsive mediation. In such a further embodiment, the command node processing unit of the system's command node may be further programmatically configured to receive an update for the environmental threshold conditions for at least one of the packages using the second communication interface. Such an update may come from the external transceiver unit over the second communication interface of the command node. The update for the environmental threshold conditions may be defined by an operator of the transit vehicle using the external transceiver unit (e.g., cockpit transceiver 25150*a* shown in FIG. 25C) or a logistics crew member of the transit vehicle using the external transceiver unit (e.g., logistics transceiver 25150*b* shown in FIG. 25C). Further, such an update for the environmental threshold conditions may be provided to the external transceiver unit from a remote control center (e.g., remote control center server 24100 in communication with the external transceiver unit 24150).

In still a further embodiment of this system, the validity of communications (e.g., broadcasted sensor data) may be confirmed or verified to provide a more secure and robust system that is less susceptible to error or spoofing by other nodes. In such a further embodiment, the command node processing unit may be programmatically configured to detect the sensor data using the first communication interface by being further operative to: (a) receive the sensor data broadcasted from a first of the ID nodes using the first communication interface; (b) confirm the validity of the received sensor data; (c) repeat (a) and (b) for the remainder of the sensor data received from any of the remaining ones of the ID nodes using the first communication interface; and (d) selectively compile the detected sensor data using only the received sensor data confirmed valid.

In more detail, the command node may confirm that it uses only valid sensor data when detecting an environmental anomaly in an active or passive manner. In an "active" example, the command node may cause the first communication interface to send an authentication request to an ID node, and receive a validation response from that ID node via the first communication interface. Such an actively requested validation response authenticates the sensor data broadcasted from that one of the ID nodes. In a "passive" example, the command node may confirm the validity of the received sensor data by being further operative to access a validation sequence for an ID node as maintained by the command node in memory (e.g., as part of security data 435 or profile data 430 on command node 26000 for that particular ID node). Such a validation sequence characterizes expected broadcasts from that particular ID node. Using such a validation sequence, the command node may then passively determine if the received sensor data from that ID node matches a predetermined one of the expected broadcasts from that ID node without the need to poll or interactively request authentication from that ID node. In more detail, the predetermined one of the expected broadcasts according to the validation sequence may be a rotating value previously received by the command node for that ID node as a way of enhancing security for the command node to better determine and confirm that ID node sensor data is coming from a valid ID node and, thus, is valid sensor data upon which to make determinations of whether an environmental anomaly exists.

Figure 27:
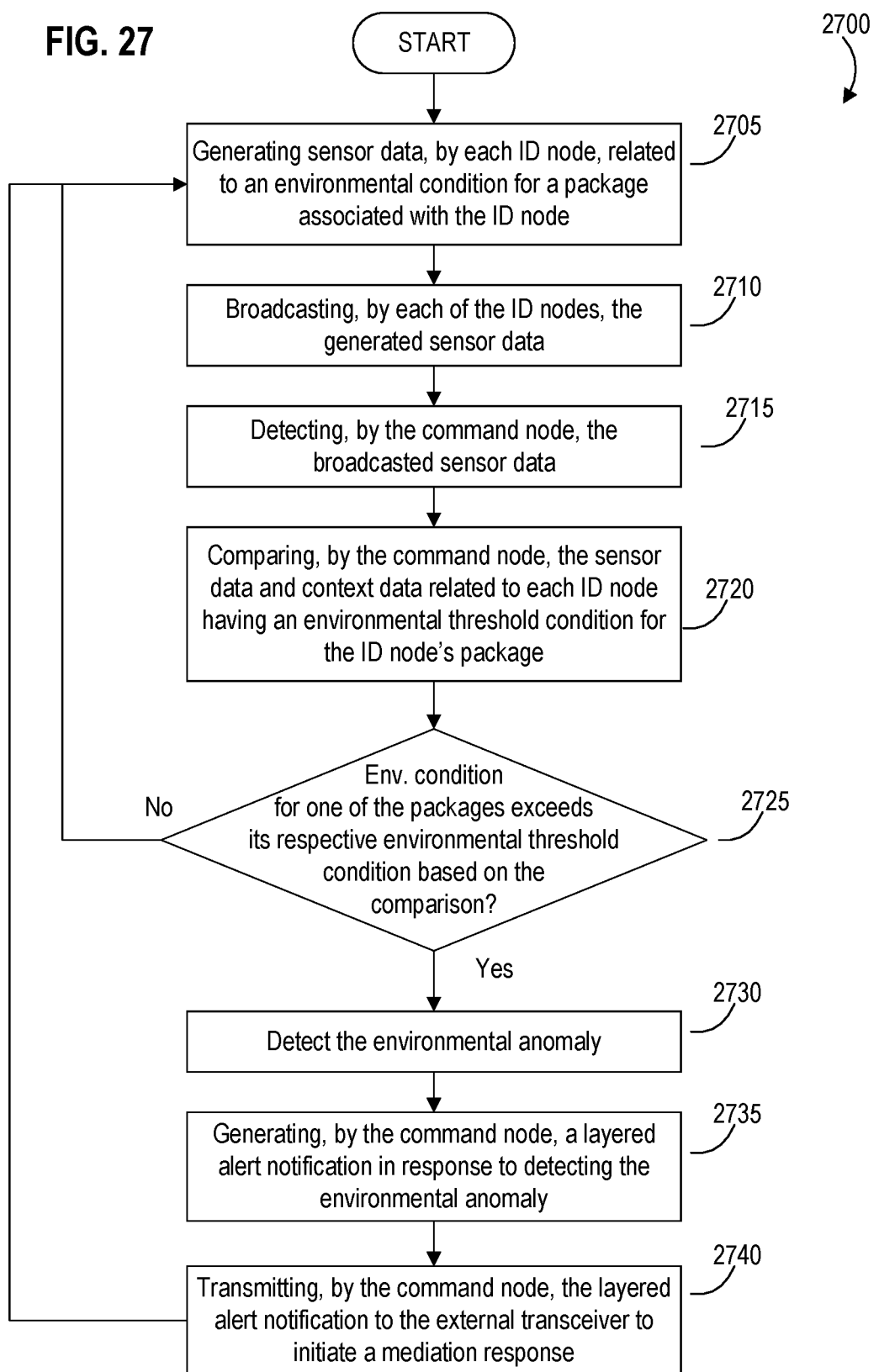
FIG. 27 is a flow diagram illustrating an exemplary method for monitoring a shipping container for an environmental anomaly using a wireless node network using sensor data from ID nodes associated with packages and with environmental threshold conditions for the packages in accordance with an embodiment of the invention.

Using the above described system embodiment that monitors a shipping container for an environmental anomaly using ID nodes associated with packages and environmental threshold conditions corresponding to the packages, a further embodiment focuses on an improved method for monitoring the shipping container using such system elements. FIG. 27 is a flow diagram illustrating an exemplary method for monitoring a shipping container for an environmental anomaly using a wireless node network using sensor data from ID nodes associated with packages and with environmental threshold conditions for the packages in accordance with an embodiment of the invention. In more detail and referring now to FIG. 27, exemplary method 2700 describes an improved method for monitoring a shipping container (e.g., ULD shipping container 24300) for an environmental anomaly using a wireless node network having at least a plurality of ID nodes (e.g., ID nodes 24120*a*-24120*c*) disposed within the shipping container and a command node (e.g., command node 24160) mounted to and associated with the shipping container, each of the ID nodes having at least one environmental sensor and being associated with a respective one of a group of packages (e.g., packages 24400*d*-24400*f*) maintained within the shipping container, and where the command node is operative to communicate with each of the ID nodes and an external transceiver unit (e.g., external transceiver 24150) associated with a transit vehicle (e.g., transit vehicle 24200, such as an aircraft, railway conveyance, a maritime vessel, or a roadway conveyance). Method 2700 begins at step 2705 with the environmental sensor or sensors on each of the ID nodes generating sensor data related to an environmental condition of the respective package associated with each of the ID nodes as the packages reside within the shipping container. In more detailed embodiment, the environmental sensor for a first of the ID nodes may be a temperature sensor while the environmental sensor for a second of the ID nodes may be a barometric pressure sensor. In another embodiment, the environmental sensor for a first of the ID nodes may be a temperature sensor while the environmental sensor for a second of the ID nodes may be one from a group consisting of a barometric pressure sensor, a radiation sensor, and a chemical sensor. In still a further embodiment, the environmental sensor for one or more of the ID nodes may have multiple sensor elements, where such sensor elements may include at least a temperature sensor element and a barometric pressure sensor element (but may also include a radiation sensor and/or a chemical sensor).

At step 2710, method 2700 proceeds with each of the ID nodes broadcasting their respectively generated sensor data. At step 2715, method 2700 has the command node detecting the sensor data broadcasted from the ID nodes. Method 2700 then proceeds to step 2720 where the command node compares the detected sensor data from each of the ID nodes and locally maintained context data related to each of the ID nodes. Such context data (e.g., context data 26560) includes at least a plurality of environmental threshold conditions respectively corresponding to the packages. In this way, a particular environmental threshold condition for one package may be different than that of another package as, for example, the material in one package may become volatile at a lower temperature than material in other packages.

At decision step 2725, method 2700 has the command node determining if an environmental condition for one of the packages exceeds its respective environmental threshold condition based upon the comparison performed in step 2720. If so, method 2700 proceeds from step 2725 directly to step 2730 where the command node detects the environmental anomaly for the shipping container because the comparison of the detected sensor data and the context data indicates an environmental condition for at least one of the packages exceeds its respective environmental threshold condition. If not, method 2700 proceeds from step 2725 back to step 2705 where the ID nodes generate more sensor data and the ID nodes continue to broadcast newly generated sensor data at step 2710 for detection and consideration by the command node in steps 2715-2725 again.

In steps 2725-2730, the command node may detect different types of environmental anomalies depending on the type of sensor data being considered. For example, a further embodiment of method 2700 may have the command node detecting the environmental anomaly as part of steps 2725-2730 when (a) the sensor data detected from one of the ID nodes comprises a temperature value; (b) the sensor data detected from a second of the ID nodes comprises a barometric pressure value; (c) the temperature value indicates the environmental condition of a first package associated with the first ID node exceeds the environmental threshold condition for the first package according to the context data for the first package; and (d) the barometric pressure value indicates the environmental condition of a second package associated with the second ID node exceeds the environmental threshold condition for the second package according to the context data for the second package.

Still further embodiments of method 2700 may use a combination of temperature and other types of sensors. For example, another embodiment of method 2700 may have the command node detecting the environmental anomaly as part of steps 2725-2730 when (a) the sensor data detected from one of the ID nodes comprises a temperature value; (b) the sensor data detected from a second of the ID nodes comprises an environmental condition value of one of a sensed barometric pressure level by the barometric sensor, a detected radiation level by the radiation sensor, or a detected chemical by the chemical sensor (e.g., the detected chemical by the chemical sensor may be indicative of an explosive, a fire, or the presence of either CO or $CO_2$); (c) the temperature value indicates the environmental condition of a first package associated with the first ID node exceeds the environmental threshold condition for the first package according to the context data for the first package; and (d) the environmental condition value indicates the environmental condition of a second package associated with the second ID node exceeds the environmental threshold condition for the second package according to the context data for the second package.

The environmental anomaly detected in step 2730 of method 2700 may come in a variety of types depending on the type of sensors used as well. For example, a further embodiment of step 2730 may have the command node detect the environmental anomaly for the shipping container to be a fire within the shipping container when the temperature value exceeds a temperature threshold maintained by the command node as part of the context data for the first package and when the barometric pressure value exceeds a pressure threshold maintained by the command node as part of the context data for the second package. Another embodiment of step 2730 may have the command node detect the environmental anomaly for the shipping container to be an explosion within the shipping container when the temperature value exceeds a temperature threshold maintained by the command node as part of the context data for the first package and when the barometric pressure value is below a pressure threshold maintained by the command node as part of the context data for the second package. Yet another embodiment of step 2730 may have the command node detect the environmental anomaly for the shipping container to be an explosion within the shipping container when the temperature value exceeds a temperature threshold maintained by the command node as part of the context data for the first package and when the barometric pressure value drops faster than a pressure drop threshold maintained by the command node as part of the context data for the second package. A further embodiment of step 2730 may have the command node detect the environmental anomaly for the shipping container to be a detected chemical related fire within the shipping container when the temperature value exceeds a temperature threshold maintained by the command node as part of the context data for the first package and when the detected chemical matches a predetermined chemical profile maintained by the command node as part of the context data for the second package. And still another embodiment of step 2730 may have the command node detect the environmental anomaly for the shipping container to be a radiation leak within the shipping container when the temperature value exceeds a temperature threshold maintained by the command node as part of the context data for the first package and when the detected radiation matches a predetermined radiation profile maintained by the command node as part of the context data for the second package.

In other embodiments, method 2700 may detect the environmental anomaly based upon relative changes in sensor data when compared to the relevant context data on environmental threshold conditions. For example, steps 2725 and 2730 may have the command node detecting an environmental anomaly when the comparison of the detected sensor data and the context data in step 2720 indicates a relative change in the environmental condition for at least one of the packages and where such a relative change exceeds its respective environmental threshold condition (which may be defined in terms of relative changes in environmental conditions, such as temperature, pressure, and the like). In a more detailed example, step 2730 may further have the command node comparing a relative change in the detected sensor data from at least one of the ID nodes and the locally maintained context data for that one of the ID nodes, which has the environmental threshold condition for at least the package with that ID node as a threshold relative environmental change condition that when exceeded is indicative of the environmental anomaly for the shipping container. As such in this example, detecting the environmental anomaly for the shipping container in this embodiment of step 2730 occurs when the comparison of the detected sensor data and the context data indicates the environmental condition for the one of the packages associated with that ID node exceeds the threshold relative environmental change condition.

At step 2735, method 2700 proceeds with the command node generating a layered alert notification related to the environmental anomaly for the shipping container in response to detecting the environmental anomaly. The layered alert notification identifies a targeted mediation recipient, identifies a targeted mediation action, and establishes a mediation response priority based upon the comparison of the received sensor data and the context data. In a further embodiment of method 2700, the targeted mediation recipient may be automatically selected by the command node based upon an excess condition on how much the detected sensor data and the context data indicates the environmental condition for at least one of the packages exceeds the environmental threshold condition for at least one of the packages. Such a targeted mediation recipient identified by the command node in the layered alert notification may be, for example, a triggered fire suppression system on the transit vehicle (e.g., exemplary fire suppression system 25010 of FIG. 25B) that is operative to automatically respond to the detected environmental anomaly based upon receipt of the layered alert notification; an operator of the transit vehicle that can alter movement of the transit vehicle; or a logistics crew member of the transit vehicle that can inspect the shipping container.

In another further embodiment of method 2700, the targeted mediation action identified by the command node in step 2735 may be automatically selected by the command node based upon an excess condition on how much the detected sensor data and the context data indicates the environmental condition for at least one of the packages exceeds the environmental threshold condition for those packages. In more detail, the targeted mediation action identified by the command node in the layered alert notification may depend upon what is loaded within the shipping container as indicated by shipping information maintained on the command node or may depend upon an excess condition on how many of the packages have their detected sensor data and their context data indicating that their environmental condition exceed the environmental threshold condition for the packages. With such information, the command node may identify an appropriate targeted mediation action, such as immediately deploying the onboard fire suppression system or, instead, identify a threat appropriate action of notifying a logistics personnel to inspect a particular one or group of packages.

The targeted mediation action in step 2735 may be identified by the command node using a variety of types of context data so that the targeted mediation action may be automatically identified with an robust and improved sense of contextual understanding of the situation. For example, in a further embodiment, method 2700 may have the command node receiving vehicle status data from the external transceiver unit associated with the transit vehicle, so that the targeted mediation action identified by the command node in the layered alert notification may depend upon a state of the transit vehicle as indicated by the vehicle status data. Such a state of the transit vehicle may include, for example, a takeoff vehicular status, a cruising vehicular status, a landing vehicular status, and an on-the-ground vehicular status. Thus, context data 26560 may include such vehicle status data, which may be used in identifying the targeted mediation action in response to detecting the environmental anomaly.

In another example, an embodiment of method 2700 may have the command node accessing container status data maintained by the command node and associated with the shipping container, so that the targeted mediation action identified by the command node in the layered alert notification depends upon a state of the shipping container as indicated in the container status data. In yet another example, an embodiment of method 2700 may have the command node detecting geolocation data related to a current location of the shipping container within the transit vehicle, so that the targeted mediation action identified by the command node in the layered alert notification depends upon the current location of the shipping container as indicated in the geolocation data. In still another example, an embodiment of method 2700 may have the command node accessing loading plan data maintained by the command node (where such loading plan data indicates a relative location of the shipping container within the transit vehicle), so that the targeted mediation action identified by the command node in the layered alert notification depends upon the relative location of the shipping container within the transit vehicle as indicated in the loading plan data. And in another example, an embodiment of method 2700 may have the command node accessing facility status data maintained by the command node and associated with a storage facility for the shipping container, so that the targeted mediation action identified by the command node in the layered alert notification depends upon a state of the storage facility as indicated in the facility status data.

The targeted mediation response identified in step 2735 may also take several forms. For example, a further embodiment may have the targeted mediation response identified by the command node in the layered alert notification be an automatic response by a triggered fire suppression system on the transit vehicle; a request to change course of the transit vehicle from an existing travel path of the transit vehicle; or a request to investigate the shipping container.

Likewise, the mediation response priority established by the command node as part of step 2735 may take several forms. For example, the command node may establish the mediation response priority as part of step 2735 by automatically selecting the mediation response priority based upon an excess condition on how much the detected sensor data and the context data indicates the environmental condition for at least one of the packages exceeds the environmental threshold condition for the package(s). In another example, the mediation response priority established by the command node as part of the layered alert notification may be established as a high priority level indicating further travel by the transit vehicle is to be at least minimized when responding to the detected environmental anomaly, or as an intermediate priority level indicating further travel by the transit vehicle is permissible when responding to the detected environmental anomaly.

At step 2740, method 2700 proceeds with the command node transmitting the layered alert notification to the transceiver unit to initiate a mediation response related to the targeted mediation action. In this way, the command node (e.g., command node 24160 as shown in FIG. 24B) automatically and responsively monitors its particular shipping container by means of the ID nodes associated with packages within the shipping container and responsively provides an enhanced type of notification in the form of the layered alert notification to the transit vehicle's external transceiver (e.g., transceiver 24150), which is used to cause the external transceiver to initiate the identified type of mediation response related to the identified type of targeted mediation action to deal with the detected environmental anomaly in a rapid, improved, and more robust manner. Thereafter, method 2700 may proceed back to step 2705 where further sensor data may be generated by each of the ID nodes.

Further embodiments of method 2700 may provide more detailed steps as well as additional steps. For example, in a more detailed embodiment, the ID nodes generate sensor data over a particular time period and the command node, as part of step 2715, may monitor the generated sensor data from each of the ID nodes over the time period to identify relative changes in the generated sensor data over the time period. Thereafter, as part of step 2720, the step of comparing may have the command node comparing the identified relative changes in the generated sensor data and locally maintained context data (e.g., context data 26560) related to those of the ID nodes that are related to the relative changes in the generated sensor data. Here, the context data stored on the command node includes at least a plurality of relative environmental threshold conditions respectively corresponding to the different packages. Further, as part of steps 2725 and 2730, the step of detecting the environmental anomaly for the shipping container may occur when the comparison of identified relative changes in the generated sensor data and locally maintained context data related to those of the ID nodes that correspond to each of the identified relative changes in the generated sensor data indicates a changed environmental condition for at least one of the packages exceeds its respective relative environmental threshold condition. Additionally, as part of step 2735, the command node may establish the mediation response priority as being based upon the comparison of the identified relative changes in the generated sensor data and the locally maintained context data related to those of the ID nodes that correspond to the relative changes in the generated sensor data.

Another more detailed embodiment of method 2700 may involve setting/adjusting the rate an ID node generates and broadcasts sensor data as a way to adaptively respond to an initially detected environmental anomaly. For example, step 2710 of broadcasting the generated sensor data by the ID nodes may have each of the ID nodes transmitting their respectively generated sensor data according to a broadcast profile maintained by each of the ID nodes, where such a broadcast profile defines a first messaging rate used to regulate how often the generated sensor data is transmitted to the command node, and where the first messaging rate is higher than a default messaging rate. This further embodiment of method 2700 may also have the command node instructing each of the ID nodes to broadcast future generated sensor data at a second messaging rate that exceeds the first messaging rate after transmitting the layered alert notification to the transceiver unit in step 2740. The first messaging rate for the ID nodes may be set with an initial value correlated to an environmental risk associated with at least one of the packages within the shipping container, and may adaptively set the second messaging rate for the ID nodes to a predetermined messaging rate based upon a type of material existing within at least one of the packages within the shipping container. This further embodiment of method 2700 may also have the command node instructing each of the ID nodes to change from the default messaging rate to the first messaging rate. In this way, the command node may adaptively change the messaging rates by which the ID nodes broadcast their sensor data depending on the detected environmental anomaly and depending on context data (e.g., context data 26560) about the makeup of packages being transported within the shipping container.

Still another embodiment of method 2700 may involve selectively and adaptively choosing which of the ID nodes available within the shipping container to use when monitoring for an environmental anomaly. For example, this further embodiment of method 2700 may have the command node select each of the ID nodes used for detecting the environmental anomaly from a larger group of network elements being loaded into the shipping container. In this way, the ID nodes that are selected are those chosen by the command node to provide the gathered sensor data for use in detecting the environmental anomaly for the shipping container. In more detail, the ID nodes selected may be identified for selection by the command node based upon contents of the packages associated with the ID nodes being selectively activated, or based upon a loading scheme for the shipping container (where such a loading scheme may be maintained in memory of the command node as loading plan data that may be stored as part of context data 26560).

Yet another embodiment of method 2700 may involve remote altering and updating of thresholds and mediation information used for detecting an environmental anomaly and how to respond to such an environmental anomaly. For example, this additional embodiment of method 2700 may have the command node receiving an update for the environmental threshold conditions for at least one of the packages. Such an update may be received from the external transceiver unit (e.g., transceiver 24150). This update received from the external transceiver may be defined by personnel on the transit vehicle (e.g., an operator or logistics personnel on the transit vehicle using the particular external transceiver unit (such as cockpit transceiver 25150*a* or logistics transceiver 25150*b*) using user input interfaces on the transceiver). Alternatively, the update may be received from a remote control center (e.g., remote control center server 24100 in communication with external transceiver 24150).

In still a further embodiment of method 2700, the validity of communications (e.g., broadcasted sensor data) may be confirmed or verified to provide a more secure and robust system that is less susceptible to error or spoofing by other nodes. In such a further embodiment of method 2700, the command node may detect the sensor data in step 2715 by (a) receiving the sensor data broadcasted from a first of the ID nodes; (b) confirming the validity of the received sensor data; (c) repeat steps (a) and (b) for the remainder of the sensor data received from any of the remaining ones of the ID nodes; and (d) compiling the detected sensor data using only the received sensor data confirmed valid in sub step (b) of modified step 2715. In more detail, the command node may confirm as part of (b) that it uses only valid sensor data when detecting an environmental anomaly in an active or passive manner. For example, confirming the validity of the received sensor data may have the command node actively sending an authentication request to the first of the ID nodes, and receiving a validation response back from that ID node that authenticates the sensor data broadcasted from that ID node. In another example, confirming the validity of the received sensor data as part of (b) may have the command node, in a more passive sense accessing a validation sequence for an ID node as maintained by the command node in memory (e.g., as part of security data 435 or profile data 430 on command node 26000 for that particular ID node). Such a validation sequence characterizes expected broadcasts from that particular ID node. Using such a validation sequence, the command node may then passively determine if the received sensor data from that ID node matches a predetermined one of the expected broadcasts from that ID node without the need to poll or interactively request authentication from that ID node. Such a predetermined one of the expected broadcasts according to the validation sequence may be a rotating value previously received by the command node for that ID node as a way of enhancing security for the command node to better determine and confirm that ID node sensor data is coming from a valid ID node and, thus, is valid sensor data upon which to make determinations of whether an environmental anomaly exists.

While exemplary method 2700 and the exemplary system described relative to FIG. 24B has the ID nodes associated with particular packages, another embodiment of a method and system that monitors for an environmental anomaly using ID nodes may be deployed where the ID nodes are not required to be associated with particular packages within the shipping container, and where the environmental threshold conditions are related to particular ID nodes. This is similar what is described above relative to FIGS. 24A and 24C where specific packages are shown, but the sensor data and relevant environmental threshold conditions focus on particular ID nodes without being tied to specific packages maintained within shipping container 24300.

Figure 28:
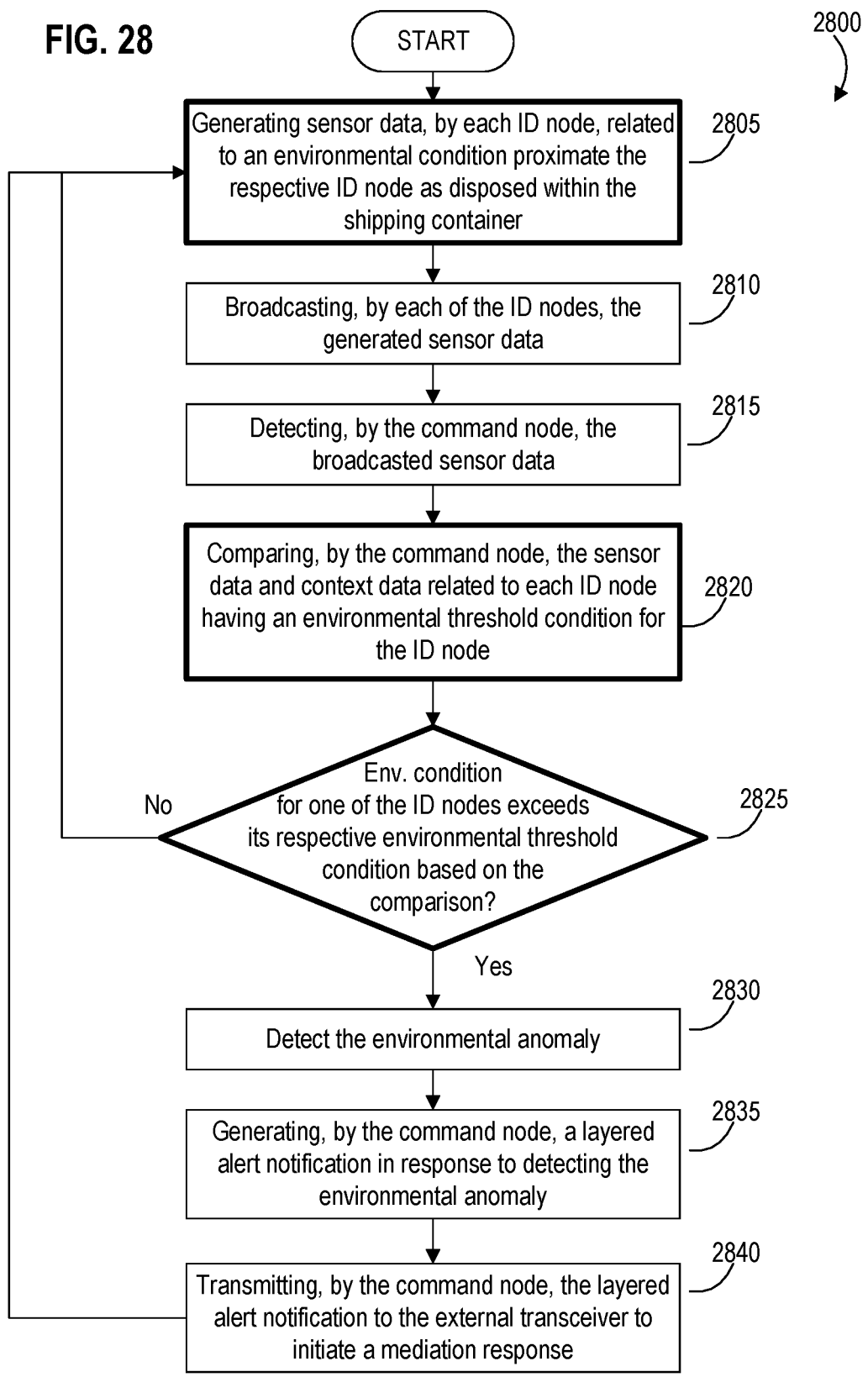
FIG. 28 is a flow diagram illustrating an exemplary method for monitoring a shipping container for an environmental anomaly using a wireless node network using sensor data from ID nodes that are disposed within the shipping container but not associated with particular packages and with environmental threshold conditions for the ID nodes in accordance with an embodiment of the invention.

FIG. 28 is a flow diagram illustrating an exemplary method for monitoring a shipping container for an environmental anomaly using a wireless node network using sensor data from ID nodes that are disposed within the shipping container but are generally not associated with particular packages and with environmental threshold conditions for the ID nodes in accordance with an embodiment of the invention. In more detail and referring now to FIG. 28, exemplary method 2800 describes an improved method for monitoring a shipping container (e.g., ULD shipping container 24300 as shown, for example in FIG. 24C) for an environmental anomaly using a wireless node network having at least a plurality of ID nodes (e.g., ID nodes 24120a-24120f shown in FIG. 24C) disposed within the shipping container and a command node (e.g., command node 24160 of FIG. 24C) mounted to and associated with the shipping container that maintains multiple packages (e.g., packages 24400a-24400c of FIG. 24C), where each of the ID nodes has at least one environmental sensor, and where the command node is operative to communicate with each of the ID nodes and an external transceiver unit (e.g., external transceiver 24150 of FIG. 24C) associated with a transit vehicle (e.g., transit vehicle 24200, which may, for example, be an aircraft, railway conveyance, a maritime vessel, or a roadway conveyance). In general, exemplary method 2800 is similar to method 2700 as described above with variations to steps 2705, 2720, and 2725 given the difference in the type of sensor data broadcast by the ID nodes and the type of environmental threshold conditions used by the command node to detect the environmental anomaly and determine what goes into the relevant layered alert notification to the external transceiver so as to initiate an appropriate mediation response to the environmental anomaly.

In more detail, method 2800 begins at step 2805 with the environmental sensor or sensors on each of the ID nodes generating sensor data related to an environmental condition proximate the respective ID node as disposed within the shipping container. In more detailed embodiment, the environmental sensor for a first of the ID nodes may be a temperature sensor while the environmental sensor for a second of the ID nodes may be a barometric pressure sensor. In another embodiment, the environmental sensor for a first of the ID nodes may be a temperature sensor while the environmental sensor for a second of the ID nodes may be one from a group consisting of a barometric pressure sensor, a radiation sensor, and a chemical sensor. In still a further embodiment, the environmental sensor for one or more of the ID nodes may have multiple sensor elements, where such sensor elements may include at least a temperature sensor element and a barometric pressure sensor element (but may also include a radiation sensor and/or a chemical sensor).

In still another further embodiment of method 2800, the ID nodes generating sensor data in step 2805 may be in two different groups—one of which ID nodes that are disposed on the shipping container itself and a second group of the ID nodes are associated with different ones of a plurality of packages disposed within the shipping container. Further still, the ID nodes generating sensor data in step 2805 may be in a third group—namely, ID nodes that are disposed within the shipping container but not affixed to the shipping container itself.

At step 2810, method 2800 proceeds with each of the ID nodes broadcasting their respectively generated sensor data about the environmental condition proximate the particular ID node within the shipping container. At step 2815, method 2800 has the command node detecting the sensor data broadcasted from the ID nodes. Method 2800 then proceeds to step 2820 where the command node compares the detected sensor data from each of the ID nodes and locally maintained context data related to each of the ID nodes. Such context data (e.g., context data 26560) includes at least a plurality of environmental threshold conditions respectively corresponding to the different ID nodes. In more detail, the environmental threshold condition for each of the ID nodes may depend on where a particular ID node is located within the shipping container or what is placed next to each of the ID nodes according to a loading scheme for the shipping container maintained in memory of the command node as loading plan data. In another example, the environmental threshold condition for each of the ID nodes as indicated by the context data may be a dynamic value that changes or is updated (as discussed herein) when what is placed next to each of the ID nodes within the shipping container changes. In this manner, a command node for the shipping container may have the environmental threshold conditions for the ID nodes within the shipping container being updated, changed, and revised as the contents of the shipping container changes and as what is in the container is moved or relocated within the shipping container.

At decision step 2825, method 2800 has the command node determining if an environmental condition for one of the ID nodes exceeds its respective environmental threshold condition based upon the comparison performed in step 2820. If so, method 2800 proceeds from step 2825 directly to step 2830 where the command node detects the environmental anomaly for the shipping container because the comparison of the detected sensor data and the context data indicates an environmental condition for at least one of the ID nodes exceeds its respective environmental threshold condition. If not, method 2800 proceeds from step 2825 back to step 2805 where the ID nodes generate more sensor data and the ID nodes continue to broadcast newly generated sensor data at step 2810 for detection and consideration by the command node in steps 2815-2825 again.

In steps 2825-2830, the command node may detect different types of environmental anomalies depending on the type of sensor data being considered. For example, a further embodiment of method 2800 may have the command node detecting the environmental anomaly as part of steps 2825-2830 when (a) the sensor data detected from one of the ID nodes comprises a temperature value; (b) the sensor data detected from a second of the ID nodes comprises a barometric pressure value; (c) the temperature value indicates the environmental condition of the first ID node exceeds the environmental threshold condition for the first ID node according to the context data for the first ID node; and (d) the barometric pressure value indicates the environmental condition of the second ID node exceeds the environmental threshold condition for the second ID node according to the context data for the second ID node.

Still further embodiments of method 2800 may use a combination of temperature and other types of sensors. For example, another embodiment of method 2800 may have the command node detecting the environmental anomaly as part of steps 2825-2830 when (a) the sensor data detected from one of the ID nodes comprises a temperature value; (b) the sensor data detected from a second of the ID nodes comprises an environmental condition value of one of a sensed barometric pressure level by the barometric sensor, a detected radiation level by the radiation sensor, or a detected chemical by the chemical sensor (e.g., the detected chemical by the chemical sensor may be indicative of an explosive, a fire, or the presence of either CO or $CO_2$); (c) the temperature value indicates the environmental condition of the first ID node exceeds the environmental threshold condition for the first ID node according to the context data for the first ID node; and (d) the environmental condition value indicates the environmental condition of the second ID node exceeds the environmental threshold condition for the second ID node according to the context data for the second ID node.

The environmental anomaly detected in step 2830 of method 2800 may come in a variety of types depending on the type of sensors used as well. For example, a further embodiment of step 2830 may have the command node detect the environmental anomaly for the shipping container to be a fire within the shipping container when the temperature value exceeds a temperature threshold maintained by the command node as part of the context data for the first ID node and when the barometric pressure value exceeds a pressure threshold maintained by the command node as part of the context data for the second ID node. Another embodiment of step 2830 may have the command node detect the environmental anomaly for the shipping container to be an explosion within the shipping container when the temperature value exceeds a temperature threshold maintained by the command node as part of the context data for the first ID node and when the barometric pressure value is below a pressure threshold maintained by the command node as part of the context data for the second ID node. Yet another embodiment of step 2830 may have the command node detect the environmental anomaly for the shipping container to be an explosion within the shipping container when the temperature value exceeds a temperature threshold maintained by the command node as part of the context data for the first ID node and when the barometric pressure value drops faster than a pressure drop threshold maintained by the command node as part of the context data for the second ID node. A further embodiment of step 2830 may have the command node detect the environmental anomaly for the shipping container to be a detected chemical related fire within the shipping container when the temperature value exceeds a temperature threshold maintained by the command node as part of the context data for the first ID node and when the detected chemical matches a predetermined chemical profile maintained by the command node as part of the context data for the second ID node. And still another embodiment of step 2830 may have the command node detect the environmental anomaly for the shipping container to be a radiation leak within the shipping container when the temperature value exceeds a temperature threshold maintained by the command node as part of the context data for the first ID node and when the detected radiation matches a predetermined radiation profile maintained by the command node as part of the context data for the second ID node.

In other embodiments, method 2800 may detect the environmental anomaly based upon relative changes in sensor data when compared to the relevant context data on environmental threshold conditions. For example, steps 2825 and 2830 may have the command node detecting an environmental anomaly when the comparison of the detected sensor data and the context data in step 2820 indicates a relative change in the environmental condition for at least one of the ID nodes and where such a relative change exceeds its respective environmental threshold condition (which may be defined in terms of relative changes in environmental conditions, such as temperature, pressure, and the like). In a more detailed example, step 2830 may further have the command node comparing a relative change in the detected sensor data from at least one of the ID nodes and the locally maintained context data for that one of the ID nodes, which has the environmental threshold condition for at least that ID node as a threshold relative environmental change condition that when exceeded is indicative of the environmental anomaly for the shipping container. As such in this example, detecting the environmental anomaly for the shipping container in this embodiment of step 2830 occurs when the comparison of the detected sensor data and the context data indicates the environmental condition for that ID node exceeds the threshold relative environmental change condition.

At step 2835, method 2800 proceeds with the command node generating a layered alert notification related to the environmental anomaly for the shipping container in response to detecting the environmental anomaly. The layered alert notification identifies a targeted mediation recipient, identifies a targeted mediation action, and establishes a mediation response priority based upon the comparison of the received sensor data and the context data. In a further embodiment of method 2800, the targeted mediation recipient may be automatically selected by the command node based upon an excess condition on how much the detected sensor data and the context data indicates the environmental condition for at least one of the ID nodes exceeds the environmental threshold condition for that ID node. Such a targeted mediation recipient identified by the command node in the layered alert notification may be, for example, a triggered fire suppression system on the transit vehicle (e.g., exemplary fire suppression system 25010 of FIG. 25B) that is operative to automatically respond to the detected environmental anomaly based upon receipt of the layered alert notification; an operator of the transit vehicle that can alter movement of the transit vehicle; or a logistics crew member of the transit vehicle that can inspect the shipping container.

In another further embodiment of method 2800, the targeted mediation action identified by the command node in step 2835 may be automatically selected by the command node based upon an excess condition on how much the detected sensor data and the context data indicates the environmental condition for at least one of the ID nodes exceeds the environmental threshold condition for that ID node. In more detail, the targeted mediation action identified by the command node in the layered alert notification may depend upon what is loaded within the shipping container as indicated by shipping information maintained on the command node or may depend upon an excess condition on how many of the ID nodes have their detected sensor data and their context data indicating that their environmental condition exceed the environmental threshold condition for the ID nodes. With such information, the command node may identify an appropriate targeted mediation action, such as immediately deploying the onboard fire suppression system or, instead, identify a threat appropriate action of notifying logistics personnel to inspect the shipping container.

The targeted mediation action in step 2835 may be identified by the command node using a variety of types of context data so that the targeted mediation action may be automatically identified with an robust and improved sense of contextual understanding of the situation. For example, in a further embodiment, method 2800 may have the command node receiving vehicle status data from the external transceiver unit associated with the transit vehicle, so that the targeted mediation action identified by the command node in the layered alert notification may depend upon a state of the transit vehicle as indicated by the vehicle status data. Such a state of the transit vehicle may include, for example, a takeoff vehicular status, a cruising vehicular status, a landing vehicular status, and an on-the-ground vehicular status. Thus, context data 26560 may include such vehicle status data, which may be used in identifying the targeted mediation action in response to detecting the environmental anomaly.

In another example, an embodiment of method 2800 may have the command node accessing container status data maintained by the command node and associated with the shipping container, so that the targeted mediation action identified by the command node in the layered alert notification depends upon a state of the shipping container as indicated in the container status data. In yet another example, an embodiment of method 2800 may have the command node detecting geolocation data related to a current location of the shipping container within the transit vehicle, so that the targeted mediation action identified by the command node in the layered alert notification depends upon the current location of the shipping container as indicated in the geolocation data. In still another example, an embodiment of method 2800 may have the command node accessing loading plan data maintained by the command node (where such loading plan data indicates a relative location of the shipping container within the transit vehicle), so that the targeted mediation action identified by the command node in the layered alert notification depends upon the relative location of the shipping container within the transit vehicle as indicated in the loading plan data. And in another example, an embodiment of method 2800 may have the command node accessing facility status data maintained by the command node and associated with a storage facility for the shipping container, so that the targeted mediation action identified by the command node in the layered alert notification depends upon a state of the storage facility as indicated in the facility status data.

The targeted mediation response identified in step 2835 may also take several forms. For example, a further embodiment may have the targeted mediation response identified by the command node in the layered alert notification be an automatic response by a triggered fire suppression system on the transit vehicle; a request to change course of the transit vehicle from an existing travel path of the transit vehicle; or a request to investigate the shipping container.

Likewise, the mediation response priority established by the command node as part of step 2835 may take several forms. For example, the command node may establish the mediation response priority as part of step 2835 by automatically selecting the mediation response priority based upon an excess condition on how much the detected sensor data and the context data indicates the environmental condition for at least one of the ID nodes exceeds the environmental threshold condition for the ID node(s). In another example, the mediation response priority established by the command node as part of the layered alert notification may be established as a high priority level indicating further travel by the transit vehicle is to be at least minimized when responding to the detected environmental anomaly, or as an intermediate priority level indicating further travel by the transit vehicle is permissible when responding to the detected environmental anomaly.

At step 2840, method 2800 proceeds with the command node transmitting the layered alert notification to the transceiver unit to initiate a mediation response related to the targeted mediation action. In this way, the command node (e.g., command node 24160 as shown in FIG. 24C) automatically and responsively monitors its particular shipping container by means of the ID nodes disposed and dispersed within the shipping container and responsively provides an enhanced type of notification in the form of the layered alert notification to the transit vehicle's external transceiver (e.g., transceiver 24150 in FIG. 24C), which is used to cause the external transceiver to initiate the identified type of mediation response related to the identified type of targeted mediation action to deal with the detected environmental anomaly in a rapid, improved, and more robust manner. Thereafter, method 2800 may proceed back to step 2805 where further sensor data may be generated by each of the ID nodes.

Further embodiments of method 2800 may provide more detailed steps as well as additional steps. For example, in a more detailed embodiment, the ID nodes generate sensor data over a particular time period and the command node, as part of step 2815, may monitor the generated sensor data from each of the ID nodes over the time period to identify relative changes in the generated sensor data over the time period. Thereafter, as part of step 2820, the step of comparing may have the command node comparing the identified relative changes in the generated sensor data and locally maintained context data (e.g., context data 26560) related to those of the ID nodes that are related to the relative changes in the generated sensor data. Here, the context data stored on the command node includes at least a plurality of relative environmental threshold conditions respectively corresponding to the different ID nodes. Further, as part of steps 2825 and 2830, the step of detecting the environmental anomaly for the shipping container may occur when the comparison of identified relative changes in the generated sensor data and locally maintained context data related to those of the ID nodes that correspond to each of the identified relative changes in the generated sensor data indicates a changed environmental condition for at least one of the ID nodes exceeds its respective relative environmental threshold condition. Additionally, as part of step 2835, the command node may establish the mediation response priority as being based upon the comparison of the identified relative changes in the generated sensor data and the locally maintained context data related to those of the ID nodes that correspond to the relative changes in the generated sensor data.

Another more detailed embodiment of method 2800 may involve setting/adjusting the rate an ID node generates and broadcasts sensor data as a way to adaptively respond to an initially detected environmental anomaly. For example, step 2810 of broadcasting the generated sensor data by the ID nodes may have each of the ID nodes transmitting their respectively generated sensor data according to a broadcast profile maintained by each of the ID nodes, where such a broadcast profile defines a first messaging rate used to regulate how often the generated sensor data is transmitted to the command node, and where the first messaging rate is higher than a default messaging rate. This further embodiment of method 2800 may also have the command node instructing each of the ID nodes to broadcast future generated sensor data at a second messaging rate that exceeds the first messaging rate after transmitting the layered alert notification to the transceiver unit in step 2840. The first messaging rate for the ID nodes may be set with an initial value correlated to an environmental risk associated with a package within the shipping container, and may adaptively set the second messaging rate for the ID nodes to a predetermined messaging rate based upon a type of material existing within at least one of the packages within the shipping container. This further embodiment of method 2700 may also have the command node instructing each of the ID nodes to change from the default messaging rate to the first messaging rate. In this way, the command node may adaptively change the messaging rates by which the ID nodes broadcast their sensor data depending on the detected environmental anomaly and depending on context data (e.g., context data 26560) about the makeup of what is being transported within the shipping container.

Still another embodiment of method 2800 may involve selectively and adaptively choosing which of the ID nodes available within the shipping container to use when monitoring for an environmental anomaly. For example, this further embodiment of method 2800 may have the command node select each of the ID nodes used for detecting the environmental anomaly from a larger group of network elements being loaded into the shipping container. In this way, the ID nodes that are selected are those chosen by the command node to provide the gathered sensor data for use in detecting the environmental anomaly for the shipping container. In more detail, the ID nodes selected may be identified for selection by the command node based upon a loading scheme for the shipping container (where such a loading scheme may be maintained in memory of the command node as loading plan data that may be stored as part of context data 26560).

Yet another embodiment of method 2800 may involve remote altering and updating of thresholds and mediation information used for detecting an environmental anomaly and how to respond to such an environmental anomaly. For example, this additional embodiment of method 2800 may have the command node receiving an update for the environmental threshold conditions for at least one of the ID nodes. Such an update may be received from the external transceiver unit (e.g., transceiver 24150 as shown in FIG. 24C). This update received from the external transceiver may be defined by personnel on the transit vehicle (e.g., an operator or logistics personnel on the transit vehicle using the particular external transceiver unit (such as cockpit transceiver 25150*a* or logistics transceiver 25150*b*)). Alternatively, the update may be received from a remote control center (e.g., remote control center server 24100 in communication with external transceiver 24150).

In still a further embodiment of method 2800, the validity of communications (e.g., broadcasted sensor data) may be confirmed or verified to provide a more secure and robust system that is less susceptible to error or spoofing by other nodes. In such a further embodiment of method 2800, the command node may detect the sensor data in step 2815 by (a) receiving the sensor data broadcasted from a first of the ID nodes; (b) confirming the validity of the received sensor data; (c) repeat steps (a) and (b) for the remainder of the sensor data received from any of the remaining ones of the ID nodes; and (d) compiling the detected sensor data using only the received sensor data confirmed valid in sub step (b) of modified step 2815. In more detail, the command node may confirm as part of (b) that it uses only valid sensor data when detecting an environmental anomaly in an active or passive manner. For example, confirming the validity of the received sensor data may have the command node actively sending an authentication request to the first of the ID nodes, and receiving a validation response back from that ID node that authenticates the sensor data broadcasted from that ID node. In another example, confirming the validity of the received sensor data as part of (b) may have the command node, in a more passive sense accessing a validation sequence for an ID node as maintained by the command node in memory (e.g., as part of security data 435 or profile data 430 on command node 26000 for that particular ID node). Such a validation sequence characterizes expected broadcasts from that particular ID node. Using such a validation sequence, the command node may then passively determine if the received sensor data from that ID node matches a predetermined one of the expected broadcasts from that ID node without the need to poll or interactively request authentication from that ID node. Such a predetermined one of the expected broadcasts according to the validation sequence may be a rotating value previously received by the command node for that ID node as a way of enhancing security for the command node to better determine and confirm that ID node sensor data is coming from a valid ID node and, thus, is valid sensor data upon which to make determinations of whether an environmental anomaly exists.

Those skilled in the art will appreciate that method 2800 as disclosed and explained above in various embodiments may be implemented using an exemplary improved monitoring system for detecting an environmental anomaly in a shipping container that maintains multiple packages and for reporting a layered alert notification related to the environmental anomaly to an external transceiver unit associated with a transit vehicle transporting the shipping container such as that explained above with reference to FIG. 24C and its exemplary elements. Such an embodiment of an improved monitoring system, as explained above relative to operations according to method 2800 and with elements from FIG. 24C, uses at least multiple ID nodes disposed within the shipping container (e.g., ID nodes 24120*a*-24120*f*) running one or more ID node monitoring program code as part of node control and management code 325 to control operations of the ID nodes to generate and broadcast sensor data, as well as a command node mounted to the shipping container (e.g., command node 24160 in FIG. 24C) running one or more parts of CN control & management code 26425 to control the operations of the command node as part of monitoring for and detecting an environmental anomaly using the ID node generated sensor data as well as generating the layered alert notification and transmitting that notification to the external transceiver unit to initiate a type of mediation response. Such code may be stored on a non-transitory computer-readable medium, such as memory storage 26415 on command node 24160 (an embodiment of exemplary command node 26000) and memory storage 315 on ID nodes 24120a-24120f (embodiments of exemplary ID node 120a). Thus, when executing such code, the ID nodes and the command node may be operative to perform operations or steps from the exemplary methods disclosed above, including method 2800 and variations of that method.

While exemplary method 2800 and the exemplary system described relative to FIG. 24C uses ID node generated sensor data (also referred to as ID node sensor data) where the ID nodes are not required to be associated with particular packages within the shipping container and where the environmental threshold conditions are related to particular ID nodes, further embodiments may extend this method and system by involving command node sensor data as well. As explained above, an exemplary command node (e.g., command node 26000 of FIG. 26) may be implemented and deployed with its own onboard sensor or sensors (e.g., sensors 26465). Thus, such additional method and system embodiments may be similar to what is described above relative to FIGS. 24A and 24C where specific packages are shown, but the ID node sensor data and relevant environmental threshold conditions focus on particular ID nodes without being tied to specific packages maintained within shipping container 24300, but can also involve sensor data generated by the command node to improve and enhance how an environmental anomaly related to the shipping container may be detected and how a mediation response may be initiated via a layered alert notification to an external transceiver associated with a transit vehicle (such as an aircraft, railway conveyance, a maritime vessel, or a roadway conveyance).

Figure 29:
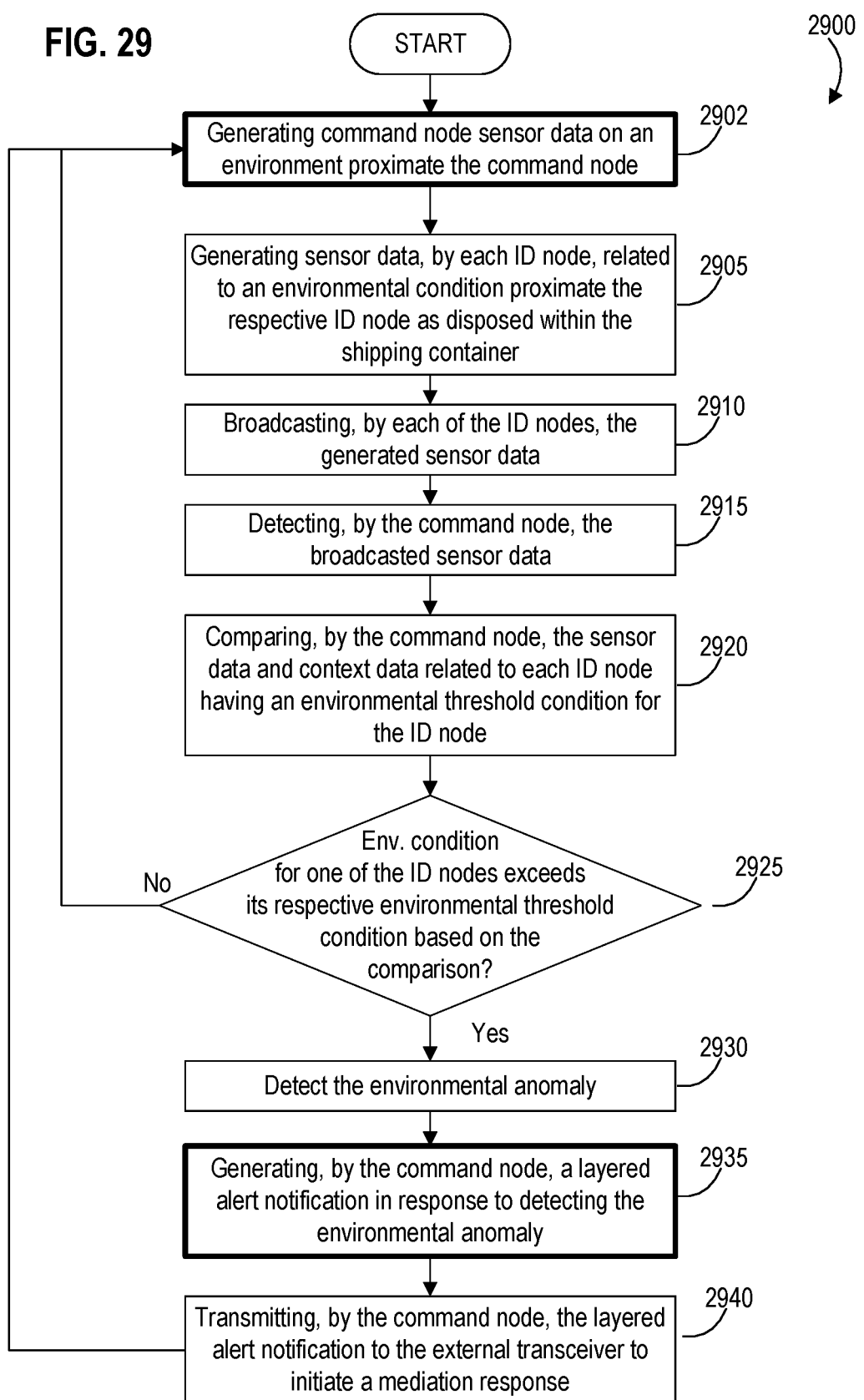
FIG. 29 is a flow diagram illustrating an exemplary method for monitoring a shipping container for an environmental anomaly using a wireless node network using ID node sensor data from ID nodes that are disposed within the shipping container but are generally not associated with particular packages and with environmental threshold conditions for the ID nodes as well as command node sensor data from a command node mounted to the shipping container in accordance with an embodiment of the invention.

FIG. 29 is a flow diagram illustrating an exemplary method for monitoring a shipping container for an environmental anomaly using a wireless node network using ID node sensor data from ID nodes that are disposed within the shipping container but are generally not associated with particular packages and with environmental threshold conditions for the ID nodes as well as command node sensor data from a command node mounted to the shipping container in accordance with an embodiment of the invention. In more detail and referring now to FIG. 29, exemplary method 2900 describes an improved method for monitoring a shipping container (e.g., ULD shipping container 24300 as shown, for example in FIG. 24C) for an environmental anomaly using a wireless node network having at least a plurality of ID nodes (e.g., ID nodes 24120a-24120f shown in FIG. 24C) disposed within the shipping container and a command node (e.g., command node 24160 of FIG. 24C) mounted to a predetermined location on the shipping container, where the shipping container maintains a plurality of packages (e.g., packages 24400a-24400c of FIG. 24C), where each of the ID nodes has at least one ID node environmental sensor, where the command node has at least one command node environmental sensor (e.g., sensor 26465 shown in FIG. 26), and where the command node is operative to communicate with each of the ID nodes and an external transceiver unit (e.g., external transceiver 24150 of FIG. 24C) associated with a transit vehicle (e.g., transit vehicle 24200, which may, for example, be an aircraft, railway conveyance, a maritime vessel, or a roadway conveyance). In general, exemplary method 2900 is similar to method 2800 as described above with the addition of step 2905 (related to generating command node sensor data by the command node) and variations to step 2835 that consider the generated command node sensor data part of detecting the environmental anomaly and determining what goes into the relevant layered alert notification to the external transceiver so as to initiate an appropriate mediation response to the environmental anomaly.

In more detail, exemplary method 2900 begins at step 2902 with generating current sensor data (also referred to current command node sensor data) using the command node's sensor(s) related to a current environment condition proximate the command node. For example, step 2902 may have exemplary command node 24160 (as shown in FIG. 24C) generating sensor data using one or more of sensor(s) 26465 (similar to sensor 360 as explained above). Such exemplary command node sensor data may be generated, for example, using a single element sensor, multiple sensor elements, or an array of sensor elements that may be of the same type or of different types of environmental sensors onboard the command node. An embodiment may have such a sensor or sensors operatively coupled to the command node's processor 26400, but may be disposed within a housing of the command node or may be deployed external to the housing while still sensing an environmental condition proximate the command node. In this manner, exemplary current command node sensor data may include a single type of sensor information or multiple types of sensor information related to a variety of environmental conditions (e.g., pressure, movement, light, temperature, humidity, chemical, radiation, magnetic field, altitude, attitude, orientation, acceleration, and the like). Further embodiment may deploy such command node sensor(s), as part of the command node operating as part of step 2902, remotely in different parts of the shipping container (e.g., along wall surfaces, the ceiling, and/or the base of the shipping container).

At step 2905, the environmental sensor or sensors on each of the ID nodes generate sensor data (also referred to as ID node sensor data) related to an environmental condition proximate the respective ID node as disposed within the shipping container. In more detailed embodiment, the environmental sensor for a first of the ID nodes may be a temperature sensor while the environmental sensor for a second of the ID nodes may be a barometric pressure sensor. In another embodiment, the environmental sensor for a first of the ID nodes may be a temperature sensor while the environmental sensor for a second of the ID nodes may be one from a group consisting of a barometric pressure sensor, a radiation sensor, and a chemical sensor. In still a further embodiment, the environmental sensor for one or more of the ID nodes may have multiple sensor elements, where such sensor elements may include at least a temperature sensor element and a barometric pressure sensor element (but may also include a radiation sensor and/or a chemical sensor).

In still another further embodiment of method 2900, the ID nodes generating ID node sensor data in step 2905 may be in two different groups—one of which ID nodes that are disposed on the shipping container itself and a second group of the ID nodes are associated with different ones of a plurality of packages disposed within the shipping container. Further still, the ID nodes generating sensor data in step 2905 may be in a third group—namely, ID nodes that are disposed within the shipping container but not affixed to the shipping container itself At step 2910, method 2900 proceeds with each of the ID nodes broadcasting their respectively generated sensor data about the environmental condition proximate the particular ID node within the shipping container. At step 2915, method 2800 has the command node detecting the sensor data broadcasted from the ID nodes. Method 2900 then proceeds to step 2920 where the command node compares the detected sensor data from each of the ID nodes and locally maintained context data related to each of the ID nodes. Such context data (e.g., context data 26560) includes at least a plurality of environmental threshold conditions respectively corresponding to the different ID nodes. In more detail, the environmental threshold condition for each of the ID nodes may depend on where a particular ID node is located within the shipping container or what is placed next to each of the ID nodes according to a loading scheme for the shipping container maintained in memory of the command node as loading plan data. In another example, the environmental threshold condition for each of the ID nodes as indicated by the context data may be a dynamic value that changes or is updated (as discussed herein) when what is placed next to each of the ID nodes within the shipping container changes. In this manner, a command node for the shipping container may have the environmental threshold conditions for the ID nodes within the shipping container being updated, changed, and revised as the contents of the shipping container changes and as what is in the container is moved or relocated within the shipping container.

At decision step 2925, method 2900 has the command node determining if an environmental condition for one of the ID nodes exceeds its respective environmental threshold condition based upon the comparison performed in step 2920. If so, method 2900 proceeds from step 2925 directly to step 2930 where the command node detects the environmental anomaly. If not, method 2900 proceeds from step 2925 back to step 2902 where the command node generates more command node sensor data and then to step 2905 where the ID nodes generate more ID node sensor data and the ID nodes continue to broadcast newly generated sensor data at step 2910 for detection and consideration by the command node in steps 2915-2925 again.

In steps 2925-2930, the command node may detect different types of environmental anomalies depending on the type of environmental sensor data being considered as generated and broadcast from the ID nodes. For example, a further embodiment of method 2900 may have the command node detecting the environmental anomaly as part of steps 2925-2930 when (a) the sensor data detected from one of the ID nodes comprises a temperature value; (b) the sensor data detected from a second of the ID nodes comprises a barometric pressure value; (c) the temperature value indicates the environmental condition of the first ID node exceeds the environmental threshold condition for the first ID node according to the context data for the first ID node; and (d) the barometric pressure value indicates the environmental condition of the second ID node exceeds the environmental threshold condition for the second ID node according to the context data for the second ID node.

Still further embodiments of method 2900 may use a combination of temperature and other types of ID node sensors. For example, another embodiment of method 2900 may have the command node detecting the environmental anomaly as part of steps 2925-2930 when (a) the sensor data detected from one of the ID nodes comprises a temperature value; (b) the sensor data detected from a second of the ID nodes comprises an environmental condition value of one of a sensed barometric pressure level by the barometric sensor, a detected radiation level by the radiation sensor, or a detected chemical by the chemical sensor (e.g., the detected chemical by the chemical sensor may be indicative of an explosive, a fire, or the presence of either CO or $CO_2$); (c) the temperature value indicates the environmental condition of the first ID node exceeds the environmental threshold condition for the first ID node according to the context data for the first ID node; and (d) the environmental condition value indicates the environmental condition of the second ID node exceeds the environmental threshold condition for the second ID node according to the context data for the second ID node.

The environmental anomaly detected in step 2930 of method 2900 may come in a variety of types depending on the type of ID node sensors used as well. For example, a further embodiment of step 2930 may have the command node detect the environmental anomaly for the shipping container to be a fire within the shipping container when the temperature value exceeds a temperature threshold maintained by the command node as part of the context data for the first ID node and when the barometric pressure value exceeds a pressure threshold maintained by the command node as part of the context data for the second ID node. Another embodiment of step 2930 may have the command node detect the environmental anomaly for the shipping container to be an explosion within the shipping container when the temperature value exceeds a temperature threshold maintained by the command node as part of the context data for the first ID node and when the barometric pressure value is below a pressure threshold maintained by the command node as part of the context data for the second ID node. Yet another embodiment of step 2930 may have the command node detect the environmental anomaly for the shipping container to be an explosion within the shipping container when the temperature value exceeds a temperature threshold maintained by the command node as part of the context data for the first ID node and when the barometric pressure value drops faster than a pressure drop threshold maintained by the command node as part of the context data for the second ID node. A further embodiment of step 2930 may have the command node detect the environmental anomaly for the shipping container to be a detected chemical related fire within the shipping container when the temperature value exceeds a temperature threshold maintained by the command node as part of the context data for the first ID node and when the detected chemical matches a predetermined chemical profile maintained by the command node as part of the context data for the second ID node. And still another embodiment of step 2930 may have the command node detect the environmental anomaly for the shipping container to be a radiation leak within the shipping container when the temperature value exceeds a temperature threshold maintained by the command node as part of the context data for the first ID node and when the detected radiation matches a predetermined radiation profile maintained by the command node as part of the context data for the second ID node.

In other embodiments, method 2900 may detect the environmental anomaly based upon relative changes in ID node sensor data when compared to the relevant context data on environmental threshold conditions. For example, steps 2925 and 2930 may have the command node detecting an environmental anomaly when the comparison of the detected ID node sensor data and the context data in step 2920 indicates a relative change in the environmental condition over a time period for at least one of the ID nodes and where such a relative change exceeds its respective environmental threshold condition (which may be defined in terms of relative changes in environmental conditions, such as temperature, pressure, and the like). In other words, the relative change in the environmental condition may be compared to a predefined threshold difference (e.g., a predefined relative temperature change over the time period). In a more detailed example, step 2930 may further have the command node comparing a relative change in the detected ID node sensor data from at least one of the ID nodes and the locally maintained context data for that one of the ID nodes, which has the environmental threshold condition for at least that ID node as a threshold relative environmental change condition that when exceeded is indicative of the environmental anomaly for the shipping container. As such in this example, detecting the environmental anomaly for the shipping container in this embodiment of step 2930 occurs when the comparison of the detected ID node sensor data and the context data indicates the environmental condition for that ID node exceeds the threshold relative environmental change condition.

In a further embodiment of method 2900, step 2930 may have the command node detecting the environmental anomaly when at least one of (a) the comparison of the detected ID node sensor data and the context data in step 2920 indicates an environmental condition proximate at least one of the ID nodes exceeds its respective environmental threshold condition, and (b) the difference between the current command node sensor data and a shipping container environmental profile exceeds a shipping container threshold condition. Thus, in this further embodiment, the process of detecting the environmental anomaly (and not just how to respond to the detected environmental anomaly) may be enhanced by considering current command node sensor data relative to the shipping container's environmental profile (e.g., maintained as part of profile data 430 on the command node) and a particular shipping container level threshold condition (e.g., maintained as part of context data 26560). In more detail, method 2900 may also include having the command node environmental sensor capturing shipping container characterization sensor data over a characterization time period, so that the shipping container characterization sensor data is related to an environment condition proximate the predetermined location on the shipping container over the characterization time period and storing the shipping container environmental profile (e.g., part of profile data 430) based on the shipping container characterization sensor data.

At step 2935, method 2900 proceeds with the command node generating a layered alert notification related to the environmental anomaly for the shipping container in response to detecting the environmental anomaly. In step 2935, exemplary method 2900 has the command node generating the layered alert notification as identifying a targeted mediation recipient, identifying a targeted mediation action, and establishing a mediation response priority based upon (a) the comparison of the received ID node sensor data and the context data from step 2920, and (b) a difference between the current command node sensor data and a shipping container environmental profile maintained by the command node (e.g., part of profile data 430 maintained on command node 26000).

In a further embodiment of method 2900, the targeted mediation recipient may be automatically selected by the command node based upon an excess condition on how much the detected ID node sensor data and the context data indicates the environmental condition for at least one of the ID nodes exceeds the environmental threshold condition for that ID node. Such a targeted mediation recipient identified by the command node in the layered alert notification may be, for example, a triggered fire suppression system on the transit vehicle (e.g., exemplary fire suppression system 25010 of FIG. 25B) that is operative to automatically respond to the detected environmental anomaly based upon receipt of the layered alert notification; an operator of the transit vehicle that can alter movement of the transit vehicle; or a logistics crew member of the transit vehicle that can inspect the shipping container.

In another further embodiment of method 2900, the targeted mediation action identified by the command node in step 2935 may be automatically selected by the command node based upon an excess condition on how much the detected ID node sensor data and the context data indicates the environmental condition for at least one of the ID nodes exceeds the environmental threshold condition for that ID node. In more detail, the targeted mediation action identified by the command node in the layered alert notification may depend upon what is loaded within the shipping container as indicated by shipping information maintained on the command node or may depend upon an excess condition on how many of the ID nodes have their detected sensor data and their context data indicating that their environmental condition exceed the environmental threshold condition for the ID nodes. With such information, the command node may identify an appropriate targeted mediation action, such as immediately deploying the onboard fire suppression system or, instead, identify a threat appropriate action of notifying logistics personnel to inspect the shipping container.

The targeted mediation action in step 2935 may be identified by the command node using a variety of types of context data so that the targeted mediation action may be automatically identified with an robust and improved sense of contextual understanding of the situation. For example, in a further embodiment, method 2900 may have the command node receiving vehicle status data from the external transceiver unit associated with the transit vehicle, so that the targeted mediation action identified by the command node in the layered alert notification may depend upon a state of the transit vehicle as indicated by the vehicle status data. Such a state of the transit vehicle may include, for example, a takeoff vehicular status, a cruising vehicular status, a landing vehicular status, and an on-the-ground vehicular status. Thus, context data 26560 may include such vehicle status data, which may be used in identifying the targeted mediation action in response to detecting the environmental anomaly.

In another example, an embodiment of method 2900 may have the command node accessing container status data maintained by the command node and associated with the shipping container, so that the targeted mediation action identified by the command node in the layered alert notification depends upon a state of the shipping container as indicated in the container status data. In yet another example, an embodiment of method 2900 may have the command node detecting geolocation data related to a current location of the shipping container within the transit vehicle, so that the targeted mediation action identified by the command node in the layered alert notification depends upon the current location of the shipping container as indicated in the geolocation data. In still another example, an embodiment of method 2900 may have the command node accessing loading plan data maintained by the command node (where such loading plan data indicates a relative location of the shipping container within the transit vehicle), so that the targeted mediation action identified by the command node in the layered alert notification depends upon the relative location of the shipping container within the transit vehicle as indicated in the loading plan data. And in another example, an embodiment of method 2900 may have the command node accessing facility status data maintained by the command node and associated with a storage facility for the shipping container, so that the targeted mediation action identified by the command node in the layered alert notification depends upon a state of the storage facility as indicated in the facility status data.

The targeted mediation response identified in step 2935 may also take several forms. For example, a further embodiment may have the targeted mediation response identified by the command node in the layered alert notification be an automatic response by a triggered fire suppression system on the transit vehicle; a request to change course of the transit vehicle from an existing travel path of the transit vehicle; or a request to investigate the shipping container.

Likewise, the mediation response priority established by the command node as part of step 2935 may take several forms. For example, the command node may establish the mediation response priority as part of step 2935 by automatically selecting the mediation response priority based upon an excess condition on how much the detected ID sensor data and the context data indicates the environmental condition for at least one of the ID nodes exceeds the environmental threshold condition for the ID node(s). In another example, the mediation response priority established by the command node as part of the layered alert notification may be established as a high priority level indicating further travel by the transit vehicle is to be at least minimized when responding to the detected environmental anomaly, or as an intermediate priority level indicating further travel by the transit vehicle is permissible when responding to the detected environmental anomaly.

At step 2940, method 2900 proceeds with the command node transmitting the layered alert notification to the external transceiver unit to initiate a mediation response related to the targeted mediation action. Thereafter, method 2900 may proceed back to steps 2902 and 2905 where further sensor data may be generated by the command node and each of the ID nodes.

Further embodiments of method 2900 may provide more detailed steps as well as additional steps. For example, in a more detailed embodiment, the ID nodes generate ID node sensor data over a particular time period and the command node, as part of step 2915, may monitor the generated ID node sensor data from each of the ID nodes over the time period to identify relative changes in the generated ID node sensor data over the time period. Thereafter, as part of step 2920, the step of comparing may have the command node comparing the identified relative changes in the generated ID node sensor data and locally maintained context data (e.g., context data 26560) related to those of the ID nodes that are related to the relative changes in the generated ID node sensor data. Here, the context data stored on the command node includes at least a plurality of relative environmental threshold conditions respectively corresponding to the different ID nodes. Further, as part of steps 2925 and 2930, the step of detecting the environmental anomaly for the shipping container may occur when the comparison of identified relative changes in the generated ID sensor data and locally maintained context data related to those of the ID nodes that correspond to each of the identified relative changes in the generated ID node sensor data indicates a changed environmental condition for at least one of the ID nodes exceeds its respective relative environmental threshold condition. Furthermore, generating the layered alert notification in step 2935 may have the command node identifying a targeted mediation recipient, identifying a targeted mediation action, and establishing a mediation response priority based upon (a) the comparison of the relative changes in the ID node sensor data to the context data and (b) a difference between relative changes in command node sensor data and a shipping container environmental profile maintained by the command node. In more detail as part of step 2935, the command node may establish the mediation response priority as being based upon (c) a relative change between the current command node sensor data related to the current environmental condition proximate the command node and a prior value for the current command node sensor data related to a prior environmental condition proximate the command node.

Another more detailed embodiment of method 2900 may involve setting/adjusting the rate an ID node generates and broadcasts ID node sensor data as a way to adaptively respond to an initially detected environmental anomaly. For example, step 2910 of broadcasting the generated ID node sensor data by the ID nodes may have each of the ID nodes transmitting their respectively generated ID node sensor data according to a broadcast profile maintained by each of the ID nodes, where such a broadcast profile defines a first messaging rate used to regulate how often the generated ID node sensor data is transmitted to the command node, and where the first messaging rate is higher than a default messaging rate. This further embodiment of method 2900 may also have the command node instructing each of the ID nodes to broadcast future generated ID node sensor data at a second messaging rate that exceeds the first messaging rate after transmitting the layered alert notification to the transceiver unit in step 2940. The first messaging rate for the ID nodes may be set with an initial value correlated to an environmental risk associated with a package within the shipping container, and may adaptively set the second messaging rate for the ID nodes to a predetermined messaging rate based upon a type of material existing within at least one of the packages within the shipping container. This further embodiment of method 2700 may also have the command node instructing each of the ID nodes to change from the default messaging rate to the first messaging rate. In this way, the command node may adaptively change the messaging rates by which the ID nodes broadcast their ID node sensor data depending on the detected environmental anomaly and, in some embodiments, depending on context data (e.g., context data 26560) about the makeup of what is being transported within the shipping container.

Still another embodiment of method 2900 may involve selectively and adaptively choosing which of the ID nodes available within the shipping container to use when monitoring for an environmental anomaly. For example, this further embodiment of method 2900 may have the command node select each of the ID nodes used for detecting the environmental anomaly from a larger group of network elements being loaded into the shipping container. In this way, the ID nodes that are selected are those specifically identified or chosen by the command node to provide the gathered ID node sensor data for use in detecting the environmental anomaly for the shipping container. In more detail, the ID nodes selected may be identified for selection by the command node based upon a loading scheme for the shipping container (where such a loading scheme may be maintained in memory of the command node as loading plan data that may be stored as part of context data 26560).

Yet another embodiment of method 2900 may involve remote altering and updating of thresholds and mediation information used for detecting an environmental anomaly and how to respond to such an environmental anomaly. For example, this additional embodiment of method 2900 may have the command node receiving an update for the environmental threshold conditions for at least one of the ID nodes. Such an update may be received from the external transceiver unit (e.g., transceiver 24150 as shown in FIG. 24C). This update received from the external transceiver may be defined by personnel on the transit vehicle (e.g., an operator or logistics personnel on the transit vehicle using the particular external transceiver unit (such as cockpit transceiver 25150*a* or logistics transceiver 25150*b*) and its user input interface(s)). Alternatively, the update may be received from a remote control center (e.g., remote control center server 24100 in communication with external transceiver 24150).

In still a further embodiment of method 2900, the validity of communications from ID nodes (e.g., broadcasted ID node sensor data) may be confirmed or verified to provide a more secure and robust system and method of operation that is less susceptible to error or spoofing by other nodes. In such a further embodiment of method 2900, the command node may detect the ID node sensor data in step 2915 by (a) receiving the ID node sensor data broadcasted from a first of the ID nodes; (b) confirming the validity of the received ID node sensor data; (c) repeat steps (a) and (b) for the remainder of the ID node sensor data received from any of the remaining ones of the ID nodes; and (d) compiling the detected ID node sensor data using only the received ID node sensor data confirmed valid in sub step (b) of modified step 2915. In more detail, the command node may confirm as part of (b) that it uses only valid ID node sensor data when detecting an environmental anomaly in an active or passive manner. For example, confirming the validity of the received ID node sensor data may have the command node actively sending an authentication request to the first of the ID nodes, and receiving a validation response back from that ID node that authenticates the ID node sensor data broadcasted from that ID node. In another example, confirming the validity of the received ID node sensor data as part of (b) may have the command node, in a more passive sense accessing a validation sequence for an ID node as maintained by the command node in memory (e.g., as part of security data 435 or profile data 430 on command node 26000 for that particular ID node). Such a validation sequence characterizes expected broadcasts from that particular ID node. Using such a validation sequence, the command node may then passively determine if the received ID node sensor data from that ID node matches a predetermined one of the expected broadcasts from that ID node without the need to poll or interactively request authentication from that ID node. Such a predetermined one of the expected broadcasts according to the validation sequence may be, for example, a rotating value previously received by the command node for that ID node as a way of enhancing security for the command node to better determine and confirm that ID node sensor data is coming from a valid ID node and, thus, is valid ID node sensor data upon which to make determinations of whether an environmental anomaly exists.

Those skilled in the art will appreciate that method 2900 as disclosed and explained above in various embodiments may be implemented using an exemplary improved monitoring system for detecting an environmental anomaly in a shipping container that maintains multiple packages and for reporting a layered alert notification related to the environmental anomaly to an external transceiver unit associated with a transit vehicle transporting the shipping container such as that explained above with reference to FIG. 24C and its exemplary elements. Such an embodiment of this exemplary improved monitoring system, as explained above relative to operations according to method 2900 and with elements from FIG. 24C, may use at least multiple ID nodes disposed within the shipping container (e.g., ID nodes 24120*a*-24120*f*) running one or more ID node monitoring program code as part of node control and management code 325 to control operations of the ID nodes to generate and broadcast ID node sensor data, as well as a command node mounted to the shipping container (e.g., command node 24160 in FIG. 24C) having a command node environmental sensor (e.g., sensor(s) 26465) running one or more parts of CN control & management code 26425 to control the operations of the command node as part of monitoring for and detecting an environmental anomaly using the ID node generated sensor data as well as generating the layered alert notification and transmitting that notification to the external transceiver unit to initiate a type of mediation response. Such code may be stored on a non-transitory computer-readable medium, such as memory storage 26415 on command node 24160 (an embodiment of exemplary command node 26000) and memory storage 315 on ID nodes 24120*a*-24120*f* (embodiments of exemplary ID node 120*a*). Thus, when executing such code, the ID nodes and the command node may be operative to perform operations or steps from the exemplary methods disclosed above, including method 2900 and variations of that method.

In yet another more detailed system embodiment, a further improved system is described for detecting and automatically reporting on an environmental anomaly in a shipping container onboard a transit vehicle where the shipping container maintains multiple packages. In general, an embodiment of this improved system is illustrated in FIG. 24A or 24B. Such an embodiment includes at least multiple ID sensor nodes disposed within the shipping container (e.g., ID nodes 24120*a*-24120*c*), a command node mounted to the shipping container (e.g., command node 24160), and a transit vehicle transceiver in communication with the command node (e.g., external transceiver 24150).

In more detail, the system's ID sensor nodes are disposed within the shipping container (e.g., ULD container 24300), where each of the ID sensor nodes are associated with a respective one of the packages (e.g., packages 24400*a*-2440*c* as shown in the system embodiment of FIG. 24A, or packages 24400*d*-24400*f* as shown in the system embodiment of FIG. 24B) maintained within the shipping container. Each of the ID sensor nodes have at least an ID sensor node processing unit (commonly referred to as an ID sensor node processor), an ID sensor node memory coupled to the ID sensor node processing unit, at least one environmental sensor, and a wireless radio transceiver (e.g., a hardware radio, a wireless transceiver implemented with a combination of hardware and software, or a software defined radio (SDR) implementation of a wireless radio transceiver). The ID sensor node's memory is operatively coupled to the ID sensor node processing unit and maintains at least an ID sensor node monitoring program code (e.g., part of the node control and management code 325). The ID sensor node's environmental sensor is configured to generate sensor data related to an environmental condition of the respective package associated with that particular ID sensor node. And the ID sensor node's wireless radio transceiver is operatively coupled to the ID sensor node processing unit, and configured to access the sensor data generated by the environmental sensor and broadcast the sensor data in response to a report command from the ID sensor node processing unit when the ID sensor node processing unit executes the ID sensor node monitoring program code. The system's command node mounted to the shipping container includes at least a command node processing unit, a command node memory coupled to the command node processing unit, and two communication interfaces each being operatively coupled to the command node processing unit. The command node memory maintains at least command node container management program code and context data related to each of the ID sensor nodes and including at least environmental threshold conditions respectively corresponding to each of the packages. As for the communication interfaces, a first one is configured to communicate with each of the ID sensor nodes using a first wireless communication format compatible with the wireless radio transceiver on each of the ID sensor nodes, while a second one is configured to communicate over a second wireless communications format with the system's transit vehicle transceiver, which has at least a display interface and a fire suppression system interface with which to communication with a fire suppression system on the transit vehicle.

In operation, the system's command node processing unit is programmatically configured, when executing the command node container management program code, to be operative to detect the sensor data broadcasted from the ID sensor nodes using the first communication interface and compare the detected sensor data from each of the ID sensor nodes and the context data related to each of the ID sensor nodes. The command node processing unit is also operative to detect the environmental anomaly for the shipping container when the comparison of the detected sensor data and the context data indicates an environmental condition for at least one of the packages exceeds its respective environmental threshold condition. In response to detecting the environmental anomaly, the command node processing unit is operative to generate a layered alert notification related to the environmental anomaly for the shipping container where the layered alert notification identifies a targeted mediation recipient, identifies a targeted mediation action, and establishes a mediation response priority based upon the comparison of the received sensor data and the context data. The command node processing unit is then operative to cause the second communication interface to transmit the layered alert notification to the transit vehicle transceiver to initiate a mediation response related to the targeted mediation action.

The system's transit vehicle transceiver, in response to receiving the layered alert notification, is operative to automatically generate a mediation message as the mediation response (where the mediation message reflects the targeted mediation action and the mediation response priority) and provide the mediation message to the targeted mediation recipient. In a further embodiment, the system's the transit vehicle transceiver may also be operative to automatically generate the mediation message as a trigger message for the fire suppression system on the transit vehicle, and provide the mediation message to the fire suppression system over the fire suppression system interface to cause the fire suppression system to automatically initiate a fire suppression response on the shipping container.

In yet a further embodiment, the system's transit vehicle transceiver may be further operative to automatically generate the mediation message as a warning message to an operator of the transit vehicle as the targeted mediation recipient, and provide the warning message to the operator of the transit vehicle using the display interface of the transit vehicle transceiver and/or to one or more logistics crew member of the transit vehicle as the targeted mediation recipient. Such a warning message may, for example, reflect the mediation response priority (e.g., an immediate priority requesting a change in direction for the transit vehicle) or be a prompted request for the logistics crew member to initiate a responsive action for the shipping container (e.g., a requested directive to inspect the shipping container or a directive to trigger the fire suppression system after an inspection of the shipping container).

Unresponsive Node Monitoring for Detecting an Environmental Anomaly

The embodiments described herein address the timely detection of an environmental anomaly related to a shipping container, especially with lithium fires within shipping containers aboard vessels/vehicles (e.g., aircrafts, vehicles, trains, ships, etc.) where damage can spread quickly and loss of life is more likely if not quickly treated. The embodiments described thus far above may rely upon sensor data generated by various nodes as part of detecting an environmental anomaly, but other embodiments may monitor the ability to communicate with such nodes (e.g., ID nodes) instead of monitoring just the sensor data generated by such nodes. In more detail, embodiments may monitor for a shift in behavior of several nodes known to be within a shipping container (not just monitoring sensor data, such as temperature or pressure data) and, in some embodiments, monitor communications from nodes and sense the situation of no longer being able to communicate with a threshold number of the nodes. As explained in more detail below, this may be context driven in that the command node may be aware that there is no other reason for the ID node to leave the container or to shut down and not communicate—i.e., the ID node is anticipated to be communicating based upon a profile or other context data. In other words, embodiments may have command node using a communication profile for monitored ID nodes that indicates when the ID nodes are supposed to broadcast. The ID node, in some cases, may be generally disposed within the shipping container unassociated with a package, may be traveling within a package, or it may be affixed to the outside of the package or integrated within packaging material of the package. Alert generation may also be layered based on, for example, which nodes are changing behavior and where the nodes are within the container.

Referring back to the illustrated example shown in FIG. 24C, an embodiment may have exemplary command node 24160 monitoring exemplary ID nodes 24120a-24120f for communications that may be broadcast from each of those nodes (not necessarily sensor data broadcasts). Some of these ID nodes (e.g., ID nodes 24120a-24120c) may be associated with respective different packages (e.g., packages 24400a-24400c), while another group of these ID nodes may not be associated with particular packages and, instead, are disposed in different parts of the shipping container (e.g., ULD container 24300) outside of the packages. Command node 24160 may monitor some or all of these ID nodes (depending on the embodiment) for an unanticipated state of ceased broadcasting from any of the monitored ID nodes according to a communication profile maintained on the command node 24160 for each the ID nodes (e.g., a communication profile stored as part of profile data 430 on the command node 24160). Based upon this monitoring, command node 24160 may sense and find a group of the monitored ID nodes should be broadcasting but have stopped broadcasting (i.e., are in an unanticipated state of ceased broadcasting). Command node 24160 may detect the environmental anomaly when a size of this initial group of the monitored but non-communicative ID nodes anticipated to be broadcasting exceeds a threshold setting maintained by the command node (e.g., as part of context data 26560 or separately stored as in another data structure in memory of the command node), and then responsively generate a layered alert notification related to the detected environmental anomaly for the shipping container. Such a layered alert notification may identify a targeted mediation recipient, identify a targeted mediation action, and establish a mediation response priority based upon a size of the sensed initial group of the ID nodes and context data related to the sensed initial group of the ID nodes. The command node 24160 may then transmit the layered alert notification to the transceiver 24150 to initiate a mediation response related to the targeted mediation action. More detailed exemplary method and system embodiments are described below that generally relate to the example elements shown in FIG. 24C as explained in more detail below.

Figure 30:
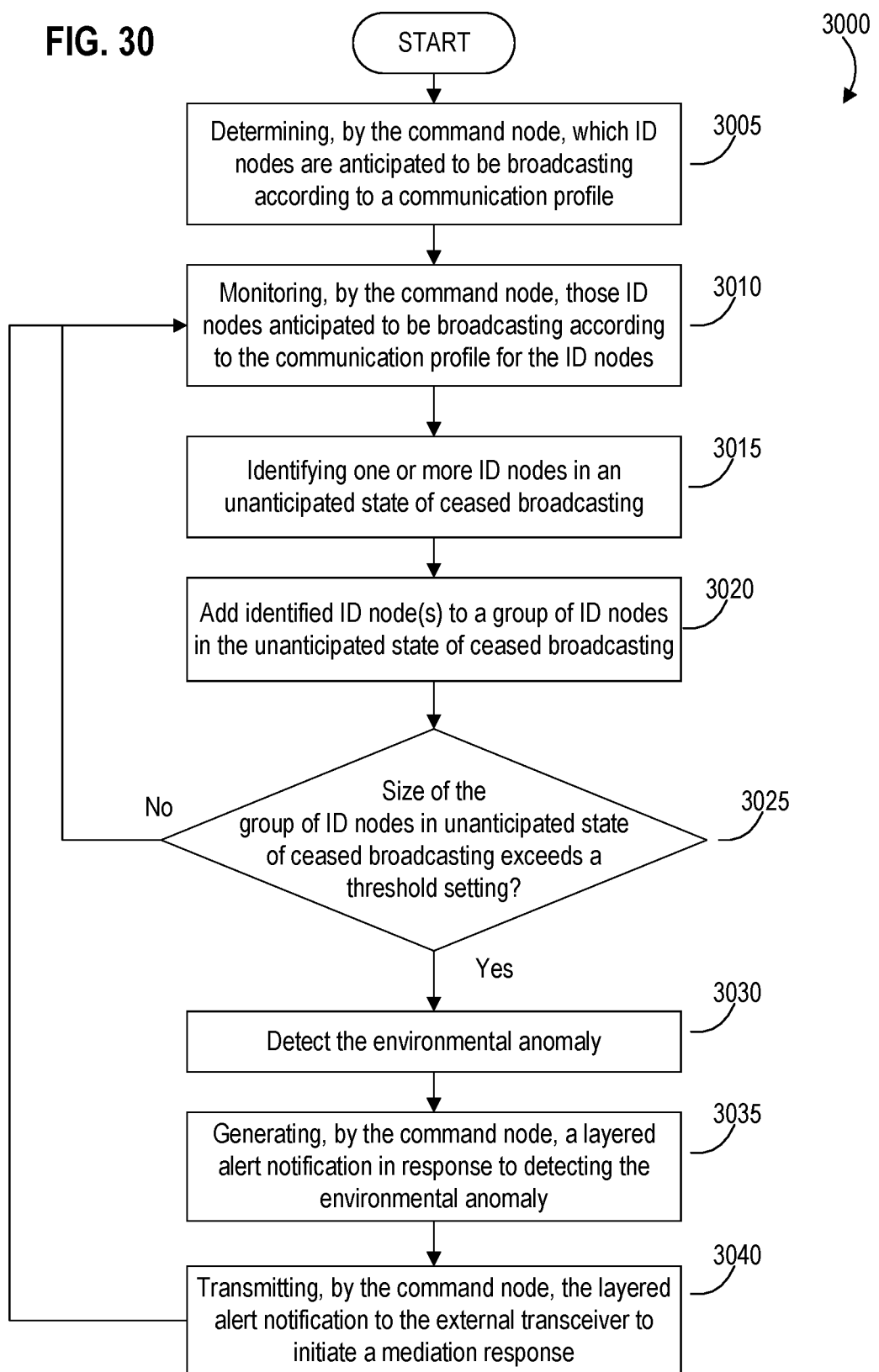
FIG. 30 is a flow diagram illustrating an exemplary method for monitoring a shipping container for an environmental anomaly using a wireless node network based upon unanticipated communications from ID nodes that are disposed within the shipping container in accordance with an embodiment of the invention.

FIG. 30 is a flow diagram illustrating an exemplary method for monitoring a shipping container (e.g., ULD shipping container 24300) for an environmental anomaly using a wireless node network based upon unanticipated communications from ID nodes (e.g., ID nodes 24120*a*-24120*f*) that are disposed within the shipping container in accordance with an embodiment of the invention. The command node operating as part of exemplary method 3000 described below may, for example, be implemented as part of the shipping container or separately from the shipping container. Such an exemplary command node (as explained in more detail above relative to exemplary command node 26000 and command node 24160) may be implemented as a type of master node capable of self-locating or as a master node without location circuitry. The exemplary ID nodes being monitored and used as part of exemplary method 3000 (such as ID nodes 24120*a*-24120*f*) may be traveling with a respective first portion of packages (e.g., one or more of packages 24400*a*-24400*c*), have one or more of them affixed to the outside of one of the packages, have one or more of them integrated as part of a package, may be deployed within the shipping container without being associated with or fixed to any particular one or more of the packages, or may be deployed as part of method 3000 where the ID nodes are disposed in a combined situation where some of the ID nodes are associated with particular packages but others are not while being disposed within the shipping container at different locations in the container.

In more detail and referring now to FIG. 30, method 3000 begins at step 3005 where the command node may initially determine which of the ID nodes in the shipping container are anticipated to be broadcasting according to a communication profile maintained on the commend node for each of the ID nodes. For example, exemplary command node 24160 may access profile data 430, which may have a communication profile on each of ID nodes 24120*a*-24120*f*. Those skilled in the art will appreciate that the communication profile may be implemented with a single data structure for all of the ID nodes disposed within the shipping container, or may be implemented in individual data structures per ID node. In more detail, the communication profile may identify a programmatic setting for a broadcast timing parameter that defines when a particular ID node is programmed to transmit an advertising message in the future to indicate to the command node whether that particular ID node is anticipated to be broadcasting. In one embodiment, the communication profile may define an anticipated broadcast behavior for a particular one of the ID nodes in the shipping container, so that the command node may sense an unanticipated state of ceased broadcasting for that particular ID node as an inoperative state of that particular ID node inconsistent with the anticipated broadcast behavior for the particular ID node. In yet another embodiment, the communication profile maintained on the command node for each of the ID nodes may define an anticipated broadcast behavior for a respective one of the ID nodes, so that the command node may sense an unanticipated state of ceased broadcasting for that respective ID node based upon such a communication profile because the respective ID node is not anticipated to be absent from the shipping container (e.g., is not with a package that has been unloaded from the container) and the sensed inoperative state of the respective ID node is inconsistent with the anticipated broadcast behavior for the respective ID node per the communication profile. In this manner, the communication profile may indicate anticipated broadcast behavior for a particular ID node and may in further embodiments be used in conjunction with context data (e.g., context data 26560), association data (e.g., association data 440), and/or location data (e.g., location data 455) so that the command node can appreciate a deeper understanding of the contextual environment for the ID nodes when determining which of the ID nodes are anticipated to be broadcasting as part of method 3000.

At step 3010, method 3000 proceeds with the command node monitoring the ID nodes for an unanticipated state of ceased broadcasting from any of the ID nodes according to a communication profile maintained on the command node for each of the ID nodes. In more detail, an embodiment of method 3000 may have the command node in step 3010 monitor those of the ID nodes anticipated to be broadcasting (per step 3005 and according to the communication profile) to identify which of those ID nodes have ceased broadcasting (i.e., are in the unanticipated state of ceased broadcasting). This may take the form of monitoring each of the ID nodes that are anticipated to be broadcasting (per the communication profile) for a shift in broadcast behavior away from the anticipated broadcast behavior for the respective ID node.

At step 3015, method 3000 continues with the command node identifying one or more ID nodes in an unanticipated state of ceased broadcasting based upon the monitoring conducted in step 3010. At step 3020, method 3000 proceeds then to have the command node add the identified ID node or nodes from step 3015 to a group of ID nodes found by the command node to be in the unanticipated state of ceased broadcasting. In this exemplary manner, the command node senses, detects, or otherwise identifies an initial group of one or more of the ID nodes to be in the unanticipated state of ceased broadcasting based upon the monitoring step 3010.

At step 3025, method 3000 proceeds to have the command node determining if the size of the group of ID nodes in the unanticipated state of ceased broadcasting exceeds a threshold setting maintained by the command node. The threshold setting, a data value maintained in a data structure (such as a threshold setting value stored as part of CN control and management code 26435 or other data structures used by such code (e.g., profile data 430, shared data 445, context data 26560, and the like)). In more detail, the threshold setting maintained by the command node may be kept on the command node's memory as a dynamic value defined by the command node based upon a material characteristic of what is contained in at least one of the packages (e.g., as indicated by package information stored in context data 26560 on what is stored within shipping container 24300). In a further embodiment, the threshold setting may be a dynamic value defined by the command node related to a count of how many of the ID nodes are disposed within the shipping container. For example, if the contents of shipping container 24300 are altered, the number of ID nodes within shipping container 24300 may decrease (e.g., an ID node with a package is removed) or may increase (e.g., an ID node with a package is added to the ULD container 24300). Command node 24160 may detect the presence of such a change in ID nodes, some of which may be or may have been part of the group of ID nodes anticipated to be broadcasting. As such, command node 24160 may dynamically update the threshold setting used in step 3025 of an embodiment of method 3000 to reflect such a change in how many ID nodes are now within shipping container 24300.

At step 3030, method 3000 has the command node detecting the environmental anomaly when the size of the sensed initial group of the ID nodes in the unanticipated state of ceased broadcasting exceeds the threshold setting maintained by the command node. As such, the environmental anomaly detected in step 3030 is based upon monitoring broadcast behavior instead of being based on the values of sensor data.

A further embodiment, may detect the environmental anomaly as part of method 3000 by also monitoring ID node sensor data broadcast by one or more of the ID nodes and/or command node sensor data generated onboard the command node. In more detail, detecting the environmental anomaly in this further embodiment of step 3030 may involve a combination of monitored broadcast behavior and a threshed setting for how many ID nodes are now in an unanticipated state of ceased broadcasting as well as when an environmental condition for one or more of the ID nodes and/or packages exceeds a relevant environmental threshold condition for the ID node/package as indicated by sensor data. As such, this further embodiment of method 3000 expands upon the detection scheme at step 3030 to be multi-variate, which in yet a further embodiment may also be implemented in a dynamic aspect of the command node's operation—e.g., the command node may initially operate to detect an environmental anomaly by monitoring broadcast behavior as described above, but once the threshold setting is exceeded, the command node may verify or confirm the environmental detection using one or more types of sensor data generated by one or more of the ID nodes and/or the command node itself.

In a further embodiment of step 3030 of method 3000, the detected environmental anomaly for the shipping container may be detected as a fire within the shipping container based upon how quickly the sensed initial group of the ID nodes have changed broadcast behavior when monitoring the ID nodes and detecting the environmental anomaly. For example, command node 24160 may use its timer 26460 as part of step 3025 to monitor the rate of how quickly the ID nodes are identified in steps 3015 and 3020 as an indicator of how quickly the sensed initial group of the ID nodes have changed broadcast behavior up to the point the size exceeds the threshold setting in step 3025. The indication that the environmental anomaly is a fire may be reported as part of the layered alert notification generated as explained below in step 3035.

In yet another embodiment of step 3030 of method 3000, the detected environmental anomaly for the shipping container may be detected as a fire within the shipping container based upon which of the ID nodes are in the sensed initial group of the ID nodes and based upon material contained in at least one of packages associated with the sensed initial group of the ID nodes as indicated in the context data related to the sensed initial group of the ID nodes. For example, command node 24160 may access context data 26560 to identify the type of material contained within the shipping container (or material contained in one of the packages associated with an unresponsive one of the ID nodes) and use this information to further detect that the environmental anomaly is a fire based on that material information. The indication that the environmental anomaly is a fire may then be reported as part of the layered alert notification generated as explained below in step 3035.

In still another embodiment of step 3030 of method 3000, the detected environmental anomaly for the shipping container may be detected as a fire within the shipping container based upon where the sensed initial group of the ID nodes are located within the shipping container according to the context data related to the sensed initial group of the ID nodes and a loading scheme for the shipping container, the loading scheme being maintained in the command node. For example, command node 24160 may access context data 26560 to identify the location of a particular ID node(s) as well as a loading scheme for what is stored within the shipping container and use this information to further detect that the environmental anomaly is a fire based on that information. Again, the indication that the environmental anomaly is a fire may then be reported as part of the layered alert notification generated as explained below in step 3035.

In another embodiment of step 3030 of method 3000, the detected environmental anomaly for the shipping container may be detected as an explosion within the shipping container. In more detail, this may be based upon how quickly the sensed initial group of the ID nodes have changed broadcast behavior when monitoring the ID nodes and detecting the environmental anomaly, or how quickly the sensed initial group of the ID nodes have changed broadcast behavior when monitoring the ID nodes and based upon material contained in at least one of packages associated with the sensed initial group of the ID nodes as indicated in the context data related to the sensed initial group of the ID nodes. The indication that the environmental anomaly is an explosion may be reported as part of the layered alert notification generated as explained below in step 3035.

At step 3035, method 3000 proceeds with the command node generating a layered alert notification related to the detected environmental anomaly for the shipping container. In this step as part of method 3000, the generated layered alert notification identifies a targeted mediation recipient, identifies a targeted mediation action, and establishes a mediation response priority based upon a size of the sensed initial group of the ID nodes and context data related to the sensed initial group of the ID nodes (e.g., context data 26560 being maintained locally on the command node 26000 as shown in FIG. 26).

In more detail, the command node may generate the layered alert notification in step 3035 based upon which of the ID nodes are (a) sensed to be part of the initial group of ID nodes in the unanticipated state of ceased broadcasting and (b) indicated by the context data related to the sensed initial group of the ID nodes to be still maintained within the shipping container. In another embodiment, the command node may generate the layered alert notification in step 3035 based upon how quickly the sensed initial group of the ID nodes have changed broadcast behavior when detecting the environmental anomaly. In still another embodiment, the command node may generate the layered alert notification as part of step 3035 based upon where the sensed initial group of the ID nodes are located within the shipping container according to the context data related to the sensed initial group of the ID nodes.

A more detailed embodiment of step 3035 may involve patterns of sensed unresponsive ID nodes. For example, the sensed initial group of the ID nodes may form a first sensed pattern of unresponsive ID nodes. The command node may then sense a subsequent group of one or more ID nodes to be in the unanticipated state of ceased broadcasting after the command node senses the initial group of the ID nodes in the unanticipated state of ceased broadcasting where the subsequent group of ID nodes is larger than the initial group of the ID nodes. The command node may then, as part of this further embodiment of method 3000, detect a further environmental anomaly when a pattern of the subsequent group of the ID nodes in the unanticipated state of ceased broadcasting exceeds a threshold pattern setting maintained by the command node when compared to the first sensed pattern of unresponsive ID nodes. In such a situation, this further embodiment of method 3000 may have the command node generating the layered alert notification as being based upon the size of the sensed initial group of the ID nodes, a size of the subsequent group of the ID nodes, a change in the pattern of the subsequent group of the ID nodes and the pattern of the initial group of the ID nodes, and context data related to the subsequent group of the ID nodes.

As part of step 3035, the targeted mediation recipient may be identified more specifically. For example, in one embodiment, the targeted mediation recipient may be automatically selected by the command node based upon an extent of how much the size of the sensed initial group of ID nodes exceeds the threshold setting. Thus, if the size of the initial group of unresponsive ID nodes is 25 and the threshold setting is 5, the command node may responsively and automatically select the targeted mediation recipient to be a fire suppression system where if the group of unresponsive ID nodes is 6 and the threshold setting is 5, the command node may select the targeted mediation recipient to be a logistics crew member of the transit vehicle that can inspect the shipping container.

As such, a further embodiment may have the targeted mediation recipient identified by the command node in the layered alert notification to be, for example, a fire suppression system operative to automatically respond to the detected environmental anomaly based upon receipt of the layered alert notification, an operator of the transit vehicle that can alter movement of the transit vehicle, or a logistics crew member of the transit vehicle that can inspect the shipping container.

As such, a further embodiment of method 3000 may further include the step of automatically dispensing, by the fire suppression system, fire suppression agent into the shipping container upon receipt of a trigger message from the external transceiver of the transit vehicle, where the trigger message being in response to the layered alert notification. In more detail, the trigger message from the external transceiver may be automatically generated by the external transceiver, or may be generated in response to input to the external transceiver from a logistics crew member of the transit vehicle after inspecting the shipping container. In an embodiment where the external transceiver is part of the fire suppression system, method 300 may further include the step of having the command node directly cause the fire suppression system to automatically dispense the fire suppression agent into the shipping container via the layered alert notification operating as the trigger message for the fire suppression system.

As part of step 3035, the targeted mediation action may also be identified more specifically. For example, the targeted mediation action may be automatically selected by the command node based upon which of the ID nodes are sensed to be the initial group of ID nodes in the unanticipated state of ceased broadcasting; based upon how quickly members of the sensed initial group of the ID nodes have changed broadcast behavior to become in the unanticipated state of ceased broadcasting; based upon a pattern of change when the initial group of the ID nodes is monitored and sensed to have changed broadcast behavior to become in the unanticipated state of ceased broadcasting; and/or based upon where the sensed initial group of the ID nodes are located within the shipping container according to the context data related to the sensed initial group of the ID nodes.

When identifying the targeted mediation action as part of the layered alert notification in step 3035, the command node may consider further contextual types of information, such as vehicle status data, container status data, geolocation data, and/or facility status data. For example, a further embodiment of method 3000 may have the command node receiving vehicle status data provided by the external transceiver unit associated with the transit vehicle. In this situation, the command node may identify the targeted mediation action in the layered alert notification as part of step 3035 depending upon a state of the transit vehicle as indicated by the vehicle status data (e.g., a takeoff vehicular status, a cruising vehicle status, a landing vehicular status, and a stationary vehicular status of the transit vehicle). Thus, when the vehicle is moving (i.e., cruising vehicle status), the command node may consider this data input to enhance and improve what targeted mediation action to identify, which may be entirely different from when the vehicle is stationary. In another example, a further embodiment of method 3000 may have the command node accessing container status data maintained by the command node and associated with the shipping container. In this situation, the targeted mediation action identified by the command node in the layered alert notification as part of step 3035 may depend upon a state of the shipping container as indicated in the container status data (e.g., a loading status, an unloading status, a secure status, an in-transit status). In still another example, a further embodiment of method 3000 may have the command node accessing geolocation data (e.g., a type of location data 455) maintained by the command node, associated with the shipping container, and related to a current location of the shipping container. In this situation, the targeted mediation action identified by the command node in the layered alert notification as part of step 3035 may depend upon the current location of the shipping container as indicated in the geolocation data. In still another example, a further embodiment of method 3000 may have the command node accessing facility status data maintained by the command node and associated with a storage facility for the shipping container. In this situation, the targeted mediation action identified by the command node in the layered alert notification as part of step 3035 may depend upon a state of the storage facility as indicated in the facility status data.

Further still, embodiments of step 3035 of method 3000 may identify the targeted mediation action an automatic response by a triggered fire suppression system on the transit vehicle; a prompted request to change course of the transit vehicle from an existing travel path of the transit vehicle and/or a prompted request to investigate the shipping container.

More detailed embodiments of step 3035 of method 3000 may have the mediation response priority automatically selected by the command node based upon an extent of how much the size of the sensed initial group of ID nodes exceeds the threshold setting. For example, the mediation response priority established by the command node as part of the layered alert notification in step 3035 may be an immediate priority level that automatically indicates further travel by the transit vehicle is permissible when responding to the detected environmental anomaly or may be a higher priority level that automatically indicates further travel by the transit vehicle is not permissible and requests immediate cessation of transit vehicle travel.

At step 3040, method 3000 proceeds with the command node transmitting the layered alert notification to the transceiver unit to initiate a mediation response related to the targeted mediation action. Again, in some embodiments, the transceiver unit may be separate from the targeted mediation recipient (e.g., a fire suppression system onboard the vehicle) but the transceiver unit in other embodiments may be built into such onboard devices related to the targeted mediation recipients (e.g., display units in a cockpit or logistics support area of the transit vehicle).

Additional embodiments of exemplary method 3000 may involve more specific details and/or additional steps. For example, monitoring for unresponsive ID nodes as part of step 3010 may, in more detail, involve monitoring a select subset of the ID nodes for the unanticipated state of ceased broadcasting from any of the ID nodes in the select subset according to a communication profile maintained on the command node for each the ID nodes in the select subset. This select subset may be less than all of the ID nodes anticipated to be broadcasting and, as such, provides a further level of improved selective targeting of which particular ID nodes to use when monitoring for broadcast behavioral changes in step 3010. As such, the command node may then sense the initial group of one or more unresponsive ID nodes from the select subset of ID nodes monitored (that should be broadcasting) and detect the environmental anomaly when the size of the sensed initial group of the ID nodes in the unanticipated state of ceased broadcasting exceeds the threshold setting maintained by the command node. In this example, the threshold setting maintained by the command node may be a dynamic value defined by the command node based upon a material characteristic of what is contained in at least one of the packages and/or a dynamic value defined by the command node related to a count of how many of the ID nodes are in the select subset of ID nodes.

In a further embodiment of method 3000, the communication profile for each of the ID nodes may be used by the command node to regulate how often each of the ID nodes broadcast. As such, method 3000 may also include the command node instructing each of the ID nodes not in the initial group of the ID nodes (the initial group being those of the ID nodes anticipated to be broadcasting that have been found unresponsive) to broadcast at a second messaging rate that exceeds an initial messaging rate after method 3000 has the command node transmitting the layered alert notification to the transceiver unit. In this way, each of the ID nodes not in the initial group of the ID nodes more frequently broadcast compared to prior to when the initial group of the ID nodes was sensed to be in the unanticipated state of ceased broadcasting. In more detail, the initial messaging rate for the ID nodes may be an initial value correlated to an environmental risk associated with at least one of the packages within the shipping container. Further, the second messaging rate for the ID nodes not in the initial group of the ID nodes may be a predetermined higher messaging rate based upon a type of material existing within at least one of the packages within the shipping container.

In yet another embodiment of method 3000, the command node may be remotely updated with threshold updates for the threshold setting maintained by the command node. For example, such a threshold update may be received by the command node from the external transceiver unit where such an update may be defined by an operator of the transit vehicle using the external transceiver unit, or a logistics crew member of the transit vehicle using the external transceiver unit. In another example, the threshold update may be provided to the external transceiver unit from a remote control center in communication with the external transceiver unit.

In like manner, a further embodiment of method 3000 may have the command node receiving a selection update for which of the ID nodes are included in the select subset of the ID nodes described above. Such a selection update may be received from the external transceiver unit (e.g., as defined by an operator of the transit vehicle using the external transceiver unit or a logistics crew member of the transit vehicle using the external transceiver unit) or from a remote control center in communication with the external transceiver unit.

In still a more detailed embodiment of method 3000, step 3010 involving monitoring those ID nodes anticipated to be broadcasting may be further implemented to confirm validity of broadcasts received from those ID nodes. In more detail, step 3010 may have the command node (a) receiving a communication broadcasted from a first of the ID nodes; (b) confirming the validity of the received communication; (c) having the command node repeat steps (a) and (b) for the remainder of the communications received from any of the remaining ones of the ID nodes; and then having the command node sensing the initial group of one or more of the ID nodes to be in the unanticipated state of ceased broadcasting based upon the command node determining which of the ID nodes are not broadcasting based upon steps (a)-(c). Step (b) of confirming may, in some embodiments, be an active type of confirmation where the command node is sending an authentication request to the first of the ID nodes, and receives a validation response from that ID node that authenticates the communication broadcasted from the first of the ID nodes. Alternatively, step (b) of confirming may, in other embodiments, be passive in that the command node may be accessing a validation sequence for the first of the ID nodes (where the validation sequence is maintained by the command node and characterizing expected broadcasts from the first of the ID nodes) and determining if the received communication from the first of the ID nodes matches a predetermined one of the expected broadcasts from the first of the ID nodes according to the validation sequence stored within the command node. Such a predetermined one of the expected broadcasts may be a rotating value previously received by the command node for the first of the ID nodes.

Those skilled in the art will appreciate that method 3000 as disclosed and explained above in various embodiments may be implemented using an exemplary improved monitoring system for detecting an environmental anomaly in a shipping container that maintains multiple packages and for reporting a layered alert notification related to the environmental anomaly to an external transceiver unit associated with a transit vehicle transporting the shipping container such as that explained above with reference to FIG. 24C and its exemplary elements. Such an embodiment of an improved monitoring system, as explained above relative to operations according to method 3000 and with elements from FIG. 24C, uses at least multiple ID nodes disposed within the shipping container (e.g., ID nodes 24120a-24120f) running one or more ID node monitoring program code as part of node control and management code 325 to control operations of the ID nodes to broadcast wireless signals (e.g., advertising signals that may include other information, such as sensor data), as well as a command node mounted to the shipping container (e.g., command node 24160 in FIG. 24C) running one or more parts of CN control & management code 26425 to control the operations of the command node as part of monitoring for and detecting an environmental anomaly based on unanticipated ID nodes that cease broadcasting (e.g., as per a communication profile for the ID node) as well as generating the layered alert notification and transmitting that notification to the external transceiver unit to initiate a type of mediation response. Such code may be stored on a non-transitory computer-readable medium, such as memory storage 26415 on command node 24160 (an embodiment of exemplary command node 26000) and memory storage 315 on ID nodes 24120a-24120f (embodiments of exemplary ID node 120a). Thus, when executing such code, the ID nodes and the command node may be operative to perform operations or steps from the exemplary methods disclosed above, including method 3000 and variations of that method.

External and Internal Monitoring for an Environmental Anomaly

Further embodiments may address enhanced detection of an environmental anomaly relative to a shipping container being transported on a transit vehicle in situations where an exemplary command node (e.g., ULD container node that is essentially a master node that may not have location circuitry for self-locating capabilities, a mobile master node deployed on or as part of the shipping container that has location circuitry for self-locating capabilities) may more broadly monitor what ID nodes are anticipated to be broadcasting within as well as around the shipping container. In particular, embodiments may deploy a container's command node to monitor ID nodes within and external to the shipping container and detect whether there is a shift in behavior for those ID nodes anticipated to be broadcasting regardless of whether the ID nodes are actually within the command node's own shipping container or disposed external to the shipping container but still within the communication range of the command node (i.e., the command node being capable of receiving communications from such an externally disposed ID node). Such a shift in behavior may be detected and take the form of, for example, an unanticipated state of ceased broadcasting from a monitored ID node that is anticipated to be broadcasting—whether within the shipping container or outside the shipping container. The cessation of broadcasting by particular ID nodes, both from within the shipping container as well as disposed outside of but near the shipping container, may operate as a detectable trigger condition indicating an environmental anomaly for the shipping container, such as a fire within the shipping container.

In such embodiments, an ID node being monitored may be considered a "package ID node" when the ID node is attached to, disposed within, travels with, or is otherwise associated as part of a package being transported on and within the temporary custody of the transit vehicle (such as an aircraft). For example, exemplary ID node 24120a shown within package 24400d in FIG. 24B may be considered an exemplary package ID node given that ID node 24120a in FIG. 24B is disposed within the package itself or may be integrated as part of the package (e.g., part of the packaging material, cushioning material, fill material, and the like). Alternatively, an exemplary ID node being monitored may be considered a "non-package ID node" when the ID node is not specifically attached to, disposed within, traveling with, nor is otherwise associated as part of a particular package or group of packages being transported on the transit vehicle. For example, exemplary ID node 24120a shown in FIG. 24C may be considered an exemplary non-package ID node given that it may simply be disposed within the shipping container (such as on a wall, on the floor, attached to the ceiling, fixed to a door, or simply placed within the interior storage area of the shipping container along with one or more packages) and not specifically associated with nor attached to any particular package or group of packages being transported on the transit vehicle.

As explained in more detail below, such embodiments may involve systems and methods where the ID nodes being monitored are package ID nodes associated with particular packages or, alternatively, are the ID nodes being monitored as non-package ID nodes. In more detail, further embodiments may have the command node monitoring a set of ID nodes within the shipping container where some are package ID nodes and some may be non-package ID nodes while also monitoring another set of ID nodes outside the shipping container where those monitored ID nodes outside the shipping container include both package ID nodes and non-package ID nodes. Additional embodiments may further vary this configuration of ID nodes being monitored by the command node—e.g., monitoring only package ID nodes within the container while also monitoring only non-package ID nodes outside the container; monitoring only non-package ID nodes within the container while also monitoring only package ID nodes outside the container. Further still, the configuration of ID nodes being monitored in embodiments may be further diversified as, for example, monitoring only package ID nodes within the container while also monitoring a combination of package and non-package ID nodes outside the container; monitoring only non-package ID nodes within the container while also monitoring a combination of package and non-package ID nodes outside the container; monitoring a combination of package and non-package ID nodes within the container while also monitoring only package ID nodes outside the container; and monitoring a combination of package and non-package ID nodes within the container while also monitoring only non-package ID nodes outside the container.

Figure 31:
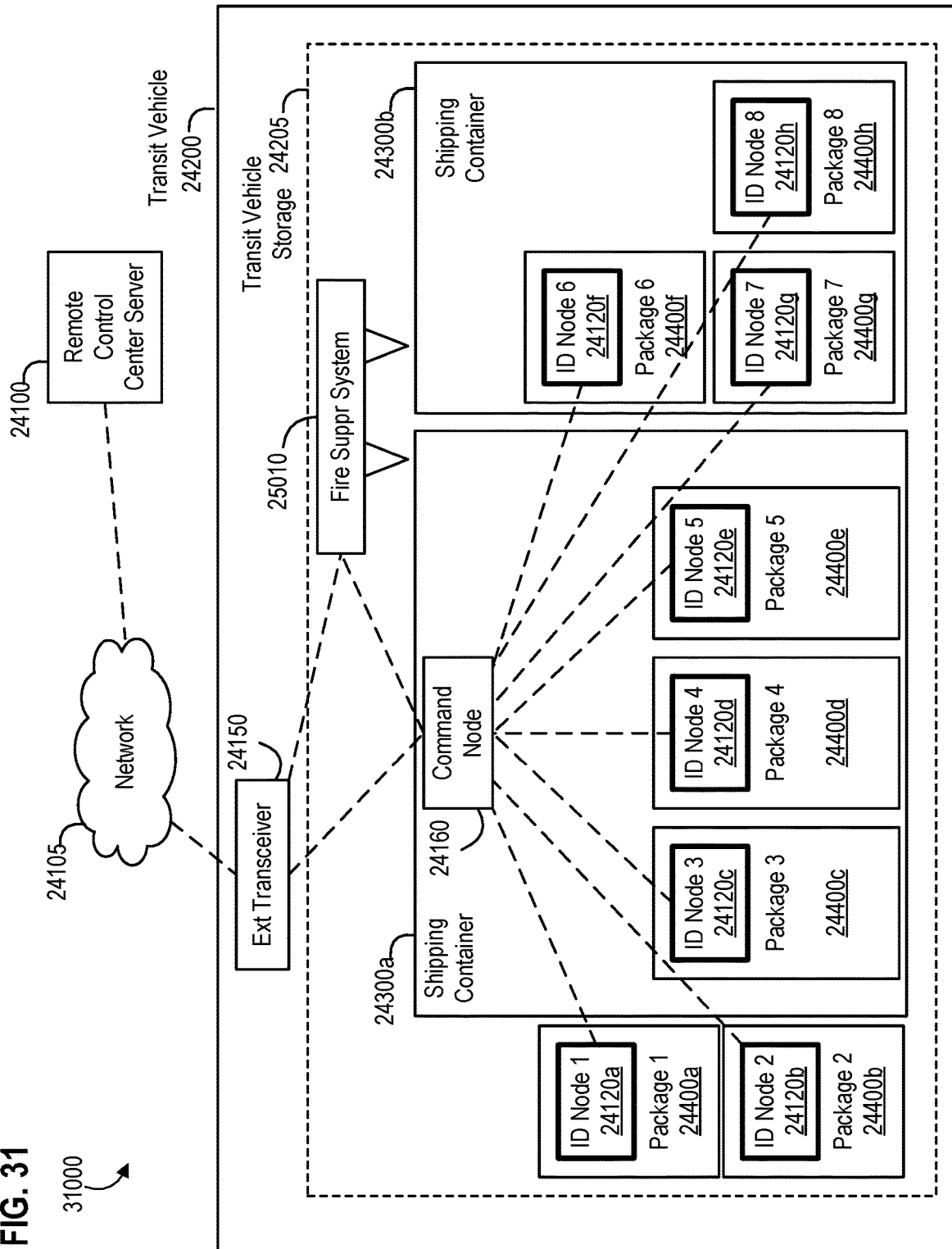
FIG. 31 is a diagram of another exemplary wireless node network used for detecting environmental anomalies using a command node associated with a shipping container being transported on a transit vehicle and ID nodes internal and external to the shipping container on the transit vehicle and where the ID nodes are each associated with packages in accordance with an embodiment of the invention.

FIGS. 31-34 illustrate various embodiments of different exemplary systems and their components where a command node may monitor different types of ID nodes within and external to a shipping container and responsively interact with an external transceiver on the transit vehicle as well as directly interact with an onboard fire suppression system on the transit vehicle. In more detail, FIG. 31 is a diagram of an exemplary wireless node network used for detecting environmental anomalies using a command node associated with a shipping container being transported on a transit vehicle and ID nodes internal and external to the shipping container on the transit vehicle and where the ID nodes are each associated with packages in accordance with an embodiment of the invention. Referring now to FIG. 31, exemplary system 32000 is illustrated showing transit vehicle 24200 having transit vehicle storage 24205 that maintains temporary custody of different shipping containers, such as container 24300a and 24300b (e.g., ULD containers, and the like), when transporting them. The transit vehicle 24000 is further equipped with an external transceiver 24150 onboard along with an exemplary onboard fire suppression system 25010 disposed in the transit vehicle storage 24205. The onboard fire suppression system 25010 may be activated by the external transceiver 24150 and/or a command node of a particular shipping container to supply fire suppression agent into one or more shipping containers (e.g., containers 24300a, 24300b) as well as into the transit vehicle storage 24205 in some embodiments (e.g., as an additional mediation response to a detected environmental anomaly related to a shipping container).

Figure 33:
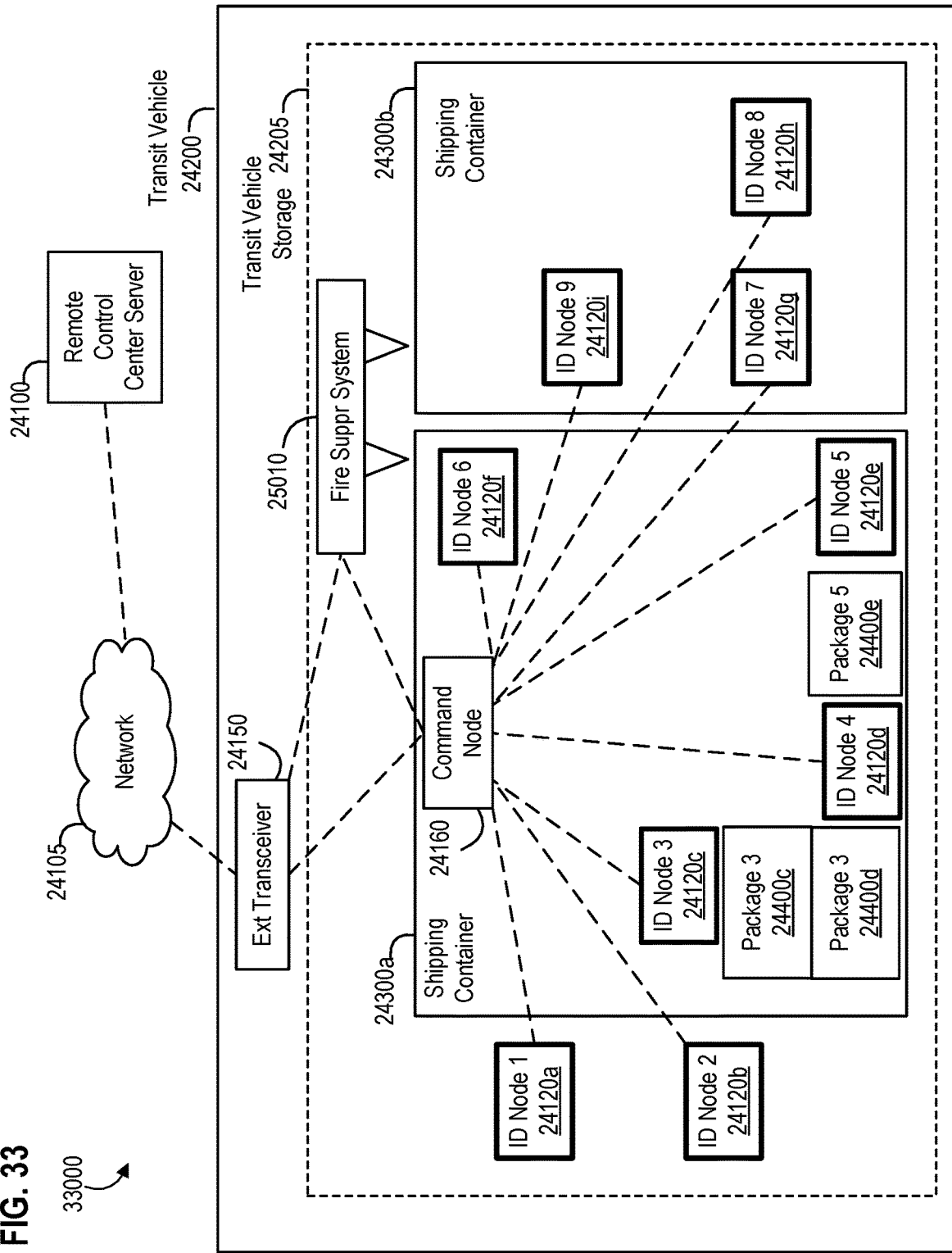
FIG. 33 is a diagram of yet another exemplary wireless node network used for detecting environmental anomalies using a command node associated with a shipping container being transported on a transit vehicle and ID nodes internal and external to the shipping container on the transit vehicle and where the ID nodes are not specifically associated with packages in accordance with an embodiment of the invention.
Figure 34:
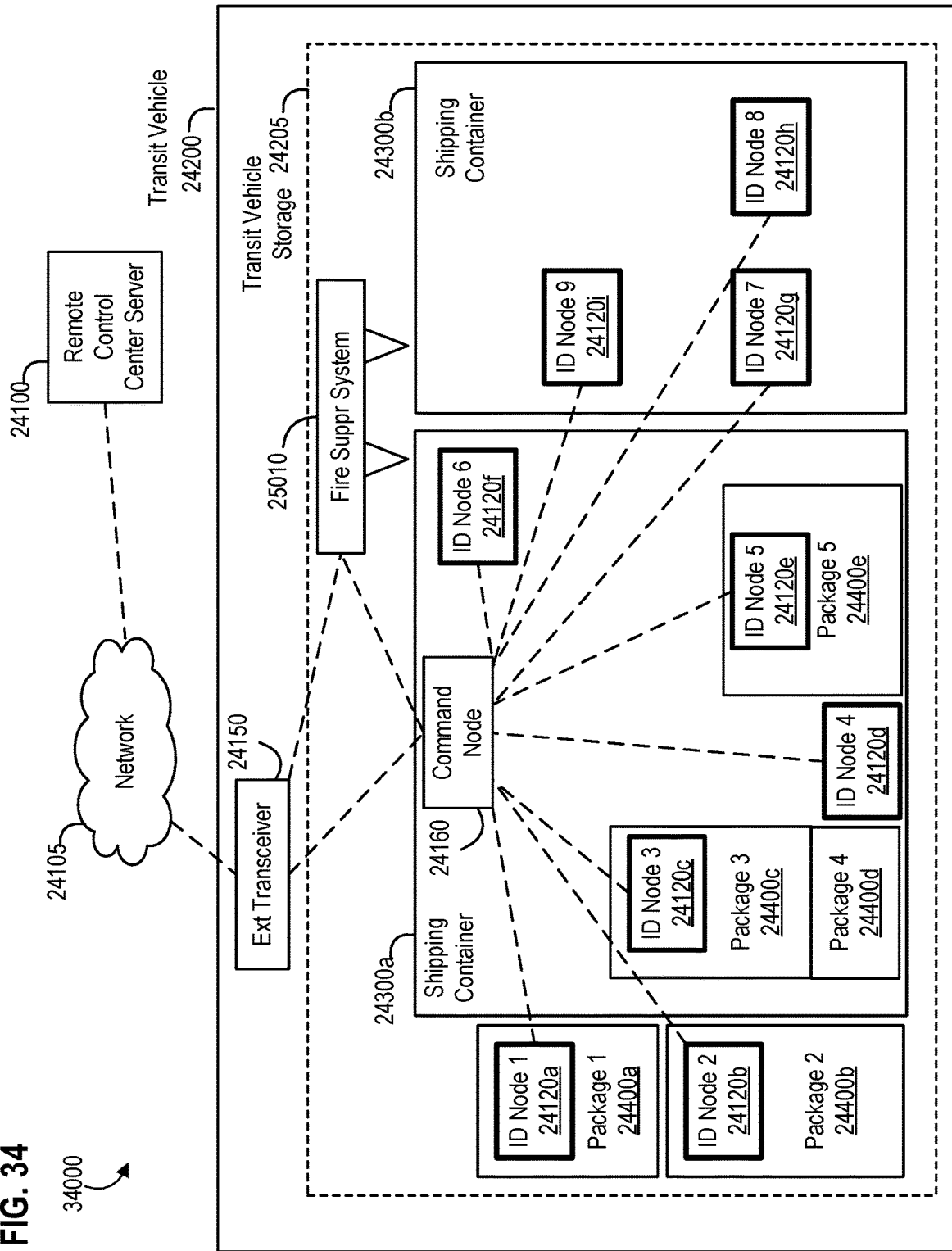
FIG. 34 is a diagram of yet another exemplary wireless node network used for detecting environmental anomalies using a command node associated with a shipping container being transported on a transit vehicle and ID nodes internal and external to the shipping container on the transit vehicle and where the ID nodes in the network are a combination of package and non-package ID nodes within and outside of the shipping container in accordance with an embodiment of the invention.

In FIGS. 31, 33, and 34, the exemplary external transceiver 24150 is disposed on transit vehicle 24200 (similar to that shown in the embodiments of FIGS. 24A-24C) and may receive alert notifications and automatically respond to such alerts by initiating a mediation response related to a particular mediation action based upon the particular environmental anomaly detected. Some responses may have the external transceiver 24150 triggering the onboard fire suppression system 25010 on transit vehicle 24200 and/or communicating with an operator or logistics crew aboard transit vehicle 24200 as explained above. Exemplary external transceiver 24150 shown in FIGS. 31, 33, and 34 may also communicate with remote control center server 24100 over network 24105 to report the detected environmental anomaly and any mediation response initiated as well as to receive information about packages onboard the transit vehicle (e.g., packages 24400a-24400h), environmental threshold conditions related to such packages, and other updated data to be used for detecting environmental anomalies and initiating responsive mediation actions.

In general, the exemplary onboard fire suppression system 25010 shown in FIGS. 31, 33, and 34 is similar to that described above relative to FIG. 25B in that it may be selectively activated with an activation control signal to the fire suppression system's controller, which then causes a fire suppression agent to be applied to a shipping container. In one embodiment, the fire suppression system's controller responds by connecting with a particular shipping container and initiates pressurized expulsion of a fire suppression agent from a fire suppression agent reservoir chamber into that particular shipping container on the transit vehicle 24200. In a more detailed embodiment, this may occur using an articulating puncture (e.g., an actuator and articulating needle) responsive to the fire suppression system's controller that forcibly creates an opening in a surface of the particular shipping container and through which the fire suppression agent may flow into the shipping container so as to address a detected environmental anomaly within that particular shipping container.

Figure 32A:
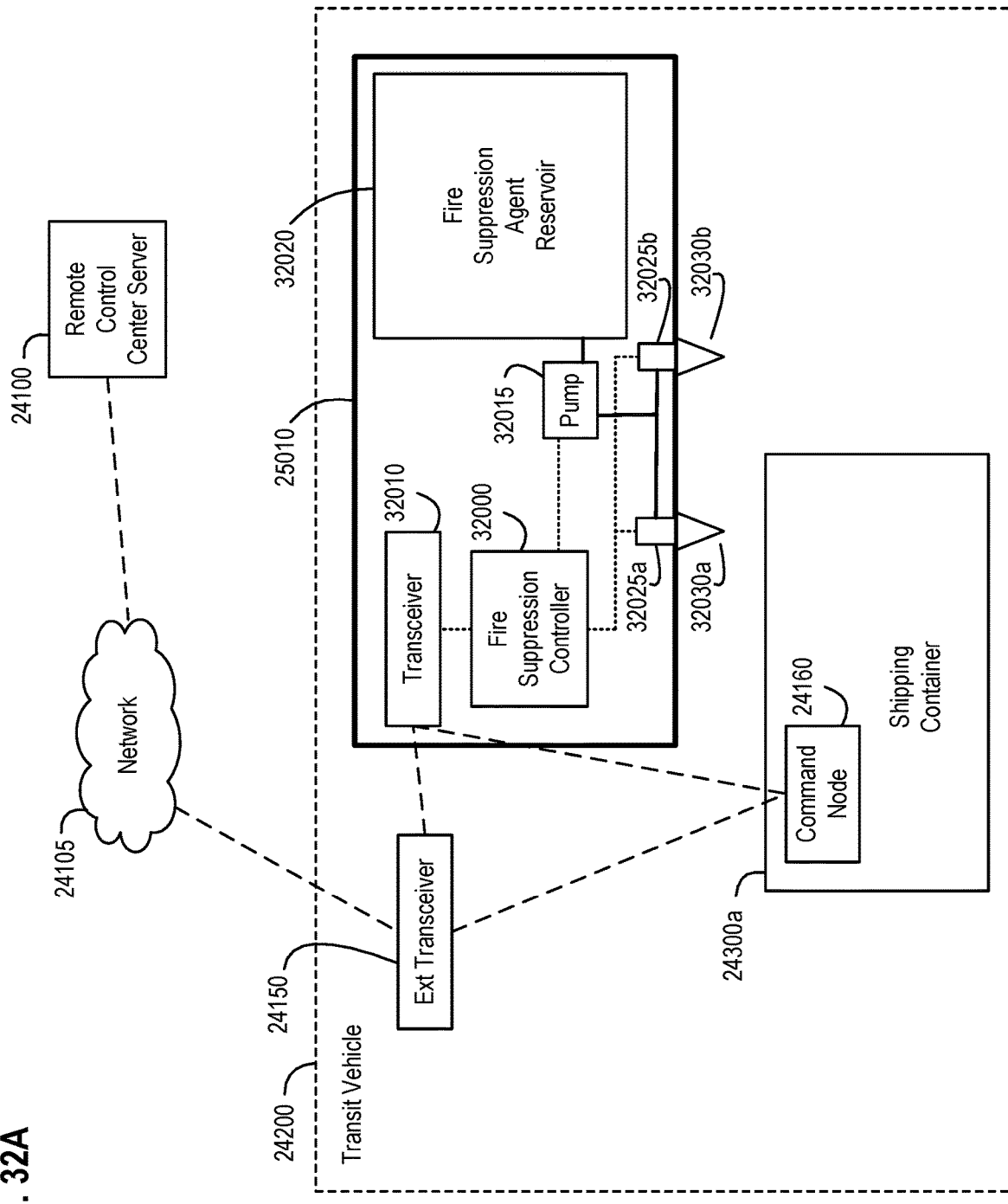
FIG. 32A-32C are a series of diagrams of an exemplary onboard fire suppression system that may be activated and deployed on a transit vehicle for initiating a mediation action in response to a detected environmental anomaly related to a shipping container being transported on the transit vehicle in accordance with an embodiment of the invention.
Figure 32B:
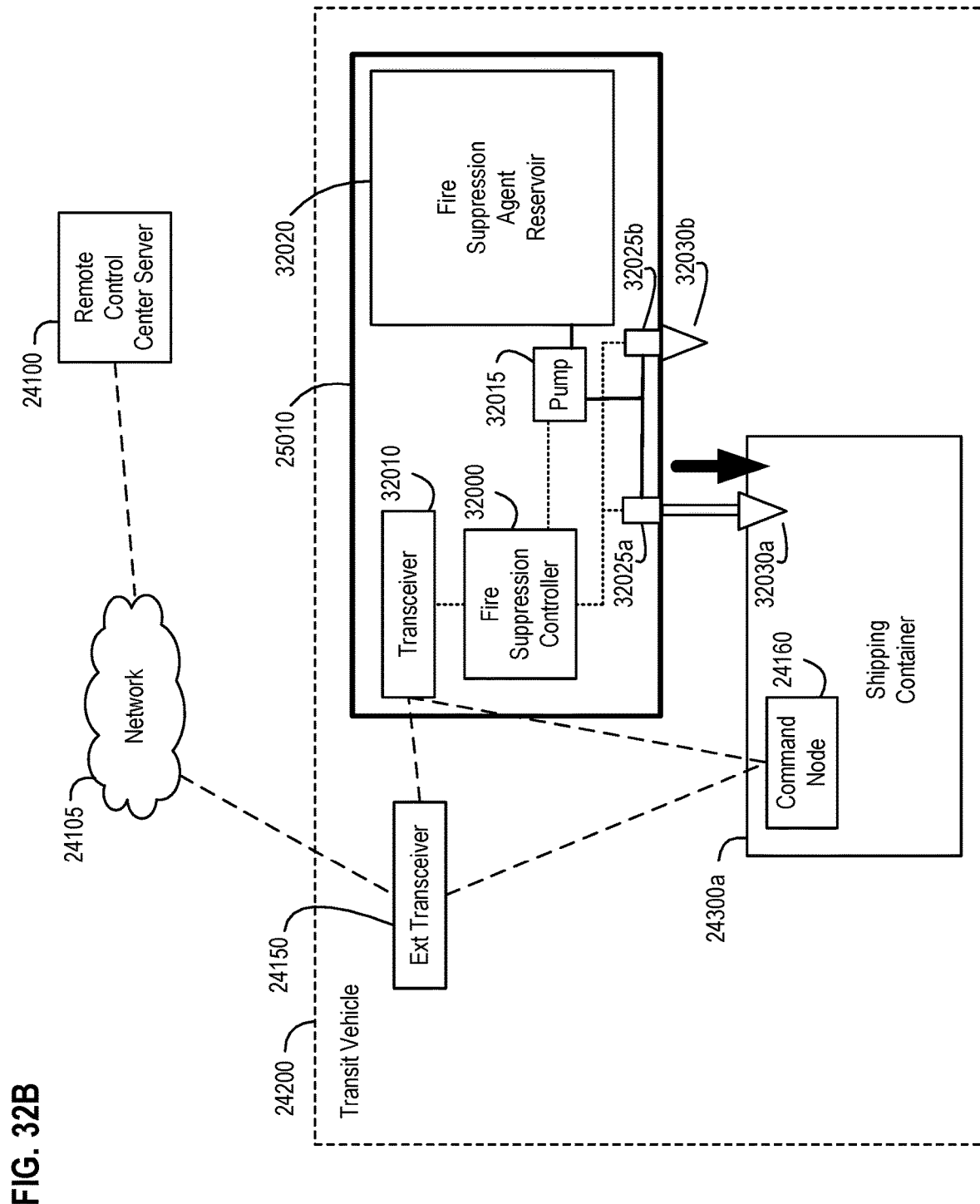
Figure 32C:
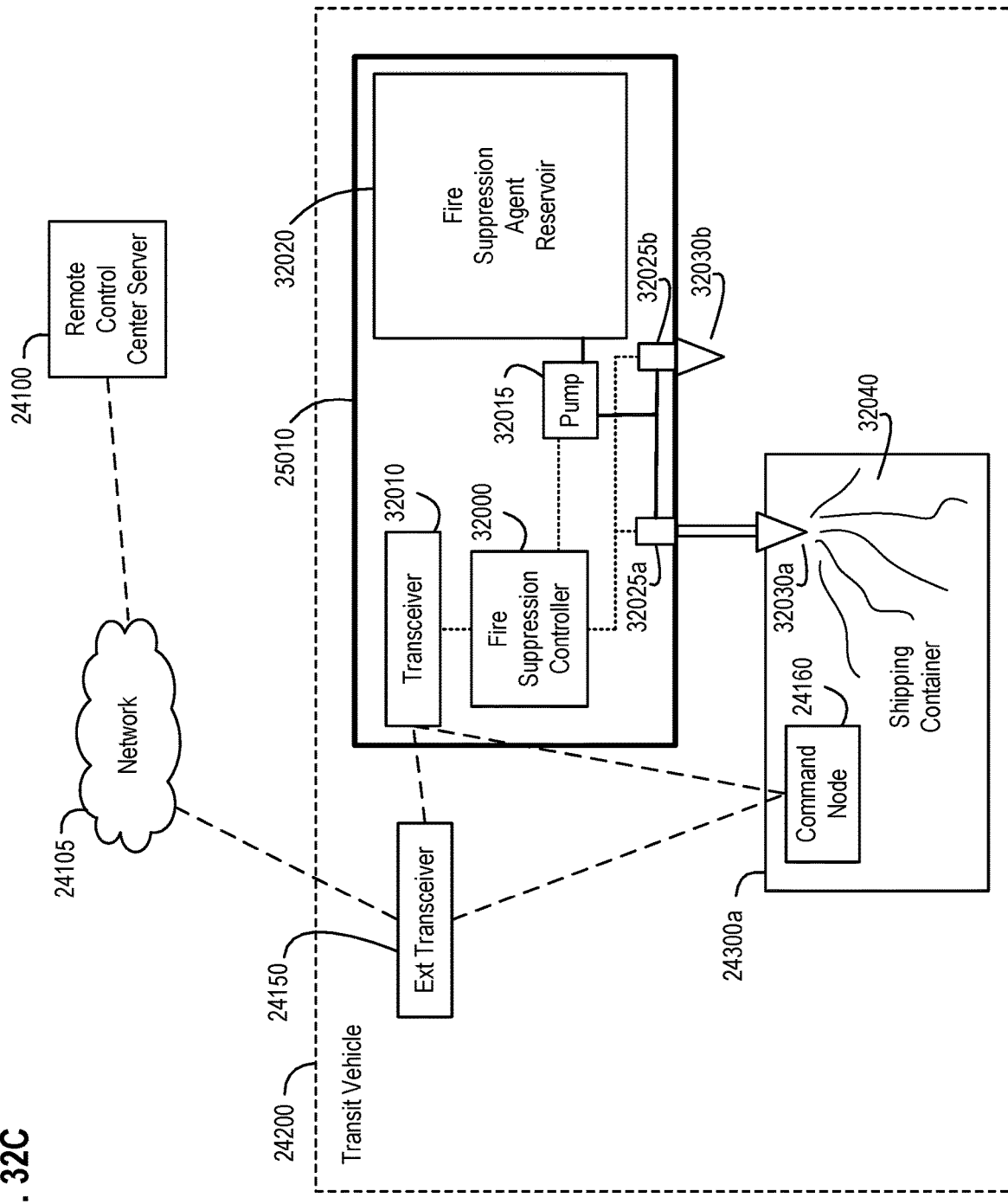

FIGS. 32A-32C provide further details on such an exemplary onboard fire suppression system through a series of diagrams of such an exemplary fire suppression system that may be activated and deployed on a transit vehicle for initiating a mediation action in response to a detected environmental anomaly related to a shipping container being transported on the transit vehicle in accordance with an embodiment of the invention. Referring now to FIG. 32A, exemplary fire suppression system 25010 (as generally discussed above) is shown in more detail as disposed on transit vehicle 24200. In this embodiment, the system 25010 generally includes at least a fire suppression controller 32000, a transceiver 32010 coupled to the controller, a pump 32015, a fire suppression agent reservoir chamber 32020 that holds a fire suppression agent, and actuators 32025a-32025b that responsively control an articulating needle 32030a-32030b as a type of dispenser coupled to the pump and that may be extended to puncture a shipping container 24300a on the transit vehicle 24200. An exemplary fire suppression controller 32000 may be implemented as a control circuit (e.g., a logic circuit, PLA, or programmable microprocessor-based controller board with memory, processing, interface circuitry, and drivers) that receives the activation control signal through transceiver 32010 to control operation of the system 25010. The transceiver 32010 may be implemented as a wired and/or wireless transceiver operative to receive an activation control signal from, for example, external transceiver 24150 on the transit vehicle and/or from a shipping container's command node (e.g., command node 24160 disposed as part of shipping container 24300a). Exemplary transceiver 32010 may also be operative to transmit status information from controller 32000 related to the state of the system (e.g., status of the fire suppression agent within reservoir chamber 32020, position of an actuator 32025a and its linked articulating needle 32030a, as well as pump status, pressure readings, and flow rates as sensed by sensors (not shown), and the like).

Exemplary pump 32015 may be implemented as an electronically activated pump to move the fire suppression agent from fire suppression agent reservoir chamber 32020 to one or more of the actuator/needle dispensers. Such an exemplary pump 32015 may include one or more selectively controlled valves to direct the output of the pump to a particular actuator/needle dispenser so that the pressurized fire suppression agent is selectively provided one or more of the actuator/needle dispensers associated with particular shipping container(s) on the transit vehicle 24200 in response to control signals sent to pump 32015 from controller 32000. Some embodiments may implement pump 32015 with multiple pumps that may be dedicated for particular sections of transit vehicle storage 24205 or for particular shipping containers or groups of shipping containers on the transit vehicle 24200. In this way, the system's fire suppression agent pump 32015 may be activated by the fire suppression controller 32000 in response to the activation control signal provided to the controller 32000 (e.g., as received by the fire suppression transceiver 32010 and passed to controller 32000, which then generates the appropriate control signals to send to pump 32015 based on the contents of the activation control signal that identify which shipping container requires a mediation response by the fire suppression system 25010, what pressure may be required, how long to apply the fire suppressant agent, and other control parameters of pump 32015 needed to provide the appropriate mediation response).

In some embodiments, fire suppression agent reservoir chamber 32020 may be implemented as non-pressurized container where the fire suppression agent flows from the chamber 32020 simply by virtue of gravity and suction from the pump 32015, which then pressurizes the fire suppression agent as it flows to the shipping container through the particular actuator/needle dispenser. In other embodiments, fire suppression agent reservoir chamber 32020 may be loaded with fire suppression agent material maintained under a particular storage pressure (i.e., pressurized on chamber 32020). As such, the combination of a pressurized release from chamber 32020 and the action of pump 32015 allows the fire suppression agent to flow to the shipping container through the particular actuator/needle dispenser.

The actuators 32025a-32025b and needles 32030a-32030b provide an articulating puncture coupled to the fire suppression agent reservoir chamber 32020 that effectively dispense and allow for selective injection of pressurized fire suppression agent into a particular shipping container on the transit vehicle 24200. Those skilled in the art will appreciate that actuators 32025a-32025b may be implemented with hydraulically and/or mechanically actuated linkages, arms, pistons, or other articulating structure that moves needles 32030a-32030b. Exemplary needles 32030a-32030b may be implemented with material of sufficient stiffness and strength to puncture the exterior of a shipping container used in an embodiment and have an input side coupled to the pump 32015 and output hole near the tip of the needle that extends into the shipping container when the needle is deployed into the shipping container.

In an embodiment, each of the actuators 32025a-32025b are coupled to and may be activated by the fire suppression system controller 32000 so that a particular actuator, such as actuator 32035a, responsively articulates, moves, and/or extends its needle 32030a from a retracted position (as shown in FIG. 32A) to an extended activated position (as shown in FIG. 32B). In this way, the extended needle 32030a and its actuator 32025a are forcibly deployed to rapidly create an opening in a shipping container (e.g., shipping container 24300a shown in FIGS. 32A-32C) in response to a deployment control signal sent from the fire suppression controller 32000 to the respective actuator (e.g., actuator 32025a) in response to the activation control signal received by the fire suppression controller 32000 via transceiver 32010. Once the dispensing articulated puncture (e.g., actuator 32025a and its related needle 32030a) is in the extended activated position as shown in FIG. 32B, fire suppression controller 32000 may send the appropriate control signals to pump 32015 based on the contents of the activation control signal, which identifies which shipping container requires a mediation response by the fire suppression system 25010 (e.g., control signals from controller 32000 to pump 32015 to selectively supply fire suppression agent from chamber 32020 to needle 32030a so that the pressurized fire suppression agent is injected within shipping container 24300a). Thus, as shown in FIG. 32C, fire suppression agent 32040 pressurized by pump 32015 may be supplied from fire suppression agent reservoir chamber 32020, then through needle 32030b so that the agent enters shipping container 24300a as a type of mediation action or response that may be directly or indirectly initiated by a shipping container's command node 24160.

While the embodiments shown in FIGS. 32A-32C illustrate exemplary onboard fire suppression system 25010 illustrate a system that may selectively dispense fire suppression agent into one or more different shipping containers being transported on transit vehicle 24200, further embodiments of onboard fire suppression system may be implemented as dedicated modules (similar to what is shown in FIG. 25B) that are each an onboard fire suppression system paired to a particular shipping container. Thus, further embodiments may deploy multiple dedicated onboard fire suppression systems that service and can respond to detected environmental anomalies in one or more different shipping containers where the shipping container's command node 24160 and/or transit vehicle's external transceiver 24150 may interact with more than one onboard fire suppression system.

As shown in FIGS. 31, 33, and 34, exemplary transit vehicle storage 24205 is shown maintaining the temporary custody of shipping containers 24300a and 24300b. Those skilled in the art will appreciate that while each of these shipping containers may have an associated command node, the illustrations in FIGS. 31, 33, and 34 focus on embodiments with highlighted details of exemplary command node 24160 mounted to shipping container 24300a and ID nodes that may be monitored by exemplary command node 24160 in different example embodiments.

Further, as shown in FIGS. 31, 33 and 34, exemplary transit vehicle storage 24205 may temporarily maintain a variety of different packages where each package may or may not be within particular shipping containers in the transit vehicle storage 24205 and the packages may or may not be associated with a specific ID node. For example, as shown in FIG. 31, the ID nodes within the transit vehicle storage 24205 are each associated with particular packages in accordance with an embodiment of the invention. In particular, as shown in FIG. 31, transit vehicle storage 24205 has packages 24400a, 24400b (and their respective ID nodes 24120a, 24120b) disposed within the transit vehicle storage 24205 but outside of both shipping container 24300a and shipping container 24300b but situated close to shipping container 24300a. Packages 24300c-24400e (and their respective ID nodes 24120c-24120e) are disposed within shipping container 24300a while packages 24400f-24400h (and their respective ID nodes 24120f-24120h) as disposed within shipping container 24300b, which is next to shipping container 24300a. Those skilled in the art will appreciate that ID nodes 24120a-24120h shown in FIG. 31 are within a communication range of command node 24160 and, thus, able to generate wireless broadcasts that may be received by command node 24160.

In another example configuration shown in FIG. 33, the ID nodes within the transit vehicle storage 24205 are not specifically associated with packages in accordance with another embodiment of the invention. In particular, as shown in FIG. 33, transit vehicle storage 24205 has packages 24400c-24400e disposed within shipping container 24300a but none of ID nodes 24120c-24120e within shipping container 24300a are specifically associated with any of packages 24400c-24400e in the container. Additionally, ID nodes 24120a-24120b are non-package ID nodes disposed outside of shipping container 24300a and shipping container 24300b but situated close to shipping container 24300a. Non-package ID nodes 24120g-24120i are disposed within shipping container 24300b, which is next to shipping container 24300a. The ID nodes not specifically associated with any package but disposed within a shipping container (such as ID nodes 24120c-24120i) may be implemented as stand-alone devices loaded into a particular shipping container but not attached, affixed, or otherwise specifically associated with a particular package in the container; integrated as part of the shipping container (e.g., as part of the walls, floor, ceiling, door, and the like), or merely attached to part of the shipping container. As with the configuration shown in FIG. 31, those skilled in the art will appreciate that ID nodes 24120a-24120h shown in FIG. 33 are within a communication range of command node 24160 and, thus, able to generate wireless broadcasts that may be received by command node 24160.

In still another example configuration shown in FIG. 34, the ID nodes within the transit vehicle storage 24205 are a combination of package ID nodes and non-package ID nodes within and outside of a particular shipping container in accordance with an embodiment of the invention. In more detail, as shown in FIG. 34, transit vehicle storage 24205 has packages 24400c-24400e disposed within shipping container 24300a. In this example, packages 24400c and 24400e have associated ID nodes 24120c and 24120e, respectively, while ID nodes 24120d and 24120f are not specifically associated with any of packages 24400c-24400e in the container. Additionally, ID nodes 24120a-24120b are package ID nodes respectively associated with packages 24400a-24400b disposed outside of shipping container 24300a and shipping container 24300b but situated close to shipping container 24300a. Non-package ID nodes 24120g-24120i are disposed within shipping container 24300b, which is next to shipping container 24300a. Again, the ID nodes not specifically associated with any package but disposed within a shipping container (such as ID nodes 24120d and 24120f-24120i) may be implemented as stand-alone devices loaded into a particular shipping container but not attached, affixed, or otherwise specifically associated with a particular package in the container; integrated as part of the shipping container (e.g., as part of the walls, floor, ceiling, door, and the like), or merely attached to part of the shipping container. As with the configuration shown in FIGS. 31 and 33, those skilled in the art will appreciate that the combination of package and non-package ID nodes 24120a-24120h shown in FIG. 33 are within a communication range of command node 24160 and, thus, able to generate wireless broadcasts that may be received by command node 24160.

Figure 35:
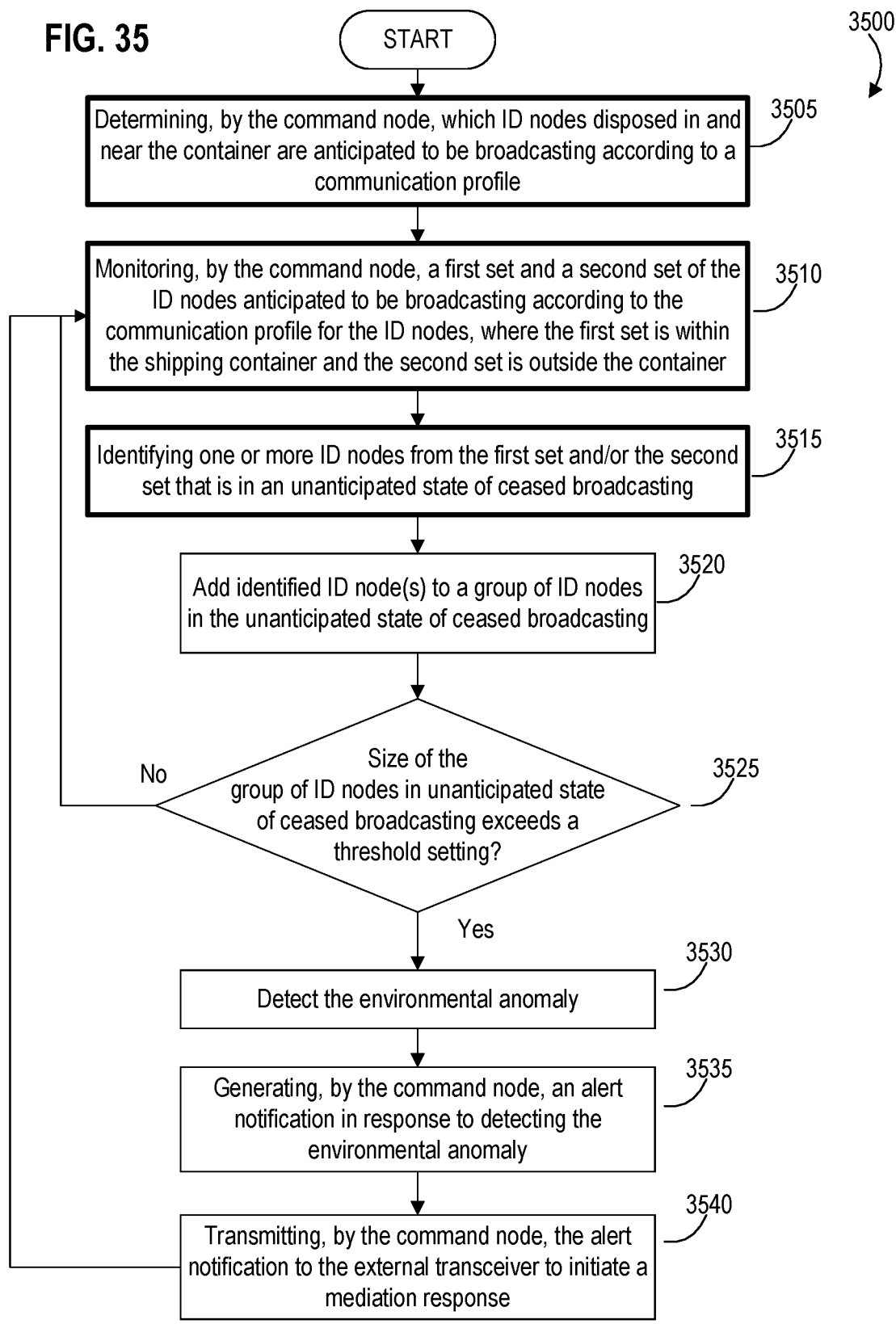
FIG. 35 is a flow diagram illustrating an exemplary method for monitoring for an environmental anomaly related to a shipping container using a wireless node network having at least a command node associated with a shipping container and ID nodes within the shipping container and outside the shipping container and where the ID nodes are not specifically associated with packages in accordance with an embodiment of the invention.

FIG. 35 is a flow diagram illustrating an exemplary method for monitoring a shipping container for an environmental anomaly using a wireless node network having at least a command node associated with a shipping container and ID nodes within the shipping container and outside the shipping container and where the ID nodes are not specifically associated with packages in accordance with an embodiment of the invention. In particular, FIG. 35 describes an exemplary improved method 3500 for monitoring for an environmental anomaly related to a shipping container (e.g., shipping container 24300a) using a wireless node network. The shipping container involved in method 3500 is being transported on a transit vehicle (e.g., transit vehicle 24200—such as an aircraft, railway conveyance, a maritime vessel, or a roadway conveyance) that also transports multiple packages (e.g., packages 24400a-24400h as shown in FIG. 31). The wireless node network involved in method 3500 has at least a plurality of ID nodes (e.g., ID node 24120a-24120h as shown in FIG. 31) and a command node associated with the shipping container (e.g., command node 241260 associated with and mounted to shipping container 24300a). The command node used as part of method 3500 may, for example, be implemented as a container node integrated as part of the shipping container or a self-locating master node implemented separately from the shipping container. The ID nodes used as part of method 3500 include a first set of the ID nodes disposed within the shipping container (e.g., ID nodes 24120c-24120e) and a second set of the ID nodes disposed outside the shipping container (e.g., ID nodes 24120a, 24120b, and 24120f-24120h). In this configuration, the command node involved in method 3500 is operative to communicate with each of the ID nodes in the first set of the ID nodes and the second ID nodes and an external transceiver unit associated with the transit vehicle (e.g., external transceiver 24150 on transit vehicle 24200).

Referring now to FIG. 35, exemplary method 3500 begins at step 3505 with the command node determining which of the ID nodes disposed in and near the shipping container are anticipated to be broadcasting according to a communication profile on what ID nodes are within and located near the shipping container. For example, command node 24160 may reference profile data 430 (as well as location data and/or association data) that may indicate what ID nodes are within shipping container 24300a or loaded within transit vehicle storage 24205. Using this information, command node 24160 may initiate communication with any ID nodes within the command node's transmission and reception range (e.g., what ID nodes may receive communications from command node 24160 and which ID nodes respond to such communications from the command node 24160). Those ID nodes that may establish initial communications with command node 24160—i.e., ID nodes within shipping container 24300a and outside of 24300a—may be identified as potential ID nodes to be monitored as part of the embodiment of method 3500 as long as the communication profile information on each of those potential ID nodes indicates the particular ID node is anticipated to be broadcasting so that the command node 24160 is able to count on communications from those ID nodes anticipated to be broadcasting under normal conditions.

At step 3510, method 3500 continues with the command node monitoring for an unanticipated state of ceased broadcasting from any of the ID nodes within the first set of the ID nodes disposed within the shipping container according to a communication profile for each the ID nodes in the first set of the ID nodes maintained on the command node, as well as monitoring for an unanticipated state of ceased broadcasting from any of the ID nodes within the second set of the ID nodes disposed outside the shipping container according to a communication profile for each the ID nodes in the second set of the ID nodes. For example, command node 24160 shown in FIG. 31 may monitor the first set of ID nodes (e.g., ID nodes 24120c-24120e disposed within shipping container 24300a) as well as monitor the second set of ID nodes (e.g., ID nodes 24120a, 24120b, and 24120f-24120h disposed outside shipping container 24300a). Command node 24160 would be monitoring those ID nodes in particular as part of step 3510 because the communication profile data on each of those nodes (as indicated in profile data 430 on command node 24160) indicates they are anticipated to be broadcasting.

At step 3515, method 3500 continues by identifying one or more ID nodes from the first set and/or second set of the monitored ID nodes as being unresponsive or in an unanticipated state of ceased broadcasting. In more detail, this may have the command node detecting an unresponsive group of the ID nodes to be in the unanticipated state of ceased broadcasting based upon the monitoring step for the first set of the ID nodes and upon the monitoring step for the second set of the ID nodes. The command node, such as command node 24160, may then determine if the unresponsive group of the ID nodes includes any from the first set of the ID nodes (i.e., those monitored ID nodes disposed within the shipping container) and if the unresponsive group of the ID nodes includes any from the second set of the ID nodes (i.e., those monitored ID nodes disposed external to the shipping container).

At step 3520, method 3500 continues with the command node adding any of the identified ID nodes from step 3515 to a group of ID nodes in the unanticipated state of ceased broadcasting. Then, at decision step 3525, method 3500 has the command node determining if the size of the group of ID nodes in the unanticipated state of ceased broadcasting exceeds a threshold setting maintained by the command node. If so, method 3500 proceeds from step 3525 directly to step 3530 where the command node detects the environmental anomaly for the shipping container because the size of the identified or otherwise sensed unresponsive group of the ID nodes in the unanticipated state of ceased broadcasting exceeds the threshold setting. If not, method 3500 proceeds from step 3525 back to step 3510. In a further embodiment of method 3500, the threshold setting maintained by the command node that is used as part of step 3525 may be set by the command node, for example, depending on a combined count of the ID nodes monitored in the first set of the ID nodes and the second set of the ID nodes; depending on a material characteristic of what is contained in at least one of a plurality of packages disposed within the shipping container; and/or depending on a material characteristic of what is contained in at least one of the packages disposed outside the shipping container but on the transit vehicle having custody of the shipping container.

For example, in an embodiment of method 3500, command node 24160 may have identified ID nodes 24120*d* and 24120*e* within the first set of monitored ID nodes within the shipping container 24300*a* as well as ID nodes 24120*f* and 24120*g* within the second set of monitored ID nodes external to shipping container 24300*a* as anticipated to be broadcasting but now being in an unanticipated state of ceased broadcasting. If the threshold setting maintained in memory of command node 24160 is three, then method 3500 would have command node 24160 determining in step 3525 that the four identified ID nodes in the group in the unanticipated state of ceased broadcasting exceeds the threshold setting. Thus, command node 24160 may detect the environmental anomaly for shipping container 24300*a* at step 3530 upon the basis of the monitoring, identifying, and decisions made by the command node in steps 3510-3525.

At step 3535, method 3500 proceeds with the command node automatically generating an alert notification about the detected environmental anomaly for the shipping container, where the alert notification has an alert level setting based upon whether the unresponsive group of the ID nodes includes any from the first set of the ID nodes and whether the unresponsive group of the ID nodes includes any from the second set of the ID nodes. In one example, the alert level setting may be implemented by the command node an initial degree of alert when the unresponsive group of the ID nodes includes only ID nodes from the second set of the ID nodes disposed outside the shipping container. As such, the generated alert notification about the detected environmental anomaly having the initial degree of alert may be generated as an automatic warning about a potential fire outside of the shipping container and/or an automatic warning about a potential fire within the shipping container.

In another example, the alert level setting may be implemented by the command node as an enhanced degree of alert when the unresponsive group of the ID nodes includes only ID nodes from the first set of the ID nodes disposed within the shipping container. As such, the generated alert notification about the detected environmental anomaly having the enhanced degree of alert may be generated as an automatic warning about a fire inside of the shipping container as the enhanced degree of alert reflects a higher confidence level that the detected environmental anomaly is the fire inside of the shipping container.

In still another example, the alert level setting may be implemented by the command node as a high degree of alert when the unresponsive group of the ID nodes includes ID nodes from both the first set of the ID nodes disposed within the shipping container and the second set of the ID nodes disposed outside the shipping container. As such, the generated alert notification about the detected environmental anomaly having the high degree of alert may be generated as an automatic warning about an explosion involving contents of the shipping container, the high degree of alert reflecting a higher confidence level that the detected environmental anomaly involves at least a spreading fire inside of the shipping container.

At step 3540, method 3500 then proceeds to have the command node transmitting the alert notification to the transceiver unit (e.g., external transceiver 24150) to initiate a mediation response related to the detected environmental anomaly.

In further embodiments, method 3500 may include further steps to refine and update for known movement of ID nodes outside of the shipping container. In more detail, a further embodiment of method 3500 may also include having the command node first requesting context data related to the ID nodes from the second set of the ID nodes that are in the unresponsive group of the ID nodes (e.g., requesting such context data from onboard storage memory in the command node, from the external transceiver, or from a remote server in communication with the external transceiver). This requested context data (e.g., context data 26560) provides information on an anticipated location of the ID nodes from the second set of the ID nodes (those outside the shipping container) that are in the unresponsive group of the ID nodes. The further embodiment of method 3500 then has the command node predicting movement of any of the ID nodes from the second set of the ID nodes that are in the unresponsive group of the ID nodes where the prediction operation is based upon whether the anticipated location of any of the ID nodes from the second set of the ID nodes within the unresponsive group of the ID nodes is beyond a reception range for the command node as disposed relative to the shipping container. The command node may then update the unresponsive group of the ID nodes to remove any of the ID nodes from the second set of the ID nodes that are (a) initially detected to be within the unresponsive group of the ID nodes and (b) that are predicted as moved beyond the reception range for the command node based upon the requested context data. The command node then may re-identify the environmental anomaly when the size of the updated unresponsive group of the ID nodes in the unanticipated state of ceased broadcasting exceeds the threshold setting maintained by the command node, and then may automatically generate a refined alert notification about the detected environmental anomaly for the shipping container. Such a refined alert notification has a revised alert level setting based upon whether the updated unresponsive group of the ID nodes includes any from the first set of the ID nodes and whether the updated unresponsive group of the ID nodes includes any from the second set of the ID nodes. This further embodiment of method 3500 then may have the command node transmitting the revised alert notification to the transceiver unit to initiate the mediation response related to the detected environmental anomaly.

In another further embodiment of method 3500, the exemplary method may include further steps to refine and update for known movement of the shipping container away from ID nodes external to the shipping container. In more detail, such a further embodiment of method 3500 may have the command node requesting context data related to the ID nodes from the second set of the ID nodes that are in the unresponsive group of the ID nodes and context data about the shipping container (e.g., requesting such context data from onboard storage memory in the command node, from the external transceiver, or from a remote server in communication with the external transceiver). Such requested data (e.g., context data 26560 and location data 455) provides information on an anticipated location of the ID nodes from the second set of the ID nodes that are in the unresponsive group of the ID nodes and an anticipated location of the shipping container. The method may proceed with predicting movement, by the command node, of the shipping container away from any of the ID nodes from the second set of the ID nodes that are in the unresponsive group of the ID nodes. Such predicted movement is based upon whether the anticipated location of any of the ID nodes from the second set of the ID nodes within the unresponsive group of the ID nodes differs from the anticipated location of the shipping container according to the requested context data. The method may then have the command node updating the unresponsive group of ID nodes to remove any of the ID nodes from the second set of the ID nodes that are (a) initially detected to be within the unresponsive group of the ID nodes and (b) that are beyond a reception range for the command node given the predicted movement of the shipping container away from any of the ID nodes from the second set of the ID nodes that are in the unresponsive group of the ID nodes. As part of this further embodiment of method 3500, the command node may then re-identify the environmental anomaly when the size of the updated unresponsive group of the ID nodes in the unanticipated state of ceased broadcasting exceeds the threshold setting maintained by the command node, and then automatically generate a refined alert notification about the detected environmental anomaly for the shipping container. The refined alert notification has a revised alert level setting based upon whether the updated unresponsive group of the ID nodes includes any from the first set of the ID nodes and whether the updated unresponsive group of the ID nodes includes any from the second set of the ID nodes. The command node may then transmit the refined alert notification to the transceiver unit to initiate the mediation response related to the detected environmental anomaly.

In still another further embodiment of method 3500, the alert notification may identify a targeted mediation recipient. In more detail, a more detailed embodiment may have step 3535 of method 3500 automatically generating the alert notification, which identifies a targeted mediation recipient that is automatically selected by the command node based upon an extent of how much the size of the unresponsive group of ID nodes exceeds a threshold setting and based upon the alert level setting. Such a targeted mediation recipient may comprise, for example, an operator of the transit vehicle that can alter movement of the transit vehicle in response to the alert level setting and/or a logistics crew member of the transit vehicle that can inspect the shipping container in response to the alert level setting.

The targeted mediation recipient, in another example, may be identified as a triggered fire suppression system (e.g., onboard fire suppression system 25010) that is operative to automatically respond to the detected environmental anomaly based upon receipt of the alert notification and based upon the alert level setting. As such, an embodiment of method 3500 may further include the step of automatically dispensing, by the fire suppression system, fire suppression agent into the shipping container upon receipt of a trigger message from the external transceiver of the transit vehicle sent in response to the alert notification. Such a trigger message from the external transceiver may be generated in response to input to the external transceiver from a logistics crew member of the transit vehicle after inspecting the shipping container.

In yet another further embodiment of method 3500, a targeted mediation action may be identified by the alert notification. In more detail, method 3500 may have the command node automatically generate the alert notification, which identifies a targeted mediation action that is automatically selected by the command node based upon an extent of how much the size of the unresponsive group of ID nodes exceeds a threshold setting and based upon the alert level setting. In even more detail, the command node may automatically select the targeted mediation action based upon, for example, how quickly members of the unresponsive group of the ID nodes have changed broadcast behavior to become in the unanticipated state of ceased broadcasting; based upon a pattern of change as members of the unresponsive group of the ID nodes are initially monitored and detected to have changed broadcast behavior to become in the unanticipated state of ceased broadcasting; or based upon where each member of the unresponsive group of the ID nodes is located relative to the shipping container according to context data related to the unresponsive group of the ID nodes.

The targeted mediation action identified by the command node may also depend upon further contextual information and may include, for example, an automatic response request for a triggered fire suppression system on the transit vehicle, a request to change course of the transit vehicle from an existing travel path of the transit vehicle; and/or a request to investigate the shipping container. In more detail, a further embodiment of method 3500 may have the command node receiving vehicle status data from the external transceiver unit associated with the transit vehicle (e.g., external transceiver 24150). In such a situation, the targeted mediation action identified in the automatically generated alert notification may depend upon a state of the transit vehicle as indicated by the vehicle status data and depends upon the alert level setting. Such a state of the transit vehicle may, for example, include a takeoff vehicular status, a cruising vehicle status, a landing vehicular status, and a stationary vehicular status. Thus, when an aircraft is stationary, the vehicle status data provides relevant input, along with the alert level setting, on what the command node may identify as the targeted mediation action. This may be different if the aircraft is taking off, which may have the targeted mediation action being an automatic prompt to abort the landing given the alert level setting so that logistics personnel may inspect the shipping container.

Similarly, the targeted mediation action identified in the automatically generated alert notification may depend upon the status of the shipping container or location data on the current location of the shipping container. Thus, a further embodiment of method 3500 may have the command node accessing container status data maintained by the command node and associated with the shipping container. In such a situation, the targeted mediation action identified by the command node in the automatically generated alert notification may depend upon a state of the shipping container as indicated in the container status data and depends upon the alert level setting. Likewise, another embodiment of method 3500 may have the command node detecting geolocation data related to a current location of the shipping container, so that the targeted mediation action identified by the command node in the automatically generated alert notification may depend upon the current location of the shipping container as indicated in the geolocation data and depends upon the alert level setting.

A further embodiment of method 3500 may have the communication profile maintained on the command node for each of the ID nodes in the first and second set of ID nodes identifying a programmatic setting for a broadcast timing parameter that defines when a respective ID node is programmed to transmit an advertising message in the future. In this way, the command node may use such information when determining when the respective ID node may be anticipated to be broadcasting. As such, the monitoring step 3510 in method 3500 may have the command node monitoring for a shift in broadcast behavior of any of the ID nodes within the first set of the ID nodes and within the second set of the ID nodes away from an anticipated broadcast behavior according to the communication profile maintained on the command node for each of the ID nodes in the first set of the ID nodes and the second set of the ID nodes.

Additionally, method 3500 may also leverage such communication profile information by further instructing each of the responsive ID nodes (i.e., those ID nodes but not in the unresponsive group of the ID nodes but anticipated to be broadcasting) to broadcast at an altered messaging rate different from an initial messaging rate after initially identifying the environmental anomaly so that each of the remaining ID nodes within the first set of the ID nodes and the second set of the ID nodes that are responsive and not included as a member of the unresponsive group of the ID nodes are operative to broadcast using the altered messaging rate compared to prior to when the unresponsive group of the ID nodes was initially identified. This further ability of the command node, as part of method 3500, to set and adjust how quickly the ID nodes are broadcasting enables a level of adjustable data quality rate changes that further enhances detecting and monitoring for an environmental anomaly associated with a shipping container near such ID nodes and related to the command node.

In more detail, method 3500 may have the command node instructing each of the responsive ID nodes (i.e., those ID nodes not in the unresponsive group of the ID nodes but anticipated to be broadcasting) to broadcast at a second messaging rate that exceeds an initial messaging rate after the command node detects the environmental anomaly so that each of the ID nodes within the first set of the ID nodes and the second set of the ID nodes but not included as a member of the unresponsive group of the ID nodes more frequently broadcasts compared to prior to when the unresponsive group of the ID nodes was detected. In a further example, the initial messaging rate may be set as an initial value correlated to an environmental risk associated with at least one of the packages—e.g., one or more packages disposed within the shipping container, one or more packages disposed outside the shipping container but within the transit vehicle having custody of the shipping container, or a combination of packages within the shipping container and disposed outside the shipping container. Further still, an embodiment may have the second messaging rate for the ID nodes not in the unresponsive group of the ID nodes being set at a predetermined higher messaging rate based upon a type of material existing within at least one of a plurality of packages disposed within the shipping container.

A further embodiment of method 3500 may also involve confirming the validity of node communications being monitored so that the command node detections of and responses to an environmental anomaly may be more robust and secure. For example, an embodiment of method 3500 may implement the monitoring step 3510 by having the command node (a) receiving a communication broadcasted from a first of the ID nodes within the first set of the ID nodes; (b) confirming, by the command node, the validity of the received communication; (c) repeating steps (a) and (b), by the command node, for the remainder of the communications received from any of the remaining ones of the ID nodes within the first set of the ID nodes; (d) receiving, by the command node, a communication broadcasted from a first of the ID nodes within the second set of the ID nodes; (e) confirming, by the command node, the validity of the received communication; and (f) repeating steps (d) and (e), by the command node, for the remainder of the communications received from any of the remaining ones of the ID nodes within the second set of the ID nodes. As such, detecting the unresponsive group of the ID nodes may then be based upon the monitoring step for the first set of the ID nodes and upon the monitoring step for the second set of the ID nodes and based upon steps (a)-(f).

Confirming the validity in steps (b) and (e) above may be accomplished in an "active" or "passive" validation process. For example, confirming the validity of the received communication in step (b) may be actively accomplished by having the command node (b1) actively sending an authentication request to the first of the ID nodes within the first set of the ID nodes; and (b2) receiving, by the command node, a validation response from the first of the ID nodes within the first set of the ID nodes that authenticates the communication broadcasted from the first of the ID nodes within the first set of the ID nodes. In like manner, confirming the validity of the received communication in step (e) may be actively accomplished by having the command node (e1) actively sending an authentication request to the first of the ID nodes within the second set of the ID nodes; and (e2) receiving, by the command node, a validation response from the first of the ID nodes within the second set of the ID nodes that authenticates the communication broadcasted from the first of the ID nodes within the second set of the ID nodes.

In a "passive" example, confirming the validity of the received communication in step (b) may be accomplished by having the command node (b1) accessing a validation sequence for the first of the ID nodes within the first set of the ID nodes, where the validation sequence is maintained by the command node and characterizes expected broadcasts from the first of the ID nodes within the first set of the ID nodes; and (b2) determining if the received communication from the first of the ID nodes within the first set of the ID nodes matches a predetermined one of the expected broadcasts from the first of the ID nodes within the first set of the ID nodes according to the validation sequence stored within the command node. The predetermined one of the expected broadcasts may be a rotating value previously received by the command node for the first of the ID nodes within the first set of the ID nodes. In like manner, confirming the validity of the received communication in step (e) may be accomplished by having the command node (e1) accessing a validation sequence for the first of the ID nodes within the second set of the ID nodes, where the validation sequence is maintained by the command node and characterizes expected broadcasts from the first of the ID nodes within the second set of the ID nodes; and (e2) determining if the received communication from the first of the ID nodes within the second set of the ID nodes matches a predetermined one of the expected broadcasts from the first of the ID nodes within the second set of the ID nodes according to the validation sequence stored within the command node. And likewise, the predetermined one of the expected broadcasts may be a rotating value previously received by the command node for the first of the ID nodes within the second set of the ID nodes.

Additional embodiments of method 3500 may involve ID nodes that are particularly disposed and configured relative to the shipping container and the packages on the transit vehicle. For example, each of the ID nodes being monitored may be associated with a respective one of the plurality of packages on the transit vehicle (e.g., as shown in FIG. 31). As such, the ID nodes may travel with their respective package, be affixed to the outside of one of the packages, and/or be integrated as part of one of the packages.

In another example, the ID nodes being monitored as part of method 3500 may involve combinations of ID nodes and packages inside and outside of the shipping container. In more detail, an embodiment of method 3500 may have the first set of the ID nodes monitored by the command node being made up of a first group of ID nodes and a second group of ID nodes, where the first group of ID nodes is associated with a first group of the packages being disposed within the shipping container and where the second group of the ID nodes is not associated with any of the packages being disposed within the shipping container. The second set of the ID nodes monitored by the command node may be made up of a third group of ID nodes and a fourth group of ID nodes, where the third group of ID nodes is associated with a third group of the packages being disposed outside the shipping container and where the fourth group of the ID nodes is not associated with any of the packages being disposed outside the shipping container and on the transit vehicle.

In still another example, the ID nodes monitored within the shipping container may be package ID nodes, while the ID nodes monitored outside the shipping container may be a combination of package ID nodes and non-package ID nodes. In more detail, an embodiment of method 3500 may have the first set of the ID nodes monitored by the command node being associated with a first group of the packages being disposed within the shipping container; and the second set of the ID nodes monitored by the command node may be made up of a third group of ID nodes and a fourth group of ID nodes, where the third group of ID nodes is associated with a third group of the packages being disposed outside the shipping container and where the fourth group of the ID nodes is not associated with any of the packages being disposed outside the shipping container and on the transit vehicle.

In yet another example, the ID nodes monitored within the shipping container may be non-package ID nodes, while the ID nodes monitored outside the shipping container may be a combination of package ID nodes and non-package ID nodes. In more detail, an embodiment of method 3500 may have the first set of the ID nodes monitored by the command node being not associated with any of the packages being disposed within the shipping container; and the second set of the ID nodes monitored by the command node may be made up of a third group of ID nodes and a fourth group of ID nodes, where the third group of ID nodes is associated with a third group of the packages being disposed outside the shipping container and where the fourth group of the ID nodes is not associated with any of the packages being disposed outside the shipping container and on the transit vehicle.

Another exemplary embodiment of method 3500 may have the ID nodes monitored within the shipping container being a combination of package and non-package ID nodes, while the ID nodes monitored outside the shipping container being package ID nodes. In more detail, such an embodiment of method 3500 may have the first set of the ID nodes monitored by the command node being made up of a first group of ID nodes and a second group of ID nodes, where the first group of ID nodes is associated with a first group of the packages being disposed within the shipping container and where the second group of the ID nodes is not associated with any of the packages being disposed within the shipping container; and where the second set of the ID nodes monitored by the command node being associated with a third group of the packages being disposed outside the shipping container and on the transit vehicle.

Further still, another embodiment of method 3500 may have the ID nodes monitored within the shipping container being a combination of package and non-package ID nodes, while the ID nodes monitored outside the shipping container being non-package ID nodes. In more detail, such an embodiment of method 3500 may have the first set of the ID nodes monitored by the command node being made up of a first group of ID nodes and a second group of ID nodes, where the first group of ID nodes is associated with a first group of the packages being disposed within the shipping container and where the second group of the ID nodes is not associated with any of the packages being disposed within the shipping container; and where the second set of the ID nodes monitored by the command node being not associated with any of the packages being disposed outside the shipping container and on the transit vehicle.

Those skilled in the art will appreciate that exemplary method 3500 as disclosed and explained above in various embodiments may be implemented using an exemplary improved monitoring system for detecting an environmental anomaly in a shipping container. Such a system may include, for example, a command node that interactively monitors ID nodes disposed within and external to the shipping container and reports an alert notification related to the environmental anomaly to cause different types of mediation responses such as that explained above with reference to FIGS. 31-34 and its exemplary elements. In more detail, such an embodiment of an improved monitoring system, as explained above relative to operations according to method 3500 and with elements from FIGS. 31-34, uses at least ID nodes disposed within and external to the shipping container (e.g., ID nodes 24120a-24120i as they appear in the exemplary configurations shown in FIGS. 31, 33, and 34) running one or more ID node monitoring program code as part of node control and management code 325 to control operations of the ID nodes to generate and broadcast wireless communications, as well as a command node mounted to the shipping container (e.g., command node 24160 in FIGS. 31, 33, and 34) running one or more parts of CN control & management code 26425 to control the operations of the command node as part of monitoring for and detecting an environmental anomaly using ID nodes anticipated to be broadcasting within and external to the shipping container as well as generating the alert notification and transmitting that notification to the external transceiver unit to initiate a type of mediation response (such as triggering onboard fire suppression system 25010). Such code may be stored on a non-transitory computer-readable medium, such as memory storage 26415 on command node 24160 (an embodiment of exemplary command node 26000) and memory storage 315 on ID nodes 24120a-24120i (embodiments of exemplary ID node 120a). Thus, when executing such code, the ID nodes and the command node may be operative to perform operations or steps from the exemplary methods disclosed above, including method 3500 and variations of that method. Further system embodiments may also include the onboard fire suppression system as a component that is caused to expel fire suppression agent into the command node's shipping container in response to the alert notification (directly) or in response to an activation control signal from the external transceiver generated as a result of the external transceiver receiving the alert notification from the command node.

Further method and system embodiments may provide further detail on situations where the command node itself may operate as a type of transceiver to directly cause initiation of a mediation response from the onboard fire suppression system. As described above relative to FIGS. 32A-32C, exemplary fire suppression system 25010 may be activated directly by the command node 24160 of a shipping container 24300a or indirectly by the command node 24160 via the alert notification sent to the external transceiver 24150, which then sends an activation control signal to exemplary fire suppression system 25010. Thus, embodiments may have command node 24160 programmed to send the alert notification directly to onboard systems (such as a display in a cockpit or logistics support area of a transit vehicle 24200, or an onboard fire suppression system on the transit vehicle 24200) without needing to involve an intermediary separate external transceiver (e.g., external transceiver 24150). Further embodiments may deploy a built-in communication interface as part of other transit vehicle electronics (e.g., a cockpit disposed transceiver) that may operate as a type of external transceiver with which to communicate with the command node 24160 of a particular shipping container 24300. Additional embodiments may also implement transceiver 24150 as being internal to the shipping container or may have the command node and internal transceiver that initiates the mediation responsive action being the same node-based transceiver device (i.e., the command node 24160 operates as the external transceiver and generates the alert notification to directly initiate the mediation responsive action).

Additional method and system embodiments may have the shipping container's command node more particularly and selectively transmit the alert notification to different targeted mediation recipients based on the alert level setting (e.g., to the external transceiver when the alert level setting is at a predetermined alert level to initiate a first mediation response related to the detected environmental anomaly, and to the onboard fire suppression system on the transit vehicle when the alert level setting is above the predetermined alert level to directly cause the onboard fire suppression system to automatically dispense a fire suppressant agent within the shipping container as a second mediation response related to the detected environmental anomaly. In these embodiments, this type of automatic selective mediation response may further enhance the contextual rapid response to any detected environmental anomaly with the shipping container.

Figure 36:
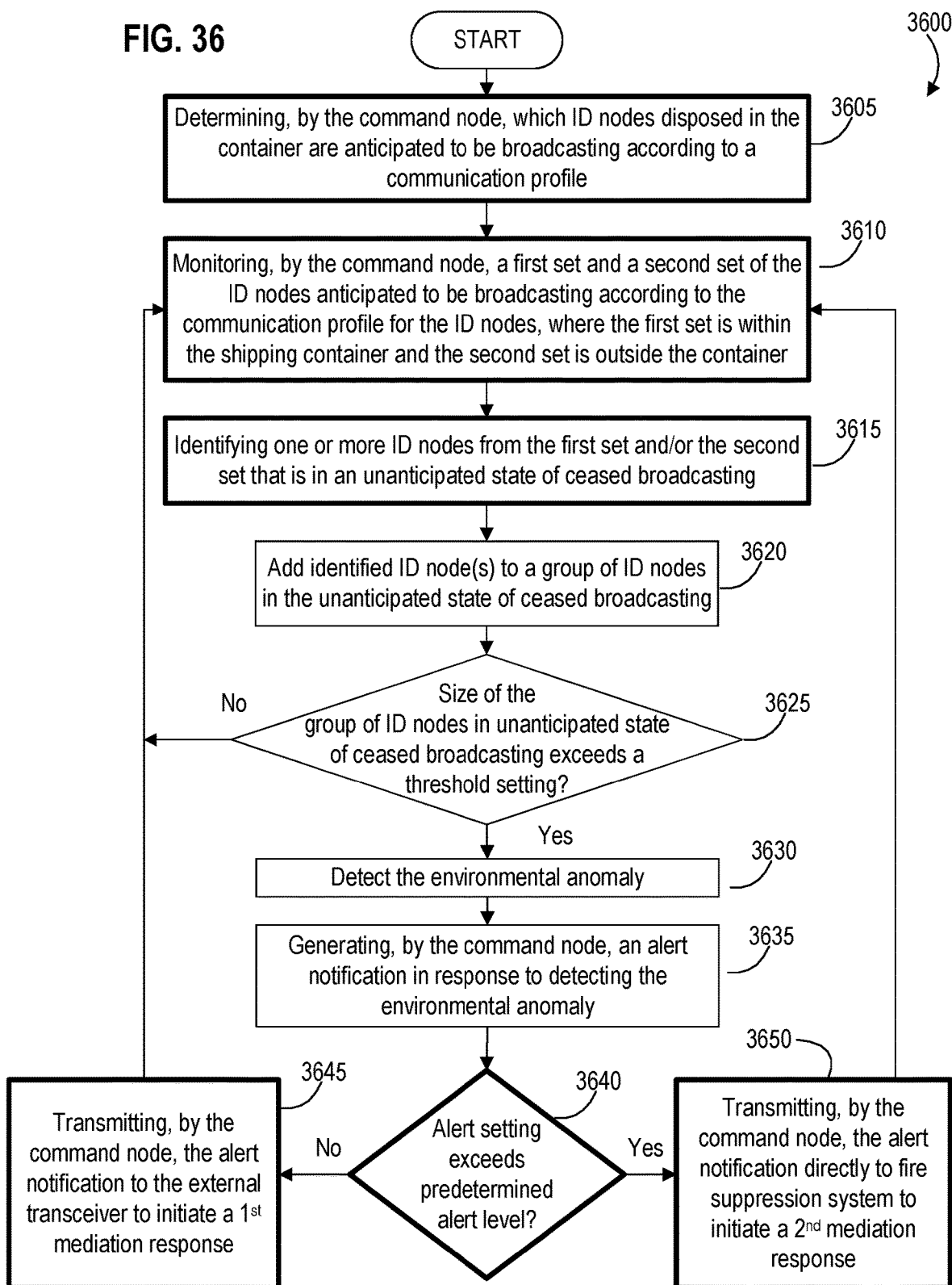
FIG. 36 is a flow diagram illustrating an exemplary method for monitoring for an environmental anomaly related to a shipping container using a wireless node network having at least a command node associated with the shipping container, ID nodes within the shipping container and outside the shipping container, and an onboard fire suppression system and external transceiver in accordance with an embodiment of the invention.

FIG. 36 is a flow diagram illustrating an exemplary method for monitoring for an environmental anomaly related to a shipping container using a wireless node network having at least a command node associated with the shipping container, ID nodes within the shipping container and outside the shipping container, and an onboard fire suppression system and external transceiver in accordance with an embodiment of the invention.

In particular, FIG. 36 describes an exemplary improved method 3600 for monitoring for an environmental anomaly related to a shipping container (e.g., shipping container 24300a) using a wireless node network. The shipping container involved in method 3600 is being transported on a transit vehicle (e.g., transit vehicle 24200—such as an aircraft, railway conveyance, a maritime vessel, or a roadway conveyance) that also transports multiple packages (e.g., packages 24400a-24400h as shown in FIG. 31). The wireless node network involved in method 3600 has at least a plurality of ID nodes (e.g., ID node 24120a-24120h as shown in FIG. 31), a command node associated with the shipping container (e.g., command node 241260 associated with and mounted to shipping container 24300a), and an onboard fire suppression system for the shipping container (e.g., fire suppression system 25010). The command node used as part of method 3600 may, for example, be implemented as a container node integrated as part of the shipping container or a self-locating master node implemented separately from the shipping container. The ID nodes used as part of method 3600 include a first set of the ID nodes disposed within the shipping container (e.g., ID nodes 24120c-24120e) and a second set of the ID nodes disposed outside the shipping container (e.g., ID nodes 24120a, 24120b, and 24120f-24120h). In this configuration, the command node involved in method 3600 is operative to communicate with each of the ID nodes in the first set of the ID nodes and the second ID nodes, the onboard fire suppression system, and an external transceiver unit associated with the transit vehicle (e.g., external transceiver 24150 on transit vehicle 24200). Notably, the embodiment of method 3600 is similar to method 3500 with the exception of the responsive actions taken by the command node when generating and transmitting the alert notification.

In more detail and referring now to FIG. 36, exemplary method 3600 begins at step 3605 with the command node determining which of the ID nodes disposed in and near the shipping container are anticipated to be broadcasting according to a communication profile on what ID nodes are within and located near the shipping container. For example, command node 24160 may reference profile data 430 (as well as location data and/or association data) that may indicate what ID nodes are within shipping container 24300a or loaded within transit vehicle storage 24205. Using this information, command node 24160 may initiate communication with any ID nodes within the command node's transmission and reception range (e.g., what ID nodes may receive communications from command node 24160 and which ID nodes respond to such communications from the command node 24160). Those ID nodes that may establish initial communications with command node 24160—i.e., ID nodes within shipping container 24300a and outside of 24300a—may be identified as potential ID nodes to be monitored as part of the embodiment of method 3600 as long as the communication profile information on each of those potential ID nodes indicates the particular ID node is anticipated to be broadcasting so that the command node 24160 is able to count on communications from those ID nodes anticipated to be broadcasting under normal conditions.

At step 3610, method 3600 continues with the command node monitoring for an unanticipated state of ceased broadcasting from any of the ID nodes within the first set of the ID nodes disposed within the shipping container according to a communication profile for each the ID nodes in the first set of the ID nodes maintained on the command node, as well as monitoring for an unanticipated state of ceased broadcasting from any of the ID nodes within the second set of the ID nodes disposed outside the shipping container according to a communication profile for each the ID nodes in the second set of the ID nodes. For example, command node 24160 shown in FIG. 31 may monitor the first set of ID nodes (e.g., ID nodes 24120c-24120e disposed within shipping container 24300a) as well as monitor the second set of ID nodes (e.g., ID nodes 24120a, 24120b, and 24120f-24120h disposed outside shipping container 24300a). Command node 24160 would be monitoring those ID nodes in particular as part of step 3510 because the communication profile data on each of those nodes (as indicated in profile data 430 on command node 24160) indicates they are anticipated to be broadcasting.

At step 3615, method 3600 continues by identifying one or more ID nodes from the first set and/or second set of the monitored ID nodes as being unresponsive or in an unanticipated state of ceased broadcasting. In more detail, this may have the command node detecting an unresponsive group of the ID nodes to be in the unanticipated state of ceased broadcasting based upon the monitoring step for the first set of the ID nodes and upon the monitoring step for the second set of the ID nodes. The command node, such as command node 24160, may then determine if the unresponsive group of the ID nodes includes any from the first set of the ID nodes (i.e., those monitored ID nodes disposed within the shipping container) and if the unresponsive group of the ID nodes includes any from the second set of the ID nodes (i.e., those monitored ID nodes disposed external to the shipping container).

At step 3620, method 3600 continues with the command node adding any of the identified ID nodes from step 3615 to a group of ID nodes in the unanticipated state of ceased broadcasting. Then, at decision step 3625, method 3600 has the command node determining if the size of the group of ID nodes in the unanticipated state of ceased broadcasting exceeds a threshold setting maintained by the command node. If so, method 3600 proceeds from step 3625 directly to step 3630 where the command node detects the environmental anomaly for the shipping container because the size of the identified or otherwise sensed unresponsive group of the ID nodes in the unanticipated state of ceased broadcasting exceeds the threshold setting. If not, method 3600 proceeds from step 3625 back to step 3610. In a further embodiment of method 3600, the threshold setting maintained by the command node that is used as part of step 3625 may be set by the command node, for example, depending on a combined count of the ID nodes monitored in the first set of the ID nodes and the second set of the ID nodes; depending on a material characteristic of what is contained in at least one of a plurality of packages disposed within the shipping container; and/or depending on a material characteristic of what is contained in at least one of the packages disposed outside the shipping container but on the transit vehicle having custody of the shipping container.

At step 3635, method 3600 proceeds with the command node automatically generating an alert notification about the detected environmental anomaly for the shipping container, where the alert notification has an alert level setting based upon whether the unresponsive group of the ID nodes includes any from the first set of the ID nodes and whether the unresponsive group of the ID nodes includes any from the second set of the ID nodes. In one example, the alert level setting may be implemented by the command node an initial degree of alert when the unresponsive group of the ID nodes includes only ID nodes from the second set of the ID nodes disposed outside the shipping container. As such, the generated alert notification about the detected environmental anomaly having the initial degree of alert may be generated as an automatic warning about a potential fire outside of the shipping container and/or an automatic warning about a potential fire within the shipping container.

In another example, the alert level setting may be implemented by the command node as an enhanced degree of alert when the unresponsive group of the ID nodes includes only ID nodes from the first set of the ID nodes disposed within the shipping container. As such, the generated alert notification about the detected environmental anomaly having the enhanced degree of alert may be generated as an automatic warning about a fire inside of the shipping container as the enhanced degree of alert reflects a higher confidence level that the detected environmental anomaly is the fire inside of the shipping container.

In still another example, the alert level setting may be implemented by the command node as a high degree of alert when the unresponsive group of the ID nodes includes ID nodes from both the first set of the ID nodes disposed within the shipping container and the second set of the ID nodes disposed outside the shipping container. As such, the generated alert notification about the detected environmental anomaly having the high degree of alert may be generated as an automatic warning about an explosion involving contents of the shipping container, the high degree of alert reflecting a higher confidence level that the detected environmental anomaly involves at least a spreading fire inside of the shipping container.

At steps 3640-3650, exemplary method 3600 differs from method 3500 described above in how the command node functions to respond to the detected environmental anomaly relative to initiating different kinds of mediation responses based upon the alert level setting. In particular, method 3600 proceeds to decision step 3640 where the command node determines if the alert level setting exceeds a predetermined alert level (such as the initial degree of alert described above). If not, step 3640 proceeds to step 3645 where the command node transmits the alert notification to the external transceiver on the transit vehicle to initiate a first mediation response related to the detected environmental anomaly before method 3600 returns to step 3610 for continued monitoring for unresponsive ID nodes anticipated to be broadcasting. But if so, step 3640 proceeds directly to step 3650 where the command node transmits the alert notification directly to the onboard fire suppression system on the transit vehicle (given the alert level setting is above the predetermined alert level) to directly cause the onboard fire suppression system to automatically dispense a fire suppressant agent within the shipping container as a second mediation response related to the detected environmental anomaly. This type of operation of method 3600 allows for a tiered approach that has the command node being configured and operative to provide direct and immediate responsive initiation of the onboard fire suppression system (rather than relying on a relayed message through the external transceiver on the transit vehicle) under certain alert level settings (based on how the environmental anomaly is detected and what ID nodes have become unresponsive within and external to the shipping container).

In further embodiments, method 3600 may include further steps to refine and update for known movement of ID nodes outside of the shipping container. In more detail, a further embodiment of method 3600 may also include having the command node first requesting context data related to the ID nodes from the second set of the ID nodes that are in the unresponsive group of the ID nodes (e.g., requesting such context data from onboard storage memory in the command node, from the external transceiver, or from a remote server in communication with the external transceiver). This requested context data (e.g., context data 26560) provides information on an anticipated location of the ID nodes from the second set of the ID nodes (those outside the shipping container) that are in the unresponsive group of the ID nodes. The further embodiment of method 3600 then has the command node predicting movement of any of the ID nodes from the second set of the ID nodes that are in the unresponsive group of the ID nodes where the prediction operation is based upon whether the anticipated location of any of the ID nodes from the second set of the ID nodes within the unresponsive group of the ID nodes is beyond a reception range for the command node as disposed relative to the shipping container. The command node may then update the unresponsive group of the ID nodes to remove any of the ID nodes from the second set of the ID nodes that are (a) initially detected to be within the unresponsive group of the ID nodes and (b) that are predicted as moved beyond the reception range for the command node based upon the requested context data. The command node then may re-identify the environmental anomaly when the size of the updated unresponsive group of the ID nodes in the unanticipated state of ceased broadcasting exceeds the threshold setting maintained by the command node, and then may automatically generate a refined alert notification about the detected environmental anomaly for the shipping container. Such a refined alert notification has a revised alert level setting based upon whether the updated unresponsive group of the ID nodes includes any from the first set of the ID nodes and whether the updated unresponsive group of the ID nodes includes any from the second set of the ID nodes. This further embodiment of method 3600 then may have the command node transmitting the refined alert notification to the external transceiver on the transit vehicle when the alert level setting is at the predetermined alert level to initiate a third mediation response related to the detected environmental anomaly (e.g., a mediation response to cause the external transceiver to generate a warning for an operator of the transit vehicle based upon the refined alert notification), and transmitting the refined alert notification directly to the onboard fire suppression system on the transit vehicle when the alert level setting is above the predetermined alert level to directly cause the onboard fire suppression system to continue to dispense the fire suppressant agent within the shipping container as part of the second mediation response related to the detected environmental anomaly.

In another further embodiment of method 3600, the exemplary method may include further steps to refine and update for known movement of the shipping container away from ID nodes external to the shipping container. In more detail, such a further embodiment of method 3600 may have the command node requesting context data related to the ID nodes from the second set of the ID nodes that are in the unresponsive group of the ID nodes and context data about the shipping container (e.g., requesting such context data from onboard storage memory in the command node, from the external transceiver, or from a remote server in communication with the external transceiver). Such requested data (e.g., context data 26560 and location data 455) provides information on an anticipated location of the ID nodes from the second set of the ID nodes that are in the unresponsive group of the ID nodes and an anticipated location of the shipping container. The method may proceed with predicting movement, by the command node, of the shipping container away from any of the ID nodes from the second set of the ID nodes that are in the unresponsive group of the ID nodes. Such predicted movement is based upon whether the anticipated location of any of the ID nodes from the second set of the ID nodes within the unresponsive group of the ID nodes differs from the anticipated location of the shipping container according to the requested context data. The method may then have the command node updating the unresponsive group of ID nodes to remove any of the ID nodes from the second set of the ID nodes that are (a) initially detected to be within the unresponsive group of the ID nodes and (b) that are beyond a reception range for the command node given the predicted movement of the shipping container away from any of the ID nodes from the second set of the ID nodes that are in the unresponsive group of the ID nodes. As part of this further embodiment of method 3600, the command node may then re-identify the environmental anomaly when the size of the updated unresponsive group of the ID nodes in the unanticipated state of ceased broadcasting exceeds the threshold setting maintained by the command node, and then automatically generate a refined alert notification about the detected environmental anomaly for the shipping container. The refined alert notification has a revised alert level setting based upon whether the updated unresponsive group of the ID nodes includes any from the first set of the ID nodes and whether the updated unresponsive group of the ID nodes includes any from the second set of the ID nodes. The command node may then transmit the refined alert notification to the external transceiver on the transit vehicle based when the alert level setting is at the predetermined alert level to initiate a third mediation response related to the detected environmental anomaly (e.g., a mediation response that causes the external transceiver to generate a warning for an operator of the transit vehicle based upon the refined alert notification on a display coupled to or integrated as part of the external transceiver), and transmit the refined alert notification directly to the onboard fire suppression system on the transit vehicle when the alert level setting is above the predetermined alert level to directly cause the onboard fire suppression system to continue to dispense the fire suppressant agent within the shipping container as part of the second mediation response related to the detected environmental anomaly.

In still another further embodiment of method 3600, the alert notification may identify a targeted mediation recipient. In more detail, a more detailed embodiment may have step 3635 of method 3500 automatically generating the alert notification, which identifies a targeted mediation recipient that is automatically selected by the command node based upon an extent of how much the size of the unresponsive group of ID nodes exceeds a threshold setting and based upon the alert level setting. Such a targeted mediation recipient may comprise, for example, an operator of the transit vehicle that can alter movement of the transit vehicle in response to the alert level setting and/or a logistics crew member of the transit vehicle that can inspect the shipping container in response to the alert level setting. Thus, the first mediation response initiated in step 3645 may be responsively causing the external transceiver to prompt the operator of the transit vehicle to alter movement of the transit vehicle in response to the alert level setting or responsively causing the external transceiver to prompt the logistics crew member of the transit vehicle to inspect the shipping container in response to the alert level setting.

In more detail, step 3635 of method 3600 may be implemented by having the command node's automatically generated alert notification identifying the first mediation response based upon an extent of how much the size of the unresponsive group of ID nodes exceeds the threshold setting and based upon the alert level setting. In this situation, the first mediation response may be automatically selected by the command node based upon, for example, how quickly members of the unresponsive group of the ID nodes have changed broadcast behavior to become in the unanticipated state of ceased broadcasting; based upon a pattern of change as members of the unresponsive group of the ID nodes are initially monitored and detected to have changed broadcast behavior to become in the unanticipated state of ceased broadcasting; and/or based upon where each member of the unresponsive group of the ID nodes is located relative to the shipping container according to context data related to the unresponsive group of the ID nodes.

The targeted mediation action identified by the command node may also depend upon further contextual information. In more detail, a further embodiment of method 3500 may have the command node receiving vehicle status data from the external transceiver unit associated with the transit vehicle (e.g., external transceiver 24150). In such a situation, the first mediation response in step 3645 may depend upon a state of the transit vehicle as indicated by the vehicle status data and depends upon the alert level setting. Such a state of the transit vehicle may, for example, include a takeoff vehicular status, a cruising vehicle status, a landing vehicular status, and a stationary vehicular status. Thus, when an aircraft is stationary, the vehicle status data provides relevant input, along with the alert level setting, on what the command node may identify as the targeted mediation action. This may be different if the aircraft is taking off, which may have the targeted mediation action being an automatic prompt to abort the landing given the alert level setting so that logistics personnel may inspect the shipping container.

Similarly, the first mediation response may depend upon the status of the shipping container or location data on the current location of the shipping container. Thus, a further embodiment of method 3600 may have the command node accessing container status data maintained by the command node and associated with the shipping container. In such a situation, the first mediation response may depend upon a state of the shipping container as indicated in the container status data and depends upon the alert level setting. Likewise, another embodiment of method 3600 may have the command node detecting geolocation data related to a current location of the shipping container, so that the first mediation response depends upon the current location of the shipping container as indicated in the geolocation data and depends upon the alert level setting.

A further embodiment of method 3600 may have the communication profile maintained on the command node for each of the ID nodes in the first and second set of ID nodes identifying a programmatic setting for a broadcast timing parameter that defines when a respective ID node is programmed to transmit an advertising message in the future. In this way, the command node may use such information when determining when the respective ID node may be anticipated to be broadcasting. As such, the monitoring step 3610 in method 3600 may have the command node monitoring for a shift in broadcast behavior of any of the ID nodes within the first set of the ID nodes and within the second set of the ID nodes away from an anticipated broadcast behavior according to the communication profile maintained on the command node for each of the ID nodes in the first set of the ID nodes and the second set of the ID nodes.

Additionally, method 3600 may also leverage such communication profile information by further instructing each of the responsive ID nodes (i.e., those ID nodes not in the unresponsive group of the ID nodes but anticipated to be broadcasting) to broadcast at an altered messaging rate different from an initial messaging rate after initially identifying the environmental anomaly so that each of the remaining ID nodes within the first set of the ID nodes and the second set of the ID nodes that are responsive and not included as a member of the unresponsive group of the ID nodes are operative to broadcast using the altered messaging rate compared to prior to when the unresponsive group of the ID nodes was initially identified. This further ability of the command node, as part of method 3500, to set and adjust how quickly the ID nodes are broadcasting enables a level of adjustable data quality rate changes that further enhances detecting and monitoring for an environmental anomaly associated with a shipping container near such ID nodes and related to the command node.

In more detail, method 3600 may have the command node instructing each of the responsive ID nodes (i.e., those ID nodes not in the unresponsive group of the ID nodes but anticipated to be broadcasting) to broadcast at a second messaging rate that exceeds an initial messaging rate after the command node detects the environmental anomaly in step 3630 so that each of the ID nodes within the first set of the ID nodes and the second set of the ID nodes but not included as a member of the unresponsive group of the ID nodes more frequently broadcasts compared to prior to when the unresponsive group of the ID nodes was detected. In a further example, the initial messaging rate may be set as an initial value correlated to an environmental risk associated with at least one of the packages—e.g., one or more packages disposed within the shipping container, one or more packages disposed outside the shipping container but within the transit vehicle having custody of the shipping container, or a combination of packages within the shipping container and disposed outside the shipping container. Further still, an embodiment may have the second messaging rate for the ID nodes not in the unresponsive group of the ID nodes being set at a predetermined higher messaging rate based upon a type of material existing within at least one of a plurality of packages disposed within the shipping container.

A further embodiment of method 3600 may also involve confirming the validity of node communications being monitored as part of step 3610 so that the command node detections of and responses to an environmental anomaly may be more robust and secure. For example, an embodiment of method 3600 may implement the monitoring step 3610 by having the command node (a) receiving a communication broadcasted from a first of the ID nodes within the first set of the ID nodes; (b) confirming, by the command node, the validity of the received communication; (c) repeating steps (a) and (b), by the command node, for the remainder of the communications received from any of the remaining ones of the ID nodes within the first set of the ID nodes; (d) receiving, by the command node, a communication broadcasted from a first of the ID nodes within the second set of the ID nodes; (e) confirming, by the command node, the validity of the received communication; and (f) repeating steps (d) and (e), by the command node, for the remainder of the communications received from any of the remaining ones of the ID nodes within the second set of the ID nodes. As such, detecting the unresponsive group of the ID nodes may then be based upon the monitoring step for the first set of the ID nodes and upon the monitoring step for the second set of the ID nodes and based upon steps (a)-(f).

Confirming the validity in steps (b) and (e) above may be accomplished in an "active" or "passive" validation process. For example, confirming the validity of the received communication in step (b) may be actively accomplished by having the command node (b1) actively sending an authentication request to the first of the ID nodes within the first set of the ID nodes; and (b2) receiving, by the command node, a validation response from the first of the ID nodes within the first set of the ID nodes that authenticates the communication broadcasted from the first of the ID nodes within the first set of the ID nodes. In like manner, confirming the validity of the received communication in step (e) may be actively accomplished by having the command node (e1) actively sending an authentication request to the first of the ID nodes within the second set of the ID nodes; and (e2) receiving, by the command node, a validation response from the first of the ID nodes within the second set of the ID nodes that authenticates the communication broadcasted from the first of the ID nodes within the second set of the ID nodes.

In a "passive" example, confirming the validity of the received communication in step (b) may be accomplished by having the command node (b1) accessing a validation sequence for the first of the ID nodes within the first set of the ID nodes, where the validation sequence is maintained by the command node and characterizes expected broadcasts from the first of the ID nodes within the first set of the ID nodes; and (b2) determining if the received communication from the first of the ID nodes within the first set of the ID nodes matches a predetermined one of the expected broadcasts from the first of the ID nodes within the first set of the ID nodes according to the validation sequence stored within the command node. The predetermined one of the expected broadcasts may be a rotating value previously received by the command node for the first of the ID nodes within the first set of the ID nodes. In like manner, confirming the validity of the received communication in step (e) may be accomplished by having the command node (e1) accessing a validation sequence for the first of the ID nodes within the second set of the ID nodes, where the validation sequence is maintained by the command node and characterizes expected broadcasts from the first of the ID nodes within the second set of the ID nodes; and (e2) determining if the received communication from the first of the ID nodes within the second set of the ID nodes matches a predetermined one of the expected broadcasts from the first of the ID nodes within the second set of the ID nodes according to the validation sequence stored within the command node. And likewise, the predetermined one of the expected broadcasts may be a rotating value previously received by the command node for the first of the ID nodes within the second set of the ID nodes.

Like method 3500, additional embodiments of method 3600 may involve ID nodes that are particularly disposed and configured relative to the shipping container and the packages on the transit vehicle. For example, each of the ID nodes being monitored may be associated with a respective one of the plurality of packages on the transit vehicle (e.g., as shown in FIG. 31). As such, the ID nodes may travel with their respective package, be affixed to the outside of one of the packages, and/or be integrated as part of one of the packages.

In another example, the ID nodes being monitored as part of method 3500 may involve combinations of ID nodes and packages inside and outside of the shipping container. In more detail, an embodiment of method 3600 may have the first set of the ID nodes monitored by the command node being made up of a first group of ID nodes and a second group of ID nodes, where the first group of ID nodes is associated with a first group of the packages being disposed within the shipping container and where the second group of the ID nodes is not associated with any of the packages being disposed within the shipping container. The second set of the ID nodes monitored by the command node may be made up of a third group of ID nodes and a fourth group of ID nodes, where the third group of ID nodes is associated with a third group of the packages being disposed outside the shipping container and where the fourth group of the ID nodes is not associated with any of the packages disposed outside the shipping container and on the transit vehicle.

In still another example, the ID nodes monitored within the shipping container may be package ID nodes, while the ID nodes monitored outside the shipping container may be a combination of package ID nodes and non-package ID nodes. In more detail, an embodiment of method 3600 may have the first set of the ID nodes monitored by the command node being associated with a first group of the packages being disposed within the shipping container; and the second set of the ID nodes monitored by the command node may be made up of a third group of ID nodes and a fourth group of ID nodes, where the third group of ID nodes is associated with a third group of the packages being disposed outside the shipping container and where the fourth group of the ID nodes is not associated with any of the packages being disposed outside the shipping container and on the transit vehicle.

In yet another example, the ID nodes monitored within the shipping container may be non-package ID nodes, while the ID nodes monitored outside the shipping container may be a combination of package ID nodes and non-package ID nodes. In more detail, an embodiment of method 3600 may have the first set of the ID nodes monitored by the command node being not associated with any of the packages being disposed within the shipping container; and the second set of the ID nodes monitored by the command node may be made up of a third group of ID nodes and a fourth group of ID nodes, where the third group of ID nodes is associated with a third group of the packages being disposed outside the shipping container and where the fourth group of the ID nodes is not associated with any of the packages being disposed outside the shipping container and on the transit vehicle.

Another exemplary embodiment of method 3600 may have the ID nodes monitored within the shipping container being a combination of package and non-package ID nodes, while the ID nodes monitored outside the shipping container being package ID nodes. In more detail, such an embodiment of method 3600 may have the first set of the ID nodes monitored by the command node being made up of a first group of ID nodes and a second group of ID nodes, where the first group of ID nodes is associated with a first group of the packages being disposed within the shipping container and where the second group of the ID nodes is not associated with any of the packages being disposed within the shipping container; and where the second set of the ID nodes monitored by the command node being associated with a third group of the packages being disposed outside the shipping container and on the transit vehicle.

Further still, another embodiment of method 3600 may have the ID nodes monitored within the shipping container being a combination of package and non-package ID nodes, while the ID nodes monitored outside the shipping container being non-package ID nodes. In more detail, such an embodiment of method 3600 may have the first set of the ID nodes monitored by the command node being made up of a first group of ID nodes and a second group of ID nodes, where the first group of ID nodes is associated with a first group of the packages being disposed within the shipping container and where the second group of the ID nodes is not associated with any of the packages being disposed within the shipping container; and where the second set of the ID nodes monitored by the command node being not associated with any of the packages being disposed outside the shipping container and on the transit vehicle.

Those skilled in the art will appreciate that exemplary method 3600 as disclosed and explained above in various embodiments may be implemented using an exemplary improved monitoring system for detecting an environmental anomaly in a shipping container. Such a system may include, for example, at least a command node that interactively monitors ID nodes disposed within and external to the shipping container and reports an alert notification related to the environmental anomaly to cause different types of mediation responses by an external transceiver on the transit vehicle and an onboard fire suppression system as that explained above with reference to FIGS. 31-34 and its exemplary elements. In more detail, such an embodiment of an improved monitoring system, as explained above relative to operations according to method 3600 and with elements from FIGS. 31-34, uses at least ID nodes disposed within and external to the shipping container (e.g., ID nodes 24120a-24120i as they appear in the exemplary configurations shown in FIGS. 31, 33, and 34) running one or more ID node monitoring program code as part of node control and management code 325 to control operations of the ID nodes to generate and broadcast wireless communications, as well as a command node mounted to the shipping container (e.g., command node 24160 in FIGS. 31, 33, and 34) running one or more parts of CN control & management code 26425 to control the operations of the command node as part of monitoring for and detecting an environmental anomaly using ID nodes anticipated to be broadcasting within and external to the shipping container as well as generating the alert notification and transmitting that notification to the external transceiver unit to initiate a type of mediation response (such as triggering onboard fire suppression system 25010). Such code may be stored on a non-transitory computer-readable medium, such as memory storage 26415 on command node 24160 (an embodiment of exemplary command node 26000) and memory storage 315 on ID nodes 24120a-24120i (embodiments of exemplary ID node 120a). Thus, when executing such code, the ID nodes and the command node may be operative to perform operations or steps from the exemplary methods disclosed above, including method 3600 and variations of that method.

A more detailed system embodiment similar to that described above (e.g., that has ID nodes and a command node performing operations or steps from the exemplary methods disclosed above, including methods 3500 and 3600 and variations of those methods) may include the fire suppression system as part of the system itself along with the command node that monitors ID nodes within and external to the shipping container. Further detailed system embodiments may also include the external transceiver as a further element that interacts with the system's command node and operates to initiate different types of mediation responses at the direction of the command node.

Monitoring for an Environmental Anomaly via Selectively Assigned ID Nodes

Additional embodiments may detect an environmental anomaly relative to a shipping container where an exemplary command node (e.g., ULD container node that is essentially a master node that may not have location circuitry for self-locating capabilities, a mobile master node deployed on or as part of the shipping container that has location circuitry for self-locating capabilities) may selectively choose or assign which of the available ID nodes are to be monitored. In other words, embodiments may have a container's command node adaptively identify, choose, or otherwise assign a subset of the available ID nodes to function as dedicated monitor beacons that are deployed within the shipping container and monitored as part of detecting an environmental anomaly related to the shipping container (e.g., a condition of the container and/or package(s) or assets within the container). In general, the available ID nodes that may be assigned may be associated with a particular package or packages within the container (e.g., traveling with the package, attached to the package, inserted within the package, integrated as part of the package, and the like), may be associated with part of the shipping container (e.g., attached to a wall, affixed to a ceiling, integrated into the floor or base of the container, and the like), or may be separately disposed within the container without being fixed to or part of the container or a package/asset within the container. As discussed in the embodiments described herein, the task of selectively assigning such a subset of ID nodes may be based upon information about the ID node itself (e.g., the node's location within the container, whether the node is on a predetermined list of ID nodes to use as dedicated beacon monitors, whether the node is passively detected to be broadcasting by the container's command node); information regarding an item, asset, or package with which the ID node may be associated (e.g., shipping information indicating the type of item or asset being shipped in a package associated with an ID node, context data or location information (a loading scheme, pattern, or plan) indicating the location of a package associated with an ID node). Further, as described in more detail below, the selective assignment of which ID nodes are used as the subset of ID nodes to be monitored may change over time given that what may be stored within the container can change as a shipping container loaded, unloaded, and/or re-arranged in transit or at any time, and ID nodes within the container may change over time (e.g., ID nodes that are attached to the shipping container may be replaced, ID nodes with packages may be removed from the container or added to the container). As explained in more detail below, FIG. 37A through FIG. 40 provide further details on such embodiments that build upon the disclosure above.

Figure 37A:
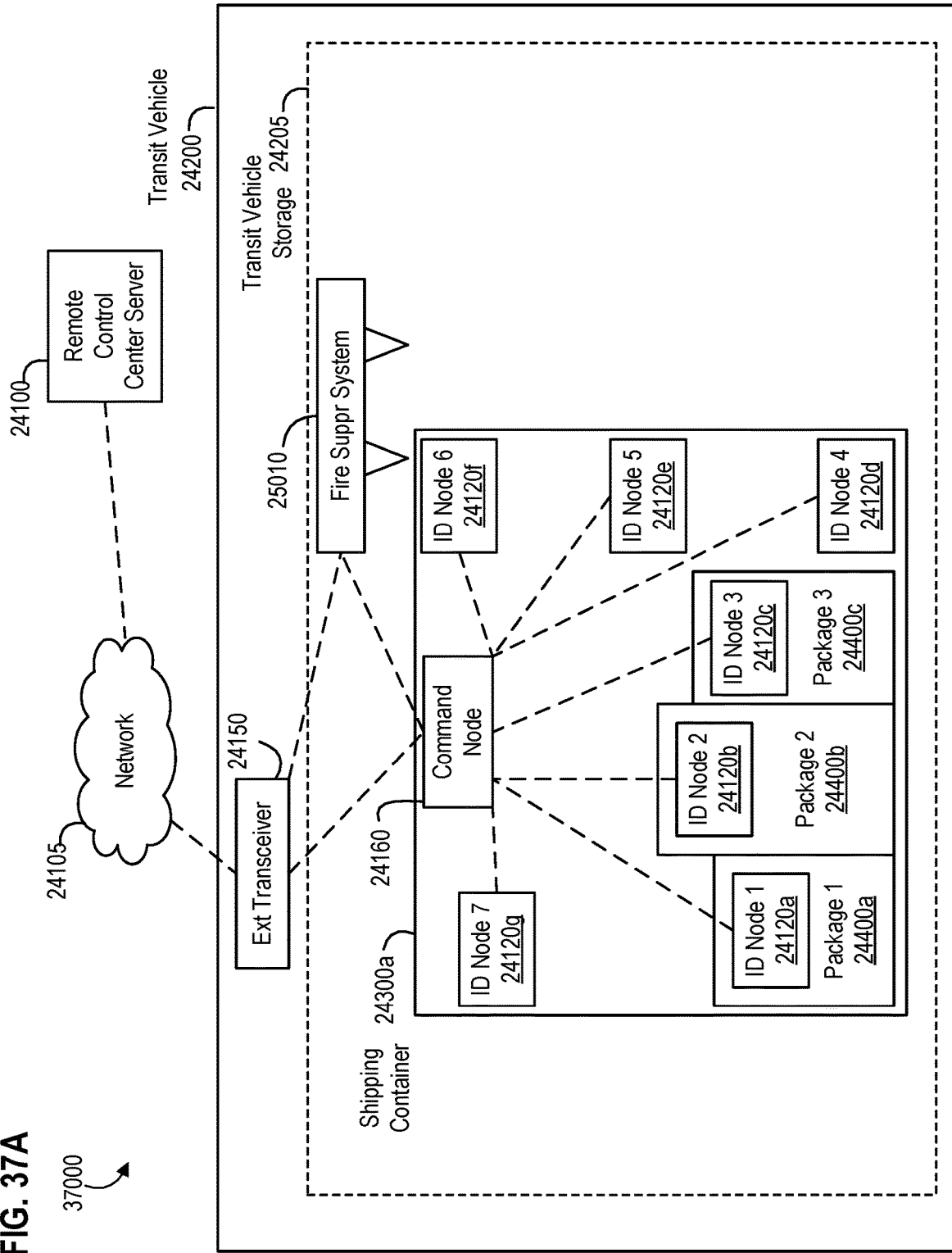
FIGS. 37A-37B are diagrams of an exemplary shipping container that leverages an exemplary wireless node network for detecting environmental anomalies associated with the shipping container using a command node mounted to the shipping container and selectively assigned ID nodes within the shipping container in accordance with an embodiment of the invention.
Figure 37B:
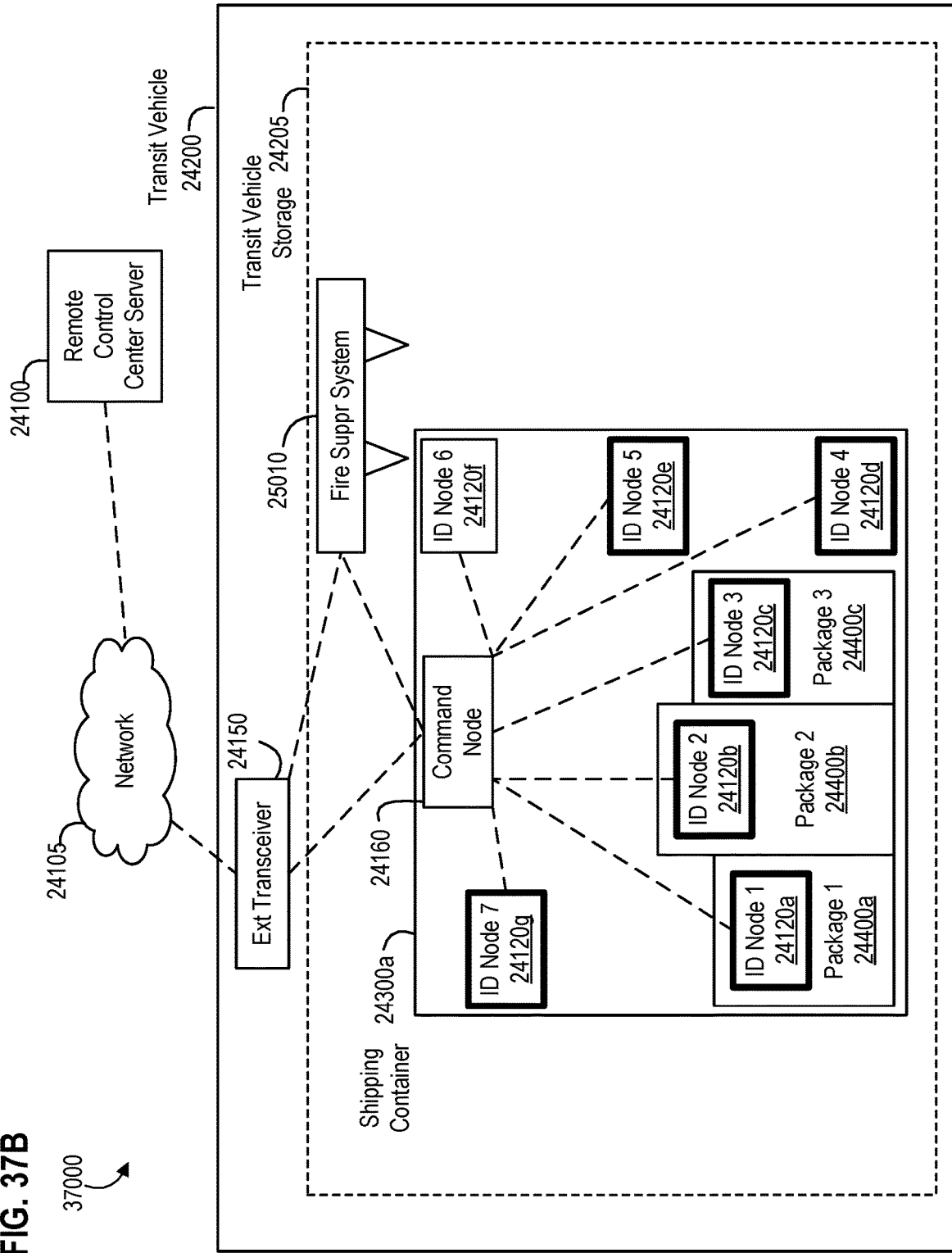

FIGS. 37A-37B are diagrams of an exemplary shipping container (container 24300a) that leverages an exemplary wireless node network for detecting environmental anomalies associated with the shipping container using a command node mounted to the shipping container and selectively assigned ID nodes within (or as part of) the shipping container in accordance with an embodiment of the invention. Referring now to FIG. 37A, an exemplary system 37000 is shown similar to what is described above with reference to, for example, FIGS. 31, 33, and 34 where a transit vehicle 24200 is shown with transit vehicle storage 24205. The transit vehicle 24200 is shown equipped with external transceiver 24150 (as previously described), which may communicate with remote control center server 24100 via network 24105 as well as communicate directly with each of command node 24160 and fire suppression system 25010. Within storage 24205, exemplary shipping container 24300a is disposed such that fire suppression system 25010 may be activated (e.g., by external transceiver 24150 or by command node 24160) to supply a fire suppression agent into shipping container 24300a (e.g., as explained with reference to FIGS. 32A-32C).

In more detail and as illustrated in FIG. 37A, the system's shipping container 24300a is deployed to include exemplary command node 24160, which may communicate with external transceiver 24150 as well as with fire suppression system 25010. Command node 24160 is further operative to communicate with various ID nodes disposed within or as part of container 24300a. For example, as shown in FIG. 37A, command node 24160 is operative to communicate with exemplary ID nodes 24120a-24120g disposed within container 24300a. Exemplary ID nodes 24120a-24120c (i.e., ID Nodes 1-3) are illustrated as being respectively associated with packages 24400a-24400c, while ID nodes 24120d-24120g (i.e., ID Nodes 4-7) are disposed within shipping container 24300a without being associated with a package. As such, ID nodes 24120d-24120g (i.e., ID Nodes 4-7) may be part of the shipping container or attached to the shipping container or may be simply an ID node disposed within the shipping container without being fixed to the shipping container and without being associated with, attached to, or disposed within a package in the shipping container.

In FIG. 37B, system 37000 is graphically depicted as having command node 24160 selectively assigning a subset of the ID nodes disposed within container 24300a (e.g., exemplary ID nodes 24120a-24120g) to function as dedicated monitor beacons deployed within shipping container 24300a. As shown in FIG. 37B, command node 24160 may have selectively assigned exemplary ID nodes 24120a-24120e and 24120g to be the subset of ID nodes disposed in the container that are to be monitored as dedicated monitor beacons. As a dedicated monitor beacon, a particular ID node within this subset (e.g., the highlighted subset of exemplary ID nodes 24120a-24120e and 24120g) will be monitored by command node 24160 for an unanticipated state of ceased broadcasting. The process of selectively assigning the particular subset of those ID nodes disposed within container 24300a to be those monitored as part of detecting an environmental anomaly related to the container may be performed in a variety of ways in different embodiments. For example, command node 24160 may selectively assign particular ID nodes disposed within the container 24300a to be part of the monitored subset of ID nodes (i.e., dedicated monitor beacons) based upon a predetermined (or updated) ID node list maintained in memory of command node 24160; based upon such a list as well as location information (e.g., a type of context data) on different ID nodes within the container 24300a; based on such a list as well as including additional ID nodes disposed within container 24300a that are not on the list but are passively detected by the command node 24160 as broadcasting; or based simply upon what ID nodes are disposed within container 24300a that are passively detected by the command node 24160. In further examples, command node 24160 may selectively assign which of the ID nodes are part of the monitored subset of ID nodes disposed within the container 24300a based on information related to a package associated with a particular ID node. For instance, command node 24160 may selectively assign which of the ID nodes are part of the subset monitored based on shipping information that indicates what type of item (or asset or object) is being shipped in the package, or based on location information that indicates where the ID node's associated package is located within the shipping container 24300a. Further still, command node 24160 may receive instructions from, for example, external transceiver 24150 or server 24100 (via transceiver 24150 or directly from server 24100) where such instructions identify the subset of which ID nodes are to function as the dedicated monitor beacons being monitored as part of detecting an environmental anomaly. Such instructions, in some embodiments, may take the form of vehicle status data associated with transit vehicle 24200 transporting shipping container 24300a and where the vehicle status data is indicative of the state of transit vehicle 24200 (e.g., a takeoff vehicular status, a cruising vehicle status, a landing vehicular status, and a stationary vehicular status) and a risk factor associated with that state of the vehicle (e.g., a lower risk factor being when the transit vehicle is in the stationary vehicular status).

Figure 38A:
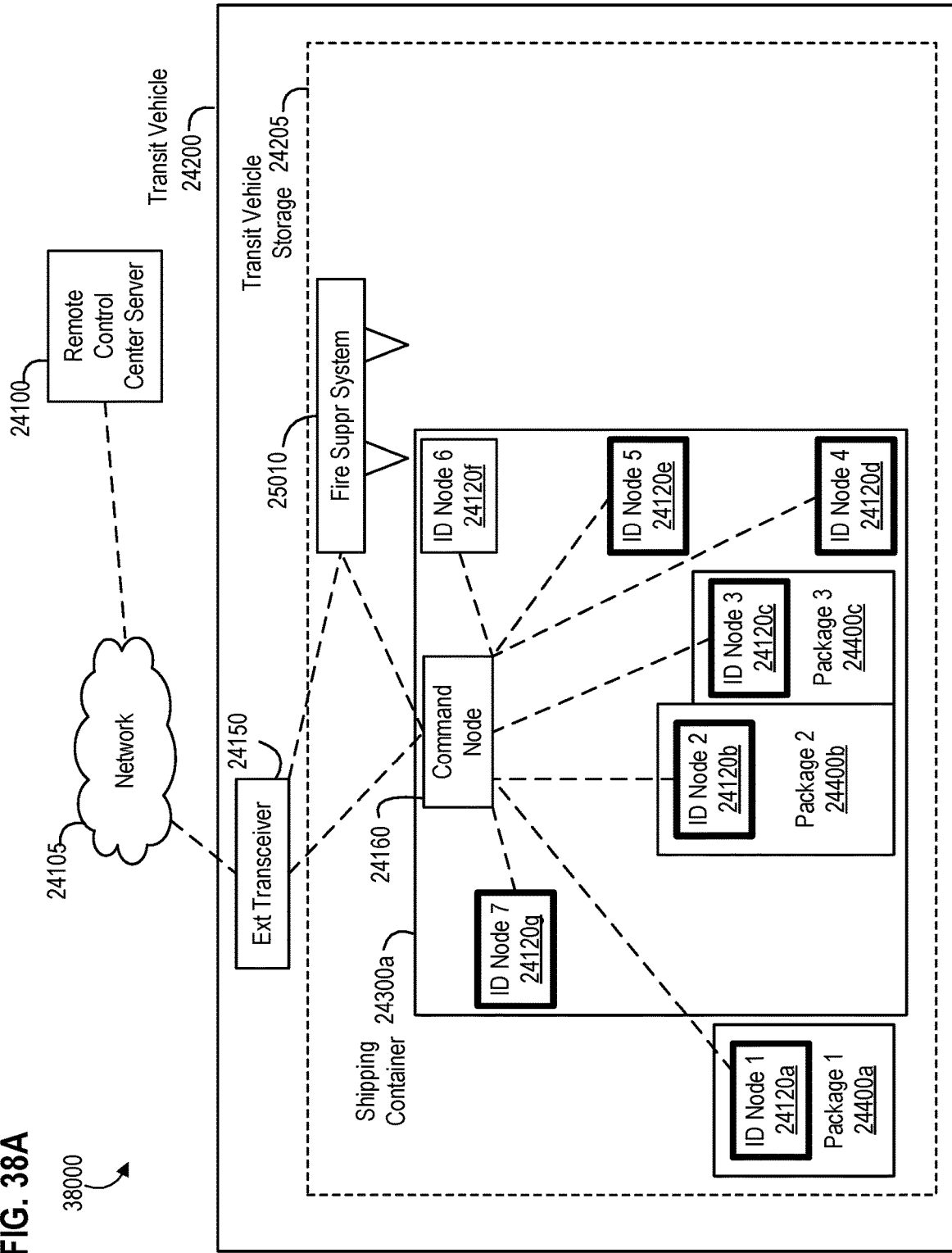
FIGS. 38A-38B are diagrams of an exemplary shipping container that leverages an exemplary wireless node network for detecting environmental anomalies associated with the shipping container using a command node mounted to the shipping container and selectively reassigned ID nodes within the shipping container when what is in shipping container changes in accordance with an embodiment of the invention.
Figure 38B:
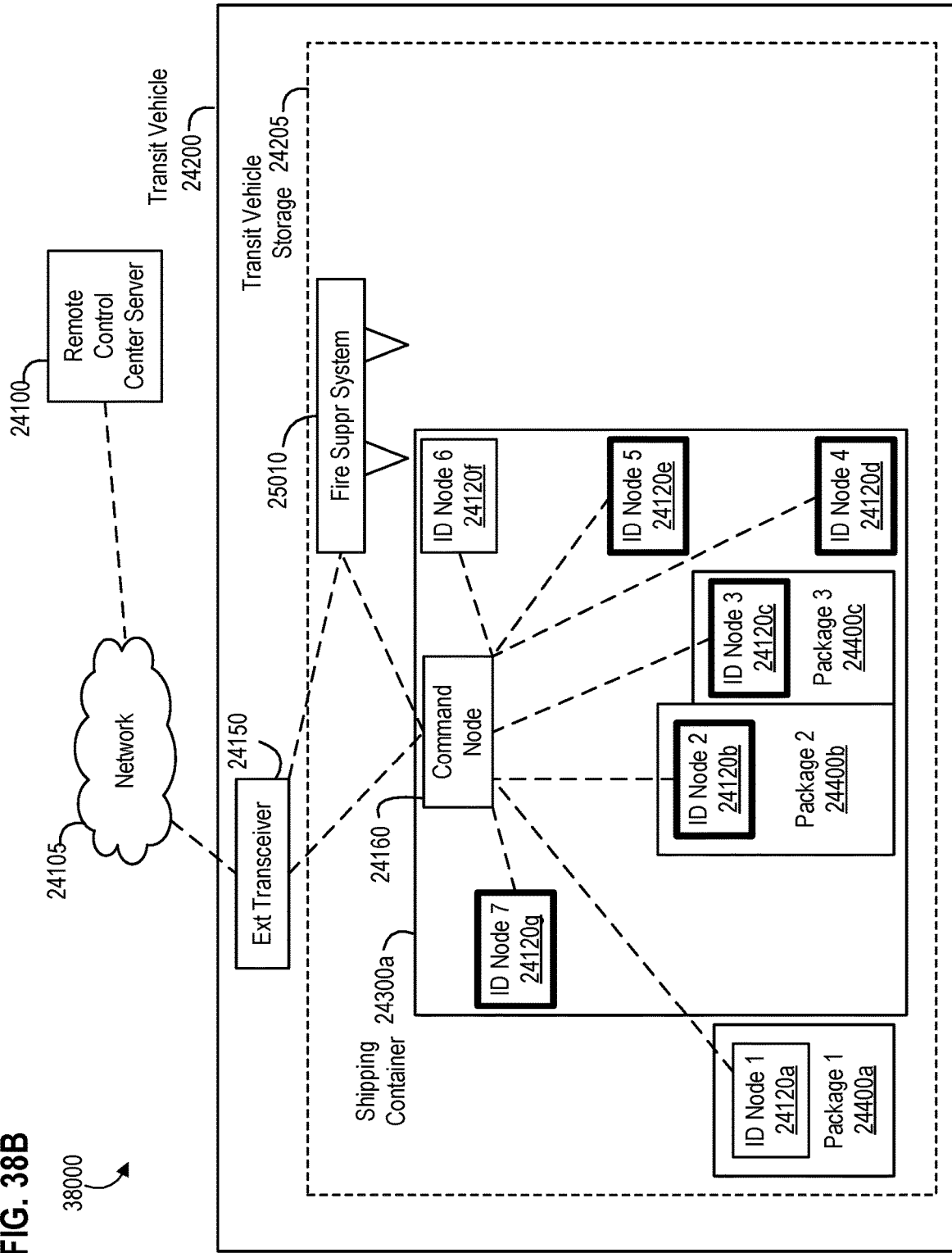

Over time, the ID nodes disposed within a particular shipping container may change. As such, embodiments may have the command node adjust which of the ID nodes are in the assigned subset of ID nodes being monitored as dedicated beacon nodes. FIGS. 38A-38B are diagrams of an exemplary shipping container that leverages an exemplary wireless node network for detecting environmental anomalies associated with the shipping container using a command node 24160 mounted to the shipping container 24300a and selectively reassigned ID nodes within the shipping container 24300a when what is in shipping container 24300a changes in accordance with an embodiment of the invention. Referring now to FIG. 38A, exemplary shipping container 24300a was originally in a configuration of having the ID nodes (i.e., ID nodes 24120a-24120g) disposed within it and where command node 24160 had selectively assigned a subset of those ID nodes (i.e., the highlighted subset of exemplary ID nodes 24120a-24120e and 24120g) as shown in FIG. 37B. But, as shown in FIG. 38A, package 24400a (having associated ID node 24120a) has been removed from container 24300a. In other words, a package having one of the selectively assigned ID nodes from the subset of monitored ID nodes (i.e., ID node 24120a) is no longer disposed within shipping container 24300a. In this situation, command node 24160 may re-assign which of the ID nodes are to be monitored as dedicated monitors beacon so that, as shown in FIG. 38B, command node 24160 has now assigned a different subset of those ID nodes (i.e., the highlighted subset of exemplary ID nodes 24120b-24120e and 24120g) to be monitored as dedicated monitor beacons. In this way, an embodiment may deploy the command node 24160 to adjust for changes (e.g., loading, unloading, and even mere re-arranging) of what is within shipping container 24300a by adaptively reassigning which ID nodes are to be monitored.

In light of the embodiments illustrated in FIGS. 37A-37B and 38A-38B, exemplary system and method embodiments may be described in more detail that involve selectively assigning particular ID nodes disposed within a shipping container (such as container 24300a) when detecting an environmental anomaly related to the shipping container. For example, FIG. 39 is a flow diagram illustrating an exemplary method for monitoring a shipping container for an environmental anomaly using a command node mounted to the shipping container and selective ones of a plurality of ID nodes disposed at different locations within the shipping container in accordance with an embodiment of the invention. In particular, FIG. 39 describes an exemplary improved method 3900 for monitoring a shipping container (e.g., shipping container 24300a) for an environmental anomaly. The shipping container involved in method 3900 may be transported on a transit vehicle (e.g., transit vehicle 24200 shown in FIGS. 37A-38B—such as an aircraft, railway conveyance, a maritime vessel, or a roadway conveyance) that may also transport multiple packages (e.g., packages 24400a-24400c as shown in FIGS. 37A-38B). The wireless node network involved in method 3900 has at least a plurality of ID nodes (e.g., ID node 24120a-24120g as shown in FIGS. 37A-38B) and a command node associated with the shipping container (e.g., command node 241260 associated with and mounted to shipping container 24300a). The command node used as part of method 3900 may, for example, be implemented as a container node integrated as part of the shipping container or a self-locating master node implemented separately from the shipping container. The ID nodes used as part of method 3900 include ID nodes disposed within the shipping container (e.g., ID nodes 24120a-24120g) and, in particular, selectively assigned ones of those ID nodes as chosen or assigned by the command node. In this configuration, the command node involved in method 3900 is operative to communicate with each of the ID nodes and an external transceiver unit associated with the transit vehicle (e.g., external transceiver 24150 on transit vehicle 24200).

Referring now to FIG. 39, exemplary method 3900 begins at step 3905 with the command node selectively assigning a subset of the ID nodes disposed within a shipping container to function as dedicated monitor beacons deployed within the shipping container. For example, exemplary command node 24160 mounted to shipping container 24300a as shown in FIG. 37A may selectively assign ID nodes 2410a-24120e and 24120g (i.e., ID nodes 1-5 and ID node 7 as shown in FIG. 37B) as the subset of ID nodes disposed within shipping container 24300a to function as dedicated monitor beacons out of those ID nodes disposed within shipping container 24300a (i.e., ID nodes 1-7).

At step 3910, method 3900 proceeds with the command node monitoring the assigned subset of the ID nodes for an unanticipated state of ceased broadcasting from any of the assigned subset of the ID nodes from step 3905. For example, command node 24160 shown in FIG. 37B may monitor the assigned subset of ID nodes 2410a-24120e and 24120g (i.e., ID nodes 1-5 and ID node 7) as they are disposed within shipping container 24300a. Those assigned ID nodes are shown dispersed within shipping container 24300a—some being disposed near the walls of the container, some being on the floor of the container, and some disposed within packages (or attached to packages). In this way, the command node 24160 is programmatically configured to allow for selective and adaptive monitoring within the shipping container 24300a. The assigned subset of ID nodes 2410a-24120e and 24120g is anticipated to be broadcasting, as may be reflected by the communication profile data on each of those nodes (as indicated in profile data 430 on command node 24160). Such a communication profile may define an anticipated periodic broadcast behavior for a node, and any shift in broadcast behavior from that anticipated behavior may be indicative of an unanticipated state of ceased broadcasting.

At step 3915, method 3900 proceeds with the command node identifying any of those in the assigned subset of the ID nodes found to be in the unanticipated state of ceased broadcasting based upon the monitoring step 3910. In more detail, monitored broadcast signals from the assigned subset of the ID nodes may indicate the source of such broadcast signals—namely, which ID node is broadcasting the signal received by the command node as part of monitoring step 3910. As such, the command node may receive and assess the received broadcast signals and identify which of the assigned subset of ID nodes are broadcasting as anticipated and which, if any, of the assigned subset of ID nodes are no longer broadcasting as anticipated. Those no longer broadcasting as anticipate are identified by the command node as part of step 3915.

At step 3920, method 3900 continues with the command node adding any of the identified ID nodes from step 3915 to an unresponsive group from the assigned subset of the ID nodes found to be in the unanticipated state of ceased broadcasting. Then, at decision step 3925, method 3900 has the command node determining if the size of the unresponsive group of the assigned subset of the ID nodes exceeds a threshold setting maintained by the command node. If so, method 3900 proceeds from step 3925 directly to step 3930 where the command node detects the environmental anomaly for the shipping container because the size of the identified or otherwise sensed unresponsive group from the assigned subset of ID nodes exceeds the threshold setting. If not, method 3900 proceeds from step 3925 back to step 3910 where monitoring of the assigned subset of ID nodes disposed within the shipping container by the command node continues.

At step 3935, method 3900 proceeds with the command node automatically generating an alert notification about the detected environmental anomaly for the shipping container, and then in step 3940, method 3900 has the command node transmitting the alert notification to the transceiver unit (e.g., external transceiver 24150) to initiate a mediation response related to the detected environmental anomaly.

In further embodiments of exemplary method 3900, step 3905 may be more detailed in how the command node selectively assigns which of the ID nodes to be part of the assigned subset of ID nodes disposed within the shipping container to function as dedicated monitor beacons. For example, a more detailed embodiment may have the command node selectively assigning the subset of ID nodes as part of step 3905 by accessing a predetermined ID node list in memory of the command node (e.g., list information on ID nodes to be monitored as part of context data 26560) and selectively assigning, by the command node, members of the subset of the ID nodes based upon which of the ID nodes are indicated in the accessed predetermined ID node list. A further embodiment may selectively assign members of the subset of the ID nodes as part of step 3905 by accessing both such a predetermine ID node list as well as context data having location information (e.g., another part of context data 26560) related to each of the ID nodes identified in the predetermined ID node list, and then selectively assigning, by the command node, members of the subset of the ID nodes based upon which of the ID nodes are indicated in the accessed predetermined ID node list and the location information related to each of the ID nodes in the subset of the ID nodes.

Still a further embodiment of method 3900 may selectively assign members of the subset of the ID nodes as part of step 3905 using such a predetermined ID node list as well as detecting what other ID nodes are broadcasting that are not on the list. In more detail, such a further embodiment of method 3900 may selectively assign members of the subset of the ID nodes as part of step 3905 by having the command node accessing a predetermined ID node list in memory of the command node; initially assigning a first set of members of the subset of the ID nodes based upon which of the ID nodes are indicated in the accessed predetermined ID node list; detecting, by the command node, a broadcast signal from one or more additional ones of the ID nodes not included in the predetermined ID node list; and selectively adding, by the command node, at least one additional ID node as an additional member of the subset of the ID nodes from the additional ones of the ID nodes not included in the predetermined ID node list.

Yet another further embodiment of method 3900 may selectively assign members of the subset of the ID nodes as part of step 3905 by having the command node detecting a broadcast signal from one or more of the ID nodes; and selectively assigning members of the subset of the ID nodes from the those of the ID nodes detected as broadcasting. In more detail, such an embodiment may selectively assign members of the subset of the ID nodes as part of step 3905 by having the command node detect one or more broadcast signals respectively from one or more of the ID nodes; accessing, by the command node, a communication profile maintained by the command node on an anticipated broadcasting state for each of the one or more of the ID nodes associated with the detected broadcast signals; and selectively assigning, by the command node, members of the subset of the ID nodes from those of the one or more of the ID nodes associated with the detected broadcast signals that are in the anticipated broadcasting state according to their respective communication profile.

In embodiments where the shipping container maintains packages respectively associated with each of the subset of the ID nodes, further embodiments of method 3900 may have the command node selectively assigning the subset of the ID nodes at step 3905 by having the command node access shipping information (e.g., a part of context data 26560 or profile data 430) on what type of item is being shipped in each of the packages associated with each of the ID nodes; and selectively assigning, by the command node, members of the subset of the ID nodes based upon the type of item being shipped in each of the packages associated with each of the ID nodes in the subset of the ID nodes. For example, the command node may selectively assign the members of the ID node subset by identifying which of the ID nodes are associated with packages containing incendiary material based upon the shipping information; and assigning the identified ID nodes associated with incendiary material as the members of the subset of the ID nodes to function as the dedicated monitor beacons. In even more detail, the command node may assign only a predetermined number of the identified ID nodes associated with incendiary material as the members of the subset of the ID nodes to function as the dedicated monitor beacons.

Further embodiments of method 3900 may selectively assign what ID nodes are in the monitored subset from step 3905 based on the package location within the shipping container. In more detail, when the shipping container maintains packages respectively associated with each of the subset of the ID nodes, a further embodiment of step 3905 may have the command node accessing context data maintained by the command node on location information related to each the packages as maintained within the shipping container, and then selectively assigning the members of the subset of the ID nodes based upon the location information related to each of the ID nodes in the subset of the ID nodes. In even more detail, a further embodiment may selectively assign such members of the subset of ID nodes by identifying which of the ID nodes are located in designated regions within the shipping container based upon the location information (e.g., a loading scheme for the packages maintained within the shipping container, where the loading scheme is part of the location information in the context data, such as context data 26560); and assigning a respective one of the ID nodes in each of the designated regions within the shipping container as the members of the subset of ID nodes to function as the dedicated monitor beacons.

Still further embodiments may identify the subset of the ID nodes to function as the dedicated monitor beacons based upon an instruction message received by the command node. Such an instruction message may be generated by a higher level element in the wireless node network, such as the external transceiver (e.g., transceiver 24150) disposed on the transit vehicle and separate from the shipping container as a higher level element of the network, or a server (e.g., server 24100) separate from the transit vehicle as an additional higher level element in the wireless node network.

Another further embodiment of method 3900 may have the command node selectively assign the subset of ID nodes in step 3905 based upon further contextual information on the transit vehicle and its status. In more detail, an embodiment of step 3905 may have the command node receiving vehicle status data provided by the external transceiver unit associated with the transit vehicle (e.g., external transceiver 24150) and then have the command node selectively assigning the subset of the ID nodes depending upon a state of the transit vehicle as indicated by the vehicle status data. In even more detail, selectively assigning the subset of the ID nodes may depend on a risk factor associated with the state of the transit vehicle as indicated by the vehicle status data. For example, when the risk factor is a first level for a first state of the transit vehicle, a number of the members selectively assigned to the subset of the ID nodes is a first value and when the risk factor is a second level for a second state of the transit vehicle where the second level is higher than the first level, the number of the members selectively assigned to the subset of the ID nodes is greater than the first value. This, effectively, allows for the command node to operate to selectively assign the members of the ID nodes to be monitored by taking into account a state of the transit vehicle (e.g., a takeoff vehicular status, a cruising vehicle status, a landing vehicular status, and a stationary vehicular status).

Embodiments of exemplary method 3900 may be extended to adapt to changes in what is stored in the shipping container (e.g., similar to that described with respect to FIGS. 38A-38B). In more detail, method 3900 may further include the step of re-assigning which of the ID nodes are members of the subset of the ID nodes when the command node detects a change in what is maintained within the shipping container (e.g., when the command node finds the location of an ID node within the subset of the ID nodes being monitored is outside the shipping container, or when the command node is notified of an ID node within the subset of the ID nodes being monitored is removed from the shipping container). More particularly, method 3900 may include re-assigning which of the ID nodes are members of the subset of the ID nodes when the command node detects movement within the shipping container using a motion detector on the command node (e.g., when sensor 26465 on command node 24160 is a motion detector, and movement within shipping container 24300a is detected via that sensor indicating a change of what is within shipping container 24300a). Such re-assigning may be initiated from updated shipping information received by the command node on updated contents to be maintained within the shipping container. As such, the command node may re-assign which of the ID nodes are members of the subset of the ID nodes when the command node detects the change in what is maintained within the shipping container based upon the updated shipping information. In such further embodiments, the re-assigning may comprise changing which of the ID nodes are part of the subset of the ID nodes when the command node detects a loading operation of the shipping container based on the updated shipping information, or detects an unloading operation of the shipping container based on the updated shipping information, or detects a re-arrangement operation of the shipping container based upon detecting a change in location of at least one of the members of the subset of the ID nodes within the shipping container.

Further embodiments of method 3900 may involve more specific mediation responses. For example, step 3940 may have the mediation response that is initiated by the alert notification transmission to be an automatic response request for the external transceiver to activate a triggered fire suppression system on the transit vehicle (e.g., exemplary fire suppression system 25010). In another example, step 3940 may have the mediation response that is initiated by the alert notification transmission to be a request to change course of the transit vehicle from an existing travel path of the transit vehicle (e.g., a requested prompt to be displayed on the external transceiver's display) or a request to investigate the shipping container (e.g., a requested prompt also displayed on the external transceiver's display).

Additional embodiment of method 3900 may involve updating information used in selectively assigning the subset of ID nodes and/or the threshold setting used for detecting the environmental anomaly. For example, a further embodiment of method 3900 may include having the command node receiving a threshold update for the threshold setting maintained by the command node used as part of step 3925. This threshold update may be received from, for example, the external transceiver unit (e.g., as defined from user input provided by an operator of the transit vehicle or a logistics crew member of the transit vehicle using the external transceiver unit). This threshold update may also be provided to the external transceiver unit (e.g., transceiver 24150) from a remote control center in communication with the external transceiver unit (e.g., server 24100). In another example, a further embodiment of method 3900 may include having the command node receiving a selection update for which of the ID nodes are selectively assigned to be in the subset of the ID nodes. This selection update may be received from, for example, the external transceiver unit (e.g., as defined from user input provided by an operator of the transit vehicle or a logistics crew member of the transit vehicle using the external transceiver unit). This selection update may also be provided to the external transceiver unit (e.g., transceiver 24150) from a remote control center in communication with the external transceiver unit (e.g., server 24100).

Embodiments of method 3900 may also implement step 3910 as monitoring that involves confirming the validity of what the command node receives. In more detail, the monitoring step 3910 of method 3900 may be implemented in a further embodiment by having the command node (a) receiving a communication broadcasted from a first of the ID nodes within the assigned subset of the ID nodes; (b) confirming the validity of the received communication; and (c) repeating steps (a) and (b) for the remainder of the communications received from any of the remaining ones of the ID nodes within the assigned subset of the ID nodes. As such, the identifying in step 3915 may then involve having the command node identifying the unresponsive group from the assigned subset of the ID nodes based upon the monitoring step and based upon steps (a)-(c).

Further detailed implements may involve active or passive validation. In an active validation example, the step of confirming the validity of the received communication in step (b) may have the command node sending an authentication request to the first of the ID nodes within the assigned subset of the ID nodes; and then receiving a validation response from the first of the ID nodes within the assigned subset of the ID nodes that authenticates the communication broadcasted from the first of the ID nodes within the assigned subset of the ID nodes. Alternatively, in a passive validation example, the step of confirming the validity of the received communication in step (b) may have the command node accessing a validation sequence for the first of the ID nodes within the assigned subset of the ID nodes, the validation sequence being maintained by the command node and characterizing expected broadcasts from the first of the ID nodes within the assigned subset of the ID nodes; and then determining if the received communication from the first of the ID nodes within the assigned subset of the ID nodes matches a predetermined one of the expected broadcasts from the first of the ID nodes within the assigned subset of the ID nodes according to the validation sequence stored within the command node. Such a predetermined one of the expected broadcasts may be a rotating value previously received by the command node for the first of the ID nodes within the assigned subset of the ID nodes.

As noted above, the ID nodes used as part of method 3900 include ID nodes disposed within the shipping container (e.g., ID nodes 24120a-24120g) and may be ID nodes respectively associated with one or more of different packages within the shipping container, where each of the ID nodes may travel with their respective one of the packages, be affixed to the outside of one of the packages, be integrated as part of one of the packages. In other embodiments, the ID nodes disposed within the container used as part of method 3900 may not be associated with any of package disposed within the shipping container and, in some cases, may be temporarily or permanently fixed to a part of the shipping container itself. In still another embodiment, the ID nodes used as part of method 3900 may be a combination of ID nodes associated with packages and ID nodes not associated with any package.

Those skilled in the art will appreciate that method 3900 as disclosed and explained above in various embodiments may be implemented using an improved monitoring system for detecting and responding to an environmental anomaly in a shipping container having a plurality of packages and being transported by a transit vehicle having an external transceiver unit separate from the shipping container such as that explained above with reference to FIGS. 27A-28B and their respective exemplary elements. Such an embodiment of an improved monitoring system, as explained above relative to operations according to method 3900 and with elements from system 37000 of FIG. 37A or system 38000 of FIG. 38A, uses at least multiple ID nodes disposed within the shipping container (e.g., ID nodes 24120a-24120g) running one or more ID node monitoring program code as part of node control and management code 325 to control operations of the ID nodes to generate and broadcast signals, as well as a command node mounted to the shipping container (e.g., command node 24160 in FIGS. 37A and 38A) running one or more parts of CN control & management code 26425 to control the operations of the command node as part of monitoring for and detecting an environmental anomaly using selectively assigned ones of the ID nodes that are monitored as dedicated monitor beacons. Such code may be stored on a non-transitory computer-readable medium, such as memory storage 26415 on command node 24160 (an embodiment of exemplary command node 26000) and memory storage 315 on ID nodes 24120a-24120g (embodiments of exemplary ID node 120a). Thus, when executing such code, the ID nodes and the command node may be operative to perform operations or steps from the exemplary methods disclosed above, including method 3900 and variations of that method.

Figure 40:
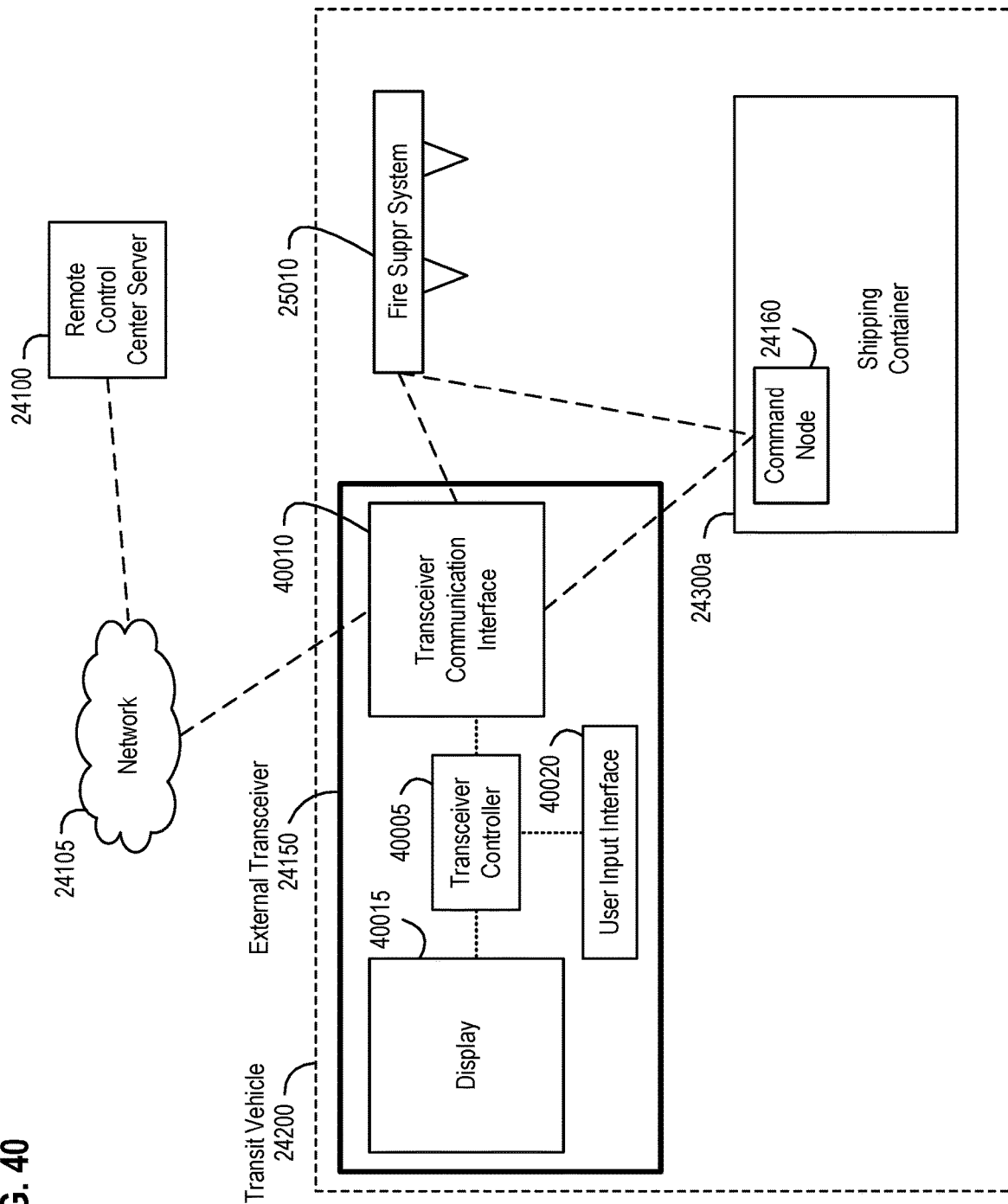
FIG. 40 is a diagram of an exemplary external transceiver that may be activated and deployed on a transit vehicle for initiating a mediation action in response to a detected environmental anomalies related to a shipping container being transported on the transit vehicle in accordance with an embodiment of the invention.

A more detailed system embodiment may include the command node (e.g., exemplary command node 24160 as shown in FIGS. 37A-38B), ID nodes disposed within the shipping container (and that may be selectively assigned to a subset of the ID nodes to function as dedicated monitor beacons, such as ID nodes 24120a-24120g as shown in FIGS. 27A-28B), as well as the external transceiver (e.g., exemplary external transceiver 24150) in communication with the command node. FIG. 40 is a diagram that provides more details regarding an exemplary external transceiver that may be activated and deployed on a transit vehicle for initiating a mediation action in response to a detected environmental anomaly related to a shipping container being transported on the transit vehicle in accordance with an embodiment of the invention. As generally explained in above, embodiments of the external transceiver 24150 may receive alert notifications from the command node 24160, and automatically respond to such alerts by initiating a mediation response related to a particular mediation action based upon the particular environmental anomaly detected. And as noted above, some mediation responses may have the external transceiver 24150 triggering a fire suppression system 25010 on transit vehicle 24200, communicating with an operator or logistics crew aboard transit vehicle 24200, and/or communicating with remote control center server 24100 over network 24105. As shown in FIG. 40, exemplary external transceiver 24150 may be implemented with a transceiver controller 40005, a transceiver communication interface 40010 coupled to the controller, a display 40015 coupled to the controller, and a user input interface 40020 coupled to the controller. In general, the transceiver controller 40005 may be implemented using a core programmable microprocessor-based controller board with memory, processing, interface circuitry, and drivers (such as the Raspberry Pi single board computer described above). The transceiver communication interface 40010 coupled to controller 40005 may be a wireless receiver/transmitter with a related antenna operative to communicate with command node 24160 and onboard fire suppression system 25010 using a wireless communication format (e.g., cellular, Wi-Fi, and the like). Transceiver communication interface 40010 may also include a wired receiver/transmitter with related driver and/or buffer circuitry that allows for communication over wired connections when desired with such other components (e.g., the fire suppression system 25010). The display 40015 may be implemented as a screen type of interface (e.g., an LCD display for the operator or crew, a touch screen display) or a more simplified set of status lights allowing more simplified prompts and feedback interaction with the operator or logistics crew that are on the transit vehicle 24200. A further embodiment of display 40015 may be implemented to display information via sound—e.g., with prompted messages being displayed as an audible message (e.g., sounds, alarms, beeps, recited oral statements corresponding to details of the message, and the like) rather than a visual message. The user input interface 40020 on the transceiver may be implemented using, for example, a touchscreen interface, interactive buttons, hardware keys, soft keys, switches, or other feedback input devices that accept information (e.g., feedback input) from users (such as the operator or logistics crew that are on the transit vehicle 24200). Such feedback input may be, for example, from a logistics crew member that was prompted to inspect a shipping container (e.g., container 24300*a*) and then provides feedback input via interface 40020. Those skilled in the art will appreciate that such exemplary components that make up exemplary external transceiver 24150 as shown in FIG. 41 may be applicable in any other embodiment that may use an external transceiver on the transit vehicle (e.g., external transceiver 25010, or cockpit transceiver 25150*a*, or logistics transceiver 25150*b*).

In light of the above-described further details of an exemplary external transceiver (which may be implemented as cockpit transceiver 25150*a* or logistics transceiver 25150*b*), further details appear below. This more detailed system embodiment includes at least multiple ID nodes disposed at different locations within the shipping container, where each of the ID nodes is configured to wirelessly transmit a broadcast signal. Such ID nodes may be, for example, ID nodes 24120*a*-24120*g* as shown in FIG. 37B disposed within shipping container 24300*a*. The system further includes a command node mounted to the shipping container, such as exemplary command node 24160 as shown in FIG. 37B. The command node further comprises a command node processing unit or processor (e.g., processor 26400), a command node memory (e.g., memory 26415 and/or memory 26420), and two communication interfaces (e.g., interfaces 26480, 26485). The command node memory is coupled to the command node processing unit and maintains at least a command node container management program code (e.g., a part of CN control and management code 26425), and a threshold setting used for identifying the environmental anomaly (e.g., another part of CN control and management code 26425). A first of the communication interfaces (e.g., short range communication interface 26480) is coupled to the command node processing unit, and configured to communicate using a first wireless communication format compatible with the broadcast signal transmitted by each of the ID nodes, while a second of the communication interfaces (e.g., medium/long range communication interface 26485) is also coupled to the command node processing unit, and is configured to communicate using a second wireless communications format (such as a cellular, Wi-Fi, or Bluetooth depending on the deployed embodiment and its environment). The system also includes an external transceiver (e.g., external transceiver 25010, or cockpit transceiver 25150*a*, or logistics transceiver 25150*b*) mounted to the transit vehicle and configured to wirelessly communicate with at least the second communication interface of the command node using the second wireless communications format.

In operation, the command node's processing unit is programmatically configured, when executing the command node container management program code, to be operative to selectively assign a subset of the ID nodes to function as dedicated monitor beacons deployed within the shipping container, and then monitor the assigned subset of the ID nodes using the first communication interface for an unanticipated state of ceased broadcasting from any of the assigned subset of the ID nodes. The command node processing unit is further programmatically configured to be operative to identify an unresponsive group from the assigned subset of the ID nodes to be in the unanticipated state of ceased broadcasting based upon the monitoring operation involving the assigned subset of the ID nodes; detect the environmental anomaly when a size of the unresponsive group of the assigned subset of the ID nodes exceeds the threshold setting maintained by the command node; automatically generate an alert notification related to the detected environmental anomaly for the shipping container; and cause the second communication interface to transmit the alert notification to the external transceiver unit to initiate a mediation response related to the detected environmental anomaly. The system's external transceiver is then operative to receive the alert notification and initiate a mediation response related to the detected environmental anomaly.

A further embodiment of such a system may equip the external transceiver to have a display interface (e.g., display 40015) that generates a mediation response prompt related to the detected environmental anomaly in response to receiving the alert notification from the command node. In more detail, the external transceiver may be operative to initiate the mediation response related to the detected environmental anomaly by generating the mediation response prompt on the display interface for an operator of the transit vehicle. Such a mediation response prompt may request a change in course of the transit vehicle from an existing travel path of the transit vehicle in response to the detected environmental anomaly. Alternatively, the external transceiver may be operative to initiate the mediation response related to the detected environmental anomaly by generating the mediation response prompt on the display interface for a logistics crew member of the transit vehicle. Such a mediation response prompt may request an inspection of the shipping container in response to the detected environmental anomaly. In this manner, the alert notification received by the system's external transceiver may prompt personnel on the transit vehicle to initiate a particular and selective type of mediation response as determined, identified, and initiated by the command node.

In still another additional embodiment of such a system, the system may further include an onboard triggered fire suppression system (e.g., exemplary fire suppression system 25010 as shown in FIGS. 32A-32C) as an element of the system. The system's onboard fire suppression system is disposed on the transit vehicle for responsively supplying a fire suppression agent to the shipping container in response to an activation signal received by the onboard triggered fire suppression system from the external transceiver. In this way, the system's external transceiver may initiate the mediation response by generating the activation signal when it receives the alert notification from the command node, which causes the external transceiver to send the activation signal to the onboard triggered fire suppression system on the transit vehicle.

In a more detailed embodiment, the system may include an onboard triggered fire suppression system (e.g., exemplary fire suppression system shown in FIGS. 32A-32C), as well as having a more detailed external transceiver deployed to have a display interface (e.g., display 40015 on exemplary transceiver 24150 shown in FIG. 40) that generates a mediation response prompt related to the detected environmental anomaly in response to receiving the alert notification from the command node. The more detailed external transceiver may also be deployed as having a user input interface (e.g., user input interface 40020 on exemplary transceiver 24150 shown in FIG. 40) that receives feedback input responsive to the mediation response prompt displayed on the display interface. As such, the system's external transceiver may then be further operative to generate the activation signal in response to receiving the feedback input, and send the activation signal to the system's onboard triggered fire suppression system on the transit vehicle. The feedback input, for example as part of this further system embodiment, may be input from a logistics crew member of the transit vehicle after an inspection of the shipping container prompted by the mediation response prompt generated on the display interface of the external transceiver. Thus, such feedback input may be provided to a user input interface on exemplary logistics transceiver 25150b by a logistics crew member on aircraft 2500 after inspecting a particular shipping container.

In still another system embodiment, an exemplary improved monitoring system may be deployed for detecting and responding to an environmental anomaly in a shipping container having a packages and being transported by a transit vehicle. In general, such a system comprises at least a command node mounted to the shipping container (e.g., affixed to the container or integrated as part of the container), ID nodes disposed within the container, and an onboard fire suppression system responsive to an activation signal sent by the command node directly to the fire suppression system. In this system embodiment, an initial mediation response is initiated directly by the command node's alert notification to the fire suppression system, while a secondary mediation response may also be initiated when the command node transmits the alert notification to an external transceiver, which may have a display for prompts involving course changes for the transit vehicle or requests to inspect the shipping container. Feedback input through the external transceiver may initiate a secondary activation of the fire suppression system.

In more detail, such an exemplary system embodiment includes at least multiple ID nodes disposed at different locations within the shipping container, where each of the ID nodes is configured to wirelessly transmit a broadcast signal. Such ID nodes may be, for example, ID nodes 24120a-24120g as shown in FIG. 37B disposed within shipping container 24300a. The system further includes a command node mounted to the shipping container, such as exemplary command node 24160 as shown in FIG. 37B. The command node further comprises a command node processing unit or processor (e.g., processor 26400), a command node memory (e.g., memory 26415 and/or memory 26420), and two communication interfaces (e.g., interfaces 26480, 26485). The command node memory is coupled to the command node processing unit and maintains at least a command node container management program code (e.g., a part of CN control and management code 26425), and a threshold setting used for identifying the environmental anomaly (e.g., another part of CN control and management code 26425). A first of the communication interfaces (e.g., short range communication interface 26480) is coupled to the command node processing unit, and configured to communicate using a first wireless communication format compatible with the broadcast signal transmitted by each of the ID nodes, while a second of the communication interfaces (e.g., medium/long range communication interface 26485) is also coupled to the command node processing unit, and is configured to communicate using a second wireless communications format (such as a cellular, Wi-Fi, or Bluetooth depending on the deployed embodiment and its environment). The system also includes an onboard triggered fire suppression system (e.g., exemplary fire suppression system 25010 as shown in FIG. 37B as well as in more detail in FIGS. 32A-32C) disposed on the transit vehicle for responsively supplying a fire suppression agent to the shipping container in response to an activation signal directly received by the onboard triggered fire suppression system from the second communication interface of the command node.

As the ID nodes broadcast, the processing unit of the system's command node is programmatically configured, when executing the command node container management program code, to be operative to selectively assign a subset of the ID nodes to function as dedicated monitor beacons deployed within the shipping container and monitor the assigned subset of the ID nodes using the first communication interface for an unanticipated state of ceased broadcasting from any of the assigned subset of the ID nodes. The command node processing unit is further operative to then identify an unresponsive group from the assigned subset of the ID nodes to be in the unanticipated state of ceased broadcasting based upon the monitoring, and then detect the environmental anomaly when a size of the unresponsive group of the assigned subset of the ID nodes exceeds the threshold setting maintained by the command node. In response to this detection, the command node processing unit is further operative to automatically generate an alert notification related to the detected environmental anomaly for the shipping container, and cause the second communication interface to transmit the alert notification to the onboard triggered fire suppression system to directly initiate a mediation response by the onboard triggered fire suppression system related to the detected environmental anomaly. The system's onboard triggered fire suppression system is then operative to receive the alert notification as the activation signal and initiate a mediation response related to the detected environmental anomaly by responsively supplying the fire suppression agent to the shipping container.

The system may further include, as an additional element, an external transceiver (e.g., exemplary external transceiver 24150) mounted to the transit vehicle and configured (e.g., as described with respect to the embodiment shown in FIG. 40 and the transceiver communication interface 40010) to wirelessly communicate with at least the second communication interface of the command node using the second wireless communications format. This system's external transceiver also has a display interface (e.g., display 40015) that generates a mediation response prompt related to the detected environmental anomaly, such as a displayed mediation prompt message. As such, the command node processing unit may be further operative to cause the second communication interface to transmit the alert notification to the external transceiver to initiate a secondary mediation response related to the detected environmental anomaly, such as requesting that an operator of the transit vehicle change the course of the transit vehicle from an existing travel path of the transit vehicle in response to the detected environmental anomaly or requesting a logistics crew member of the transit vehicle conduct an inspection of the shipping container in response to the detected environmental anomaly.

In more detail, the system's external transceiver may also include a user input interface (e.g., user input interface 40020) that may receive feedback input (e.g., input from a logistics crew member of the transit vehicle after an inspection of the shipping container) responsive to the mediation response prompt displayed on the display interface. As such, the external transceiver may then generate a secondary activation signal in response to receiving the feedback input, and transmit the secondary activation signal to the onboard triggered fire suppression system on the transit vehicle. The system's onboard triggered fire suppression system may then supply an additional amount of the fire suppression agent to within the shipping container in response to receiving the secondary activation signal from the external transceiver.

Figure 41A:
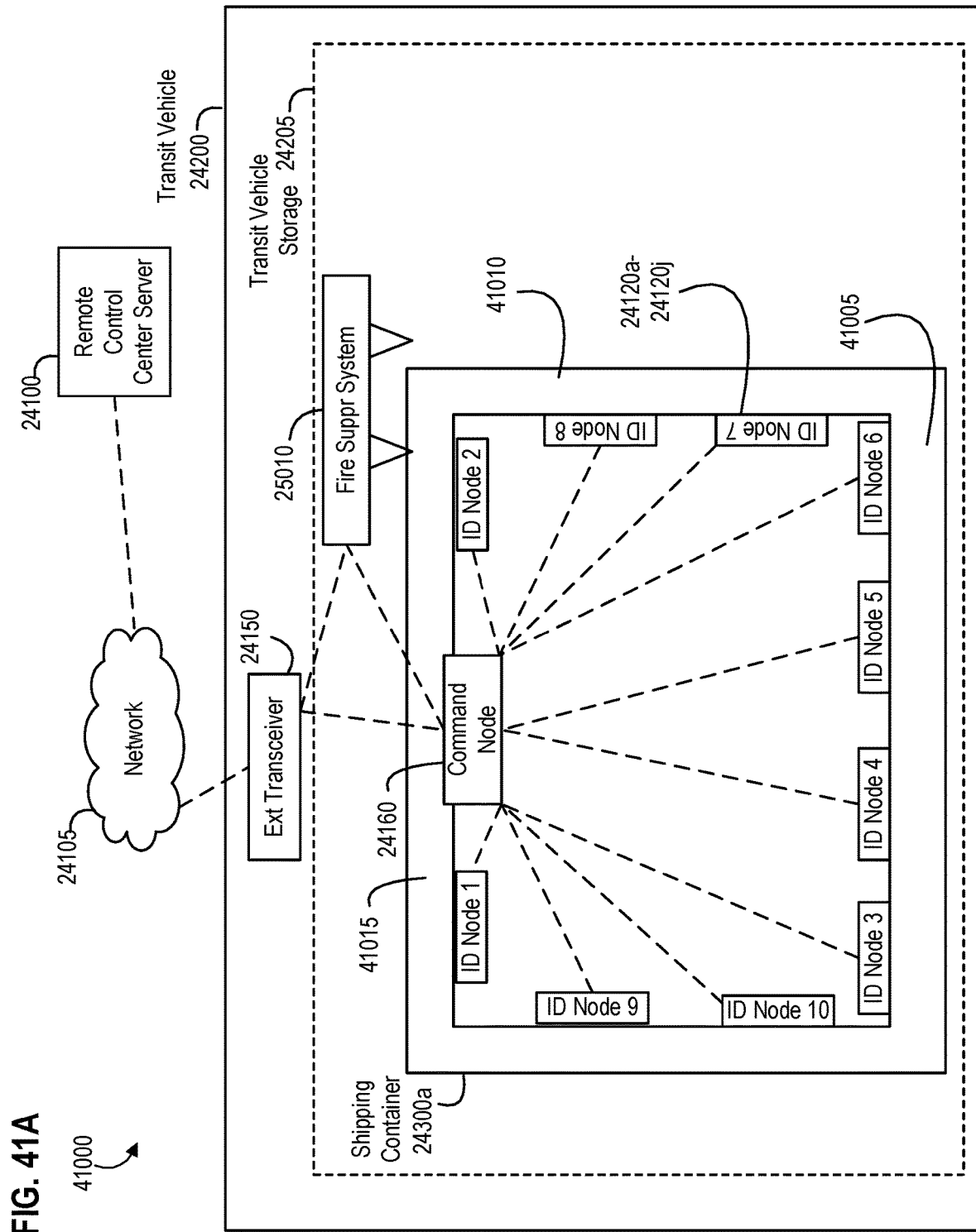
FIGS. 41A-41D are diagrams of an exemplary enhanced shipping container that transports packages and self-monitors for an environmental anomaly using selectively assigned ID nodes in accordance with an embodiment of the invention.
Figure 41B:
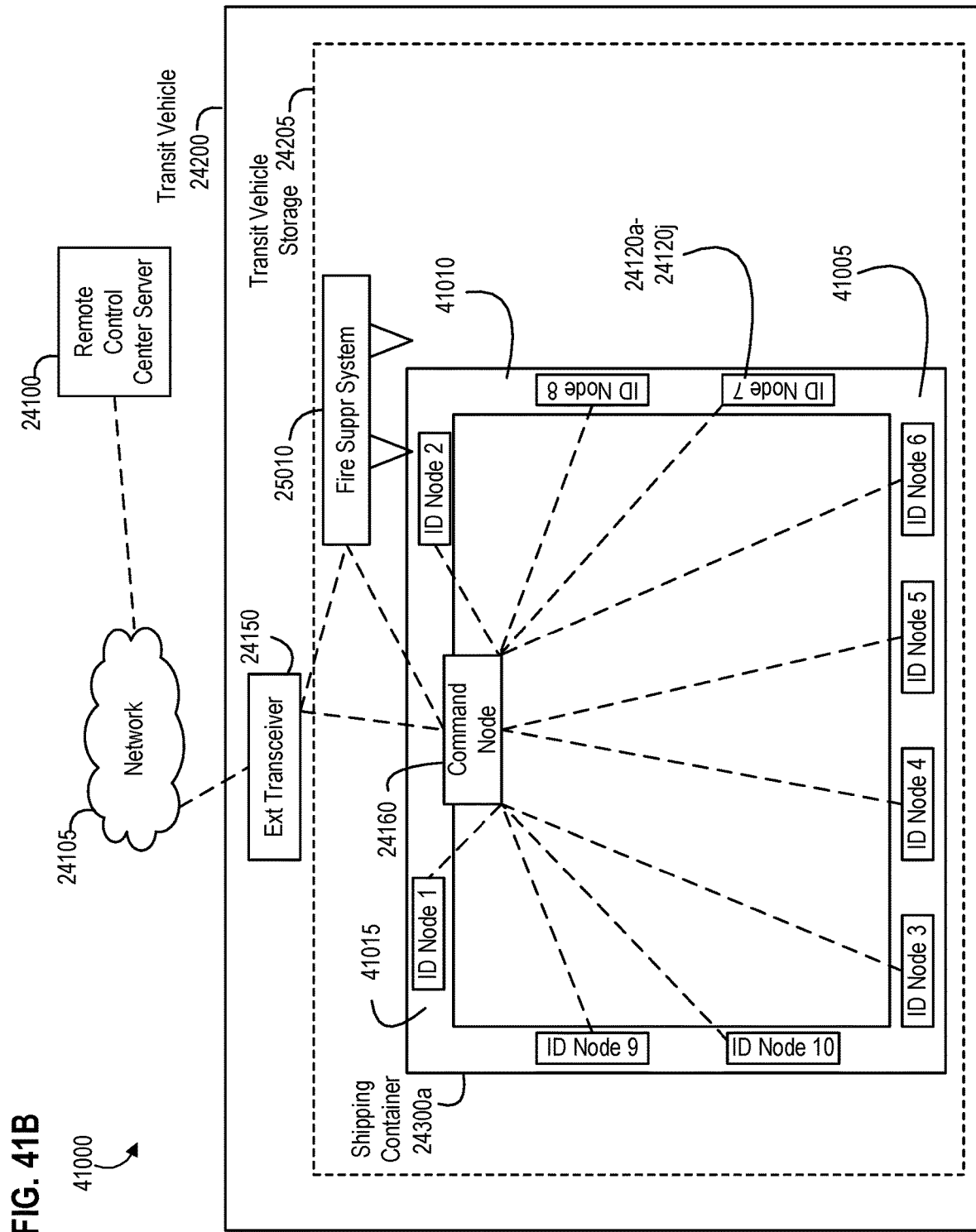
Figure 41C:
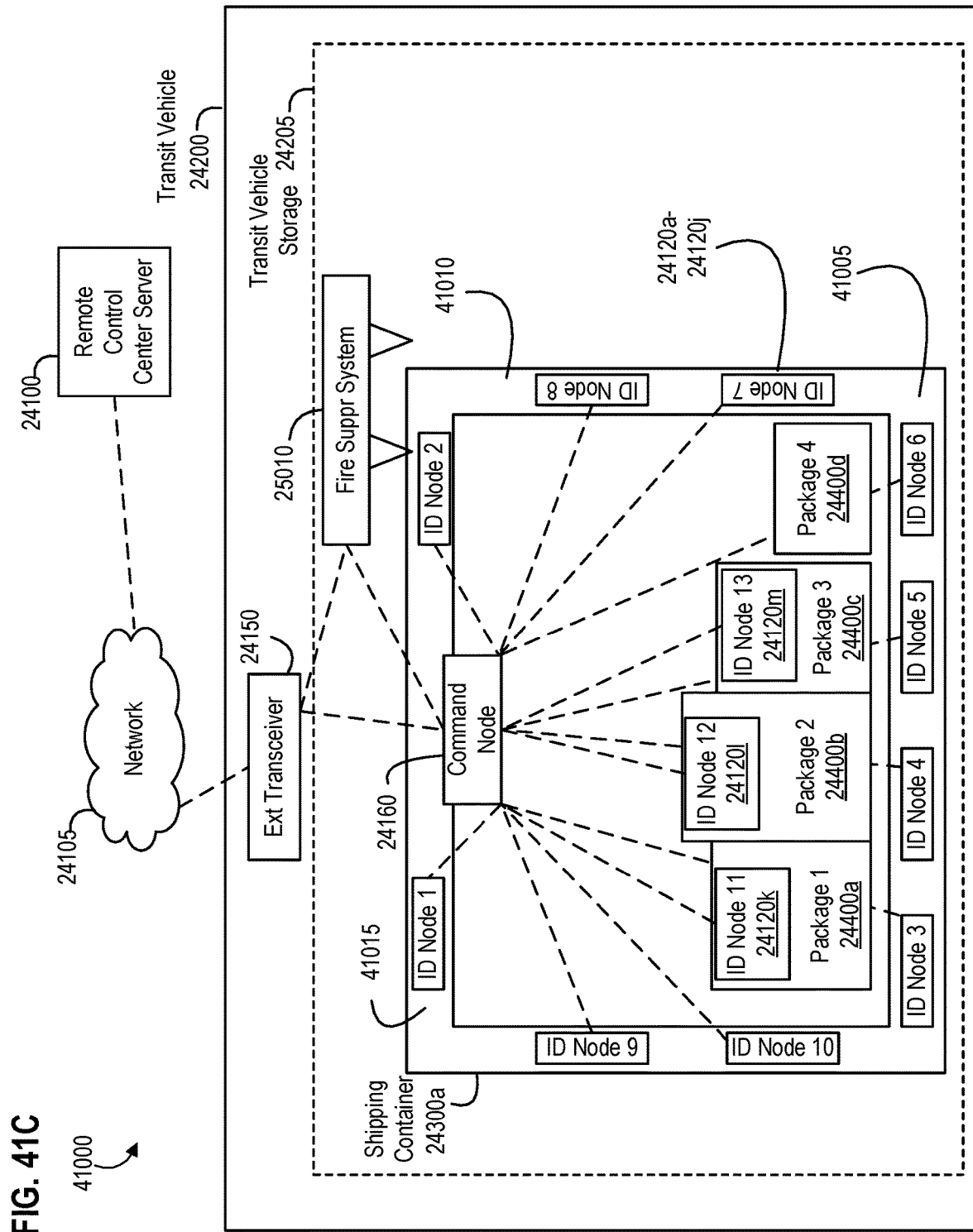
Figure 41D:
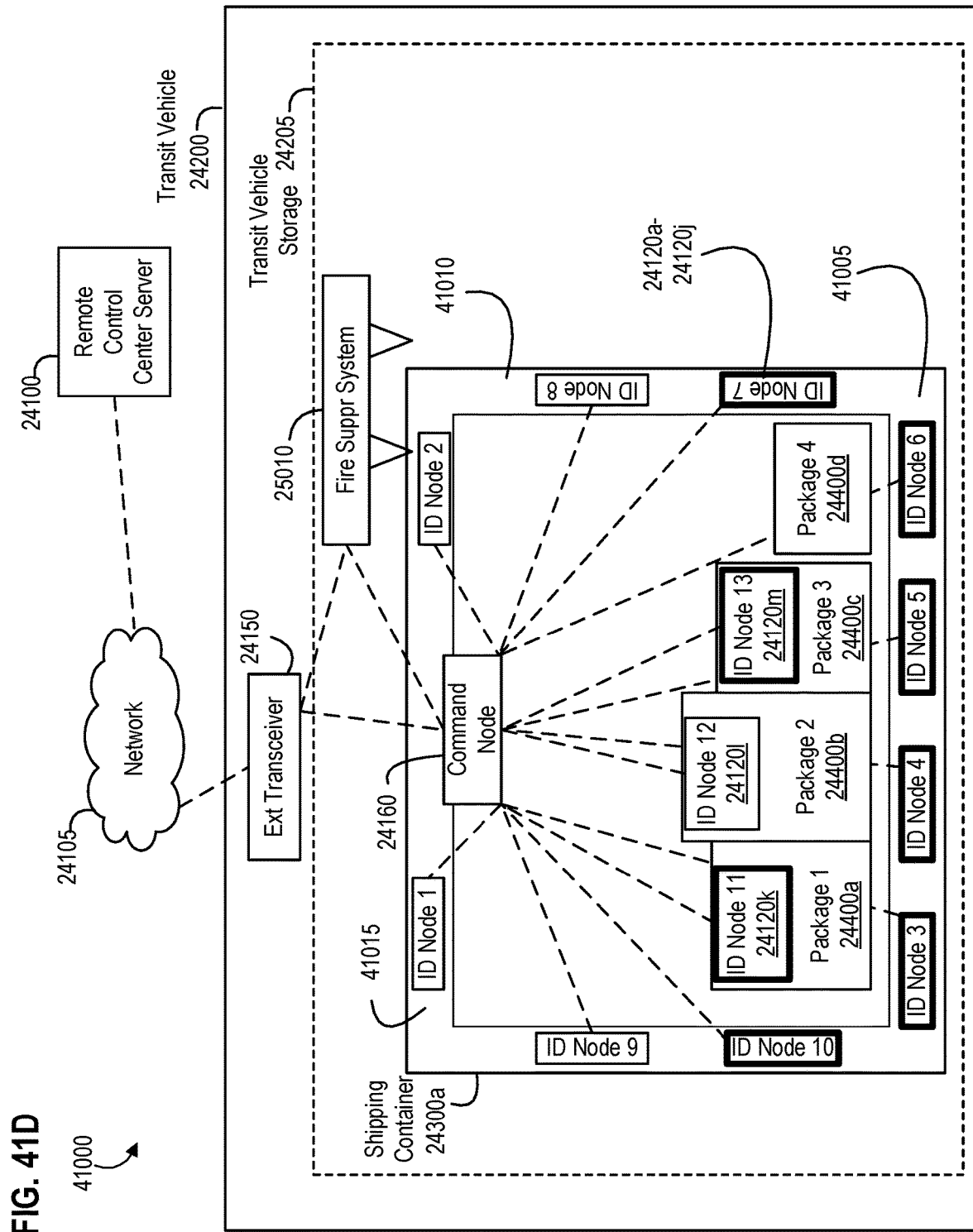

Further embodiments that involve a command node interacting with selectively assigned ID nodes when monitoring for and detecting an environmental anomaly may focus on the shipping container itself as a specially enhanced and improved type of apparatus. FIGS. 41A-41D are diagrams of different exemplary improved and enhanced shipping containers that transports packages and self-monitors for an environmental anomaly using selectively assigned ID nodes in accordance with an embodiment of the invention. FIG. 41A shows such an enhanced shipping container with ID nodes attached to parts of the shipping container, while FIG. 41B shows ID nodes integrated into parts of the shipping container. FIG. 41C shows packages loaded into such an enhanced shipping container and FIG. 41D illustrates how the container's command node may selectively assign particular ones of the container's ID nodes as a subset of ID nodes to use for monitoring for and detecting an environmental anomaly related to the shipping container.

Referring now to FIG. 41A, further details of an embodiment of exemplary shipping container 24300a are shown. In particular, FIG. 41A illustrates shipping container 24300a as having command node 24160 mounted to it as well as ID nodes 1-10 (24120a-24120j, respectively) disposed within container 24300a. In general, the exemplary shipping container 24300a has a base 41005, a plurality of walls 41010 coupled to the base 41005, a ceiling 41015 coupled to the walls 41010 so as to enclose the walls 41010 and base 41005. As such, the base 41005, the walls 41010, and the ceiling 41015 collectively define an interior storage space within the shipping container 24300a. While not shown in FIG. 41A, those skilled in the art will appreciate that an embodiment of shipping container 24300a may further include at least one selectively securable door (e.g., a lid as part of the ceiling, an access hatch or door as part of at least one of the walls) that provides securable access into the interior storage space of the shipping container.

ID nodes 1-10 (24120a-24120j) disposed within container 24300a, as shown in FIG. 41A, are located in different locations along the interior of the shipping container 24300a. In more detail, ID nodes 1-2 are each disposed at different locations as part of ceiling 41015; ID nodes 3-6 are each disposed at different locations as part of floor/base 41005; and ID nodes 7-10 are each disposed at different locations as part of walls 41010. As disposed on these different locations within the shipping container 24300a, each of ID nodes 1-10 are configured to wirelessly transmit a broadcast signal (e.g., an advertising signal broadcast by the ID node that may be requesting information, reporting status information on the node, transmitting sensor data gathered by the ID node, relaying shared sensor data from another ID node, and the like). As shown in FIG. 41A, exemplary ID nodes 1-10 (24120a-24120j) may be disposed on the different locations as being fixed to an interior surface of the shipping container, or removable and only temporarily attached to the shipping container. Thus, an embodiment may use some or all of the ID nodes disposed within shipping container 24300a as being replaceable to allow for periodic replacement (e.g., swapping out ID nodes that need charging, repair, or replacement) with the same type of ID node or with a different ID node having batteries that have a longer charge life, having longer range or different communication capabilities (e.g., use a longer range communicating format to better communicate with command node 24160), or having specialized sensors (e.g., an ID node used for monitoring special and/or hazardous items being shipped within the container where the sensors on the ID node may correspond to particular risks associated with such items, correspond to temperature or other environmental conditions critical for monitoring such items, and the like).

Alternatively, the ID nodes disposed within the shipping container may be integrated into parts of the shipping container as shown in FIG. 41B. Referring now to FIG. 41B, exemplary ID nodes 1-10 (24120a-24120j) disposed within container 24300a are located in different locations of the shipping container 24300a, but are shown as disposed as integrated parts of shipping container 24300a. As shown, ID nodes 1-2 are each disposed at different locations as integrated parts of ceiling 41015 (e.g., within the ceiling); ID nodes 3-6 are each disposed at different locations as integrated parts of floor/base 41005; and ID nodes 7-10 are each disposed at different locations as integrated parts of different walls 41010.

FIG. 41C shows exemplary ID nodes 1-10 (24120a-24120j) disposed within container 24300a after packages 24400a-24400d have been loaded into container 24300a. As shown in FIG. 41C, packages 24400a-24400c are each associated with ID nodes 24120k-24120m, respectively. In more detail, each of packages 24400a-24400c may have their respective ID nodes 24120k-24120m attached to the outside of the respective package, inserted within the interior of the respective package, attached to the item/asset within the respective package, or integrated as parts of the respective package in such a way that the ID node and its associated package are logically related to one another as well as physically traveling together within the shipping container 24300a.

The command node 24160 mounted to shipping container 24300a, as shown in FIG. 41C, is similar to the command node used in other system embodiments described above in that it has a command node processing unit; a command node memory coupled to the processor and maintaining at least a command node container management program code used to selectively assign ID nodes to be monitored when detecting an environmental anomaly, and a threshold setting used for identifying the environmental anomaly; and two communication interfaces—one for transmitting and receiving in a first wireless communication format compatible with the broadcast signal transmitted by each of the ID nodes, and the other for transmitting and receiving in a second wireless communications format (e.g., cellular, Wi-Fi, or other formats). In more detail, the enhanced shipping container's command node may, for example, be implemented as a container node integrated as part of the shipping container or, alternatively, be implemented as self-locating master node implemented separately from the shipping container (but where it may be simply attached to the container).

In operation, the enhanced shipping container's command node processor is programmatically configured, when executing the command node container management program code, to be operative to selectively assign a subset of the ID nodes to function as dedicated monitor beacons deployed as part of the shipping container (e.g., selectively assigning ID nodes 3-7, 10, 11, and 13 as illustrated in FIG. 41D); monitor the assigned subset of the ID nodes using the first communication interface for an unanticipated state of ceased broadcasting from any of the assigned subset of the ID nodes; identify an unresponsive group from the assigned subset of the ID nodes to be in the unanticipated state of ceased broadcasting based upon the monitoring step; detect the environmental anomaly when a size of the unresponsive group of the assigned subset of the ID nodes exceeds the threshold setting maintained by the command node; automatically generate an alert notification related to the detected environmental anomaly for the shipping container; and cause the second communication interface to transmit the alert notification to directly cause a mediation response related to the detected environmental anomaly.

In more detail, a further apparatus embodiment may have the command node's processor causing the second communication interface to transmit the alert notification to directly cause the mediation response by being further operative to cause the second communication interface to transmit the alert notification to a fire suppression apparatus disposed outside the shipping container (e.g., fire suppression system 25010 shown in FIG. 41D) to cause the fire suppression apparatus to responsively supply a fire suppression agent to the shipping container as the mediation response (as explained in more detail with respect to FIGS. 32A-32C). In this way, alert notification transmitted by the enhanced shipping container's command node 24160 to the fire suppression system 25010 activates the fire suppression system 25010 to cause the fire suppression system to pierce shipping container 24300a and inject fire suppression agent into the interior storage space of the shipping container as the mediation response.

Still another embodiment of such an enhanced shipping container apparatus may have the command node's processor causing the second communication interface to transmit the alert notification to directly cause the mediation response by being further operative to cause the second communication interface to transmit the alert notification to an external transceiver disposed outside of the shipping container (e.g., external transceiver 24150, cockpit transceiver 25150a, or logistics transceiver 25150b). In this way, the alert notification sent by the command node's second communication interface causes the external transceiver to generate a prompt to investigate the shipping container or to change course from a transit path related to the shipping container.

In yet another embodiment of such an enhanced shipping container apparatus may have the command node's memory maintaining a predetermined ID node list identifying those of the ID nodes to be monitored. As such, the command node's processor may then be operative to selectively assign the subset of the ID nodes by being further programmatically configured to be operative to access the predetermined ID node list from the command node memory, and selectively assign members of the subset of the ID nodes based upon which of the ID nodes disposed within the shipping container are indicated in the accessed predetermined ID node list.

In a similar way, another embodiment of such an enhanced shipping container apparatus may have the command node's memory maintaining a predetermined ID node list identifying those of the ID nodes to be monitored as well as context data on location information related to a location for each of the ID nodes disposed as part of the shipping container. As such, the command node's processor may then be operative to selectively assign the subset of the ID nodes by being further programmatically configured to be operative to access the predetermined ID node list and the context data from the command node memory, and selectively assign members of the subset of the ID nodes based upon which of the ID nodes are indicated in the accessed predetermined ID node list and the location information related to each of the ID nodes in the subset of the ID nodes.

In even more detail, another embodiment of such an enhanced shipping container apparatus may have the command node's memory maintaining a predetermined ID node list identifying those of the ID nodes to be monitored. As such, the command node's processor may then be operative to selectively assign the subset of the ID nodes by being further programmatically configured to be operative to access the predetermined ID node list from the command node memory; initially assign a first set of members of the subset of the ID nodes based upon which of the ID nodes are indicated in the accessed predetermined ID node list; cause the first communication interface to detect a broadcast signal from one or more additional ones of the ID nodes not included in the predetermined ID node list; and selectively add at least one additional ID node as an additional member of the subset of the ID nodes from the additional ones of the ID nodes not included in the predetermined ID node list.

In still another embodiment, the enhanced shipping container apparatus may selectively assign the subset of ID nodes to be monitored in more of a passive detection manner. In particular, such an embodiment of the enhanced shipping container apparatus may have the command node processing unit being operative to selectively assign the subset of the ID nodes by being further programmatically configured to be operative to cause the first communication interface to detect the broadcast signal from one or more of the ID nodes, and selectively assign members of the subset of the ID nodes from the ID nodes detected as broadcasting. In more detail, the embodiment of the enhanced shipping container apparatus may have the command node's memory maintaining a communication profile (e.g., part of profile data 430) that identifies an anticipated broadcasting state for ID nodes disposed within the enhanced shipping container. As such, the command node processing unit may be operative to selectively assign the subset of the ID nodes by being further programmatically configured to be operative to cause the first communication interface to detect one or more of the broadcast signals respectively from one or more of the ID nodes; access the communication profile from the command node memory to determine the anticipated broadcasting state for each of the one or more of the ID nodes associated with the detected broadcast signals; and selectively assign members of the subset of the ID nodes from those of the one or more of the ID nodes associated with the detected broadcast signals that are in the anticipated broadcasting state according to their respective communication profile.

The enhanced shipping container's command node may, in some embodiments, receive (via the second communication interface) an instruction message that identifies the subset of the ID nodes to function as the dedicated monitor beacons. Such an instruction message received by the command node may be generated by an external transceiver disposed outside and separate from the shipping container (e.g., exemplary external transceiver 24150) or a server (e.g., server 24100) in communication with the shipping container's command node (e.g., either directly between command node 24160 and server 24100 or indirectly from command node 24160 and at least one intermediary device (e.g., external transceiver 24150) in communication with server 24100.

Embodiments of the enhanced shipping container may adapt which ID nodes are monitored as part of detecting an environmental anomaly based upon what may be stored within the container. In particular, an embodiment may have the command node processing unit being further operative to re-assign which of the ID nodes are the members of the subset of the ID nodes being monitored when the command node detects a change in what is maintained within the shipping container. In more detail, the command node element of the enhanced shipping container apparatus may include a motion detector (e.g., a type of sensor 26465) coupled to the command node processing unit. Such a motion detector is disposed within the shipping container and operative to generate a movement detection signal upon detecting movement within the shipping container. As such, he command node processing unit may then be operative to detect the change in what is maintained within the shipping container based upon the movement detection signal from the motion detector within the shipping container. For example, the motion detector may generate a movement detection signal when the container is being loaded, unloaded, or packages/items/assets are moved within the container.

In another example, the command node processing unit on the enhanced shipping container apparatus may be operative to detect the change in what is maintained within the shipping container (and responsively re-assign which ID nodes to use as the monitored subset) based upon receiving updated shipping information on updated contents to be maintained within the shipping container. As such, the shipping container's command node may detect a loading operation, an unloading operation, or a re-arrangement operation of the shipping container based on the updated shipping information. Such a re-arrangement operation of the shipping container, which may cause such re-assigning of the ID nodes in the subset, may be also be based upon detecting a change in location of at least one of the members of the subset of the ID nodes within the shipping container.

In even more detail, another embodiment of such an enhanced shipping container apparatus may have the command node's memory maintaining a communication profile that identifies an anticipated broadcasting state for each of ID nodes within the shipping container apparatus. As such, the command node's processor may then be operative to selectively assign the subset of the ID nodes by being further programmatically configured to be operative to monitor the assigned subset of the ID nodes for the unanticipated state of ceased broadcasting from any of the assigned subset of the ID nodes according to the communication profile maintained in the command node memory. Such a communication profile, in more detail, may define an anticipated periodic broadcast behavior for the member of the assigned subset of the ID nodes, so that the command node processing unit may be operative to monitor the assigned subset of the ID nodes for the unanticipated state of ceased broadcasting by being further operative to monitor for a shift in broadcast behavior of any of the members of the assigned subset of the ID nodes away from the anticipated broadcast behavior for the respective member of the assigned subset of the ID nodes.

Embodiments of the enhanced shipping container may have its command node access and use contextual type of data when selectively assigning which ID nodes to use as part of the monitored subset. In particular, the enhanced shipping container's command node processor may receive vehicle status data provided by the external transceiver via the second communication interface; and then be operative to selectively assign the subset of the ID nodes depending upon a state of the transit vehicle (e.g., a takeoff vehicular status, a cruising vehicle status, a landing vehicular status, and a stationary vehicular status) as indicated by the vehicle status data or, in more detail, depending on a risk factor associated with the state of the transit vehicle as indicated by the vehicle status data. For example, the risk factor associated with a particular state of the vehicle may allow for different numbers of ID nodes to be assigned to the monitored subset. As such, when the risk factor is a first level for a first state of the transit vehicle, a number of the members selectively assigned to the subset of the ID nodes may be a first value. When the risk factor is a second level for a second state of the transit vehicle where the second level is higher than the first level, the number of the members selectively assigned to the subset of the ID nodes may be greater than the first value. Thus, under certain conditions where the vehicle status data reflects a higher risk factor, the command node may selectively assign an increased number of ID nodes disposed within the enhanced shipping container to be monitored as part of detecting an environmental anomaly related to the enhanced shipping container.

In a further embodiment, the enhanced shipping container's command node processing unit may receive a threshold update for the threshold setting over the second communication interface from, for example, from the external transceiver unit (e.g., as defined by an operator of the transit vehicle using the external transceiver unit, or as defined by a logistics crew member of the transit vehicle using the external transceiver unit). Such a threshold update may be provided to the external transceiver unit from a remote control center (e.g., server 24100 as shown in FIG. 41D) in communication with the external transceiver unit. In like manner, the enhanced shipping container's command node processing unit may receive a selection update over the second communication interface, where the selection update has updated information on which of the ID nodes are selectively assigned to be in the subset of the ID nodes (e.g., updated information for the predetermined ID node list that may be used by the command node to know which ID nodes disposed within the enhanced shipping container to monitor). Such a selection update may be provided, for example, from the external transceiver unit (e.g., as defined by an operator of the transit vehicle using the external transceiver unit, or as defined by a logistics crew member of the transit vehicle using the external transceiver unit). Such a threshold update may be provided to the external transceiver unit from a remote control center (e.g., server 24100 as shown in FIG. 41D) in communication with the external transceiver unit. In this way, an embodiment of the enhanced shipping container may be adaptively and automatically repurposed and updated on which ID nodes to use as dedicated monitor beacons and what type of threshold setting to use based on how the container may be deployed and what the container may be carrying.

Additionally, an embodiment of the enhanced shipping container may have its command node confirming the validity of broadcasts received from the ID nodes. In particular, an embodiment may have the enhanced command node processor being operative to monitor the assigned subset of the ID nodes for the unanticipated state of ceased broadcasting by being further operative to (a) receive a communication broadcasted from a first of the ID nodes within the assigned subset of the ID nodes over the first communication interface; (b) confirm the validity of the received communication; and then (c) repeating (a) and (b) for the remainder of the communications received from any of the remaining ones of the ID nodes within the assigned subset of the ID nodes. As such, the command node may be operative to then identify the unresponsive group from the assigned subset of the ID nodes based upon the monitoring step and based upon steps (a)-(c). In a further "active" validation example, the command node processing unit may confirm the validity of the received communication in (b) by being further operative to (b1) send, via the first communication interface, an authentication request to the first of the ID nodes within the assigned subset of the ID nodes; and (b2) receive, via the first communication interface, a validation response from the first of the ID nodes within the assigned subset of the ID nodes that authenticates the communication broadcasted from the first of the ID nodes within the assigned subset of the ID nodes. In a further "passive" validation example, the command node memory may maintain a validation sequence for the first of the ID nodes within the assigned subset of the ID nodes, where the validation sequence characterizes expected broadcasts from the first of the ID nodes within the assigned subset of the ID nodes; and then the command node processor may confirm the validity of the received communication in (b) by being further operative to (b1) access the validation sequence from the command node memory; and (b2) determine if the received communication from the first of the ID nodes within the assigned subset of the ID nodes matches a predetermined one of the expected broadcasts from the first of the ID nodes within the assigned subset of the ID nodes according to the validation sequence stored within the command node. Such a predetermined one of the expected broadcasts may be implemented as a rotating value previously received by the command node over the second communication interface for the first of the ID nodes within the assigned subset of the ID nodes.

Enhanced Deployment of ID Nodes for Detecting Environmental Anomaly

As noted in the embodiments described above, an exemplary command node (e.g., a container node that is essentially a master node that may not have location circuitry for self-locating capabilities, or a mobile master node deployed on or as part of the shipping container that has location circuitry for self-locating capabilities) may selectively choose, assign, or designate which of the available ID nodes are to be monitored as part of detecting an environmental anomaly. However, at times, one of the assigned ID nodes to be monitored may fall outside a reception range of the command node. As such, further embodiments may have an ID node within a container being designated (or pre-designated) as listeners/bridging nodes so that other ID nodes that are to be used for monitoring environmental anomalies but located outside the command node's reception range (e.g., remotely located ID nodes functioning as monitor beacons) can still communicate with the command node and participate as part of an enhanced monitoring system for shipping container environmental anomalies.

In some embodiments, this may be helpful when proactively setting up the set of monitoring ID nodes so as to accommodate shipped items known to shield communications with certain nodes. In further embodiments, as the container is loaded, the command node mounted on the shipping container may "see" or be able to communicate with an ID node designated for monitoring environmental anomalies (i.e., one from the group of monitor beacons), but then detects a drop in signal strength from that ID node. The command node may then adaptively and responsively re-program another ID node to operate as a bridged listening node for the ID node desired to be one of the container's environmental anomaly detecting elements but no longer able to be received by the command node as it was earlier in the container loading process. In further embodiments, the command node may dynamically alter how often the ID nodes report based on a density of RF broadcasters within the reception range of the command node (e.g., lowering a reporting interval when the density of RF broadcasters is above a threshold RF visibility limit, and increasing a reporting interval when such a density falls below the threshold limit). Embodiments may also have the command node instructing particular ID nodes functioning as members of the group of monitor beacons to dynamically adjust their respective RF broadcast signal output power as packages are loaded to help increase the likelihood of still "seeing" node-enabled packages at extreme reaches of the container relative to the command node.

Figure 42A:
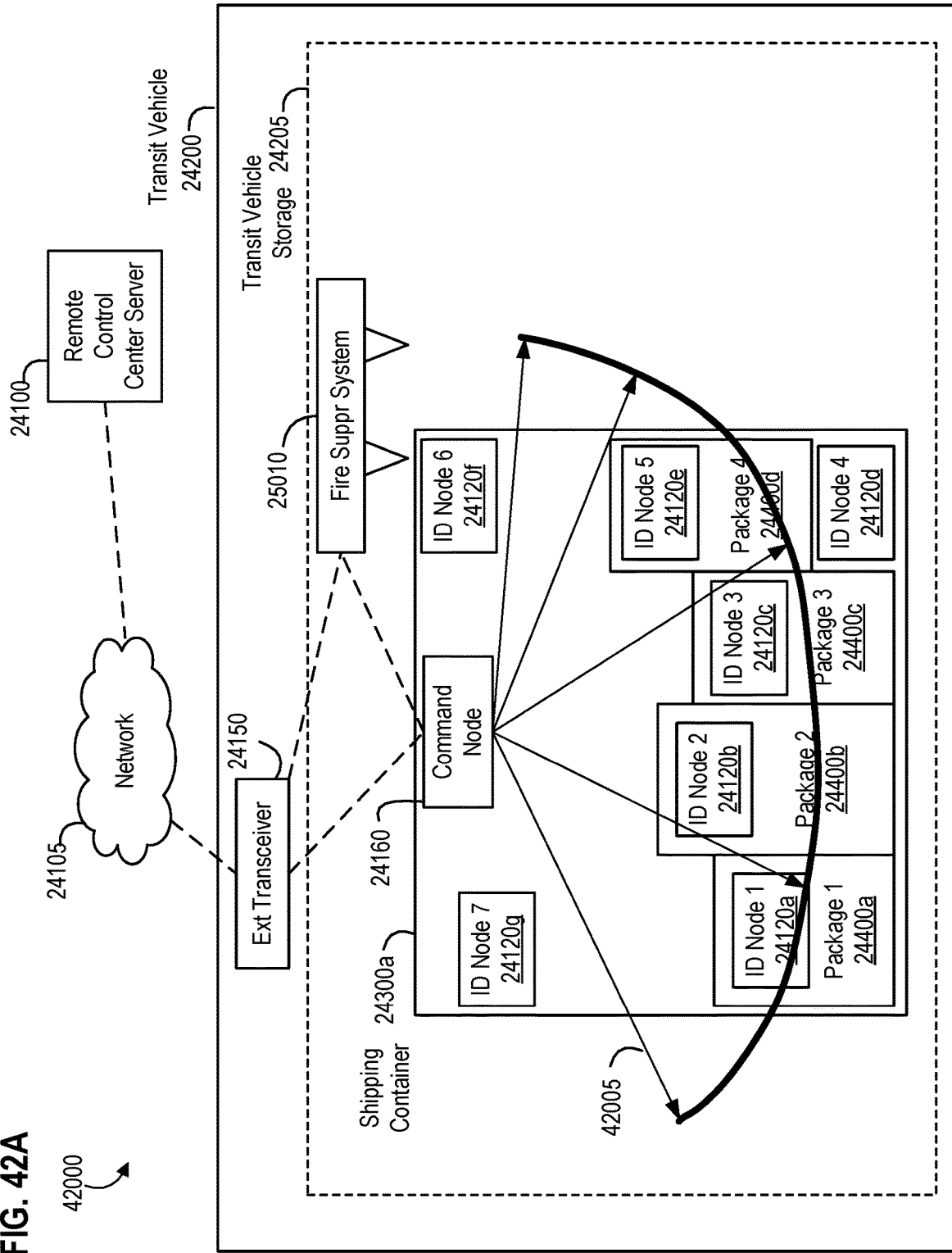
FIGS. 42A-42C are diagrams of an exemplary shipping container that leverages an exemplary wireless node network for detecting environmental anomalies associated with the shipping container using a command node mounted to the shipping container and selectively assigned ID nodes within the shipping container as a group of monitor beacons including a dedicated bridging node for a remote monitor beacon in accordance with an embodiment of the invention.
Figure 42B:
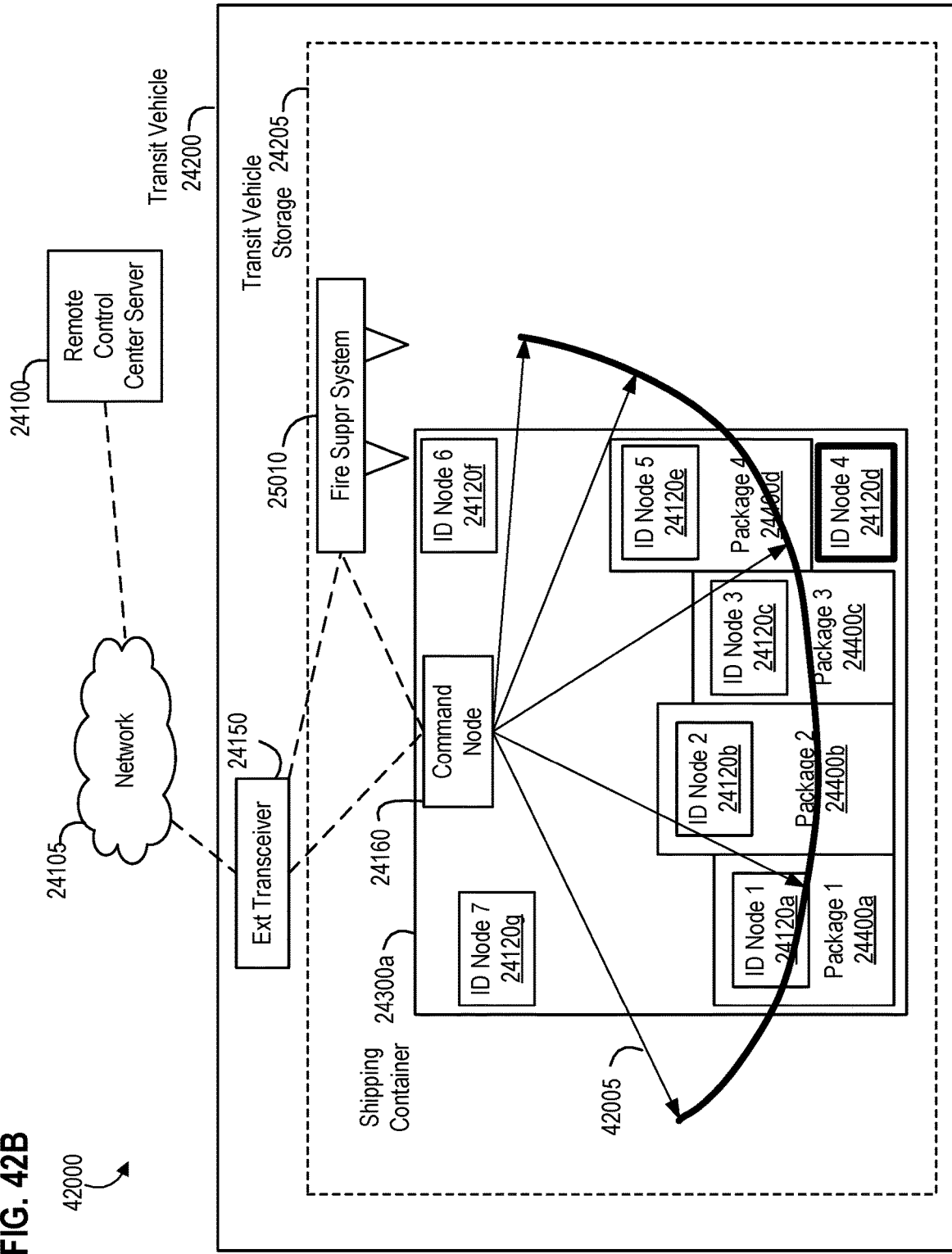
Figure 42C:
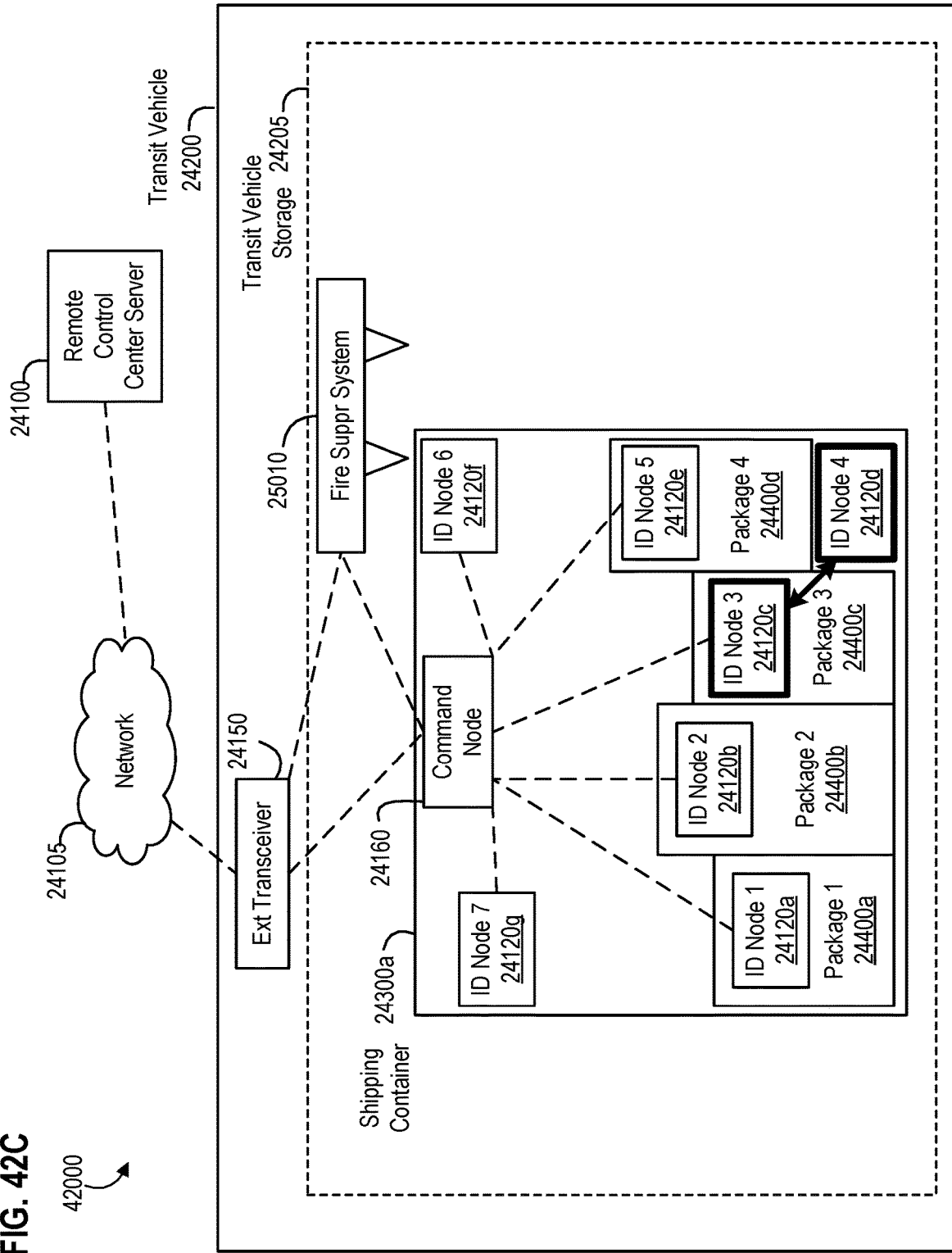
Figure 43:
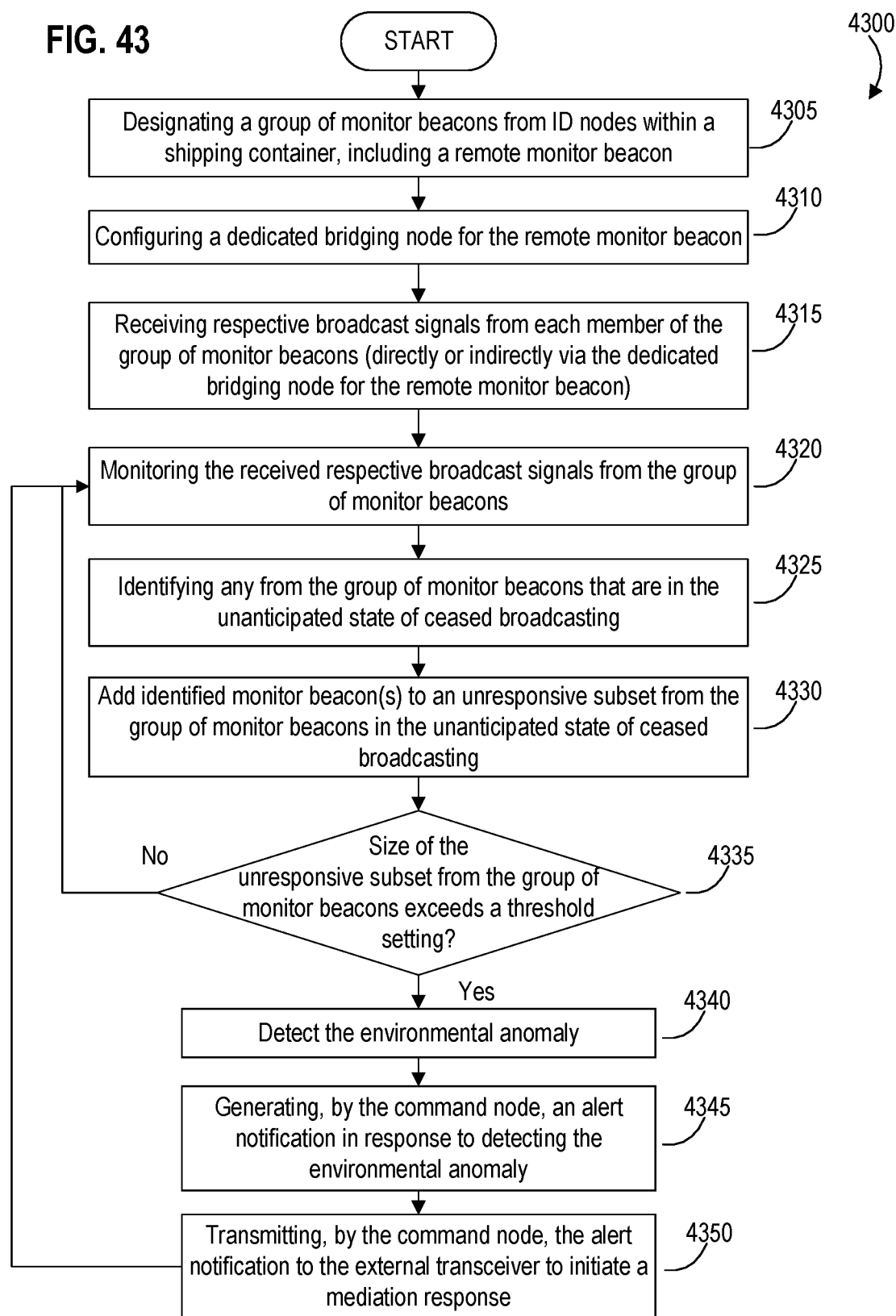
FIG. 43 is a flow diagram illustrating an exemplary method for adaptively monitoring for an environmental anomaly using a group of monitor beacons including a dedicated bridging node for a remote monitor beacon in accordance with an embodiment of the invention.

Further details of exemplary embodiments are illustrated in FIGS. 42A-43. FIGS. 42A-42C are diagrams of an exemplary shipping container that leverages an exemplary wireless node network for detecting environmental anomalies associated with the shipping container using a command node mounted to the shipping container and selectively assigned ID nodes within the shipping container as a group of monitor beacons including a dedicated bridging node for a remote monitor beacon in accordance with an embodiment of the invention. Referring now to FIG. 42A, exemplary system 42000 is shown with exemplary shipping container 24300a having command node 24160 mounted to the shipping container 24300a and ID nodes 24120a-24120g (also referred to as ID nodes 1-7) disposed at different locations within container 24300a. ID nodes 1, 2, 3, and 5 are associated with respective ones of packages 24400a-24400d maintained within shipping container 24300a, while ID nodes 4, 6, and 7 are not associated with any particular package maintained within container 24300a. Notably, as shown in FIG. 42A, ID node 4 is disposed along the floor or base of shipping container 24300a and is not associated with any particular package within container 24300a. In an example, ID node 4 may be operative to wirelessly broadcast a signal (e.g., an advertising signal, a signal having sensor data generated by ID node 4, and the like), which may be received by command node 24160. However, as packages are loaded within shipping container 24300*a* (such as package 3 and package 4 (i.e., packages 24400*c* and 24400*d*)), the material within such packages may reduce the reception range 42005 of command node. In other words, with packages loaded within shipping container 24300*a*, ID node 4 may be beyond the reception range 42005 of command node 24160 where command node 24160 could receive wirelessly broadcast signals from ID node 4 prior to particular packages having been loaded into container 24300*a*. Thus, as shown in FIG. 42B, if command node 24160 initially selected ID node 4 as part a group of the ID nodes to be monitor beacons selected (e.g., ID nodes 1, 2, 4, and 5 deployed in different locations within the container 24300*a* and chosen for monitoring as part of detecting an environmental anomaly within the shipping container 24300*a*), ID node 4 may be or have become a remote monitor beacon because it is or has become located outside of a reception range 42005 for the short range communication interface 26480 used by the command node 24160 to communicate with ID nodes. Rather than simply dropping ID node 4 from the group of monitor beacons, command node 24160 may still include ID node 4 as part of the selected group of monitor beacons (e.g., ID nodes 1, 2, 4, and 5) by programmatically configuring another of the ID nodes in the shipping container (e.g., ID node 3) to be a dedicated bridging node as shown in FIG. 42C. As such, dedicated bridging ID node 3, as configured to relay communications in such an embodiment, is operative to provide a dedicated intermediary communication link between the command node 24160 and the remote monitor beacon (i.e., ID node 4 in this example). ID node 3, as the dedicated bridging node, is located and deployed within the reception range 42005 of the first communication interface 26480 on the command node 24160 and a broadcast range of the remote monitor beacon so that the command node 24160 may receive signals broadcast by ID node 4 (the remote monitor beacon) as relayed by ID node 3 (the dedicated bridging node for such a remote monitor beacon). In this way, while materials in package 3 and package 4 may shield, attenuate, and/or otherwise interfere with communications between command node 24160 and ID node 4, the use of ID node 3 as a dedicated bridging node permits the continued ability of command node 24160 to use ID node 4 as a monitor beacon for detecting an environmental anomaly. While the embodiments shown in FIGS. 42A-42C illustrate how the command node 24160 may configure an ID node to be a dedicated bridging node for a remote monitor beacon, those skilled in the art will appreciate that a system involving such a command node 24160 may configure multiple ID nodes to be different dedicated bridging nodes for different remote monitor beacons used when detecting an environmental anomaly on shipping container 24300*a*.

In more detail, an embodiment of an improved system for adaptively monitoring for an environmental anomaly related to a shipping container (e.g., container 24300*a*) maintaining a plurality of packages (e.g., packages 1-4) may generally have multiple ID nodes (e.g., ID nodes 1-7) disposed as different locations within the shipping container and a command node (e.g., command node 24160) mounted to the shipping container. The system may have the shipping container being transported by a transit vehicle (such as an airplane, a railway conveyance, a maritime vessel, and a roadway conveyance). The system's command node has at least a command node processing unit (commonly referred to as a processor), a command node memory, and two communication interfaces with which the command node uses to the communicate with ID nodes within the shipping container and to communication with further elements (e.g., exemplary external transceiver 24150 (which may be a mobile handheld transceiver or a transceiver fixed to a relative location, such as on transit vehicle 24200), exemplary onboard triggered fire suppression system 25010), such as explained with reference to FIG. 26 and exemplary command node 26000. The system's command node may, for example, be implemented as a container node integrated as part of the shipping container or, alternatively, a master node implemented separately from the shipping container but attached to the container. In more detail, the system's command node has command node memory coupled to the command node processing unit and maintaining at least a command node container management program code (e.g., CN control and management code 26425), and a threshold setting used for identifying the environmental anomaly (e.g., a threshold setting as part of code 26425). The command node's first communication interface (e.g., interface 26480) is coupled to the command node processing unit and is configured to communicate using a first wireless communication format compatible with each of the ID nodes (e.g., Bluetooth Low Energy, ZigBee, and the like). The command node's second communication interface (e.g., interface 26485) is also coupled to the command node processing unit and is configured to communicate with devices disposed separately from the shipping container (e.g., an external transceiver unit associated with a transit vehicle transporting the shipping container, an onboard fire suppression system) using a second wireless communications format.

In operation, the system's command node is specially programmed, adapted, and configured, when executing the command node container management program code, to be operative to first select a group of monitor beacons from the ID nodes disposed within the shipping container. Each in the selected group of monitor beacons are what the command node will monitor as part of detecting any environmental anomaly related to the shipping container. Each member of the group of monitor beacons broadcasts according to a communication profile associated with that member of the group of monitor beacons (e.g., a communication profile that is part of profile data 430). Each member of the group of monitor beacons is deployed at a different location within the shipping container, and where the group of monitor beacons includes at least a remote monitor beacon located outside a reception range of the first communication interface on the command node. For example, command node 24160 may select ID nodes 1, 2, 4, and 5 (as shown in FIG. 42A-C) to be a group of monitor beacons where ID node 4 is a remote monitor beacon as it is outside the reception range 42005 of the command node. In more detail, the remote monitor beacon may be located outside the reception range of the command node as a result of at least one of the packages being loaded within the shipping container (such as when package 4 shown in FIG. 42C is loaded within shipping container 24300*a* and placed on top of ID node 4). Prior to such loading, the command node processing unit may initially receive the respective broadcast signal directly from the remote monitor beacon before the relevant package(s) is loaded within the shipping container, and then the command node processing unit may detect the loss of direct reception of the respective broadcast signal from the remote monitor beacon after the at least one of the packages is loaded within the shipping container.

The command node processing unit is further operative, as part of the system's operation, to programmatically configure at least another of the ID nodes not included in the selected group of monitor beacons to be a dedicated bridging node (e.g., ID node 3 as shown in FIG. 42C). The dedicated bridging node provides a dedicated intermediary communication link between the command node and the remote monitor beacon. In other words, the dedicated bridging node is deployed within the reception range of the first communication interface on the command node and a broadcast range of the remote monitor beacon so as to operate as a relay type of node to enable the command node to effectively receive wirelessly broadcast signals from the remote monitor beacon via relayed communications from the dedicated bridging node to the command node. In more detail, such a dedicated monitor beacon may be a pre-designated one of the ID nodes not included in the group of monitor beacons to be the dedicated bridging node, or may be an adaptively designated one of the ID nodes not included in the group of monitor beacons to be the dedicated bridging node (such as when the command node detects a drop in signal strength from one member of the group of monitor beacons). For example, the command node may detect, using the first communication interface, the drop in signal strength transmitted from a member of the group of monitor beacons as the shipping container is being loaded, and then responsively and programmatically configure a second of the ID nodes not included in the group of monitor beacons to be the dedicated bridging node providing the dedicated intermediary communication link between the command node and the one member of the group of monitor beacons.

The command node processing unit of the system's command node is further operative to receive, via the first communication interface, a respective broadcast signal from each respective member of the group of monitor beacons. In more detail, the command node directly receives the respective broadcast signal from the group of monitor beacons not including the remote monitor beacon, but indirectly receives the respective broadcast signal from the remote monitor beacon through the dedicated intermediary communication link provided by the dedicated bridging node. As such, the command node processing unit is then operative to monitor the received respective broadcast signals from the group of monitor beacons for an unanticipated state of ceased broadcasting from any of the group of monitor beacons; identify an unresponsive subset from the group of monitor beacons to be in the unanticipated state of ceased broadcasting based upon the monitoring step; and detect the environmental anomaly when a size of the unresponsive subset of the group of monitor beacons exceeds the threshold setting maintained by the command node in the command node memory.

Once detected, the command node processing unit is then operative to automatically generate an alert notification related to the detected environmental anomaly for the shipping container, and cause the second communication interface to transmit the alert notification to initiate a mediation response related to the detected environmental anomaly. The system may further include an external transceiver unit disposed separately from the shipping container (e.g., exemplary external transceiver 24150 (mobile or a fixed transceiver), cockpit transceiver 25150*a*, or logistics transceiver 25150*b*). The transmitted alert notification may be sent to the external transceiver, which is operative to receive the alert notification and initiate the mediation response related to the detected environmental anomaly (as described in more detail above related to mediation prompts to be displayed and requesting feedback input related to such a detected environmental anomaly). The system, in a further embodiment, may include an onboard fire suppression system (e.g., fire suppression system 25010) disposed separately from the shipping container and that can supply a fire suppression agent within the shipping container. The transmitted alert notification, in this embodiment, may be sent directly to the onboard fire suppression system by the command node so that the onboard fire suppression system receives the alert notification and responsively initiates the mediation response related to the detected environmental anomaly (e.g., supplies the fire suppression agent to the interior of the shipping container).

In a further embodiment of this system, the command node processing unit may select the group of monitor beacons by being further programmatically configured to be operative to cause the first communication interface to transmit a monitor activation command to each of the group of monitor beacons to cause each of the group of monitor beacons to broadcast the respective broadcast signal from each of the group of monitor beacons.

In further embodiments, the system's command node may dynamically alter how often the ID node members of the group of monitor beacons broadcast. In more detail, the command node processing unit may be further operative to transmit, via the first communication interface, an instruction to a first member of the group of monitor beacons to change how often that member of the group of monitor beacons broadcasts its respective broadcast signal. Such an instruction may cause that member of the group of monitor beacons to change how often the first member of the group of monitor beacons broadcasts its respective broadcast signal based upon an active broadcasting density within the range of the first member of the group of monitor beacons. In another example, such an instruction may be a command to cause the first member of the group of monitor beacons to lower a reporting interval of how often the first member of the group of monitor beacons broadcasts its respective broadcast signal when the active broadcasting density is above an RF visibility limit, or to increase a reporting interval of how often the first member of the group of monitor beacons broadcasts its respective broadcast signal when the active broadcasting density is below an RF visibility limit. In still another example, the command node processing unit may be operative to transmit, via the first communication interface, an instruction to each member of the group of monitor beacons to change how often each member of the group of monitor beacons broadcasts its respective broadcast signal (as opposed to only one member).

In still other embodiments, the system's command node may dynamically alter the RF output power of the monitor beacons (i.e., those ID nodes selected to be part of the group of monitor beacons) as packages are loaded. In more detail, the command node processing unit may be further operative to transmit, via the first communication interface, an instruction to a first member of the group of monitor beacons to change a power level setting for how the first member of the group of monitor beacons broadcasts its respective broadcast signal. Such an instruction may cause that member of the group of monitor beacons to change the power level setting for how that member of the group of monitor beacons broadcasts its respective broadcast signal based upon context data accessible by the command node (e.g., context data 26560) and related to a proximity environment of that particular member of the group of monitor beacons (e.g., what items are in packages next to or within a predetermined distance to that member of the group of monitor beacons, what is in a package associated with that member of the group of monitor beacons). In still another example, the command node processing unit may be further operative to transmit, via the first communication interface, an instruction to each member of the group of monitor beacons to change a respective power level for how each member of the group of monitor beacons broadcasts its respective broadcast signal. Such changes for different members may be different depending on what is disposed next to or near respective members of the group of monitor beacons.

A further embodiment of the system's ID nodes, which may be part of the group of monitor beacons, may be associated with particular packages. In more detail, an embodiment may have the command node operative to select at least a portion of the group of monitor beacons as having ID nodes associated with respective ones of the packages maintained within the shipping container (e.g., ID node 1, 2, and 5 as shown in FIG. 42C). In another embodiment, at least a portion of the group of monitor beacons may include ID nodes traveling with respective ones of the packages maintained within the shipping container, or affixed to respective ones of the plurality of packages maintained within the shipping container, or integrated within respective ones of the plurality of packages maintained within the shipping container.

In further embodiments where packages may be associated with the ID nodes, the command node memory may have shipping information (e.g., a type of data that is part of association data 440) on what type of item is being shipped in each of the packages associated with each of the ID nodes. As such, the command node processing unit may select the group of monitor beacons by being further operative to access the shipping information from the command node memory, and selectively assign the members of the group of monitor beacons based upon the type of item being shipped in each of the packages associated with each of the ID nodes in the group of the monitor beacons as reflected in the accessed shipping information. In a more detailed embodiment, the command node processing unit may selectively assign the members of the group of monitor beacons by being further operative to identify which of the ID nodes are associated with packages containing predetermined target material for observation according to the accessed shipping information, and assign the identified ID nodes associated with the predetermined target material for observation as members of the group of monitor beacons. Such predetermined target material may include, for example, incendiary material, corrosive material, explosive material, flammable material, or acidic material. In another embodiment, the command node processing unit may selectively assign the members of the group of monitor beacons by being further operative to identify which of the ID nodes are associated with packages containing such predetermined target material for observation according to the accessed shipping information, and assign only a predetermined number of the identified ID nodes associated with the predetermined target material for observation as members of the group of monitor beacons.

Further embodiments provide more details on why an ID node in the group of monitor beacons may be unresponsive. For example, in one further embodiment, at least one of the ID nodes from the identified unresponsive subset from the group of monitor beacons is in the unanticipated state of ceased broadcasting due to mechanical damage. In more detail, the mechanical damage may, for example, be damage resulting from an impact to the ID node and damage resulting from exposure to a predetermined target material (such as a corrosive material, an explosive material, or a flammable material). Further still, the mechanical damage may be damage rendering the ID node from the identified unresponsive subset from the group of monitor beacons to be inoperable as a result of an impact to the at least one of the ID nodes from the identified unresponsive subset from the group of monitor beacons; corrosive damage to the ID node from the identified unresponsive subset from the group of monitor beacons; explosive damage to the ID node from the identified unresponsive subset from the group of monitor beacons; or flammable damage (e.g., heat damage, burn damage) to the ID node from the identified unresponsive subset from the group of monitor beacons.

In a further embodiment, at least one of the ID nodes from the identified unresponsive subset from the group of monitor beacons may have a particular type of ID node enclosure having an outer exposed material is generally designed or engineered to fail. In other words, the node enclosure or part of the enclosure may lose structural integrity or break apart when exposed to an environmental anomaly, which may cause the ID node's battery to be disconnected. A portion of the enclosure may, for example, be weakened in a targeted way based on a particular material anomaly to be detected. For instance, the node enclosure may react with a predetermined chemical material (or a predetermined incendiary material, predetermined flammable material, or a predetermined corrosive material). As such, an ID node with this ID node enclosure becomes inoperable and uncommunicative after the outer exposed material has reacted with the predetermined material that may come from an environmental anomaly. In an example, a node enclosure made with a starch at a targeted point of the node enclosure so that, when that part dissolves when exposed to liquid or another predetermined chemical, the portion of the node enclosure holding the battery may separate and, as a result, disconnect the battery in this example. In another example, the node enclosure or a part of the enclosure may be made from a material which has chemical reaction with specific components related to types of environmental anomalies (e.g., copper connectors as part of the node enclosure that may operate as battery terminals may dissolve when exposed to an acidic environment. Still another example may have a node enclosure or portion thereof and/or an electric pathway part of the enclosure being built of a material with a melting point at or lower than a targeted environmental anomaly (temperature of a lithium-ion battery fire).

In still further embodiments, the threshold setting or the selection criteria for which ID nodes are part of the group of monitor beacons may be remotely updated. For example, a further embodiment of the system may have the command node processing unit being further operative to receive, via the second communication interface, a threshold update for the threshold setting maintained by the command node. Such a threshold update may be received from an external transceiver unit (e.g., exemplary external transceiver 24150) and defined by an operator of the transit vehicle using the external transceiver unit or a logistics crew member of the transit vehicle using the external transceiver unit. The threshold update may, in another example, be provided to the external transceiver unit from a remote control center (e.g., server 24100) in communication with the external transceiver unit. In another example, another further embodiment of the system may have the command node processing unit being further operative to receive, via the second communication interface, a selection update for which of the ID nodes are selected to be in the group of monitor beacons. Such a selection update may be received from an external transceiver unit (e.g., exemplary external transceiver 24150) and defined by an operator of the transit vehicle using the external transceiver unit or a logistics crew member of the transit vehicle using the external transceiver unit. The selection update may also be provided to the external transceiver unit from a remote control center (e.g., server 24100) in communication with the external transceiver unit.

Another embodiment may include the external transceiver as an element of the improved system. In more detail, another embodiment of an improved system for adaptively monitoring for an environmental anomaly related to a shipping container maintaining packages. The system generally includes multiple ID nodes disposed at different locations within the shipping container (where each of the ID nodes are configured to wirelessly broadcast a signal), a command node mounted to the shipping container (as described above), and an external transceiver disposed separately from the shipping container that is configured to wirelessly communicate with at least the second communication interface of the command node using the second wireless communications format. The command node processing unit is programmatically configured, when executing the command node container management program code in its memory, to be operative to first select a group of monitor beacons from the ID nodes. Each member of the group of monitor beacons is deployed at a different location within the shipping container and broadcasts according to a communication profile associated with that member of the group of monitor beacons, and where the group includes at least a remote monitor beacon located outside a reception range of the first communication interface on the command node. In this improved system, the command node processing unit is also operative to programmatically configure at least another of the ID nodes not included in the group of monitor beacons to be a dedicated bridging node providing a dedicated intermediary communication link between the command node and the remote monitor beacon. The dedicated bridging node is deployed within the reception range of the first communication interface on the command node and a broadcast range of the remote monitor beacon. The command node processing unit is then operative to receive, via the first communication interface, a respective broadcast signal from each respective member of the group of monitor beacons, where the command node directly receives the respective broadcast signal from the group of monitor beacons not including the remote monitor beacon, and where the command node indirectly receives the respective broadcast signal from the remote monitor beacon through the dedicated intermediary communication link provided by the dedicated bridging node. The command node processing unit is then operative to monitor the received respective broadcast signals from the group of monitor beacons for an unanticipated state of ceased broadcasting from any of the group of monitor beacons; identify an unresponsive subset from the group of monitor beacons to be in the unanticipated state of ceased broadcasting based upon the monitoring step; detect the environmental anomaly when a size of the unresponsive subset of the group of monitor beacons exceeds a threshold setting maintained by the command node; automatically generate an alert notification related to the detected environmental anomaly for the shipping container; and cause the second communication interface to transmit the alert notification to the external transceiver to initiate a mediation response related to the detected environmental anomaly. The improved system's external transceiver is then operative to receive the alert notification and initiate the mediation response related to the detected environmental anomaly.

In a further embodiment, the improved system's external transceiver may have a display interface (e.g., display 40015) that generates a mediation response prompt related to the detected environmental anomaly in response to receiving the alert notification from the command node. In more detail, the external transceiver may initiate the mediation response related to the detected environmental anomaly by generating the mediation response prompt on the display interface for an operator of a transit vehicle transporting the shipping container. The mediation response prompt may, for example, request the operator change in course of the transit vehicle from an existing travel path of the transit vehicle in response to the detected environmental anomaly or request a logistics crew member to inspect the shipping container.

Another embodiment of the improved system may include an onboard triggered fire suppression system disposed separately from the shipping container, such as exemplary fire suppression system 25010. The onboard triggered fire suppression system responsively supplies a fire suppression agent to the shipping container in response to an activation signal received by the onboard triggered fire suppression system. As such, the system's external transceiver may initiate the mediation response by (a) generating the activation signal in response to receiving the alert notification from the command node and (b) sending the activation signal to the onboard triggered fire suppression system. In more detail, the system's external transceiver may include a display interface that generates a mediation response prompt related to the detected environmental anomaly in response to receiving the alert notification from the command node, and a user input interface that receives feedback input responsive to the mediation response prompt displayed on the display interface. As such, the improved system's external transceiver may be further operative to generate the activation signal in response to receiving the feedback input, and send the activation signal to the onboard triggered fire suppression system. The feedback input may, for example, be input from a logistics crew member of the transit vehicle of a transit vehicle transporting the shipping container after an inspection of the shipping container prompted by the mediation response prompt generated on the display interface of the external transceiver.

In still another embodiment of an improved system for adaptively monitoring for an environmental anomaly may involve having the onboard fire suppression system directly initiated by the command node to provide the mediation response. As such, this further embodiment may include multiple ID nodes disposed at different locations within the shipping container, a command node (as described above) mounted to the shipping container, and an onboard triggered fire suppression system disposed separately from the shipping container and operative to responsively supply a fire suppression agent to the shipping container in response to an activation signal received by the onboard triggered fire suppression system from the second communication interface. The command node's processing unit is programmatically configured, when executing the command node container management program code, to be operative to select the group of monitor beacons from the ID nodes (as described above to include a remote monitor beacon located outside a reception range of the first communication interface on the command node); programmatically configure at least another of the ID nodes not included in the group of monitor beacons to be a dedicated bridging node (as described above); receive a respective broadcast signal from each respective member of the group of monitor beacons (directly or indirectly from the remote monitor beacon vis the dedicated bridging node); monitor the received respective broadcast signals from the group of monitor beacons for an unanticipated state of ceased broadcasting from any of the group of monitor beacons; identify an unresponsive subset from the group of monitor beacons to be in the unanticipated state of ceased broadcasting based upon the monitoring step; detect the environmental anomaly when a size of the unresponsive subset of the group of monitor beacons exceeds a threshold setting maintained by the command node; automatically generate an alert notification related to the detected environmental anomaly for the shipping container; and cause the second communication interface to transmit the alert notification to the onboard triggered fire suppression system to directly initiate a mediation response by the onboard triggered fire suppression system related to the detected environmental anomaly. The system's onboard triggered fire suppression system is then operative to receive the alert notification as the activation signal and initiate the mediation response related to the detected environmental anomaly by responsively supplying the fire suppression agent to the shipping container.

A further embodiment may add an external transceiver disposed separately from the shipping container, where the external transceiver is configured to wirelessly communicate with at least the second communication interface of the command node using the second wireless communications format, and where the external transceiver further has a display interface that generates a mediation response prompt related to the detected environmental anomaly. As such, the command node processing unit may be further operative to cause the second communication interface to transmit the alert notification to the external transceiver to initiate a secondary mediation response related to the detected environmental anomaly. In one example, the secondary mediation response may be generating the mediation response prompt on the display interface of the external transceiver, where the mediation response prompt requests a change in course of a transit vehicle transporting the shipping container from an existing travel path of the transit vehicle in response to the detected environmental anomaly. In another example, the secondary mediation response may be generating the mediation response prompt on the display interface of the external transceiver, where the mediation response prompt requests an inspection of the shipping container in response to the detected environmental anomaly. The system's external transceiver may further include a user input interface that receives feedback input responsive to the mediation response prompt displayed on the display interface (e.g., feedback input in the form of input received after an inspection of the shipping container prompted by the mediation response prompt generated on the display interface of the external transceiver), where the external transceiver is further operative to generate a secondary activation signal in response to receiving the feedback input, and transmit the secondary activation signal to the onboard triggered fire suppression system. As such, the onboard triggered fire suppression system may then supply an additional amount of the fire suppression agent to within the shipping container in response to receiving the secondary activation signal from the external transceiver.

The operation of such exemplary improved systems may also take the form of methods for adaptively monitoring for an environmental anomaly using a group of monitor beacons including a dedicated bridging node for a remote monitor beacon. FIG. 43 is a flow diagram illustrating such an exemplary method for adaptively monitoring for an environmental anomaly using a group of monitor beacons including a dedicated bridging node for a remote monitor beacon in accordance with an embodiment of the invention. Referring now to FIG. 43, method 4300 uses elements of a wireless node network having at least ID nodes (e.g., ID nodes 1-5 shown in FIG. 42C) disposed within the shipping container (e.g., exemplary shipping container 24300a) and a command node (e.g., exemplary command node 24160) associated with the shipping container maintaining packages (e.g., packages 1-4 shown in FIG. 42C), where the command node is operative to communicate with each of the ID nodes and an external transceiver unit (e.g., exemplary external transceiver 24150 as disposed on transit vehicle 24200) associated with a transit vehicle (e.g., an airplane, a railway conveyance, a maritime vessel, and a roadway conveyance).

The ID nodes used as part of method 4300 may be not be associated with any particular package in the shipping container. However, in some embodiments of method 4300, the ID nodes used as all or at least a portion of the group of monitor beacons may be ID nodes associated with respective ones of the packages maintained within the shipping container. Such ID nodes associated with packages may travel with a respective package, be affixed to a respective package, or be integrated within a respective package.

Method 4300 begins at step 4305 with the command node designating a group of monitor beacons from the ID nodes. Each member of the group of monitor beacons broadcasts according to a communication profile associated with that member of the group of monitor beacons, and each member is an ID node deployed at a different location within the shipping container. As designated or selected by the command node as part of step 4305, the group of monitor beacons includes at least a remote monitor beacon located outside a reception range of the command node. For example, exemplary command node 24160 may designate ID nodes 1, 2, 4, and 5 as a group of monitor beacons shown within shipping container 24300 in FIG. 42A-42C, where ID node 4 is a remote monitor beacon located outside reception range 42005 for command node 24160. In more detail, step 4305 may be implemented by the command node transmitting a monitor activation command to each of the group of monitor beacons to cause each ID node in the group of monitor beacons to broadcast the respective broadcast signal from each of the group of monitor beacons.

The remote monitor beacon designated as part of step 4305 may be located outside the reception range of the command node as a result of at least one of the packages being loaded within the shipping container. For example, ID node 4 (as shown in FIG. 42C) may qualify as a remote monitor beacon once package 4 has been loaded into shipping container 24300a, which may place materials within package 4 in a location that attenuates or shields electronic signals and effectively reduces the reception range of the command node 24160 so as to no longer receive wireless signals broadcast from ID node 4. As such, the command node 24160 may initially receive broadcast signals directly from ID node 4 (the remote monitor beacon) before package 4 is loaded within the shipping container, but not after package 4 is loaded. In such a situation, the command node 24160 may detect the loss of direct reception of a respective broadcast signal from ID node 4 (i.e., the remote monitor beacon) after package 4 is loaded within the shipping container and, thus, render ID node 4 as a remote monitor beacon.

In a further embodiment of step 4305 when designating the group of monitor beacons, each of the ID nodes designated as a monitor beacon may be associated with a respective package maintained within the shipping container. As such, designating the group of monitor beacons by the command node in step 4305 may have the command node accessing shipping information on what type of item is being shipped in each of the packages associated with each of the ID nodes, and then selectively assigning members of the group of monitor beacons based upon the type of item being shipped in each of the packages associated with each of the ID nodes in the group of the monitor beacons as reflected in the accessed shipping information. In more detail, selectively assigning such members may be implemented with the command node identifying which of the ID nodes are associated with packages containing predetermined target material for observation according to the accessed shipping information, and then assigning the identified ID nodes associated with the predetermined target material for observation material as the members of the group of monitor beacons. Such predetermined target material for observation may include, for example, incendiary material, corrosive material, explosive material, flammable material, or acidic material. Further still, selectively assigning such members may be implemented by the command node identifying which of the ID nodes are associated with packages containing predetermined target material for observation material, and then assigning only a predetermined number of the identified ID nodes associated with the predetermined target material for observation material as members of the group of monitor beacons.

At step 4310, method 4300 has the command node programmatically configuring another of the ID nodes not included in the group of monitor beacons to be a dedicated bridging node for the remote monitor beacon. The dedicated bridging node (e.g., ID node 3 as shown in FIGS. 42A-42C) provides a dedicated intermediary communication link between the command node and the remote monitor beacon (e.g., ID node 4) as the dedicated bridging node is deployed within the reception range of the command node and a broadcast range of the remote monitor beacon. For example, ID node 4, as a remote monitor beacon, may wirelessly broadcast a signal that can be received by ID node 3, as a dedicated bridging node, and relayed to the command node 24160 by ID node 3.

In a further embodiment of step 4310, the command node may programmatically configure such a dedicated monitor beacon by programmatically configuring a pre-designated one of the ID nodes not included in the group of monitor beacons to be the dedicated bridging node. As such, ID node 3 may be pre-designated as a dedicated bridging node. In another example, ID nodes not associated with particular packages but fixed to or integrated as part of the shipping container may be pre-designated due to their deployment location within the shipping container (e.g., being deployed along a periphery of the container but not at the base of the container, while the command node may be located more central to the container for more optimum reception range coverage).

In still another embodiment, step 4310 may have the command node programmatically configuring the dedicated bridging node as the container is being loaded. For example, the command node, as part of step 4310, may programmatically configure an adaptively designated one of the ID nodes not included in the group of monitor beacons to be the dedicated bridging node when the command node detects a drop in signal strength from one member of the group of monitor beacons. This may be accomplished by having the command node detecting the drop in signal strength transmitted from the one member of the group of monitor beacons as the shipping container is being loaded, and then programmatically configuring a second ID node not included in the group of monitor beacons to be the dedicated bridging node providing the dedicated intermediary communication link between the command node and the one member of the group of monitor beacons.

At step 4315, method 4300 continues with the command node receiving a respective broadcast signal from each respective member of the group of monitor beacons (directly from the group of monitor beacons not including the remote monitor beacon, and indirectly from the remote monitor beacon through the dedicated intermediary communication link provided by the dedicated bridging node). In some embodiments, method 4300 may also have the command node instructing a member of the group of monitor beacons to change how often that member of the group of monitor beacons broadcasts its respective broadcast signal. How often may depend upon an active broadcasting density within the range of that member of the group of monitor beacons as known or detected by the command node. The instruction to change how often a member of the group of monitor beacons broadcasts may lower a reporting interval when the active broadcasting density is above an RF visibility limit, or may increase the reporting interval when the active broadcasting density is below an RF visibility limit. Furthermore, another embodiment of method 4300 may have the instruction sent to each member of the group of monitor beacons so as to have the command node change how often each member of the group of monitor beacons broadcasts its respective broadcast signal.

In a further embodiment, method 4300 may also have the command instruction a member of the group of monitor beacons to change a power level setting for how that member of the group of monitor beacons broadcasts its respective broadcast signal. Such an instruction may, for example, change the power level setting for how that member of the group of monitor beacons broadcasts its respective broadcast signal based upon context data accessible by the command node and where the context data is related to a proximity environment of the first member of the group of monitor beacons. Such an instruction, in another embodiment, may be sent by the command node to each member of the group of monitor beacons to change a respective power level for how each member of the group of monitor beacons broadcasts its respective broadcast signal. In this way, the command node may interact with the particular monitor beacons in a way to proactively adjust for what materials may be next to the monitor beacons that may interfere with communications from the monitor beacon to the command node.

At step 4320, method 4300 proceeds with the command node monitoring the received respective broadcast signals from the group of monitor beacons for an unanticipated state of ceased broadcasting from any of the group of monitor beacons.

At step 4325, method 4300 has the command node identifying any from the group of monitor beacons that are in the unanticipated state of ceased broadcasting and then adding, in step 4330, those identified members of the group of monitor beacons to an unresponsive subset from the group of monitor beacons to be in the unanticipated state of ceased broadcasting based upon the monitoring step 4320. Thus, at step 4330, method 4300 has the command node adding any of the identified ID nodes from step 4325 to the unresponsive subset of those ID nodes in the group of monitor beacons that are identified to be in the unanticipated state of ceased broadcasting. Then, at decision step 4335, method 4300 has the command node determining if a size of the unresponsive subset of the group of monitor beacons exceeds a threshold setting maintained by the command node. If so, method 4300 proceeds from step 4335 directly to step 4340 where the command node detects the environmental anomaly for the shipping container because the size of the unresponsive group of monitor beacons exceeds the threshold setting. If not, method 4300 proceeds from step 4335 back to step 4320.

At step 4340, method 4300 proceeds with the command node detecting the environmental anomaly when the size of the unresponsive subset of the group of monitor beacons exceeds the threshold setting maintained by the command node. In response, to detecting the environmental anomaly in step 4340, method 4300 then moves to step 4345 where the command node automatically generates an alert notification related to the detected environmental anomaly for the shipping container.

At step 4350, method 4300 proceeds with the command node transmitting the alert notification to the external transceiver unit (e.g., exemplary external transceiver 24150, exemplary cockpit transceiver 25150*a*, or exemplary logistics transceiver 25150*b*) to initiate a mediation response related to the detected environmental anomaly.

In a further embodiment of method 4300, the method may also include having the command node altering the threshold setting related to detecting the environmental anomaly or altering which ID nodes are to be selected as monitor beacons. In more detail, a further embodiment of method 4300 may have the command node receiving a threshold update for the threshold setting maintained by the command node from, for example, the external transceiver unit (e.g., as defined by an operator of the transit vehicle using the external transceiver unit; as defined by a logistics crew member of the transit vehicle using the external transceiver unit; or as provided to the external transceiver unit from a remote control center in communication with the external transceiver unit). Another embodiment of method 4300 may have the command node receiving a selection update for which of the ID nodes are designated to be in the group of monitor beacons, where the selection update may be received from the external transceiver unit (e.g., as defined by an operator of the transit vehicle using the external transceiver unit; as defined by a logistics crew member of the transit vehicle using the external transceiver unit; or as provided to the external transceiver unit from a remote control center in communication with the external transceiver unit).

Enhanced Container for Environmental Anomaly Monitoring

Further detailed embodiments focus on improved shipping container systems and apparatus that have sensor-based ID nodes attached to (e.g., permanently or removably), affixed to, installed on, or integrated as part of the shipping container. Using such sensor-based ID nodes disposed on or as part of the different parts of the shipping container along with a command node mounted to (e.g., permanently or removably) or integrated as part of the shipping container, these further embodiments provide a container-centric base-level apparatus and system for sensor-based detecting an environmental anomaly related to the container. Such further embodiments may also include enhanced communication interfaces that take advantage of low power, improved range communication formats. For example, the communication interfaces deployed on exemplary sensor-based ID nodes and/or an exemplary command node may use LPWAN (Low Power Wide Area Network) connectivity, such as LTE 5G, LTE-M, and NB-IOT (NarrowBand IoT). LPWAN, also commonly referred to low-power wide-area (LPWA) network or just low-power network (LPN), is a type of wide-area network wireless communication format that allows for extended range, low-bandwidth communications for power sensitive application, such as with devices that are battery powered devices (e.g., ID nodes, mobile master nodes, container nodes, command nodes, and the like). Exemplary types of LPWAN may include ultra-narrowband (UNB) technology from Sigfox, random phase multiple access (RPMA) technology from Ingenu, and other long-range WAN protocol (LoRaWAN) technology as promoted by the LoRa Alliance of companies (e.g., IBM, MicroChip, Cisco, Semtech, Singtel, KPN, Bouygues Telecom). LTE-M is a communication technology that allows a node-based device (such as a sensor-based ID node or command node) to directly connect to a Long Term Evolution (4G) cellular network without a gateway and on batteries. NB-IOT is a low-power communication technology that applies a narrowband approach to cellular IoT (Internet of Things) communications allowing for usage of parts of the GSM spectrum bandwidth in unused 200 kHz bands.

Figure 44:
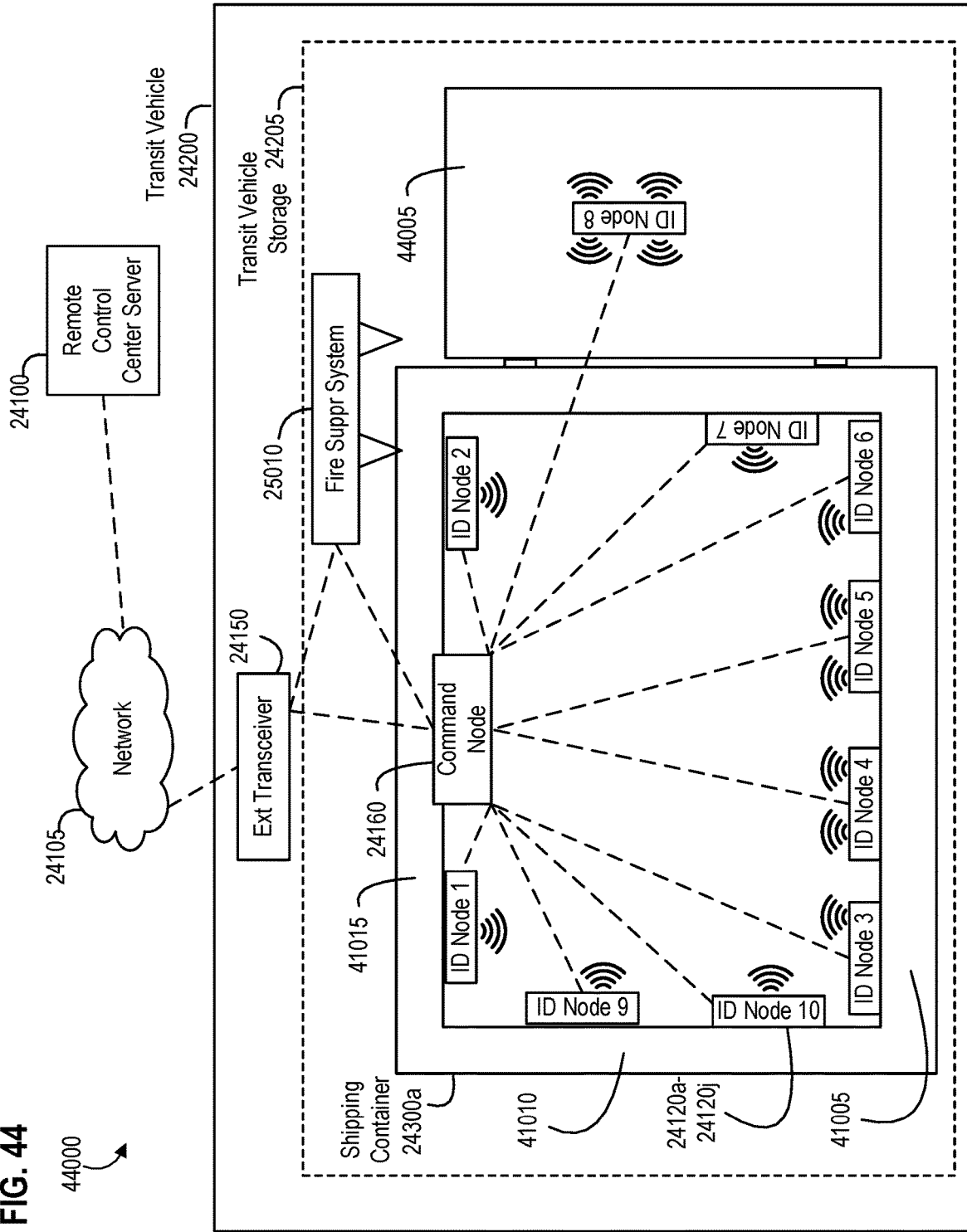
FIG. 44 is a diagram of an exemplary enhanced shipping container that transports packages and self-monitors for an environmental anomaly using sensor-based ID nodes in accordance with an embodiment of the invention.

FIG. 44 is a diagram of an exemplary enhanced shipping container that can transport packages and self-monitors for an environmental anomaly using sensor-based ID nodes disposed within in accordance with an embodiment of the invention. Referring now to FIG. 44, exemplary system 44000 is shown with exemplary transit vehicle 24200 and its transit vehicle storage 24205 along with an external transceiver 24150 and fire suppression system 25010 as described in embodiments above (e.g., similar to that shown in FIG. 41A with exemplary system 41000). System 44000 further includes exemplary enhanced shipping container 24300*a*, which has command node 24160 mounted to it as well as ID nodes 1-10 (24120*a*-24120*j*, respectively) disposed within container 24300*a*.

As shown in FIG. 44, the exemplary shipping container 24300*a* has a base 41005, a plurality of walls 41010 coupled to the base 41005, a ceiling 41015 coupled to the walls 41010 so as to enclose the walls 41010 and base 41005. In other words, the walls 41010 and ceiling 41015 coupled to walls 41010 are a type of enclosing structure that is coupled to the base 41005. As coupled to the base 41005, they collectively define an interior storage space within the shipping container 24300*a* that may maintain packages for transport on the transit vehicle 24200. Exemplary shipping container 24300*a*, as shown in FIG. 44, further illustrates a selectively securable door 44005 hinged to one of the walls 41010 that provides securable access into the interior storage space of the shipping container.

ID nodes 1-10 (24120*a*-24120*j*) are sensor-based ID nodes disposed within container 24300*a*, as shown in FIG. 44, and are located in different locations along the interior of the shipping container 24300*a*. In more detail, ID nodes 1-2 are each disposed at different locations as part of ceiling 41015; ID nodes 3-6 are each disposed at different locations as part of floor/base 41005; and ID nodes 7, 9, and 10 are each disposed at different locations as part of walls 41010. ID node 8, as shown in FIG. 44, is disposed on or as part of the door 44005 (which may be considered part of the wall when secured in place). As disposed or installed on these different locations within the shipping container 24300*a*, each of the sensor-based ID nodes may be removably attached, permanently affixed, or integrated as part of the different parts of the shipping container. For example, when an embodiment replaceably attaches some or all of the ID nodes within shipping container 24300*a*, those replaceably attached sensor-based ID nodes may be removed and replaced to allow for periodic replacement (e.g., swapping out ID nodes that need charging, repair, or replacement) with the same type of sensor-based ID node or with a different ID node having batteries that have a longer charge life, having longer range or different communication capabilities (e.g., use a longer range communicating format to better communicate with command node 24160), or having specialized sensors (e.g., an ID node used for monitoring special and/or hazardous items being shipped within the container where the sensors on the ID node may correspond to particular risks associated with such items, correspond to temperature or other environmental conditions critical for monitoring such items, and the like).

Each of ID nodes 1-10 shown in FIG. 44 are implemented as sensor-based ID nodes having at least an ID node processing unit (also called a processor, such as ID node processor 300), an ID node memory coupled to the processor (e.g., memory 315, 320), at least one environmental sensor operatively coupled to the processor (e.g., sensors 360), and a wireless radio transceiver also operatively coupled to the processor (e.g., communication interface 375). The ID node memory on each sensor-based ID node in FIG. 44 maintains an ID node monitoring program (e.g., as part of the node control and management code 325). Essentially, the ID node monitoring program, when executed on a respective sensor-based ID node, programmatically configures the ID node processor to receive sensor data from the environmental sensor and cause the sensor data to be broadcast via the wireless radio transceiver. In other words, the wireless radio transceiver is configured (via the operation of the ID node monitoring program and interaction of the ID node processing unit with the wireless radio transceiver) to effectively access the sensor data generated by the environmental sensor(s) and broadcast the sensor data in response to a report command from the ID node processing unit when the ID node processing unit executes the ID node monitoring program code.

Exemplary command node 24160 shown in FIG. 44 is mounted (temporarily or permanently) to shipping container 24300a. As such, command node 24160 includes at least a command node processing unit (e.g., processor 26400), a command node memory (e.g., 26415, 26420) coupled to the command node processor and that maintains a command node container management program code (e.g., as part of the CN control and management code 26425), and two communications interfaces. The first communication interface is coupled to the command node processor, and is configured to communicate with each of the sensor-based ID nodes using a first wireless communication format compatible with the wireless radio transceiver on each of the sensor-based ID nodes. The second communication interface is also coupled to the command node processing unit, and is configured to communicate with at least an external transceiver unit associated with a transit vehicle transporting the shipping container using a second wireless communications format.

In operation, the command node processing unit of the shipping container's command node is programmatically configured, when executing the command node container management program code, to be operative to detect the sensor data broadcasted from the sensor-based ID nodes using the first communication interface; responsively identify the environmental anomaly for the shipping container when the detected sensor data does not include the sensor data from at least a threshold number of the sensor-based ID nodes, and when the detected sensor data indicates an environmental condition that exceeds an environmental threshold; generate a layered alert notification related to the environmental anomaly for the shipping container in response to identifying the environmental anomaly for the shipping container (where the layered alert notification identifies a targeted mediation recipient, identifies a targeted mediation action, and establishes a mediation response priority); and then causes the second communication interface to transmit the layered alert notification to the transceiver unit to initiate a mediation response related to the targeted mediation action.

In more detail, the enhanced shipping container 24300a shown in FIG. 44 may use relative sensor data generated and monitored over time. For example, each of the sensor-based ID nodes used as part of the enhanced shipping container apparatus is further operative to incrementally generate the sensor data over a time period using the environmental sensor on each of the respective sensor-based ID nodes. As such, the command node processing unit of the container's command node is further programmatically configured to monitor the generated sensor data from each of the sensor-based ID nodes over the time period to identify relative changes in the generated sensor data over the time period. The command node processor may be programmatically configured to then compare the identified relative changes in the generated sensor data and context data (e.g., context data 26560) locally maintained on the command node memory related to those of the sensor-based ID nodes that are related to the relative changes in the generated sensor data. Such context data in this further embodiment includes at least a relative environmental threshold condition respectively corresponding to the shipping container. The command node processor may be programmatically configured to then identify the environmental anomaly for the shipping container when the comparison of identified relative changes in the generated sensor data and the context data indicates a changed environmental condition for the shipping container that exceeds the relative environmental threshold condition.

In a further embodiment of the enhanced shipping container 24300a, the sensors used on the deployed sensor-based ID nodes within container 24300a may be different types of environmental sensors. For example, an environmental sensor for a first of the sensor-based ID nodes may be implemented with a temperature sensor while the environmental sensor for a second of the sensor-based ID nodes may be implemented with a barometric pressure sensor. As such and in more detail, the command node processing unit of the container's command node may be further programmatically configured to responsively identify the environmental anomaly for the shipping container when (a) the sensor data detected from the first sensor-based ID node is a temperature value; (b) the sensor data detected from the second sensor-based ID node is a barometric pressure value; (c) the temperature value indicates a first local environmental condition proximate the first sensor-based ID node exceeds the environmental threshold condition for the shipping container according to first context data locally maintained on the command node memory related to that first sensor-based ID node (where the first context data includes at least a temperature threshold condition for the shipping container); and (d) the barometric pressure value indicates a second local environmental condition proximate the second sensor-based ID node exceeds the environmental threshold condition for the shipping container according to second context data locally maintained on the command node memory related to that second sensor-based ID node (where the second context data includes at least a barometric pressure threshold condition for the shipping container). In some embodiments, one sensor-based ID node may have an environmental sensor implemented by a temperature sensor while the environmental sensor for another sensor-based ID node may be implemented with a barometric pressure sensor, a radiation sensor, or a chemical sensor. Further still, the environmental sensor for a sensor-based ID node may be implemented with multiple sensor elements (such as a temperature sensor element and a barometric pressure sensor element).

In another embodiment of the enhanced shipping container, the identified environmental anomaly may be based on sensor data compared to profile data maintained on the command node. The profile data, which may be maintained as a type of context data locally maintained on the command node memory (e.g., profile data 430 on memory 26415/26420 of command node 26000), may provide a time-based profile of sensor data that is indicative of a particular environmental anomaly. Such a time-base profile of temperature data, for example, may indicate a lithium-ion battery fire for a particularly rapid rise in temperature over time to a particular range of temperatures within that time frame. Such a temperature profile, as sensed by a temperature sensor, may be used to detect the environmental anomaly as well as the type of environmental anomaly that can be used by the command node to generate the appropriate alert notification to initiate the appropriate mediation response. Another example may have a pressure profile which, when matched over time, may indicate an explosion (e.g., a sudden increase in pressure, then followed by a rapid drop in pressure).

A further embodiment where a sensor on the sensor-based ID node is a barometric pressure sensor, the context data reflecting a pressure profile of pressure values over time that may be detected in a particular pattern that when matched indicates In another embodiment of the enhanced shipping container, the identified environmental anomaly may be based on sensor data from a combination of temperature information with other types of sensor data. For example and in more detail, the command node processing unit may be further programmatically configured to responsively identify the environmental anomaly when: (a) the sensor data detected from the first sensor-based ID node is a temperature value; (b) the sensor data detected from the second sensor-based ID node is an environmental condition value of either a sensed barometric pressure level by the barometric sensor, a detected radiation level by the radiation sensor, or a detected chemical by the chemical sensor; (c) the temperature value indicates a first local environmental condition proximate the first sensor-based ID node exceeds the environmental threshold condition for the shipping container according to first context data related to the first sensor-based ID node (where the first context data includes at least a temperature threshold condition for the shipping container); and (d) the environmental condition value indicates a second local environmental condition proximate the second sensor-based ID node exceeds the environmental threshold condition for the shipping container according to second context data related to the second sensor-based ID node (where the second context data includes at least an environmental threshold condition for the shipping container corresponding to the type of sensor data detected from the second of the sensor-based ID nodes). In this example, the detected chemical may be indicative of an explosive within the shipping container, a fire within the shipping container, or may be one of either CO or $CO_2$ disposed within the shipping container.

In still another embodiment of the enhanced shipping container, the identified environmental anomaly for the shipping container may, for example, be a fire within the shipping container when the sensor data from the temperature sensor comprises a temperature value exceeding a temperature threshold maintained by the command node in the command node memory as part of context data for the shipping container and when the sensor data from the barometric pressure sensor is a barometric pressure value exceeding a pressure threshold maintained by the command node in the command node memory as part of the context data for the shipping container. In another example, the identified environmental anomaly for the shipping container may be an explosion within the shipping container when the sensor data from the temperature sensor is a temperature value exceeding a temperature threshold maintained by the command node in the command node memory as part of context data for the shipping container and when the sensor data from the barometric pressure sensor is a barometric pressure value that is below a pressure threshold maintained by the command node in the command node memory as part of the context data for the shipping container. In still another example, the identified environmental anomaly for the shipping container comprises an explosion within the shipping container when the sensor data from the temperature sensor is a temperature value exceeding a temperature threshold maintained by the command node in the command node memory as part of context data for the shipping container and when the sensor data from the barometric pressure sensor is a barometric pressure value drops faster than a pressure drop threshold maintained by the command node in the command node memory as part of the context data for the shipping container. In an additional example, the identified environmental anomaly for the shipping container may be a detected chemical-related fire and/or a detected chemical that is related to a fire within the shipping container when the sensor data from the temperature sensor is a temperature value exceeding a temperature threshold maintained by the command node in the command node memory as part of context data for the shipping container and when the sensor data from the chemical sensor matches a predetermined chemical profile maintained by the command node in the command node memory as part of the context data for the shipping container. In a further example, the identified environmental anomaly for the shipping container may be a radiation leak within the shipping container when the sensor data from the temperature sensor is a temperature value exceeding a temperature threshold maintained by the command node in the command node memory as part of context data for the shipping container and when the sensor data from the radiation sensor matches a predetermined radiation profile maintained by the command node in the command node memory as part of the context data for the shipping container. As such, sensor information as well as context data (including profile information on what may be stored within the shipping container) may be leveraged to allow the enhanced shipping container to better and more precisely identify the particular environmental anomaly.

When detecting sensor data broadcasted by the different sensor-based ID nodes, the container's command node may set or adjust how often that sensor data is broadcast. For example, the command node processing unit of the command node may be further operative to detect the sensor data broadcasted from the sensor-based ID nodes by being operative to (a) detect the sensor data broadcasted by the sensor-based ID nodes according to a broadcast profile maintained by each of the sensor-based ID nodes (where the broadcast profile (e.g., part of profile data 430 on command node 24160) defines a first messaging rate used to regulate how often the generated sensor data is transmitted to the command node such that the first messaging rate is higher than a default messaging rate); and (b) cause the first communication interface to instruct each of the sensor-based ID nodes to broadcast future generated sensor data at a second messaging rate that is higher/faster than the first messaging rate after causing the second communication interface to transmit the layered alert notification to the transceiver unit. Further, the command node processing unit of the command node may also cause the first communication interface to instruct each of the sensor-based ID nodes to change from the default messaging rate to the first messaging rate, which may be established or set as an initial value correlated to an environmental risk associated with material maintained within the shipping container.

When the enhanced shipping container's command node generates the layered alert notification, further embodiments may implement this functionality in more detail with respect to how to select the targeted mediation recipient. For example, the container's command node may be further programmatically configured to automatically select the targeted mediation recipient based upon at least one of (a) how many of the sensor-based ID nodes were not detected above the threshold number of the sensor-based ID nodes and (b) how much the environmental condition exceeds the environmental threshold. As such, the targeted mediation recipient identified by the command node in the layered alert notification may be a triggered fire suppression apparatus (e.g., exemplary onboard triggered fire suppression system 25010 as shown in FIG. 44 and explained in more detail with reference to FIGS. 32A-32C) on the transit vehicle that is operative to automatically respond to the detected environmental anomaly based upon receipt of the layered alert notification. Another targeted mediation recipient that may be identified by the command node in the layered alert notification is an operator of the transit vehicle that can alter movement of the transit vehicle. Further, still another targeted mediation recipient identified by the command node in the layered alert notification may be a logistics crew member of the transit vehicle that can inspect the shipping container.

When the enhanced shipping container's command node generates the layered alert notification, further embodiments may implement this functionality in more detail with respect to how to select the particular targeted mediation action that is initiated in response to the detected environmental anomaly in the shipping container. For example, the container's command node may be further programmatically configured to automatically select the targeted mediation action based upon at least one of (a) how many of the sensor-based ID nodes were not detected above the threshold number of the sensor-based ID nodes and (b) how much the environmental condition exceeds the environmental threshold. In more detail, the targeted mediation action identified by the command node in the layered alert notification depends upon what is loaded within the shipping container as indicated by the shipping information maintained on the command node memory.

The targeted mediation action may also depend on further information, such as vehicle status data (indicating a status of the transit vehicle transporting the enhanced shipping container) and/or container status data. For example, the enhanced shipping container's command node processing unit may be further programmatically configured to receive vehicle status data from the external transceiver unit of the transit vehicle using the second communication interface and maintain the vehicle status data in the command node memory. With the vehicle status data, the targeted mediation action identified in the layered alert notification may depend upon a state of the transit vehicle as indicated by the vehicle status data. Examples of such a state of the transit vehicle may include a takeoff vehicular status, a cruising vehicular status, a landing vehicular status, or an on-the-ground vehicular status. As such, when the transit vehicle is in the state of being on-the-ground, the command node is automatically equipped with information to more quickly and safely identify the targeted mediation action (e.g., inspect the shipping container) that may be different than a targeted mediation action identified when the transit vehicle is in a cruising statue (e.g., change course to stop or land the vehicle). As such, safety advantages abound for the transit vehicle, personnel involved with the transit vehicle, as well as property being transported by the transit vehicle.

In another example, the command node memory may maintain container status data corresponding to the shipping container. With this container status data, the targeted mediation action in the command node generated layered alert notification may depend upon a state of the shipping container as indicated in the container status data maintained on the command node memory.

Information on the location of the shipping container within the transit vehicle may also be leveraged by the enhanced shipping container's command node to better identify a targeted mediation action. For example, the enhanced shipping container's command node may further include location circuitry (similar to location circuitry 475 used on a master node) coupled to the command node processing unit, where the command node's location circuitry detects geolocation data related to a current location of the shipping container within the transit vehicle. With such geolocation data, the targeted mediation action in the command node generated layered alert notification may depend upon the current location of the shipping container as indicated in the geolocation data. For example, the identified targeted mediation action may include an inspection of the shipping container if the container is located in certain spots on the transit vehicle, but may include an automated immediate activation of an onboard fires suppression system when the container is located near particular parts of the transit vehicle deemed more critical than others (e.g., a fuel supply, an oxygen system, and the like).

Loading plan data may also be used by the enhanced shipping container's command node when identifying an appropriate targeted mediation response. For example, the command node memory may maintain loading plan data indicating the relative location of the shipping container within the transit vehicle. With such loading plan data, the targeted mediation action identified by the command node in the layered alert notification may depend upon the relative location of the shipping container within the transit vehicle as indicated in the loading plan data.

Likewise, facility status data associated with a storage facility for the enhanced shipping container may also be used when identifying an appropriate targeted mediation response. In more detail, the targeted mediation action identified by the command node in the layered alert notification may depends upon a state of the storage facility as indicated in the facility status data maintained within the command node memory.

In further embodiments, the command node processing unit may establish the mediation response priority (as part of the layered alert notification) in more detail. For example, the enhanced shipping container's command node may be further programmatically configured to automatically establish the mediation response priority based upon at least one of (a) how many of the sensor-based ID nodes were not detected above the threshold number of the sensor-based ID nodes and (b) how much the environmental condition exceeds the environmental threshold. As such, the mediation response priority may be established by the command node as a high priority level indicating further travel by the transit vehicle is to be at least minimized as part of the mediation response, or an intermediate priority level indicating further travel by the transit vehicle is permissible as part of the mediation response.

In still further embodiments of an enhanced shipping container apparatus as noted above, the command node processing unit may take further steps to verify or validate the sensor data received so as to address the potential for spoofing of sensor data or taking mediation responsive actions unnecessarily. For example, the command node processing unit may detect the sensor data using the first communication interface by being operative to (a) receive the sensor data broadcasted from a first sensor-based ID node using the first communication interface; (b) confirm the validity of the received sensor data; (c) repeat (a) and (b) for the remainder of the sensor data received from any of the remaining sensor-based ID nodes using the first communication interface; and (d) selectively compile the detected sensor data using only the received sensor data confirmed valid. In a further example, the command node processor may confirm the validity of the received sensor data in an "active" manner by being further operative to cause the first communication interface to send an authentication request to the first sensor-based ID node, and receive a validation response from that first sensor-based ID node via the first communication interface. Such a validation response may authenticate the sensor data broadcasted from the particular sensor-based ID node. In another example, the command node processor may confirm the validity of the received sensor data in a "passive" manner by being further operative to access a validation sequence for the first sensor-based ID node (where the validation sequence is maintained in the command node memory and characterizes expected broadcasts from that particular sensor-based ID node) and determine if the received sensor data from the first sensor-based ID node matches a predetermined one of the expected broadcasts from that sensor-based ID node according to the validation sequence stored within the command node memory. Such a predetermined one of the expected broadcasts may be a rotating value previously received by the command node for the first sensor-based ID node.

In still further embodiments of this enhanced shipping container apparatus, as shown in FIG. 44, the communication interface on the command node to communicate outside the shipping container may be enhanced with more long range, low power technology, such as a low power wide area network (LPWAN) interface operative to communicate as the second wireless communications interface format. In more detail, such a second communication interface format may be implemented as a narrow band Internet of Things (NB-IoT) format, or a long term evolution (LTE) category M1 format.

While the enhanced shipping container apparatus embodiments described above generates the layered alert notification and transmits that notification to an external transceiver to initiate the mediation response, another embodiment of such an enhanced shipping container apparatus is described below where the sensor-based ID nodes and the command node are explicitly types of replaceable wireless network elements that may be removed and replaced as line replaceable modules for the enhanced shipping container apparatus. In this way, such further embodiments of the enhanced shipping container apparatus may be re-configured to handle and effectively self-monitor different types of packages being transported within the interior storage apparatus' shipping container for an environmental anomaly.

In more detail, this other embodiment of an enhanced shipping container apparatus includes at least a shipping container housing, multiple sensor-based ID nodes removably attached to different parts of the shipping container housing, and a command node removably mounted to the shipping container housing. The shipping container housing (e.g., exemplary shipping container 24300*a* as shown in FIG. 44), in this embodiment, has at least a base portion (e.g., base 41005), and an enclosing structure (e.g., walls 41010, ceiling 41015, and door 44005) that is coupled to the base portion and that defines an interior storage space within the shipping container housing. The sensor-based ID nodes are removably attached to different parts of the shipping container housing, such as to the base, walls, door, and/or ceiling. Each of the sensor-based ID nodes are a first type of replaceable wireless network elements deployed on the shipping container (e.g., a sensor-equipped ID node wireless network element, such as exemplary ID node 120*a* as shown in FIG. 3 or exemplary sensor-based ID nodes as shown in FIG. 44). Consistent with the description of such exemplary sensor-based ID nodes, each has at least an ID node enclosure for housing one or more components of the ID node, an ID node processing unit disposed within the ID node enclosure; an ID node memory coupled to the ID node processing unit and maintaining at least an ID node monitoring program code; at least one environmental sensor operatively coupled to the ID node processing unit and configured to generate sensor data related to an environmental condition proximate the respective sensor-based ID node; and a wireless radio transceiver coupled to the ID node processing unit. The sensor-based ID node's wireless radio transceiver is configured to access the sensor data generated by the environmental sensor and broadcast the sensor data in response to a report command from the ID node processing unit when the ID node processing unit executes the ID node monitoring program code.

The ID node enclosure for each of the sensor-based ID nodes may be implemented to house all or a portion of the components of the sensor-based ID node. For example, the ID node processor, memory, and wireless radio transceiver may be fixed relative to the ID node enclosure and disposed within the enclosure, while one or more of the environmental sensors may be operatively coupled to the processor and be disposed so as to have sufficient exposure to the environment outside of the ID node enclosure for sensing such an environment. Those skilled in the art will further appreciate that exemplary environmental sensors used with a sensor-based ID node may be remote from the ID node enclosure—e.g., one or more sensors that have connections back to the ID node processor but that are disposed external to the ID node enclosure in one or more locations near the sensor-based ID node's enclosure. In this manner, a sensor-based ID node may deploy an array of similar or different types of environmental sensors that may be disposed in, on, or external to the ID node enclosure while each sensor is still operatively coupled to the ID node processor.

Such an ID node enclosure may be sized to fit within recessed sections of the shipping container housing in some embodiments. As such, a sensor-based ID node may be removably attached to a particular part of the shipping container housing within such a recessed section of the shipping container house so as to not protrude from the interior surface of the shipping container housing. Those skilled in the art will appreciate that the command node may similarly be removably disposed or mounted within a recessed section of the shipping container housing. The shipping container housing may further include securing straps, pockets, clamps, restraining hardware, screws, bolts, or other fasteners that may be used to hold the sensor-based ID node/command node in place relative to the shipping container housing.

The command node is removably mounted to the shipping container as a second type of replaceable wireless network element deployed on the shipping container (e.g., an exemplary command node wireless network element, such as exemplary command node 26000 as shown in FIG. 26 or exemplary command node 24160 as shown in at least FIG. 44). Consistent with the description of such an exemplary command node, the command node in this embodiment has at least a command node processing unit; a command node memory coupled to the command node processing unit and maintaining at least command node container management program code; and two different communications interfaces coupled to the command node processing unit. A first of the communication interfaces is configured to communicate with each of the sensor-based ID nodes using a first wireless communication format compatible with the wireless radio transceiver on each of the sensor-based ID nodes, while a second of the communication interfaces is operative to communicate outside the shipping container housing using a second wireless communications format.

In operation, the command node processing unit of the apparatus's command node is programmatically configured, when executing the command node container management program code, to be operative to detect the sensor data broadcasted from the sensor-based ID nodes using the first communication interface; responsively identify the environmental anomaly for the shipping container when the detected sensor data does not include the sensor data from at least a threshold number of the sensor-based ID nodes and when the detected sensor data indicates an environmental condition that exceeds an environmental threshold; generate a layered alert notification related to the environmental anomaly for the shipping container in response to identifying the environmental anomaly for the shipping container, wherein the layered alert notification identifies a targeted mediation recipient, identifies a targeted mediation action, and establishes a mediation response priority; and cause the second communication interface to broadcast a layered alert notification that initiates a mediation response related to the targeted mediation action.

Further variations of this embodiment of an enhanced shipping container apparatus (i.e., the embodiment having sensor-based ID nodes and a command node as replaceable wireless network elements that are explicitly removable and replaceable as line replaceable modules) may be implemented with the same enhancements, details, and variations of the previously described embodiment of an enhanced shipping container apparatus.

Coordinated Response when Monitoring for Environmental Anomaly

Further embodiments provide a level of redundancy by deploying one or more backup types of command nodes. When monitoring wireless ID nodes within a shipping container, the use of such backup types of command nodes provides further robust decision points that can take over for a primary command node monitoring for an environmental anomaly related to a shipping container. Given an anticipated hostile or hazardous environment within a shipping container when and where an environmental anomaly may occur (e.g., a fire, explosion, chemical leak, radiation leak, and the like), deploying backup types of command nodes as additional types of networked wireless nodes serves to enhance systems and methods that monitor the shipping container to detect an environmental anomaly. In other words, enhancing and improving such monitoring and detection embodiments with redundant command nodes for the shipping container allows a system or method to more robustly handle detection, reporting, and initiating of mediation responses related to such environmental anomalies with the shipping container.

In general, exemplary types of backup command nodes may include a designated survivor command node mounted to the shipping container that may take over the monitoring, detecting, and responsive notification and mediation response initiation activities from a primary command node once that primary command node has become inoperative (e.g., once the designated survivor command node detects that the primary command node has become inoperative). Another type of backup command node may come in the form of one from multiple possible survivor command nodes where each may be deployed in different parts of the shipping container so as to spread the risk of where an intense environmental anomaly may erupt that may render a wireless node inoperative in that vicinity. As such, when the primary command node has become inoperative (e.g., is no longer in a normal operating state), one of the possible survivor command nodes may be selected (e.g., based upon a priority rank associated with each possible survivor command node) to quickly and responsively take over so as to operate as the designated survivor command node performing the primary command node's container monitoring operations given detection that the primary command node is no longer operative.

Figure 45A:
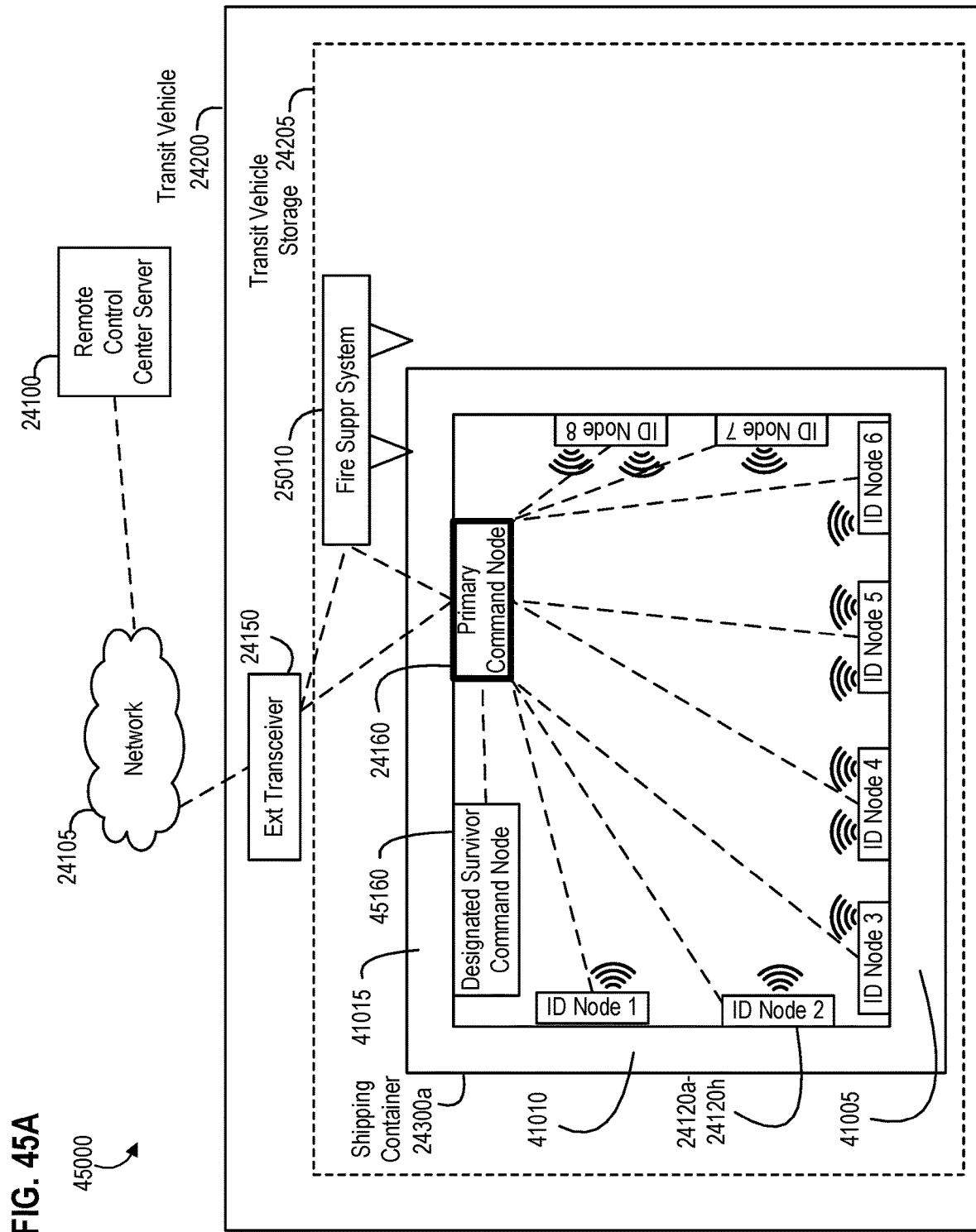
FIGS. 45A-45B are diagrams of an exemplary adaptive wireless node network system for monitoring a shipping container for an environmental anomaly using a primary command node and a designated survivor command node in accordance with an embodiment of the invention.
Figure 45B:
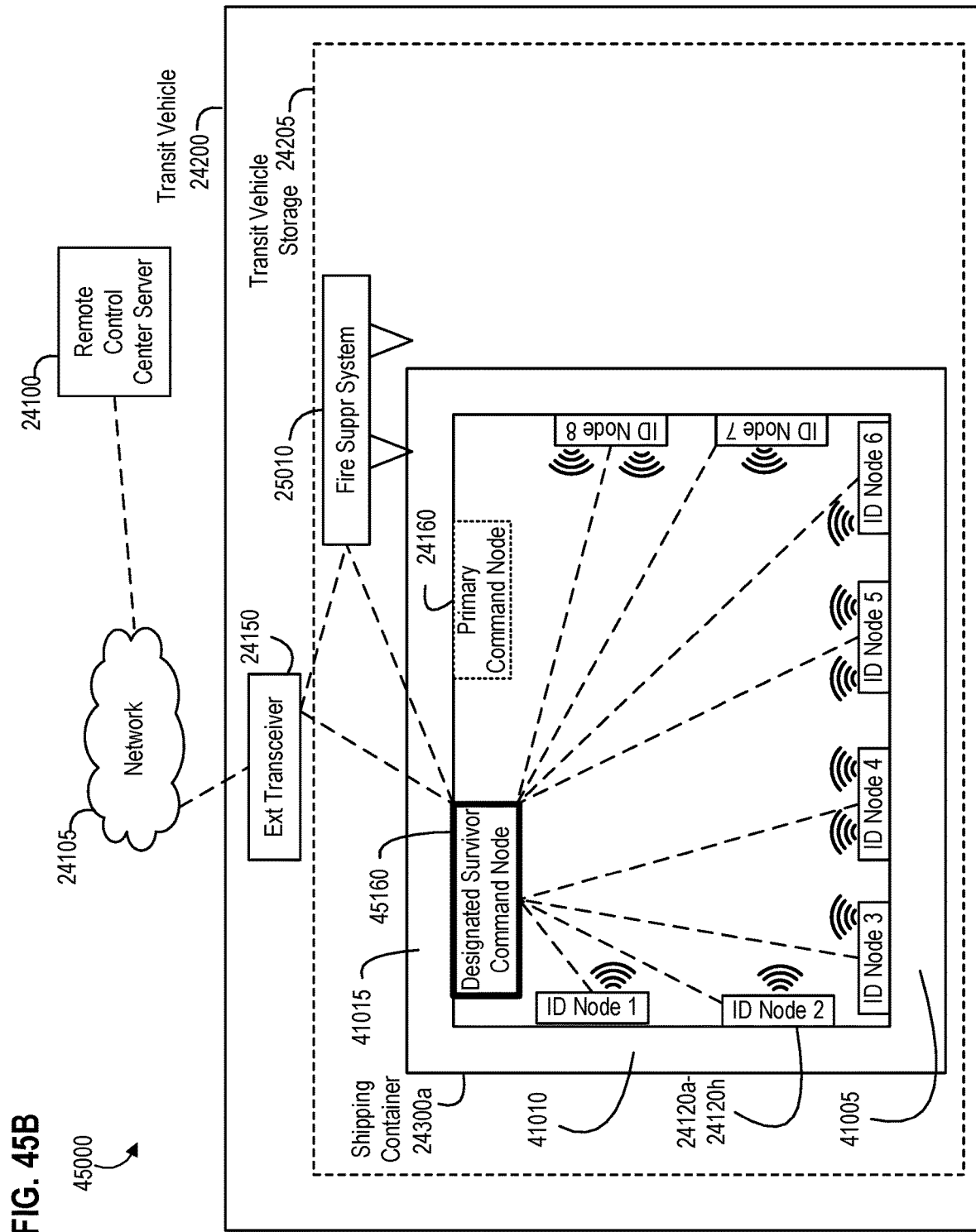

FIGS. 45A-45B are diagrams of an exemplary adaptive wireless node network system for monitoring a shipping container for an environmental anomaly using an exemplary primary command node and an exemplary designated survivor command node in accordance with an embodiment of the invention. Referring now to FIG. 45A, exemplary system 45000 is shown with exemplary transit vehicle 24200 and its transit vehicle storage 24205 along with an external transceiver 24150 and fire suppression system 25010 as described in embodiments above (e.g., similar to that shown in FIG. 41A with exemplary system 41000). System 44000 further includes exemplary shipping container 24300a as configured to include a primary command node 24160 mounted to it, a designated survivor command node 45160 mounted to it, as well as ID nodes 1-8 (24120a-24120h, respectively) as shown disposed within container 24300a.

ID nodes 1-8 shown in FIGS. 45A-46B (24120a-24120h) are a group of wireless ID nodes disposed within container 24300a, and are disposed within the shipping container 24300a. Each of ID nodes 1-8 are operative to broadcast one or more wireless signals via a wireless radio transceiver, where those wireless signals represent ongoing signal activity from that respective ID node (i.e., indicating normal operation of the ID node). While each of ID nodes 1-8, as shown in FIGS. 45A-46B, are not illustrated as being associated with particular objects (such as packages), those skilled in the art will appreciate that any or all of ID nodes 1-8 may be associated with one or more objects being transported in the shipping container 24300a (e.g., similar to the example shown in FIG. 24B where exemplary ID nodes are disposed within particular packages being transported in shipping container 24300). As such, each of the wireless ID nodes 1-8 may be removably attached, permanently affixed, or integrated as part of the different parts of the shipping container in a particular example. Further, in another example, each of the wireless ID nodes 1-8 may be associated with, travel with, attached to (removably or permanently) an object (such as a package) being transported within the shipping container 24300*a*.

Each of ID nodes 1-8 shown in FIGS. 45A-46B may further be implemented as sensor-based wireless ID nodes having at least an ID node processing unit (also called a processor, such as ID node processor 300), an ID node memory coupled to the processor (e.g., memory 315, 320), at least one environmental sensor operatively coupled to the processor (e.g., sensors 360), and a wireless radio transceiver also operatively coupled to the processor (e.g., communication interface 375). The ID node memory on each sensor-based ID node in FIG. 44 maintains an ID node monitoring program (e.g., as part of the node control and management code 325). Essentially, the ID node monitoring program, when executed on a respective sensor-based ID node, programmatically configures the ID node processor to receive sensor data from the environmental sensor and cause the sensor data to be broadcast via the wireless radio transceiver. In other words, the wireless radio transceiver is configured (via the operation of the ID node monitoring program and interaction of the ID node processing unit with the wireless radio transceiver) to effectively access the sensor data generated by the environmental sensor(s) and broadcast the sensor data in response to a report command from the ID node processing unit when the ID node processing unit executes the ID node monitoring program code.

Exemplary primary command node 24160 shown in FIGS. 45A-46B is disposed (temporarily, removably, or permanently) within shipping container 24300*a* at, for example, a predetermined location within the container, on a predetermined location of the container, or associated with a particular package or object within the container. As such, command node 24160 includes at least a command node processing unit (e.g., processor 26400), a command node memory (e.g., 26415, 26420) coupled to the command node processor and that maintains a command node container management program code (e.g., as part of the CN control and management code 26425 and that implements a primary container monitoring operation), and two communications interfaces. The first communication interface is coupled to the command node processor, and is configured to communicate with each of the wireless ID nodes 1-8 using a first wireless communication format compatible with the wireless radio transceiver on each of the wireless ID nodes 1-8. The second communication interface is also coupled to the command node processing unit, and is configured to communicate with at least an external transceiver unit (e.g., exemplary transceiver 24150 or a transceiver 32010 component of fire suppression system 25010) associated with a transit vehicle transporting the shipping container using a second wireless communications format.

In its normal operating state, the command node processing unit of primary command node 24160 is programmatically configured, when executing the command node container management program code (implementing executable instructions that carry out the primary container monitoring operation as set forth below), to be operative to monitor signal activity from the ID nodes 1-8; responsively identify the environmental anomaly based upon the monitored signal activity from the ID nodes; generate a layered alert notification related to the environmental anomaly for the shipping container in response to identifying the environmental anomaly for the shipping container (where the layered alert notification identifies a targeted mediation recipient, identifies a targeted mediation action, and establishes a mediation response priority); and transmits the layered alert notification to the external transceiver (via the second communication interface on primary command node 24160) to initiate a mediation response related to the targeted mediation action.

In more detail, the identified targeted mediation recipient may be a triggered fire suppression apparatus on the transit vehicle that supplies a fire suppression agent into the shipping container as the mediation response, or personnel related to operations of the transit vehicle that are prompted by the external transceiver as the mediation response. Additionally, the targeted mediation action identified by the primary command node in the layered alert notification may be identified based upon an extent of an observed drop in the monitored signal activity from the ID nodes and what is loaded within the shipping container as indicated by shipping information maintained on the primary command node. Further still, the mediation response priority established by the primary command node in the layered alert notification may be established based upon an extent of an observed drop in the monitored signal activity from the ID nodes, where the extent of the observed drop reflects a priority level for the mediation response priority that indicates one type of permissive status condition for further travel by the transit vehicle.

In more detail and as part of this exemplary primary container monitoring operation, primary command node 24160 may monitor signal activity from the wireless ID nodes 1-8 by detecting sensor data broadcast from each of the ID nodes. As such, primary command node 24160 may be further configured to responsively identify the environmental anomaly for the shipping container when, for example, the detected sensor data does not include the sensor data from at least a threshold number of the ID nodes or when the detected sensor data indicates an environmental condition that exceeds an environmental threshold. The environmental condition and the environmental threshold may, for example, be related to detected temperature, detected pressure, detected radiation, or the detected presence of a particular chemical (e.g., when the detected chemical presence is indicative of an explosive within the shipping container or a fire within the shipping container).

Additionally, the primary command node may detect the sensor data broadcasted from the ID nodes according to a broadcast profile maintained by each of the ID nodes. Such a broadcast profile may define a first messaging rate used by the particular ID node to regulate how often the generated sensor data is broadcast, where the first messaging rate is higher than a default messaging rate. As such, the primary command node may instruct each of the ID nodes to change from the default messaging rate to the first messaging rate. The primary command node may also, in some embodiments, instruct each of the ID nodes to broadcast future generated sensor data at a second messaging rate that exceeds the first messaging rate after the primary command node transmits the layered alert notification to the external transceiver associated with the transit vehicle as part of the primary container monitoring operation. In a more detailed embodiment, the first messaging rate for the ID nodes may be an initial value correlated to an environmental risk associated with material maintained within the shipping container.

As part of this adaptive system 45000, and embodiment may have exemplary designated survivor command node 45160 within the shipping container 24300*a*. Further embodiments may have designated survivor command node 45160 being disposed (temporarily, removably, or permanently) within shipping container 24300a at, for example, a predetermined location within the container, on a predetermined location of the container, or associated with a particular package or object within the container. As shown in FIGS. 45A-45B, designated survivor command node 45160 is a container node mounted to the shipping container 24300a and operative to also directly communicate with the ID nodes 1-8 disposed internal to the shipping container and to directly communicate with the external transceiver associated with the transit vehicle.

Typically, exemplary designated survivor command node 45160 may be disposed remotely within shipping container 24300a with respect to the position of the primary command node 24160 (e.g., on opposing sides of the shipping container relative to each other) so as to increase the chance that any environmental anomaly within shipping container 24300a that renders primary command node 24160 to be inoperative (e.g., out of its normal operating state of conducting the primary container monitoring operation set forth above), will still have designated survivor command node 45160 being operative and able to take over the primary container monitoring operation from the now inoperative primary command node 24160. In other words, designated survivor command node 45160 is configured to communicate with the primary command node 24160, as shown in FIG. 45A, and operate as the primary command node when the designated survivor command node 45160 is unable to communicate with the primary command node 24160, as shown in FIG. 45B where primary command node 24160 is no longer operative or able to communicate with designated survivor command node 45160 (e.g., because of damage to primary command node 24160 from an environmental anomaly or another malfunction in the primary command node 24160).

For example, the system's designated survivor command node 45160 may periodically communicate with primary command node 24160 to ensure normal operation (as shown in FIG. 45A), but initiate taking over as the primary command node (e.g., conducting the primary container monitoring operation as shown in FIG. 45B) when the primary command node 24160 ceases to respond, such as when the designated survivor command node 45160 fails to receive a response from the primary command node 24160 within a threshold reporting interval. In another example, the primary command node 24160 may, as part of the primary container monitoring operation, periodically send a status message to the designated survivor command node 45160 without prompting so that when the designated survivor command node 45160 fails to receive a timely and expected status message from the primary command node 24160, the designated survivor command node 45160 responsively takes over for the primary command node 24160 as described.

In still another example, the designated survivor command node may not wait for the primary command node to become inoperative or incommunicative before taking on the functionality and responsibility of the primary command node. Instead, the designated survivor command node 45160 may be monitoring the ID nodes for signal activity and then preemptively coordinate with the primary command node 24160 so as to take over the primary container monitoring operation from the primary command node 24160 when the monitored signal activity from the ID nodes 1-8 indicates less than a threshold number of the ID nodes are broadcasting.

Figure 46A:
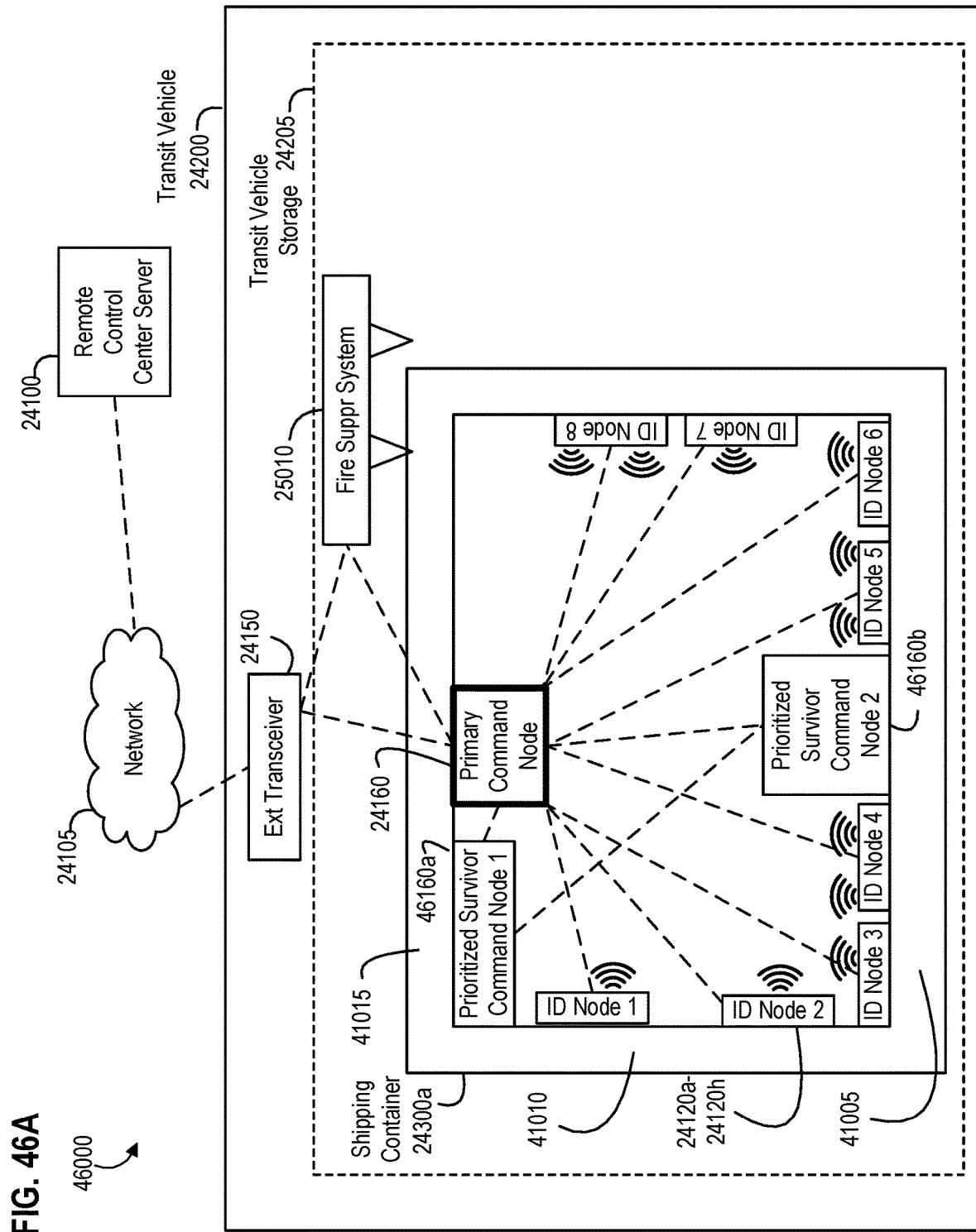
FIGS. 46A-46B are diagrams of an exemplary adaptive wireless node network system for monitoring a shipping container for an environmental anomaly using a primary command node and multiple prioritized survivor command nodes in accordance with an embodiment of the invention.
Figure 46B:
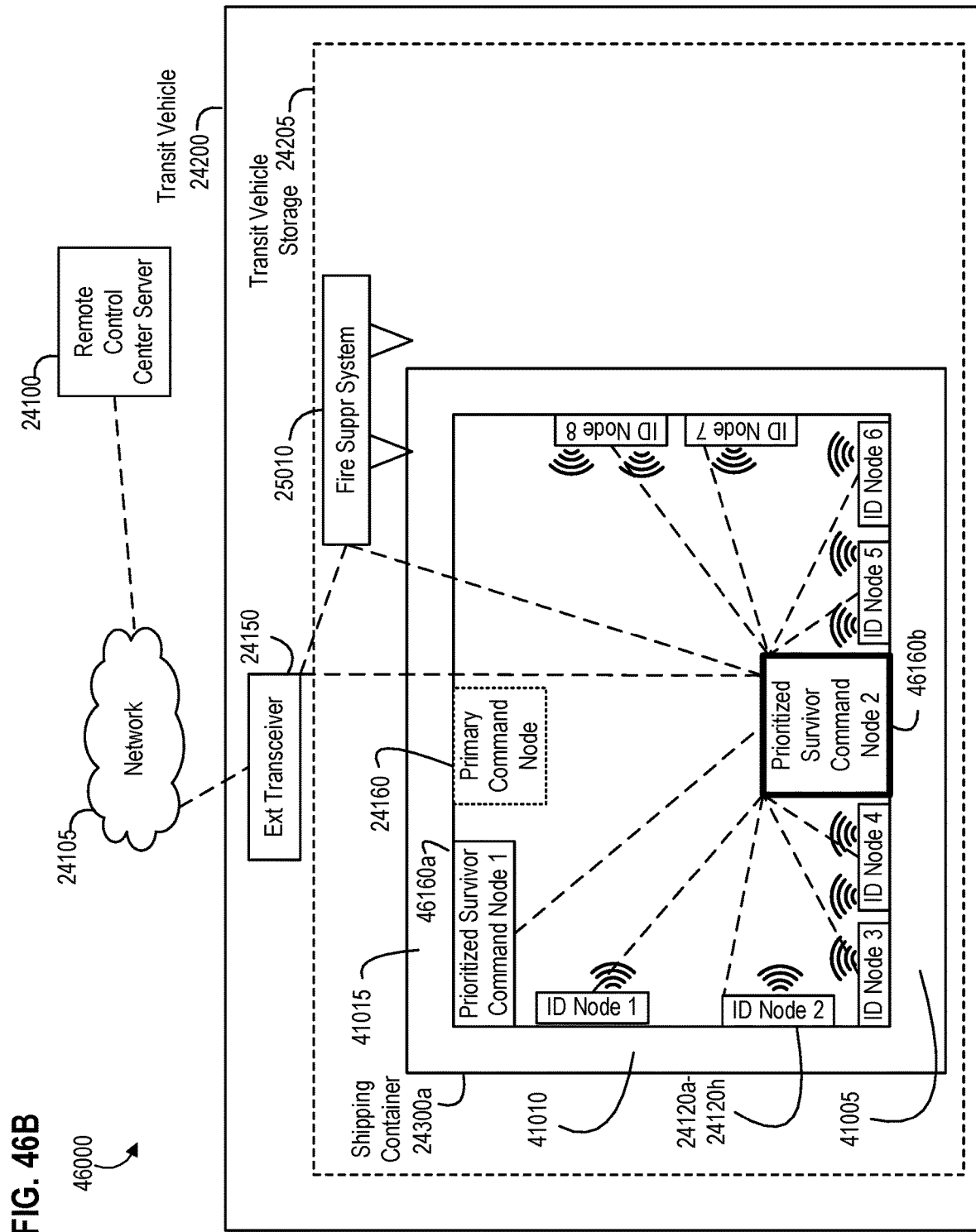

In a further embodiment, the adaptive system may use one of multiple prioritized survivor command nodes disposed within the shipping container as the system's designated survivor command node, which takes over from the primary command node when the primary command node is rendered inoperative and uncommunicative. FIGS. 46A-46B are diagrams of an exemplary adaptive wireless node network system for monitoring a shipping container for an environmental anomaly using a primary command node and one of multiple prioritized survivor command nodes used as the designated survivor command node in accordance with an embodiment of the invention. Referring now to FIG. 46A, exemplary system 46000 is shown largely the same as that shown with system 45000 in FIG. 45A, but now including two prioritized survivor command nodes 46160a, 46160b shown in FIG. 46A instead of the lone designated survivor command node 45160 shown in FIG. 45A. As such, the designated survivor command node as described as part of an adaptive system may be implemented by one the prioritized survivor command nodes 46160a, 46160b associated with the primary command node 24160 shown in FIG. 46A. Each of the prioritized survivor command nodes 46160a, 46160b may be implemented as a container node operative to directly communicate with the ID nodes 1-8 disposed internal to the shipping container 24300a as well as to directly communicate with the external transceiver 24150 (or the transceiver implemented as part of fire suppression system 25010) associated with the transit vehicle. Each of the prioritized survivor command nodes 461060a, 46160b is disposed within the shipping container 24300a (e.g., disposed within the shipping container at different physical locations within the shipping container, such as having a first prioritized survivor command node 46160a disposed on the ceiling 41015 of container 24300a while a second prioritized survivor command node 46160b is disposed on the base 41005 of the container 24300a). Each of the prioritized survivor command nodes 46160a, 46160b also has a priority rank (e.g., data that is part of CN control and management code 26425) used to determine which of these node will take the place of the inoperative primary command node as the designated survivor command node. The respective priority rank of each of the prioritized survivor command nodes may be related to their respective distance from the primary command node—i.e., the closer the particular prioritized survivor command node is to the primary command node, the lower the rank that particular prioritized survivor command node has. In other words, a highly ranked prioritized survivor command node may be a greater distance from the primary command node than others of the prioritized survivor command nodes.

As such, each of prioritized survivor command nodes 46160a, 46160b is configured to communicate with the primary command node 24160 and others of the prioritized survivor command nodes (as reflected in FIG. 46A) and to selectively operate as the primary command node 24160 when higher priority ranked ones of the prioritized survivor command nodes 46160a, 46160b are unable to communicate with the primary command node 24160. For example, For example, each of the system's prioritized survivor command nodes 46160a, 46160b may periodically communicate with primary command node 24160 to ensure normal operation. When the primary command node 24160 ceases to respond (e.g., no response within a threshold reporting interval), the higher priority ranked one of prioritized survivor command nodes 46160a, 46160b initiates taking over within the adaptive monitoring system as the primary command node (e.g., conducting the primary container monitoring operation). In another example, the primary command node 24160 may, as part of the primary container monitoring operation, periodically send a status message to each of the prioritized survivor command nodes 46160a, 46160b without prompting so that when the prioritized survivor command nodes fail to receive a timely status message from the primary command node 24160, the prioritized survivor commander node with the higher priority ranking take over for the primary command node 24160 as described. The determination of which of the multiple prioritized survivor command nodes has the highest priority ranking (and is still functional to take on the operation of the primary command node), the prioritized survivor commands 46160a, 46160b may communicate with each other to compare priority rankings. This may be implemented as a collective request sent between the multiple prioritized survivor command nodes, once the primary command node is determined not to be responsive or to be in operative (e.g., no response within the threshold reporting interval). Each of the prioritized survivor command nodes that remain functional (as some may be damaged and in operative as the primary command node is) responds to the others of the prioritized survivor command nodes with its respective priority ranking so that only the one with the highest priority ranking of those prioritized survivor command nodes left operating may be the designated survivor command node that takes over the functionality of conducting the primary container monitoring operation as was being performed by the primary command node. As such, those skilled in the art can appreciate that further failure handoffs may take place with others of the prioritized survivor command nodes taking over the functionality of conducting the primary container monitoring operations when the prioritized survivor command node operating as the designated survivor command node is also rendered inoperative and uncommunicative. As such, an embodiment of such an adaptive monitoring system may use "layers" of redundant types of command nodes to continue the primary container monitoring operations.

Figure 47:
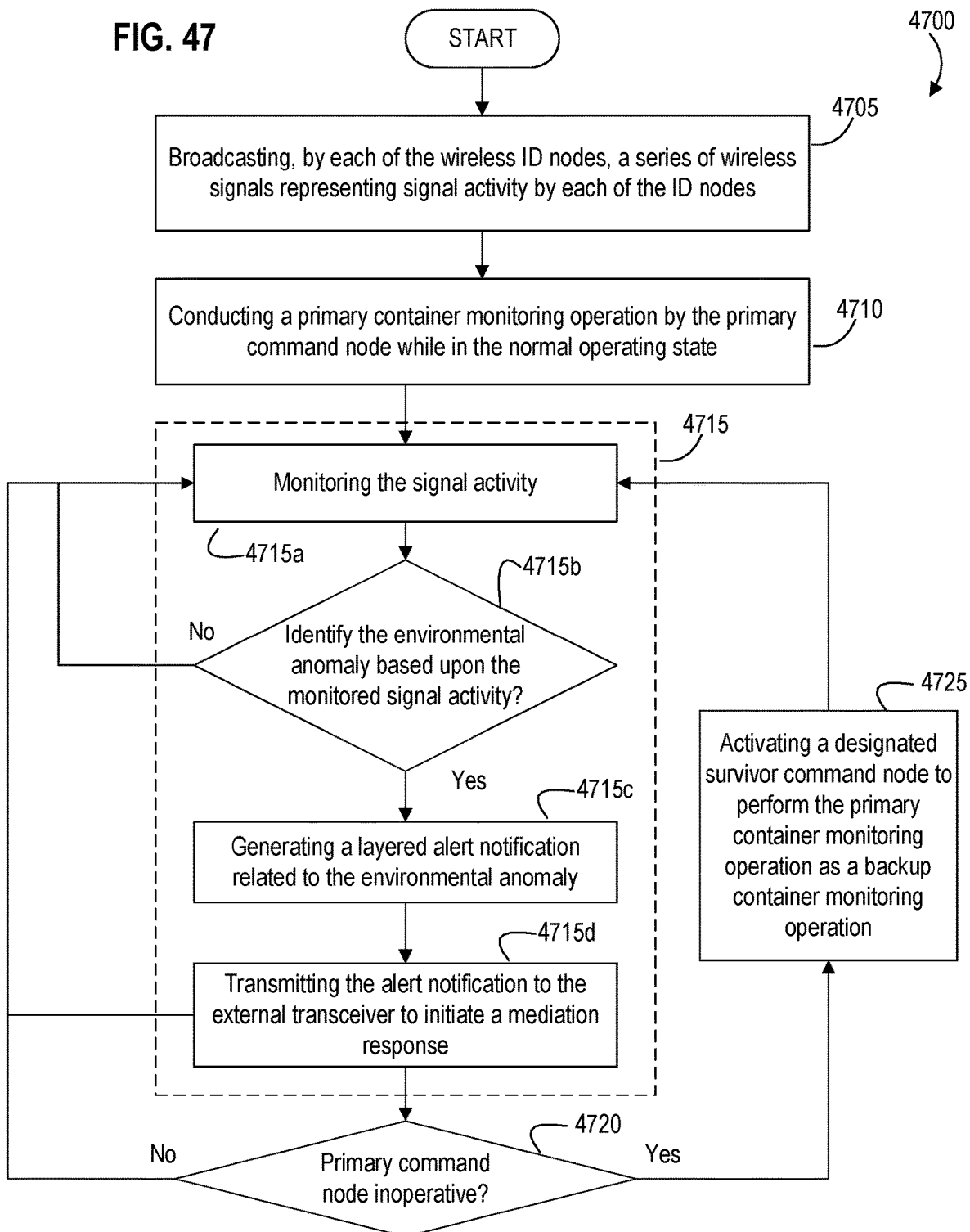
FIG. 47 is a flow diagram illustrating an exemplary method for adaptively monitoring a shipping container for an environmental anomaly using a primary command node and a designated survivor command node in accordance with an embodiment of the invention.

The above-described adaptive monitoring system embodiments may also be used to implement embodiments of an improved method for adaptively monitoring a shipping container for an environmental anomaly. FIG. 47 is a hybrid flow diagram illustrating an exemplary method for adaptively monitoring a shipping container for an environmental anomaly using a primary command node and a designated survivor command node that depends upon the operating state of the primary command node in accordance with an embodiment of the invention. As shown in FIG. 47, exemplary method 4700 is an improved method for adaptively monitoring a shipping container (e.g., shipping container 24300a) for an environmental anomaly using elements of wireless node network having at least a group of wireless ID nodes (e.g., ID nodes 1-8 as shown in FIGS. 45A-46B) disposed within the shipping container, a primary command node (e.g., primary command node 24160) disposed within the shipping container and a designated survivor command node (e.g., designed survivor command node) mounted to the shipping container.

Referring now to FIG. 47, exemplary method 4700 begins at step 4705 with each in the group of the wireless ID nodes broadcasting a series of wireless signals representing signal activity by each in the group of the wireless ID nodes. The series of wireless signals need not be periodic, but generally includes multiple signals over time that may be detected by another node, such as the primary command node 24160 and designed survivor command node 45160 so as to reflect an operative state of the broadcasting ID node.

At step 4710, method 4700 continues with the primary command node conducting a primary container monitoring operation 4715 while the primary command node is in a normal operating state (e.g., while primary command node 24160 is operating normally, has not entered a state of ceased communications, is responsively communicative with other nodes, such as the designated survivor command node 45150, and the like). The primary container monitoring operation 4710 is essentially a series of sub steps 4715a-4715d performed by the primary command node (e.g., exemplary primary command node 24160) while the primary command node remains in the normal operating state. However, should the operating state of the primary command node change to become inoperative or incommunicative, the primary command node is then no longer able to perform the primary container monitoring operation 4715 and that task will shift (as explained above) to the designated survivor command node as part of step 4725.

In more detail, after step 4710, method 4700 has the primary command node proceeding to sub step 4715a where the primary command node monitors the signal activity from each in the group of the wireless ID nodes. For example, such monitoring of the signal activity may involve detecting sensor data broadcast from each in the group of the wireless ID nodes (when the ID nodes deployed as used in method 4700 are sensor-based wireless ID nodes, such as ID nodes 1-8 as described above). In a further embodiment of method 4700 as part of sub step 4715a when monitoring the signal activity involves detecting sensor data broadcast from each in the group of the wireless ID nodes, the step of detecting the sensor data broadcasted from each in the group of the wireless ID nodes may be implemented with the primary command node detecting the sensor data broadcasted by each in the group of the wireless ID nodes according to a broadcast profile maintained by each of the group of the wireless ID nodes. The broadcast profile (e.g., part of exemplary profile data 330) defines a first messaging rate used to regulate how often the generated sensor data is broadcast, where the first messaging rate is higher than a default messaging rate. As such, the primary command node may then instruct each of the group of the wireless ID nodes to broadcast future generated sensor data at a second messaging rate that exceeds the first messaging rate after the primary command node transmits the layered alert notification to the external transceiver associated with the transit vehicle as part of sub step 4715d. Such instructions from the primary command node may instruct each of the group of the wireless ID nodes to change from the default messaging rate to the first messaging rate (e.g., a messaging rate for the ID nodes that has an initial value correlated to an environmental risk associated with material maintained within the shipping container).

At sub step 4715b, method 4700 continues with the primary command node determining if it can responsively identify the environmental anomaly based upon the monitored signal activity from the ID nodes. If so, sub step 4715b proceeds to sub step 4715c. Otherwise, sub step 4715b returns back to monitoring signal activity from the wireless ID nodes in sub step 4715a. In more detail as part of sub step 4715b and when, the primary command node may responsively identify the environmental anomaly for the shipping container when the detected sensor data does not include the sensor data from at least a threshold number of the wireless ID nodes, or when the detected sensor data indicates an environmental condition that exceeds an environmental threshold. In a further embodiment, the primary command node may responsively identify the environmental anomaly for the shipping container when the detected sensor data does not include the sensor data from at least a threshold number of the wireless ID nodes, and when the detected sensor data indicates an environmental condition that exceeds an environmental threshold. The environmental condition and the environmental threshold in such embodiments may be related to detected temperature, detected pressure, detected radiation, or conditions and thresholds related to a detected chemical presence (such as the detected chemical presence is indicative of an explosive within the shipping container or the detected chemical presence is indicative of a fire within the shipping container).

At sub step 4715c, method 4700 continues with the primary command node generating a layered alert notification related to the environmental anomaly for the shipping container in response to identifying the environmental anomaly for the shipping container in sub step 4715b. Such a layered alert notification identifies a targeted mediation recipient, identifies a targeted mediation action, and establishes a mediation response priority. In more detail, the identified targeted mediation recipient may be identified as a triggered fire suppression apparatus (e.g., exemplary fire suppression system 25010) on the transit vehicle that supplies a fire suppression agent into the shipping container as the mediation response, or personnel (e.g., an operator or logistics crew) related to operations of the transit vehicle that are prompted by the external transceiver as the mediation response. The targeted mediation action identified by the primary command node in the layered alert notification may also be identified based upon an extent of an observed drop in the monitored signal activity from the ID nodes and what is loaded within the shipping container as indicated by shipping information maintained on the primary command node. Additionally, the mediation response priority established by the primary command node in the layered alert notification may be established based upon an extent of an observed drop in the monitored signal activity from the wireless ID nodes, where the extent of the observed drop reflects a priority level for the mediation response priority that indicates one of different permissive status conditions for further travel by the transit vehicle.

At step 4715d, method 4700 then has the primary command node transmitting the layered alert notification to an external transceiver disposed separate from the shipping container to initiate a mediation response related to the targeted mediation action.

Thus, the sub steps 4715a-4715d essentially make up the process involved with the primary container monitoring operation 4715 performed while the primary command node is operative and communicative (e.g., in a normal state of operation). In more detail, the primary command node performing sub steps 4715a-4715d may be implemented as a container node mounted to the shipping container and operative to directly communicate with each in the group of the wireless ID nodes disposed internal to the shipping container and to directly communicate with the external transceiver (e.g., external transceiver 24150 or the transceiver part of fire suppression system 25010) associated with the transit vehicle However, step 4720 of method 4700 determines if the primary command node has been rendered inoperative (i.e., the primary command node is no longer operative and able to perform the primary container monitoring operation 4715). In more detail, the designated survivor command node determines if the primary command node is no longer operative (e.g., primary command node 24160 is not responsive to communications sent by designated survivor command node 45160 to primary command node 24160; primary command node is no longer sending out status messages anticipated to be broadcast and received by the designated survivor command node 45160) as part of step 4720. As such and if step 4720 determines the primary command node is still operative, step 4720 proceeds back to step 4710. But if step 4720 determines the primary command is inoperative, step 4720 proceeds to step 4725 where the designated survivor command node is activated to step into the role of the primary command node and begin performing a backup container monitoring operation (i.e., the same container monitoring operation 4715 involving sub steps 4715(a)-(d) of the primary container monitoring operation but now performed by the designated survivor command node in place of the inoperative primary command node). Stated another way in more detail, step 4725 may involve activating the backup container monitoring operation with the designated survivor command node performing sub steps (a)-(d) of the primary container monitoring operation 4715 by a container node mounted to the shipping container operating as the designated survivor command node. As such, the designated survivor command node may then directly communicate with each in the group of the wireless ID nodes disposed internal to the shipping container as part of performing the primary container monitoring operation 4715 and directly communicate with the external transceiver (e.g., external transceiver 24150 or the transceiver within fire suppression system 25010) associated with the transit vehicle A further embodiment of method 4700 may use one of multiple different prioritized survivor command nodes as the designated survivor command node involved in steps 4720 and 4725. For example, the step of activating the backup container monitoring operations in step 4725 by the designated survivor command node when the primary command node becomes inoperative may further involve identifying one of multiple prioritized survivor command nodes associated with the primary command node to be the designated survivor command node based upon a priority rank related each of the prioritized survivor command nodes (e.g., a priority rank related to how far away the particular prioritized survivor command node is from the primary command node as disposed within the shipping container as the prioritized survivor command nodes are typically disposed at different physical locations within the container, such as on opposing sides of the shipping container). As such, the one of the prioritized survivor command nodes identified to be the designated survivor command node when the primary command node becomes inoperative may be the highest priority one of the prioritized survivor command nodes that remains operative when the primary command node becomes inoperative. In a further example, the one of the prioritized survivor command nodes may be identified to be the designated survivor command node from the others of the prioritized survivor command nodes when higher priority ranked ones of the prioritized survivor command nodes are unable to communicate with the primary command node (e.g., the higher priority ranked ones are no longer operative as well and, thus, an operative but next lower priority ranked one of the prioritized survivor command nodes may be used as that designated survivor command node).

Another further embodiment of method 4700 may have step 4725 activating the backup container monitoring operation by activating the backup container monitoring operation by the designated survivor command node when the designated survivor command node is unable to communicate with the primary command node within a threshold reporting interval. In another example, the step of activating the backup container monitoring operation may involve preemptively activating the backup container monitoring operation by the designated survivor command node when the monitored signal activity from each in the group of the wireless ID nodes indicates less than a threshold number of the wireless ID nodes are broadcasting.

Transitioned Monitoring Management for Environmental Anomaly

While the embodiments described above leverage another backup type of command node within the shipping container, there are further embodiments that may transfer or transition the primary monitoring operation related to monitoring wireless ID node signal activity within the shipping container from a command node mounted to the shipping container to an external master node that can at least temporarily take over the primary monitoring operation. For example, if a shipping container is at a particular known or designated location (e.g., a location within the transit vehicle, at a particular storage facility, and the like), a master node disposed separately and outside of the shipping container at that location may associate with the shipping container's command node and take some of the processing burden off the shipping container's command node. In particular, for example, arriving at that location can have the primary task of monitoring ID nodes for an environmental anomaly shifting from the container's command node to the external master node (passively monitoring the container's ID nodes), which may free up the command node for other management responsibilities or help save battery life on the command node itself. When leaving that known location, the responsibility may transition back from the external master node to the container's command node. Some embodiments may have the shipping container's command node initiating such a transition of the primary monitoring operation for detecting the environmental anomaly with an instruction to the external master node. Other embodiments may have the external master node proactively being the device that initiates the transition of primary monitoring operations from the shipping container's command node. Still further embodiments may have the shipping container's command node initiating such a transition of primary monitoring operations when detecting it is close enough to the external master node and when the command node senses its own battery level is below a threshold where the transition of such monitoring operations helps the command node preserve battery power and extend its battery life.

Figure 48A:
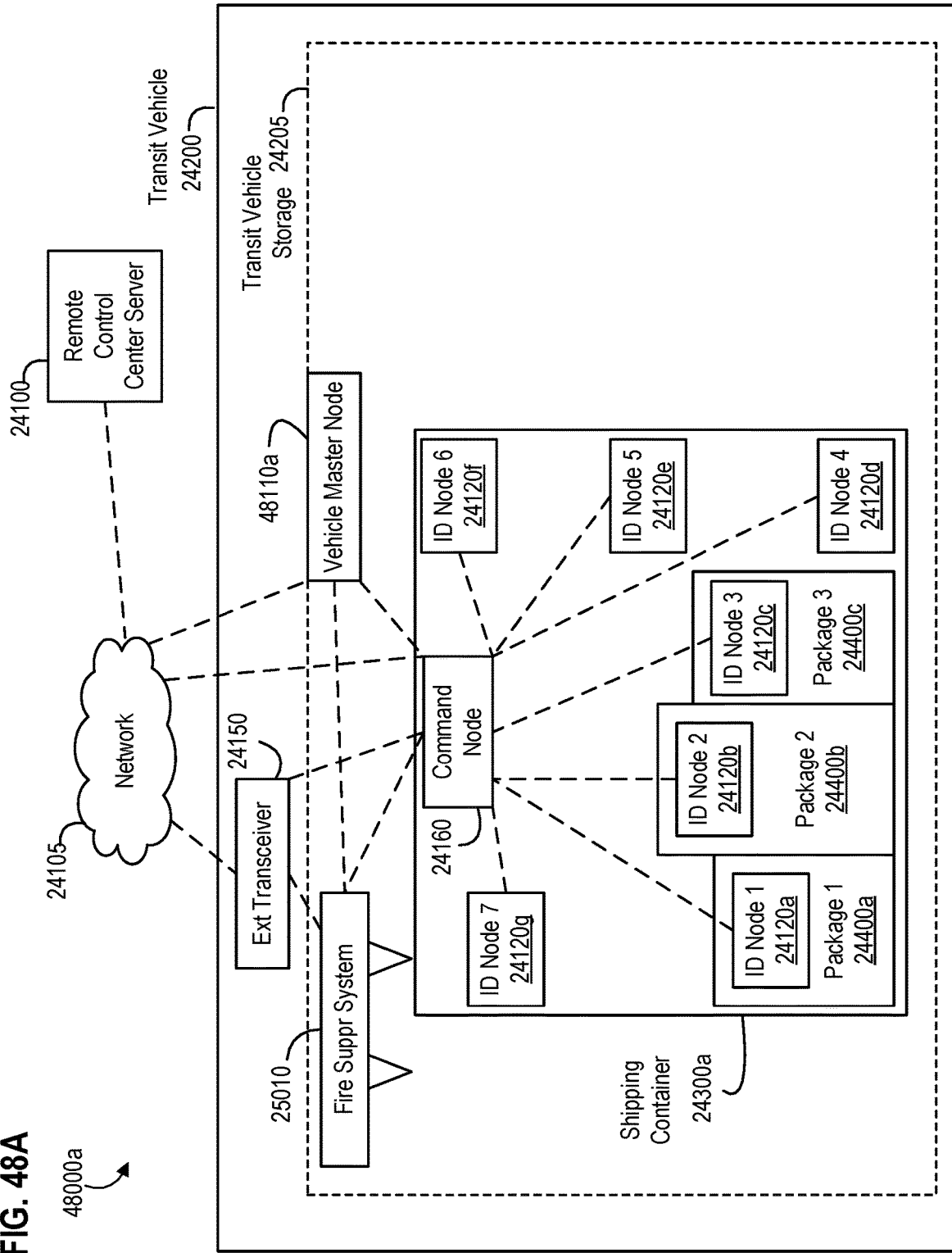
FIGS. 48A-48C are diagrams of an exemplary dynamic monitoring system for identifying and responding to an environmental anomaly related to a shipping container using wireless ID nodes, a command node as a primary monitor and external master node that is operative to temporarily operate as the primary monitor for the environmental anomaly in accordance with an embodiment of the invention.
Figure 48B:
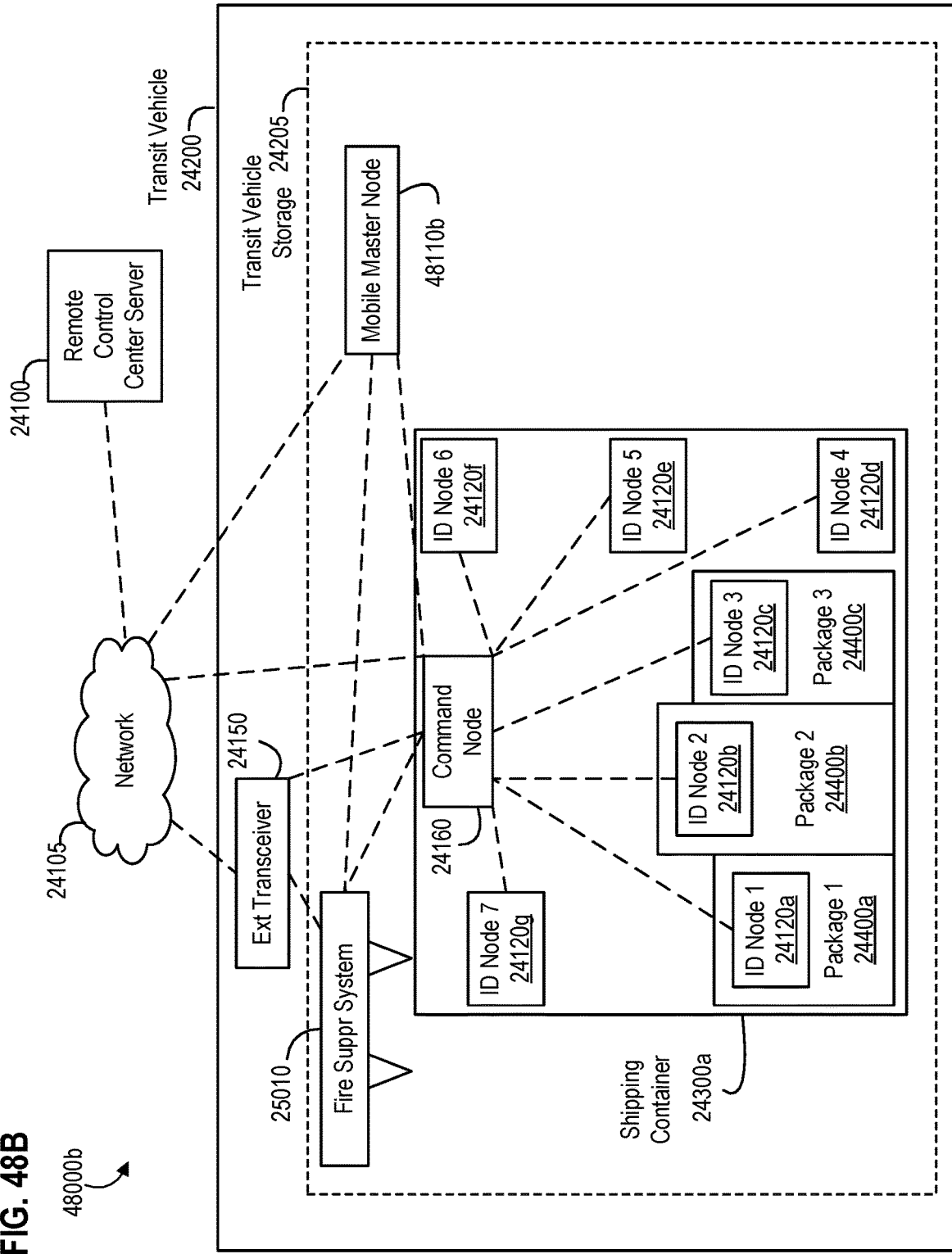
Figure 48C:
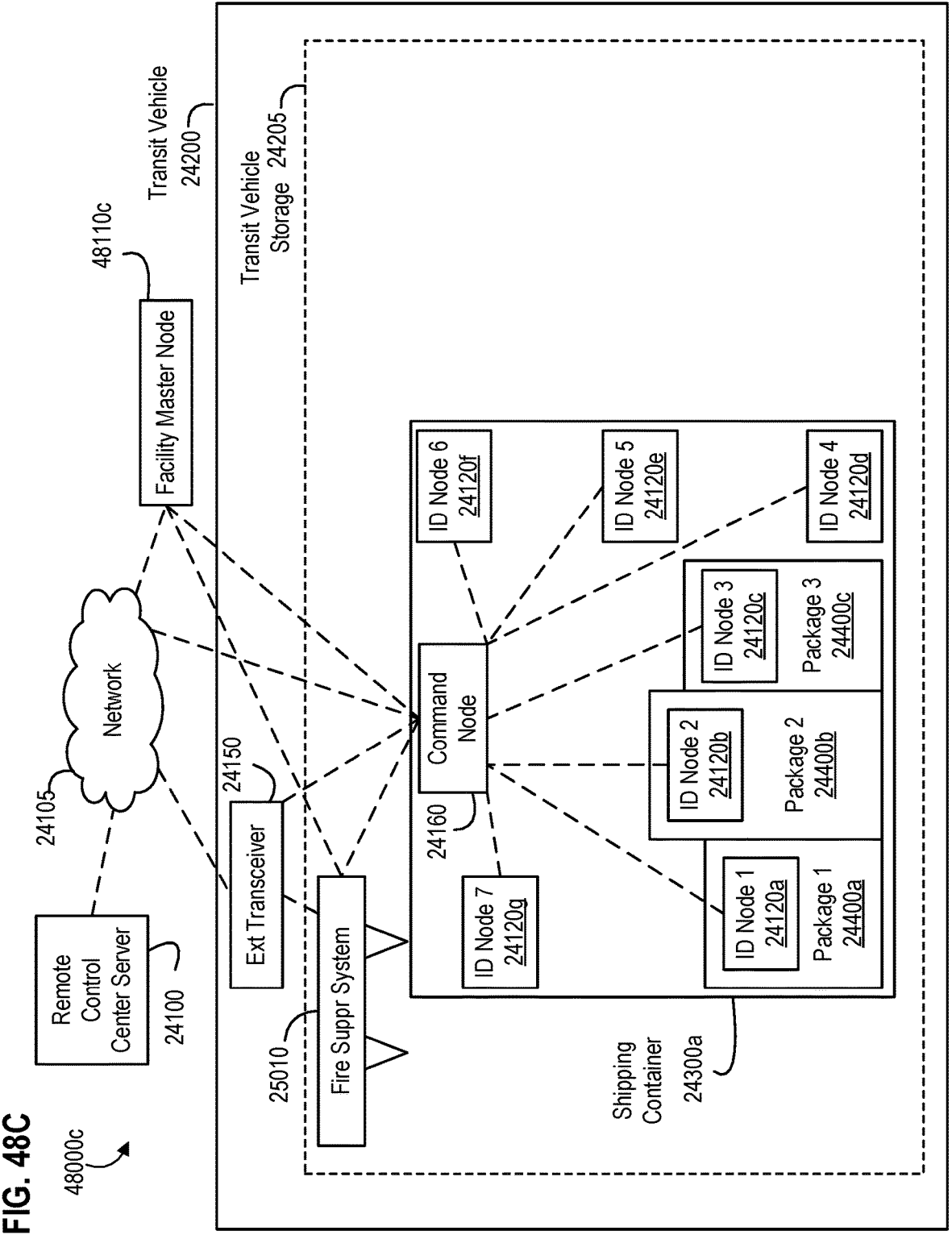

FIGS. 48A-48C are diagrams of an exemplary dynamic monitoring system for identifying and responding to an environmental anomaly related to a shipping container using wireless ID nodes, a command node as a primary monitor and external master node that is operative to temporarily operate as the primary monitor for the environmental anomaly in accordance with an embodiment of the invention. Referring now to FIG. 48A, an exemplary system 48000a is shown similar to what is described above with reference to, for example, FIGS. 37A-37B, where a transit vehicle 24200 is shown with transit vehicle storage 24205. The transit vehicle 24200 is shown equipped with external transceiver 24150 (as previously described), which may communicate with remote control center server 24100 via network 24105 as well as communicate directly with each of command node 24160 and wireless transceiver equipped fire suppression system 25010. Within storage 24205, exemplary shipping container 24300a is disposed such that fire suppression system 25010 may be activated (e.g., by external transceiver 24150 or by command node 24160) to supply a fire suppression agent into shipping container 24300a (e.g., as explained with reference to FIGS. 32A-32C).

In more detail and as illustrated in FIG. 48A, the system's shipping container 24300a is deployed to include exemplary command node 24160, which may communicate with external transceiver 24150 as well as with fire suppression system 25010. Command node 24160 is further operative to communicate with various ID nodes disposed within or as part of container 24300a. For example, as shown in FIG. 48A, command node 24160 is operative to communicate with exemplary ID nodes 24120a-24120g (e.g., ID nodes 1-7) disposed within container 24300a. Exemplary ID nodes 24120a-24120c (i.e., ID Nodes 1-3) are illustrated as being respectively associated with packages 24400a-24400c, while ID nodes 24120d-24120g (i.e., ID Nodes 4-7) are disposed within shipping container 24300a without being associated with a package. As such, ID nodes 24120d-24120g (i.e., ID Nodes 4-7) may be part of the shipping container or attached to the shipping container or may be simply an ID node disposed within the shipping container without being fixed to the shipping container and without being associated with, attached to, or disposed within a package in the shipping container.

Exemplary system 48000a illustrated in FIG. 48A shows an additional external master node, exemplary vehicle master node 48110a, that may be used to temporarily operate as the primary monitor for an environmental anomaly. This additional external master node may be implemented as a type of master node described relative to FIG. 4 and exemplary master node 110a. The external master node, as part of the embodiments described relative to FIGS. 48A-49B, is a master node that is disposed separately from the shipping container 24300a and operative to temporarily perform as the primary monitor of signal activity from ID nodes 1-7 under particular conditions where that primary monitoring operation has been transitioned off the shipping container's own command node 24160 as described in more detail below. For example, as part of system 48000a, vehicle master node 48110a is disposed separate from the shipping container 24300a and is mounted as part of the transit vehicle 24200 (e.g., disposed in a known location within the transit vehicle 24200). As such, vehicle master node 48110a may have a known relative location as disposed on transit vehicle 24200 and relative to the movable location of the command node 24160 (i.e., the location of command node 24160 as mounted to container 24300a as the container 24300a moves relative to the transit vehicle 24200 and within the transit vehicle storage 24205).

While only one vehicle master node 48110a is illustrated in FIG. 48A, embodiments of system 48000a may deploy more than one vehicle master node 48110a on transit vehicle 24200. Further, while the description herein describes the particular interactions between vehicle master node 48110a and command node 24160 within shipping container 24300a, those skilled in the art will appreciate that vehicle master node 48110a may concurrently interact with and take over primary monitoring operations from multiple different command nodes deployed on different shipping containers on transit vehicle 24200 and that similar concurrent interacts may take place with other such command nodes on those different shipping containers. As such, the vehicle master node 48110a in system 48000a provides a robust wireless node network element that can help manage and offload monitoring operations involving the detection of environmental anomalies with one or more shipping containers on transit vehicle 24200.

In another example, as shown in FIG. 48B, exemplary system 48000b deploys an external master node as a mobile master node 48110b. Referring now to FIG. 48B, mobile master node 48110b is disposed separately from shipping container 24300a, but may move relative to the command node 24160 of container 24300a. In this situation, the distance between the command node 24160 of container 24300a and mobile master node 48110b may change based upon movement of the container 24300a, movement of the mobile master node 48110b, or the combined movement of both the container 24300a and mobile master node 48110b. While the embodiment of system 48000b is shown in the context of what is on transit vehicle 24200, an embodiment of system 48000b may be deployed outside of a transit vehicle environment where the mobile master node 48110b and shipping container 24300a may be operating more generally to monitor for an environmental anomaly and transition such a primary monitoring operation from the container's command node 24160 to the mobile master node 48110b.

In another example, as shown in FIG. 48C, exemplary system 48000c deploys an external master node as a facility master node 48110c. Referring now to FIG. 48C, facility master node 48110b is disposed separately from shipping container 24300a, and may be located at a storage facility used to temporarily house transit vehicle 24200. Thus, exemplary facility master node 48110c is disposed external to shipping container 24300a and outside of transit vehicle 24200, but is still close enough and operative to communicate with ID nodes 1-7 within container 24300a so that facility master node 48110c may temporarily take over the functions of the primary monitor operations typically performed by command node 24160 of container 24300a.

Figure 49A:
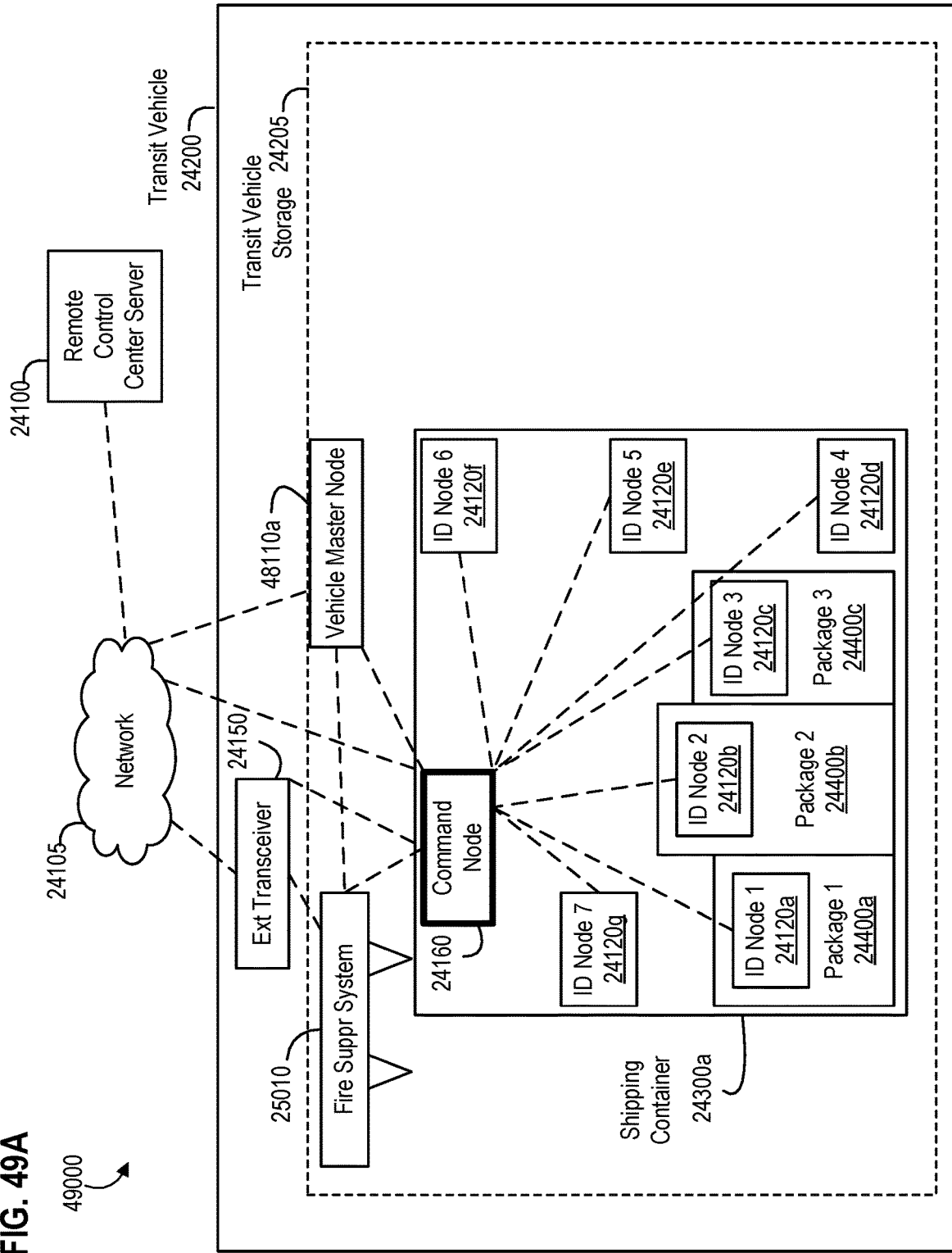
FIGS. 49A-49B are diagrams illustrating primary monitor transitions within an exemplary dynamic monitoring system for identifying and responding to an environmental anomaly related to a shipping container using wireless ID nodes, a command node as a primary monitor and external master node that is operative to temporarily operate as the primary monitor for the environmental anomaly in accordance with an embodiment of the invention.
Figure 49B:
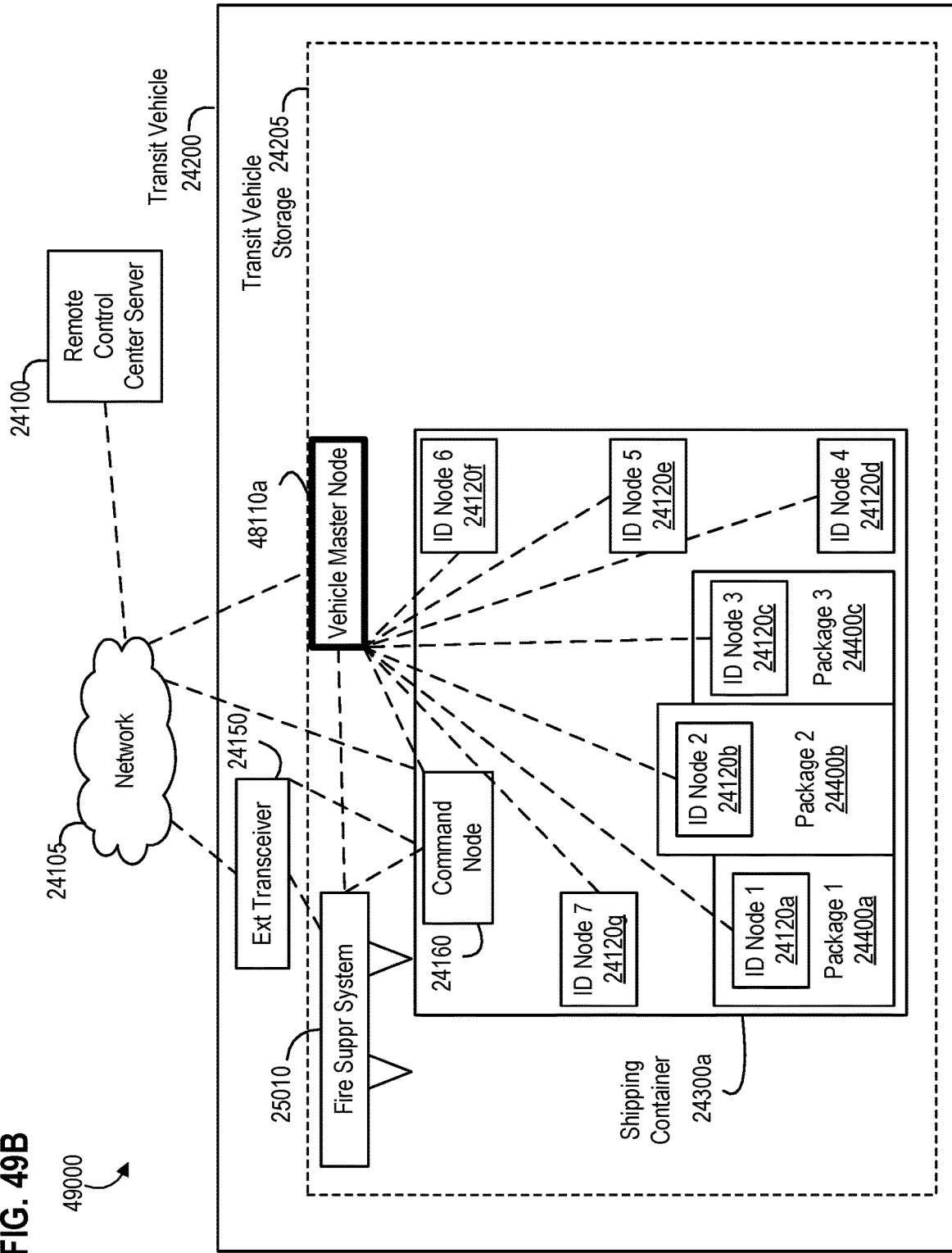

FIGS. 49A-49B are diagrams illustrating examples where primary monitor operations are transitioned within an exemplary dynamic monitoring system for identifying and responding to an environmental anomaly related to a shipping container. Referring now to FIG. 49A illustrating exemplary system 49000 (similar to that shown in FIG. 48A), system 49000 uses wireless ID nodes1-7, command node 24160 as the current primary monitor for an environmental anomaly, and external vehicle master node 48110a that is operative to temporarily operate as the primary monitor for the environmental anomaly in place of command node 24160 in accordance with an embodiment of the invention. In more detail and as shown in FIG. 49A, exemplary command node 24160 is configured to operate as the primary monitor for an environmental anomaly in that command node 24160 is shown at least wirelessly monitoring signal activity being broadcast from ID nodes 1-7 disposed within shipping container 24300a. Such signal activity may, for example, be advertising signals broadcast from ID nodes 1-7. Such advertising signals may, in some instances, include sensor data generated by respective ones of ID nodes 1-7.

As part of exemplary system 49000, command node 24160 may determine it is located within a threshold distance from the known location of the external vehicle master node (e.g., via node locating techniques described above, via signaling with or from server 24100, via signaling with or from vehicle master node 48110a). As such, command node 24160 may dynamically instruct the external vehicle master node 48110a to temporarily operate as the primary monitor for the environmental anomaly related to shipping container 24300a. In more detail, such a threshold distance within which the command node 24160 should be from vehicle master node 48110a may be a distance predetermined so that exemplary vehicle master node 48110a may be ensured to reliable receive communications from ID nodes 1-7 under normal conditions (e.g., broadcasted signals from ID nodes 1-7, which may include sensor data from ID nodes 1-7, when no environmental anomaly is present). As a result, vehicle master node 48110a then temporarily begins to operate as the primary monitor for any environmental anomaly within shipping container 24300a as shown in FIG. 49B where vehicle master node 48110a is shown at least wirelessly monitoring signal activity being broadcast from ID nodes 1-7 disposed within shipping container 24300a.

In light of such exemplary systems and their components as described in each of FIGS. 48A-49B, further more detailed embodiments of dynamically transitioning systems that monitor a shipping container for an environmental anomaly related to the shipping container are described below. For example, one embodiment of such a dynamically transitioning system may generally include a group of wireless ID nodes (e.g., ID nodes 1-7 as shown in FIG. 48A) disposed within a shipping container (e.g., exemplary container 24300a being transported by transit vehicle 24200 including an external transceiver 24150), a command node (e.g., exemplary command node 24160 as shown in FIG. 48A), and an external master node (e.g., exemplary vehicle master node 48110a as shown in FIG. 48A).

The group of wireless ID nodes disposed within the shipping container have some of the ID nodes (which may or may not be implemented as sensor-based ID nodes) associated with one or more objects being transported in the shipping container (e.g., ID nodes 1-3 being associated with packages 1-3 as shown in FIG. 48A). As part of this embodiment, the system's command node is mounted to the shipping container and operative to directly communicate with the ID nodes disposed internal to the shipping container. As such, the command node is configured (e.g., via program code that is part of command node control and management code 26425 and with wireless communication interfaces 26480, 26485) to operate as a primary monitor for the environmental anomaly.

The system's command node performs the primary monitor operations by, for example, being operative to (a) wirelessly monitor signal activity being broadcast from the ID nodes; (b) responsively identify the environmental anomaly based upon the monitored signal activity from the ID nodes (e.g., which ID nodes are broadcasting, what sensor data is being broadcasted compared to particular thresholds, and the like); (c) generate the layered alert notification related to the environmental anomaly for the shipping container in response to identifying the environmental anomaly for the shipping container (where the layered alert notification identifies a targeted mediation recipient, identifies a targeted mediation action, and establishes a mediation response priority); and (d) transmit the layered alert notification to the external transceiver to initiate a mediation response related to the targeted mediation action. Thus, as deployed within the shipping container, the system's command node is programmatically configured to perform and conduct at least operations (a)-(d) as the primary monitor for the shipping container's environmental anomaly.

The system's external master node in this embodiment (even when it is selected from one of many external support master nodes disposed throughout the transit vehicle) is disposed at a known location within the transit vehicle, such as a particular location within a storage area of the transit vehicle (e.g., disposed on the ceiling or within the floor within the middle of storage 24205 of transit vehicle 24200). For example, the external master node may be implemented by exemplary vehicle master node disposed at a particular location on transit vehicle 24200. The system's external master node may be a particular one of many vehicle master nodes deployed along the transit vehicle storage 24205 so as to provide differently located external master nodes that may communicate with the command node 24160 of container 24300a while also be able to communicate with the ID nodes 1-7 within container 24300a given the relative location of the particular external master node to the command node 24160 of container 24300a. In more detail, such an external master node may be implemented as a dual wireless transceiver based processing device mounted on the transit vehicle (e.g., a master node 110a having two wireless transceivers 480, 485), where one of the dual wireless transceivers (e.g., interface 480) is operative to wirelessly monitor the signal activity being broadcast from the ID nodes and a second of the dual wireless transceivers (e.g., interface 485) is operative to wirelessly transmit the layered alert notification to the external transceiver to initiate the mediation response related to the targeted mediation action.

Within this system embodiment, the system's command node is further configured to dynamically instruct the external master node to temporarily operate as the primary monitor for the environmental anomaly when the command node determines a current location of the command node to be within a threshold distance from the known location of the external master node. For example, as shown in FIG. 49A, command node 24160 is initially operating as the primary monitor for the environmental anomaly (e.g., conducting at least operations (a)-(d) as the primary monitor for the shipping container's environmental anomaly as described above). However, container 24300a may be located to be within a threshold distance of vehicle master node 48110a (or relocated to come within the threshold distance of vehicle master node 48110a). Under such conditions, the command node 24160 in container 24300a may instruct vehicle master node 48110a to temporarily operate as the primary monitor for the environmental anomaly as it related to shipping container 24300a as shown in FIG. 49B (e.g., conducting at least operations (a)-(d) as the primary monitor for the environmental anomaly as described above for shipping container 24300a).

In more detail, the command node may dynamically instruct the external master node to temporarily operate as the primary monitor for the environmental anomaly by being further operative to detect an advertising signal broadcast from the external master node as the command node approaches the known location of the external master node (e.g., as command node 24160 within shipping container 24300a moves towards the location of vehicle master node 48110a as located within the transit vehicle 24200). As the command node approaches the external master node, the command node may then dynamically instruct the external master node to temporarily operate as the primary monitor for the environmental anomaly involving functions (a)-(d) as described above in response to detecting the advertising signal broadcast from the external master node. Thus, the command node may "sense" the external master node from the detected advertising signal emanating from the external master node (e.g., an advertising signal that may not have been prompted by the command node but, instead, is more passively detected so as to indicate being within the threshold distance so as to enable the external master node to be able to take over the primary monitor functions from the command node, which involves monitoring signal activity of ID nodes within the command node's shipping container).

In another example, a logical association may be established between the command node and external master node as part of transitioning primary monitor duties by the system's command node. Such an association may be authorized by a separate server (such as server 24100) and may be tracked by such a server to manage the current logical associations between particular node elements used as part of this dynamic system that monitors for an environmental anomaly. For example, the system's command node may dynamically instruct the external master node to temporarily operate as the primary monitor for the environmental anomaly by being further operative to first detect an advertising signal broadcast from the external master node as the command node approaches the known location of the external master node; then generate association data on the command node (e.g., association data 440) to associate the command node with the external master node and reflect an authorized pairing of the command node and the external master node; and dynamically instruct the external master node to temporarily operate as the primary monitor for the environmental anomaly involving functions (a)-(d) as the command node transitions to a non-monitoring mode in response to associating the command node with the external master node. Such a non-monitoring mode of the command node allows the external master node to be temporarily responsible for performing at least the primary monitor functions (a)-(d) noted above, while allowing the command node to offload the processing burden and power usage that comes with such primary monitor operations (e.g., allows command node 24160 to enter a low power mode to save on battery power, allows command node 24160 to focus on other management duties with respect to ID nodes disposed within shipping container 24300a without having to incur the processing overhead and power drain from its onboard battery system related to the primary monitor duties as set forth at least by functions (a)-(d) above).

In even more detail, the system's command node may dynamically instruct the external master node to temporarily operate as the primary monitor for the environmental anomaly by being further operative to first detect the current location of the command node (e.g., via self-location using GPS circuitry on the command node, via location data 455 maintained in memory of the command node, via location data received requested and received by the command node) and determine if the command node's current location is within the threshold distance from the external master node. When the current location of the command node is within the threshold distance from the external master node, the command node may then generate association data on the command node to associate the command node with the external master node. Such generated association data reflects a logical and authorized pairing of the command node and the external master node. The command node may then dynamically instruct the external master node to temporarily operate as the primary monitor for the environmental anomaly involving functions (a)-(d) as the command node transitions to a non-monitoring mode in response to associating the command node with the external master node, where the command node's non-monitoring mode allows the external master node to be temporarily responsible for performing functions (a)-(d).

In a further example, the command node may dynamically instruct the external master node to temporarily operate as the primary monitor for the environmental anomaly by being further operative to first broadcast a transition command to the external master node as the command node approaches the known location of the external master node, and then receive an acknowledgement message from the external master node in response to the transition comment. Such an acknowledgement message is indicative of the external master node receiving the transition command from the command node. The command node may then generate association data (e.g., generate and store data maintained as part of association data 440 in memory of the command node) to associate the command node with the external master node and reflect an authorized pairing of the command node and the external master node. Thereafter, the command node may dynamically instruct the external master node to temporarily operate as the primary monitor for the environmental anomaly involving functions (a)-(d) as the command node transitions to a non-monitoring mode in response to associating the command node with the external master node, where the non-monitoring mode of the command node allows the external master node to be temporarily responsible for performing functions (a)-(d).

In another example, the transition may be based upon a transition command sent by the command node without requiring the particulars of establishing a formal and logical association between the command node and the external master node. For example, the command node may dynamically instruct the external master node to temporarily operate as the primary monitor for the environmental anomaly by being further operative to broadcast a transition command from the command node to the external master node as the command node approaches the known location of the external master node, and then receive an acknowledgement message by the command node from the external master node in response to the transition comment. Such an acknowledgement message is indicative of the external master node receiving the transition command from the command node. Accordingly, in response to receiving the acknowledgement message, the command node may then dynamically instruct the external master node to temporarily operate as the primary monitor for the environmental anomaly involving functions (a)-(d) as the command node transitions to a non-monitoring mode in response to associating the command node with the external master node, where the non-monitoring mode of the command node allows the external master node to be temporarily responsible for performing functions (a)-(d).

In a further embodiment, the system's command node may later resume primary monitor operations. For example, the system's command node (e.g., command node 24160) may subsequently instruct the external master node to transition out of its role as the primary monitor for the environmental anomaly in order allow the command node to resume operating as the primary monitor for the environmental anomaly responsible for performing functions (a)-(d). Such a transition back to the command node may happen when the command node (e.g., the shipping container 24300*a* with command node 24160) moves outside the threshold distance from the external master node (e.g., when the command node determines a subsequent location of the command node is no longer within the threshold distance from the known location of the external master node).

In an example where the command node and the external master node associated as part of transitioning the primary monitor operation temporarily to the external master node, the command node may determine that its subsequent location is no longer within the threshold distance from the known location of the external master node. As a result, the command node may subsequently instruct the external master node to transition from the primary monitor for the environmental anomaly in order allow the command node to resume operating as the primary monitor for the environmental anomaly responsible for performing functions (a)-(d); and alter the association data on the command node to reflect a disassociation of the command node and the external master node in response to when the command node resumes operating as the primary monitor for the environmental anomaly.

As mentioned above, embodiments of a dynamic monitoring system may have the external master node being one of multiple different external master nodes disposed at different respectively known locations within the transit vehicle. In other words, the group of different external master nodes may be referenced as external support master nodes as disposed at locations within the transit vehicle, and the system's external master node may be one of these different externally disposed master nodes (e.g., the vehicle master node 48110*a*). As such, the command node may be configured to dynamically instruct one of the external support master nodes (e.g., vehicle master node 48110*a* if other vehicle master nodes are deployed at different locations on transit vehicle 24200) to temporarily operate as the primary monitor for the environmental anomaly when the command node determines the current location of the command node to be within the threshold distance from the respectively known location of the one of the external support master nodes.

In further embodiments where multiple external master nodes may be disposed on the transit vehicle, the command node may transition the primary monitor operations to different external master nodes. For example, the command node may be further configured to dynamically instruct a second of the external support master nodes to temporarily operate as the primary monitor for the environmental anomaly from the one of the external support master nodes when the command node determines a subsequent location of the command node to be within the threshold distance from the respectively known location of the second of the external support master nodes.

In like fashion, another example may have the primary monitor duties going to one external master node, then back to the command node, and then subsequently to another external master node. For example and in more detail, the command node may subsequently instruct the one of the external support master nodes to transition from the primary monitor for the environmental anomaly in order allow the command node to resume operating as the primary monitor for the environmental anomaly responsible for performing functions (a)-(d); and then dynamically instruct a second of the external support master nodes to temporarily operate as the primary monitor for the environmental anomaly when the command node determines a subsequent location of the command node to be within the threshold distance from the respectively known location of the second of the external support master nodes.

As mentioned above, an effect of transitioning the primary monitor operation functions (a)-(d) from the command node to the external master may include power savings on the command node. As such, an example may have the command node being operative to shift to a reduced power operating mode after dynamically instructing the external master node to temporarily operate as the primary monitor for the environmental anomaly. The reduced power operating mode, in general, is for the command node to conduct normal operations other than the primary monitor operation functions (a)-(d), but may further have the command node enter a sleep or hibernate mode where the command node temporarily goes into a minimal power draw state or turns off particular circuitry within the command node to save power but where the command may re-activate such circuitry to "wake" from such a reduced power operating mode. In more detail, the command node may be operative to shift to such a reduced power operating mode after receiving an acknowledgement message from the external master node, where the acknowledgement message indicates that the external master node is temporarily operating as the primary monitor for the environmental anomaly. This may provide some overlapping monitoring functionality by the command node and the external master node before the external master node issues the acknowledgement message and the command node is assured the transition of primary monitoring duties have been at least temporarily effective.

In still a further example, the command node may be operative to shift to such a reduced power operating mode after dynamically instructing the external master node to temporarily operate as the primary monitor for the environmental anomaly when (a) the command node determines a current location of the command node to be within a threshold distance from the known location of the external master node and (b) the command node determines a battery status level for the command node is less than a battery level threshold. As such, the command node may detect the battery status level and compare it to a battery level threshold in some instances before or as a condition for transitioning the primary monitor operation functions (a)-(d) to the external master node.

In another embodiment of a dynamic monitoring system for identifying and responding to an environmental anomaly related to a shipping container, the system's external master node may not be specifically located at a particular or known location (e.g., it may not be located a predetermined location in the transit vehicle's storage area). Instead, the system's external master node may, for example, be a mobile master node (e.g., mobile master node 48110b) that may be untethered to a specific or fixed location. Such an embodiment of a dynamically transitioning system may generally include a group of wireless ID nodes (e.g., ID nodes 1-7 as shown in FIG. 48B) disposed within a shipping container (e.g., exemplary container 24300a being transported by transit vehicle 24200 including an external transceiver 24150), a command node (e.g., exemplary command node 24160 as shown in FIG. 48B), and an external master node (e.g., exemplary mobile master node 48110b as shown in FIG. 48B).

The group of wireless ID nodes in this embodiment are disposed within the shipping container where at least a portion of the ID nodes (which may or may be implemented as sensor-based ID nodes) are respectively associated with one or more objects being transported in the shipping container (e.g., ID nodes 1-3 being associated with packages 1-3 as shown in FIG. 48A). The system's command node in this embodiment is mounted to the shipping container and operative to directly communicate with the ID nodes disposed internal to the shipping container. As such, the command node is configured (e.g., via program code that is part of command node control and management code 26425 and with wireless communication interfaces 26480, 26485) to operate as a primary monitor for the environmental anomaly.

Similar the prior embodiment, this embodiment's command node performs the primary monitor operations by, for example, being operative to (a) wirelessly monitor signal activity being broadcast from the ID nodes; (b) responsively identify the environmental anomaly based upon the monitored signal activity from the ID nodes (e.g., which ID nodes are broadcasting, what sensor data is being broadcast compared to particular thresholds, and the like); (c) generate the layered alert notification related to the environmental anomaly for the shipping container in response to identifying the environmental anomaly for the shipping container (where the layered alert notification identifies a targeted mediation recipient, identifies a targeted mediation action, and establishes a mediation response priority); and (d) initiate a mediation response related to the targeted mediation action by broadcasting the layered alert notification. Thus, as deployed within the shipping container, the system embodiment's command node is programmatically configured to perform and conduct at least operations (a)-(d) as the primary monitor for the shipping container's environmental anomaly.

The system's external master node in this further embodiment is disposed separately from the command node and, as a type of master node, is configured to communicate with the command node over its wireless communication interfaces.

In more detail, such an external master node may be implemented as a dual wireless transceiver based processing device mounted on the transit vehicle (e.g., a master node 110a having two wireless transceivers 480, 485), where one of the dual wireless transceivers (e.g., interface 480) is operative to wirelessly monitor the signal activity being broadcast from the ID nodes and a second of the dual wireless transceivers (e.g., interface 485) is operative to wirelessly transmit the layered alert notification to the external transceiver to initiate the mediation response related to the targeted mediation action.

Within this further system embodiment, the system's command node is configured to dynamically instruct the external master node to temporarily operate as the primary monitor for the environmental anomaly when the command node determines a current location of the command node to be within a threshold distance from a current location of the external master node. For example, command node 24160 may determine it is located within a threshold distance from a current location of the externally disposed mobile master node 48110b (e.g., via self-location using GPS circuitry on the command node 24160, via location data 455 maintained in memory of the command node 24160, via location data received requested and received by the command node 24160, via node locating techniques described above to determine the location of the mobile master node 48110b, via signaling with or from server 24100, via signaling with or from mobile master node 48110b requesting such location information).

In more detail, command node in this embodiment may dynamically instruct the external master node to temporarily operate as the primary monitor for the environmental anomaly by being further operative to detect an advertising signal broadcast from the external master node as the distance between the command node and the external master node decreases (i.e., the command node and external master node close in relative to each other), and dynamically instruct the external master node to temporarily operate as the primary monitor for the environmental anomaly involving functions (a)-(d) in response to detecting the advertising signal broadcast from the external master node.

The system embodiment may specifically have the external master node being a mobile external master node (e.g., mobile master node 48110b) movably disposed external to the command node. As such, the command node may dynamically instruct the mobile external master node to temporarily operate as the primary monitor for the environmental anomaly by being further operative to detect an advertising signal broadcast from the mobile external master node as a distance between the command node and the mobile external master node decreases as a result of the mobile external master node moving closer to the command node, and dynamically instruct the mobile external master node to temporarily operate as the primary monitor for the environmental anomaly involving functions (a)-(d) in response to detecting the advertising signal broadcast from the mobile external master node.

In another example, the system's command node may dynamically instruct the external master node to temporarily operate as the primary monitor for the environmental anomaly using associations by being further operative to detect an advertising signal broadcast from the external master node as the command node approaches the location of the external master node; generate association data on the command node to associate the command node with the external master node and reflect an authorized pairing of the command node and the external master node; and dynamically instruct the external master node to temporarily operate as the primary monitor for the environmental anomaly involving functions (a)-(d) as the command node transitions to a non-monitoring mode in response to associating the command node with the external master node (where the command node's non-monitoring mode allows the external master node to be temporarily responsible for performing functions (a)-(d) and where the command node no longer operates in a manner to perform functions (a)-(d)).

In a more detailed another example involving association data, the system's command node may dynamically instruct the external master node to temporarily operate as the primary monitor for the environmental anomaly by being further operative to detect the current location of the command node and the external master node; determine if the current location of the command node is within the threshold distance from the current location of the external master node; generate association data on the command node to associate the command node with the external master node when the current location of the command node is within the threshold distance from the current location of the external master node, the generated association data reflecting an authorized pairing of the command node and the external master node; and dynamically instruct the external master node to temporarily operate as the primary monitor for the environmental anomaly involving functions (a)-(d) as the command node transitions to a non-monitoring mode in response to associating the command node with the external master node (where the non-monitoring mode of the command node allows the external master node to be temporarily responsible for performing functions (a)-(d) and where the command node no longer operates in a manner to perform functions (a)-(d)).

In yet another example, the command node may dynamically instruct the external master node to temporarily operate as the primary monitor for the environmental anomaly based on a transition command by being further operative to broadcast a transition command from the command node to the external master node as the command node approaches the external master node, and receive an acknowledgement message by the command node from the external master node in response to the transition command (where such an acknowledgement message indicates the external master node received the transition command from the command node). The command node may then be further operative to generate association data on the command node to associate the command node with the external master node and reflect an authorized pairing of the command node and the external master node, and dynamically instruct the external master node to temporarily operate as the primary monitor for the environmental anomaly involving functions (a)-(d) as the command node transitions to a non-monitoring mode in response to associating the command node with the external master node, the non-monitoring mode of the command node allowing the external master node to be temporarily responsible for performing functions (a)-(d).

Another example may have the command node dynamically instructing the external master node to temporarily operate as the primary monitor for the environmental anomaly by being further operative to broadcast a transition command from the command node to the external master node as the command node approaches the external master node; receive an acknowledgement message by the command node from the external master node in response to the transition command (where the acknowledgement message receipt of the transition command from the command node); and then respond by dynamically instructing the external master node to temporarily operate as the primary monitor for the environmental anomaly involving functions (a)-(d) as the command node transitions to a non-monitoring mode in response to associating the command node with the external master node, the non-monitoring mode of the command node allowing the external master node to be temporarily responsible for performing functions (a)-(d).

In a further embodiment, the above-described system may have the command node later resuming the primary monitor operation from the external master node. For example and in more detail, the command node may subsequently instruct the external master node to transition from the primary monitor for the environmental anomaly in order allow the command node to resume operating as the primary monitor for the environmental anomaly responsible for performing functions (a)-(d). Such a subsequent instruction may be sent by the command node when the command node determines a subsequent location of the command node is no longer within the threshold distance from the external master node. As such, the command node may send this subsequent instruction and may also, in some embodiments, alter the association data on the command node to reflect a disassociation of the command node and the external master node in response to when the command node resumes operating as the primary monitor for the environmental anomaly.

A further embodiment of the above-described system embodiment may further include an external transceiver disposed on a transit vehicle transporting the shipping container. As such, the command node may then initiate the mediation response related to the targeted mediation action by broadcasting the layered alert notification to the external transceiver disposed on a transit vehicle transporting the shipping container. In more detail, such an external transceiver disposed on the transit vehicle may be implemented as a display-based external transceiver (e.g., exemplary transceiver 24150 that may include a display 40015 as shown in FIG. 40) operative to receive the layered alert notification and generate a prompt notification on the display that provides mediation instructions on the targeted mediation action. Such a prompt notification may include instructions for an operator of the transit vehicle to change course of the transit vehicle as the mediation instructions, or instructions for a logistics crew on the transit vehicle to inspect the shipping container as the mediation instructions. Alternatively, such an external transceiver disposed on the transit vehicle may be implemented as a wireless transceiver equipped fire suppression system (e.g., exemplary fire suppression system 25010 having transceiver communication interface 32010 as shown in FIGS. 32A-32C) operative to receive the layered alert notification and supply a fire suppression agent into the shipping container as the targeted mediation action.

A further system embodiment may have the external master node initiating a request to serve as the primary monitor. In more detail, such a further embodiment may include the group of ID nodes and command node as described above, and also include an external master node disposed at a known location within the transit vehicle. The external master node is configured to communicate with the command node and, in particular, is further configured to (a) dynamically instruct the command node to stop operating as the primary monitor for the environmental anomaly (i.e., the primary monitor operating functions (a)-(d) described above) and (b) temporarily operate as the primary monitor for the environmental anomaly when the external master node determines a current location of the command node to be within a threshold distance from the location of the external master node.

Further still, another system embodiment may rely upon a backend server to initiate changing which of the command node or the external master node is to be operating as the primary monitor for an environmental anomaly related to a shipping container. For example, such a dynamically transitioning system for monitoring a shipping container for an environmental anomaly related to the shipping container includes a group of wireless ID nodes disposed within the shipping container (e.g., ID nodes 1-7 as shown in FIG. 49A within shipping container 24300*a*), a command node mounted to the shipping container (e.g., command node 24160), an external master node disposed separate from the shipping container and on the transit vehicle (e.g., vehicle master node 48110*a*, which is configured to communicate with the command node), and a backend remote server (e.g., server 24100) configured to communicate with the command node and with the external master node over a network (e.g., network 24105).

In this additional system embodiment (similar to the other dynamic system embodiments described above), the command node is operative to directly communicate with the ID nodes disposed internal to the shipping container and is configured to operate as a primary monitor for the environmental anomaly by being operative to (a) wirelessly monitor signal activity being broadcast from the ID nodes; (b) responsively identify the environmental anomaly related to the shipping container based upon the monitored signal activity from the ID nodes; (c) generate the layered alert notification related to the environmental anomaly related to the shipping container in response to identifying the environmental anomaly for the shipping container (where the layered alert notification identifies a targeted mediation recipient, identifies a targeted mediation action, and establishes a mediation response priority); and (d) transmit the layered alert notification to the external transceiver to initiate a mediation response related to the targeted mediation action). The backend remote server is further configured, when the backend remote server determines a current location of the command node to be within a threshold distance from a current location of the external master node, to be operative to (i) instruct the command node to stop operating as the primary monitor for the environmental anomaly related to the shipping container, and (ii) instruct the external master node to temporarily operate as the primary monitor for the environmental anomaly related to the shipping container.

The backend server's instructions may also be authenticated as part of changing responsibility for the primary monitor operation for an environmental anomaly related to the shipping container. For example, the command node may be further configured to transmit an authentication request to the backend remote server. Such an authentication request is related to an instruction for the command node to stop operating as the primary monitor for the environmental anomaly related to the shipping container. The command node may then be further operative to cease operating as the primary monitor for the environmental anomaly related to the shipping container when the command node receives an acknowledgement message from the backend remote server confirming the instruction for the command node to stop operating as the primary monitor for the environmental anomaly related to the shipping container. In like manner, the external master node may be further configured to transmit an authentication request to the backend remote server (where the authentication request is related to an instruction for the external master node to begin temporarily operating as the primary monitor for the environmental anomaly related to the shipping container) and begin temporarily operating as the primary monitor for the environmental anomaly related to the shipping container when the external master node receives an acknowledgement message from the backend remote server confirming the instruction for the external master node to begin temporarily operating as the primary monitor for the environmental anomaly related to the shipping container.

At a later point in time, the command node in this embodiment may resume primary monitor operations at the instruction of the backend server. For example, the backend remote server may instruct the external master node to stop temporarily operating as the primary monitor for the environmental anomaly related to the shipping container, and instruct the command node to resume operating as the primary monitor for the environmental anomaly related to the shipping container.

Additionally, the system's backend server may also transition the primary monitor duties for the shipping container from one external master node to another external master node. For example, the backend remote server may be further configured to be operative to instruct the external master node to stop temporarily operating as the primary monitor for the environmental anomaly related to the shipping container, and instruct another external master node to begin temporarily operating as the primary monitor for the environmental anomaly related to the shipping container. As such, the backend server may directly and actively manage which of the potential external master nodes disposed near a shipping container may be deployed to temporarily take over the primary monitoring for an environmental anomaly related to the shipping container, as well as moving such monitoring responsibilities between different external master nodes as needed (e.g., as the shipping container moves between locations where different external master nodes are disposed).

Further still, the system's backend server may direct the transition of the primary monitoring operation responsibilities from one external master node, back to the command node, and then to anther external master node. For example, the backend remote server may be further configured to be operative to instruct the external master node to stop temporarily operating as the primary monitor for the environmental anomaly related to the shipping container; instruct the command node to resume operating as the primary monitor for the environmental anomaly related to the shipping container; instruct the command node to stop operating as the primary monitor for the environmental anomaly related to the shipping container after having resumed operating as the primary monitor; and then instruct another external master node to temporarily operate as the primary monitor for the environmental anomaly related to the shipping container.

In still a further system embodiment, the system's command node may be further configured to dynamically instruct the external master node (or another shipping container's command node or a secondary command node deployed within the same shipping container) to temporarily operate as the primary monitor for the environmental anomaly when the command node determines a current location of the command node to be within a threshold distance from the known location of the external master node (or the other shipping container's command node or the second command node deployed within the same shipping container). For example, as shown in FIG. 49A, command node 24160 is initially operating as the primary monitor for the environmental anomaly (e.g., conducting at least operations (a)-(d) as the primary monitor for the shipping container's environmental anomaly as described above). However, container 24300a may be located to be within a threshold distance of vehicle master node 48110a (or relocated to come within the threshold distance of vehicle master node 48110a or located to be within a communication distance to another shipping container's command node or a secondary command node deployed within container 24300a). Under such conditions, the command node 24160 in container 24300a may instruct vehicle master node 48110a (or the other shipping container's command node) to temporarily operate as the primary monitor for the environmental anomaly as it relates to shipping container 24300a as shown in FIG. 49B (e.g., conducting at least operations (a)-(d) as the primary monitor for the environmental anomaly as described above for shipping container 24300a). Further, in this situation, command node 24160 in container 24300a may dispense with expending battery power and processing cycles to perform operations (a)-(d) and, instead, become an enhanced sensor-based ID node to be monitored by vehicle master node 48110a by using one or more sensors (e.g., 26465) on command node 24160 in container 24300a and broadcast sensor data generated by command node 24160 to vehicle master node 48110a. As such, vehicle master node 48110a may perform the (a) wirelessly monitor signal activity being broadcast from the ID nodes (now including signal activity broadcast from command node 24160 as an additional sensor-based ID node using the command node's own sensors); (b) responsively identify the environmental anomaly based upon the monitored signal activity from the ID nodes (e.g., which ID nodes are broadcasting including the command node operating as the enhanced sensor-based ID node, what sensor data is being broadcasted (including the command node's sensor data) compared to particular thresholds, and the like). In this way, the command node's own sensors (which may have a broader array of sensors, more accurate sensors, and more sensing elements) may allow this type of monitor responsibility shift to provide an even greater level of sensing and better use of command node battery power and compute cycles to more accurately detect potential environmental anomalies. In this example, command node 24160 may also similarly transition back to assuming operations (a)-(d) as well and similar to that described above.

Integrated Fire Suppression System

As shown and described in embodiments above, an exemplary fire suppression system (such as exemplary onboard triggered fire suppression system 25010) may be activated and deployed on a transit vehicle for initiating a mediation action in response to a detected environmental anomaly related to a shipping container being transported on the transit vehicle. As noted above, an embodiment of such an exemplary fire suppression system 25010 as shown in FIGS. 32A-32C may generally include at least a fire suppression controller 32000, a transceiver 32010 coupled to the controller, a pump 32015, a fire suppression agent reservoir chamber 32020 that holds a fire suppression agent, and actuators 32025a-32025b that responsively control an articulating needle 32030a-32030b as a type of dispenser coupled to the pump and that may be extended to puncture a shipping container 24300a on the transit vehicle 24200. Further embodiments may implement such an exemplary fire suppression system with an integrated master node, which may allow the fire suppression system to take on the primary monitoring operation involving monitoring signal activity from ID nodes and/or sensor data from various types of sensors associated with the fire suppression system. In more detail, such a further embodiment of the fire suppression system may deploy additional sensors for monitoring the inside and/or outside of the shipping container to further assess environmental conditions of the shipping container itself and/or conditions within the container. Thus, rather than having a command node within the shipping container conduct the primary monitoring operation and coordinate separately with an onboard fire suppression system, embodiments may have the onboard fire suppression system take on the primary monitoring responsibility for detecting an environmental anomaly as well as provide for advanced assessments involved in such detecting and improved mediation responses. Furthermore, similar to that described above, having the onboard fire suppression system take on the primary monitoring responsibility for detecting an environmental anomaly may let the command node within the shipping container assume the role of an enhanced ID node using the command node's wider array of more powerful and/or sensitive sensors (given the availability of more power from the command node's battery or if the command node is powered via a line connection to the shipping container and to an external power source (e.g., a generator onboard the transit vehicle)).

Figure 50A:
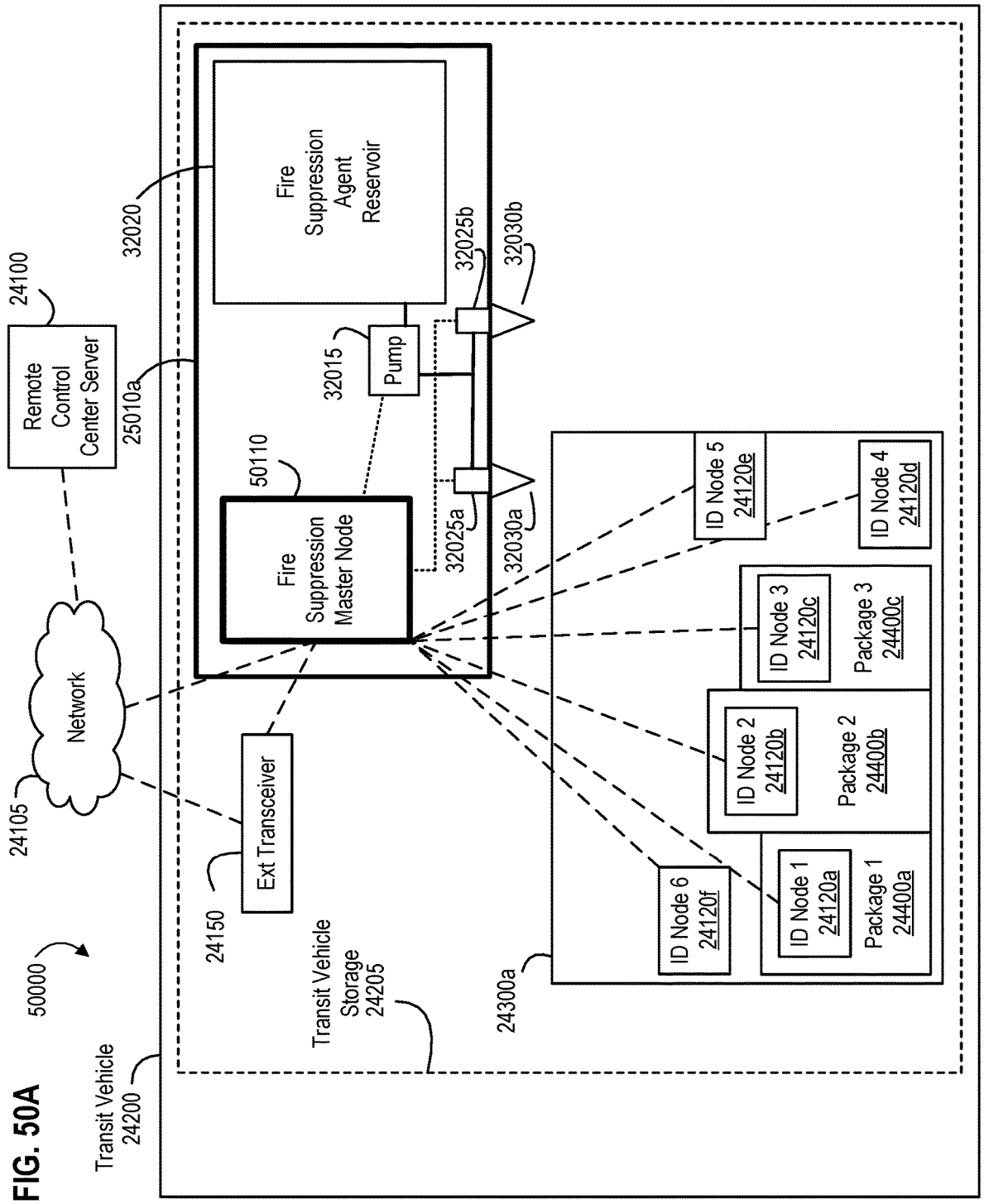
Figure 50C:
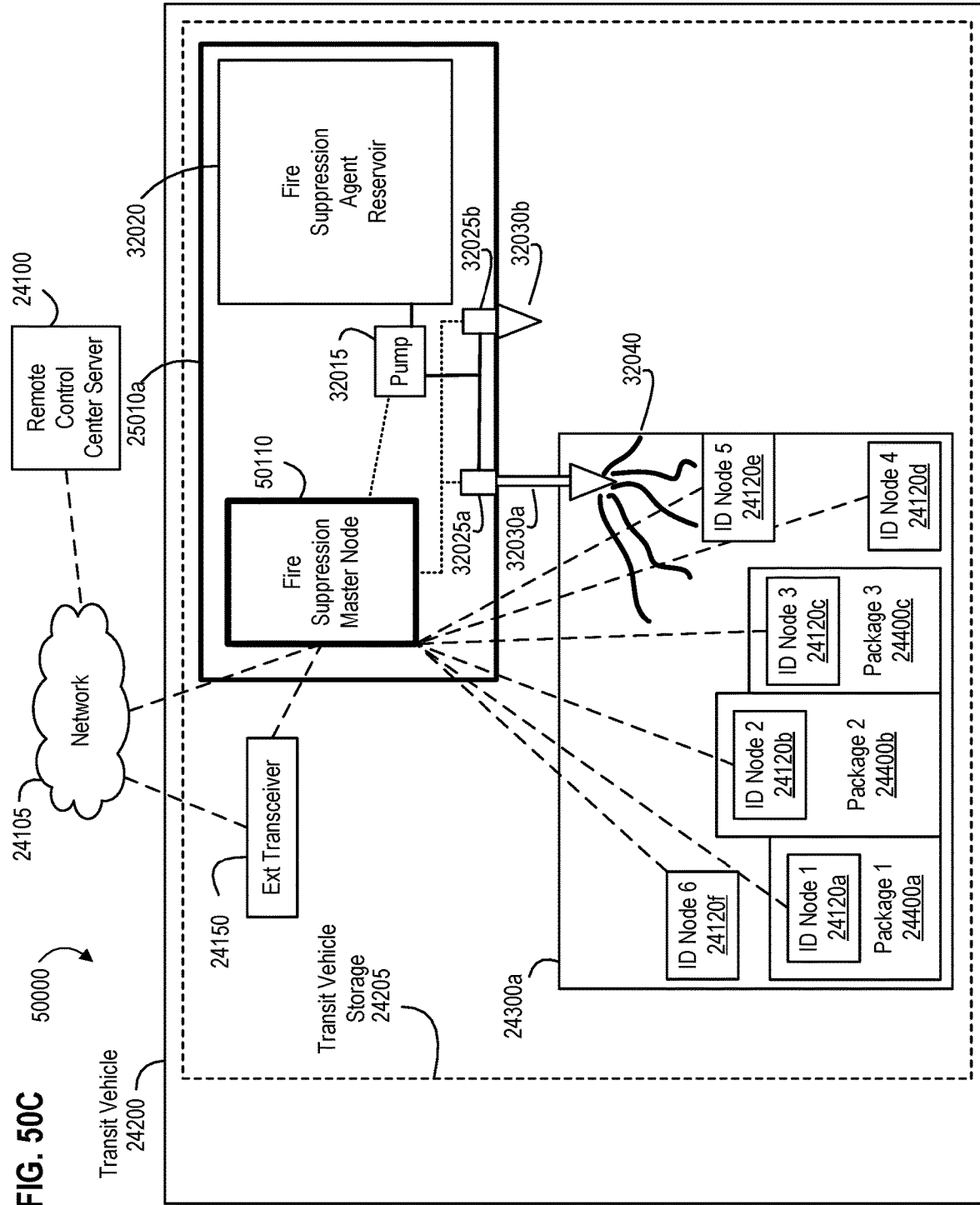

FIGS. 50A-50C are a series of diagrams of another exemplary onboard fire suppression system having an integrated master node and be activated and deployed on a transit vehicle for monitoring for an environmental anomaly and initiating a mediation action in response to a detected environmental anomaly related to a shipping container being transported on the transit vehicle in accordance with an embodiment of the invention. Referring now to FIG. 50A, exemplary system 50000 is shown as having similar components illustrated and described relative to FIG. 32A, but includes a different embodiment of the fire suppression system when compared to system 25010 shown in FIG. 32A. In particular, exemplary onboard fire suppression system 25010a is illustrated in FIGS. 50A-50C with similar components as fire suppression system 25010 from FIGS. 32A-32C, but exemplary fire suppression system 25010a includes fire suppression master node 50110 (e.g., a type of master node 110a as described above) in place of the transceiver 32010 and fire suppression controller 32000 of system 25010 shown in FIG. 32A. In general, fire suppression master node 50110 has functionality that is programmatically configured by virtue its master node management and control code (e.g., code 425) as explained in more detail below. Similar to the fire suppression controller 32000 from fire suppression system 25010, the exemplary fire suppression master node 50110 in fire suppression system 25010*a* is also operative generate the pump control input for pump 32015 and cause the articulating delivery nozzle 32030*a*, 32030*b* to deploy (via actuators 32025*a*, 32025*b*) and deliver the fire suppressant material to the shipping container.

Additionally, the fire suppression master node 50110 is programmatically configured to operate as a primary monitor for the environmental anomaly related to shipping container 24300*a* in how it can interact with ID nodes 1-6 and respond accordingly. In more detail and as fire suppression master node 50110 executes its master node management and control code, fire suppression master node 50110 becomes programmatically configured to be operative to (a) wirelessly monitor the signals being broadcast from the ID nodes 1-6; (b) responsively identify the environmental anomaly based upon the monitored signals broadcast from the ID nodes 1-6 (e.g., advertising signals, signals including sensor data, and the like); (c) generate a layered alert notification related to the environmental anomaly for the shipping container in response to identifying the environmental anomaly for the shipping container (where the layered alert notification identifies a targeted mediation action and establishes a mediation response priority); and (d) initiate a mediation response by the fire suppression system 25010*a* related to the targeted mediation action and the mediation response priority (such as dispensing the fire suppression agent material into the shipping container 24300*a*). As such, the fire suppression master node 50110 may take on the role of the shipping container's command node in such embodiments.

As shown in FIG. 50B (similar to that shown in FIG. 32B), actuators may be activated by the fire suppression master node 50110 so that a particular actuator, such as actuator 32035*a*, responsively articulates, moves, and/or extends its needle 32030*a* (part of an exemplary articulating delivery nozzle) from a retracted position to an extended activated position (as shown in FIG. 50B). In this way, the extended needle 32030*a* and its actuator 32025*a* (collectively an example of an articulating delivery nozzle) are forcibly deployed to rapidly create an opening in a shipping container (e.g., shipping container 24300*a* shown in FIGS. 50A-50C) in response to a deployment control signal sent from the fire suppression master node 50110 to the respective actuator (e.g., actuator 32025*a*) as part of initiating a type of mediation action as part of the above described primary monitoring operation (d). Once the dispensing articulated puncture (e.g., actuator 32025*a* and its related needle 32030*a*, collectively considered a type of articulating delivery or dispensing nozzle) is in the extended activated position as shown in FIG. 50B, fire suppression master node 50110 may send the appropriate control signals to pump 32015 based on the particular shipping container monitored that indicates there is an environmental anomaly warranting such a mediation response by the fire suppression system 25010*a* (e.g., control signals from master node 50110 to pump 32015 to selectively supply fire suppression agent from chamber 32020 to needle 32030*a* so that the pressurized fire suppression agent is injected within shipping container 24300*a*). Thus, as shown in FIG. 50C, fire suppression agent 32040 pressurized by pump 32015 (and, in some cases, pressurized as agent 32040 is stored within chamber 32020) may be supplied from fire suppression agent reservoir chamber 32020, then through needle 32030*b* so that the agent enters shipping container 24300*a* as a type of mediation action or response that may be directly or indirectly initiated by the fire suppression system 25010*a* (more particularly, by the system's fire suppression master node 50110).

As shown in FIG. 50B, an embodiment of system 25010*a* may have a part of the articulating delivery nozzle that is being inserted into shipping container 24300*a* deployed with one or more shipping container sensors (e.g., sensors 50010 on the delivery end portion 50005 of needle 32030*a*). Such shipping container sensors are operatively coupled (e.g., via wiring or via a wireless connection, such as with RF sensors) to the fire suppression master node 50110. As such, the insertion of a portion of needle 32030*a* (including the delivery end 50005) into the shipping container 24300*a* allows for the fire suppression master node 50110 to expand its available sensory input with which to monitor the interior of the shipping container 24300*a*.

Figure 51:
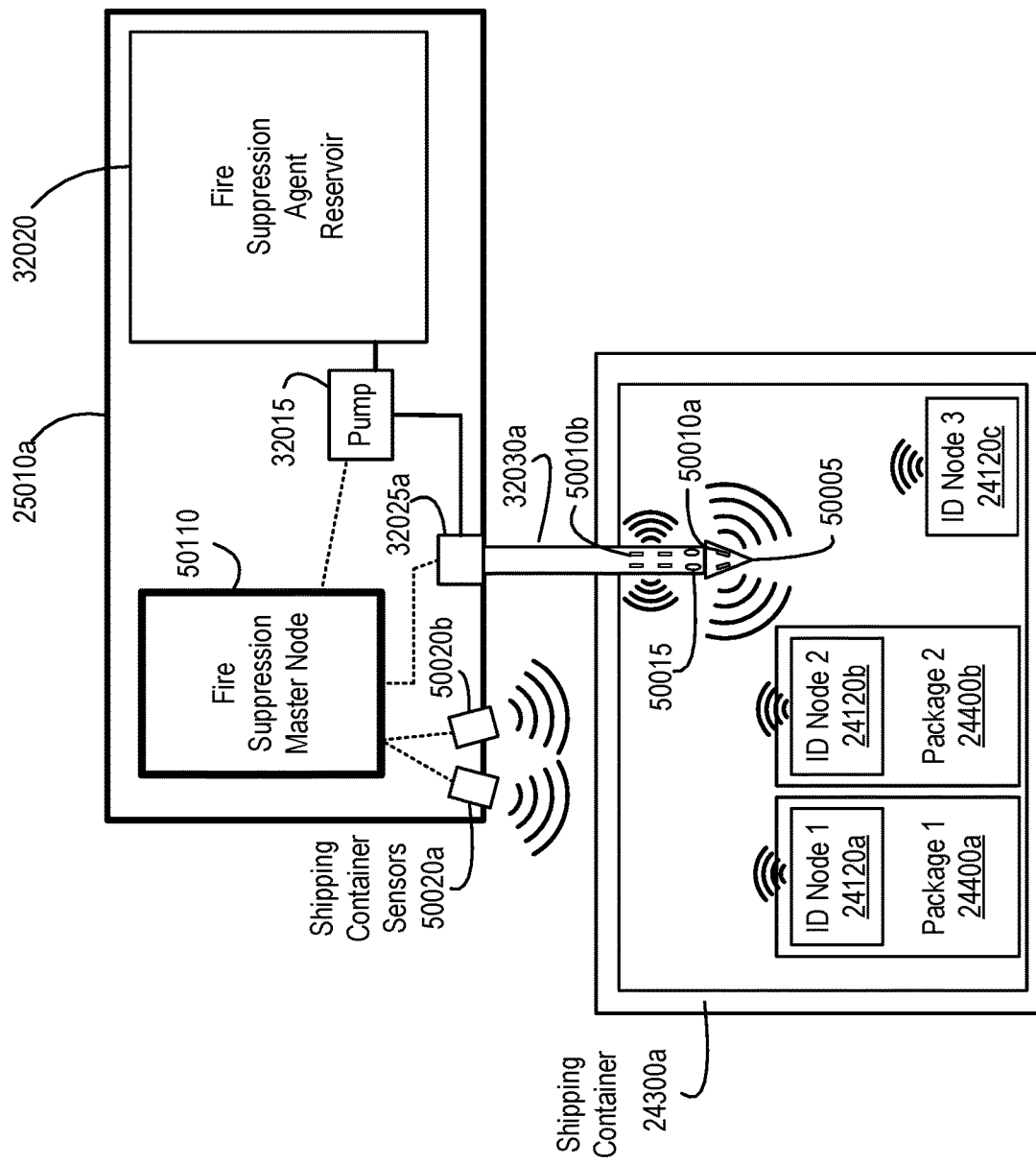
FIG. 51 is a diagram illustrating an exemplary onboard fire suppression system having an integrated master node coupled to exemplary shipping container sensors that may be deployed as part of the fire suppression system to provide for further monitoring and assessment of an environmental anomaly related to a shipping container in accordance with an embodiment of the invention.

FIG. 51 provides further details regarding an embodiment of fire suppression system 25010*a* where more shipping container sensors are deployed that may assist with monitoring and further assessment regarding any environmental anomaly detected relative to shipping container 24300*a* as well as refining how the system 25010*a* may advantageously respond. Referring now to FIG. 51, further details are illustrated regarding the articulating delivery nozzle shown having been inserted into shipping container 24300*a*. The exemplary articulating delivery nozzle (as implemented in this embodiment with actuator 32025*a*, its related needle 32030*a*, and apertures 50015 through which fire suppressant agent 32040 may flow), is equipped with shipping container sensors 50010*a* on the delivery end portion 50005 of needle 32030*a* along with additional shipping container sensors 50010*b* disposed elsewhere on needle 32030*a* that are located below the shipping container's housing (i.e., on a shaft of needle 32030*a* where sensors 50010*b* are exposed to the interior of shipping container 24300*a* once the needle 32030*a* punctures shipping container 24300*a*). Still further shipping container sensors (not shown) may be deployed on needle 32030*a* at one or more points that remain outside of the insertion point into the shipping container 24300*a*, but operate as exemplary shipping container sensors coupled to the fire suppression master node and generating sensor data relevant to the area outside of the insertion point on the shipping container 24300*a*. As noted above, these exemplary shipping container sensors on the articulating delivery nozzle are operatively coupled (e.g., via wiring or via a wireless connection, such as with RF sensors) to the fire suppression master node 50110 so that the fire suppression master node 50110 may gather sensor data from such shipping container sensors and use this sensor data in further assessments and actions to be taken related to a detected environmental anomaly within shipping container 24300*a*.

As shown in FIG. 51, exemplary fire suppression system 25010*a* may include additional shipping container sensors 50020*a*, 50020*b* disposed outside the shipping container 24300*a* being monitored. As shown in FIG. 51, sensors 50020*a*, 50020*b* focus on the exterior of the shipping container 24300*a* so as to generate sensor data indicative of conditions on the exterior surface of shipping container 24300*a*. As such, this further type of sensor on system 25010*a* may monitor the shipping container 24300*a* from the outside in conjunction with, for example, sensor-based ID nodes 1-6 within the shipping container, delivery end disposed sensors 50010*a*, and/or needle shaft disposed sensors 50010*b*. Those skilled in the art will appreciate that such additional shipping container sensors, while disposed on and as part of fire suppression system 25010*a*, provide the fire suppression master node 50110 more diverse sensing capabilities to better assess and respond to any detected environmental anomaly within or related to shipping container 24300a.

In light of the above description of exemplary system 50000, including details on exemplary fire suppression system 25010a, an embodiment of an improved system on a transit vehicle for coordinated mediation action in response to an identified environmental anomaly on a shipping container being transported by the transit vehicle can be described in more detail as follows. This system embodiment generally includes at least multiple wireless ID nodes (e.g., ID nodes 1-6) and a fire suppression system (e.g., fire suppression system 25010a) that may be disposed on a transit vehicle. The wireless ID nodes are disposed at different locations within the shipping container (e.g., ID nodes 1-6 shown in different locations within container 24300a). Each of the ID nodes are at a low level of a hierarchical wireless node network and are respectively configured and operative to broadcast signals over a first wireless communication path. In some embodiments, the ID nodes may be implemented as sensor-based wireless ID nodes (e.g., similar to that explained above with ID node 120a in FIG. 3, as wells as each of ID nodes 1-6 that may have one or more sensors). Each of such ID nodes may generally include an ID node processor, ID node memory, at least one environmental sensor, and a wireless radio transceiver. The ID node memory is coupled to the ID node processor, and maintains at least an ID node monitoring program code that provide programmatic functionality for the sensor-based ID node when executed by the ID node processor. The environmental sensor (such as a temperature sensor, a chemical sensor, a pressure sensor, and the like) is configured to generate sensor data related to an environmental condition proximate the respective wireless ID node. The ID node's wireless radio transceiver is coupled to the ID node processing unit and, for example, is configured to access the sensor data generated by the at least one environmental sensor and broadcast the sensor data in response to a report command from the ID node processor when the ID node processing unit executes the ID node monitoring program code.

The system's fire suppression system (e.g., exemplary fire suppression system 25010a) generally includes at least a fire suppressant material reservoir (e.g., chamber 32020), a fire suppressant material pump (e.g., pump 32015), an articulating delivery nozzle (e.g., actuator 32025a and its related articulating needle 32030a), and a wireless transceiver-based controller operating as a master node at a middle level of the hierarchical wireless node network (e.g., fire suppression master node 50110). The fire suppressant material reservoir is a chamber or container that temporarily maintains a fire suppressant material. In some embodiments, such material may be maintained under a storage level of pressure so as to provide initial pressurized force with which the material exits the reservoir chamber (in addition to the or in place of the pump action). The fire suppressant material pump is connected to the fire suppressant material reservoir and responsive to a pump control input to activate pumping the fire suppressant material from the fire suppressant material reservoir. The articulating delivery nozzle is connected to the fire suppressant material pump that receives the pumped fire suppressant material and deploys from a retracted or default position (e.g., as shown in FIG. 50A) to an extended position (e.g., as shown in FIGS. 50B and 50C) to deliver the fire suppressant material to the shipping container. The wireless transceiver-based controller on the fire suppression system is implemented and operates as a master node (e.g., fire suppression master node 50110, which is an implementation of exemplary master node 110) at a middle level of the hierarchical wireless node network. The fire suppression system's master node is operative to generate the pump control input and cause the articulating delivery nozzle to deploy and deliver the fire suppressant material to the shipping container. Additionally, the master node of the fire suppression system is further configured to operate as a primary monitor for the environmental anomaly by being operative to: (a) wirelessly monitor the signals being broadcast from the ID nodes; (b) responsively identify the environmental anomaly based upon the monitored signals broadcast from the ID nodes; (c) generate a layered alert notification related to the environmental anomaly for the shipping container in response to identifying the environmental anomaly for the shipping container (where the layered alert notification identifies a targeted mediation action and establishes a mediation response priority); and (d) initiate a mediation response by the fire suppression system related to the targeted mediation action and the mediation response priority.

In one embodiment, the monitored signals from the ID node may not necessarily include sensor data. As such, wirelessly monitoring the signals being broadcast from the ID nodes; (b) responsively identifying the environmental anomaly based upon the monitored signals broadcast from the ID nodes by the master node may be based upon missing ID nodes that appear to no longer be broadcasting. For example, the system's fire suppression master node may be further operative to responsively identify the environmental anomaly based upon the monitored signals broadcast from the ID nodes by being operative to identity of the environmental anomaly for the shipping container when the signals broadcast from the ID nodes as wirelessly monitored by the master node indicate at least a threshold number of the wireless ID nodes are in a state of ceased broadcasting. Once a threshold number of ID nodes are identified as no longer broadcasting, the master node in the fire suppression system may identify that an environmental anomaly exists and take further steps to respond as noted above and below in further examples and embodiments.

In another exemplary embodiment, when the system's ID nodes are implemented as sensor-based ID nodes where each broadcasts sensor data as part of the signals broadcast over the first wireless communication path, the system's master node of the fire suppression system may be programmatically configured to initiate the mediation response as part of (d) as a stepped mediation response that involves initiating a first stage response that further assesses the identified environmental anomaly using the sensor data from at least one or more of the wireless ID nodes, and initiating a second stage response that causes deployment of the fire suppressant material to the shipping container based upon and in response to the further assessment of the identified environmental anomaly in the first stage response. In more detail, the master node of the fire suppression system may be programmatically configured to initiate the first stage response by being configured and operative to detect sensor data from the monitored signals being broadcasted from the wireless sensor-based ID nodes; refine the identity of the environmental anomaly for the shipping container when the detected sensor data does not include the sensor data from at least a threshold number of the wireless sensor-based ID nodes, and further refine the identity of the environmental anomaly for the shipping container when the detected sensor data indicates an environmental condition that exceeds an environmental threshold.

In another example, the fire suppression system may include shipping container sensors (e.g., sensors 50010, 50010a, 50010b) coupled to the master node. Such shipping container sensors provide sensor data to the fire suppression master node about the shipping container. As such, the master node of the fire suppression system may be programmatically configured to be further operative to (d) initiate the mediation response as a stepped mediation response by being operative to (1) initiate a first stage response that further assesses the identified environmental anomaly using at least one or more of the shipping container sensors, and (2) initiate a second stage response that causes deployment of the fire suppressant material to the shipping container based upon and in response to the further assessment of the identified environmental anomaly in (1). In more detail, initiating the first stage response may have the fire suppression master node being configured and operative to detect sensor data from the shipping container sensors (when the shipping container sensors, such as sensors 50020a, 50020b, are disposed outside the shipping container and focus on the exterior of the shipping container); and refine the identity of the environmental anomaly for the shipping container when the detected sensor data indicates an environmental condition that exceeds an environmental threshold.

In another embodiment, at least one or more of the shipping container sensors may be disposed on the articulating delivery nozzle (e.g., sensor 50010a or sensor 50010b) so that when then the articulating delivery nozzle is disposed within the shipping container, those shipping container sensors are exposed to an interior of the shipping container. As such, n the master node of the fire suppression system may be programmatically configured to initiate the first stage response by detecting sensor data from the at least one or more of the shipping container sensors, and refining the identity of the environmental anomaly for the shipping container when the detected sensor data indicates an environmental condition that exceeds an environmental threshold. The detected sensor data from such shipping container sensors may, for example, include a detected temperature, a detected radiation level, or a detected chemical (such as CO or $CO_2$ disposed within the shipping container, a chemical indicative of an explosive within the shipping container, or a indicative of a fire within the shipping container).

In a more detailed embodiment, the shipping container sensors may be disposed on a delivery end of the articulating delivery nozzle (such as sensor 50010 on delivery end 50005 of needle 32030a). In such an embodiment, when then the articulating delivery nozzle is deployed with the delivery end puncturing and disposed within the shipping container (e.g., as shown in FIG. 50B or 51), the shipping container sensors on the delivery end are exposed to an interior of the shipping container. For example, as shown in FIG. 50B, sensors 50010 are exposed to the interior of shipping container 24300a when the delivery end 50005 of articulating nozzle 32030a has punctured the housing of the shipping container 24300a. Likewise, as shown in FIG. 51, sensors 50010a on delivery end 50005 are exposed to the interior of shipping container 24300a when the delivery end of articulating nozzle 32030a has punctured the housing of the shipping container 24300a.

In another embodiment, another combination of shipping container sensors may be used as part of the system. For example, a first portion of the shipping container sensors (e.g., sensors 50010a, 50010b) in this embodiment may be disposed on the articulating delivery nozzle such that when then the articulating delivery nozzle (e.g., collectively the actuator 32025a that articulates needle 32030a) is deployed within the shipping container, the first portion of the shipping container sensors are exposed to an interior of the shipping container. In this example, a second portion of the shipping container sensors (e.g., sensors 50020a, 50020b) may be disposed outside the shipping container and focusing on the exterior of the shipping container. In this configuration, the system's fire suppression master node may be programmatically configured to initiate the first stage response by being configured and operative to detect sensor data from the first portion of the shipping container sensors and the second portion of the shipping container sensors, and refine the identity of the environmental anomaly for the shipping container when the detected sensor data indicates an environmental condition that exceeds an environmental threshold. In this way, the fire suppression master node may rely upon differently disposed sensors other than the ID node sensors within the shipping container to initiate the first stage response.

In still another embodiment, three types of sensors may be used—namely, sensors in the ID nodes, shipping container sensors exposed to the interior of the shipping container, and shipping container sensors focusing on the outside of the shipping container. For example, each of the system's wireless ID nodes may be implemented as a sensor-based ID node operative to broadcast sensor data as part of the signals broadcast over the first wireless communication path. Additionally, a first portion of the system's shipping container sensors may be disposed on a delivery end of the articulating delivery nozzle such that when then the articulating delivery nozzle is deployed with the delivery end puncturing and disposed within the shipping container, that portion of the shipping container sensors are exposed to an interior of the shipping container. Furthermore, a second portion of the system's shipping container sensors may be disposed outside the shipping container and focusing on the exterior of the shipping container. As such, the system's fire suppression master node may be programmatically configured to initiate the first stage response by being configured and operative to: detect first sensor data from the first portion of the shipping container sensors; detect second sensor data from the second portion of the shipping container sensors; detect third sensor data from the monitored signals being broadcasted from the wireless sensor-based ID nodes; and refine the identity of the environmental anomaly for the shipping container when a collective assessment of the first sensor data, the second sensor data, and the third sensor data indicates an environmental condition that exceeds an environmental threshold.

The system's master node may be further configured to operate as the primary monitor for the environmental anomaly by being further operative to (e) transmit the layered alert notification to a targeted mediation recipient according to the mediation response priority. For example, such a targeted mediation recipient may be an external transceiver on the transit vehicle (e.g., external transceiver 24150) having a display (e.g., a display in a cockpit or logistics support area of a transit vehicle 24200, such as display 40015) used by an operator of the transit vehicle that can alter movement of the transit vehicle or a logistics crew member of the transit vehicle that can inspect the shipping container.

The system's master node, in another example embodiment, may be further programmatically configured to identify the targeted mediation action based at least upon how many of the wireless ID nodes were not detected, and if that number of undetected wireless ID nodes was above a threshold number of the wireless ID nodes. Having the current number of undetected wireless ID nodes (i.e., those ID nodes no longer broadcasting signals and in a state of ceased broadcasting) being above such a threshold may allow the fire suppression master node to identify a particular targeted mediation action (e.g., automatically and immediately cause the fire suppression system to dispense the fire suppression agent, rather than cause a prompted mediation response message to be displayed to the operator or crew of the transit vehicle requesting that the shipping container be inspects or that the vehicle change course). In a further example, the targeted mediation action identified by the master node depends upon what is loaded within the shipping container as indicated by shipping information maintained on the master node of the fire suppression system. In another example, the master node may be further programmatically configured to identify the targeted mediation action based upon at least one of (a) how many of the wireless ID nodes were not detected as broadcasting above the threshold number of the wireless sensor-based ID nodes and (b) how much an environmental condition (based on sensor data from the ID nodes) exceeds the environmental threshold. This may also depend upon what is loaded within the shipping container as indicated by shipping information maintained on the master node of the fire suppression system.

In a further example of such a system embodiment, the master node may be further programmatically configured to automatically establish the mediation response priority based upon at least one of (a) how many of the wireless ID nodes were not detected as still broadcasting above the threshold number of the wireless ID nodes and (b) how much the environmental condition exceeds the environmental threshold. For instance, the established mediation response priority may be a high priority level indicating further travel by the transit vehicle is to be at least minimized as part of the mediation response or, for example, an intermediate priority level indicating further travel by the transit vehicle is permissible as part of the mediation response.

In still another example of such a system embodiment, the master node may adjust how the ID nodes broadcast. In one example, the master node may be further operative to wirelessly monitor the signals being broadcast from the ID nodes by being operative to: detect the signals broadcasted by the wireless ID nodes according to a broadcast profile maintained by each of the wireless ID nodes (e.g., broadcast profile information as part of profile data 330 that defines a first messaging rate used to regulate how often the signals are broadcast from an ID node to the master node (where the first messaging rate is higher than a default messaging rate)); and instruct each of the wireless ID nodes to broadcast future signals at a second messaging rate that exceeds the first messaging rate after initiating the mediation response. In more detail, the master node may instruct each of the wireless ID nodes to change from the default messaging rate to the first messaging rate (e.g., an initial messaging rate value correlated to an environmental risk associated with material maintained within the shipping container). Thus, for more volatile or risky materials within a particular shipping container, the master node may have a higher or faster messaging rate than normal so as to keep closer tabs on the material and stay situated to more rapidly and robustly provide an immediate and tailored mediation response to address any detected environmental anomaly.

In another example (where the ID nodes broadcast generated or shared/acquired sensor data), the master node may be further operative to detect the sensor data from the monitored signals being broadcast from the wireless sensor-based ID nodes by being operative to: detect the sensor data broadcasted by the wireless sensor-based ID nodes according to a broadcast profile maintained by each of the wireless sensor-based ID nodes (e.g., broadcast profile information as part of profile data 330 that defines a first messaging rate used to regulate how often the signals are broadcast from an ID node to the master node (where the first messaging rate is higher than a default messaging rate)); and instruct each of the wireless sensor-based ID nodes to broadcast future generated sensor data at a second messaging rate that exceeds the first messaging rate after initiating the mediation response. In more detail, the master node may instruct each of the wireless ID nodes to change from the default messaging rate to the first messaging rate (e.g., an initial messaging rate value correlated to an environmental risk associated with material maintained within the shipping container).

In a further example, the fire suppression master node may be further programmatically configured to operate as a primary monitor for the environmental anomaly by being further operative to receive an altered trigger limit related to the targeted mediation action and initiate the mediation response using the altered trigger limit related to the targeted mediation action. Such a trigger limit may take the form of a limit or threshold used to identify the environmental anomaly when compared to monitored signals broadcast from the ID nodes. Such an altered trigger limit may come from, for example, the external transceiver on the transit vehicle (e.g., as defined by an operator of the transit vehicle using the external transceiver or a logistics crew member of the transit vehicle using the external transceiver or as provided to the external transceiver of the transit vehicle from a remote control center in communication with the external transceiver).

Further still, another embodiment may have the master node being configured to receive a request to initiate a secondary mediation response by the fire suppression system related to the targeted mediation action and the mediation response priority. Such a request may be provided to the master node from the external transceiver in response to the layered alert notification. For example, the master node 50110 in the fire suppression system 25010a may provide an immediate and quick initial mediation response, but after an inspection prompted by the transmitted layered alert notification, the external transceiver 24150 may receive input from a crew member via the display or user input interfaces that responsively sends a request to fire suppression master node 50110 for a secondary mediation response (e.g., additional fire suppressant agent material to be dispensed into shipping container 24300a).

Figure 52:
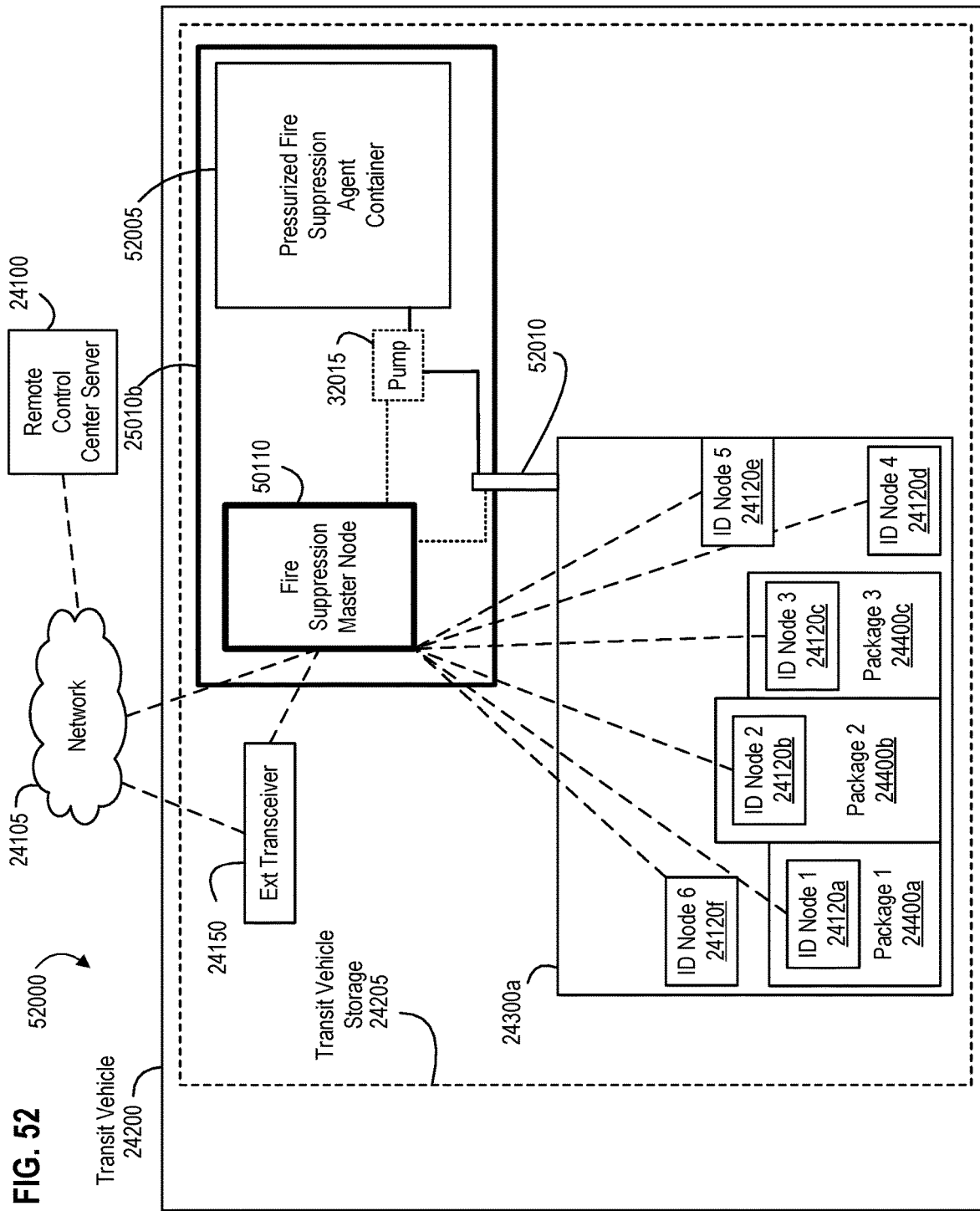
FIG. 52 is a diagram illustrating still another exemplary onboard fire suppression system having a pressurized fire suppression material container and a controlled release nozzle that can be actuated to deliver fire suppression material to a shipping container being monitored by the master node-enabled fire suppression system in accordance with an embodiment of the invention.

While the system embodiment above is explained using an exemplary fire suppression system 25010a, a further system embodiment may use an alternatively configured fire suppression system 25010b as shown in FIG. 52 with similar functionality as the system embodiment described above, but using a pressurized fire suppression material container 52005 and a controlled release nozzle 52010 instead of an articulating delivery nozzle that may puncture the shipping container and have shipping container sensors disposed on that articulating delivery nozzle. As such, similar system functionality as described in the various embodiments above (e.g., such as that described and supported by FIGS. 50A-50C and 51) will also apply to the embodiment shown in FIG. 52.

In more detail and referring now to FIG. 52, exemplary system 52000 has exemplary fire suppression system

25010b disposed on transit vehicle 24200 transporting shipping container 24300a. The fire suppression system 25010b generally includes pressurized fire suppressant material container (e.g., chamber or container 52005), a fire suppressant material pump (e.g., pump 32015), a controlled or actuated release nozzle (e.g., having an electronically controlled release valve to selectively open and close), and a wireless transceiver-based controller operating as a master node at a middle level of the hierarchical wireless node network (e.g., fire suppression master node 50110) that performs the similar primary monitor functions as described above. In more detail, the exemplary release nozzle 52010 on fire suppression system 25010b is operatively coupled to the pressurized fire suppressant material container 52005 so that nozzle 52010 may provide fire suppressant material to shipping container 24300a. Nozzle 52010 may include an electronically activated valve that selectively opens in response to an activation input signal from fire suppression master node 50110 in order to control the flow of the fire suppressant material from the pressurized fire suppressant material container (via pump action should an embodiment of fire suppression system 25010b include pump 32015 or via pressurized release/gravity when no pump is implemented on an embodiment of fire suppression system 25010b) so that the fire suppressant material may be delivered to the shipping container 24300a. As such, those skilled in the art will appreciate that further examples of system 52000 shown in FIG. 52 may substitute pressurized fire suppression material container 52005 with a non-pressurized container for the fire suppression agent.

Enhanced Container for Rapid Environmental Anomaly Response & Fire Suppression

Still further embodiments addressing shipping container environmental anomalies include another type of enhanced shipping container improved to have integrated fire suppression materials and panels as part of the container itself and systems using such enhanced shipping containers. In general, an exemplary embodiment of such an enhanced shipping container may have one or more added or integral fire suppression panels that are part of or attached to one or more internal parts of the container (such as a top portion (e.g., lid, ceiling, cap, roof) or wall). The fire suppression panels have internal exposure, are engineered to melt due to high heat, and quickly release an amount of fire suppression material. This may be considered an initial or first type of mediation response, and may be coordinated with ID node monitoring within the shipping container, so that an external fire suppression system has more time to punch through the container and have a secondary release of additional fire suppression material. Such an enhanced shipping container having one or more fire suppression panels provides a vessel for transporting items, objects, or packages that can, by its structural design, halt or minimize an environmental anomaly (such as a fire) within that transport vessel.

While some embodiments may have a single enhanced shipping container with one or more fire suppression panels designed to distribute the fire suppression material contained or simply that are part of such fire suppression panels, a further embodiment may deploy such enhanced containers in a nested fashion. More specifically, a further embodiment may have a shipping container enhanced with one or more integral fire suppression panels where the container encompasses another enhanced container with further fire suppression panels. Still further embodiments may use multiple layers of fire suppression panels as a composite or collective panel for a particular shipping container so that the distributed release of fire suppression material may be staged as the interior exposed temperature sensitive material of each different layer reaches its respective melting point to release and distribute its respective amount of fire suppression material.

Figure 53A:
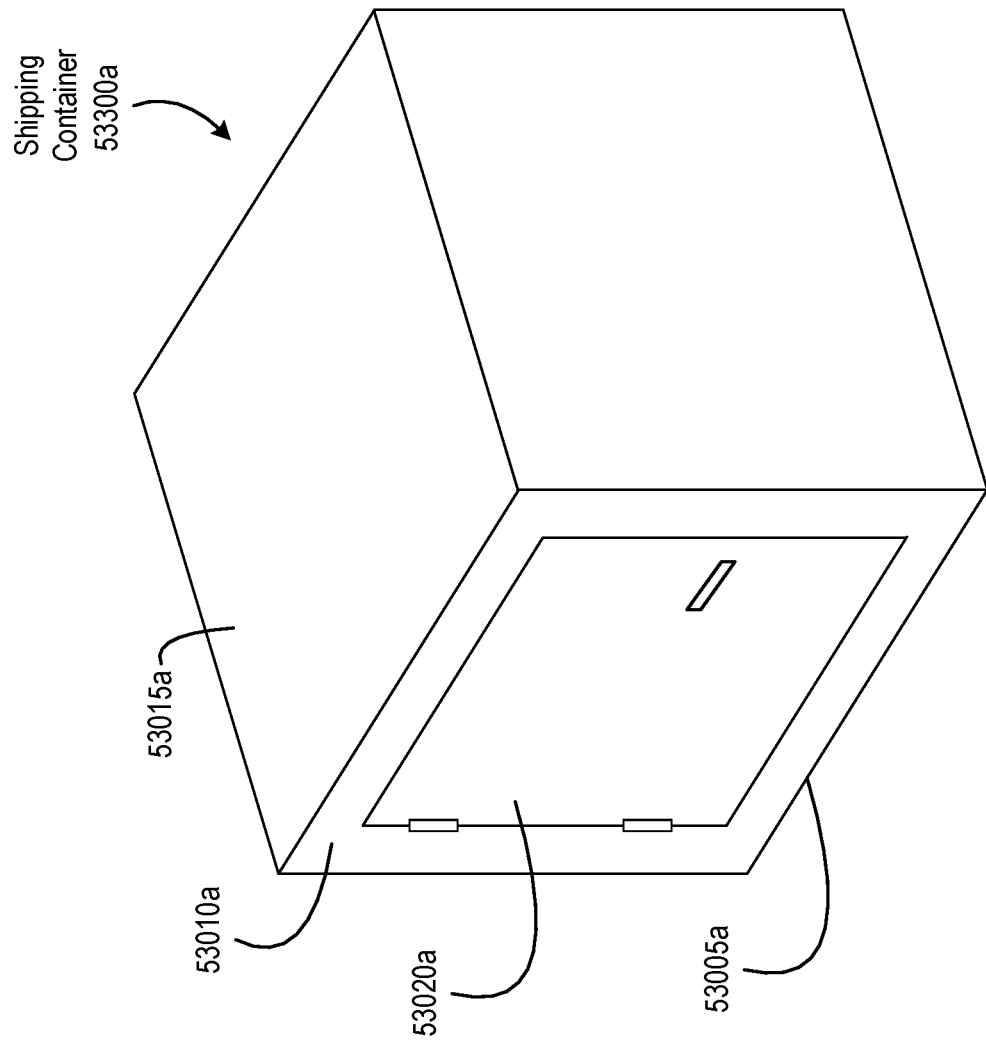
FIGS. 53A-53D are a series of diagrams of exemplary shipping containers that may be deployed in accordance with an embodiment of the invention.

FIGS. 53A-53D are a series of diagrams of exemplary shipping containers that may be deployed in accordance with an embodiment of the invention as having one or more fire suppression panels. Referring now to FIG. 53A, exemplary shipping container 53300a is shown in perspective (similarly disposed as described above with respect to exemplary shipping container 24300a) as generally having a container base portion 53005a, multiple container walls 53010a vertically disposed relative to the base 53005a, a container top portion 53015a, and a resealable access closure 53020a (e.g., a door, hatch, screen, webbing, and the like) on one of the walls 53010a providing selective access to within the container 53300a. The container base portion 53005a may support any packages that are maintained within container 53300a. As shown in FIG. 53A, the walls 53010a generally having one edge coupled to the container base 53005a and another edge coupled to the top or lid 53015a (as well as the other edges being coupled to other walls). In this configuration, the container base 53005a, the container walls 53010a, and the container top 53015a collectively define an interior storage space of container 53300a, which may maintaining packages being shipped (e.g., items, assets, objects whether enclosed in packaging material or not).

In general, an exemplary shipping container's base, walls, and top may be separate structural elements of the container that are attached to each other (e.g., welded, bolted, molded, screwed, glued, or other wised made to be fixed relative to each other), but such elements of the container may also be part of a singular integrated container. For example, the shipping container may have a base, walls, and a top while such structural elements are portions of a singular enclosing structure that defines the interior storage space of the container. In other words, some of the container's base, walls, and a top may be integrated to each other as part of the same enclosing structure (e.g., walls and base, walls to each other, walls to the container top).

Another embodiment of an exemplary shipping container that may be deployed with fire suppression panels may have a base and one or more walls, but not include a top and may not fully enclose to form a sealed unit. As such, this type of shipping container may still have an interior storage space relative to above the base and next to the walls where packages may be maintained as supported by the base while having less than a fully encompassing enclosure structure to seal off the shipping container. Those skilled in the art will appreciate that the wall may have one or more integrated or attached fire suppression panels as described in more detail below.

As shown in FIG. 53A, the resealable access closure 53020a on one of the walls 53010a provides selective access to within the container 53300a. Such a closure may be implemented with a rigid door on hinges with a handle and lock, but other exemplary closures may take the form of a flexible structure (e.g., thick plastic sheet, webbing, reinforced screens, and the like) that may be selectively released to gain access to within the container 53300a and then secured in place to help prevent contents (e.g., packages) from falling out of the container 53300a.

Figure 53B:
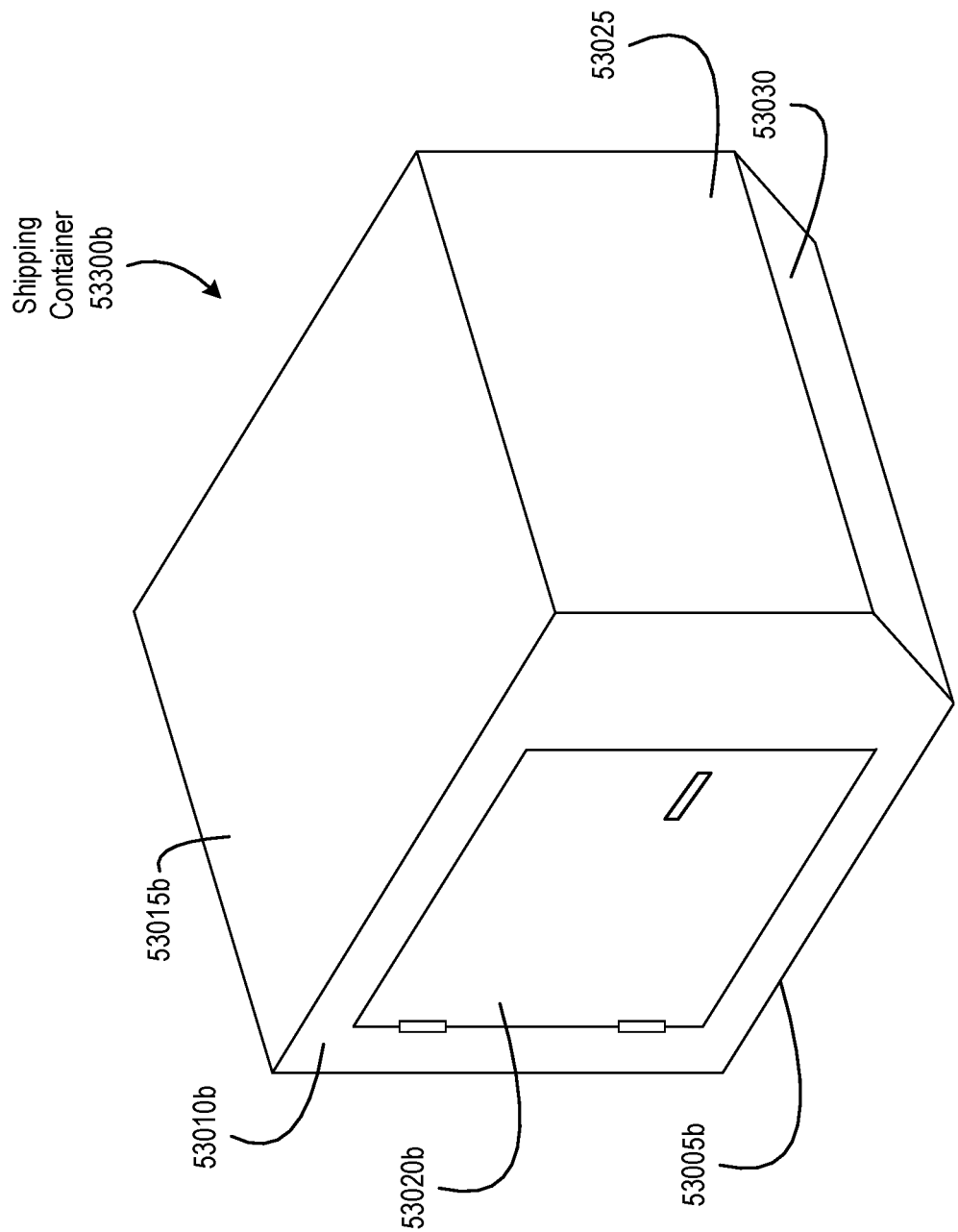

FIG. 53B illustrates an alternative embodiment an exemplary shipping container more in the form of a unit load device (ULD) type of container. Such a ULD container is commonly used to transport items on aircraft as the container's physical configuration is adapted to make better use of available cargo space onboard the aircraft. Referring now to FIG. 53B, exemplary shipping container 53300*b* is illustrated with similar features that that shown for shipping container 53300*a*, but with a modified wall that includes a vertical top wall portion 53025 and an angled bottom wall portion 53030. Those skilled in the art will appreciate that the remaining base 53005*b*, walls 53010*b*, top portion 53015*b*, and resealable access closure 53020*b* as shown on exemplary shipping container 53300*b* are similar to the corresponding parts of shipping container 53300*a* described above.

Figure 53C:
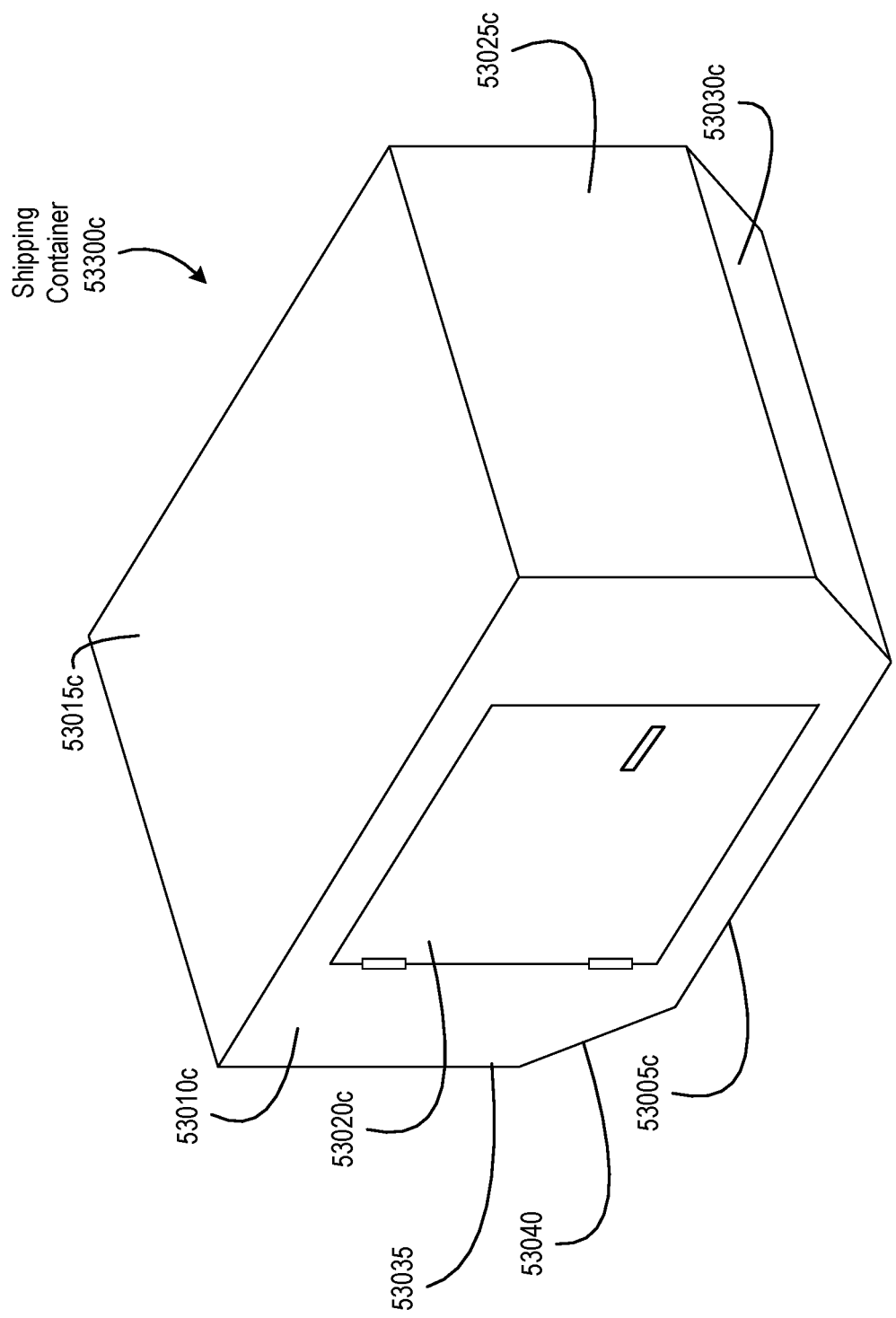

While the exemplary shipping container 53300*b* shown in FIG. 53B is typically targeted for use on wide-body aircraft, where two of such containers may be deployed to span the cargo width of the aircraft (where the each container's modified wall extends towards outward the aircraft fuselage), a further embodiment of an exemplary shipping container 53300*c* is shown in FIG. 53C may be one used in cargo areas on narrower aircraft. As shown in FIG. 53C, exemplary shipping container 53300*c* has two sides with modified walls (e.g., a first modified wall having a vertical top wall portion 53025*c* and an angled bottom wall portion 53030*c* and a second modified wall, on the opposing side of the container, having a similar vertical top wall portion 53035 and a similar angled bottom wall portion 53040. As such, certain walls on exemplary shipping containers (such as containers 53300*b* and 53300*c*) may not be simply vertical walls, but may include multiple wall panels or portions that make up the walls and that function to help enclose the container and define the interior storage space of the container.

Figure 53D:
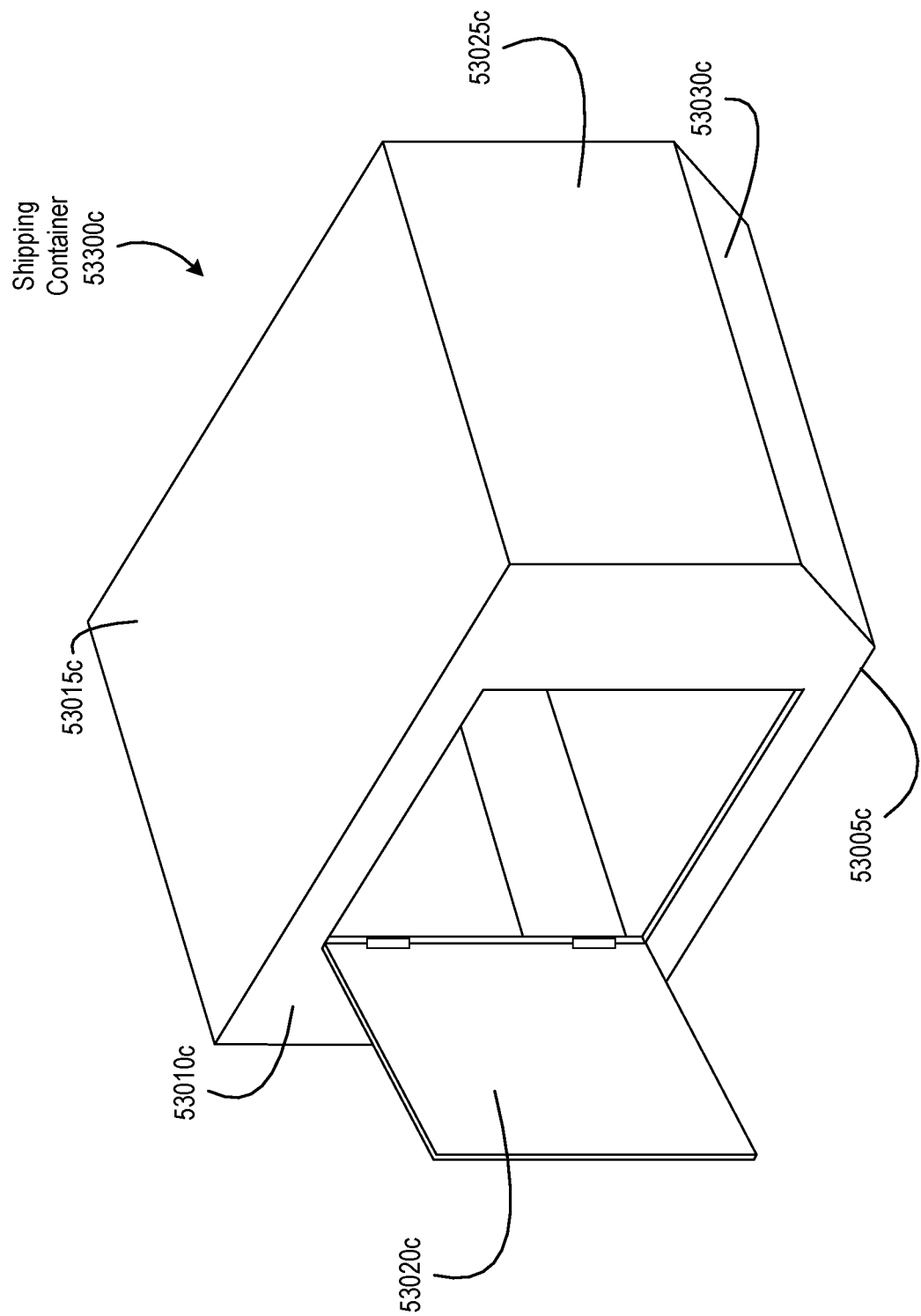

FIG. 53D illustrates the interior storage space on exemplary shipping container 53300*c*. Referring now to FIG. 53D, shipping container 53300*c* has its resealable access closure 53020*c* (e.g., door or hatch) in an open position showing the interior storage space where items may be maintained. Such items, for example, may include packages (e.g., objects and items whether enclosed in packaging materials or not), exemplary wireless ID nodes that may broadcast wireless signals, and command nodes that may monitor those wireless signals and initiate mediation responses when detecting an environmental anomaly based upon such monitoring.

As generally mentioned above, an exemplary shipping container (such as those described in each of FIGS. 53A-53D) may be enhanced and improved with one or more added or integral fire suppression panels that are part of or attached to one or more internal parts of the shipping container. In generally, exemplary fire suppression panels may be located on one or more of the container's top portion (e.g., lid, ceiling, cap, and roof) or any wall (including any resealable access closure that is considered part of a wall). An exemplary fire suppression panel is generally disposed (whether integrated into or attached such parts of the shipping container) so as to have internal exposure to the interior storage area of the shipping container. As composed, an exemplary fire suppression panel is deployed so as to have its interior facing surface designed so as to purposefully melt due to high heat conditions within the interior storage area of the shipping container (due to an environmental anomaly) and so that the panel may release or distribute an amount of fire suppression material maintained behind the interior facing surface as a result.

Figure 54:
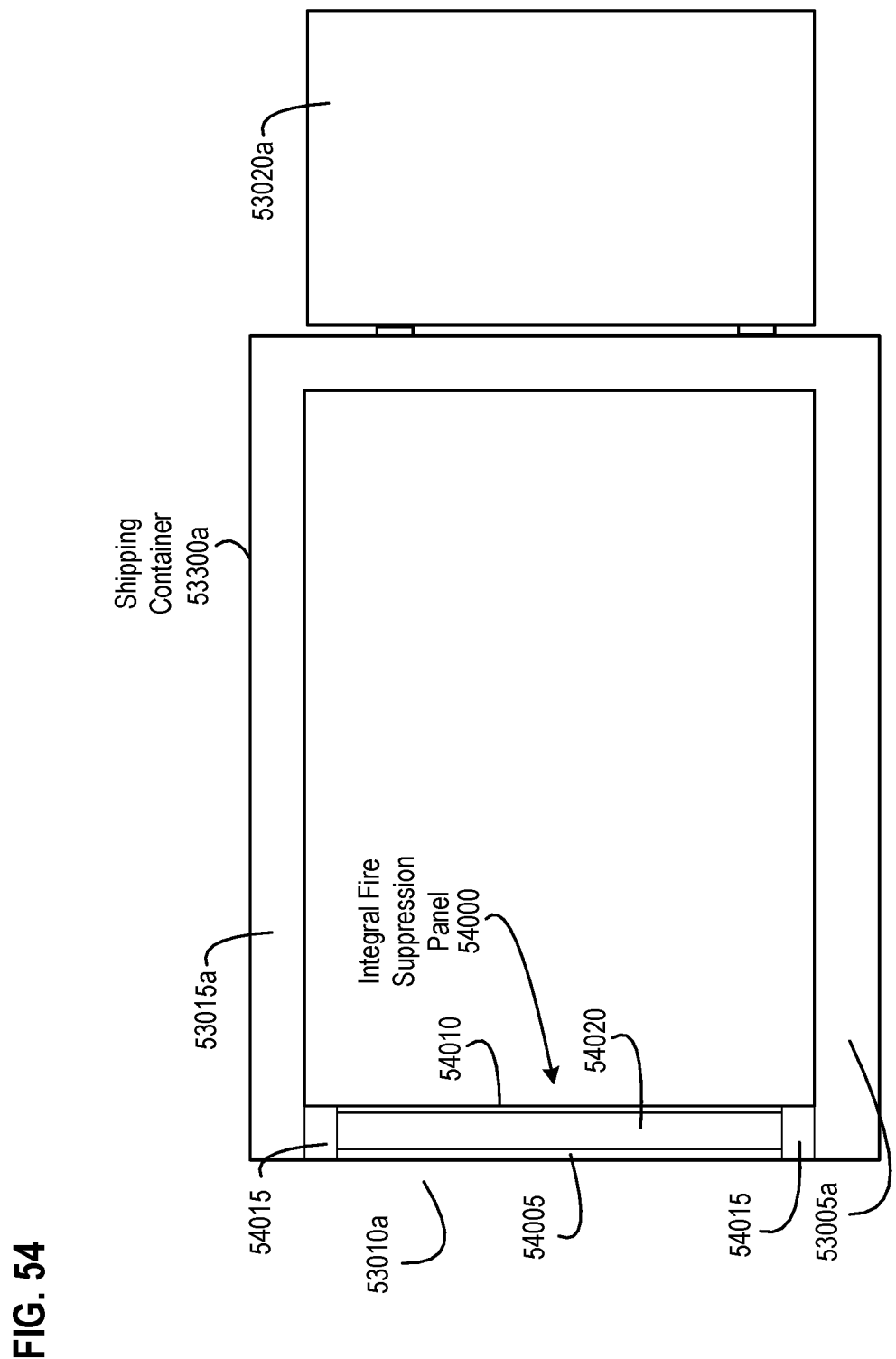
FIG. 54 is a diagram illustrating an exemplary shipping container enhanced with an exemplary fire suppression panel implemented within or as part of one of the container's walls in accordance with an embodiment of the invention.
Figure 55:
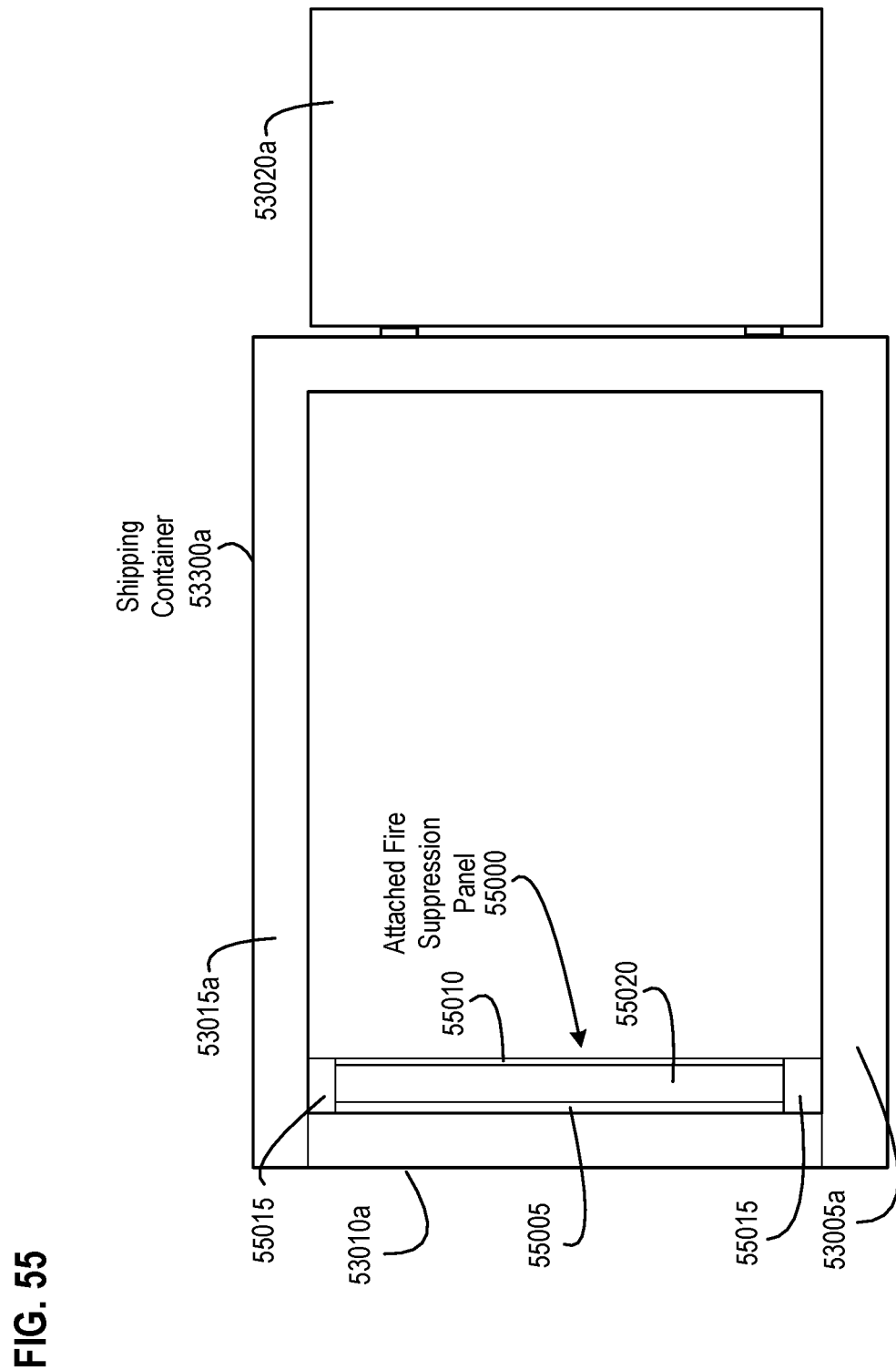
FIG. 55 is a diagram illustrating an exemplary shipping container enhanced with an alternative exemplary fire suppression panel attached to one of the container's walls in accordance with an embodiment of the invention.

FIGS. 54 and 55 provide further details on different embodiments of exemplary fire suppression panels. In particular, FIG. 54 is a diagram illustrating an exemplary shipping container enhanced with an exemplary fire suppression panel implemented as being integrated as part of or within at least part of a shipping container's walls in accordance with an embodiment of the invention. Referring now to FIG. 54, exemplary shipping container 53300*a* is illustrated in cross section showing details of an exemplary fire suppression panel 54000 integrated as part of one of the container's walls 53010*a*. In more detail and as shown in FIG. 54, exemplary fire suppression panel 54000 is shown as having a support sheet 54005 made from a fire resistant material and an interior exposed sheet 54010 made from a temperature sensitive material. Support sheet 54005 provides integral structural support for the wall 53010*a* (or for the top portion 53015*a* if disposed on such a part of the shipping container 53300*a*) in a manner that allows for structural integrity of the container 53300*a* even if the interior exposed sheet 54010 is not present (e.g., has melted, at least in part, as designed to do when exposed to high heat from a fire or explosive event). A sealed boundary 54015 connects the support sheet 54005 and the interior exposed sheet 54010 on peripheral edges of each of the support sheet 54005 and the interior exposed sheet 54010 in a way that the combination of the sealed boundary 54015, the support sheet 54005, and the interior exposed sheet 54010 define a holding cavity within which integrated fire suppressant agent material 54020 may be kept. Such material 54020 (also referred to as fire suppression material) is released or distributed internally when the temperature sensitive material of the interior exposed sheet 54010 has melted or given way in the face of an environmental anomaly (e.g., heat from a fire, explosion, or heat caused by a chemical reaction or condition) within the container 53300*a*. In other words, the temperature sensitive material of the interior exposed sheet 54010 purposefully releases the integrated fire suppressant material 54020 from within the holding cavity when the temperature sensitive material of the interior exposed sheet 54010 is exposed to a threshold temperature (e.g., a melting point temperature for the temperature sensitive material) and, thus, distributes the integrated fire suppressant material 54020 within the holding cavity as that cavity is no longer contained under the conditions of the environmental anomaly. In more detail, the temperature sensitive material of the interior exposed sheet 54010 releases the integrated fire suppressant material 54020 from within the holding cavity and operates as a purposefully designed heat sensitive aperture to the holding cavity maintaining the integrated fire suppressant material 54020. This purposeful release occurs as intended when the temperature sensitive material melts due to a heat environment that exceeds the threshold temperature. The resulting release of the integrated fire suppressant material 54020 is into the interior storage space and may be released onto at least a portion of the packages maintained within the container 53300*a*.

While FIG. 54 illustrates exemplary sealed boundary 54015 (e.g., a sealed edge or frame for panel 54000) as a separate structure from the wall 53010*a*, those skilled in the art will appreciate that sealed boundary 54015 may be implemented to include part of the wall (or top portion) where that part of the container abuts each of support sheet 54005 and interior exposed sheet 54010 on their respective peripheral edges and that part of the container works with support sheet 54005 and interior exposed sheet 54010 to seal and contain the integrated fire suppressant agent material 54020. Furthermore, exemplary integrated fire suppression panel 54000 may be implemented as part of as other walls shown on container 53300*a*, or as part of or as the top portion 53015*a* shown on container 53300*a*. Additionally, an embodiment may deploy multiple integrated fire suppression panels on different parts of container 53300a, such as integrated into cutout or recessed portions of a container's walls 53010a or top/lid/ceiling portion 53015a.

Further embodiments may deploy multiple integrated fire suppression panel layers where each layer has a temperature sensitive sheet that is internally exposed. The outer most layer may include a support sheet, but each of the other layers moving inward may essentially include layers of fire suppressant agent material and temperature sensitive interior exposed sheets where each layer may have a common designed temperature melting point or, alternatively, have the interior exposed sheet of each successive layer having different temperature melting points so as to further stage the release of the layers of fire suppressant agent material.

Those skilled in the art will appreciate the while an integrated fire suppression panel, such as panel 54000, may take the form of a larger panel of the interior exposed temperature sensitive sheet, further embodiments may deploy the panel as having the interior exposed sheet made from similar material as that of the outer support sheet, but with one or more apertures forming essentially one or more release points with temperature sensitive layers disposed within the apertures. When the temperature sensitive layer disposed within the apertures are exposed to their designed melting point, the fire suppressant material contained behind such temperature sensitive layers may be release through the apertures (e.g., a pressurized release of the fire suppressant material through multiple different apertures on the internal side of the fire suppressant panel).

FIG. 55 is a diagram illustrating an exemplary shipping container enhanced with an alternative exemplary fire suppression panel 55000 attached to one of the container's walls 53010a in accordance with an embodiment of the invention. Referring now to FIG. 55, a cross sectional view of a similar exemplary fire suppression panel 55000 that may be separate from the wall 53010a or top/ceiling portion 53015a of container 53300a, but attached to any of the interior surfaces of the walls or ceiling to provide an additional fire suppression measure. As shown in FIG. 55, exemplary attached fire suppression panel 55000 is similarly composed as panel 54000 in that is includes a support sheet 55005 made from a fire resistant material (where the support sheet is attached in this embodiment to the interior surface of wall 53010a), an interior exposed sheet 55010 made from a temperature sensitive material as described above, and a sealed boundary 55015 connecting the support sheet 55005 and the interior exposed sheet 55010 on peripheral edges of each of the support sheet 55005 and the interior exposed sheet 55010 (where the combination of the sealed boundary 55015, the support sheet 55005, and the interior exposed sheet 55010 defines a holding cavity for temporarily maintaining integrated fire suppression material 55020 that occupies the holding cavity within the fire suppression panel 55000). Similar to that described above for exemplary integrated fire suppression panel 54000, the temperature sensitive material of the interior exposed sheet 55010 releases the integrated fire suppressant material 55020 within the holding cavity when the temperature sensitive material of the interior exposed sheet 55010 is exposed to a threshold temperature (such as that generated from an environmental anomaly, e.g., a fire, an explosion, a chemical leak, and the like). In more detail, the temperature sensitive material of the interior exposed sheet 55010 of the attached fire suppression panel 55000 may release and distribute the integrated fire suppressant material 55020 held within the holding cavity when the temperature sensitive material melts when exposed to the threshold temperature or when the temperature sensitive material releases the integrated fire suppressant material in response to a breakdown of the temperature sensitive material due to a heat environment that exceeds the threshold temperature. Such a designed release of the integrated fire suppression material 55020 into the interior storage space of container 53300a may be onto at least a portion of the packages near the fire suppression panel depending on what has been loaded within the container 53300a and where such packages are within the container.

Further examples may have the integrated fire suppressant material 55020 maintained within the holding cavity under pressure so that as any of the temperature sensitive material of the interior exposed sheet 55010 melts or gives way as it is designed to do, the pressurized fire suppressant material 55020 is expelled from the holding cavity at that point for enhanced distribution onto at least a portion of the packages near the fire suppression panel.

A further example may have the interior exposed sheet 55010 made as having apertures in the sheet and where the only temperature sensitive material in sheet 55010 is disposed within such apertures (e.g., temperature sensitive plugs in each of a series of distributed apertures at different locations on the interior exposed sheet 55010). In this way, an embodiment of fire suppression panel 55000 may hold fire suppressant material 55020 under pressure between support sheet 55005 and the aperture laden interior exposed sheet 55010 where each aperture is temporarily plugged with temperature sensitive material that may purposefully give way at a predetermined pressure to release the fire suppressant material 55020 while enhancing the structural support of the panel (given the entire interior exposed sheet would not give way in this embodiment).

While only one attached fire suppressant panel 55000 is shown in FIG. 55, further embodiments may deploy multiple attached fire suppression panels disposed on different parts of container 53300a, such as fixed to or attached to one or more locations on the container's walls 53010a or top/lid/ceiling portion 53015a. In still further embodiments, the attached fire suppressant panel or panels maybe fixed to or removably mounted within cutout or recessed portions of the container's walls 53010a or top/lid/ceiling portion 53015a so as to provide replaceable panels that may be dynamically staged and placed into different targeted parts of the container depending on the character and nature of what may be transported within the container and where such material (e.g., packages with such material) is loaded within the container.

Figure 56A:
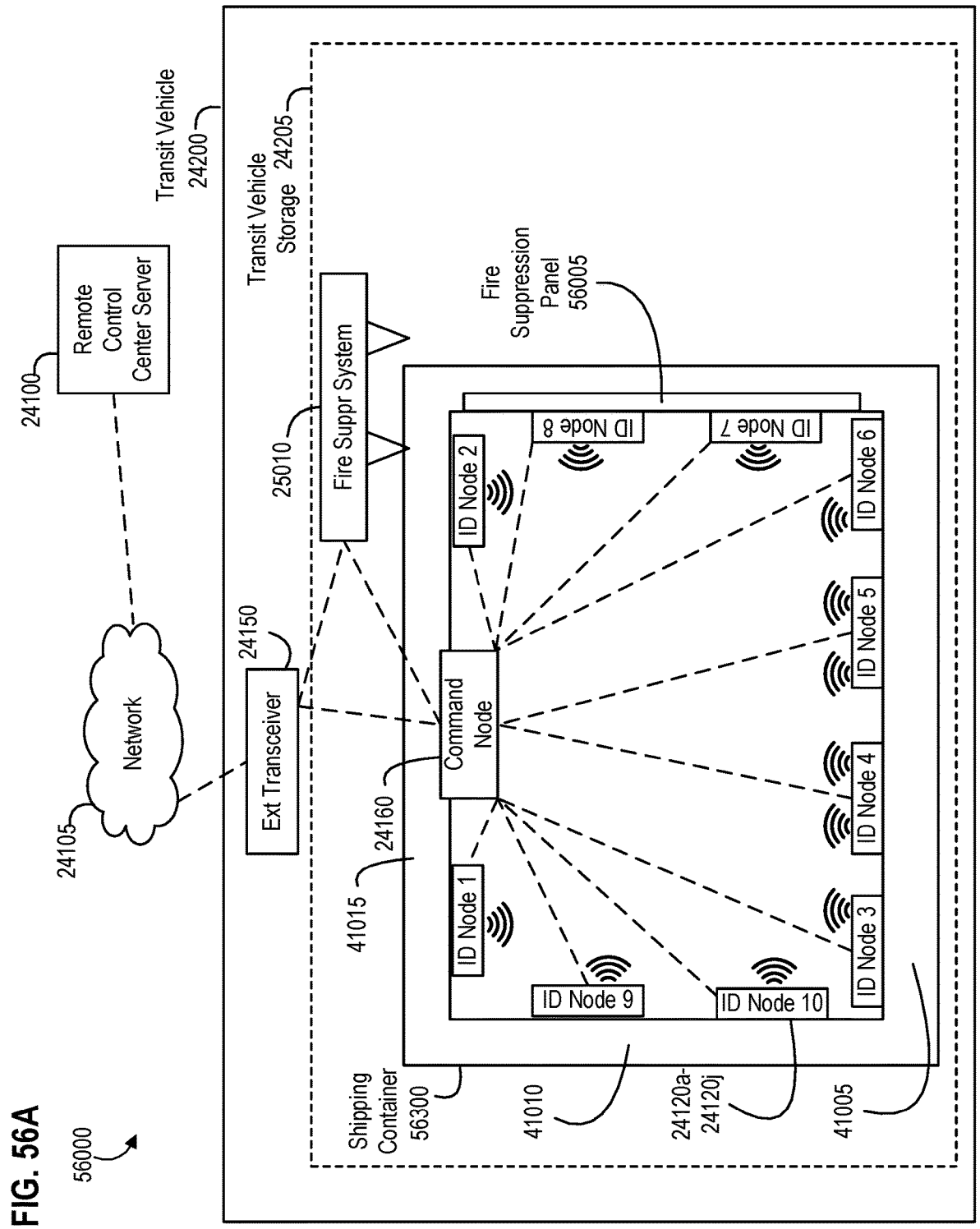
Figure 56B:
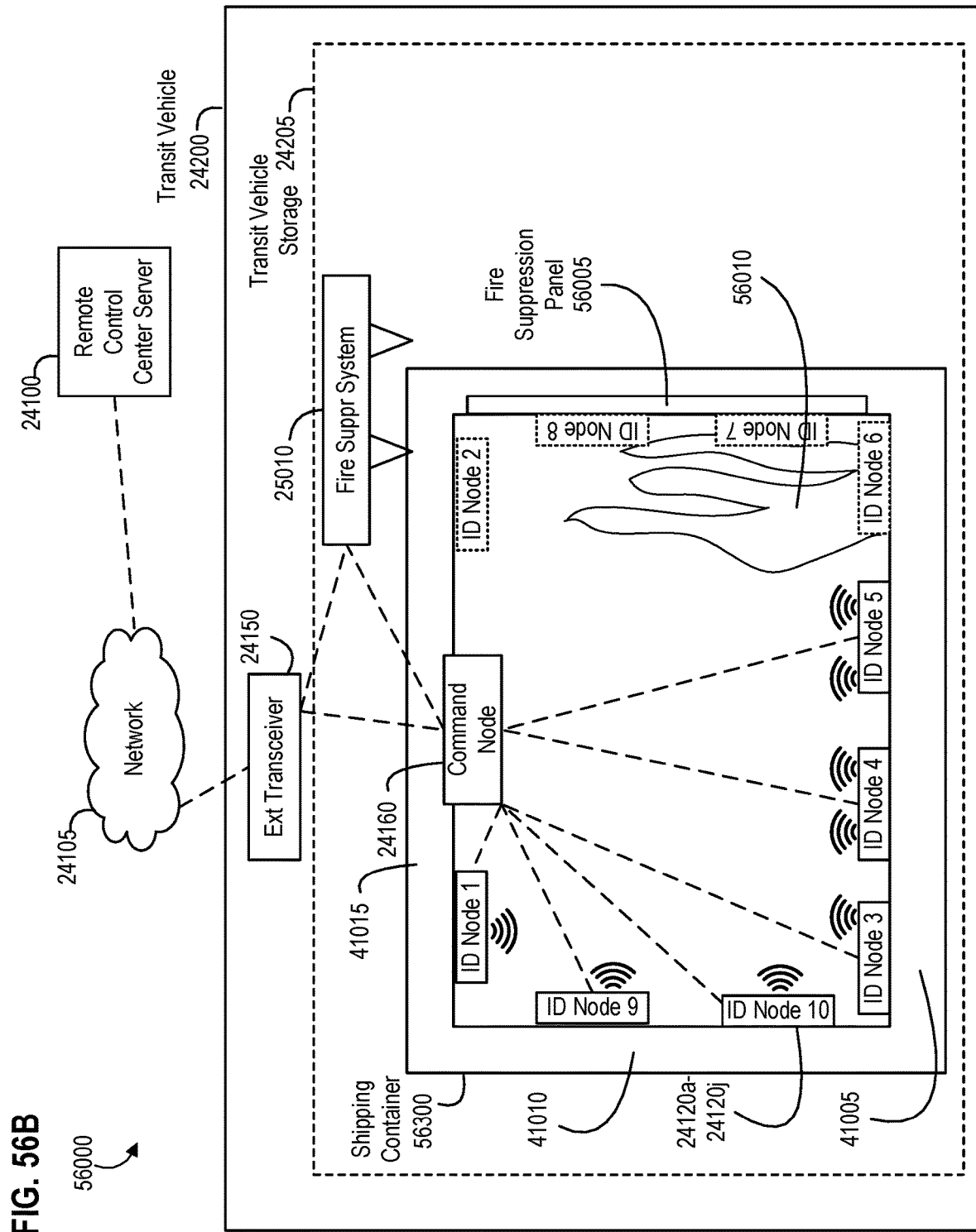

Enhanced shipping containers deployed with either integrated or attached fire suppression panels (such as panels 54000 and 55000) may be incorporated into systems that use a network of wireless nodes (such as ID nodes and command nodes) to detect an environmental anomaly related to the shipping container and respond with multiple mediation responses. FIGS. 56A-56D are a series of diagrams illustrating details of and operations involving an enhanced shipping container having at least one fire suppression panel and as used in an improved system for coordinated mediation action in response to an identified environmental anomaly related to the shipping container in accordance with an embodiment of the invention. Referring now to FIG. 56A, system 56000 is illustrated with similar components as shown in FIG. 44. However, shipping container 24300a shown in FIG. 44 is replaced with exemplary enhanced shipping container 56300 shown in FIGS. 56A-56D as part of system 56000. In more detail, exemplary shipping container 56300 is shown having a container base portion 41005 that may support packages loaded within container 56300, and an enclosing structure coupled to the container base portion (e.g., walls 41010 and top portion 41015). Such enclosing structure and the container base portion 41005 define an interior storage space for maintaining any packages loaded within container 56300.

Notably, at least a part of the enclosing structure includes a fire suppression panel 56005 disposed to the interior storage space of the container. The fire suppression panel 56005 as noted above, may be integrated as part of the enclosing structure (e.g., one of the walls 41010) or simply attached to the interior of the enclosing structure (e.g., attached to a recessed area on one of the walls 41010). As disposed relative to the enclosing structure of container 56300, fire suppression panel 56005 having temperature sensitive material on an interior exposed surface of the fire suppression panel (e.g., an interior exposed sheet as described above relative to exemplary panels 55000, 56000). The fire suppression panel 56005 internally contains integrated fire suppression material (such as material 54020, 55020) next to the temperature sensitive material on the interior exposed surface. As such, the temperature sensitive material on the interior exposed surface of panel 56005 will fail to contain the integrated fire suppressant material within the fire suppression panel 56005 when the temperature sensitive material is exposed to a threshold temperature (e.g., heat that exceeds the threshold temperature from a fire within the container 56300, from an explosion within the container 56300, or from a chemical condition or reaction that generates such heat within the container 56300).

Exemplary shipping container 56300 shown in FIG. 56A also includes multiple wireless sensor-based ID nodes 1-10 (also referenced as 24120a-24120j, respectively) disposed at different locations within the enhanced shipping container 56300 and a command node 24160 mounted to the shipping container 56300 (e.g., fixed or removably attached to the ceiling within shipping container 56300). ID nodes 1-2 are disposed along the ceiling on the top 41015 of container 56300, ID nodes 3-6 are disposed along the base 41005, and ID nodes 7-10 are disposed along the walls 41010 of container 56300. While not shown as being associated with, packed into, affixed to, or traveling with any particular package, those skilled in the art will appreciate in light of the description above that embodiments may deploy particular ID nodes on or integral to parts of the container, any package with in the container, or freely disposed within the container without being fixed to, attached, or associated with any particular package or particular part of the container. Each of ID nodes 1-10 are at a low level of a hierarchical wireless node network, where command node 24160 is disposed at a middle level of such a network (and where further elements, such as external transceiver 24150 and remote server 24100 are disposed higher within the network) and each of the ID nodes are respectively configured and operative to broadcast signals that may be received by command node 24160.

Similar to that described above, command node 24160 has at least a processor, a memory coupled to the processor, and a dual transceiver communication interface that is configured to communicate with ID nodes 1-10 as well as communicate with external transceiver 24150 and onboard fire suppression system 25010. As deployed as part of system 56000, the command node's memory includes a command node container management program code (e.g., code 26425). In this particular embodiment as illustrated in FIG. 56A-56D, the processor on command node 24160 executes the command node container management program code, which then programmatically configures the processor on command node 24160 to be specially operative to detect the sensor data broadcasted from the sensor-based ID nodes 1-10 using one of the communication interfaces on the command node 24160; responsively identify the environmental anomaly for the shipping container 56300 (e.g., a fire 56010 within container 56300 shown in FIG. 56B) when the detected sensor data indicates release of the integrated fire suppression material 56020 from the fire suppression panel 56005 as a first level mediation response (as shown in FIG. 56C); generate a layered alert notification related to the environmental anomaly for the shipping container in response to identifying the environmental anomaly for the shipping container (wherein the layered alert notification identifies a targeted mediation recipient, identifies a targeted mediation action, and establishes a mediation response priority; and cause the command node's communication interface to transmit the layered alert notification to the external transceiver 24150 to initiate a secondary mediation response related to the targeted mediation action.

As part of this system embodiment, the command node's processor may be programmatically configured to be operative to also identify the environmental anomaly for the shipping container 56300 when the detected sensor data indicates at least one of (a) when the detected sensor data does not include the sensor data from at least a threshold number of the sensor-based ID nodes; and (b) when the detected sensor data indicates an environmental condition that exceeds an environmental threshold.

Figure 56D:
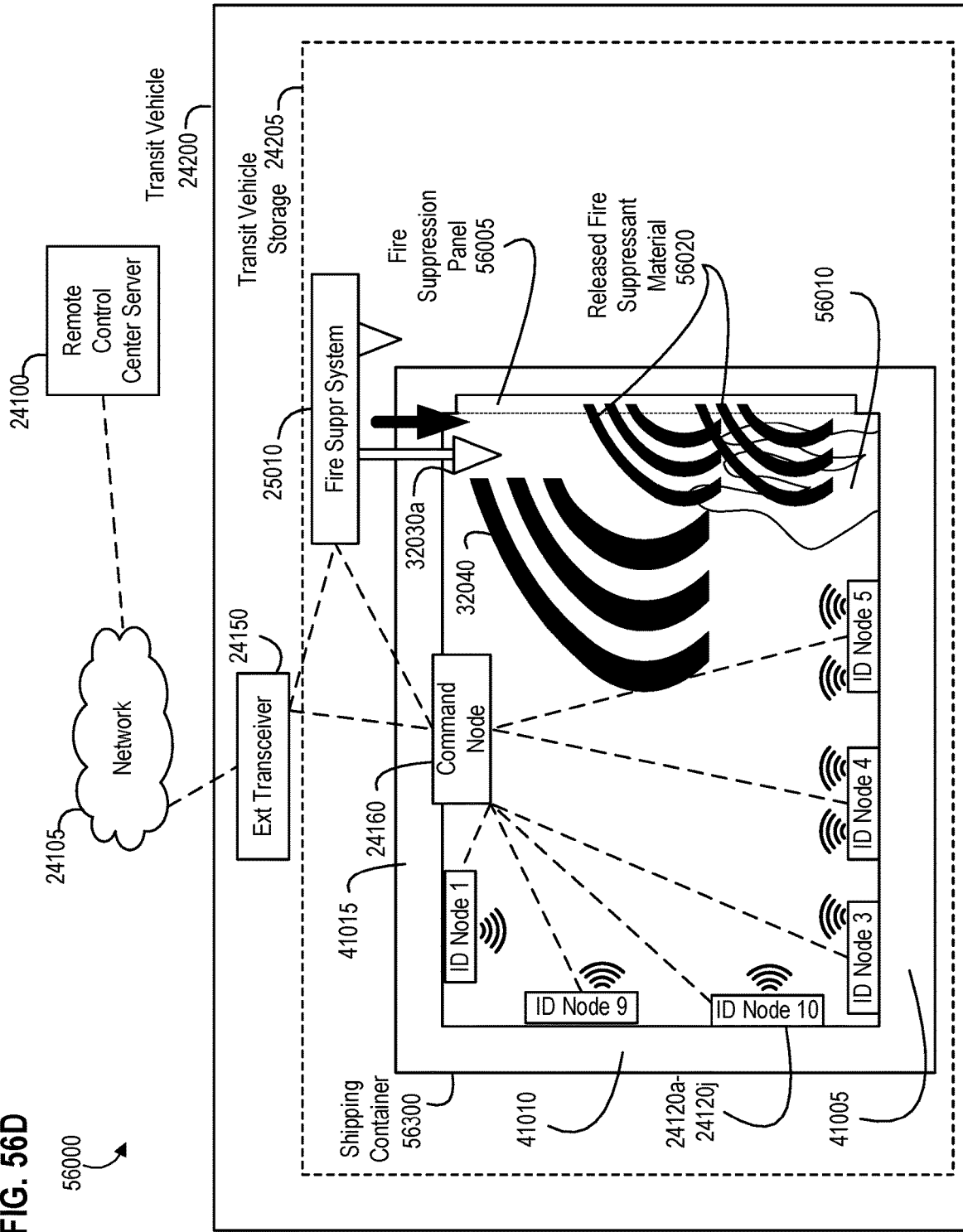

Furthermore, the secondary mediation response may, for example, be implemented as causing the external transceiver 24150 to generate a secondary mediation response notification for an operator of the transit vehicle as the targeted mediation recipient (e.g., a prompt message for such an operator on a display of the external transceiver where such a prompt message requests the operator of the transit vehicle to alter movement of the transit vehicle). In another example, the secondary mediation response may be causing the external transceiver 24150 to generate a secondary mediation response notification for a logistics crew member of the transit vehicle as the targeted mediation recipient (e.g., a prompt message for such a crew member on a display of the external transceiver where such a prompt message requests the logistics crew member to inspect the enhanced shipping container). In still another example, the secondary mediation response may be causing the external transceiver to generate a secondary mediation response notification that activates fire suppression system 25010 within the transit vehicle 24200 and outside the enhanced shipping container 56300. In response, the fire suppression system 25010 operates as the targeted mediation recipient to dispense additional fire suppression material 32040 within the enhanced shipping container as the secondary mediation response related to the targeted mediation action. In another embodiment, the command node itself is operative to directly initiate the secondary mediation response by directly activating fire suppression system 25010, which then responsively punctures container 56300 and injects additional pressurized fire suppressant material 32040 from fire suppression system 25010 as shown in FIG. 56D.

A further extension of such a system embodiment may expressly include the fire suppression system, such as system 25010, as a further element of the system that includes supplemental fire suppressant material 34020; a delivery nozzle 32030a that deploys to deliver the supplemental fire suppressant material to within the enhanced shipping container 56300, and a fire suppressant pump (such as pump 32015) that activates to cause the supplemental fire suppressant material 32040 to flow through the delivery nozzle 32030*a* and into shipping container 56300. As such, this system's command node processor may then be programmatically further operative to cause one of its communication interfaces to transmit the layered alert notification to the external transceiver 24150 to activate the fire suppression system 25010 to dispense the supplemental fire suppression material 32040 as a secondary level mediation response related to the targeted mediation action. Alternatively, this system's command node processor may be programmatically further operative to cause one of its communication interfaces to transmit the layered alert notification directly to the fire suppression system 25010 (without involving external transceiver 24150) to dispense the supplemental fire suppression material 32040 as a secondary level mediation response related to the targeted mediation action.

Node Enhanced Battery, Battery Packs, and Battery Packages

Additional embodiments may provide further improvements to environmental anomaly detection and mediation responses using enhanced sensor-based nodes (such as sensor-based ID nodes) that may be directly incorporated into, disposed as part of, or otherwise associated with a battery (such as a lithium-based or lithium-ion battery), pack of batteries, or battery packaging so as to enable integrated environmental anomaly detection and reporting at that low level of a wireless node network. For example, travel suit cases may have internal batteries that offer a level of convenience to a traveler by allowing the traveler to charge a personal device (e.g., smartphone, laptop, tablet) while that device is secured within the suit case. And while this may be a convenience to the traveler, such a charging situation may create a overheating situation resulting in a type of environmental anomaly unintended by the traveler but potentially catastrophic in the context of occurring while on an aircraft carrying other travelers, crew, and cargo. The ability to use a node-enhanced battery in such a situation allows for advantageous monitoring for environmental anomalies in an advantageous and novel manner (e.g., by a vehicle master node (or aircraft master node) that monitors sensor data from different node-enhanced batteries on board the aircraft and provides alert notifications to flight personnel relative to potential dangers, such as overheating of particular batteries during use on the aircraft or overheating of particular batteries when simply stored on the aircraft).

Exemplary embodiments may have an associated sensor-based ID node being disposed and operative to sense and communicate the battery's charge status and/or temperature at one or more locations of the battery, battery pack, or packaging of such a battery or group of batteries. Such a sensor-based ID node may be associated with the battery (its parts or with multiple batteries) as, for example, an integrated assembly of the sensor-based ID node and the battery (or its parts or with the group of batteries) where the ID node may not be separable from the assembly and may also be powered by the battery it may be monitoring. Another example may have the sensor-based ID node as a separate device (with or without its own power supply), but still being integrated with the battery it is associated with for monitoring purposes. Still another example may have the sensor-based ID node as a removable device with its own power supply and that is externally attached to the battery (its parts or with multiple batteries) to be monitored but in a manner that has the sensor-based ID node as a replaceable or swappable device relative to the battery.

Self-sensing in this manner can advantageously activate the ID node (even if in a low power mode) to cause the generation and transmission of a relevant alert notification that depends on the temperature and/or battery status to intelligently initiate mediation responses. In some embodiments, the battery package may include multiple ID nodes, multiple sensors with a single ID node, or involve a network of a master node (e.g., a command node, such as exemplary command node 24160) and several ID nodes as part of the package depending on the size and type of battery package. Embodiments may have the ID nodes maintain data that identifies the specific associated battery or batteries, as well as the type or characteristic category of such batteries, where such information may be used as part of determining a relevant and appropriate mediation response.

Figure 57:
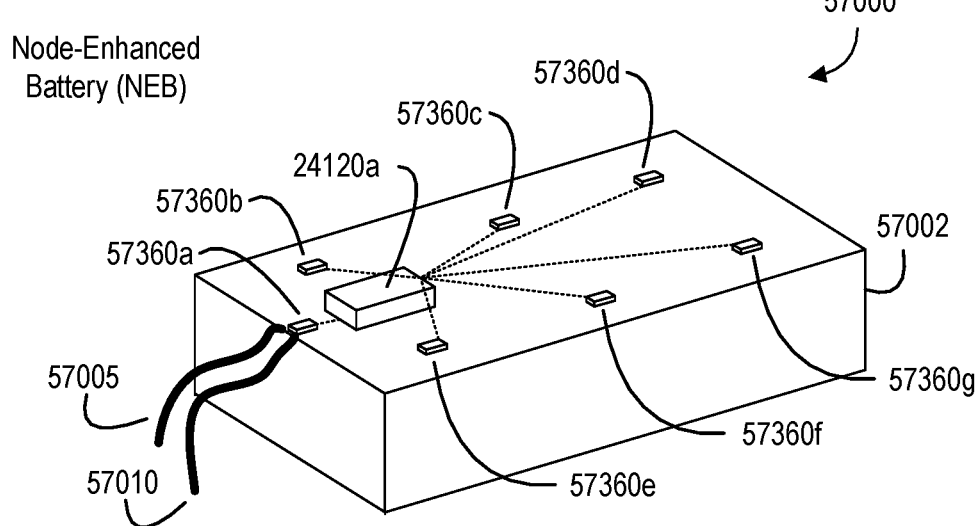
FIG. 57 is a diagram illustrating an exemplary node-enabled battery system having integrated environmental detection and reporting functionalities in accordance with an embodiment of the invention.

FIG. 57 is a diagram illustrating an exemplary node-enabled battery system having integrated environmental detection and reporting functionalities in accordance with an embodiment of the invention. Referring now to FIG. 57, an exemplary node-enhanced battery system 57000 (NEB, also referenced as a node-enabled battery system) is shown having a battery 57002, such as a lithium-ion battery. Those skilled in the art will appreciate that battery 57002 may comprise a housing and multiple battery cells that are commonly coupled to form a power source. In other words, the battery 57002 may have multiple battery packs based upon different battery cells (e.g., lithium battery cells). A terminal part of such a battery 57002 includes battery terminal connections 57005, 57010 through which electricity may be made available to tap into the power source of battery 57002.

Exemplary system 57000 further includes a sensor-based ID node 24120*a* attached to the battery 57002. As shown in FIG. 57, ID node 24120*a* is mounted on the battery 57002, but further implementations may attach ID node 24120*a* in a manner that incorporates the ID node 24120*a* into the physical structure of the battery 57002 (e.g., integrates ID node 24120*a* as part of battery 57002). Exemplary sensor-based ID node 24120*a* (e.g., an implementation of ID node 120*a* explained above and with reference to FIG. 3) includes a node processor, a node memory storage coupled to the node processor, a wireless communication interface coupled to the processor, as well as one or more sensors coupled to the processor. The node memory storage maintains at least a battery monitoring program code and a battery threshold metric value (e.g., as part of the node control and management code 325 stored on memory 320 of ID node 120*a*). The wireless communication interface (e.g., variable power short range communication interface 375) may be a low power communication interface capable of Bluetooth Low Energy formatted communications. The sensor(s) deployed as part of sensor-based ID node 24120*a* is generally operative to sense a battery status condition for the battery 57002. Such a sensor (e.g., sensor 360) may be integrated and deployed with ID node 24120*a*, but may be remotely disposed (e.g., sensors 57360*a*-57360*g*) at different locations on the battery 57002 (e.g., sensor 57360*a* disposed at the terminals 57005, 570010 to sense the charge status condition of the battery 57002; sensors 57360*b*-57360*g* disposed on dispersed and different locations on the housing of the battery 57002). Further embodiments may have the sensor or sensors disposed within battery 57002 to detect a charge status condition or temperature, for example, from within battery 57002.

As part of system 57000, the processor of sensor-based ID node 24120*a* is programmatically configured, when executing the battery monitoring program code, to be operative to receive status data from the sensor (where the status data reflects the battery status condition as sensed by the sensor);

automatically trigger generation of a layered alert notification related to the battery when the received status data is inconsistent with the battery threshold metric value; and cause the wireless communication interface to broadcast the layered alert notification to initiate a mediation response related to the battery status condition for the battery.

In more detail, the battery status condition sensed by the sensor on the sensor-based node may be a charge status condition of the battery (e.g., a voltage level indicative of the charge status of battery 57002). As such, the node processor may be programmatically configured to be operative to automatically trigger generation of the layered alert notification (a) when the battery threshold metric value is a threshold voltage value and (b) when the received status data on the charge status condition of the battery is less than that threshold voltage value.

In another example, the battery status condition sensed by the sensor on the sensor-based node on battery 57002 may be a temperature condition of the battery. As such, the node processor may be programmatically configured to be operative to automatically trigger generation of the layered alert notification (a) when the battery threshold metric value is a threshold temperature value and (b) when the received status data on the temperature condition of the battery exceeds that threshold temperature value.

As noted, exemplary sensor-based ID node 24120a is shown equipped with multiple battery sensors 57360a-57360g disposed on different points of the battery 57002. In this configuration, an embodiment may have the battery status condition sensed by each of the battery sensors being temperature conditions of the battery 57002, where each of the temperature conditions corresponds to the respective different point on (or in) the battery 57002 where the respective battery sensor is disposed. As such, the node processor on ID node 24120a may be programmatically configured to be operative to receive the status data by receiving individual status information from each of the battery sensors as the status data. Furthermore, the node processor may be programmatically configured to be operative to automatically trigger generation of the layered alert notification related to the battery by automatically triggering generation of the layered alert notification related to the battery 57002 when at least one of the received individual status information reflects that at least one of the temperature conditions of the battery exceeds a threshold temperature value for the battery.

In some embodiments, the node processor may be programmatically configured to be operative to receive the status data by receiving individual status information from each of the battery sensors as the status data over a time period. In this situation, the node processor may also be programmatically configured to be operative to automatically trigger generation of the layered alert notification by being further operative to monitor the received individual status information from each of the battery sensors over the time period to identify relative changes in the individual status information over the time period, and automatically trigger generation of the layered alert notification related to the battery when at least one of the identified relative changes in the individual status information over the time period exceeds a time-based relative temperature change threshold for the battery.

As briefly mentioned above, the system's sensor-based ID node 24120a may be activated and "wake" from a low power mode based upon the sensor data. For example, the node processor may be programmatically configured, when executing the battery monitoring program code, to be operative to automatically activate the sensor-based node (such as ID node 24120a shown in FIG. 57) from a low power mode when the received status data is inconsistent with the battery threshold metric value maintained in the sensor-based node memory.

As explained above, the node processor of sensor-based ID node 24120a may programmatically be configured so as to be operative to automatically trigger generation of a layered alert notification related to the battery 57002 when the received status data is inconsistent with the battery threshold metric value. The layered alert notification generated may depend on a number for factors. For example, such a layered alert notification may, for example, be generated based upon a level of inconsistency between the received status data and the battery threshold metric value, based upon how much the charge status condition differs from the threshold voltage value, based upon how much the temperature condition of the battery 57002 exceeds the threshold temperature value, based upon how much at least one of the temperature conditions of the battery exceeds the threshold temperature value for the battery 57002, and/or based upon how many of the battery sensors have their respective battery status condition exceeding the threshold temperature value for the battery.

In another example of system 57000, the layered alert notification may identify battery 57002 so that those elements receiving the layered alert notification will be informed that it is specifically battery 57002 having an inconsistent battery status condition relative to thresholds for that battery. In more detail, the node memory storage on sensor-based ID node 24120a may maintain battery specifier data related to the battery 57002 (e.g., exemplary battery specifier data related to battery 57002 as part of profile data 330 maintained in memory of ID node 24120a). As such, the layered alert notification related to battery 57002 may include an identification of battery 57002 based upon the battery specifier data (e.g., information on a unique identifier for battery 57002, information on a characteristic category of battery 57002 (such as a lithium-ion type of battery)). Such battery specifier data may be pre-programmed into the node memory of ID node 24120a when the ID node is associated with the battery 57002 (e.g., during manufacture, during packaging for transport, and the like). This may be accomplished by having the node processor being further programmatically configured to be operative to receive the battery specifier data over the wireless communication interface and store the battery specifier data within the node memory storage.

Figure 59:
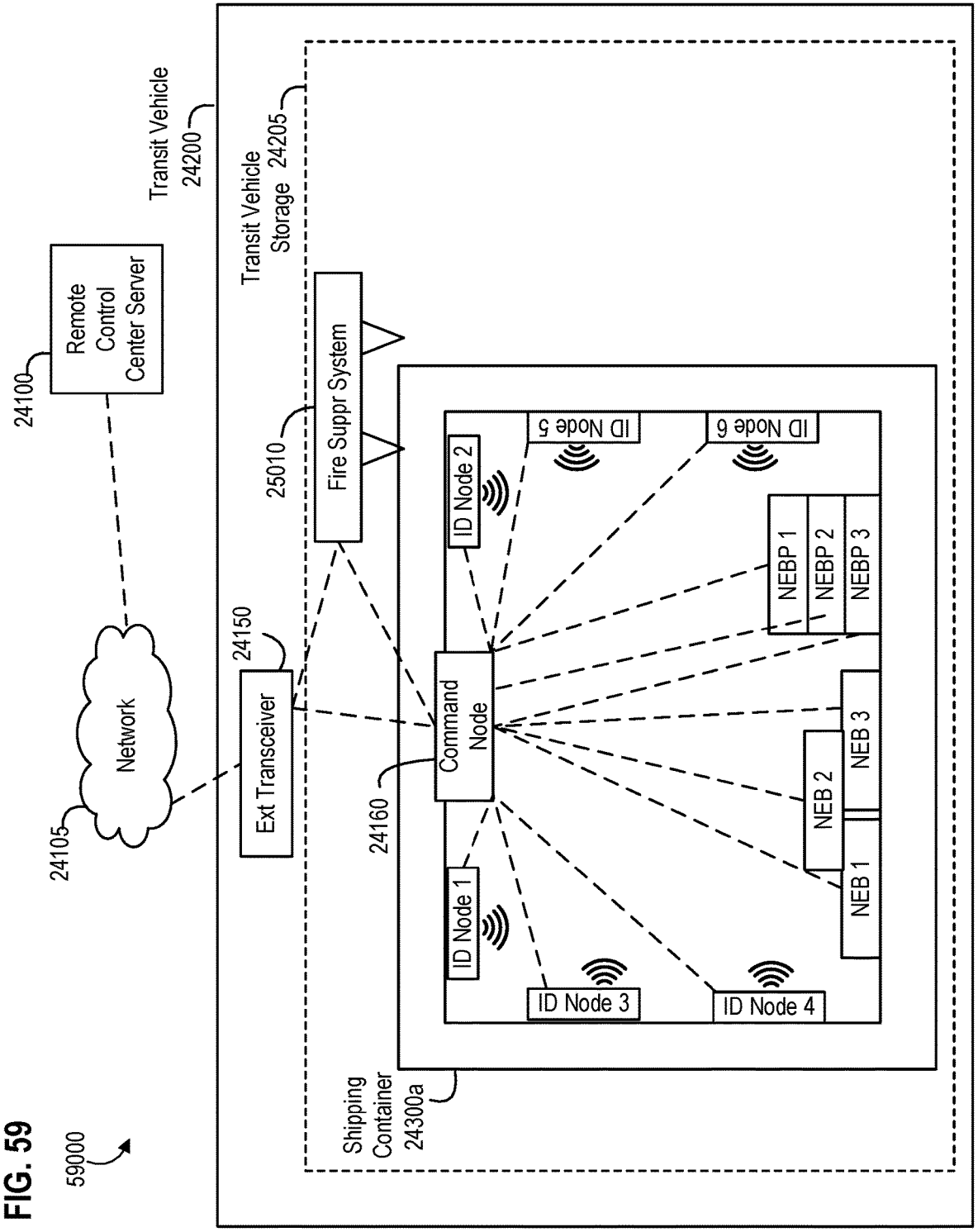
FIG. 59 is a diagram illustrating an exemplary improved system for coordinated mediation action in response to an identified environmental anomaly related to the shipping container transporting at least one node-enabled battery system and at least one node-enabled package system for a battery in accordance with an embodiment of the invention.

As noted above, the node processor of ID node 24120a in system 57000 is operative to cause the wireless communication interface of ID node 24120a to broadcast the layered alert notification to initiate a mediation response related to the battery status condition for battery 57002. Such a mediation response may be a request for intervention in the transport of battery 57002. For example, as shown in FIG. 59, system 59000 is shown with similar components as system 44000 in FIG. 44, but FIG. 59 shows several node-enhanced battery systems (e.g., NEB 1, NEB 2, NEB 3) within shipping container 24300a. In this example, the sensor-based ID node as part of NEB1 may cause its wireless communication interface to broadcast a layered alert notification to initiate a mediation response related to the battery status condition for the battery of NEB 1. Such a mediation response may be a request for intervention in the transport of NEB 1 (notably, the battery within NEB 1). As such, the layered alert notification may be received by command node 24160, which may direct external transceiver 24150 to display a prompt message requesting intervention (e.g., a change in course of transit vehicle 24200 or an inspection be conducted of NEB 1). In another example, the mediation response may be a request for automatic fire suppression intervention for the battery (e.g., where command node 24160 responds to the layered alert notification broadcast from the ID node in NEB1, and directs fire suppression system 25010 to dispense fire suppressant material within shipping container 24300a to as to intervene in response to the notification from NEB 1).

Figure 58:
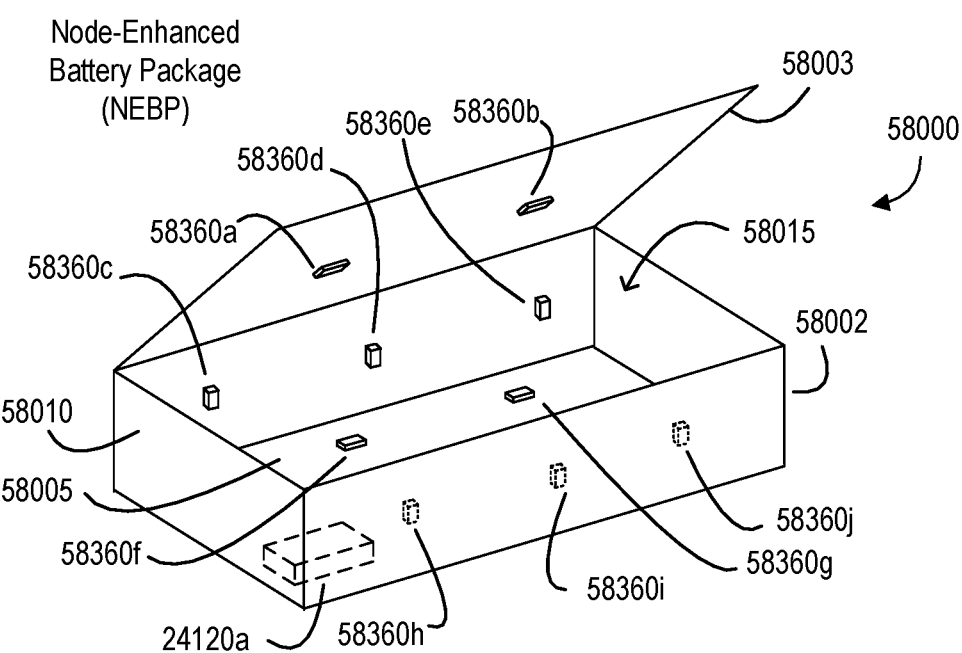
FIG. 58 is a diagram illustrating an exemplary node-enabled package system for a battery having integrated environmental detection and reporting functionalities in accordance with an embodiment of the invention.

FIG. 58 is a diagram illustrating an exemplary node-enabled package system for a battery having integrated environmental detection and reporting functionalities in accordance with an embodiment of the invention. Referring now to FIG. 58, an exemplary node-enhanced battery package system 58000 (NEBP, also referenced as a node-enabled battery package system) is shown having a battery package 58002 configured to as a type of housing that packages a battery (e.g., a lithium-ion battery). Such a package 58002 may, in some embodiments, be implemented as packaging that encloses a battery (such as that shown in FIG. 58) in a sealable package that may selectively opened/closed, but package 58002 may be implemented as a housing that conformally holds multiple battery cells that make up the battery. In other words, an embodiment of package 58002 may be similar to battery 57002 (which has battery cells and a housing to contain such cells together as a unit) but does not include the actual battery cells. As such, an embodiment of system 58000 may have battery package 58002 along with a sensor-based node 24120a attached to the package 58002 without having power cells or fuel cells that power a battery that may be further inserted into and contained by package 58002. As shown in FIG. 58, exemplary package 58002 includes a base 58005, walls 58010, and a lid or top 58003 that collectively define an interior space 58015 within which a battery may be disposed and monitored as part of system 58000.

Exemplary system 58000 further includes a sensor-based ID node 24120a attached to the battery package 58002. As shown in FIG. 58, ID node 24120a is mounted on or within package 58002, but further implementations may attach ID node 24120a in a manner that incorporates the ID node 24120a into the physical structure of the package 58002 (e.g., integrates ID node 24120a as part of package 58002). Similar to that shown in FIG. 57, exemplary sensor-based ID node 24120a (e.g., an implementation of ID node 120a explained above and with reference to FIG. 3) used as part of system 58000 and shown in FIG. 58 includes a node processor, a node memory storage coupled to the node processor, a wireless communication interface coupled to the processor, as well as one or more sensors coupled to the processor and disposed on parts of package 58002. The node memory storage maintains at least a battery monitoring program code and a battery threshold metric value (e.g., as part of the node control and management code 325 stored on memory 320 of ID node 120a). The wireless communication interface (e.g., variable power short range communication interface 375) may be a low power communication interface capable of Bluetooth Low Energy formatted communications. The sensor(s) deployed as part of sensor-based ID node 24120a is generally operative to sense a battery status condition for the battery to be held by package 58002. Those skilled in the art will appreciate that such a sensor (e.g., sensor 360) may be integrated and deployed with ID node 24120a, but may be remotely disposed (e.g., sensors 58360a-58360j) at different locations on the battery package 58002.

As part of system 58000, the processor of sensor-based ID node 24120a shown in FIG. 58 is programmatically configured, when executing the battery monitoring program code, to be operative to receive status data from the sensor (where the status data reflecting the battery status condition as sensed by the sensor); automatically trigger generation of a layered alert notification related to the battery when the received status data is inconsistent with the battery threshold metric value; and cause the wireless communication interface to broadcast the layered alert notification to initiate a mediation response related to the battery status condition for the battery held by battery package 58002.

In more detail, the battery status condition sensed by the sensor on the sensor-based node may be a charge status condition of the battery held in package 58002 (e.g., a voltage level indicative of the charge status of a battery held in package 58002). In more detail, an example may have a sensor on sensor-based ID node 24120a shown in FIG. 58 that is placed on a location of package 58002 and connected to terminals of the battery held in package 58002. As such, the node processor may be programmatically configured to be operative to automatically trigger generation of the layered alert notification (a) when the battery threshold metric value is a threshold voltage value and (b) when the received status data on the charge status condition of the battery held by package 58002 is less than that threshold voltage value.

In another example, the battery status condition sensed by the sensor on the sensor-based node on package 58002 may be a temperature condition of the battery held in package 58002. As such, the node processor may be programmatically configured to be operative to automatically trigger generation of the layered alert notification (a) when the battery threshold metric value is a threshold temperature value and (b) when the received status data on the temperature condition of the battery held by package 58002 exceeds that threshold temperature value.

As noted, exemplary sensor-based ID node 24120a is shown in FIG. 58 as part of system 58000 equipped with multiple battery sensors 58360a-58360j disposed on different points of the battery package 58002. In this configuration, an embodiment may have the battery status condition sensed by each of the battery sensors being temperature conditions of the battery held in package 58002, where each of the temperature conditions corresponds to the respective different point on (or in) the battery package 58002 where the respective battery sensor is disposed. As such, the node processor on ID node 24120a of package 58002 may be programmatically configured to be operative to receive the status data by receiving individual status information from each of the battery sensors as the status data. Furthermore, the node processor may be programmatically configured to be operative to automatically trigger generation of the layered alert notification related to the battery housed by the battery package 58002 by automatically triggering generation of the layered alert notification related to the battery 57002 when at least one of the received individual status information reflects that at least one of the temperature conditions of the battery housed by the battery package 58002 exceeds a threshold temperature value for the battery housed by the battery package 58002.

In some embodiments, the node processor may be programmatically configured to be operative to receive the status data by receiving individual status information from each of the battery sensors as the status data over a time period. In this situation, the node processor may also be programmatically configured to be operative to automatically trigger generation of the layered alert notification by being further operative to monitor the received individual status information from each of the battery sensors over the time period to identify relative changes in the individual status information over the time period, and automatically trigger generation of the layered alert notification related to the battery housed by the battery package 58002 when at least one of the identified relative changes in the individual status information over the time period exceeds a time-based relative temperature change threshold for the battery housed by package 58002.

Similar to that described above in system 57000, the sensor-based ID node 24120a in system 58000 may be activated and "wake" from a low power mode based upon the sensor data. For example, the node processor may be programmatically configured, when executing the battery monitoring program code, to be operative to automatically activate the sensor-based node (such as ID node 24120a shown in FIG. 58) from a low power mode when the received status data is inconsistent with the battery threshold metric value maintained in the sensor-based node memory.

As explained above, the node processor of sensor-based ID node 24120a in system 58000 may programmatically be configured so as to be operative to automatically trigger generation of a layered alert notification related to the battery housed by package 58002 when the received status data is inconsistent with the battery threshold metric value. The layered alert notification generated may depend on a number for factors. For example, such a layered alert notification may, for example, be generated based upon a level of inconsistency between the received status data and the battery threshold metric value, based upon how much the charge status condition differs from the threshold voltage value, based upon how much the temperature condition of the battery housed by package 58002 exceeds the threshold temperature value, based upon how much at least one of the temperature conditions of the battery housed by package 58002 exceeds the threshold temperature value for that battery, and/or based upon how many of the battery sensors have their respective battery status condition exceeding the threshold temperature value for the battery housed by package 58002.

In another example of system 58000, the layered alert notification may identify the battery housed by package 58002 so that those elements receiving the layered alert notification will be informed that it is specifically the battery housed by package 58002 having an inconsistent battery status condition relative to thresholds for that battery. In more detail, the node memory storage on sensor-based ID node 24120a as part of system 58000 may maintain battery specifier data related to the battery housed by package 58002 (e.g., exemplary battery specifier data related to the battery housed by package 58002 as part of profile data 330 maintained in memory of ID node 24120a). As such, the layered alert notification related to the battery housed by package 58002 may include an identification of the battery housed by package 58002 based upon the battery specifier data (e.g., information on a unique identifier for the battery housed by package 58002, information on a characteristic category of the battery housed by package 58002 (such as a lithium-ion type of battery)). Such battery specifier data may be preprogrammed into the node memory of ID node 24120a when the ID node is associated with the battery housed by package 58002 (e.g., during manufacture, during packaging for transport, and the like). This may be accomplished by having the node processor being further programmatically configured to be operative to receive the battery specifier data over the wireless communication interface and store the battery specifier data within the node memory storage.

As noted above, the node processor of ID node 24120a in system 58000 is operative to cause the wireless communication interface of the package's ID node 24120a to broadcast the layered alert notification to initiate a mediation response related to the battery status condition for the battery housed by package 58002. Such a mediation response may be a request for intervention in the transport of package 58002 (including the battery housed by package 58002). For example, as shown in FIG. 59, system 59000 is shown with similar components as system 44000 in FIG. 44, but FIG. 59 further shows several node-enhanced battery package systems (e.g., NEBP 1, NEBP 2, NEBP 3) within shipping container 24300a. In this example, the sensor-based ID node as part of NEBP 1 may cause its wireless communication interface to broadcast a layered alert notification to initiate a mediation response related to the battery status condition for the battery housed within the package of NEBP 1. Such a mediation response may be a request for intervention in the transport of NEBP 1 (notably, the battery housed within NEBP 1). As such, the layered alert notification may be received by command node 24160, which may direct external transceiver 24150 to display a prompt message requesting intervention (e.g., a change in course of transit vehicle 24200 or an inspection be conducted of NEBP 1). In another example, the mediation response may be a request for automatic fire suppression intervention for the battery housed within the node-enhanced battery package system (e.g., where command node 24160 responds to the layered alert notification broadcast from the ID node in NEBP 1, and directs fire suppression system 25010 to dispense fire suppressant material within shipping container 24300a to as to intervene in response to the notification from NEBP 1).

In a further embodiment, system 58000 may be modified so that multiple sensor-based ID nodes are attached to (or integrated as part of) the battery package, instead of using a single sensor-based ID node 24160a in or on package 58002 as shown in FIG. 58. In this further embodiment, each of the multiple sensor based ID nodes is similarly configured as node 24160a as explained above with reference to and as shown in FIG. 58. As such, the sensor (or sensors) for each of the sensor-based nodes are disposed at differing locations on the battery package, where each of the sensors is operative to sense a battery status condition for the battery housed within the battery package.

The node processor in each of this further system embodiment's sensor-based nodes is programmatically configured, when executing the battery monitoring program code, to be operative to receive status data from that node's sensor (where the status data reflects the battery status condition as sensed by that particular sensor); automatically trigger generation of a layered alert notification related to the battery housed within the package when the received status data is inconsistent with the battery threshold metric value; and cause the wireless communication interface to broadcast the layered alert notification to initiate a mediation response related to the battery status condition for the battery housed within this system's battery package.

In more detail, the further system embodiment may have the sensor for one of the sensor-based nodes be coupled to the terminals of the battery housed within the battery package so that the sensor data reflects a charge status condition of the battery. As such, the node processor of that sensor-based node may be programmatically configured to be operative to automatically trigger generation of the layered alert notification when the battery threshold metric value comprises a threshold voltage value and when the received status data on the charge status condition of the battery housed within the package is less than the threshold voltage value.

The battery status condition sensed by the sensor on the sensor-based nodes may, in other examples, be a temperature condition relative to the location on the battery package associated with the respective sensor on the particular one of the sensor-based nodes. As such, the node processor of each of the sensor-based nodes may be programmatically configured to be operative to automatically trigger generation of the layered alert notification when the battery threshold metric value comprises a threshold temperature value and when the received status data on the temperature condition relative to the location on the battery package associated with the respective sensor on the sensor-based nodes exceeds the threshold temperature value.

Similar to the embodiments described above relative to system 58000, this further embodiment may have the node processor operative to receive the status data over a time period. In such a situation, the node processor of each of the sensor-based nodes may be programmatically configured to be operative to automatically trigger generation of the layered alert notification by being further operative to monitor the received status data over the time period to identify relative changes in the received status over the time period, and automatically trigger generation of the layered alert notification related to the battery housed within the package when at least one of the identified relative changes in the received status data over the time period exceeds a time-based relative temperature change threshold for the battery housed within the package.

In more detail, the node processor of each of the sensor-based nodes in this further embodiment may be programmatically configured, when executing the battery monitoring program code, to be operative to automatically activate the respective sensor-based node from a low power mode when the received status data is inconsistent with the battery threshold metric value.

The layered alert notification generated by the node processor in each of the sensor-based nodes in this further embodiment may be based upon a variety of factors. For example, it may be based upon a level of inconsistency between the received status data and the battery threshold metric value; based upon how much the charge status condition differs from the threshold voltage value; and/or based upon how much the temperature condition of the battery housed within the system's battery package exceeds the threshold temperature value.

Similar to the embodiments described above, the mediation response may involve a request for intervention in transport of the battery housed within the package or a request for automatic fire suppression intervention for the battery housed by the battery package.

Additionally, this further system embodiment may have the node memory storage on each of the sensor-based nodes maintaining battery specifier data related to the battery housed with the package as described above (e.g., exemplary battery specifier data related to a battery housed within package 58002 as part of profile data 330 maintained in memory of ID node 24120*a* and other ID nodes disposed on package 58002). As such, the layered alert notification related to the battery housed within the package in this system embodiment may include an identification of that battery based upon the battery specifier data (e.g., information on a unique identifier for the battery, information on a characteristic category of the battery (such as a lithium-ion type of battery)). Such battery specifier data may be preprogrammed into the node memory of each sensor-based node on the package when the battery to be housed within the battery package is assembled with the package (e.g., during manufacture, during packaging for transport, and the like). This may be accomplished by having the node processor for each sensor-based node being further programmatically configured to be operative to receive the battery specifier data over the wireless communication interface and store the battery specifier data within the node memory storage.

Figure 60A:
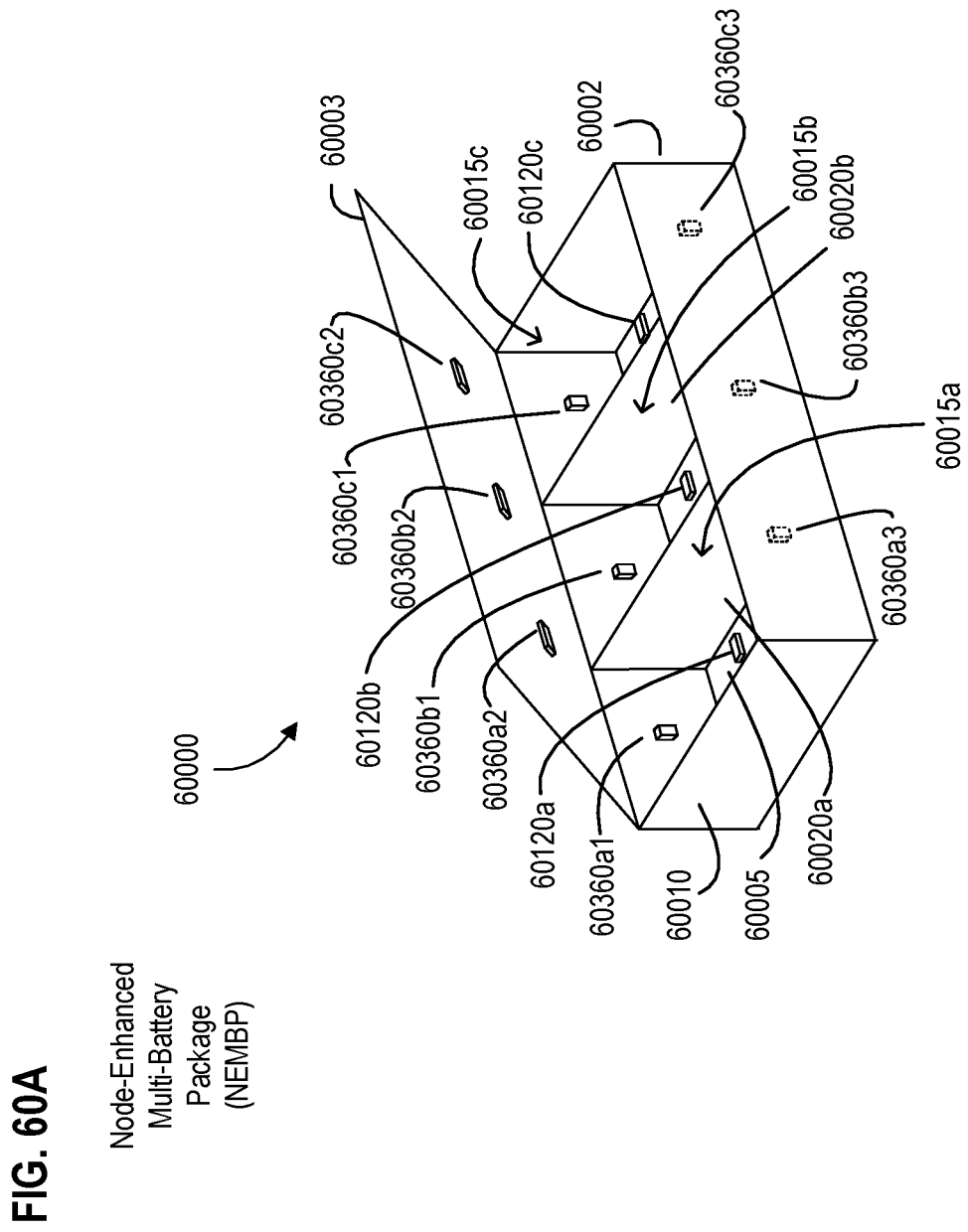
FIG. 60A is a diagram illustrating an exemplary multi-node-enabled package system for transporting multiple batteries having integrated environmental detection and reporting functionalities in accordance with an embodiment of the invention.

Another embodiment of an alternative type of node-enhanced (or node-enabled) battery package is configured to house multiple batteries where each is monitored by a sensor-based node (e.g., sensor-based wireless ID node 24160*a*). This additional embodiment extends the battery package generally to have different battery storage locations within the package and where specific sensor-based nodes are deployed on or as part of the package to individually monitor batteries housed within each of the different battery storage locations within the package. FIG. 60A is a diagram illustrating an exemplary multi-node-enabled package system for transporting multiple batteries having integrated environmental detection and reporting functionalities in accordance with an embodiment of the invention. Referring now to FIG. 60A, an exemplary multi-node-enhanced multi-battery package system 60000 (NEMBP, also referenced as a node-enabled multi-battery package system) is shown having a battery package 60002 configured to as a type of housing that packages multiple batteries (e.g., different batteries that may include one or more lithium-ion batteries). Such a package 60002 may, in some embodiments, be implemented as packaging that encloses the batteries (such as that shown in FIG. 60A) in a sealable package that may be selectively opened/closed, but package 60002 may be implemented as a housing that conformally holds multiple batteries in different battery storage locations 60015*a*-60015*c* defined within package 60002. In other words, an embodiment of package 60002 may provide battery storage locations 60015*a*-60015*c* but does not include the actual batteries that will be disposed within them (a further embodiment may include the batteries as part of system 60000).

As shown in FIG. 60A, exemplary package 60002 includes a base 60005 that supports the batteries to be housed within package 60002; and an enclosing structure coupled to base 60005 having, for example, walls 60010 and a lid or top 60003. The enclosing structure (e.g., walls 60010 and lid 60003) and the base 60005 collectively define an interior storage space within the battery package 60002 for maintaining the batteries. In particular and as shown in FIG. 60A, package 60002 include further interspersed separators 60020*a*, 60020*b* that divide the interior storage space and define the different battery storage locations 60015*a*-60015*c* within the interior storage space where different batteries may be housed and be monitored by different sensor-based ID nodes 60120*a*-60120*c* disposed in a respective one of locations 60015*a*-60015*c*.

As shown in FIG. 60A, ID nodes 24120*a*-24120*c* are each mounted on or within package 60002 in respectively different battery storage locations 60015*a*-60015*c*, but further implementations may attach each of ID nodes 24120*a*-24120*c* in a manner that incorporates the particular ID node into the physical structure of the package 60002 (e.g., integrates ID node as part of package 60002). Similar to that shown in FIGS. 57 and 58, each of exemplary sensor-based ID nodes 24120a-24120c (e.g., an implementation of ID node 120a explained above and with reference to FIG. 3) used as part of system 60000 and shown in FIG. 60A includes a node processor, a node memory storage coupled to the node processor, a wireless communication interface coupled to the processor, as well as one or more sensors coupled to the processor and disposed on parts of package 60002. The node memory storage maintains at least a battery monitoring program code and a battery threshold metric value (e.g., as part of the node control and management code 325 stored on memory 320 of ID node 120a). The wireless communication interface (e.g., variable power short range communication interface 375) may be a low power communication interface capable of Bluetooth Low Energy formatted communications. The sensor(s) deployed as part of each of sensor-based ID nodes 24120a-24120c is generally operative to sense a battery status condition for the battery held by package 60002 in the particular one of the battery locations 60015a-60015c associated with the particular sensor-based ID node having that sensor(s). Those skilled in the art will appreciate that such a sensor (e.g., sensor 360) may be integrated and deployed with its respective ID node, but may be remotely disposed (e.g., sensors 60360a1-60360c3) at different locations within the different battery storage locations 60015a-60015c of the battery package 60002. For example, within battery storage location 60015a, sensor-based ID node 24120a is coupled to each of sensors 60360a1-60360a3. In like manner, within battery storage location 60015b, sensor-based ID node 24120b is coupled to each of sensors 60360b1-60360b3. Similarly, within battery storage location 60015c, sensor-based ID node 24120c is coupled to each of sensors 60360c1-60360c3. In this way, package 60002 offers different storage locations 60015a-60015c for different batteries that will be monitored by their own sensor-based node capable as part of system 60000.

Figure 61:
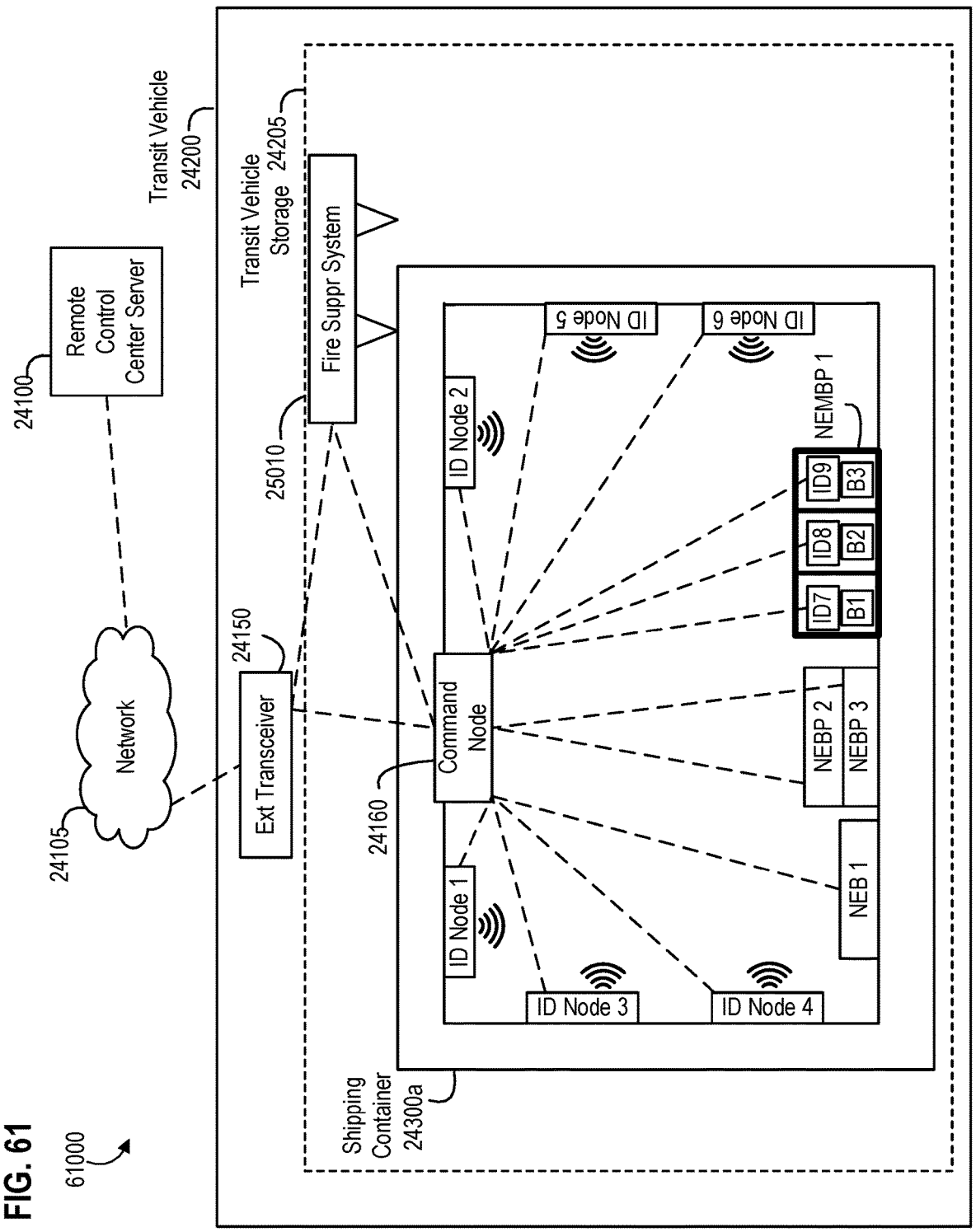
FIG. 61 is a diagram illustrating an exemplary improved system for coordinated mediation action in response to an identified environmental anomaly related to the shipping container transporting an exemplary node-enabled battery system, an exemplary node-enabled package system for a battery, and an exemplary multi-node-enabled package system for transporting multiple batteries in accordance with an embodiment of the invention.

FIG. 61 is a diagram illustrating an exemplary improved system for coordinated mediation action in response to an identified environmental anomaly related to the shipping container transporting an exemplary node-enabled battery system, an exemplary node-enabled package system for a battery, and an exemplary multi-node-enabled package system for transporting multiple batteries in accordance with an embodiment of the invention. Referring now to FIG. 61, system 61000 is shown with similar components as system 59000 shown in FIG. 59. In particular, as it relates to the NEB and NEBP systems shown in FIG. 61, functionality of system 61000 that has exemplary command node 24160 (a type of master node) interacting with the NEB and NEBP systems shown and operating as has been described above relative to FIG. 59. However, exemplary system 61000 illustrates an exemplary multi-node-enabled package system (i.e., NEMBP 1) that may be implemented as exemplary system 6000 and also interact with command node 24160. In more detail, the wireless communication interface coupled to the node processor on each of the sensor-based ID nodes 24120a-24120c disposed in package 60002 of system 60000 (e.g., NEMBP 1 shown in FIG. 61) is configured to wirelessly communicate with the command node 24160.

As shown in system 61000, the node processor in each of the ID nodes deployed in NEMBP 1 is programmatically configured, when executing the battery monitoring program code, to be operative to receive status data from the sensor of the respective ID node (where the status data reflects the battery status condition for the particular battery disposed in the one of the battery storage locations 60015a-60015c associated with the respective ID node on NEMBP 1). The node processor in each of the ID nodes deployed in NEMBP 1 is further programmatically configured to be operative to, when the received status data from a particular ID node is inconsistent with the battery threshold metric value, automatically trigger generation of a layered alert notification related to the respective battery disposed in that ID node's battery storage location; and then cause the wireless communication interface of that the ID node to broadcast the layered alert notification to the command node 24160.

Figure 60B:
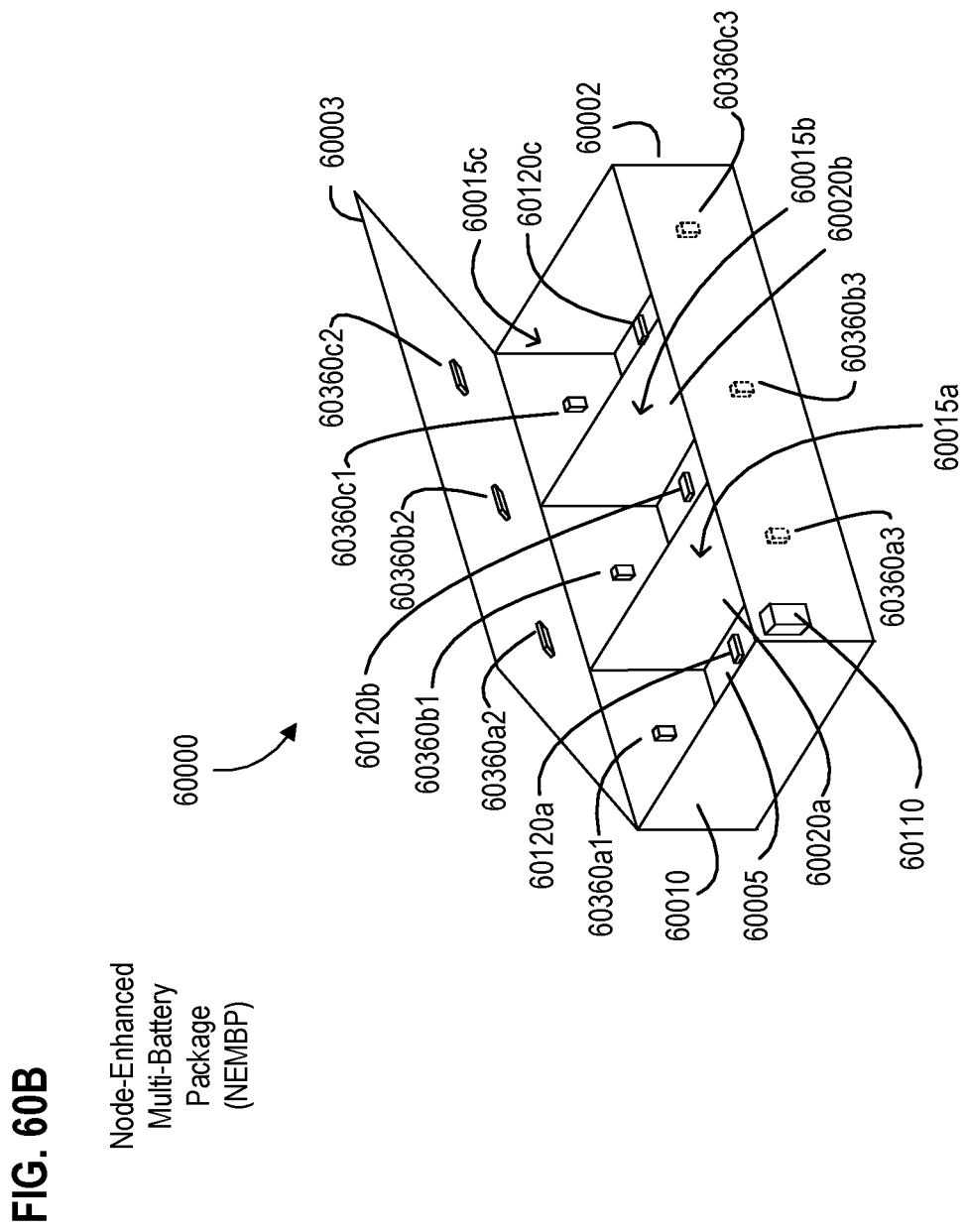
FIG. 60B is a diagram illustrating an exemplary multi-node-enabled package system for transporting multiple batteries having integrated environmental detection and reporting functionalities and a package master node in accordance with an embodiment of the invention.

A further embodiment of NEMBP 1 (e.g., system 60000) as shown in FIG. 60B includes an exemplary master node 60110 attached to battery package 60002 separate from each of the ID nodes 24120a-24120c. Exemplary master node 60110 is disposed on or within package 60002, is affixed in a temporary or removable manner, and is operative to communicate with an external node, such as command node 24160 or in some instances directly with external transceiver 24150 or onboard fire suppression system 25010. The exemplary master node 60110, as an additional management node component attached to and associated with multiple battery package 60002 (NEMBP 1), is configured to receive the layered alert notification from any of the ID nodes 24120a-24120c; responsively identify an environmental anomaly for a particular one of the batteries housed within NEMBP 1 based upon the layered alert notification and an identification of which of the ID nodes 24120a-24120c transmitted the layered alert notification; and transmit a package level alert notification to the external node (e.g., the command node 24160 disposed within shipping container 24300a, external transceiver 24150, and/or fire suppression system 25010) to initiate a mediation response related to the battery status condition for the batteries in NEMBP 1 (i.e., at least one of those batteries) where the package level alert notification identifies the environmental anomaly for the batteries.

In more detail, exemplary system 61000 may have the sensor for one of the sensor-based ID nodes in NEMBP 1 be coupled to terminals of the particular battery disposed in the particular battery storage location associated with that ID node so that the sensor data reflects a charge status condition of that particular one of the batteries housed within NEMBP 1. As such, the node processor of that sensor-based node may be programmatically configured to be operative to automatically trigger generation of the layered alert notification when the battery threshold metric value comprises a threshold voltage value and when the received status data on the charge status condition of the battery housed within that location of the package is less than the threshold voltage value.

The battery status condition sensed by the sensor on the sensor-based nodes may, in other examples, be a temperature condition relative to the location on the battery package (e.g., a temperature condition associated with the one of the batteries disposed in one of the battery storage locations 60015a-60015c). As such, the node processor of each of the sensor-based ID nodes may be programmatically configured to be operative to automatically trigger generation of the layered alert notification when the battery threshold metric value comprises a threshold temperature value and when the received status data on the temperature condition relative to the location on the battery package associated with the respective sensor on the sensor-based ID nodes exceeds the threshold temperature value.

Similar to the embodiments described above relative to system 58000, system 61000 (using components of NEMBP 1) may have the node processor of each of the ID nodes operative to receive the status data over a time period. In such a situation, the node processor of each of the sensor-based ID nodes may be programmatically configured to be operative to automatically trigger generation of the layered alert notification by being further operative to monitor the received status data over the time period to identify relative changes in the received status over the time period, and automatically trigger generation of the layered alert notification related to the particular battery housed within the battery storage location associated with that ID node when at least one of the identified relative changes in the received status data over the time period exceeds a time-based relative temperature change threshold for that battery.

In more detail, the node processor of each of the sensor-based nodes in this embodiment may be programmatically configured, when executing the battery monitoring program code, to be operative to automatically activate the respective sensor-based ID node from a low power mode when the received status data is inconsistent with the battery threshold metric value.

The layered alert notification generated by the node processor in each of the sensor-based ID nodes in NEMBP 1 as part of system 61000 may be based upon a variety of factors. For example, it may be based upon a level of inconsistency between the received status data and the battery threshold metric value; based upon how much the charge status condition differs from the threshold voltage value; and/or based upon how much the temperature condition of the particular one of the batteries housed within the system's battery package 60002 exceeds the threshold temperature value.

Similar to the embodiments described above, the mediation response as part of system 61000 may involve a request for intervention in transport of the particular one of the batteries housed within the package 60002 of NEMBP 1 or a request for automatic fire suppression intervention for the particular one of the batteries housed within the package 60002 of NEMBP 1.

Additionally, exemplary system 61000 may have the node memory storage on each of the sensor-based ID nodes in NEMBP 1 maintaining battery specifier data related to the particular battery located in the storage location of that ID node as described above (e.g., exemplary battery specifier data related to a battery housed within one of the locations 60015a-60015c of package 60002 as part of profile data 330 maintained in memory of ID node 24120a and other ID nodes disposed on package 60002). As such, the layered alert notification may include an identification of that battery based upon the battery specifier data (e.g., information on a unique identifier for the battery, information on a characteristic category of the battery (such as a lithium-ion type of battery)). Such battery specifier data may be pre-programmed into the node memory of each sensor-based ID node in NEMBP 1 when the different batteries to be housed within the battery package 60002 are placed or assembled with the package (e.g., during manufacture, during packaging for transport, and the like). This may be accomplished by having the node processor for each sensor-based ID node in NEMBP 1 being further programmatically configured to be operative to receive the battery specifier data over the wireless communication interface and store the battery specifier data within its own node memory storage.

In still a further embodiment of system 61000 that uses NEMBP 1, the package level alert notification transmitted by the package's master node adaptively identifies the mediation response depending upon the identification of which of the ID nodes in NEMBP 1 transmitted the layered alert notification. Expanding on this further, an embodiment may have the node memory storage on each of the ID nodes in NEMBP 1 further maintaining usage context data (e.g., part of profile data 330) related to the particular battery that is disposed in the battery storage location associated with the respective one of the ID nodes. As such, the package level alert notification transmitted by the master node may adaptively identify the mediation response depending upon (a) the identification of which of the ID nodes transmitted the layered alert notification, and (b) based upon the usage context data and/or characteristic category (e.g., type) related the one of the batteries disposed in the one of the battery storage locations associated with the respective one of the ID nodes transmitting the layered alert notification.

In one embodiment, such usage context data may indicate an active usage status of the battery in NEMBP 1. Examples of such an active usage status may be a present battery charging state (e.g., a standby state, a charging state, and a discharging state) or a current battery health state (e.g., charge cycle count, delivered voltage, internal resistance, current charge capacity, and the like). In some embodiments, the ID node sensor disposed with a battery within NEMBP1 may be a power sensor (e.g., a type of sensor 360 connected to a battery, such as sensor 57360a connected to terminals 57005 and 57010 of battery 57002 shown in FIG. 57). Such a power sensor is operative to detect the active usage status of the battery. In this situation, the advertising signals broadcast by the that ID node may include usage context data indicating the active usage status as detected by the power sensor and, in some embodiments, may allow command node 24160 to identify or update the usage context data when wirelessly monitoring the advertising signals.

In another embodiment, the usage context data may indicate a location of the battery pack used in NEMBP 1. For example, the usage context data may include information on the battery pack's proximity to other important items (e.g., mission critical or sensitive electronics that may be damaged by smoke or heat) or dangerous/hazardous materials within container 24300a or situated near the location of NEMBP 1 as disposed within container 24300a (e.g., materials that may catch fire and cause a larger explosion). The usage context data may indicate a risk factor associated with the location of the NEMBP 1 battery—e.g., information on whether the battery pack is within a specific distance from fuel used by the transit vehicle 24200 so that an anomaly with the battery pack may cause a larger issue with such fuel (such as flames that may cause a larger explosion). As such, consideration of usage context data of these types allow command node 24160 to dynamically adjust the type of mediation response to automatically and quickly initiate the appropriate mediation response.

Layered Initiation of Mediated Environmental Anomaly Response Using Node-Enhanced Battery and Multi-Mode Triggering The embodiments above describe an exemplary node-enhanced or node-enabled battery as an apparatus (e.g., NEB1 explained as exemplary node-enhanced battery (NEB) 57000) or system of elements or a component of a larger system. However, further embodiments described below may deploy such an exemplary node-enhanced or node-enabled battery as part of different systems for layered initiation of a mediation response to a battery-related environmental anomaly. In general, when a node-enabled battery device suddenly ceases to broadcast where contextually it should still be broadcasting (e.g., detected based on a change in broadcasted advertising messages expected to be broadcast from the particular wireless node disposed with the device), an initially small temperature rise detected by a secondary device near the node-enabled battery device (or within the same shipping container as the device) may indicate an environmental anomaly issue. From a system perspective, that change may be detected by a managing device—e.g., a command node or master node—that is also in contact with the secondary device (who sends sensor data indicating the small temperature rise to the managing device). In such embodiments, the managing device interacts with both the node-enhanced battery device as well as a nearby secondary sensor-based device in making a determination that there may be an environmental anomaly.

More specifically, the managing device may receive and use both sensor-based information (e.g., the environmental sensor data, such as temperature data) as well as non-environmental detected information (e.g., the existence or absence of expected advertising signals) in making this determination of whether there is a potential environmental anomaly. Such multi-mode detection embodiments may be particularly helpful when a fire spreads rapidly, the broadcasting devices may be disappearing so quickly that relying solely upon changing values of environmental sensor data may not provide enough reaction time and may lead to catastrophic damage (e.g., loss of a shipping container before the container command node may sense a sufficient an increase in temperature to warrant transmitting an alert notification to initiate a mediation response). The use of multi-mode detection embodiments that monitor for an environmental anomaly may generally involve a first triage level, and then get further data to verify or get higher quality data (issue command or request supporting information from other network devices) as a second triage level before initiating the mediation response.

The term "mediation" is used as a broad term which may include activating an automate fire suppression system, initiate manual fire suppression, informing the pilot or operator of a transit vehicle to prepare for landing, signaling a remote system to prepare for emergency/initiate rescue, and the like. Exemplary mediation responses may also include informing customers their packages are lost and to initiate replacement as a mode to handle critical inventory or just-in-time operations who will be impacted by diverted vehicles (e.g., aircraft), packages damaged by fire suppression (or other mediation), or critical loss of items.

Figure 62:
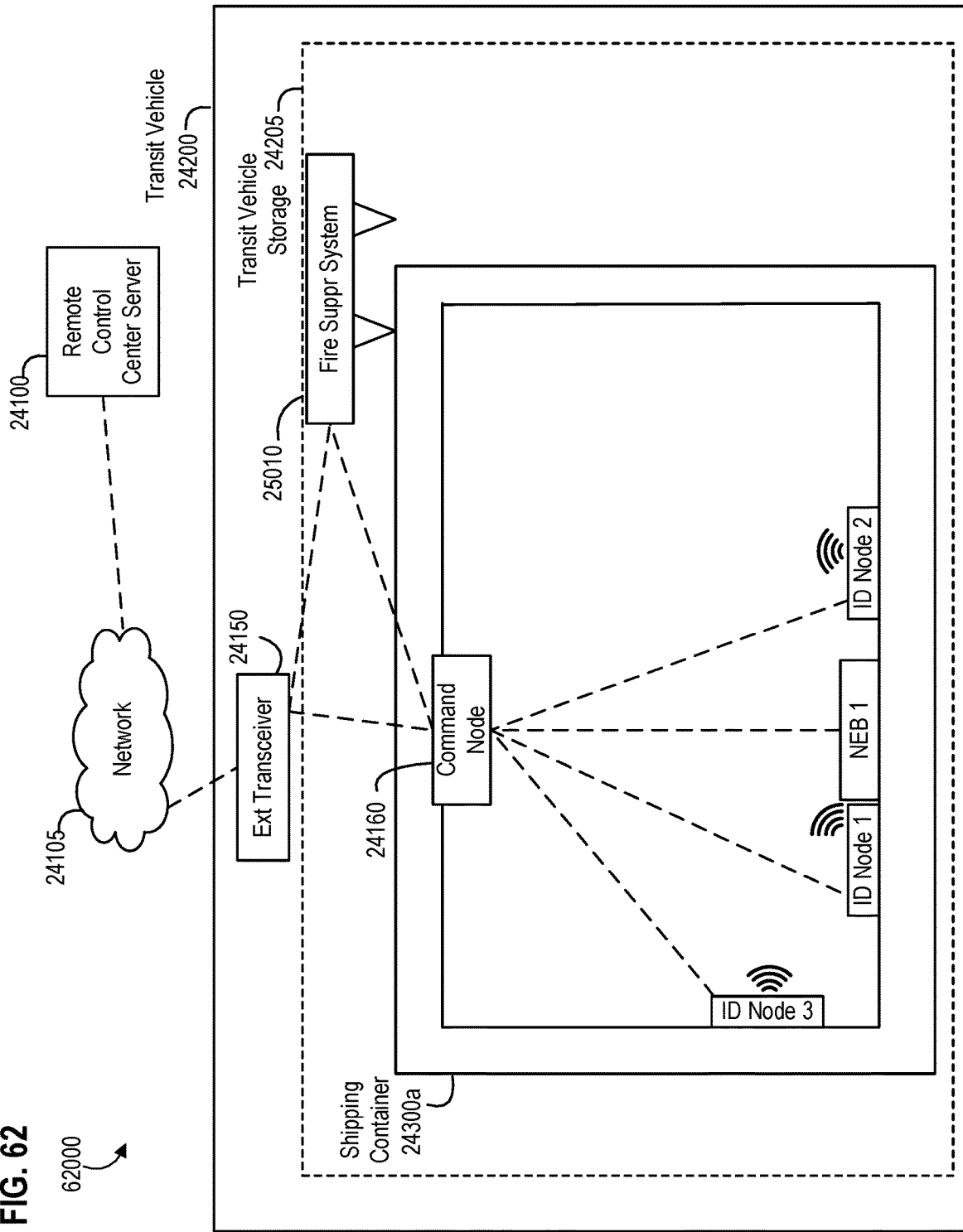
FIG. 62 is a diagram illustrating an exemplary system for layered initiation of a mediation response to a battery-related environmental anomaly involving a node-enabled battery apparatus, at least one secondary sensor-based ID node, and a command node in accordance with an embodiment of the invention.

FIG. 62 is a diagram illustrating an exemplary system for layered initiation of a mediation response to a battery-related environmental anomaly involving a node-enabled battery apparatus, at least one secondary sensor-based ID node, and a command node in accordance with an embodiment of the invention. Referring now to FIG. 62, exemplary system 62000 illustrates an exemplary system for layered initiation of a mediation response to a battery-related environmental anomaly and is shown with similar components as shown in system 59000 of FIG. 59, but is simplified to show an exemplary node-enhanced battery system, NEB 1 (also referenced as a node-enabled battery apparatus), wireless sensor-based ID nodes 1-3, and exemplary command node 24160 disposed within shipping container 24300a. Consistent with the prior description of an exemplary node-enabled battery (as a system or apparatus of distinct parts), NEB 1 in system 62000 generally includes at least one battery (e.g., battery 57002), and a wireless node (e.g., ID node 24120a shown in FIG. 57 to be part of the node-enhanced battery system 57000) disposed with the battery (e.g., attached to the battery or integrated with the battery itself).

The wireless node component of NEB 1 has a wireless communication interface operative to broadcast a plurality of advertising signals over time. Wireless sensor-based ID nodes 1-3 are shown in FIG. 62 as different secondary sensor-based nodes where each has an environmental sensor and a wireless communication interface operative to broadcast environmental sensor data generated by the environmental sensor. For example, ID node 1 shown in FIG. 62 is disposed next to or proximate NEB 1 (e.g., ID node 1 is next to with no intervening batteries, shipments, packages, or other objects between the node-enabled battery apparatus (NEB 1) and ID node 1). Command node 24160 of system 62000 is in wireless communication with NEB 1 and each of the secondary sensor-based nodes (e.g., ID nodes 1-3).

As part of system 62000, command node 24160 is programmatically configured (via program code, such as part of command node management and control code 26425 when executing on the processor 26400 of command node 24160) to be operative to conduct multiple levels of battery-related anomaly monitoring. In particular, command node 24160 is advantageously operative to conduct an initial level of battery-related anomaly monitoring by wirelessly monitoring the advertising signals broadcast by NEB 1 for an unanticipated state of ceased broadcasting of NEB 1 according to a communication profile maintained on the command node (e.g., a communication profile for NEB1 as reflected in part of profile data 430 stored on command node 24160); and wirelessly monitoring the broadcasted environmental sensor data from a secondary sensor-based node (e.g., ID node 1). Command node 24160 is further programmatically operative to identify an initial level of the battery-related environmental anomaly based on the initial level of battery-related monitoring when both the unanticipated state of ceased broadcasting is detected and the monitored broadcasted environmental sensor data reflects at least a first threshold difference change in the environmental sensor data; conduct a secondary level of battery-related anomaly monitoring of broadcasts from the secondary sensor-based node (e.g., ID node 1) in response to the identified initial level of the battery-related environmental anomaly; and initiate the mediation response to the battery-related environmental anomaly based upon the secondary level of battery-related anomaly monitoring by broadcasting a layered alert notification.

Command node 24160, as part of system 62000, may be further configured to be operative to conduct the secondary level of battery-related anomaly monitoring by wirelessly monitoring the advertising signals broadcast by NEB 1 for an additional unanticipated state of ceased broadcasting according to the communication profile maintained on command node 24160 for the wireless node in NEB 1, and wirelessly monitoring for additional environmental sensor data from ID node 1 (as the secondary sensor-based node) to verify the initial level of the battery-related environmental anomaly.

In some embodiments of system 62000, the reporting rate from the secondary sensor-based node may be changed as a refinement. For example, command node 24160 may be further programmatically configured to be operative to conduct the secondary level of battery-related anomaly monitoring by instructing ID node 1 (as the secondary sensor-based node) to broadcast the environmental sensor data at a second messaging rate that exceeds an initial messaging rate (e.g., a rate of broadcasting set as an initial value correlated to an environmental risk associated with the battery 57002 of NEB 1). The second messaging rate for ID node 1 (as the secondary sensor-based node) may be a predetermined higher messaging rate based upon a type of material existing within battery 57002 of NEB 1. Once instructing ID node 1 to use the second messaging rate, the command node may initiate the mediation response to the battery-related environmental anomaly in response to the secondary level of battery-related anomaly monitoring by broadcasting the layered alert notification when both another unanticipated state of ceased broadcasting is detected and the broadcasted environmental sensor data broadcast at the second messaging rate reflects at least the first threshold difference change in the environmental sensor data.

In a further embodiment of system 62000, command node 24160 may be further programmatically configured to be operative to conduct the secondary level of battery-related anomaly monitoring by being operative to (a) wirelessly monitor the advertising signals broadcast by NEB 1 for an additional unanticipated state of ceased broadcasting according to the communication profile maintained on command node 24160 for the wireless node of NEB 1; (b) wirelessly monitor for additional environmental sensor data from ID node 1 (as the secondary sensor-based node) to verify the initial level of the battery-related environmental anomaly; and (c) identify the secondary level of battery-related anomaly when both another unanticipated state of ceased broadcasting is detected and the broadcasted environmental sensor data reflects at least a second threshold difference change in the environmental sensor data (where the second threshold difference change is greater than the first threshold difference change).

In additional embodiments of system 62000, command node 24160 may initiate different types of mediation responses. For example, the broadcasted layered alert notification from command node 24160 may cause activation of an automatic fire suppression system (e.g., exemplary onboard fire suppression system 25010) targeting the container 24300a having the battery of NEB 1. In another example, the broadcasted layered alert notification from command node 24160 may be a message requesting manual fire suppression of the battery (e.g., a message that directs a display on external transceiver 24150 to display a prompted message that requests manual fire suppression for the battery in NEB 1). In a further example, the broadcasted layered alert notification from command node 24160 may be a message requesting preparations to cease transportation of the battery in NEB 1 (e.g., a message providing guidance to a preferred location, such as where the transit route started, a close by intermediate destination, and the like). In still another example, the broadcasted layered alert notification from command node 24160 may be a message to inform an entity associated with the battery in NEB 1 (e.g., a battery supplier, shipping client for that battery, a recipient that is to receive the battery after transport, and the like) that the battery needs replacement.

As shown in FIG. 62, an embodiment of system 62000 may include more than one container deployed sensor-based nodes (such as ID nodes 2-3 in addition to ID node 1 considered as the secondary sensor-based node). As such, command node 24160 may be further programmatically operative to conduct the initial level of battery-related anomaly monitoring by wirelessly monitoring the advertising signals broadcast by the node-enabled battery apparatus, NEB 1, for the unanticipated state of ceased broadcasting according to the communication profile maintained on the command node for the node-enabled battery apparatus; and wirelessly monitoring the broadcasted environmental sensor data from each of the container deployed sensor-based nodes, ID nodes 1-3. In this further example, command node 24160 may identify the initial level of the battery-related environmental anomaly based on the initial level of battery-related monitoring when both (a) the unanticipated state of ceased broadcasting is detected and (b) the monitored broadcasted environmental sensor data from at least one of ID nodes 1-3 deployed in shipping container 24300a reflects at least a first threshold difference change in the environmental sensor data received from the at least one of ID nodes 1-3.

As part of NEB 1 used in system 62000, the wireless node disposed with the battery in NEB 1 may maintain battery specifier data related to the particular battery used in NEB 1 (e.g., battery 57002). Exemplary battery specifier data related to the battery with the wireless node of NEB 1 may be maintained, for example, as part of profile data 330 maintained in memory of ID node 24120a shown as part of NEB 1 (also explained as node-enhanced battery system 57000). As such, the layered alert notification related to the battery in NEB 1 may include an identification of that battery based upon the battery specifier data (e.g., information on a unique identifier for the battery, information on a characteristic category of the battery (such as a lithium-ion type of battery)). Such battery specifier data may be preprogrammed into the node memory of the wireless node of NEB 1 when the wireless node is associated with the battery of NEB 1 (e.g., during manufacture, during packaging for transport, and the like).

Embodiments of system 62000 may have the mediation response depending upon usage context data maintained relative to the battery in NEB 1 as well. For example, as part of exemplary system 62000 shown in FIG. 62, command node 24160 may be further programmatically configured to be operative to identify the mediation response based upon the secondary level of battery-related anomaly monitoring as well as upon usage context data related to the battery in NEB 1. In one embodiment, such usage context data may indicate an active usage status of the battery in NEB 1. Examples of such an active usage status may be a present battery charging state (e.g., a standby state, a charging state, and a discharging state) or a current battery health state (e.g., charge cycle count, delivered voltage, internal resistance, current charge capacity, and the like).

In some embodiments, the wireless node disposed with the battery in NEB 1 may be deployed with a power sensor (e.g., a type of sensor 360 connected to a battery, such as sensor 57360a connected to terminals 57005 and 57010 of battery 57002 shown in FIG. 57). Such a power sensor is operative to detect the active usage status of the battery in NEB 1. In this situation, the advertising signals broadcast by the wireless node in NEB 1 may include usage context data indicating the active usage status as detected by the power sensor and, in some embodiments, may allow command node 24160 to identify or update the usage context data when wirelessly monitoring the advertising signals.

In another embodiment, the usage context data may indicate a location of the battery used in NEB 1. For example, the usage context data may include information on the battery's proximity to other important items (e.g., mission critical or sensitive electronics that may be damaged by smoke or heat) or dangerous/hazardous materials within container 24300a or situated near the location of NEB 1 as disposed within container 24300a (e.g., materials that may catch fire and cause a larger explosion). The usage context data may indicate a risk factor associated with the location of the NEB 1 battery—e.g., information on whether the battery in NEB 1 is within a specific distance from fuel used by the transit vehicle 24200 so that an anomaly with the NEB 1 battery may cause a larger issue with such fuel (such as flames that may cause a larger explosion). As such, consideration of usage context data of these types allow command node 24160 to dynamically adjust the type of mediation response to automatically and quickly initiate the appropriate mediation response.

Figure 63:
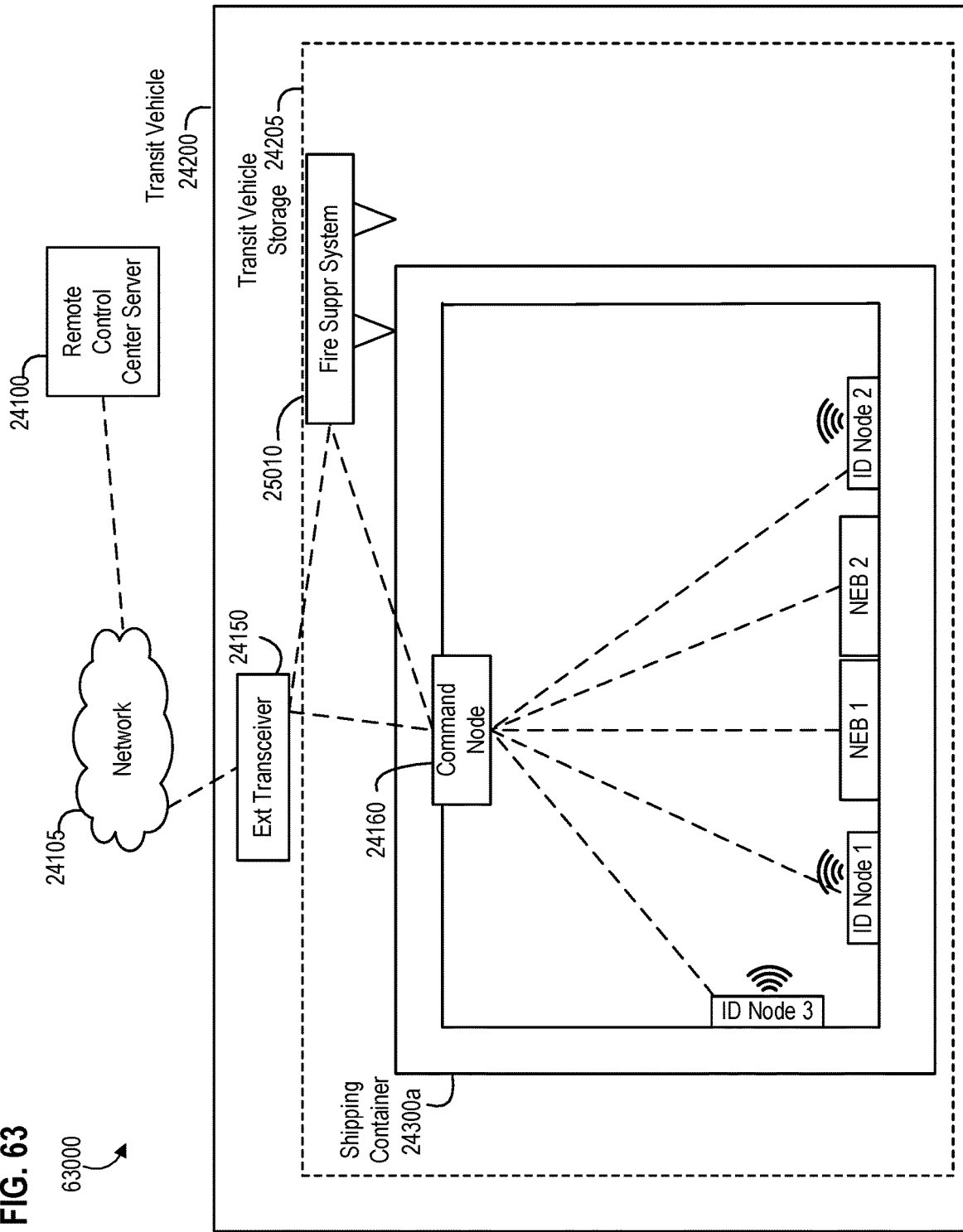
FIG. 63 is a diagram illustrating an exemplary system for layered initiation of a mediation response to a battery-related environmental anomaly involving multiple node-enabled battery apparatus, at least one secondary sensor-based ID node, and a command node in accordance with an embodiment of the invention.

Similar to system 62000, further embodiments may monitor multiple node-enabled or enhanced batteries as part of a system that initiates a mediation response to a battery-related environmental anomaly. FIG. 63 is a diagram illustrating an exemplary system for layered initiation of a mediation response to a battery-related environmental anomaly involving multiple node-enabled battery apparatus, at least one secondary sensor-based ID node, and a command node in accordance with an embodiment of the invention. Referring now to FIG. 63, exemplary system 63000 is similar to that shown and explained above relative to system 62000 of FIG. 62, but system 63000 includes both NEB 1 and NEB 2 as shown in FIG. 63 and disposed within shipping container 24300*a* along with sensor-based ID nodes 1-3. As such, an embodiment of system 63000 includes wireless nodes, where each of the wireless nodes is disposed with one of a subset of batteries that may be in shipping container 24300*a*. For example, exemplary shipping container 24300*a* may be transporting a large number of batteries, but a subset of such batteries may include the batteries that are part of NEB 1 and NEB 2. Each of NEB 1 and NEB 2 include wireless nodes (e.g., ID nodes) that a wireless communication interface that broadcast advertising signals over time. The wireless node disposed with the battery in each of NEB 1 and NEB 2 may be attached to or integrated as part of the respective battery. As part of exemplary system 63000, sensor based ID node 1 is disposed within shipping container 24300*a* as shown in FIG. 63. As explained before, ID node 1, as a secondary sensor-based node, has an environmental sensor (e.g., sensor 360) and a wireless communication interface (e.g., interface 375) operative to broadcast environmental sensor data generated by the environmental sensor. The command node of system 63000 (command node 24160 as shown in FIG. 63) is attached to the container and is in wireless communication with each of the wireless nodes in NEB 1 and NEB 2, as well as with ID node 1 (the secondary sensor-based node).

As part of system 63000, command node 24160 is programmatically configured (via program code, such as part of command node management and control code 26425 when executing on the processor 26400 of command node 24160) to be operative to conduct multiple levels of battery-related anomaly monitoring involving multiple wireless nodes as well as the secondary sensor-based node. In particular, command node 24160 is advantageously operative to conduct an initial level of battery-related anomaly monitoring by being operative to wirelessly monitor the advertising signals broadcast by each of the wireless nodes in NEB 1 and NEB 2 for an unanticipated state of ceased broadcasting for at least these wireless nodes according to a communication profile maintained on command node for each of the wireless nodes in NEB 1 and NEB 2, and wirelessly monitor the broadcasted environmental sensor data from the secondary sensor-based node (e.g., ID node 1). Command node 24160 is further programmatically operative to identify an initial level of the battery-related environmental anomaly based on the initial level of battery-related monitoring when both the unanticipated state of ceased broadcasting is detected and the monitored broadcasted environmental sensor data reflects at least a first threshold difference change in the environmental sensor data. Command node 24160 is further programmatically operative to conduct a secondary level of battery-related anomaly monitoring of broadcasts from ID node 1 (as the secondary sensor-based node) in response to the identified initial level of the battery-related environmental anomaly, and initiate the mediation response to the battery-related environmental anomaly based upon the secondary level of battery-related anomaly monitoring by broadcasting a layered alert notification.

Command node 24160, as part of system 63000, may be further configured to be operative to conduct the secondary level of battery-related anomaly monitoring by wirelessly monitoring the advertising signals broadcast by the wireless nodes in NEB 1 and NEB 2 for an additional unanticipated state of ceased broadcasting according to the communication profile maintained on command node 24160 for the wireless nodes in NEB 1 and NEB 2, and wirelessly monitoring for additional environmental sensor data from ID node 1 (as the secondary sensor-based node) to verify the initial level of the battery-related environmental anomaly.

As with system 62000, some embodiments of system 63000 may have the reporting rate from ID node 1 (as the secondary sensor-based node) being changed as a refinement. For example, command node 24160 may be further programmatically configured to be operative to conduct the secondary level of battery-related anomaly monitoring by instructing ID node 1 (as the secondary sensor-based node) to broadcast the environmental sensor data at a second messaging rate that exceeds an initial messaging rate (e.g., a rate of broadcasting set as an initial value correlated to an environmental risk associated with the battery in NEB 1 or the battery in NEB 2). The second messaging rate for ID node 1 (as the secondary sensor-based node) may be a predetermined higher messaging rate based upon a type of material existing within the battery of NEB 1 or NEB 2. Once instructing ID node 1 to use the second messaging rate, the command node may initiate the mediation response to the battery-related environmental anomaly in response to the secondary level of battery-related anomaly monitoring by broadcasting the layered alert notification when both another unanticipated state of ceased broadcasting is detected and the broadcasted environmental sensor data broadcast at the second messaging rate reflects at least the first threshold difference change in the environmental sensor data.

In a further embodiment of system 63000, command node 24160 may be further programmatically configured to be operative to conduct the secondary level of battery-related anomaly monitoring by being operative to (a) wirelessly monitor the advertising signals broadcast by the wireless nodes in NEB 1 and NEB 2 for an additional unanticipated state of ceased broadcasting according to the communication profile maintained on command node 24160; (b) wirelessly monitoring for additional environmental sensor data from ID node 1 (as the secondary sensor-based node) to verify the initial level of the battery-related environmental anomaly; and (c) identify the secondary level of battery-related anomaly when both another unanticipated state of ceased broadcasting is detected and the broadcasted environmental sensor data reflects at least a second threshold difference change in the environmental sensor data (where the second threshold difference change is greater than the first threshold difference change).

In additional embodiments of system 63000, command node 24160 may initiate different types of mediation responses. For example, the broadcasted layered alert notification from command node 24160 may cause activation of an automatic fire suppression system (e.g., exemplary onboard fire suppression system 25010) targeting the container 24300*a* having the battery of NEB 1 and NEB 2. In another example, the broadcasted layered alert notification from command node 24160 may be a message requesting manual fire suppression of one of the batteries in NEB 1 or NEB 2 (e.g., a message that directs a display on external transceiver 24150 to display a prompted message that requests manual fire suppression for the battery in NEB 1 or NEB 2). In a further example, the broadcasted layered alert notification from command node 24160 may be a message requesting preparations to cease transportation of the battery in NEB 1 or NEB 2 (e.g., a message providing guidance to a preferred location, such as where the transit route started, a close by intermediate destination, and the like). In still another example, the broadcasted layered alert notification from command node 24160 may be a message to inform an entity associated with the battery in NEB 1 or NEB 2 (e.g., a battery supplier, shipping client for that battery, a recipient that is to receive the battery after transport, and the like) that the battery needs replacement.

As part of NEB 1 or NEB 2 used in system 63000, the wireless node disposed with the battery in NEB 1 and the wireless node disposed with the battery in NEB 2 may each maintain battery specifier data related to the respective associated battery used in NEB 1 or NEB 2. Exemplary battery specifier data related to the particular battery may be maintained, for example, as part of profile data 330 maintained in memory of the wireless node shown as part of NEB 1 and NEB 2. As such, the layered alert notification related to the battery in NEB 1 or NEB 2 may include an identification of the particular battery in NEB 1 or NEB 2 based upon the battery specifier data. Such battery specifier data may be pre-programmed into the node memory of the wireless nodes of NEB 1 and NEB 2 when the respective wireless node is associated with the respectively associated battery (e.g., during manufacture, during packaging for transport, and the like).

Similar to embodiments of system 62000, embodiments of system 63000 may have the mediation response depending upon usage context data maintained relative to the battery in NEB 1 and NEB 2. For example, as part of exemplary system 63000 shown in FIG. 63, command node 24160 may be further programmatically configured to be operative to identify the mediation response based upon the secondary level of battery-related anomaly monitoring as well as upon usage context data related to the subset of batteries (e.g., the batteries in NEB 1 and NEB 2). In one embodiment, such usage context data may indicate an active usage status of the particular battery. Examples of such an active usage status may be a present battery charging state (e.g., a standby state, a charging state, and a discharging state) or a current battery health state (e.g., charge cycle count, delivered voltage, internal resistance, current charge capacity, and the like).

In some embodiments, the wireless nodes disposed with the batteries in NEB 1 and NEB 2 may be deployed with a power sensor (e.g., a type of sensor 360 connected to a battery, such as sensor 57360a connected to terminals 57005 and 57010 of battery 57002 shown in FIG. 57). Such a power sensor is operative to detect the active usage status of the particular one of the batteries. In this situation, the advertising signals broadcast by the wireless nodes in system 63000 may include usage context data indicating the active usage status as detected by the power sensor and, in some embodiments, may allow command node 24160 to identify or update the usage context data when wirelessly monitoring the advertising signals.

In another embodiment, the usage context data may indicate a location of the battery used in NEB 1 and NEB 2. For example, the usage context data may include information on the battery's proximity to other important items (e.g., mission critical or sensitive electronics that may be damaged by smoke or heat) or dangerous/hazardous materials within container 24300a or situated near the location of NEB 1 or NEB 2 as disposed within container 24300a (e.g., materials that may catch fire and cause a larger explosion). The usage context data may indicate a risk factor associated with the location of the NEB 1 battery and a risk factor associated with the location of the NEB 2 battery—e.g., information on whether that particular battery is within a specific distance from fuel used by the transit vehicle 24200 so that an anomaly with that battery may cause a larger issue with such fuel (such as flames that may cause a larger explosion). As such, consideration of usage context data of these types allow command node 24160 to dynamically adjust the type of mediation response to automatically and quickly initiate the appropriate mediation response.

A further embodiment of system 63000 as illustrated in FIG. 63 may include multiple wireless nodes disposed with respective different batteries (e.g., the ID nodes disposed with each of the batteries in NEB 1 and NEB 2), multiple secondary sensor-based nodes disposed at different locations within the shipping container (e.g., sensor-based ID nodes 1-3 located separately within shipping container 24300a), a command node attached to the shipping container (e.g., command node 24160 attached to shipping container 24300a), and further include an external transceiver in communication with the command node (e.g., exemplary external transceiver 24150) and disposed external to the shipping container (e.g., external to shipping container 24300a and disposed on transit vehicle 24200).

In this further embodiment of system 63000, command node 24160 is programmatically configured (via program code, such as part of command node management and control code 26425 when executing on the processor 26400 of command node 24160) to be operative to conduct an initial level of battery-related anomaly monitoring by being operative to wirelessly monitor the advertising signals broadcast by each of the wireless nodes for an unanticipated state of ceased broadcasting associated with at least one of the wireless nodes according to a communication profile maintained on the command node for each of the wireless nodes, and wirelessly monitoring the broadcasted environmental sensor data from each of the secondary sensor-based nodes; identify an initial level of the battery-related environmental anomaly based on the initial level of battery-related monitoring when both the unanticipated state of ceased broadcasting is detected for at least one of the wireless nodes and the monitored broadcasted environmental sensor data from the secondary sensor-based nodes reflects at least one of the secondary sensor-based nodes detects a first threshold difference change in the environmental sensor data within the first time period. Command node 24160 is further programmatically operative, as part of this further embodiment of system 63000, to conduct a secondary level of battery-related anomaly monitoring of broadcasts from the secondary sensor-based nodes in response to the identified initial level of the battery-related environmental anomaly over a second time period, and initiate the mediation response to the battery-related environmental anomaly based upon the secondary level of battery-related anomaly monitoring by broadcasting a layered alert notification to the external transceiver. In response, this further embodiment of system 6300 has the external transceiver (e.g., external transceiver 24150) receiving the layered alert notification and responsively initiating the mediation response to the battery-related environmental anomaly.

This further embodiment of system 63000 may have command node 24160 further programmatically configured to be operative to conduct the secondary level of battery-related anomaly monitoring by wirelessly monitoring the advertising signals broadcast by the wireless nodes for an additional unanticipated state of ceased broadcasting in the second time period according to the communication profile, and wirelessly monitoring for additional environmental sensor data from the secondary sensor-based nodes to verify the initial level of the battery-related environmental anomaly.

This further embodiment of system 63000 may have command node 24160 being further programmatically configured to be operative to conduct the secondary level of battery-related anomaly monitoring by instructing some or all of the secondary sensor-based nodes to broadcast their respective environmental sensor data at a second messaging rate that exceeds an initial broadcast rate. Such an initial messaging rate for the secondary sensor-based nodes may be implemented with an initial value correlated to an environmental risk associated with one or more of the batteries associated with the wireless nodes (e.g., the batteries in NEB 1 and NEB 2) or other batteries within the shipping container 24300*a*. The second messaging rate may be implemented at a predetermined higher messaging rate based upon a type of material existing within one or more of the batteries associated with the wireless nodes (e.g., the batteries in NEB 1 and Neb 2) or other batteries within the shipping container 24300*a*. In more detail, command node 24160 may, as part of the further embodiment of system 63000, be further programmatically configured to be operative to initiate the mediation response to the battery-related environmental anomaly in response to the secondary level of battery-related anomaly monitoring by broadcasting the layered alert notification to the external transceiver when both another unanticipated state of ceased broadcasting is detected and the broadcasted environmental sensor data broadcast at the second messaging rate reflects at least the first threshold difference change in the environmental sensor data over the second time period.

In this further embodiment of system 63000, command node 24160 may be further programmatically configured to be operative to conduct the secondary level of battery-related anomaly monitoring by being operative to wirelessly monitor the advertising signals broadcast by the wireless nodes (e.g., those wireless nodes in each of NEB 1 and NEB 2) for an additional unanticipated state of ceased broadcasting in the second time period according to the communication profile maintained on the command node, wirelessly monitor for additional environmental sensor data from the secondary sensor-based nodes to verify the initial level of the battery-related environmental anomaly, and identify the secondary level of battery-related anomaly when both another unanticipated state of ceased broadcasting is detected and the broadcasted environmental sensor data reflects at least a second threshold difference change in the environmental sensor data over the second time period, wherein the second threshold difference change is greater than the first threshold difference change.

In this further embodiment of system 63000, the external transceiver may be implemented by an integrated transceiver interface of an automatic fire suppression system (e.g., transceiver 32010 of fire suppression system 25010). As such, the broadcasted layered alert notification from command node 24160 causes the external transceiver (e.g., transceiver 32010) to activate the automatic fire suppression system (e.g., system 25010) targeting the container. In another example, the external transceiver in this further embodiment of system 63000 may be a display where visual and/or audible messages may be presented. As such, the broadcasted layered alert notification from command node 24160 may cause the display (e.g., display 40015) on the external transceiver to generate a message requesting manual fire suppression of the container either visually, through sound, or via a special alarm generated reflecting the particular message for a manual fire suppression request; or generate a message requesting preparations to cease transportation of the container (e.g., a message that provides guidance to a preferred location). In a further example, the broadcasted layered alert notification from command node 24160 causes the external transceiver (e.g., external transceiver 25010) to activate generate a message to inform an entity associated with the batteries that at least one of the batteries needs replacement. This may be implemented as a message from external transceiver 25010 to remote server 24100, which may then relay such a message to the intended recipient entity about the necessity of such a replacement.

This further embodiment of system 63000 may also make use of battery specifier data and usage context data as described above when generating the layered alert notification and identifying the appropriate mediation response.

Figure 64:
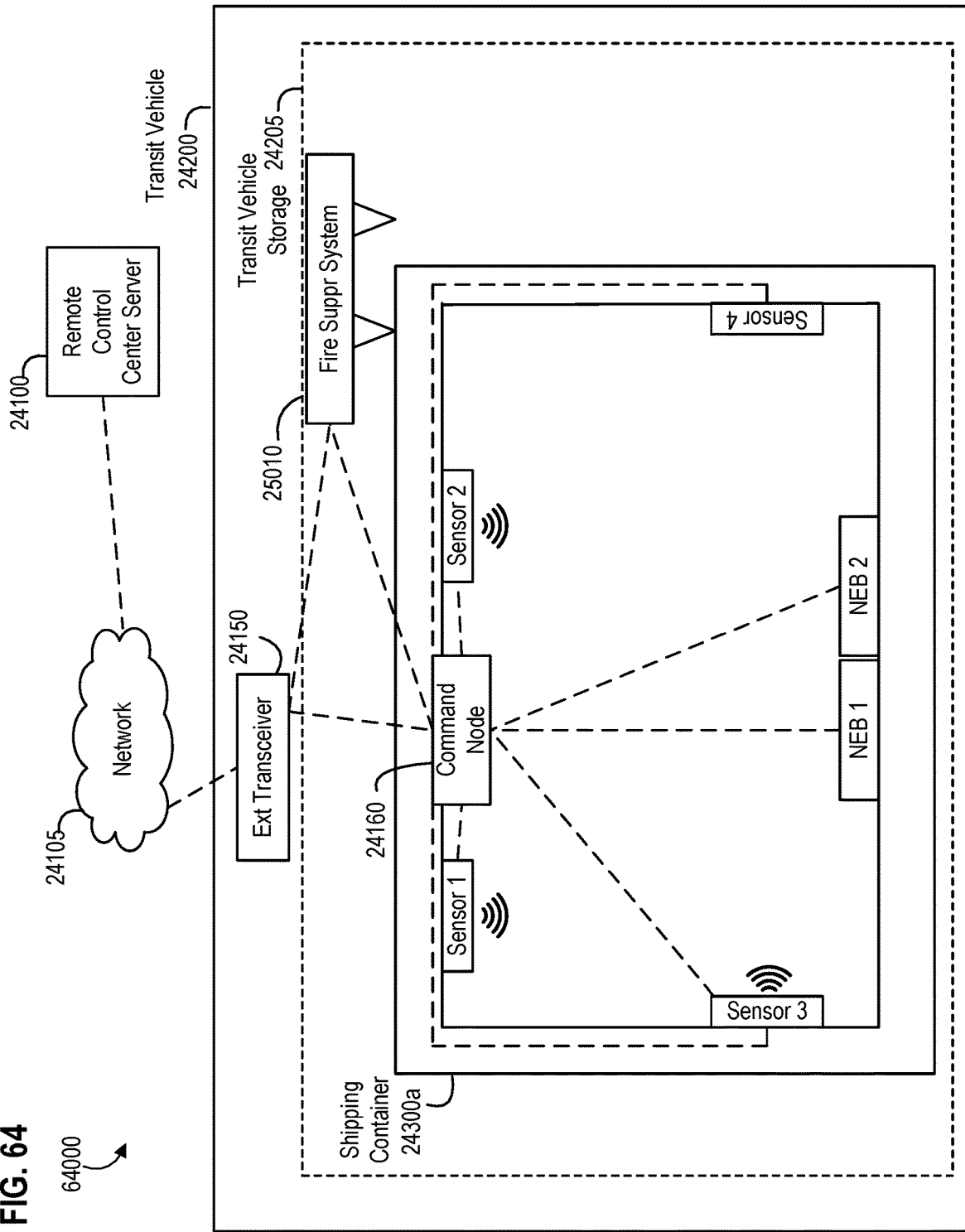
FIG. 64 is a diagram illustrating an exemplary system for layered initiation of a mediation response to a battery-related environmental anomaly involving a node-enabled battery apparatus, and a command node deployed with multiple environmental sensors in accordance with an embodiment of the invention.

In still another embodiment, the command node may monitoring a wireless node disposed with at least one of the batteries in a shipping container while also monitoring sensor data generated by the command node's own sensors (e.g., sensors 26465 on exemplary command node 26000). Thus, rather than monitoring separate sensor-based nodes disposed in the container, the command node relies upon and monitors its own environmental sensors as part of a system for layered initiation of a mediation response to an environmental anomaly. FIG. 64 is a diagram illustrating an exemplary system for layered initiation of a mediation response to a battery-related environmental anomaly involving a node-enabled battery apparatus, and a command node deployed with multiple environmental sensors in accordance with an embodiment of the invention. Referring now to FIG. 64, exemplary system 64000 is shown with a similar shipping container 24300*a* on a transit vehicle 24200 having an external transceiver 24150 and an onboard fire suppression system 25010. The shipping container 24300*a* shown in FIG. 64 has exemplary command node 24160 disposed on the container 24300*a* (e.g., attached to, temporarily or permanently fixed to, or integrated as part of container 24300*a*) and wireless nodes disposed with each of NEB 1 and NEB 2 (e.g., two of the possible node-enabled batteries that may be maintained within container 24300*a*). Such wireless nodes may be disposed with the batteries of NEB 1 or NEB 2 by being attached to or integrated with the respective one of the batteries.

As illustrated in FIG. 64, command node 24160 includes multiple environmental sensors (e.g., sensors 1-4) disposed within the container as part of the command node 24160, even if some or all of such sensors are remotely coupled back to command node 24160 (e.g., an RF environmental sensor that is wirelessly coupled to the processor in command node 24160 or other wired environmental sensors coupled to the processor in command node 24160). The command node 24160 generates environmental sensor data upon environmental conditions at different locations within the container 24300*a* as sensed by each of the environmental sensors 1-4. Command node also has a wireless communication interface with which it can communicate with the wireless nodes within NEB 1 and NEB 2.

As part of system 64000, command node 24160 is programmatically configured to be operative to conduct an initial level of battery-related anomaly monitoring by being further operative to wirelessly monitor the advertising signals broadcast by the wireless node in, for example, NEB 1, for an unanticipated state of ceased broadcasting during a first time period according to a communication profile maintained on command node 24160 for that wireless node; wirelessly monitor the environmental sensor data generated from the command node's sensors 1-4 over the first time period; and identify an initial level of the battery-related environmental anomaly based on the initial level of battery-related monitoring when both the unanticipated state of ceased broadcasting is detected and the monitored broadcasted environmental sensor data reflects at least a first threshold difference change in the environmental sensor data. Command node 24160, as part of system 64000, is also programmatically configured to be operative to conduct a secondary level of battery-related anomaly monitoring over a second time period of at least the environmental sensor data generated by sensors 1-4 in response to the identified initial level of the battery-related environmental anomaly, and initiate the mediation response to the battery-related environmental anomaly based upon the secondary level of battery-related anomaly monitoring by broadcasting a layered alert notification.

In a further embodiment of system 64000, command node 24160 may be further configured to be operative to conduct the secondary level of battery-related anomaly monitoring by wirelessly monitoring the advertising signals broadcast by the wireless node in NEB 1, for example, for an additional unanticipated state of ceased broadcasting over the second time period according to the communication profile maintained on command node 24160 for NEB 1, and wirelessly monitoring for additional environmental sensor data from the environmental sensors 1-4 over the second time period to verify the initial level of the battery-related environmental anomaly.

In still another embodiment of system 64000, command node 24160 may be further programmatically configured to be operative to conduct the secondary level of battery-related anomaly monitoring by generating the environmental sensor data at a second detection rate that exceeds an initial detection rate (e.g., a rate set at an initial value correlated to an environmental risk associated with one or more of the batteries on the shipping container). The second detection rate may be a predetermined higher detection rate based upon a type of material existing within one or more of the batteries on the shipping container. For example, the command node may be further programmatically configured to be operative to initiate the mediation response to the battery-related environmental anomaly in response to the secondary level of battery-related anomaly monitoring by broadcasting the layered alert notification when both (a) another unanticipated state of ceased broadcasting is detected over the second time period and (b) the monitored environmental sensor data detected by sensors 1-4 over the second time period at the second detection rate reflects at least the first threshold difference change in the environmental sensor data over the second time period.

In another embodiment of system 64000, command node 24160 may be further programmatically configured to be operative to conduct the secondary level of battery-related anomaly monitoring by being operative to wirelessly monitor the advertising signals broadcast by the system's wireless node (e.g., the ID node in NEB 1) for an additional unanticipated state of ceased broadcasting over the second time period according to the communication profile; wirelessly monitor for additional environmental sensor data from sensors 1-4 over the second time period to verify the initial level of the battery-related environmental anomaly; and identify the secondary level of battery-related anomaly when both another unanticipated state of ceased broadcasting is detected during the second time period and the broadcasted environmental sensor data reflects at least a second threshold difference change in the environmental sensor data (where the second threshold difference change is greater than the first threshold difference change).

In embodiments of system 64000, similar to the other embodiments described above, there may be different types of initiated mediation responses based on the broadcasted layered alert notification. For example, the broadcasted layered alert notification from command node 24160 may cause activation of an automatic fire suppression system targeting the container (e.g., fire suppression system 25010). In another example, the broadcasted layered alert notification from command node 24160 may be a message requesting manual fire suppression for the container, a message requesting preparations to cease transportation of the batteries within the container (such as guidance to a preferred locations), or a message to inform an entity associated with the batteries that the at least one battery needs replacement as described in more detail above relative to system 63000 and its various embodiments.

Embodiments of system 64000 may also make use of battery specifier data and usage context data as described above when generating the layered alert notification and identifying the appropriate mediation response.

Backup Validation of Detected Environmental Anomaly

Additional embodiments have the capability of validating or verifying a detected environmental anomaly before acting upon such a detected issue to issue alerts or notifications that cause or initiate appropriate mediation responses. This may help prevent issues of a particular command node begins to malfunction, especially as the command node may be disposed within the shipping container where such an environmental anomaly may occur. For example, a command node's wireless communication interface may begin to fail which may otherwise indicate wireless nodes around the command node being monitored appear to cease broadcasting. If the command node's wireless communication was normally operating, no longer detecting wireless nodes broadcasting when they are anticipated to be broadcasting may indicate the presence of an environmental anomaly (e.g., fire) within the command node's shipping container. But with the command node's wireless communication beginning to fail, there may be no environmental anomaly and simply the wireless communication interface is broken. Thus, by deploying an enhanced shipping container with multiple command nodes (a primary that conducts what may be considered primary monitoring, and a secondary that conducts a verification of what the primary has detected to be an environmental anomaly where either or both may be deployed with their own respective command node sensors) itself or as part of a system, embodiments described below help avoid such mistaken detections of environmental anomalies. Further embodiments may use redundant transceivers as part of the wireless communication interface in a shipping container's command node where one transceiver performs the primary monitoring operation and the second transceiver may perform the verification operation to ensure there was no issue with the first transceiver that detected an environmental anomaly.

Figure 65:
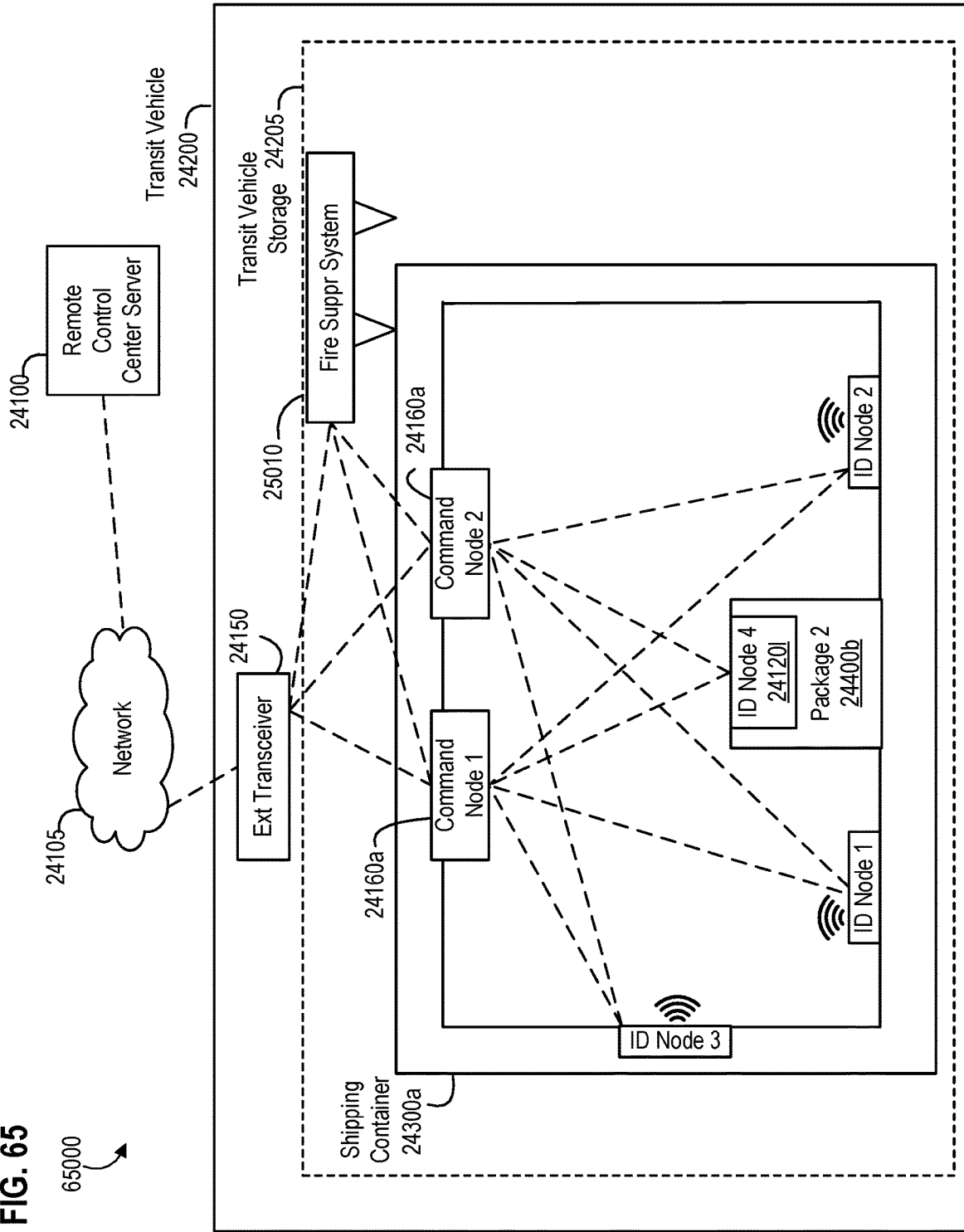
FIG. 65 is a diagram illustrating an exemplary enhanced system for detecting and verifying an environmental anomaly within an improved shipping container having primary and secondary command nodes in accordance with an embodiment of the invention.

FIG. 65 is a diagram illustrating an exemplary enhanced system for detecting and verifying an environmental anomaly within an improved shipping container having primary and secondary command nodes in accordance with an embodiment of the invention. Referring now to FIG. 65, exemplary system 65000 is shown with similar components as system 44000 in FIG. 44 (e.g., transit vehicle 24200, remote server 24100, network 24015, external transceiver 24150, onboard fire suppression system 25010, and shipping container 24300*a*), but FIG. 65 illustrates the exemplary shipping container 24300*a* as housing multiple command nodes (e.g., command node 1 also referenced as 24160*a*, command node 2 also referenced as 24160*b*) and sensor-based ID nodes 1-4 shown disposed in different locations within the container 24300*a*.

In more detail, sensor-based ID nodes 1-2 are shown disposed on the bottom floor of shipping container 24300*a* (sitting freely or attached) while sensor-based ID node 3 is integrated as part of the container 24300*a* on a wall of the container. Sensor-based ID node 4 is associated with (e.g., attached to or disposed within) package 2 24400*b* as shown in FIG. 65. As implementations of an exemplary ID node 120*a* having one or more sensors 360, each of sensor-based ID nodes 1-4 shown in FIG. 65 has an ID node processor, an environmental sensor, and a wireless radio transceiver (which may be implemented as a software defined radio (SDR)). The ID node's sensor is coupled to the ID node processor and generates sensor data related to an environmental condition proximate the respective sensor-based ID node within the shipping container. The wireless radio transceiver is also coupled to the ID node processor and operative to broadcast signals that include the sensor data in response to a command from the ID node's processor. As such, each of the sensor-based ID nodes 1-4 shown in FIG. 65 generate sensor data from and about the environment proximate their respective locations within shipping container 24300*a*.

Each of command node 1 and command node 2 shown in FIG. 65 may be implemented similarly to that explained above relative to exemplary command node 26000, where each command node has at least a command node processor coupled to one or more communications interfaces and may also include one or more environmental sensors so that the respective command node may monitor its own generated sensor data as well as the sensor data from monitored sensor-based ID nodes. In one embodiment, each command node's communications interface may be operative to communicate with the sensor-based ID nodes 1-4, the other command node, as well as externally disposed components, such as external transceiver 24150 and/or fire suppression system 25010. However in another embodiment, a first communication interface may be operative to communicate with each of the sensor-based ID nodes 1-4 using a first wireless communication format compatible with the wireless radio transceiver on each of the sensor-based ID nodes, while a second communication interface is operative to communicate with the external transceiver associated with the transit vehicle using a second wireless communication format compatible with the external transceiver (as well as other command nodes). Those skilled in the art will also appreciate the each of command node 1 and command node 2 may be implemented as a master node (e.g., exemplary master node 110*a* that may include its own sensors as well as location circuitry that enables the master node to self-locate).

In operation and as part of an embodiment of system 65000, a first of the command nodes in shipping container 24300*a* (e.g., command node 1) is programmatically configured via its onboard executing programming (e.g., code that is part of command node control and management code 26425 on command node 1) to be operative to detect the sensor data broadcasted from the sensor-based ID nodes 1-4 using the first communication interface on command node, responsively identify the environmental anomaly for the shipping container based upon the sensor data detected by command node 1, and transmit a validation request over the second communication interface of command node 1 to command node 2 (where the validation request is a request to verify the environmental anomaly for the shipping container 24300*a* identified by command node 1). The second of the command nodes (e.g., command node 2) is programmatically configured via its onboard executing programming (e.g., additional code that is part of command node control and management code 26425 on command node 2) to be operative to detect the sensor data broadcasted from the sensor-based ID nodes 1-4 using the first communication interface on command node 2, receive the validation request from command node 1, verify the environmental anomaly for the shipping container 24300*a* in response to the validation request and based upon the sensor data detected by command node 2, and broadcast a verification message over the second communication interface of command node 2 based upon whether the environmental anomaly for the shipping container 24300*a* is verified by command node 2. In this way, command node 1 and command node 2 advantageous interact to allow for validation of their monitoring and verification of the environmental anomaly detected prior to sending out the verification message, which can initiate a mediation response.

In more detail, the exemplary system 65000 may have command node 2 broadcasting the verification message as a validated alert notification (e.g., an instruction) to the external transceiver 24150 to cause the external transceiver 24150 to initiate a mediation response to the environmental anomaly. In one example, the mediation response may cause the external transceiver 24150 to generate a secondary mediation response notification for an operator of the transit vehicle as a targeted mediation recipient (e.g., a prompted visual or audible message generated as the second mediation response notification requesting the operator of the transit vehicle to alter movement of the transit vehicle 24200). In another example, the mediation response may cause the external transceiver 24150 to generate a similar type of secondary mediation response notification for a logistics crew member of the transit vehicle 24200 as a targeted mediation recipient (e.g., a prompted visual or audible message generated as the secondary mediation response notification requesting the logistics crew member to inspect the enhanced shipping container 24300*a*). In still another example, the mediation response may cause the external transceiver 24150 to generate a secondary mediation response notification that activates fire suppression system 25010 within the transit vehicle 24200 and outside the shipping container 24300*a*.

In an embodiment of system 65000, it may be the first command node that notifies the external transceiver. For example, command node 2 may broadcast the verification message by transmitting the verification message to command node 1, which is further programmatically configured to transmit a validated alert notification over the second communication interface of command node 1 in response to receipt of the verification message from command node 2. With command node 1 transmitting the validated alert notification (as an instruction) to the external transceiver 24150, command node 1 may cause the external transceiver 24150 to initiate a mediation response to the environmental anomaly. As such and in one example, the mediation response may cause the external transceiver 24150 to generate a secondary mediation response notification for an operator of the transit vehicle as a targeted mediation recipient, where the second mediation response notification requests the operator of the transit vehicle to alter movement of the transit vehicle 24200. In another example, the mediation response causes the external transceiver 24150 to generate a secondary mediation response notification for a logistics crew member of the transit vehicle as a targeted mediation recipient (where the secondary mediation response notification requests the logistics crew member to inspect the enhanced shipping container 24300a). In still another example, the mediation response may cause the external transceiver 24150 to generate a secondary mediation response notification that activates fire suppression system 25010 within the transit vehicle 24200 and outside the shipping container 24300a.

An embodiment of system 65000 may have command node 1 being further configured to responsively identify the environmental anomaly for the shipping container 24300a when (a) the broadcasted sensor data detected by command node 1 does not include sensor data from at least a threshold number of the sensor-based ID nodes 1-4 and (b) the broadcasted sensor data detected by command node 1 indicates an environmental condition that exceeds an environmental threshold maintained by command node 1. Likewise, further details on how command node 2 verifies the environmental anomaly as part of an embodiment of system 65000 may have command node 2 being further configured to responsively verify the environmental anomaly for the shipping container 24300a when (a) the broadcasted sensor data detected by command node 2 does not include sensor data from at least a threshold number of the sensor-based ID nodes and (b) the broadcasted sensor data detected by the command node 2 indicates an environmental condition that exceeds an environmental threshold maintained by command node 2.

When command node 2 is verifying the environmental anomaly, an embodiment may adjust messaging rates as a way to adjust data quality and refine the verification process. For example, an embodiment may have each of sensor-based ID nodes 1-4 maintaining a broadcast profile that defines a first messaging rate and a second messaging rate (where first messaging rate is slower than the second messaging rate). These two messaging rates may regulate how often the sensor data generated by a respective sensor-based ID node is broadcast. Command node 1 may be further operative to detect the sensor data broadcasted from the sensor-based ID nodes 1-4 using the first messaging rate. However, in this embodiment, command node 2 may be further operative to verify the environmental anomaly in response to the validation request by instructing each of the sensor-based ID nodes 1-4 to broadcast future generated sensor data at the second messaging rate, detect the sensor data broadcasted from the sensor-based ID nodes 1-4 using the second messaging rate over the first communication interface on command node 2, and verify the environmental anomaly for the shipping container based upon the sensor data detected by the second of the command nodes broadcast by the sensor-based ID nodes using the second messaging rate.

Rather than using multiple command nodes (such as command node 1 and command node 2), another system embodiment may provide similar verification functionality by using multiple transceivers within a particular command node where one transceiver does the primary monitoring and the other transceiver performs a type of redundant verification. For example, such an embodiment may generally include multiple sensor-based ID nodes (e.g., ID nodes 1-4 shown in FIG. 65) and a multi-transceiver equipped command node (e.g., exemplary command node 24160a or command node 1 shown in FIG. 65). The sensor-based ID nodes 1-4 as similarly configured as described above. In this embodiment, command node 1 is mounted to the shipping container 24300a (as shown in FIG. 65), and includes at least a processor and two communication interfaces coupled to the processor. The first communication interface has a first transceiver and a second transceiver where both are operative to communicate with each of the sensor-based ID nodes 1-4 using a first wireless communication format compatible with the wireless radio transceiver on each of the sensor-based ID nodes. The second communication interface is operative to communicate with the external transceiver 24150 associated with the transit vehicle 24200 using a second wireless communication format compatible with the external transceiver 24150 (and command node 2).

In operation and as part of this additional embodiment, command node 1 is programmatically configured to be operative to detect the sensor data broadcasted from the sensor-based ID nodes 1-4 using the first transceiver of the first communication interface on command node 1; responsively identify the environmental anomaly for the shipping container 24300a based upon the sensor data detected using the first transceiver of the first communication interface on command node 1; verify the environmental anomaly for the shipping container based upon the sensor data as detected by the second transceiver of the first communication interface of command node 1; and broadcast a verification message over the second communication interface based upon whether the environmental anomaly for the shipping container is verified using the sensor data as detected by the second transceiver of the first communication interface of command node 1. Thus, in this additional embodiment the same command node performs both the primary monitoring operating that may detect the environmental anomaly and the verification process using different transceivers on the same command node.

This additional system embodiment may have command node 1 being further programmatically configured to broadcast the verification message as a validated alert notification (e.g., an instruction) over the second communication interface to the external transceiver to cause the external transceiver 24150 to initiate a mediation response to the environmental anomaly. Such a mediation response, for example, may cause the external transceiver 24150 to generate a secondary mediation response notification for an operator of the transit vehicle 24200 as a targeted mediation recipient (where the second mediation response notification is a prompted visual or audio request for the operator of the transit vehicle 24200 to alter movement of the transit vehicle 24200). In another example, the mediation response may cause the external transceiver 24150 to generate a secondary mediation response notification for a logistics crew member of the transit vehicle 24200 as a targeted mediation recipient (where the secondary mediation response notification is a prompted visual or audio request for the logistics crew member to inspect the enhanced shipping container 24300a). In still another example, the mediation response may cause the external transceiver 24150 to generate a secondary mediation response notification that activates fire suppression system 25010 within the transit vehicle 24200 and outside the shipping container 24300a.

Further still, the additional system embodiment may have the command node 1 identifying the anomaly for the shipping container when (a) the broadcasted sensor data detected using the first transceiver does not include the sensor data from at least a threshold number of the sensor-based ID nodes and (b) the broadcasted sensor data detected using the first transceiver indicates an environmental condition that exceeds an environmental threshold. Similarly, this single command node system embodiment may have command node 1 being further configured to verify the environmental anomaly for the shipping container when (a) the broadcasted sensor data detected using the second transceiver does not include the sensor data from at least a threshold number of the sensor-based ID nodes and (b) the broadcasted sensor data detected using the second transceiver indicates an environmental condition that exceeds an environmental threshold.

When command node 1 is verifying the environmental anomaly in this additional system embodiment, a further embodiment may adjust messaging rates as a way to adjust data quality and refine the verification process. For example, a further embodiment may have each of sensor-based ID nodes 1-4 maintaining a broadcast profile that defines a first messaging rate and a second messaging rate (where first messaging rate is slower than the second messaging rate). These two messaging rates may regulate how often the sensor data generated by a respective sensor-based ID node is broadcast. Command node 1 may be further operative to detect the sensor data broadcasted from the sensor-based ID nodes 1-4 using the first transceiver when the sensor-based ID nodes 1-4 broadcast using the first messaging rate. Command node may also be operative to verify the environmental anomaly in response to the validation request by being operative to instruct each of the sensor-based ID nodes 1-4 to broadcast future generated sensor data at the second messaging rate using the second transceiver; detect the sensor data broadcasted from the sensor-based ID nodes 1-4 at the second messaging rate using the second transceiver; and verify the environmental anomaly for the shipping container 24300*a* based upon the sensor data detected by the second transceiver using the second messaging rate.

Still with reference to FIG. 65, an exemplary enhanced shipping container apparatus for detecting and verifying an environmental anomaly may be implemented with exemplary shipping container 24300*a*, exemplary sensor-based ID nodes 1-4, and exemplary command nodes 1 and 2. As shown in FIG. 65, exemplary shipping container 24300*a* is essentially an enclosure that may have a container base portion, walls coupled to the container base portion along one edge, and a container top portion coupled to another edge on each of the container walls. As such, the container base portion, the container walls and the container top portion collectively define an interior storage space within container 24300*a*. And while not specifically shown in FIG. 65, at least one of the container walls provides a resealable access closure that provides selective access to the interior storage space so that packages (such as package 2 24400*b*) or other items (such as ID nodes 1 and 2) may be placed into or removed from the interior storage space of shipping container 24300*a*.

As part of this exemplary enhanced shipping container apparatus embodiment, command node 1 and command node 2 are mounted to shipping container 24300*a* (e.g., along the ceiling within container 24300*a*). Each of command node 1 and command node 1 include at least a command node processor, and a communication interface operatively coupled to the command node processor. The communication interface is operative to communicate with each of the sensor-based ID nodes 1-4 and operative to communicate with the external transceiver 24150 associated with the transit vehicle 24200. As such, the communication of command nodes 1 and 2 may be implemented with a single wireless radio transceiver (e.g., LPWAN, LTE-M1, NB-IOT, or the like whether implemented in hardware, a combination of hardware and software, or as a software defined radio (SDR)) that is capable of short range communications with the sensor-based ID nodes 1-4 but also capable of longer range communications without sacrificing battery life on the command nodes.

In operation, the command nodes (e.g., command node 1 and command node 2) of such an exemplary enhanced shipping container apparatus generally perform the primary monitoring and detecting operation as well as the verification process. In particular, command node 1 in this apparatus embodiment is programmatically configured to be operative to detect the sensor data broadcasted from the sensor-based ID nodes 1-4 using the communication interface on command node 1; responsively identify the environmental anomaly for the shipping container 24300*a* based upon the sensor data detected by command node 1; and transmit a validation request over the communication interface of command node 1 to command node 2 (where the validation request is a request to verify the environmental anomaly for the shipping container 24300*a* identified by command node 1). Command node 2, in this apparatus embodiment, is programmatically configured to be operative to detect the sensor data broadcasted from the sensor-based ID nodes 1-4 using the communication interface on command node 2; receive the validation request from command node 1; verify the environmental anomaly for the shipping container 24300*a* in response to the validation request and based upon the sensor data as detected by command node 2; and broadcast a verification message over the communication interface of command node 2 based upon whether the environmental anomaly for the shipping container 24300*a* is verified by command node 2. Command node 2 may broadcast the verification message as a validated alert notification (e.g., an instruction) to external transceiver 24150 to cause the external transceiver 24150 to initiate a mediation response to the environmental anomaly. The mediation response initiated by the external transceiver 24150 may, for example, cause the external transceiver 24150 to generate a secondary mediation response notification for an operator of the transit vehicle 24200 as a targeted mediation recipient (where the second mediation response notification may be a prompted visual or audio request for the operator of the transit vehicle to alter movement of the transit vehicle). In another example, the mediation response may cause the external transceiver 24150 to generate a secondary mediation response notification for a logistics crew member of the transit vehicle as a targeted mediation recipient, the secondary mediation response notification requesting the logistics crew member to inspect the enhanced shipping container. In still another example, the mediation response may cause the external transceiver 24150 to generate a secondary mediation response notification that activates a fire suppression apparatus (e.g., onboard fire suppression system 25010) within the transit vehicle and outside the shipping container.

This exemplary apparatus embodiment may have command node 2 broadcasting the verification message by first transmitting the verification message to command node 1, which then transmits a validated alert notification (e.g., an instruction to external transceiver 24150) over the communication interface on command node 1 in response to receipt of the verification message from command node 2. As such, the transmitted validated alert notification to the external transceiver 24150 causes the external transceiver 24150 to initiate a mediation response to the environmental anomaly. As noted above, the mediation response may cause the external transceiver 24150 to generate a secondary mediation response notification for an operator of the transit vehicle as a targeted mediation recipient (where the second mediation response notification requests the operator of the transit vehicle to alter movement of the transit vehicle). In another example, the mediation response may cause the external transceiver 24150 to generate a secondary mediation response notification for a logistics crew member of the transit vehicle as a targeted mediation recipient (where the secondary mediation response notification requests the logistics crew member to inspect the enhanced shipping container 24300a). In still another example, the mediation response may cause the external transceiver 24150 to generate a secondary mediation response notification that activates a fire suppression apparatus (e.g. fire suppression system 25010) within the transit vehicle and outside the shipping container. In a further embodiment, such an external transceiver instructed to initiate the mediation response may be a transceiver-equipped fire suppression system. As such, the mediation response may directly cause the transceiver-equipped fire suppression system (e.g., fire suppression system 25010 having transceiver 32010) to dispense a fire suppression material into the shipping container.

Embodiments of the enhanced shipping container apparatus may provide more details on how to identify the environmental anomaly from the sensor data and how to verify the environmental anomaly from the sensor data. For example, command node 1 as part of such an embodiment may be further configured to responsively identify the environmental anomaly for the shipping container when (a) the broadcasted sensor data detected by command node 1 does not include the sensor data from at least a threshold number of the sensor-based ID nodes and (b) the broadcasted sensor data detected by command node 1 indicates an environmental condition that exceeds an environmental threshold. In another example, command node 2 as part of such an embodiment may be further configured to responsively verify the environmental anomaly for the shipping container when (a) the broadcasted sensor data detected by command node 2 does not include the sensor data from at least a threshold number of the sensor-based ID nodes and (b) the broadcasted sensor data detected by command node 2 indicates an environmental condition that exceeds an environmental threshold.

As with the system embodiments described above, when verifying the environmental anomaly, the enhanced shipping container apparatus may adjust messaging rates as a way to adjust data quality and refine the verification process. For example, each of sensor-based ID nodes 1-4 may maintain a broadcast profile that defines a first messaging rate and a second messaging rate (where first messaging rate is slower than the second messaging rate). These two messaging rates may regulate how often the sensor data generated by a respective sensor-based ID node is broadcast. Command node 1 may be further operative to detect the sensor data broadcasted from the sensor-based ID nodes 1-4 using the first messaging rate. Command node 2, in this embodiment, may be further operative to verify the environmental anomaly in response to the validation request by being operative to instruct each of the sensor-based ID nodes 1-4 to broadcast future generated sensor data at the second messaging rate; detect the sensor data broadcasted from the sensor-based ID nodes 1-4 using the second messaging rate using the communication interface on command node 2; and verify the environmental anomaly for the shipping container 24300a based upon the sensor data detected by command node 2 and broadcast by the sensor-based ID nodes 1-4 using the second messaging rate.

In still another embodiment, the enhanced shipping container apparatus may have at least one of the sensor-based ID nodes be an integrated sensor-based ID node (e.g., exemplary sensor-based ID node 3 as shown in FIG. 65) located on the shipping container 24300a as part of some part of the container 24300a (e.g., the floor/base, walls, ceiling, door, etc.)

Figure 66:
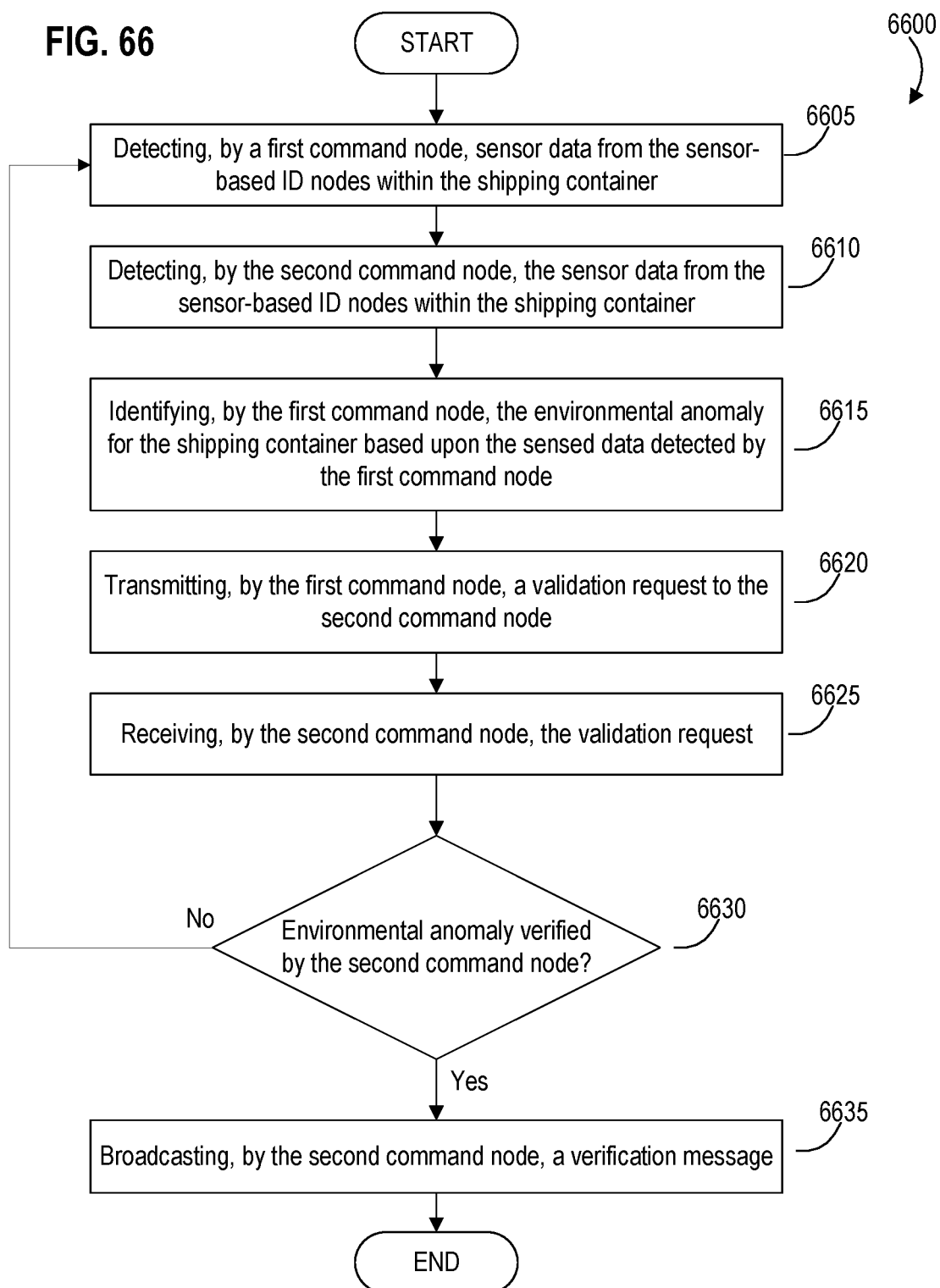
FIG. 66 is a flow diagram illustrating an exemplary enhanced method for detecting and verifying an environmental anomaly related to a shipping container using a first command node mounted to the shipping container, a second command node mounted to the shipping container, and a plurality of sensor-based ID nodes disposed in different locations within the shipping container in accordance with an embodiment of the invention.

Yet another embodiment focuses on the operation of such an enhanced shipping container apparatus as a method for detecting and verifying an environmental anomaly. FIG. 66 is a flow diagram illustrating an exemplary enhanced method for detecting and verifying an environmental anomaly related to a shipping container (e.g., shipping container 24300a) using a first command node (e.g., command node 1) mounted to the shipping container, a second command node (e.g., command node 2) mounted to the shipping container, and a plurality of sensor-based ID nodes (e.g., sensor equipped ID nodes 1-4 shown disposed in different locations within the shipping container 24300a) in accordance with an embodiment of the invention. Referring now to FIG. 66, exemplary method 6600 is described as starting at step 6605 where the first command node is detecting sensor data generated by and broadcast from the sensor-based ID nodes 1-4. At step 6610, method 6600 proceeds with detecting, by the second command node (command node 2), the sensor data generated and broadcast from the sensor-based ID nodes 1-4. As such, steps 6605 and 6610 collectively have each of command nodes 1 and 2 independently monitoring sensor data generated and broadcast by the sensor-based ID nodes 1-4 disposed in different locations of shipping container 24300a.

Primary monitoring operations by the first command node (command node 1) involves steps 6615 and 6620. As such, at step 6615, method 6600 proceeds with responsively identifying, by the first command node (command node 1), the environmental anomaly for the shipping container based upon the sensor data detected by the first command node. In more detail, step 6615 may have the first command node identifying the environmental anomaly for the shipping container in a multi-mode manner when (a) the broadcasted sensor data detected by the first command node does not include the sensor data from at least a threshold number of the sensor-based ID nodes and (b) the broadcasted sensor data detected by the first command node indicates an environmental condition that exceeds an environmental threshold.

At step 6620, method 6600 proceeds with transmitting, by the first command node, a validation request to the second command node (command node 2). The validation request is a request to verify the environmental anomaly for the shipping container identified by the first command node. At step 6625, method 6600 proceeds with the second command node receiving the validation request from the first command node so that the second command node may begin the verification process.

At decision step 6630, method 6600 has the second command node determining if the environmental anomaly is verified. If not, step 6630 proceeds directly back to steps 6605 and 6610 where further sensor data is detected by the first and second command nodes. However, if the environmental anomaly is verified (i.e., the second command node (command node 2) verifies the environmental anomaly for the shipping container in response to the validation request and based upon the sensor data detected in step 6610 by the second command node), step 6630 proceeds to step 6635. In more detail, step 6630 may have the second command node determining such a verification by responsively verifying the environmental anomaly for the shipping container also in a multi-mode manner when (a) the broadcasted sensor data detected by the second command node does not include the sensor data from at least a threshold number of the sensor-based ID nodes and (b) the broadcasted sensor data detected by the second command node indicates an environmental condition that exceeds an environmental threshold.

At step 6635, method 6600 proceeds with broadcasting, by the second command node, a verification message based upon whether the environmental anomaly for the shipping container is verified by the second command node.

A further embodiment of method 6600 may have step 6635 transmitting, by the second command node, a validated alert notification to an external transceiver to cause the external transceiver to initiate a mediation response to the environmental anomaly. Such a validated alert notification may be implemented as an instruction to cause the external transceiver to initiate the mediation response to the environmental anomaly. Such a mediation response, for example, may cause the external transceiver to generate a secondary mediation response notification for an operator of the transit vehicle as a targeted mediation recipient, the second mediation response notification requesting the operator of the transit vehicle to alter movement of the transit vehicle. In another example, the mediation response may cause the external transceiver to generate a secondary mediation response notification for a logistics crew member of the transit vehicle as a targeted mediation recipient, the secondary mediation response notification requesting the logistics crew member to inspect the enhanced shipping container. In still another example, the mediation response may cause the external transceiver to generate a secondary mediation response notification that activates a fire suppression system (e.g., fire suppression system 25010) that targets the shipping container.

In another embodiment of method 6600, step 6635 may be implemented by transmitting, by the second command node, the verification message to the first command node, which then further has method 6600 transmitting, by the first command node, a validated alert notification to an external transceiver in response to receipt of the verification message from the second command node and to cause the external transceiver to initiate a mediation response to the environmental anomaly. Such a validated alert notification may be an instruction to cause the external transceiver to initiate the mediation response to the environmental anomaly. The initiated mediation response may, for example, cause the external transceiver to generate a secondary mediation response notification for an operator of the transit vehicle as a targeted mediation recipient (where the second mediation response notification requests the operator of the transit vehicle to alter movement of the transit vehicle). In another example, the initiated mediation response may cause the external transceiver to generate a secondary mediation response notification for a logistics crew member of the transit vehicle as a targeted mediation recipient (where the secondary mediation response notification requests the logistics crew member to inspect the enhanced shipping container). In still another example, the initiated mediation response may cause the external transceiver to generate a secondary mediation response notification that activates a fire suppression system (e.g., system 25010) within the transit vehicle and outside the shipping container.

In some embodiments of method 6600, the step of transmitting the validated alert notification to the external transceiver further may be accomplished by transmitting the validated alert notification to a transceiver-equipped fire suppression system as the external transceiver (e.g., system 25010 being equipped with its own transceiver 32010 as shown in FIG. 32C and capable of communication with the command nodes as shown in FIG. 65). Such a validated alert notification may be an instruction for the transceiver-equipped fire suppression system to activate and dispense fire suppression material into the shipping container.

Still further embodiments of method 6600 may have the step of detecting the sensor data by the first command node in step 6605 be implemented as detecting, by the first command node, the sensor data as broadcast from the sensor-based ID node at a first messaging rate, where the first messaging rate and a second messaging rate being defined in a broadcast profile maintained on each of the sensor-based ID nodes, and where each of the first messaging rate and the second messaging rate regulates how often the sensor data generated by a respective sensor-based ID node is broadcast. As part of this embodiment, the first messaging rate is slower than the second messaging rate. As such, the step of verifying the environmental anomaly in response to the validation request as part of step 6630 may be implemented as instructing, by the second command node, each of the sensor-based ID nodes to broadcast future generated sensor data at the second messaging rate; detecting, by the second command node, the sensor data broadcasted from the sensor-based ID nodes using the second messaging rate; and verifying, by the second command node, the environmental anomaly for the shipping container based upon the sensor data detected by the second command node and broadcast by the sensor-based ID nodes using the second messaging rate.

Autonomous Mediation Involving Secure & Trusted Node Interactions

While an exemplary environmental anomaly may be fire within a shipping container or within a package on a shipping container, those skilled in the art will appreciate than an environmental anomaly may generally include a wide variety of arising conditions that are dangerous when related to a shipping container and especially when the shipping container is being transported on a transit vehicle, such as an aircraft. For example, an environmental anomaly may present emergency conditions with intense and rapidly spreading harmful, toxic, or otherwise dangerous conditions (e.g., caustic chemical reactions releasing toxic fumes that may be detected by sensors; explosions that may rapidly spread within a container; extremely flammable goods igniting, combusting, and spreading within the container; or highly combustible fuel vaporizing and catching fire). In such emergency conditions, components used as part of systems and methods that detect and respond to such environmental anomalies may need to quickly and autonomously work in a trusted mode. This may, for example, involve components that validate the communicating/alert issuing device or data itself broadcast from the device, secure communications between devices (e.g., those broadcasting sensor data and those monitoring/reporting based on such sensor data), and components with an overall ability to establish trusted machine-to-machine (M2M) associations or partners in the context of systems and methods that detect and respond to such environmental anomalies. In a particular example, this may include using particular trusted/known sensors (e.g., sensor-based ID nodes) to avoid a situation where a shipping container may contain other sensors or devices that may attempt to spoof the monitoring device (e.g., command nodes) into relying upon the untrusted sensor and device, which may intentionally cease broadcasting to trigger a mediation response under false pretenses. As a way of achieving such autonomy where speed may be achieved without reliance upon delayed device-to-device interactions (e.g., delays or lags when the monitoring device has to confirm connections with a server request for credentials), the monitoring device may locally cache credentials for connecting with nodes in its vicinity as part of such systems and methods that detect and respond to such environmental anomalies. Such systems and methods may also, in some embodiments, involve validation of the message itself as alternative or in addition to validating the device broadcasting the message (e.g., a sensor-based ID node broadcasting signals having sensor data that may be monitored by a command node).

Figure 67:
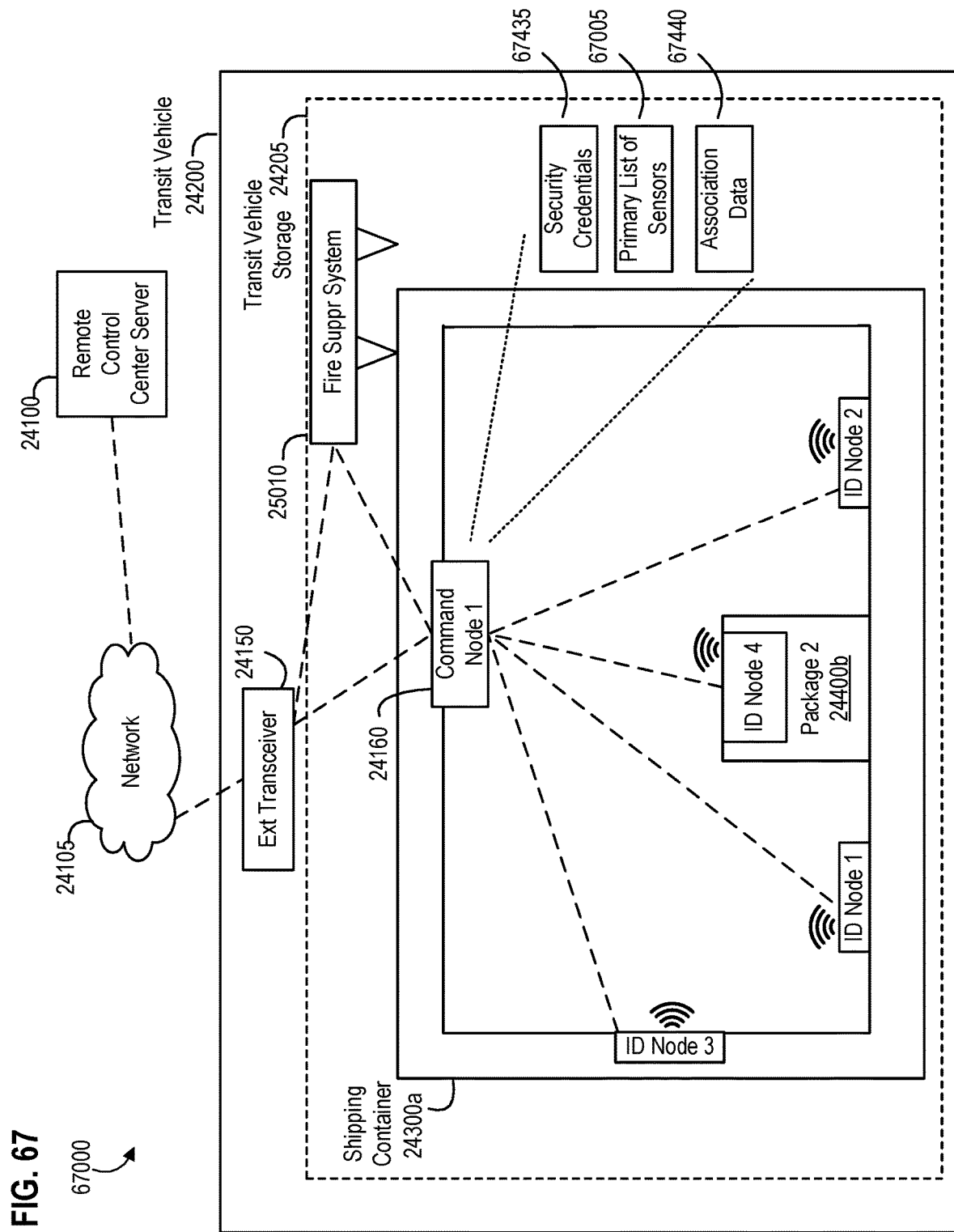
FIG. 67 is a diagram illustrating an exemplary system for securely monitoring a shipping container for an environmental anomaly using elements of a wireless node network that interact with an external transceiver associated with a transit vehicle having at least temporary custody of the shipping container in accordance with an embodiment of the invention.

FIG. 67 is a diagram illustrating an exemplary system for securely monitoring a shipping container for an environmental anomaly using elements of a wireless node network that interact with an external transceiver associated with a transit vehicle having at least temporary custody of the shipping container in accordance with an embodiment of the invention. Referring now to FIG. 67, exemplary system 67000 is shown with similar components as system 65000 in FIG. 65 (e.g., transit vehicle 24200, remote server 24100, network 24015, external transceiver 24150, onboard fire suppression system 25010, and shipping container 24300a), but FIG. 67 illustrates the exemplary shipping container 24300a as housing one command node (e.g., command node 1 also referenced as 24160a) and sensor-based ID nodes 1-4 shown disposed in different locations within the container 24300a.

In more detail, sensor-based ID nodes 1-2 are shown in FIG. 67 being disposed on the bottom floor of shipping container 24300a (sitting freely or attached) while sensor-based ID node 3 is integrated as part of the container 24300a on a wall of the container. Sensor-based ID node 4 is associated with (e.g., attached to or disposed within) package 2 24400b as shown in FIG. 67. As implementations of an exemplary ID node 120a having one or more sensors 360, each of sensor-based ID nodes 1-4 shown in FIG. 67 has an ID node processor, an environmental sensor, and a wireless radio transceiver (which may be implemented in hardware, in a combination of hardware/software/or as a software defined radio (SDR)). The environmental sensor in each ID node is coupled to the ID node processor and generates sensor data related to an environmental condition proximate the respective sensor-based ID node within the shipping container. The wireless radio transceiver is also coupled to the ID node processor and operative to broadcast signals that include the sensor data (in additional to a validation record used to confirm the sensor data broadcast as part of the signal is from that particular ID node) in response to a command from the ID node's processor. As such, each of the sensor-based ID nodes 1-4 shown in FIG. 67 generate sensor data from and about the environment proximate their respective locations within shipping container 24300a.

Exemplary command node 1 illustrated in FIG. 67 may be implemented similarly to that explained above relative to exemplary command node 26000, where the command node has at least a command node processor coupled to one or more wireless transceiver-based communications interfaces as well as a command node memory. In one embodiment, the command node's communications interface may be operative to communicate with sensor-based ID nodes 1-4 as well as externally disposed components, such as external transceiver 24150 and/or fire suppression system 25010. However in another embodiment with multiple communication interfaces, a first communication interface may be operative to communicate with each of sensor-based ID nodes 1-4 using a wireless communication format compatible with the wireless radio transceiver on each of sensor-based ID nodes 1-4, while a second communication interface is operative to communicate with the external transceiver 24150 associated with the transit vehicle 24200 using a second wireless communication format compatible with the external transceiver (as well as other command nodes that may be disposed on the transit vehicle 24200 in other shipping containers). Those skilled in the art will also appreciate command node 1 may be implemented as a master node (e.g., exemplary master node 110a that may include its own sensors as well as location circuitry that enables the master node to self-locate) or a container node that may not have location circuitry. Further, command node 1 may be integrated as part of the shipping container 24300a or be implemented separately (as a separate device) but removably mounted to the shipping container 24300a.

The memory on command node 1 as shown in the embodiment illustrated in FIG. 67 may store and maintain at least command node container management program code (e.g., code that is part of command node control and management code 26425 on command node 1), security credentials 67435 specific to one from a subset of sensor-based ID nodes 1-4 that are to be trusted (e.g., a type of security data 435 explained generally above), a primary list of sensors 67005, and association data 67440 (e.g., a type of association data 440 explained above). Such information on the memory of command node 1 may be initially downloaded from or provided by external transceiver 24150 (as a type of master node that may periodically update nodes lower in the network), which may obtain such information initially from remote server 24100 that may manage such information (e.g., authorize what devices are trusted sensors via establishing the security credentials 67435, generating the primary list of sensors 67005, and authorizing any associations reflected by association data). In more detail, an command node may include the requisite security credentials on which devices are to be trusted at the time of manufacture, thus allowing the command node to validate the sensor-based ID nodes around the particular command node as secure or trusted sensors. Alternatively, another example may have the exemplary command node obtaining the requisite security credentials 67435, primary list of sensors 67005, and any authorizations for association from the backend infrastructure (e.g., external transceiver 24150 and/or remote server 24100) so that the exemplary command node may operate autonomously if not in contact with such backend infrastructure.

In operation and as part of an embodiment of system 67000, command node 1 is programmatically configured via its onboard executing programming (e.g., the command node container management program code that is part of command node control and management code 26425) to be operative to identify which of sensor-based ID nodes 1-4 are trusted sensors disposed within the shipping container 24300a based the security credentials 67435. Those identified are considered confirmed sensor-based ID nodes (e.g., sensor-based ID nodes 1-3 may have security credentials 67435 cached on command node 1 that identify them as trusted sensors and, thus, confirmed sensor-based ID nodes while sensor-based ID node 4 may not have a corresponding security credential within those stored on command node 1). Command node 1 is further programmatically configured to be operative to monitor, via the wireless transceiver-based communication interface, only the confirmed ones of the sensor-based ID nodes (e.g., ID nodes 1-3) for sensor data broadcast from each of the confirmed sensor-based ID nodes while disregarding any sensor data broadcast from those of the sensor-based ID nodes not identified as being confirmed sensor-based ID nodes; detect the environmental anomaly for the shipping container based upon the sensor data monitored from at least one of the confirmed sensor-based ID nodes; automatically generate an alert notification related to the detected environmental anomaly for the shipping container; and cause the wireless transceiver-based communication interface to transmit the alert notification to the external transceiver to initiate a mediation response related to the detected environmental anomaly. As such, this system embodiment relies upon the security credentials to ensure only trusted sensors are monitored when detecting and responding to an environmental anomaly related to the shipping container 24300a.

The processor in command node 1 may, in some embodiments, be further programmatically configured to download the security credentials 67435 (and/or an update for such credentials) and maintain security credentials 67435 as cached security credentials on the command node memory.

Device associations may also be used to identify which of the sensor-based ID nodes are trusted sensors. For example, the command node processor of command node 1 may be programmatically configured to identify which of sensor-based ID nodes 1-4 are trusted sensors by being further programmatically configured to be operative to access one of the security credentials 67435 specific to a particular one of sensor-based ID nodes 1-4 to determine whether that sensor-based ID node is one of the trusted sensors; and establish a trackable association between command node 1 and that sensor-based ID node by generating association data 67440 reflecting the trackable association when the one of the security credentials 67435 specific to the particular one of the sensor-based ID nodes indicates that sensor-based ID node is one of the trusted sensors. As such, the established trackable association confirms that the particular one of the sensor-based ID nodes 1-4 is one of the trusted sensors and reflects that the particular one of sensor-based ID nodes 1-4 is one of the confirmed sensor-based ID nodes (e.g., one of ID nodes 1-3 given the security credentials 67435). In a further embodiment, the trackable association between command node 1 and the particular one of sensor-based ID nodes 1-4 may reflect a permissive secure connection between command node 1 and that particular sensor-based ID node over and through which that sensor-based ID node may securely broadcast its sensor data. In another example, the trackable association between command node 1 and the particular one of the sensor-based ID nodes may also reflect an authorized logical pairing of the command node and that particular sensor-based ID node. As such, the association data generated in that example indicates the authorized logical pairing of command node 1 and that particular one of sensor-based ID nodes 1-4.

In a further embodiment of such a system, the command node processor of command node 1 may be programmatically configured to access the relevant security credentials by being further programmatically configured to be operative to generate a security credential request specific to one of the sensor-based ID nodes 1-4 when none of the security credentials 67435 on the command node memory are specific to that particular one of sensor-based ID node 1-3. Such a security credential request may be transmitted, for example, to external transceiver 24150 or sent to server 24100 as a further level of making sure a particular one of the sensor-based ID nodes in shipping container 24300a may or may not be a trusted sensor and appropriate to monitor when attempting to detect and respond to an environmental anomaly in shipping container 24300a.

As noted above, the command node memory on command node 1 may include and maintain a primary list of sensors 67005 (e.g., as a type of association data 440 related to particular sensors, and which may be updated from external transceiver 24150). As such, the command node processor in command node 1 may be programmatically configured to identify which of sensor-based ID nodes 1-4 are trusted sensors by being further programmatically configured to be operative to access the primary list of sensors 67005 from the command node memory, compare the primary list of sensors 67005 against each of the sensor-based ID nodes 1-4 (e.g., identification information on each of sensor-based ID nodes 1-5 that may be kept as part of sensor data 445) so as to identify a particular subset of sensor-based ID nodes 1-4 on the primary list of sensors 67005; and identify which of the subset of the sensor-based ID nodes is confirmed to be one of the trusted sensors based upon the security credentials and the primary list of sensors.

In a further embodiment, such a system may have command node 1 validating not only the trusted sensors, but also what sensor data is to be trusted based on the sensor data and signals sending the sensor data. For example, the command node processor of command node 1 may be further programmatically configured to be operative to validate the sensor data broadcast from each of the confirmed sensor-based ID nodes (e.g., confirmed ID nodes 1-3) upon receiving the sensor data broadcast from each of the confirmed sensor-based ID nodes, and then detect the environmental anomaly for the shipping container based only upon the sensor data validated by command node 1. In more detail, the command node processor of command node 1 may be programmatically configured to validate the sensor data by being further programmatically configured to cause the wireless transceiver-based communication interface to transmit a validation request to one or more of the confirmed sensor-based ID nodes, and then receive (via the wireless transceiver-based communication interface on command node 1) a validation confirmation from the respective confirmed sensor-based ID node in response to the validation request. Such a validation confirmation indicates that the respective one of the confirmed sensor-based ID nodes receiving the validation request previously broadcast at least part of the sensor data.

In still another embodiment, such a system may have the command node processor of command node 1 being programmatically configured to validate the sensor data by being further programmatically configured to determine which of the sensor data received by the command node during monitoring is valid by assessing a validation record within each of the received sensor data broadcast from each of the confirmed sensor-based ID nodes without requiring the command node to transmit a validation request to each of the confirmed sensor-based ID nodes. For example, command node 1 may monitor a confirmed sensor-based ID node (such as ID node 1) and receive sensor data from ID node 1. The sensor data broadcast from ID node 1 may include a validation record (e.g., a security data structure) that securely reflects and ensures that sensor data from ID node 1 is truly from ID node 1 without incurring the burden of transmitting a validation request to ID node 1 to ensure it was ID node 1 that generated the specific sensor data. In a further example, such a security data structure may be implemented as a hash key generated by confirmed sensor-based ID node 1 that broadcasts the sensor data received by command node 1. Such a hash key may be used by command node 1 as a key into the block or table of sensor data to validate whether it was confirmed sensor-based ID node 1 that actually generated the sensor data sent to command node 1.

Systems may use the sensor data from confirmed sensor-based ID nodes in various ways when detecting an environment anomaly. For example, the command node processor of command node 1 may be programmatically configured to detect the environmental anomaly when the sensor data monitored from at least one of the confirmed sensor-based ID nodes comprises temperature sensor data above a threshold value; or when the sensor data monitored from each of the confirmed sensor-based ID nodes identifies one or more missing confirmed sensor-based ID nodes that are anticipated to be broadcasting; or when the sensor data monitored from each of the confirmed sensor-based ID nodes identifies an unanticipated state of ceased broadcasting from any (or a threshold number) of the confirmed sensor-based ID nodes.

Identifying what sensor-based ID nodes are trusted sensors may, in some embodiments, involve vehicle status data provided by the external transceiver 24150 associated with transit vehicle 24200. For example, the command node processor of command node 1 may be further programmatically configured to receive initial or updated vehicle status data from the external transceiver 24150 associated with transit vehicle 24200, and then identify which of the sensor-based ID nodes is one of the trusted sensors based upon one of the security credentials specific to a respective one of the sensor-based ID nodes and upon a state of the transit vehicle as indicated by the vehicle status data. Such as state of the transit vehicle, as reflected by the vehicle status data, may include a takeoff vehicular status, a cruising vehicle status, a landing vehicular status, and a stationary vehicular status.

Figure 68:
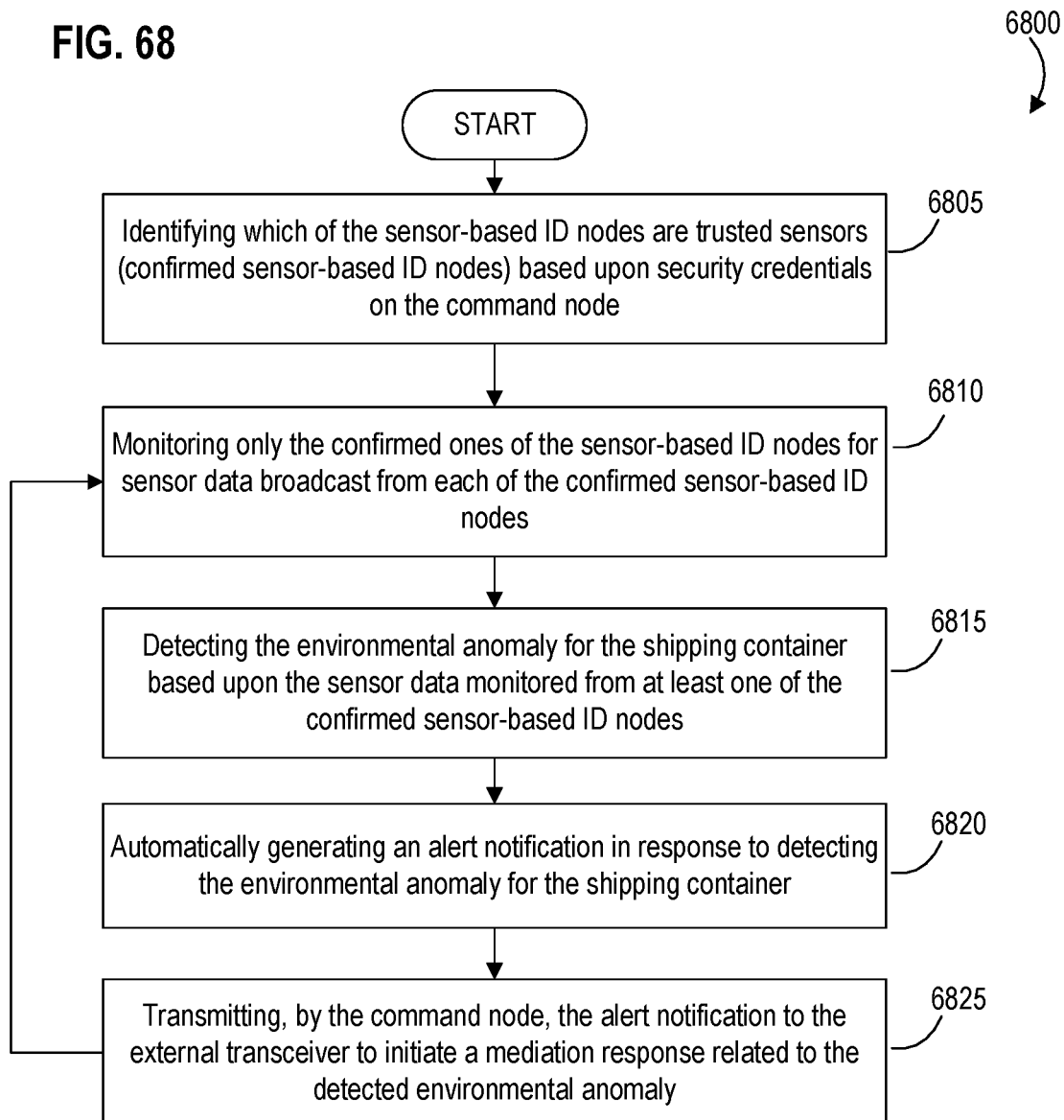
FIG. 68 is a flow diagram illustrating an exemplary method for securely monitoring a shipping container for an environmental anomaly based upon confirmed sensor-based ID nodes used as trusted sensors in accordance with an embodiment of the invention.

Components from the system embodiment described above and its variations may be deployed as operational elements that perform an exemplary method for securely monitoring such a shipping container. FIG. 68 is a flow diagram illustrating an exemplary method for securely monitoring a shipping container for an environmental anomaly based upon confirmed sensor-based ID nodes used as trusted sensors in accordance with an embodiment of the invention. Such an exemplary method 6800 as described on FIG. 68 generally includes multiple sensor-based ID nodes (e.g., ID nodes 1-4 shown in FIG. 67) disposed within the shipping container (e.g., shipping container 24300*a*) and a command node (e.g., command node 1) associated with the shipping container and operative to communicate with each of the sensor-based ID nodes and an external transceiver (e.g., external transceiver 24150) associated with a transit vehicle (e.g., transit vehicle 24200) having at least temporary custody of the shipping container. The sensor-based ID nodes used as part of method 6800 may have at least one being disposed on part of the shipping container (e.g., ID node 1 shown in FIG. 67 being disposed on a base or floor of shipping container 24300*a*) or affixed to an object being transported within the shipping container (e.g., ID node 4 being affixed or attached to package 2 being transported within shipping container 24300*a*). The command node used as part of method 6800 may be implemented, for example, as a container node integrated as part of the shipping container or a master node associated with the shipping container and implemented separately from the shipping container while attached to the shipping container. Further, the transit vehicle used as part of method 6800 may be, for example, an airplane, a railway conveyance, a maritime vessel, or a roadway conveyance.

Referring now to FIG. 68, exemplary method 6800 begins at step 6805 with the command node identifying which of the sensor-based ID nodes is one of the trusted sensors disposed within the shipping container based upon a security credential specific to a respective one of the sensor-based ID nodes, the identified ones of the sensor-based ID nodes being confirmed sensor-based ID nodes. Such a security credential may be cached on the command node or, in some embodiments, method 6800 may also have the command node downloading the security credential and storing as the cached security credential on the command node. In more detail, an embodiment may have step 6805 identifying which of the sensor-based ID nodes is one of the trusted sensors by having the command node obtaining the security credential specific to a particular one of the sensor-based ID nodes to determine whether that particular sensor-based ID node is one of the trusted sensors; and establishing an active association between the command node and that particular sensor-based ID node when the security credential specific to the particular one of the sensor-based ID nodes indicates that particular sensor-based ID node is one of the trusted sensors. Such an established active association confirms that the particular one of the sensor-based ID nodes is one of the trusted sensors and reflects that the particular one of the sensor-based ID nodes is one of the confirmed sensor-based ID nodes. In even more detail, obtaining the security credential described above may have the command node accessing a memory on the command node for a cached copy of the security credential specific to the particular one of the sensor-based ID nodes, or requesting the security credential specific to the particular one of the sensor-based ID nodes from the external transceiver (e.g., external transceiver 24150). Such an active association between the command node and the particular one of the sensor-based ID nodes may, for example, reflect a permissive secure connection between the command node and the particular one of the sensor-based ID nodes over which the particular one of the sensor-based ID nodes securely broadcasts its sensor data. In another example, the active association between the command node and the particular one of the sensor-based ID nodes may reflect an authorized logical pairing of the command node and the particular one of the sensor-based ID nodes, where the active association is represented by association data generated by the command node and maintained on the command node (e.g., association data 67440 shown in FIG. 67). Further still, an embodiment may have step 6805 identifying which of the sensor-based ID nodes is one of the trusted sensors by the command node generating such association data reflecting an authorized logical pairing of the command node and a particular one of the sensor-based ID nodes when the security credential specific to the particular one of the sensor-based ID nodes permits the logical pairing of the command node and the particular one of the sensor-based ID nodes.

At step 6810, method 6800 proceeds with the command node monitoring only the confirmed ones of the sensor-based ID nodes for sensor data broadcast from each of the confirmed sensor-based ID nodes. For example, if the confirmed sensor-based ID nodes include only ID nodes 1-3 and the ID node 4 with package 2 has not been identified as being a trusted sensor, then monitoring as part of step 6810 has command node 1 only monitoring sensor data broadcast from each of ID nodes 1-3 and only ID nodes 1-3 as those sensor-based ID nodes are the trusted sensors identified by command node 1.

At step 6815, method 6800 proceeds with the command node detecting the environmental anomaly for the shipping container based upon the sensor data monitored from at least one of the confirmed sensor-based ID nodes. In more detail, an embodiment of step 6815 may have the command node detecting the environmental anomaly for the shipping container when the sensor data monitored from the at least one of the confirmed sensor-based ID nodes comprises sensor data (e.g., temperature data, pressure data, and the like) is above a threshold value.

In another example, detecting the environmental anomaly may occur as part of step 6815 when the sensor data monitored from each of the confirmed sensor-based ID nodes identifies one or more missing ones of the confirmed sensor-based ID nodes. Stated another way, step 6815 may have the command node detecting the environmental anomaly for the shipping container when the sensor data monitored from each of the confirmed sensor-based ID nodes (e.g., ID nodes 1-3) identifies an unanticipated state of ceased broadcasting from any of the confirmed sensor-based ID nodes (e.g., such as when ID node 2 ceases broadcasting). In more detail, detecting the environmental anomaly may have the command node identifying an unresponsive group from the confirmed sensor-based ID nodes to be in the unanticipated state of ceased broadcasting based upon the monitoring in step 6810, and then detect the environmental anomaly for the shipping container when a size of the identified unresponsive group from the confirmed sensor-based ID nodes exceeds a threshold setting maintained by the command node.

At step 6820, method 6800 proceeds with the command node automatically generating an alert notification related to the detected environmental anomaly for the shipping container. Then, at step 6825, method 6800 proceeds with the command node transmitting the alert notification to the external transceiver to initiate a mediation response related to the detected environmental anomaly (such as generating a prompt message as described above or activating a fire suppression system (e.g., fire suppression system 25010)).

In a further embodiment of method 6800, step 6805 may deploy a two-stage confirmation using both a primary list of sensors (e.g., primary list of sensors 67005 maintained on command node 1 that maybe provided and updated by external transceiver 24150) as well as security credentials (e.g., 67435) maintained on the command node. For example, in such a further embodiment of method 6800, the step of identifying which of the sensor-based ID nodes is one of the trusted sensors may have the command node accessing a primary list of sensors maintained on the command node; comparing the primary list of sensors against each of the sensor-based ID nodes to identify a subset of the sensor-based ID nodes confirmed to be on the primary list of sensors; and identifying which of the subset of the sensor-based ID nodes is one of the trusted sensors based upon the security credential specific to a respective one of the subset of the sensor-based ID nodes, where the identified ones from the subset of the sensor-based ID nodes being the confirmed sensor-based ID nodes.

In still another further embodiment of method 6800, validation of the sensor data itself may be performed. For example, in this further embodiment, method 6800 may also have the command node validating the sensor data broadcast from each of the confirmed sensor-based ID nodes upon receiving the sensor data broadcast from each of the confirmed sensor-based ID nodes. As such, the detecting operation in step 6815 may then have the command node detecting the environmental anomaly for the shipping container based only upon the sensor data validated by the command node. In one example, the validating step may involve having the command node transmitting a validation request to a respective one (or all) of the confirmed sensor-based ID nodes, and receiving a validation confirmation from the respective one (or all) of the confirmed sensor-based ID nodes in response to the validation request. Such a validation confirmation indicates that the respect one (or each) of the confirmed sensor-based ID nodes receiving the validation request previously broadcast at least part of the sensor data.

In another example, the validating step may involve having the command node determining which of the sensor data received by the command node during monitoring is valid by assessing a validation record within each of the received sensor data broadcast from each of the confirmed sensor-based ID nodes without requiring the command node to transmit a validation request to each of the confirmed sensor-based ID nodes. Such a validation record may be implemented as a security data structure (e.g., a hash key as generally described above) with which the command node can process to ensure one of the confirmed sensor-based ID nodes generated the sensor data monitored and received by the command node.

A further embodiment of method 6800 may have the command node receiving vehicle status data provided by the external transceiver associated with the transit vehicle. As such, the identifying operation of step 6805 may be performed by having the command node identifying which of the sensor-based ID nodes is one of the trusted sensors disposed within the shipping container based upon (a) the security credential specific to the respective one of the sensor-based ID nodes and (b) a state of the transit vehicle as indicated by the vehicle status data (e.g., where the state of the transit vehicle may be a takeoff vehicular status, a cruising vehicle status, a landing vehicular status, and a stationary vehicular status).

Figure 69:
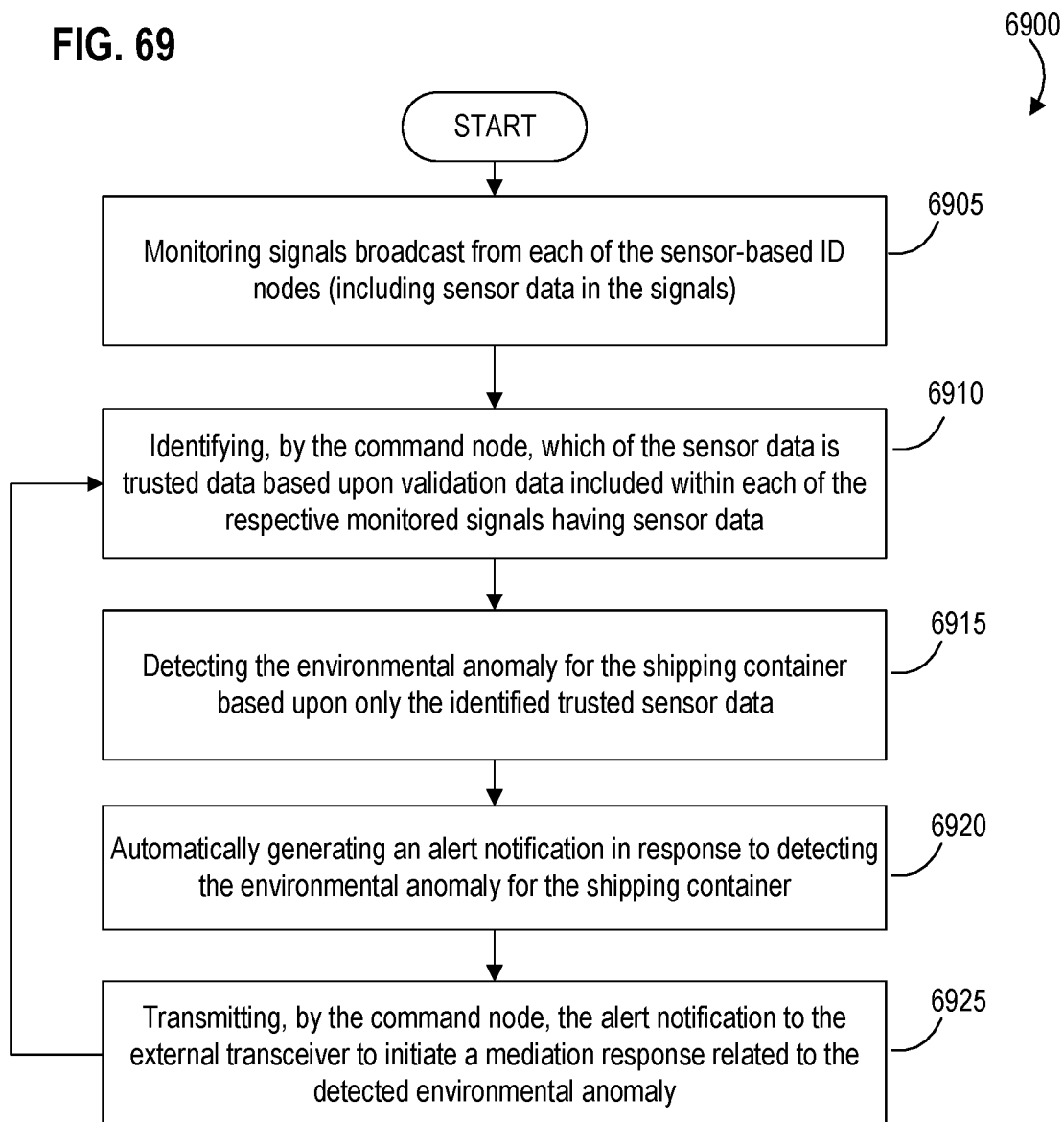
FIG. 69 is a flow diagram illustrating an exemplary method for securely monitoring a shipping container for an environmental anomaly based upon confirmed sensor data used as trusted sensor data in accordance with an embodiment of the invention.

FIG. 69 is a flow diagram illustrating an alternative exemplary method for securely monitoring a shipping container for an environmental anomaly based upon confirmed sensor data used as trusted sensor data in accordance with an embodiment of the invention. Such an exemplary method 6900 as described on FIG. 69 generally includes multiple sensor-based ID nodes (e.g., ID nodes 1-4 shown in FIG. 67) disposed within the shipping container (e.g., shipping container 24300*a*) and a command node (e.g., command node 1) associated with the shipping container and operative to communicate with each of the sensor-based ID nodes and an external transceiver (e.g., external transceiver 24150) associated with a transit vehicle (e.g., transit vehicle 24200) having at least temporary custody of the shipping container. The sensor-based ID nodes used as part of method 6900 may have at least one being disposed on part of the shipping container (e.g., ID node 1 shown in FIG. 67 being disposed on a base or floor of shipping container 24300*a*) or affixed to an object being transported within the shipping container (e.g., ID node 4 being affixed or attached to package 2 being transported within shipping container 24300*a*). The command node used as part of method 6900 may be implemented, for example, as a container node integrated as part of the shipping container or a master node associated with the shipping container and implemented separately from the shipping container while attached to the shipping container. Further, the transit vehicle used as part of method 6900 may be, for example, an airplane, a railway conveyance, a maritime vessel, or a roadway conveyance.

Referring now to FIG. 69, exemplary method 6900 begins at step 6905 with the command node (e.g., command node 1 shown in FIG. 67) monitoring signals broadcast from each of the sensor-based ID nodes (e.g., sensor-based ID nodes 1-4 shown in FIG. 67) where the monitored signals include sensor data generated from each of the sensor-based ID nodes.

At step 6910, method 6900 has the command node identifying which of the sensor data is trusted sensor data based upon validation data included within each of the respective monitored signals that includes the sensor data. In more detailed example, identifying which of the sensor data is trusted sensor data may have the command node assessing a validation record as part of the validation data and doing so without requiring the command node to transmit a validation request to each of the sensor-based ID nodes.

In still another example, an embodiment of step 6910 may have the command node identifying which of the sensor data is trusted sensor data by accessing a file or data structure representing a primary list of sensors maintained on the command node (e.g., primary list of sensors 67005), and comparing the primary list of sensors against the validation data included with the sensor data in each of the respective signals broadcast from the sensor-based ID nodes to identify a subset of the sensor data confirmed to be generated by one from the primary list of sensors. Such an identified subset of the sensor data is determined, by the command node, to be the trusted sensor data. In more detail, the validation data may be implemented as a security data structure (e.g., a hash key for the validation record as generated by the one of the sensor-based ID nodes that broadcasts the sensor data related to the validation data) with which the command node can process to ensure that the sensor data related to the validation record was generated by a one of the sensor-based ID nodes on the primary list of sensors.

At step 6915, method 6900 has the command node detecting the environmental anomaly for the shipping container based upon only the identified trusted sensor data. In more detail, step 6915 may have the command node detecting the environmental anomaly for the shipping container when the identified trusted sensor data has at least a portion being temperature sensor data above a threshold value. In another example, step 6915 may have the command node detecting the environmental anomaly when the identified trusted sensor data identifies one or more missing ones of the sensor-based ID nodes anticipated to be broadcasting (e.g., the missing sensor-based ID nodes anticipated to be broadcasting trusted sensor data have entered a state of ceased broadcasting unexpectedly).

At step 6920, method 6900 has the command node automatically generating an alert notification related to the detected environmental anomaly for the shipping container and then, at step 6925, transmitting the alert notification to the external transceiver to initiate a mediation response related to the detected environmental anomaly (such as generating a prompt message as described above or activating a fire suppression system (e.g., fire suppression system 25010)).

Those skilled in the art will appreciate that method 6900 as disclosed and explained above in various embodiments may be implemented using an exemplary system for securely monitoring a shipping container for an environmental anomaly such as that explained above with reference to FIG. 67 and its exemplary elements. Such an embodiment of this exemplary secure monitoring system, as explained above relative to operations according to method 6900 and with elements from FIG. 67, may at least use multiple ID nodes disposed within the shipping container (e.g., ID nodes 1-4) running one or more ID node monitoring program code as part of node control and management code 325 to control operations of the ID nodes to generate and broadcast ID node sensor data, as well as a command node mounted to the shipping container (e.g., command node 24160 or command node 1 shown in FIG. 67) running one or more parts of CN control & management code 26425 (e.g., the command node container management program code that is part of command node control and management code 26425) to control the operations of the command node as part of securely monitoring a shipping container for an environmental anomaly using the trusted sensor data. Such code may be stored on a non-transitory computer-readable medium, such as memory storage 26415 on command node 24160 (also referenced as command node 1, which is an embodiment of exemplary command node 26000) and memory storage 315 on ID nodes 1-4 (embodiments of exemplary ID node 120*a*). Thus, when executing such code, the ID nodes and the command node may be operative to perform operations or steps from the exemplary methods disclosed above, including method 6900 and variations of that method.

Node-Enhanced Detection Blanket

While the embodiments described above had ID nodes disposed within the shipping container, further embodiments may have ID nodes integrated as part of a blanket-type of structure that may be placed under packages (e.g., prior to loading packages into a shipping container) or may be quickly added as packages are loaded to deploy an arrangement of ID nodes (e.g., a geographically dispersed group of ID nodes distributed in different locations within the shipping container, even if some of the group are close to each other or are on contact with each other) that may communicate with the shipping container's command node. Such a node-enhanced/enabled sheet or blanket type of structure (e.g., rigid or flexible) having such integrated ID nodes may be added but kept loose within the shipping container in some embodiments, but also may be added and secured to part of the shipping container to help prevent movement of packages beneath such node-enhanced blanket structure (generally referred to here as a detection blanket having integrated ID nodes for environmental anomaly detection). In further embodiments, such a detection blanket may be made from fire/heat/chemical/radiation resistant material to help contain any environmental anomaly involving exposure to fire, intense heat, caustic chemicals, and/or radioactive materials leaking out from protective packaging. The detection blanket (as well as the enclosure on the integrated ID nodes), in other embodiments, may be designed to fail or break down at particular temperatures or under certain environmental conditions indicative of types of environmental anomalies. The description that follows and FIGS. 70-76 as explained below provide further details of such further embodiments.

Figure 70:
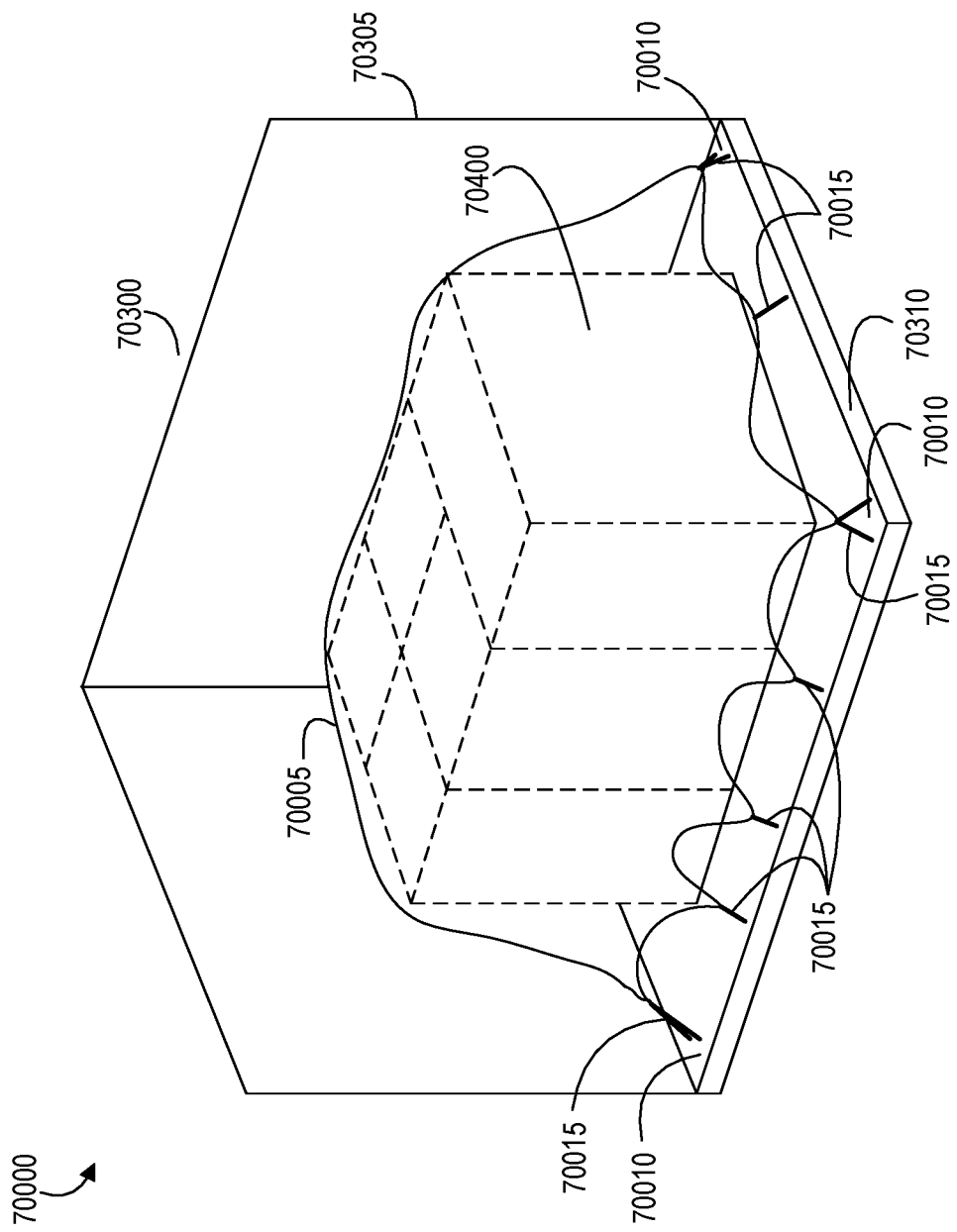
FIG. 70 is a diagram illustrating an exemplary node-enhanced detection blanket shown in perspective within a cutaway view of a shipping container in accordance with an embodiment of the invention.

FIG. 70 is a diagram generally illustrating an exemplary node-enhanced detection blanket shown in perspective within a cutaway view of an exemplary shipping container in accordance with an embodiment of the invention. Referring now to FIG. 70, an exemplary system 70000 is shown having shipping container 70300 and exemplary detection blanket 70005, which is shown covering and securing packages 70400 within container 70300. While exemplary shipping container 70300 is shown in perspective having walls 70305 and base 70310, the cutaway view shown in FIG. 70 does not show a top/lid for the container 70300 nor some of the walls for purposes of viewing the interior contents more clearly. As disposed within shipping container 70300, packages 70400 are secured by the exemplary detection blanket 70005, which is connected to the container 70300 at attachment points 70010 using tie-down straps 70015. While not shown in FIG. 70, exemplary detection blanket 70005 has multiple integrated nodes that may be sensor-based nodes (e.g., ID node devices that generate and broadcast sensor data) or nodes that simply broadcast advertising signals periodically so as to be detected by a command node mounted to the shipping container (not shown in FIG. 70). In general, detection blanket 70005 may be implemented as a single solid panel, a group of multiple connected panels, or flexible material (e.g., cargo net, webbing, braided net, reinforced tarp, and the like) that are integrated with one or more ID nodes (such as sensor-based ID nodes) as will be explained in more detailed examples below.

Figure 71:
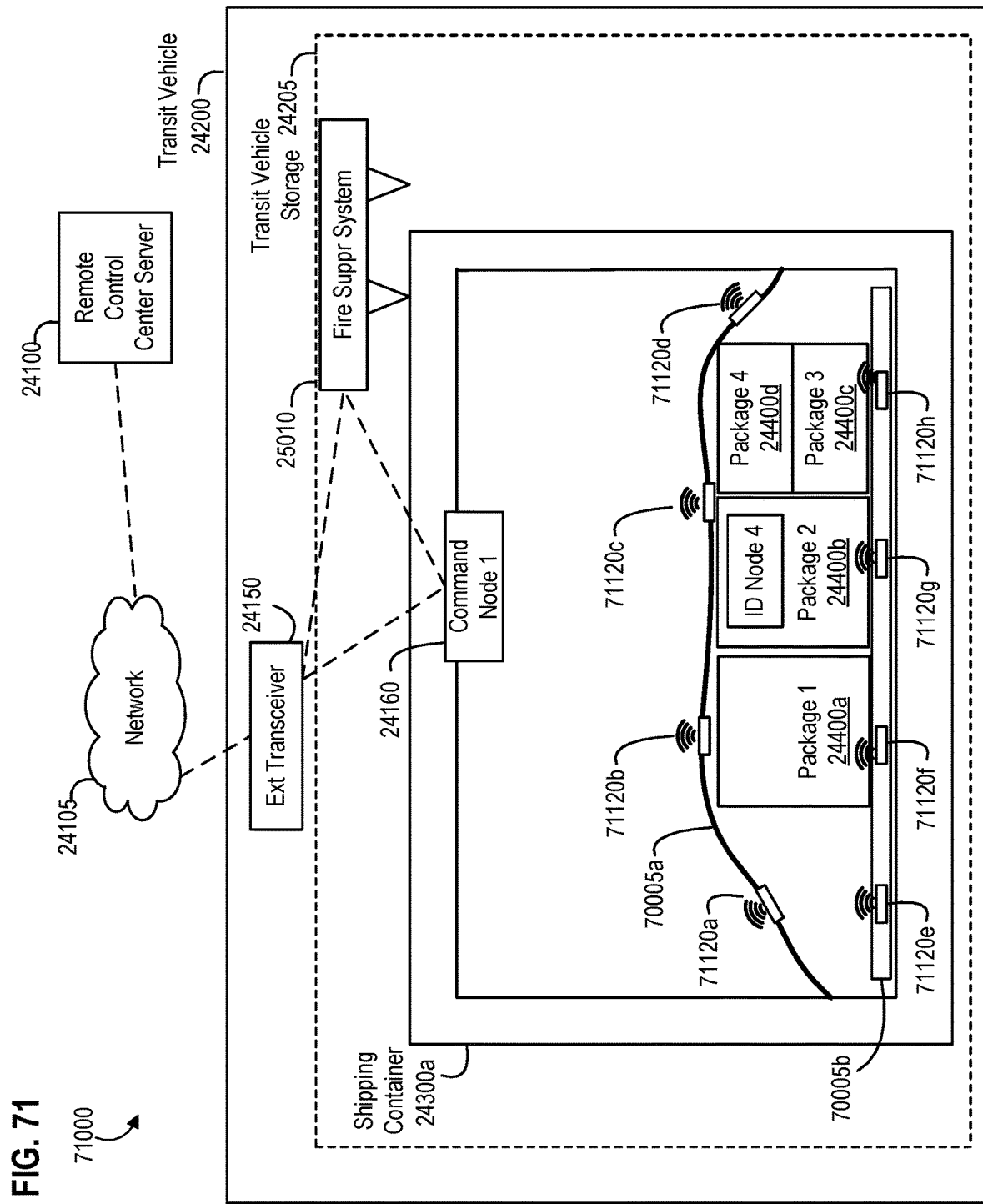
FIG. 71 is a diagram illustrating an exemplary system for enhanced detecting of an environmental anomaly relative to packages maintained in a shipping container using multiple types of node-enabled detection blankets below and above the packages in accordance with an embodiment of the invention.

FIG. 71 provides further details on such nodes integrated into and as part of different types of exemplary detection blankets. In particular, FIG. 71 is a diagram illustrating an exemplary system for enhanced detecting of an environmental anomaly relative to packages maintained in a shipping container using multiple types of node-enabled detection blankets below and above the packages in accordance with an embodiment of the invention. Referring now to FIG. 71, exemplary system 71000 is shown with similar components as system 65000 in FIG. 65 (e.g., transit vehicle 24200, remote server 24100, network 24015, external transceiver 24150, onboard fire suppression system 25010, and shipping container 24300*a*), but FIG. 71 illustrates the exemplary shipping container 24300*a* as housing a command node (e.g., command node 1 also referenced as 24160 as shown in FIG. 71) and packages 1-4 (also referenced as packages 24400*a*-24400*d*). Additionally, FIG. 71 shows two different embodiments of node-enabled detection blankets 70005*a*, 70005*b* disposed relative to packages 1-4.

Exemplary node-enabled detection blanket 70005*b* is shown as a rigid type detection blanket disposed at the bottom of shipping container 24300*a* and including sensor-based ID nodes 71120*e*-71120*h* integrated as part of the detection blanket 70005*b* in a geographically disperse configuration relative to the detection blanket so as to cover different parts of the detection blanket and the areas proximate the respective ID nodes 71120*e*-71120*h*. As implementations of an exemplary ID node 120*a* having one or more sensors 360, each of sensor-based ID nodes 71120*e*-71120*h* shown in FIG. 71 as part of exemplary detection blanket 70005*b* (as well as sensor-based ID nodes 71120*a*-71120*d* shown in FIG. 71 as part of exemplary detection blanket 70005*a*) has an ID node processor, an environmental sensor, and a wireless radio transceiver (which may be implemented in hardware, in a combination of hardware/software/or as a software defined radio (SDR)). The environmental sensor in each ID node is coupled to the ID node processor and generates sensor data related to an environmental condition proximate the respective sensor-based ID node within the shipping container. Such sensor data is indicative of the environmental anomaly when the sensor data generated is above a threshold condition for the at least one environmental sensor. The wireless radio transceiver is also coupled to the ID node processor and operative to broadcast signals that include the sensor data (in additional to a validation record used to confirm the sensor data broadcast as part of the signal is from that particular ID node) in response to a command from the ID node's processor. Stated another way, the wireless radio transceiver in each of ID nodes 71120*e*-71120*h* are configured to access the sensor data generated by its environmental sensor and broadcast the sensor data in response to a report command from the ID node processor when the ID node processor executes the ID node monitoring program code (e.g., code that is part of node control and management code 325 in memory 315, 320 of the ID node). As such, each of the sensor-based ID nodes 71120*e*-71120*h* integrated as part of detection blanket 70005*b* shown in FIG. 71 generate sensor data from and about the environment proximate their respective locations within shipping container 24300*a*.

In general, detection blankets 70005*a*, 70005*b* as illustrated in FIG. 71 have different regions where ID nodes may be integrated as parts of the detection blankets. Thus, while ID nodes may be placed close together or even touching one another as integrated into parts of the detection blanket (e.g., where some of the ID nodes may form a sensing array of nodes), some embodiments may disposed the ID nodes in a regionally dispersed and distributed configuration of the sensor-based ID nodes having different ones of the sensor-based ID nodes disposed and integrated into different ones of the respective regions of the detection blanket.

As shown in FIG. 71, packages 1-4 are positioned on top of node-enabled detection blanket 70005*b* and then covered with another detection blanket—e.g., a flexible type of detection blanket (e.g., exemplary detection blanket 70005*a*). As noted above, exemplary detection blanket 70005*a* has integrated sensor-based ID nodes 71120*a*-71120*d*. But rather than being made of a rigid core material as blanket 70005*b* (as explained in more detail in FIG. 72), exemplary detection blanket 70005*a* allows for the detection blanket 70005*b* to more flexibly cover or conform to items/objects around the blanket, such as packages 1-4. For example, detection blanket 70005*a* may be selectively connected to multiple attachment points (e.g., hooks, eyes, recessed anchors, and the like) within the shipping container 24300*a* to physically restrain movement of packages 1-4 as shown in FIG. 71. In a further example, detection blanket 70005*a* may be selectively connected to one or more of such attachment points (e.g., hooks, eyes, recessed anchors, and the like) within the shipping container 24300*a* to at least partially physically restrain movement of the detection blanket 70005*a* itself as shown in FIG. 71 even though such attachment may not physically restrain movement of any of packages 1-4.

Figure 72:
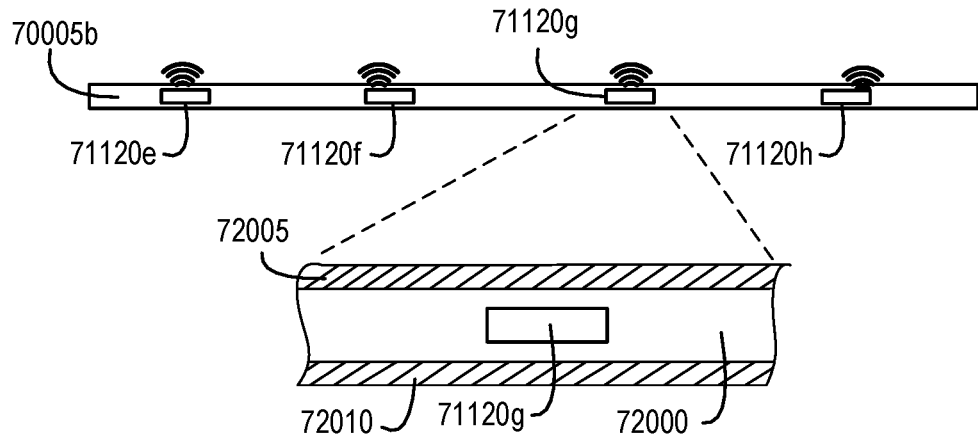
FIG. 72 is a diagram illustrating an exemplary rigid type of node-enabled detection blanket in accordance with an embodiment of the invention.

As noted above, an exemplary detection blanket may be implemented, for example, as a single solid panel, a group of multiple connected panels, or with flexible material (e.g., cargo net, webbing, braided net, reinforced tarp, and the like) that are integrated with one or more ID nodes (such as sensor-based ID nodes). FIG. 72 is a diagram illustrating details of an exemplary single solid rigid panel type of node-enabled detection blanket 70005*b* in accordance with an embodiment of the invention. As shown in FIG. 72, exemplary detection blanket 70005*b* is reproduced with a close up sectional view illustrating how blanket 70005*b* has a rigid core 72000 with cushioning sheets 72005, 72010 attached to either side of the rigid core sheet 7200. In this manner, exemplary detection blanket 70005*b* may function on the floor of shipping container 24300*a* (or as one of different rigid separators between packages).

Figure 73:
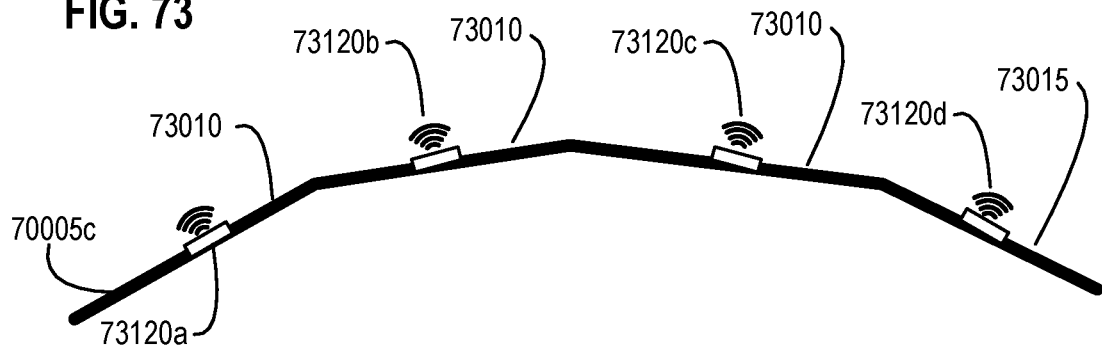
FIG. 73 is a diagram illustrating an exemplary node-enabled detection blanket having multiple panels in accordance with an embodiment of the invention.

FIG. 73 is a diagram illustrating an exemplary node-enabled detection blanket 70005*c* having multiple interconnected panels in accordance with an embodiment of the invention. Referring now to FIG. 73, exemplary detection blanket 70005*c* is shown having multiple flexibly connected panels 73010, wherein one or more of the sensor-based ID nodes (such as sensor-based ID nodes 73120*a*-73120*d*-similarly configured as ID nodes 71120*a*-71120*d* described above) are integrated into a different one of the flexibly connected panels 73010 as part of the geographically disperse configuration. In a further embodiment, one or more of the flexibly connected panels of exemplary detection blanket 70005*b* may not have an integrated sensor-based ID node and, instead, may implement a fire suppression panel having integrated fire suppression material that is passively releasable from the fire suppression panel when the fire suppression panel is exposed to a threshold temperature. An example of such a fire suppression panel is explained in more detail above as panel 54000 used as part of a shipping container, but in these embodiments such a panel may be used as part of or as one of the flexibly connected panels of an exemplary detection blanket so as to have its interior facing surface melt due to high heat conditions near the panel (due to an environmental anomaly) and quickly release an amount of fire suppression material maintained behind the interior facing surface as a result.

Figure 74:
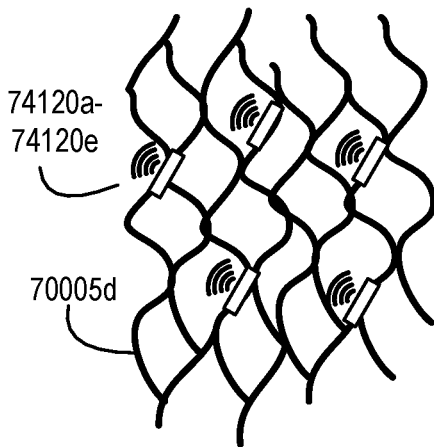
FIG. 74 is a diagram illustrating an exemplary flexible webbing type of node-enabled detection blanket in accordance with an embodiment of the invention.

FIG. 74 is a diagram illustrating further details of an exemplary flexible webbing type of node-enabled detection blanket 70005*d* in accordance with an embodiment of the invention. As shown in FIG. 74, exemplary detection blanket 70005*d* is implemented with a webbing (e.g., cargo net, braided webbing, and the like) where sensor-based ID nodes 74120*a*-74120*e* (similarly configured as ID nodes 71120*a*-71120*d* described above) are attached to or integrated into different respective parts of the webbing as part of the geographically disperse configuration. With such a type of detection blanket, an embodiment may implement the environmental sensor on at least one of the sensor-based ID nodes 74120*a*-74120*e* as a continuity sensor configured to generate sensor data indicative of a damaged status of the part of the webbing associated with the particular sensor-based ID node. The sensor data generated by the continuity sensor may exceed the threshold condition when the sensor data changes from a predetermined first state indicative of no damage to that part of the webbing associated with that sensor-based ID node to a second state indicating that part of the webbing associated with that particular sensor-based ID node has broken (e.g., is burned in two, separated, or otherwise is no longer in one piece). Such a continuity sensor may be implemented with a fuse-based sensor reactive to heat, where a particular temperature causes the fuse in the sensor to trip or open, triggering a change in state for the sensor data generated. As such, the second state indicates that the part of the webbing association with that particular sensor-based ID node has been exposed to a predetermined temperature as the threshold condition that changes the fused-based sensor from the first state to the second state.

In another embodiment where one or more of sensor-based ID nodes 74120*a*-74120*e* are integrated as part of the webbing, the webbing material itself can serve as a type of node enclosure for a particular integrated sensor-based ID node. In more detail, one or more of sensor-based ID nodes 74120*a*-74120*e* may be disposed within a section of the webbing material so as to be encompassed by the webbing material. Depending on the material chosen for such webbing material, exposure to an environmental anomaly (e.g., fire, chemical, and the like) may damage the webbing material proximate the integral sensor-based ID node so as to expose the components of the integral sensor-based ID node to the environmental anomaly. Thus, once the webbing based node enclosure has given way, which exposes the otherwise enclosed ID node, the ID node may cease operation or may detect a particular environmental condition that crosses a threshold for indicating the environmental anomaly. And, as explained above, should the enclosed ID node's sensor be implemented with a continuity sensor, the enclosed ID node sensor may also detect a particular state indicative of damage to the webbing due simply to the lack of enclosure protection from the webbing section that normally encloses that ID node.

These different embodiments of exemplary detection blankets may deploy a variety of different types of sensors as well as a mix of different sensors on a given detection blanket. For example, the environmental sensor for one of the sensor-based ID nodes in an exemplary detection blanket may be a temperature sensor while the environmental sensor for another sensor-based ID node in the detection blanket may be a barometric pressure sensor. In another example, the environmental sensor for one of the sensor-based ID nodes in an exemplary detection blanket may have multiple sensor elements, such as a temperature sensor element and a barometric pressure sensor element. In still another example, the environmental sensor for one of the sensor-based ID nodes in an exemplary detection blanket may be a temperature sensor while the environmental sensor for another of the sensor-based ID nodes in the detection blanket may be a radiation sensor or a chemical sensor.

Examples of node-enabled detection blankets may also use particular sensors in a proactively layered failure configuration as part of such an apparatus that may be used to detect an environmental anomaly. For example, an embodiment of a node-enabled detection blanket may have a first group of the sensor-based ID nodes that cease to broadcast the sensor data generated by each of the first group of sensor-based ID nodes when the environmental sensor in each of the first group of sensor-based ID nodes indicates a first temperature value exceeding a first temperature threshold while a second group of sensor-based ID nodes in the detection blanket continue to broadcast the sensor data generated by each of the second group of the sensor-based ID nodes. In more detail, such a second group of sensor-based ID nodes in the detection blanket may cease to broadcast the sensor data generated by each of the second group of sensor-based ID nodes when the environmental sensor in each of the second group of sensor-based ID nodes indicates a second temperature value exceeding a second temperature threshold while a third group of the sensor-based ID nodes in the detection blanket continue to broadcast the sensor data generated by each of the third group of the sensor-based ID nodes (where the first temperature threshold is lower than the second temperature threshold). In this manner, the configuration of particular sensors and their designed in capacity to cease broadcasting once certain temperatures are reached provides the ability of a monitoring command node to quickly assess such layered failures built into such an exemplary detection blanket and detect a particular environmental anomaly on such a monitored basis without regard to actual sensor data values.

Figure 75:
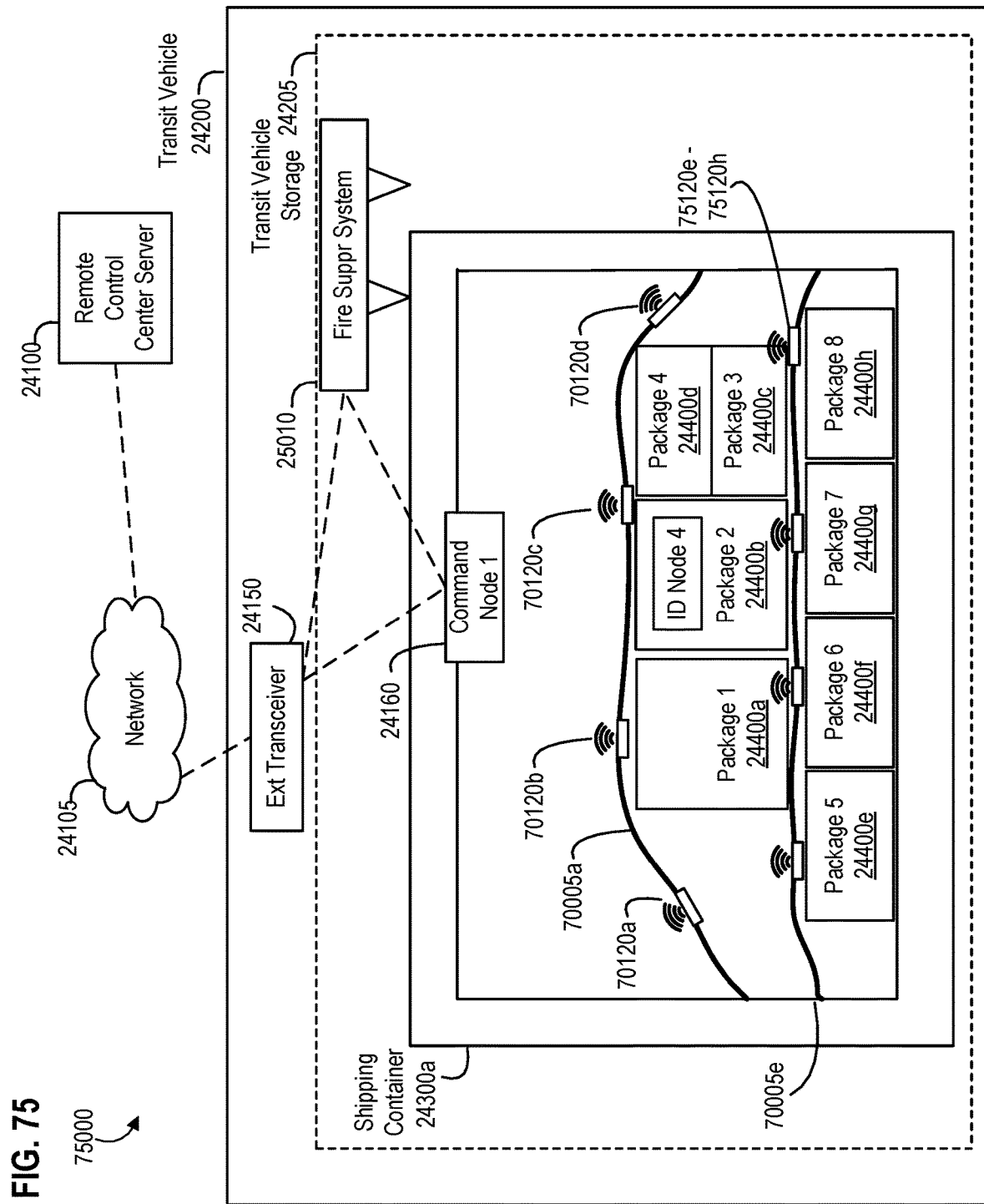
FIG. 75 is a diagram illustrating another exemplary system for enhanced detecting of an environmental anomaly relative to packages maintained in a shipping container using multiple node-enabled detection blankets disposed relative to different layers of the packages in accordance with an embodiment of the invention.

FIG. 75 is a diagram illustrating another exemplary system for enhanced detecting of an environmental anomaly relative to packages maintained in a shipping container using multiple node-enabled detection blankets disposed relative to different layers of the packages in accordance with an embodiment of the invention. Referring now to FIG. 75, exemplary system 75000 is shown similar to that shown with system 71000 in FIG. 71, but system 75000 has shipping container 24300*a* loaded with further packages and deploys a different combination of node-enabled detection blankets 70005*a*, 70005*e*. In more detail, shipping container 24300*a* as shown in FIG. 75 now has packages 5-8 loaded on the floor of container 24300 with exemplary node-enabled detection blanket 70005*e* on top of those packages. Blanket 70005*e* is shown in the example of FIG. 75 as a flexible material type of node-enabled detection blanket having sensor-based ID nodes 75120e-75120h integrated as part of detection blanket 70005e. The same combination of packages 1-4 and node-enabled detection blanket 70005a are shown on top of detection blanket 70005e with each of blankets 70005a and 70005 selectively attached to different attachment points within shipping container 24300a to physically restrain the collective movement of packages 1-8. In a further example illustrated in FIG. 75, detection blanket 70005a may be selectively connected to one or more of such attachment points (e.g., hooks, eyes, recessed anchors, and the like) within the shipping container 24300a to at least partially physically restrain movement of the detection blanket 70005a itself as shown in FIG. 75 even though such attachment may not physically restrain movement of any of packages 1-8.

In the context of the environment shown in FIG. 75 and explained above where command node 1 may monitor signals from each of the node-enabled detection blankets 70005a, 70005e (as well as other ID nodes disposed within shipping container 24300a, such as ID node 4 that is associated with package 4) and respond with notifications to further elements of system 75000 (e.g., external transceiver 24150, fire suppression system 25010), further system embodiments may be described as follows.

For example, an exemplary system for enhanced detecting of an environmental anomaly may include detection blanket 70005a disposed within shipping container 24300a and proximate to packages (such as packages 1-4) within the shipping container. The system further includes sensor-based ID nodes 70120a-70120d integrated as part of detection blanket 70005a in a geographically disperse configuration relative to the detection blanket 70005a. As described above, each of the integrated sensor-based ID nodes 70120a-70120d have an ID node processor, an ID node memory coupled to the ID node processor, an environmental sensor, and an ID node wireless radio transceiver. The ID node memory maintains at least an ID node monitoring program code (e.g., code that is part of node control and management code 325) that, when executing, controls the operation of the respective integrated ID node as part of this system. The environmental sensor (or sensors on the ID node) are configured to generate sensor data related to an environmental condition adjacent the environmental sensor (such as sensor data on temperature). The ID node wireless radio transceiver is operatively responsive to the ID node processor, and is configured to access the sensor data generated by the environmental sensor and broadcast the sensor data in response to a report command from the ID node processor when the ID node processor executes the ID node monitoring program code.

The system embodiment further includes command node 1 mounted on the shipping container 24300a. As noted above, command node 1 has a command node processor, a command node memory, and a command node wireless transceiver. The command node memory operatively is coupled to the command node processor and maintains at least command node container management program code (e.g., code that is part of CN control and management code 26435). The command node wireless transceiver communication interface is operatively responsive to the command node processor and is configured to communicate with each of the sensor-based ID nodes of the detection blanket and with the external transceiver. In some embodiments, the command node wireless transceiver communication interface may be implemented with separate communication interfaces, where a first communication interface is operatively responsive to the command node processor and configured to communicate with each of sensor-based ID nodes 70120a-710120d of the detection blanket 70005a over a first wireless communication path, while a second communication interface is also operatively responsive to the command node processor and configured to communicate with at least external transceiver 24150 (and with fire suppression system 25010 in some embodiments) using a second wireless communications path distinct from the first wireless communication path.

During operation of such a system embodiment, the command node processor of command node 1 is programmatically configured, when executing the command node container management program code, to be operative to detect the sensor data broadcasted from sensor-based ID nodes 70120a-70120d of detection blanket 70005a using the command node wireless transceiver communication interface; responsively identify the environmental anomaly for the shipping container 24300a based upon values of the detected sensor data; generate an alert notification related to the identified environmental anomaly for the shipping container 24300a; and cause the command node wireless transceiver communication interface to transmit the alert notification to at least external transceiver 24150 to initiate a mediation response related to the identified environmental anomaly.

In more detail, the system embodiment may have the command node processor of command node 1 being further programmatically operative to identify detection blanket 70005a by communicating with at least one of sensor-based ID nodes 70120a-70120d of detection blanket 70005. The sensor data generated by ID nodes in a detection blanket may include identification information about the detection blanket associated with a particular ID node in that blanket.

The system embodiment may also have the command node processor of command node 1 be further programmatically configured to responsively identify the environmental anomaly for shipping container 24300a based upon values of the detected sensor data by being further operative to detect the environmental anomaly for the shipping container when the detected sensor data from at least one of sensor-based ID nodes 70120a-70120d exceeds an environmental threshold condition. For example, command node 1 may detect such an environmental anomaly when: (a) the sensor data detected from a first of sensor-based ID nodes 70120a-70120d in detection blanket 70005a comprises a temperature value; (b) the sensor data detected from a second of the sensor-based ID nodes 70120a-70120d in detection blanket 70005a comprises an environmental condition value of one of a sensed barometric pressure level, a detected radiation level, or a detected chemical (e.g., a chemical indicative of a fire, explosive, CO, or $CO_2$); (c) the temperature value indicates the environmental condition adjacent the first of these ID nodes exceeds a temperature threshold condition; and (d) the environmental condition value indicates the environmental condition adjacent the second of these ID nodes exceeds an environmental threshold condition associated with the environmental sensor of that second ID node.

Such a system embodiment may detect various types of environmental anomalies. For example, the detected environmental anomaly for shipping container 24300a may be a fire within shipping container 24300a when command node 1 determines that, based upon the sensor data, (a) the temperature value from the first of sensor-based ID nodes 70120a-70120d in detection blanket 70005a exceeds the temperature threshold condition; and (b) the environmental condition value as the sensed barometric pressure level from the second of these sensor-based ID nodes exceeds a pressure threshold as the environmental threshold condition. In another example, the detected environmental anomaly for shipping container 24300*a* may be an explosion within shipping container 24300*a* when command node 1 determines that, based upon the sensor data, (a) the temperature value from the first of the sensor-based ID nodes 70120*a*-70120*d* in detection blanket 70005*a* exceeds the temperature threshold condition; and (b) the environmental condition value as the sensed barometric pressure level from the second of these sensor-based ID nodes is detected below a pressure threshold as the environmental threshold condition. In still another example, the detected environmental anomaly for shipping container 24300*a* may be an explosion within shipping container 24300*a* when command node 1 determines that, based upon the sensor data, (a) the temperature value from the first of the sensor-based ID nodes 70120*a*-70120*d* in detection blanket 70005*a* exceeds the temperature threshold condition; and (b) the environmental condition value as the sensed barometric pressure level from the second of these sensor-based ID nodes is detected to be dropping faster than a pressure drop threshold as the environmental threshold condition. In another example, the detected environmental anomaly for shipping container 24300*a* may be a detected chemical fire within shipping container 24300*a* when command node 1 determines that, based upon the sensor data, (a) the temperature value from the first of the sensor-based ID nodes 70120*a*-70120*d* in detection blanket 70005*a* exceeds the temperature threshold condition; and (b) the environmental condition value as the detected chemical from the second of these sensor-based ID nodes matches a predetermined chemical profile maintained by command node 1 in the command node memory (e.g., as part of profile data 430). In yet another example, detected environmental anomaly for the shipping container may be a detected radiation leak within shipping container 24300*a* when command node 1 determines that, based upon the sensor data, (a) the temperature value from the first of the sensor-based ID nodes 70120*a*-70120*d* in detection blanket 70005*a* exceeds the temperature threshold condition; and (b) the environmental condition value as the detected radiation from the second of these sensor-based ID nodes matches a predetermined radiation profile maintained by command node 1 in the command node memory (e.g., as part of profile data 430).

Another exemplary system for enhanced detecting of an environmental anomaly may involve similar system elements (e.g., detection blanket 70005*a* having integrated ID nodes 70120*a*-70120*d*, and command node 1), but have the command node alternatively configured via its programming to monitor for unresponsive ones of ID nodes 70120*a*-70120*d* within detection blanket 70005*a*. In more detail, such a system embodiment may have the command node processor of command node 1 being programmatically configured, when executing the command node container management program code, to be operative to identify detection blanket 70005*a* by responsively communicating with each of ID nodes 70120*a*-70120*d* of detection blanket 70005*a* (without necessarily receiving sensor data from such nodes) and comparing the responsive ones of these ID nodes with a blanket identification profile maintained by the command node in the command node memory (e.g., part of profile data 430); monitor the advertising messages broadcasted from ID nodes 70120*a*-70120*d* of detection blanket 70005*a* using the command node wireless transceiver communication interface to identify an unanticipated state of ceased broadcasting from any of these ID nodes; responsively identify the environmental anomaly for shipping container 24300*a* when a number of ID nodes 70120*a*-70120*d* identified to be in the unanticipated state of ceased broadcasting exceeds a threshold setting maintained by command node 1; generate an alert notification related to the identified environmental anomaly for shipping container 24300*a*; and cause the command node wireless transceiver communication interface to transmit the alert notification to external transceiver 24150 to initiate a mediation response related to the identified environmental anomaly.

As the monitoring by command node 1 in this system embodiment involves monitoring for ceased broadcasting status of particular ID nodes, a further embodiment may have command node 1 monitoring to take advantage of a proactively layered failure configuration of the ID nodes integrated into detection blanket 70005*a*. For example and consistent with the prior description of a proactively layered failure configuration of a detection blanket's integrated ID nodes, the ID nodes 70120*a*-70120*d* integrated as part of detection blanket 70005*a* may include a first group and a second group, where the first group are integrated ID nodes operative to cease broadcasting advertising messages when a temperature adjacent that first group exceeds a first temperature threshold while the second group are integrated ID nodes that continue to broadcast advertising messages at that first temperature threshold. In a further example, the second group of ID nodes may cease broadcasting when a temperature adjacent the second group of the ID nodes exceeds a second temperature threshold while a third group of the integrated ID nodes continue to broadcast the advertising messages. In this example, the first temperature threshold is lower than the second temperature threshold. As such, the command node processor of command node 1 in the system may be further programmatically configured to responsively identify the environmental anomaly as a first level anomaly for shipping container 24300*a* when command node 1 ceases to detect the advertising messages from any of the first group of integrated ID nodes in detection blanket 70005*a*, and may also responsively identify the environmental anomaly as a second level anomaly for shipping container 24300*a* when command node 1 ceases to detect the advertising messages from any of the second group of integrated ID nodes in detection blanket 70005*a*.

A further exemplary system for enhanced detecting of an environmental anomaly may involve similar system elements (e.g., detection blanket 70005*a* having integrated ID nodes 70120*a*-70120*d*, and command node 1), but also include a second detection blanket (e.g., detection blanket 70005*e* having integrated ID nodes 75120*e*-75120*h*) as part of the system. As such, the system includes a first detection blanket 70005*a* disposed within shipping container 24300*a* and proximate at least a first group of the packages 1-4 within the shipping container, where detection blanket 70005*a* has a first group of sensor-based ID nodes 70120*a*-70120*d* integrated as part of the first detection blanket 70005*a*. Each of the first group of sensor-based ID nodes 70120*a*-70120*d* are disposed as part of the first detection blanket 70005*a* in a first geographically disperse configuration and include at least a first environmental sensor configured to generate first detection blanket sensor data related to an environmental condition adjacent the first environmental sensor and a first wireless radio transceiver configured to broadcast the first detection blanket sensor data. The system also includes a second detection blanket 70005*e* disposed within shipping container 24300*a* and proximate at least a second group of the packages 5-8 within shipping container 24300*a*, where the second detection blanket 70005*e* has a second group of sensor-based ID nodes 75120*e*-75120*h* integrated as part of the second detection blanket 70005*e*. Each of the second group of sensor-based ID nodes 75120*e*-75120*h* are disposed as part of the second detection blanket 70005*e* in a second geographically disperse configuration and include at least a second environmental sensor configured to generate second detection blanket sensor data related to an environmental condition adjacent the second environmental sensor and a second wireless radio transceiver configured to broadcast the second detection blanket sensor data.

The system's command node, command node 1 on shipping container 24300*a* as described above, includes at least a command node processor, a command node memory operatively coupled to the command node processor (maintaining at least command node container management program code (e.g., code that may be part of CN control and management code 26425)), and a command node wireless transceiver communication interface. The command node wireless transceiver communication interface (which may be implemented as a single transceiver interface or dual transceivers) is operatively responsive to the command node processor, and configured to communicate with each of the sensor-based ID nodes of both detection blankets 70005*a*, 70005*e* as well as with the external transceiver 24150 (and with fire suppression system 25010 in some embodiments).

During operation of the multiple detection blanket system embodiment, the command node processor of command node 1 is programmatically configured, when executing the command node container management program code, to be operative to detect a first signal from one of the first group of sensor-based ID nodes (e.g., ID nodes 70120*a*-70120*d*) in the first detection blanket 70005*a* to register the first detection blanket 70005*a* as a first monitoring blanket within the shipping container 24300*a*, and detect a second signal from one of the second group of sensor-based ID nodes (e.g., ID nodes 75120*e*-75120*h*) in the second detection blanket 70005*e* to register the second detection blanket 70005*e* as a second monitoring blanket within the shipping container. Command node 1 is further programmatically configured to be operative to then detect the first detection blanket sensor data broadcasted from the first group of the sensor-based ID nodes in the first detection blanket using the command node wireless transceiver communication interface; detect the second detection blanket sensor data broadcasted from the second group of the sensor-based ID nodes in the first detection blanket using the command node wireless transceiver communication interface; responsively identify the environmental anomaly for the shipping container based upon values of at least one of the detected first detection blanket sensor data and the detected second detection blanket sensor data; generate an alert notification related to the identified environmental anomaly for the shipping container; and cause the command node wireless transceiver communication interface to transmit the alert notification to external transceiver 24150 to initiate a mediation response related to the identified environmental anomaly.

As part of this multiple detection blanket system, the first detection blanket may be disposed below or above the first group of the packages. Likewise, embodiments may have the second detection blanket being disposed above or below the second group of the packages.

An embodiment of such a multiple detection blanket system may have one of the detection blankets having at least a first rigid sheet within which the first group of sensor-based ID nodes is integrated in the first geographically disperse configuration, while the second detection blanket has at least a second rigid sheet within which the second group of sensor-based ID nodes is integrated in the second geographically disperse configuration.

Alternatively, the first and second blankets may be made of flexible cargo webbing. In more detail, an embodiment may have the first detection blanket being implemented with cargo webbing, where each of the first group of sensor-based ID nodes are integrated into a different part of that cargo webbing as part of the first geographically disperse configuration. Likewise, the second detection blanket may also be implemented cargo webbing, where each of the second group of sensor-based ID nodes are integrated into a different part of that cargo webbing as part of the second geographically disperse configuration. In more detail when the detection blankets are implemented with cargo netting, an environment sensor on the sensor-based ID nodes integrated as part of such detection blankets may be implemented as a fuse-based continuity sensor that is reactive to heat and configured to generate sensor data indicative of a damaged status of that part of the cargo webbing associated with respective integrated sensor-based ID nodes.

In still another embodiment, one detection blanket may have a rigid core structure while the other has a flexible webbing structure. In more detail, the first detection blanket may be implemented with a rigid sheet (or multiple rigid panels) within which the first group of sensor-based ID nodes is integrated in the first geographically disperse configuration, while the second detection blanket may be implemented with cargo webbing within which second group of sensor-based ID nodes is integrated as part of the second geographically disperse configuration.

In a further embodiment of such a multiple detection blanket system, the command node processor of command node 1 may be further programmatically operative to identify the first detection blanket and the second detection blanket by communicating with at least one within the first group of sensor-based ID nodes and with at least one within the second group of sensor-based ID nodes.

Figure 76A:
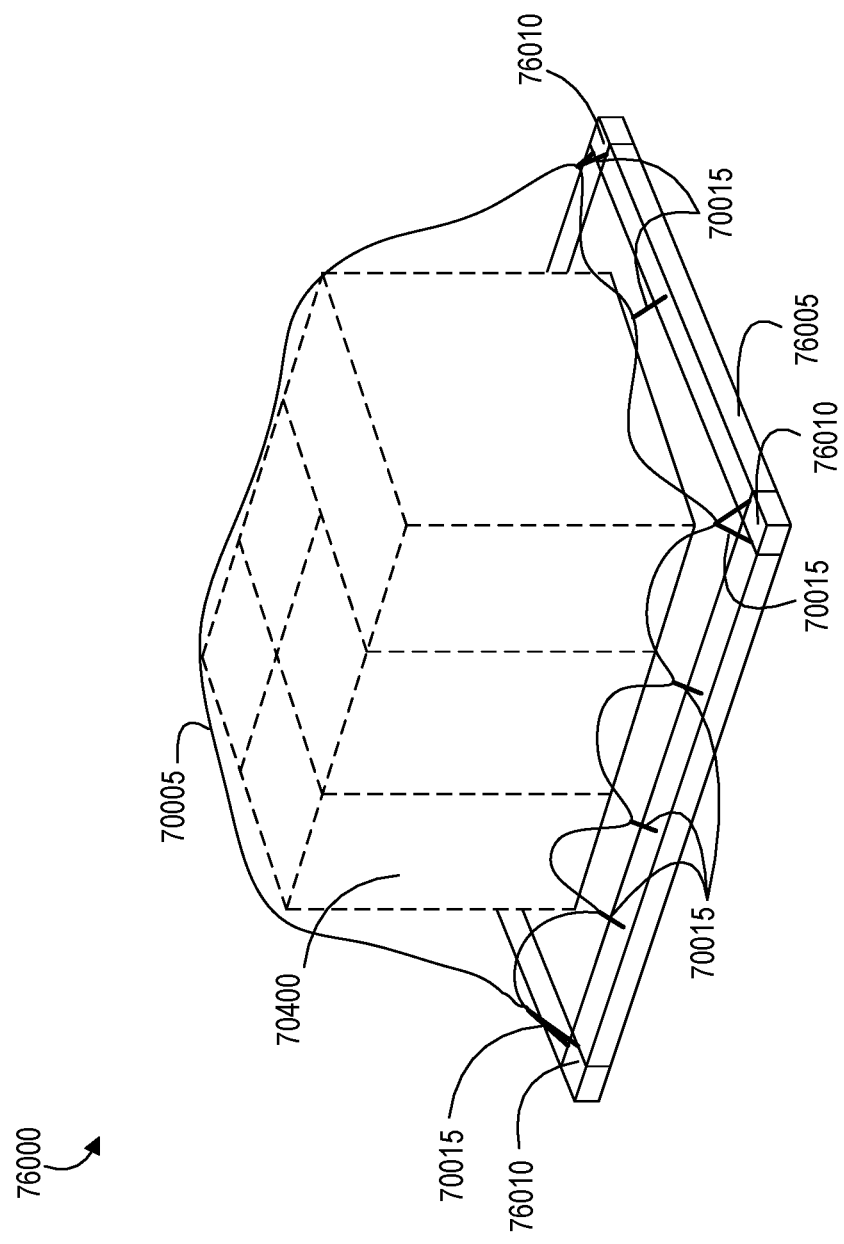
FIGS. 76A-76C are a series of diagrams illustrating an exemplary shipping container having an exemplary base pallet with an exemplary node-enabled detection blanket attached to the base pallet along with additional features that may be deployed as part of the exemplary node-enabled detection blanket in accordance with an embodiment of the invention.
Figure 76B:
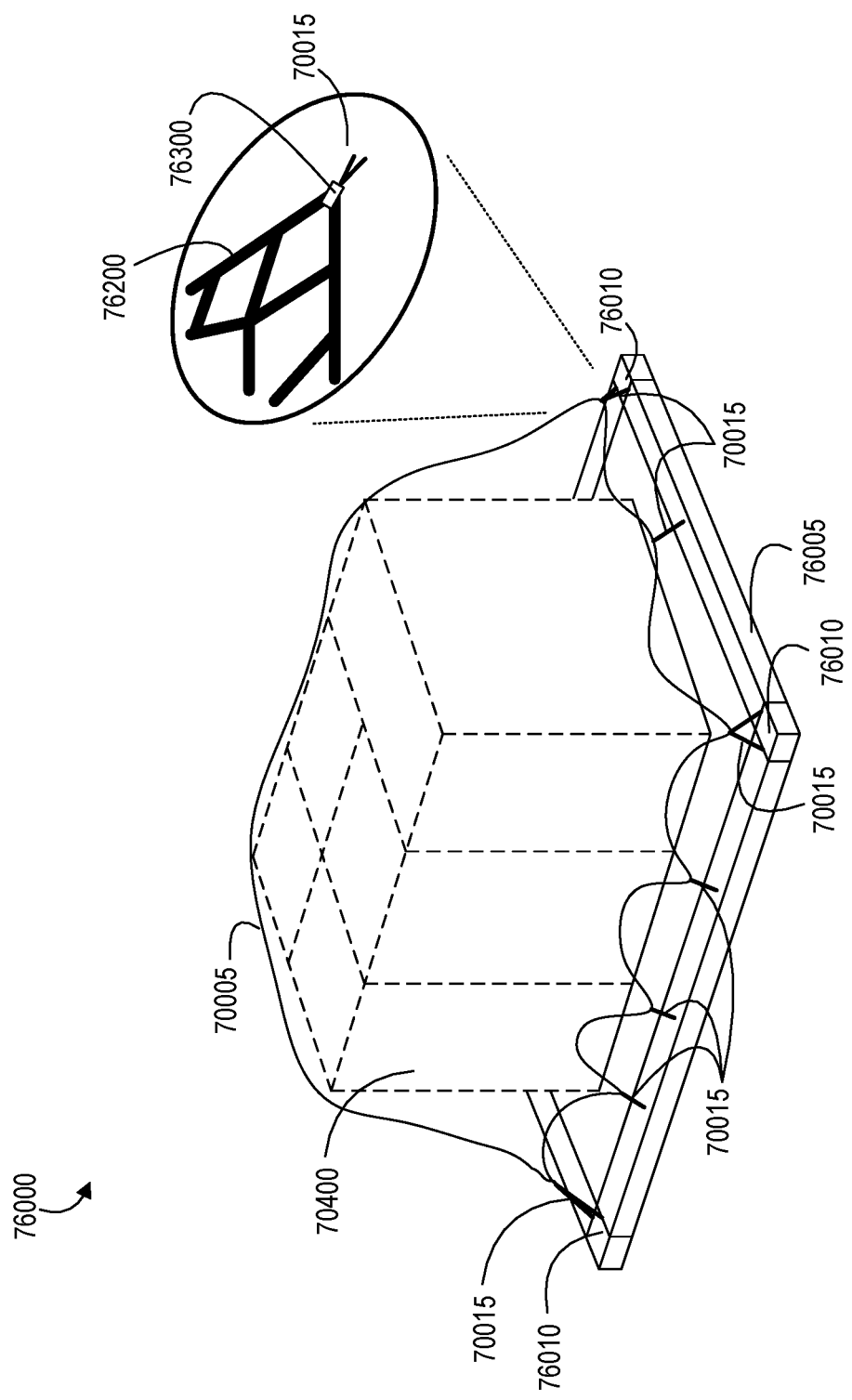
Figure 76C:
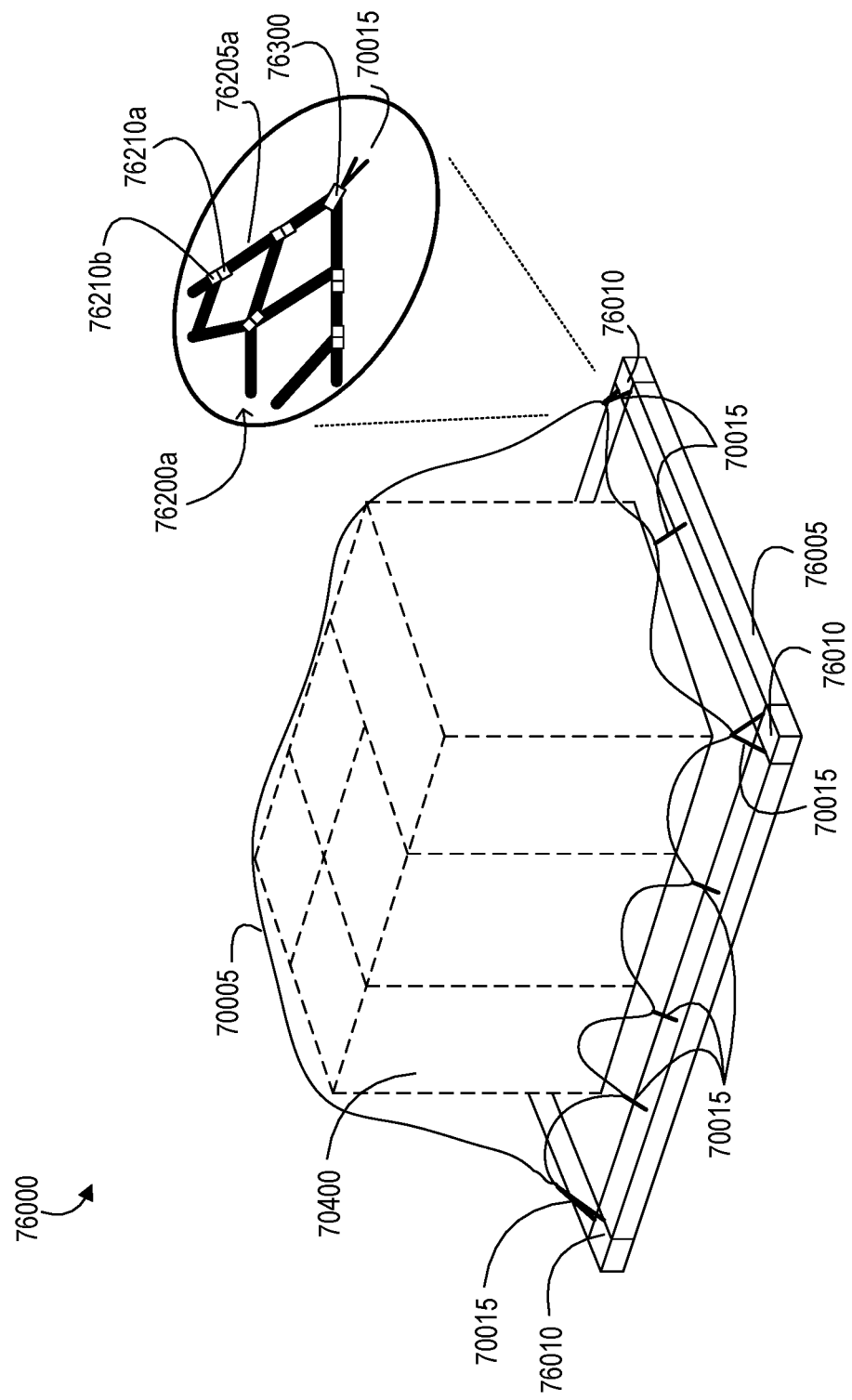

While the exemplary shipping container 24300*a* described with respect to various embodiments involving exemplary detection blankets have been containers having a base, walls, and a top/lid that enclose the container and define an interior storage area within the shipping container, further embodiments of exemplary shipping containers may also include a pallet-based container having a securing structure attached to the pallet to at least temporarily hold what is supported on the pallet in place. FIGS. 76A-76C are a series of diagrams illustrating an exemplary shipping container implemented with an exemplary base pallet and an exemplary node-enabled detection blanket attached to the base pallet along with additional features that may be deployed as part of the exemplary node-enabled detection blanket in accordance with an embodiment of the invention.

FIG. 76A is a diagram illustrating an exemplary shipping container having an exemplary base pallet with a node-enabled detection blanket attached to the base pallet as a type of securing structure that encloses packages maintained on the base pallet in accordance with an embodiment of the invention. Referring now to FIG. 76A, those skilled in that art will appreciate that exemplary pallet-based container 76000 is illustrated supporting a group of packages 70400. Exemplary node-enabled detection blanket 70005 shown in FIG. 76A is able to function as part of shipping container 76000 as it covers packages 70400 and may attach via tie-downs 70015 to different attachment points 76010 on pallet 76005. While not shown in FIG. 76A as it may be hidden within or mounted to pallet 76005 (or within a package 70400), shipping container 76000 may have an exemplary command node (such as command node 1 as explained in the various embodiments above) that may monitor integrated ID nodes within detection blanket 70005, detect an environment anomaly related to shipping container 76000 similar to that described in embodiments above, and report relevant alert notifications that may initiate a mediation response by other devices (e.g., external transceiver 24150 or fire suppression system 25010) similar to that described in the various embodiments describe above.

FIGS. 76B and 76C each provide further details related to various embodiments of exemplary node-enabled detection blanket 70005 as implemented with webbing material. In more detail and referring now to FIG. 76B, a magnified view of part of exemplary node-enabled detection blanket 70005 made from flexible webbing 76200, which may have one or more of the blanket's sensor-based ID nodes disposed on or within the webbing 76200. As shown in FIG. 76B, a connection point 76300 (e.g., a clasp, clip, connector, snap, and the like) is shown attached to an attachment point 76010 (e.g., a hook, eye, recessed anchor, and the like) on the shipping container's base via tie down straps 70015 secured to part of the base of the container (e.g., base pallet 76005). Exemplary connection point 76300, in a particular embodiment, may be a connector having an integrated one of the sensor-based ID nodes in the blanket 70005. As such, the environmental sensor on that sensor-based ID node integrated into connection point 76300 may, for example, be implemented as a continuity sensor (e.g., RF sensor, NFC sensor, and the like) configured to generate sensor data indicative of an attachment status of the connection point 76300 to an attachment point on the shipping container (attachment point 76010 on the shipping container's base having tie down straps 70015 that may be attached to connection point 76300). The attachment status may then be reported as a type of sensor data, and may be used by a command node as part of monitoring for and detecting an environmental anomaly as the state of such a monitored attachment may help indicate whether a fire or explosion has occurred.

In FIG. 76C, an alternative embodiment of such exemplary flexible webbing 76200 is illustrated with a magnified portion of exemplary detection blanket 70005 shown made from multiple connectable webbing sections 76205a that make up a connected webbing 76200a. Each connectable webbing section 76205a, in this example, is shown having connectors on ends of the section (e.g., a first connector 76210a to connect to another connector 76210b on another webbing section). Such connectors may be implemented with single or multiple connectors depending on the webbing section configurations being attached to each other to form the connected webbing. An embodiment may have one or more sensors integrated into such connectors that are coupled to an ID node disposed on the particular webbing section having such connectors. Such sensors may, for example, be temperature or pressure sensors that generate environmental sensor data about the surrounding environment near the connectors. However, in another example, such sensors may be implemented with a continuity sensor configured to generate sensor data indicative of an attachment status of the sensor's connector to another webbing section's connector. The attachment status in this situation may then be reported as a type of sensor data, and may be used by a command node as part of monitoring for and detecting an environmental anomaly as the state of such a monitored attachment may help indicate whether a fire or explosion has occurred. Such attachment status, as sensor data, may be monitored to detect a change in connection of the detection blanket's webbing, which may be indicative of an environmental anomaly (e.g., a fire burned through the webbing section or the connection no longer exists due to the fire). Further, such a change of attachment status may be used by the command node in combination of other sensor data (e.g., an increase in temp, a change in pressure that may match a pressure profile) to provide further detailed sensor data with which the command node may use to not only detect the environmental anomaly, but to adaptive generate an alert notification and fashion the appropriate information as part of the notification to initiate an appropriate mediation response as discussed in embodiments herein.

A further example may have wiring run through sections of the webbing so as to be connected to form a network of wiring that may be centrally monitored or sensed with a single ID node. In this way, any break of the webbing may be sensed by the ID node and reflected in the sensor data generated by that ID node. Further still, if the wiring is power wiring, any break may cause the ID node to cease broadcasting when anticipated to be broadcasting and, as such, any such break may be detected as relevant to detecting an environmental anomaly as well as what any sensor data may substantively indicate.

Still further embodiments may deploy one or more detection blankets within a shipping container and have a command node perform multi-mode triggering to detect an environmental anomaly (e.g., monitor both sensor data values as compared to sensor threshold as well as the number of unresponsive integrated ID nodes that are expected and anticipated to be broadcasting under normal conditions). More embodiments may combine the use of attachment status sensor data as part of the monitoring of signals and signal activity to detect an environmental anomaly.

Adaptive and Prioritized Node Reporting

In various embodiments described above, a command node (as part of a system that monitors different ID nodes for sensor data being generated by such ID nodes for purposes of detecting an environmental anomaly) is described as having the ability to selectively set and adjust rates for obtaining sensor data from the sensor-based ID nodes being monitored. Further embodiments expand on these principles in varying messaging rates on what is reported from a selective one or more of the ID nodes, as well as modifying what is monitored (e.g., which ID nodes are monitored, what type of data should be considered when monitoring, and the like) as a way of prioritizing or selectively prioritizing what may be considered in an adaptive manner as the command node continues monitoring to detect the environmental anomaly. As such, these further embodiments involve the command node refining how it interacts with the sensor-based ID nodes that generate the sensor data as well as modifying what is particularly monitored out of the potential available sensor data from the ID nodes so as to improve the focus and speed of detecting an environmental anomaly by dispensing with processing overhead with less relevant sensor data as the command node hones in on making the determination that an environmental anomaly exists within the shipping container and rapidly responding to that determination by initiating a mediation response.

FIG. 77 is a flow diagram illustrating an exemplary adaptive method for monitoring a shipping container for an environmental anomaly using a wireless node network as a command node refines monitoring when detecting the environmental anomaly in accordance with an embodiment of the invention. Such an exemplary method 7700 as described on FIG. 77 generally includes multiple sensor-based ID nodes (e.g., ID nodes 1-7 shown in FIG. 37A) disposed within the shipping container (e.g., shipping container 24300a) and a command node (e.g., command node 24160) associated with the shipping container and operative to communicate with each of the sensor-based ID nodes and an external transceiver (e.g., external transceiver 24150) associated with a transit vehicle (e.g., transit vehicle 24200) having at least temporary custody of the shipping container. The sensor-based ID nodes used as part of method 7700 each have at least one environmental sensor. These sensor-based ID nodes may have one or more being disposed on or integrated as part of the shipping container (e.g., ID nodes 4-7 shown in FIG. 37A being disposed on or integrated as part of a wall within shipping container 24300a) or associated with an object being transported within the shipping container (e.g., ID nodes 1-3 being affixed or attached to packages 1-3 or disposed within packages 1-3 being transported within shipping container 24300a). The command node used as part of method 7700 may be implemented, for example, as a container node integrated as part of the shipping container, mounted to the shipping container, or a master node associated with the shipping container and implemented separately from the shipping container while attached to the shipping container. Further, the transit vehicle used as part of method 6900 may be, for example, an airplane, a railway conveyance, a maritime vessel, or a roadway conveyance.

Referring now to FIG. 77, exemplary method 7700 begins at step 7705 with the environmental sensor on each of the ID nodes generating sensor data related to an environmental condition proximate the respective ID node as disposed within the shipping container. For example, each of ID nodes 1-7 as shown in FIG. 37A have sensors (e.g., temperature sensors, pressure sensors, chemical sensors, radiation sensors, or the like) that generate sensor data reflective of the environmental condition next to each of ID nodes 1-7.

At step 7710, method 7700 continues with each of the sensor-based ID nodes periodically broadcasting the sensor data generated by each of the ID nodes over time. For example, ID nodes 1-7 shown in FIG. 37A will be, over time, broadcasting their respectively generated sensor data via advertising signals transmitted over the wireless radio transceiver in each of ID nodes 1-7.

At step 7715, method 7700 continues with the command node monitoring a first group of the sensor data broadcast from each of the ID nodes. This is done over a first time period to detect an initial environmental threshold condition related to the shipping container. In the example illustrated with the components shown on FIG. 37A, exemplary command node 24160 may be programmatically configured (via code executing on the processor of command node 24160) to monitor the sensor data broadcast by ID nodes 1-7 over a first time period. During that time period, command node 24160 may compare the sensor data from each of ID nodes 1-7 against an initial environmental threshold setting (e.g., a first stage temperature value indicative of a possible fire or other abnormal heat generating event, such as a dangerous chemical reaction, within shipping container 24300a).

At step 7720, if the command node fails to detect an initial environmental threshold condition related to the shipping container, the method 7700 proceeds back to step 7715 for further monitoring. However, if the command node detects an initial environmental threshold condition related to the shipping container as part of step 7720, method 7700 proceeds directly to step 7725.

At step 7725, method 7700 continues with the command node monitoring a subsequent group of the sensor data broadcast from each of the ID nodes over a second time period under a modified monitoring parameter in an effort to detect a secondary environmental threshold condition related to the shipping container as the environmental anomaly. In one example, step 7725 may have the modified monitoring parameter defining which of the ID nodes to consider when detecting the secondary environmental threshold condition. In this way, the command node may refine which ID nodes are prioritized when monitoring to detect the environmental anomaly. In more detail, when each of the ID nodes is associated with one of a plurality of packages, the modified monitoring parameter may define which of the ID nodes to consider when detecting the secondary environmental threshold condition based upon a type of material within the packages as associated with a respective one of the ID nodes according to shipping information maintained by the command node. Such shipping information may identify what is in the particular package associated with a given ID node, the type of material within that package, and whether that material may be designated as hazardous, flammable, combustible or have another designation that may cause the command node to consider prioritizing monitoring of that particular ID node's sensor data relevant to such material.

In another example of step 7725, the modified monitoring parameter may define one or more types of the sensor data (e.g., temperature sensor data, pressure sensor data, chemical sensor data, and radiation sensor data) being broadcast from the ID nodes to consider when detecting the secondary environmental threshold condition. For instance, with reference to FIG. 37A, command node 24160 may refine what is to be monitored when detecting the secondary environmental threshold condition (e.g., an environmental condition that is indicative of the environmental anomaly) with a modified monitoring parameter that limits the type of sensor data considered by command node 24160 as part of step 7725 to just temperature data, and ignore sensor data of other types coming from the ID nodes generating sensor data. Which type of sensor data to focus on at step 7725 may also depend upon what, if any, type of material is associated with the ID nodes and is being transported within the shipping container 24300a.

In still another example of step 7725, the step of monitoring the subsequent group of the sensor data over the second time period under the modified monitoring parameter may have the command node instructing each of the ID nodes to change a messaging rate used to regulate how often the generated sensor data is broadcast during the second time period. This may increase or decrease the messaging rate to use during the second time period. In more detail, a further example may instruct a first group of the ID nodes to increase the messaging rate from a default messaging rate used during the first time period to a higher secondary messaging rate used during the second time period, and then monitoring the subsequent group of the sensor data broadcast from only the first group of the ID nodes over the second time period to detect the secondary environmental threshold condition related to the shipping container as the environmental anomaly. In this way, the command node is able to adapt by selectively choosing to prioritize sensor data coming from just that group of ID nodes and to make the sensor data coming from that group of ID nodes come quicker so that the command node may better and more quickly detect the environmental anomaly so as to enhance how the command node responds in a timely manner to initiate a mediation response.

At step 7730, method 7700 has the command node determining if it has detected the secondary environmental threshold condition related to the shipping container. If not, step 7730 proceeds back to step 7725 for continued monitoring. But if so, step 7730 has method 7700 proceeding directly to step 7735 where the command node generates an alert notification related to the environmental anomaly for the shipping container in response to detecting the secondary environmental threshold condition.

At step 7740, method 7700 continues with the command node transmitting the alert notification to the external transceiver (e.g., external transceiver 24150 or a transceiver interface in fire suppression system 25010) to initiate a mediation response related to the environmental anomaly. The mediation response related to the environmental anomaly may, for example, cause a fire suppression system (e.g., fire suppression system 25010) to dispense fire suppressant material into the shipping container; cause the generation of a prompted message requesting an inspection of the shipping container (e.g., on a display of external transceiver 24150 disposed in a logistics support area of the transit vehicle 24200); or cause the generation of a prompted message requesting the transit vehicle alter course as a result of the environmental anomaly (e.g., on a display of external transceiver disposed in the cockpit of the transit vehicle 24200).

Those skilled in the art will appreciate that method 7700 as disclosed and explained above in various embodiments may be implemented using an exemplary adaptive monitoring system for detecting an environmental anomaly in a shipping container such as that explained above with reference to FIG. 37A and its exemplary elements. Such an embodiment of this exemplary adaptive monitoring system, as explained above relative to operations according to method 7700 and with elements from FIG. 37A, may use at least multiple sensor-based ID nodes disposed within the shipping container (e.g., ID nodes 1-7 shown in FIG. 37A) running one or more ID node monitoring program code as part of node control and management code 325 to control operations of the ID nodes to generate and broadcast ID node sensor data, as well as a command node mounted to the shipping container (e.g., command node 24160 shown in FIG. 37A) running one or more parts of CN control & management code 26425 (e.g., the command node container management program code that is part of command node control and management code 26425) to control the operations of the command node as part of adaptively monitoring a shipping container for an environmental anomaly. Such code may be stored on a non-transitory computer-readable medium, such as memory storage 26415 on command node 24160 of FIG. 37A (which is an embodiment of exemplary command node 26000) and memory storage 315 on sensor-based ID nodes 1-7 of FIG. 37A (embodiments of exemplary ID node 120a). Thus, when executing such code, the ID nodes and the command node may be operative to perform operations or steps from the exemplary methods disclosed above, including method 7700 and variations of that method.

Command Node Deployed with a Package

Several embodiments described above include an exemplary command node that is mounted to or part of a shipping container that maintains multiple packages as it is transported on a transit vehicle. Examples of such a "shipping container command node" include exemplary command node 26000 as described with reference to FIG. 26 as well as exemplary command node 24160 described in the various examples and embodiments above. However, a further embodiment of an exemplary command node (e.g., command node 26000, which may have its own sensors 26465) may be implemented as an exemplary package command node. In general, an exemplary package command node is disposed with a shipment package (e.g., a package to be transported within a shipping container). Such an exemplary command node may have a node enclosure or housing that may be located separately within the shipment package to travel with the shipment package as the shipment package is transported within the shipping container. The exemplary package command node may be disposed within the shipment package, attached (permanently or temporarily) to the shipment package, or be integrated as part of the shipment package. As such, the exemplary package command node may monitor surrounding ID nodes (e.g., sensor-based ID nodes that generate sensor data reflecting environmental conditions relative to their respective location in the shipping container, as the nodes and/or sensor data may be verified or validated to be trusted data or sensor data from trusted sensors) and take appropriate mediation action itself to directly initiate such mediation responses or notify the shipping container command node that may be responsible for initiating such mediation responses.

Indeed, some embodiments of an exemplary package command node may be deployed as a type of nested command node. For example, an exemplary package command node may be disposed with a large shipment package (e.g., palletized group of objects or packages) where another package command node may be deployed within or as part of further components within that large shipment package. In this way, some embodiments may have a system of multiple package command nodes that may be nested in layers of a wireless node network where a lower level package command node may monitor and report on any detected anomaly it detects relative to a subset of ID nodes within the shipping container. Such a lower level package command node may report such detections through alerts up to the next level package command node, which may then report the same up through a chain of network levels (depending on the implementation of such a system) to the shipping container command node.

As such, the deployment of a package command node as part of a system for detecting an environmental anomaly relative to a shipping container allows for further detailed monitoring on a distributed basis (e.g., where the package command node or nodes handle the primary monitoring operations relative to selective portions of the available ID nodes within the shipping container and offload the shipping container command node either temporarily or as a normal mode of environmental anomaly detection operation) while the shipping container command node monitors the different package container nodes and coordinates/initiates an appropriate mediation response via interaction with devices outside the shipping container (e.g., transceivers that interact with the transit vehicle's crew or transceivers that are part of an onboard fire suppression system).

Figure 78:
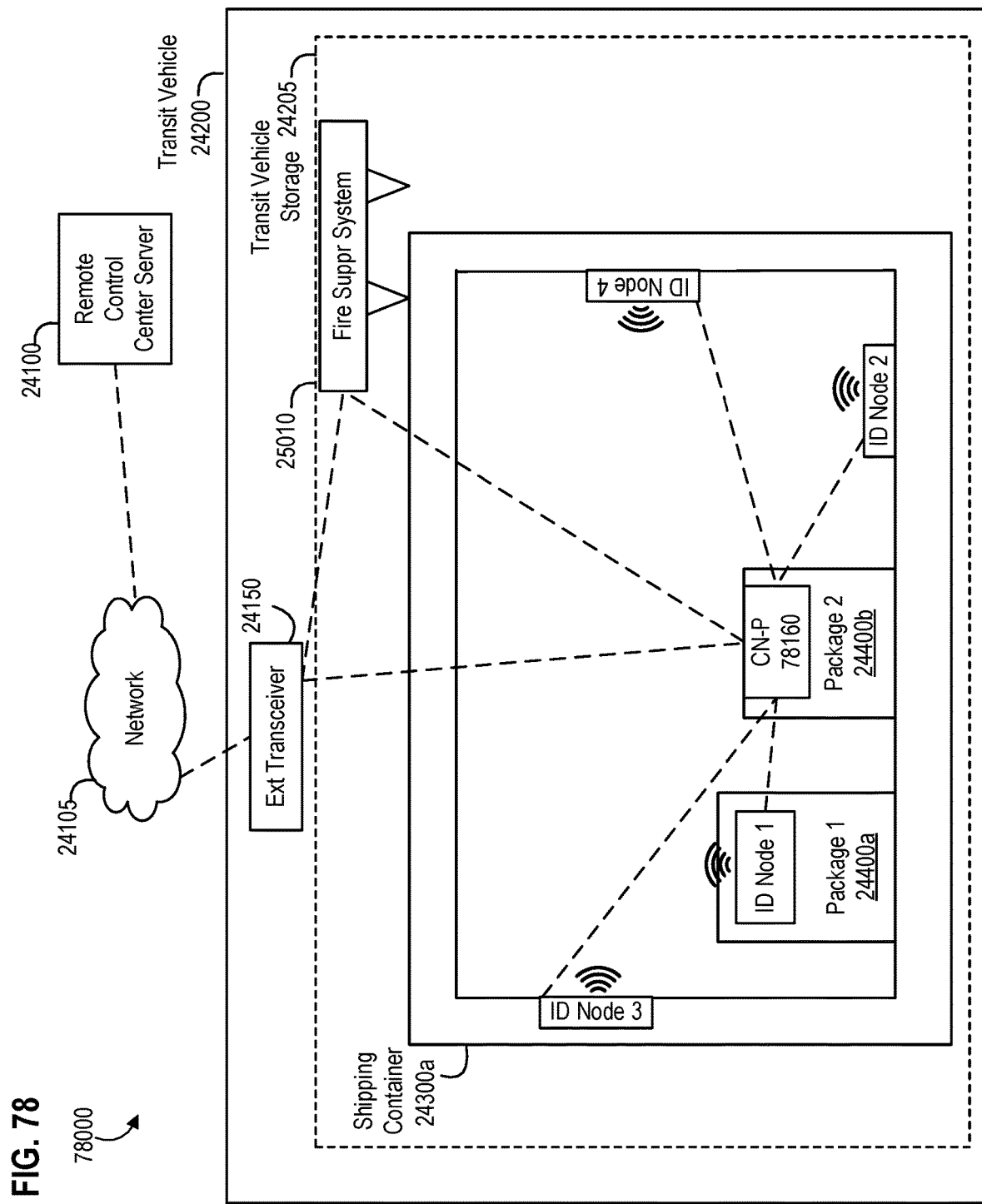
FIG. 78 is a diagram illustrating an exemplary system for detecting an environmental anomaly related to a shipment package for transport within a shipping container on a transit vehicle having an external transceiver where the system includes an exemplary package command node in accordance with an embodiment of the invention.

FIG. 78 is a diagram illustrating an exemplary system for detecting an environmental anomaly related to a shipment package for transport within a shipping container on a transit vehicle having an external transceiver where the system includes an exemplary package command node in accordance with an embodiment of the invention. Referring now to FIG. 78, exemplary system 78000 is shown with similar components as system 67000 in FIG. 67 (e.g., transit vehicle 24200, remote server 24100, network 24015, external transceiver 24150, onboard fire suppression system 25010, and shipping container 24300a), but FIG. 78 illustrates the exemplary shipping container 24300a without a shipping container command node (such as command node 1 shown in FIG. 67) but includes an exemplary package command node (e.g., package command node 78160 also referenced as CN-P) and sensor-based ID nodes 1-4 shown disposed in different locations within the container 24300*a*.

In more detail, sensor-based ID node 1 is shown in FIG. 78 as being associated with (e.g., attached to or disposed within) package 1 (also referenced as package 24400*a*) within shipping container 24300*a*. Sensor-based ID node 2 is shown in FIG. 78 being disposed on the bottom floor of shipping container 24300*a* (sitting freely or attached). Sensor-based ID node 3 is shown in FIG. 78 as integrated as part of the container 24300*a* on a wall of the container, and sensor-based ID node 4 is shown in FIG. 78 as attached to another wall of container 24300*a*. As implementations of an exemplary ID node 120*a* having one or more sensors 360, each of sensor-based ID nodes 1-4 shown in FIG. 78 has an ID node processor, an environmental sensor, and a wireless radio transceiver (which may be implemented in hardware, in a combination of hardware/software/or as a software defined radio (SDR)). The environmental sensor in each ID node is coupled to the ID node processor and generates sensor data related to an environmental condition proximate, nearby, or otherwise next to the respective sensor-based ID node within the shipping container. The wireless radio transceiver is also coupled to the ID node processor and operative to broadcast signals that include the sensor data (in additional to a validation record used to confirm the sensor data broadcast as part of the signal is from that particular ID node) in response to a command from the ID node's processor. As such, each of the sensor-based ID nodes 1-4 shown in FIG. 78 generate sensor data from and about the environment proximate, nearby, next to, or otherwise at their respective locations within shipping container 24300*a*.

Exemplary package command node 78160 (CN-P) illustrated in FIG. 78 may be implemented similarly to that explained above relative to exemplary command node 26000. For example, exemplary package command node 78160 is enclosed in a housing that is disposed with package 2 (as an exemplary shipment package). As such, exemplary package command node 78160 may be deposited within package 2, attached to either the inside or outside of package 2, or placed within a pouch or other holder that is attached to package 2. Similar to exemplary command node 26000, exemplary package command node 78160 has at least a command node processor coupled to one or more wireless transceiver-based communications interfaces as well as a command node memory. In one embodiment, the package command node's communications interface may be operative to communicate with sensor-based ID nodes 1-4 as well as externally disposed components, such as external transceiver 24150 and/or fire suppression system 25010 located outside shipping container 24300*a*. However in another embodiment with multiple communication interfaces, a first communication interface on the package command node may be operative to communicate with each of sensor-based ID nodes 1-4 using a wireless communication format compatible with the wireless radio transceiver on each of sensor-based ID nodes 1-4, while a second communication interface is operative to communicate with the external transceiver 24150 associated with the transit vehicle 24200 using a second wireless communication format compatible with the external transceiver (as well as other package command nodes that may be disposed in shipping container 24300*a*, or other transceivers on the transit vehicle 24200 outside of container 24300*a*, or in further nested package command nodes within package 2 (not shown)). Those skilled in the art will also appreciate exemplary package command node 78160 may be implemented as a master node (e.g., exemplary master node 110*a* that may include its own sensors as well as location circuitry that enables the master node to self-locate) or a container node that may not have location circuitry. Further, exemplary package command node 78160 may be integrated as part of package 2 or be implemented separately (as a separate device) but removably mounted to package 2.

The command node memory on package command node 78160 as shown in the embodiment illustrated in FIG. 78 may store and maintain at least command node container management program code that has program code governing operations on package command node 78160 when detecting and responding to environmental anomalies (e.g., package command node environmental detection program code that is part of command node control and management code 26425 on the memory of package command node 78160). While not shown in FIG. 78, those skilled in the art will appreciate the package command node 78160 may also maintain security credentials (such as security credentials 67435 shown in FIG. 67 relative to memory in command node 1) specific to one or more of sensor-based ID nodes 1-4 that are to be trusted (e.g., a type of security data 435 explained generally above).

In operation and as part of an apparatus working in an embodiment of system 78000 (e.g., package command node 78160 shown in FIG. 78), the processor of package command node 78160 is programmatically configured via its onboard executing programming (e.g., the package command node environmental detection program code that is part of command node control and management code 26425) to be operative to detect the sensor data broadcasted from the sensor-based ID nodes 1-4 using the command node wireless transceiver communication interface; responsively identify the environmental anomaly for the shipping container 24300*a* when the detected sensor data from the sensor-based ID nodes 1-4 indicates an environmental condition that exceeds an environmental threshold; generate an alert notification related to the environmental anomaly for the shipping container 24300*a* in response to identifying the environmental anomaly for the shipping container 24300*a*; and cause the command node wireless transceiver communication interface to transmit the alert notification to the external transceiver to initiate a mediation response related to the environmental anomaly.

Similar to exemplary command node 26000 (which has onboard sensors 26465), an embodiment of package command node 78160 may include at least one environmental sensor disposed with package 2 and operatively coupled to the command node processor of package command node 78160. Such an environmental sensor is operative to generate shipment package sensor data related to environmental conditions in or on package 2. As such, the command node processor of package command node 78160 may be programmatically configured to be operative to responsively identify the environmental anomaly for shipping container 24300*a* by being further programmatically configured to responsively identify the environmental anomaly for shipping container 24300*a* when at least one of the detected sensor data (i.e., the detected sensor data from the sensor-based ID nodes 1-4 and the detected shipment package sensor data from the package command node's own sensor(s)) indicates the environmental condition exceeds the environmental threshold.

In more detail, an embodiment of exemplary package command node 78160 may have its command node processor programmatically configured to be operative to responsively identify the environmental anomaly for the shipping container by being further programmatically configured to responsively identify the environmental anomaly for the shipping container when at least one of (a) the detected sensor data from the sensor-based ID nodes 1-4 indicates the environmental condition exceeds the environmental threshold, and (b) when the detected sensor data from the sensor-based ID nodes 1-4 does not include the sensor data from at least a threshold number of the sensor-based ID nodes 1-4. For example, the command node memory on package command node 78160 may maintain context data (e.g., part of context data 26560) identifying the particular ones of sensor-based ID nodes 1-4 anticipated to be broadcasting. As such, the command node processor of package command node 78160 may responsively identify the environmental anomaly for shipping container 24300a by being further programmatically configured to responsively identify the environmental anomaly for the shipping container when at least one of (a) the detected sensor data from the sensor-based ID nodes 1-4 indicates the environmental condition exceeds the environmental threshold, and (b) when the detected sensor data from those of sensor-based ID nodes 1-4 anticipated to be broadcasting according to the context data does not include sensor data from at least a threshold number of those sensor-based ID nodes anticipated to be broadcasting. Such context data that may identify those of sensor-based ID nodes anticipated to be broadcasting may have been received by package command node 78160 from external transceiver 24150 (which may have received such context data from remote control center server 24100). As the server 24100 may the device managing the different node elements of system 78000, server 24100 may track which ID nodes (or other nodes) are anticipated to be broadcasting and when. Such information may be provided as context information to other node elements of the network (such as external transceiver 24150 and package command node 78160).

While package command node 78160 transmits the alert notification to the external transceiver to initiate a mediation response related to the environmental anomaly, such a mediation response may come in different forms. For example, the mediation response initiated with the transmitted alert notification may be implemented as an instruction to activate a triggered fire suppression system on the transit vehicle (e.g., fire suppression system 25010) and in communication with external transceiver 24150. In another example, the mediation response initiated with the transmitted alert notification may be implemented as an instruction to generate a prompted request to change course of the transit vehicle from an existing travel path of the transit vehicle, or an instruction to generate a prompted request to investigate the shipping container.

Package command node 78160 may also, as part of identifying the environmental anomaly, verify or validate what ID node is providing the sensor data to avoid errors or spoofing ID nodes from providing inaccurate or unreliable sensor data. For example, command node memory on package command node 78160 may maintain security credentials associated with trusted sensors for use with environmental anomaly detection. As such, the command node processor of package command node 78160 may responsively identify the environmental anomaly for the shipping container by being further programmatically configured to identify which of the sensor-based ID nodes 1-4 maintained within shipping container 24300a is one of the trusted sensors disposed within the shipping container based the security credentials.

The identified ones of sensor-based ID nodes 1-4 are then considered being confirmed sensor-based ID nodes. As such, the command node processor of package command node 78160 may then monitor, via the command node wireless transceiver communication interface, only the confirmed ones of sensor-based ID nodes 1-4 for sensor data broadcast from each of the confirmed sensor-based ID nodes (while disregarding any sensor data broadcast from those of sensor-based ID nodes 1-4 not identified as being confirmed sensor-based ID nodes); and identify the environmental anomaly for shipping container 24300a when the monitored sensor data broadcast from each of the confirmed sensor-based ID nodes indicates an environmental condition that exceeds the environmental threshold.

Package command node 78160 may, as part of identifying the environmental anomaly, verify or validate the sensor data itself to better ensure the sensor data is to be trusted and relied upon for any environmental anomaly detection and responsive actions. For example, the command node processor of package command node 78160 may be further programmatically configured to be operative to validate the sensor data broadcast from each of sensor-based ID nodes 1-4 upon receiving the sensor data. As such, the command node processor of package command node 78160 may be programmatically operative to responsively identify the environmental anomaly for shipping container 24300a by being further programmatically configured to detect the environmental anomaly for shipping container 24300a when the sensor data validated by the package command node 78160 indicates the environmental condition that exceeds the environmental threshold. In more detail, the command node processor of package command node 78160 may validate the sensor data by being further programmatically configured to determine which of the sensor data received by the command node processor during monitoring is valid by assessing a validation record within each of the received sensor data broadcast from each of sensor-based ID nodes 1-4 without requiring the command node processor to cause the command node wireless transceiver to transmit a validation request to each of sensor-based ID nodes 1-4.

A further embodiment illustrated in FIG. 78 includes a system embodiment that deploys package command node 78160 with package 2 as explained above (including each variation and further detailed features and operational capabilities) as well as each of sensor-based ID nodes 1-4 as they generate sensor data and interact with package command node 78160 as described above. In other words, the apparatus of exemplary package command node 78160 (as described generally and in more detail in the various embodiments above) may be used as an element, in combination with each of sensor-based ID nodes 1-4, in a system embodiment that detects an environmental anomaly related to a shipment container on a transit vehicle.

Figure 79A:
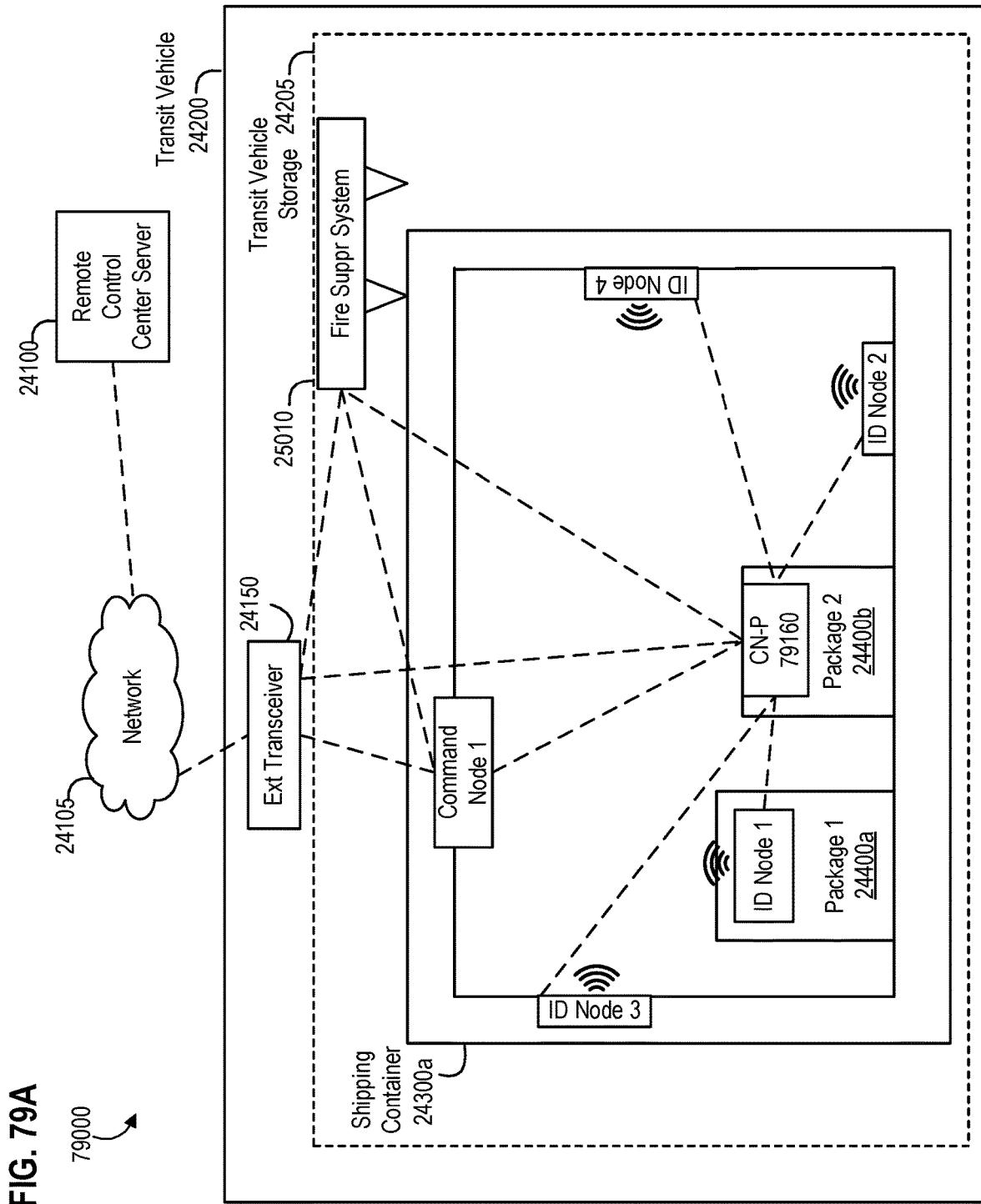
FIGS. 79A-79C are diagrams illustrating an exemplary system for detecting an environmental anomaly related to a shipment package for transport within a shipping container on a transit vehicle having an external transceiver where the system includes an exemplary package command node that interacts and works with an exemplary shipping container command node in accordance with an embodiment of the invention.
Figure 79B:
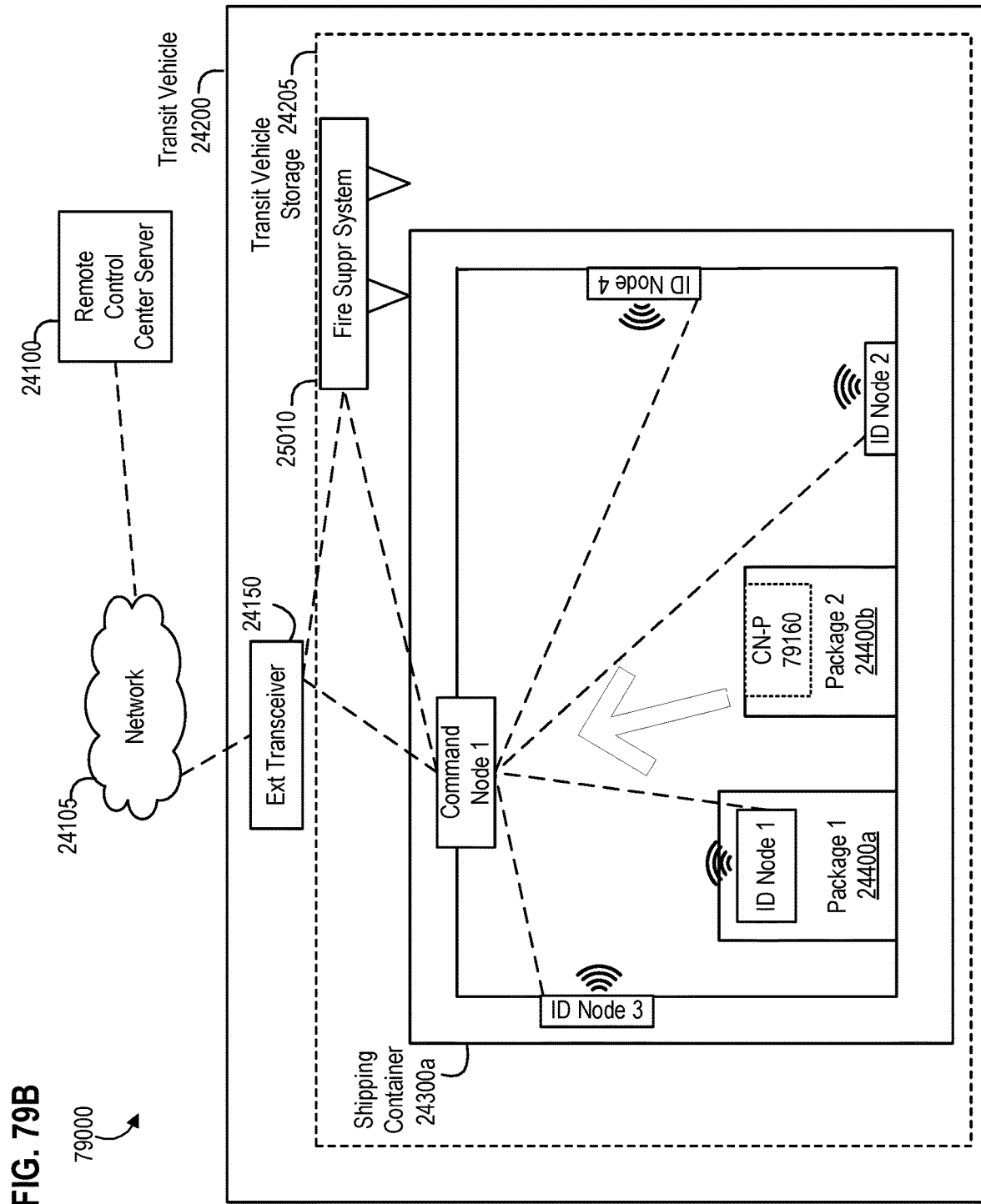
Figure 79C:
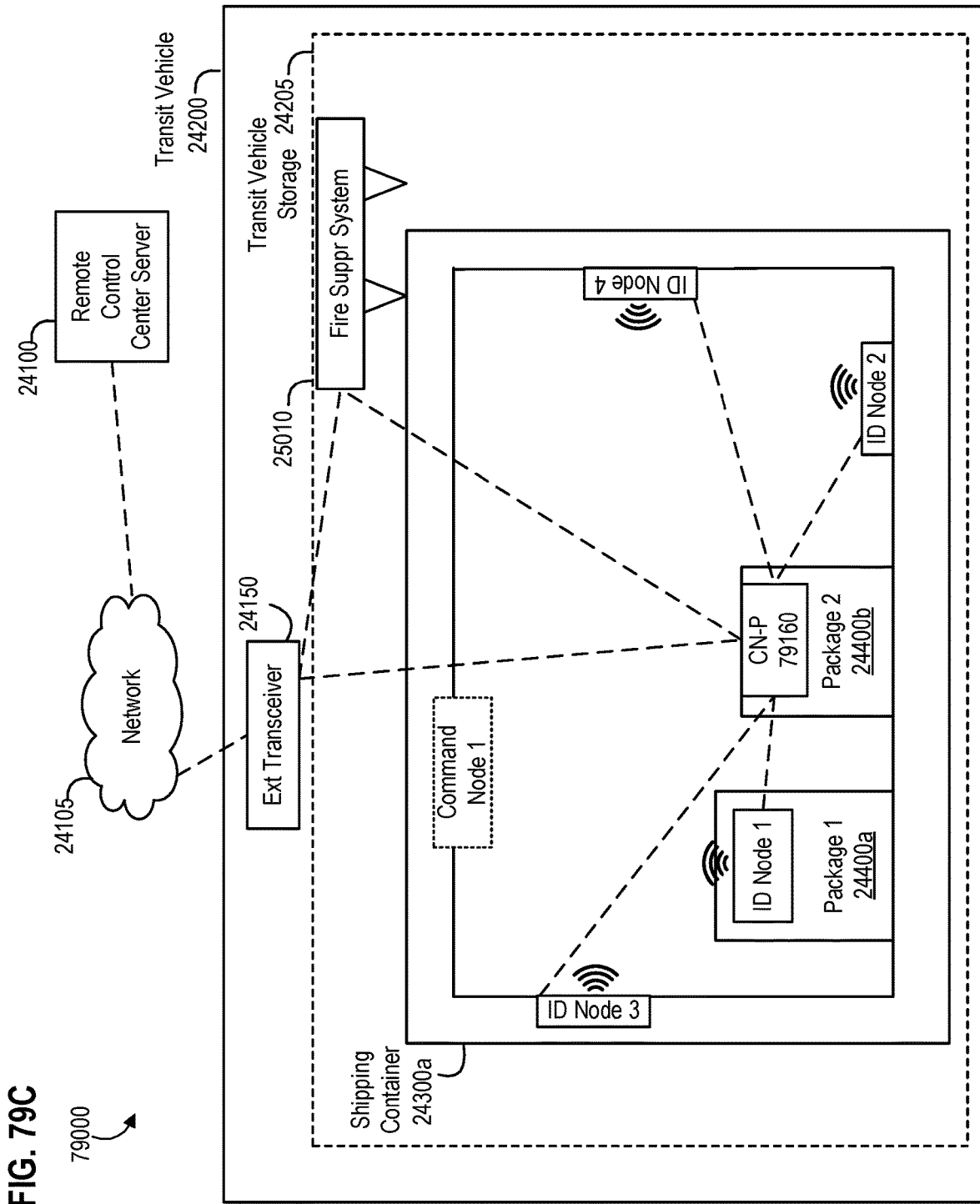

Still further embodiments involve a similar system of components (e.g., package command node 78160 and sensor-based ID nodes 1-4 as shown in FIG. 78) with the addition of a shipping container command node at a network layer above the package command node 78160. FIGS. 79A-79C are diagrams illustrating an exemplary system for detecting an environmental anomaly related to a shipment package for transport within a shipping container on a transit vehicle having an external transceiver where the system includes an exemplary package command node 78160 that interacts and works with an exemplary shipping container command node (e.g., command node 1 as generally explained in embodiments above) in accordance with an embodiment of the invention. Referring now to FIG. 79A, exemplary system 79000 is shown with similar components as system 67000 in FIG. 67 (e.g., transit vehicle 24200, remote server 24100, network 24015, external transceiver 24150, onboard fire suppression system 25010, and shipping container 24300*a*), but FIG. 79A illustrates the exemplary shipping container 24300*a* including exemplary shipping container command node 1 mounted to shipping container 24300*a* as well as exemplary package command node 78160 (also referenced as CN-P) and sensor-based ID nodes 1-4 shown disposed in different locations within the container 24300*a*. As shown in FIG. 79A, each sensor-based ID nodes 1-4 generate sensor data from different parts of shipping container 24300*a* as explained above. Package command node 78160 is similarly disposed as explained above with a package command node housing disposed with the shipment package (package 2), a package command node processor disposed within the package command node housing of package command node 78160, a package command node memory coupled to the package command node processor and within the package command node housing (maintaining at least package-level environmental detection program code—program code governing operations on package command node 78160 as shown in FIG. 79A when detecting and responding to environmental anomalies (e.g., package command node environmental detection program code that is part of command node control and management code 26425 on the memory of package command node 78160). Package command node 78160 shown in FIG. 79A as part of system 79000 also has a package command node wireless transceiver communication interface disposed within the package command node housing and operatively responsive to the package command node processor, the package command node wireless transceiver communication interface is configured to communicate with at least each of sensor-based ID nodes 1-4 within shipping container 24300*a*.

The exemplary shipping container command node (command node 1) is mounted to shipping container 24300*a* and is operative to communicate with the package command node 78160 and with an external transceiver (such as external transceiver 24150 or the transceiver-equipped fire suppression system 25010 as shown in FIG. 79A). Exemplary shipping container command node, as an implementation of exemplary command node 26000, includes at least a shipping container command node processor, a shipping container command node memory, and a shipping container command node wireless transceiver communication interface. In more detail, the shipping container command node memory on command node 1 is coupled to the shipping container command node processor and maintains at least shipping container-level environmental detection program code (e.g., program code that is part of command node control and management code 26425 on the memory of shipping container command node 1 shown in FIG. 79A). The shipping container command node wireless transceiver communication interface is operatively responsive to the shipping container command node processor and is configured to communicate with package command node 78160 as well as with external transceivers outside shipping container 24300 (e.g., external transceiver 24150 or the transceiver-equipped fire suppression system 25010 as shown in FIG. 79A).

During system operation of this embodiment, the command node processor of package command node 78160 is programmatically configured, when executing the package-level environmental detection program code, to be operative to detect the sensor data broadcasted from sensor-based ID nodes 1-4 using the package command node wireless transceiver communication interface; responsively identify the environmental anomaly for shipping container 24300*a* when the detected sensor data from sensor-based ID nodes 1-4 indicates an environmental condition that exceeds an environmental threshold; generate an alert notification related to the environmental anomaly for shipping container 24300*a* in response to identifying the environmental anomaly for shipping container 24300*a*; and cause the package command node wireless transceiver communication interface to transmit the alert notification to the shipping container command node (e.g., command node 1 mounted to shipping container 24300*a*).

Furthermore, during system operation of this embodiment, the shipping container command node processor of shipping container command node 1 is programmatically configured, when executing the shipping container-level environmental detection program code, to be operative to receive (using the shipping container command node wireless transceiver communication interface) the alert notification from package command node 78160, and responsively cause the shipping container command node wireless transceiver communication interface to instruct the external transceiver (e.g., external transceiver 24150) to initiate a mediation response for shipping container 24300*a* related to the environmental anomaly.

The system's package command node may identify the environmental anomaly based upon sensor data and/or unresponsive ID nodes. For example, the package command node processor of package command node 78160 may responsively identify the environmental anomaly for shipping container 24300*a* by being further programmatically configured to responsively identify the environmental anomaly for shipping container 24300*a* when at least one of (a) the detected sensor data from sensor-based ID nodes 1-4 indicates an environmental condition that exceeds the environmental threshold, and (b) when the detected sensor data from the sensor-based ID nodes 1-4 (i.e., detected sensor data from any of sensor-based ID nodes 1-4) does not include sensor data from at least a threshold number of sensor-based ID nodes 1-4 as some of the ID node may no longer be functioning as a result of the environmental anomaly. In more detail, when package command node 78160 maintains context data identifying which of sensor-based ID nodes 1-4 are anticipated to be broadcasting, the package command node processor of package command node 78160 may identify the environmental anomaly for shipping container 24300*a* by being further programmatically configured to responsively identify the environmental anomaly for shipping container 24300*a* when at least one of (a) the detected sensor data from sensor-based ID nodes 1-4 indicates an environmental condition that exceeds the environmental threshold, and (b) when the detected sensor data from those of sensor-based ID nodes 1-4 anticipated to be broadcasting according to the context data does not include sensor data from at least a threshold number of the sensor-based ID nodes anticipated to be broadcasting.

The context data used by package command node 78160 may be provided by different entities in system 79000. For example, the package command node processor of package command node 78160 may be further programmatically configured to be operative to receive the context data from external transceiver 24150 (which may have received the context data from remote server 24100). In another example, the shipping container command node memory of command node 1 may maintains the context data, provide the context data to package command node 78160 but may have received such context data from external transceiver 24150 (which may have received the context data from remote server 24100).

The system's shipping container command node (i.e., command node 1 mounted to shipping container 24300*a*) instruct the external transceiver to initiate a mediation response for shipping container 24300*a* related to the environmental anomaly in several ways. For example, the mediation response initiated by shipping container command node 1 may be implemented as an instruction to external transceiver 24150 to activate onboard triggered fire suppression system 25010 on transit vehicle 24200 given external transceiver 24150 is in communication with fire suppression system 25010 as shown in FIG. 79A. In another example, the mediation response initiated by shipping container command node 1 may be implemented as an instruction to external transceiver 24150 to generate a prompted request to change course of transit vehicle 24200 from an existing travel path of transit vehicle 24200 (e.g., via a visual or audio prompt generated by external transceiver 24150), or as an instruction external transceiver 24150 to generate a prompted request to investigate the shipping container (e.g., via a visual or audio prompt). In a further embodiment, such a prompted request may take the form of a wireless message generated by external transceiver 24150 and transmitted to a user access device (e.g., a handheld communication device, such as a handheld radio transceiver, laptop, ruggedized mobile tablet) used by crew on transit vehicle 24200).

The system's package command node 78160 may also identify the environmental anomaly using only verified/validated ID nodes confirmed to be trusted sensors and/or using only verified or validated sensor data as explained above relative to the embodiment shown in FIG. 78 (e.g., the functionality described relative to how exemplary package command node 78160 may use security credentials to validate and confirm which of ID nodes 1-4 are trusted sensors and/or use validation records to validate what sensor data is trusted sensor data).

Further embodiments of the system shown in FIG. 79A (system 79000 which has at least shipping container command node 1, package command node 78160, and sensor-based ID nodes 1-4) may involve additional system operations of such components when either the shipping command node or the package command node becomes unresponsive. Referring now to FIG. 79B, an example is shown where package command node 78160 has become unresponsive and is not functioning as indicated by its inability to communicate with shipping container command node 1. This may be due to damage from an environmental anomaly localized to package command node 78160 for the time being (but with the likelihood that such an environmental anomaly may spread further). As such, an embodiment may have the shipping container command node processor of command node 1 essentially taking over the primary monitoring operations of the sensor data generated by sensor-based ID nodes 1-4. In more detail, the shipping container command node processor of command node 1 may be further programmatically configured to be operative, upon detecting package command node is unresponsive to a status inquiry message from shipping container command node a to package command node 78160, to detect the sensor data broadcasted from sensor-based ID nodes 1-4 using the shipping container command node wireless transceiver communication interface; responsively identify the environmental anomaly for shipping container 24300*a* when the detected sensor data from sensor-based ID nodes 1-4 indicates an environmental condition that exceeds an environmental threshold; generate the alert notification related to the environmental anomaly for shipping container 24300*a* in response to identifying the environmental anomaly for the shipping container; and cause the shipping container command node wireless transceiver communication interface to transmit the alert notification to an external transceiver (e.g., external transceiver 24150 or the transceiver interface of fire suppression system 25010) to initiate the mediation response related to the environmental anomaly.

In an alternative embodiment related to this additional functionality, the shipping container command node 1 may simply generate and transmit the alert notification to an external transceiver (e.g., external transceiver 24150 or the transceiver interface of fire suppression system 25010) to initiate the mediation response related to the environmental anomaly immediately upon detecting package command node 78160 is unresponsive to a status inquiry message from the shipping container command node. In this way, while one embodiment of the system has the shipping container command node taking over monitoring responsibility when the package command node becomes unresponsive, the other embodiment of the system may deem the unresponsiveness of the package command node to be of such importance so as to justify an automatic and immediate alert notification transmission to initiate an appropriate mediation response. This, in some embodiments, may have the shipping container command node determining to, immediately and without further monitoring, transmitting the alert notification to initiate the appropriate mediation response depending upon context data (e.g., shipping information on what type of material is being transported within the package associated with the now unresponsive package command node). In other words, if the material in the shipment package associated with the package command node is of a predetermined category of material (e.g., lithium-ion battery material, combustible material, an extremely flammable material, a certain type of chemical, a radioactive material, and the like) as indicated by context data on the shipping container command node, this fact along with the unresponsiveness of the package command node may have the shipping container command node foregoing further monitoring activity and immediately transmitting the alert notification to initiate an appropriate mediation response.

Referring now to FIG. 79C, a different example is shown where package command node 78160 is still functional, but shipping container command node 1 has become unresponsive and is not functioning as indicated by its inability to communicate with package command node 78160. This may be due to damage from an environmental anomaly localized to shipping container command node 1 for the time being (but with the likelihood that such an environmental anomaly may spread further). As such, an embodiment may have the package command node processor of package command node 78160 essentially taking over alert notification operations in response to any environmental anomaly detected based on the sensor data generated by sensor-based ID nodes 1-4. In more detail, the package command node processor may be further programmatically configured to be operative, upon detecting that shipping container command node 1 is unresponsive to a status inquiry message from package command node 78160 to shipping container command node 1, to cause the package command node wireless transceiver communication interface to transmit the alert notification to an external transceiver (e.g., external transceiver 24150 or the transceiver interface of fire suppression system 25010) to initiate the mediation response related to the environmental anomaly.

It should be emphasized that the sequence of operations to perform any of the methods and variations of the methods described in the embodiments herein are merely exemplary, and that a variety of sequences of operations may be followed while still being true and in accordance with the principles of the present invention.

At least some portions of exemplary embodiments outlined above may be used in association with portions of other exemplary embodiments to better monitor for environmental anomalies, enhance detection of various different types of environmental anomalies, and advantageously initiate selective mediation responses using adaptive, integrated, and cooperative elements of a wireless node network or use such nodes and network elements as part of a hierarchical node network. Moreover, at least some of the exemplary embodiments disclosed herein may be used independently from one another and/or in combination with one another and may have applications to devices and methods not disclosed herein.

For example, many of the embodiments above describe using particular wireless communication interfaces when communicating to ID nodes and different wireless communication interfaces when communicating with other node elements of the network (e.g., command nodes, external transceivers, onboard fire suppression systems, mobile handheld user access devices, and the like). Depending on the type of wireless transceiver implemented on a particular node, such a node may be able to perform the same functionality with a single wireless transceiver or a node having two different wireless communication interfaces without veering from principles of the described invention herein. Thus, for example, transmitting a layered alert notification from a command node (e.g., command node 26000, command node 26140, and the like) may be accomplished with either a first or second communication interface or simply by a single wireless transceiver-based communication interface (e.g., such as one using LPWAN connectivity) capable of communication with ID nodes as well as the other node devices described herein.

Those skilled in the art will readily appreciate that operations of such an exemplary wireless node network, as set forth herein, are not limited to detecting a fire within a shipping container on an aircraft, but may be used to manage logistics related to the packages being transported within the shipping container as well as the transit vehicle itself Those skilled in the art will appreciate that embodiments may provide one or more advantages, and not all embodiments necessarily provide all or more than one particular advantage as set forth here. Additionally, it will be apparent to those skilled in the art that various modifications and variations can be made to the structures and methodologies described herein. Thus, it should be understood that the invention is not limited to the subject matter discussed in the description. Rather, the present invention is intended to cover modifications and variations.

While numerous embodiments and variations of such embodiments are described above, what follows below is a listing of an exemplary claim set focusing on one or more aspects of the different embodiments described above.

What is claimed is:

1. An improved system on a transit vehicle for coordinated mediation action in response to an identified environmental anomaly on a shipping container being transported by the transit vehicle, the transit vehicle including an external transceiver, the system comprising:
    a plurality of wireless ID nodes disposed at different locations within the shipping container, wherein each of the ID nodes being at a low level of a hierarchical wireless node network and each of the ID nodes being respectively configured and operative to broadcast signals over a first wireless communication path;
    a fire suppression system disposed on the transit vehicle transporting the shipping container, the fire suppression system comprising at least
        a fire suppressant material reservoir that temporarily maintains a fire suppressant material,
        a fire suppressant material pump connected to the fire suppressant material reservoir and responsive to a pump control input to activate pumping the fire suppressant material from the fire suppressant material reservoir,
        an articulating delivery nozzle connected to the fire suppressant material pump that receives the pumped fire suppressant material and deploys to deliver the fire suppressant material to the shipping container, and
        a wireless transceiver-based controller operating as a master node at a middle level of the hierarchical wireless node network, the master node being operative to generate the pump control input and cause the articulating delivery nozzle to deploy and deliver the fire suppressant material to the shipping container;
    wherein the master node of the fire suppression system is further configured to operate as a primary monitor for the environmental anomaly by being operative to:
        (a) wirelessly monitor the signals being broadcast from the ID nodes,
        (b) responsively identify the environmental anomaly based upon the monitored signals broadcast from the ID nodes,
        (c) generate a layered alert notification related to the environmental anomaly for the shipping container in response to identifying the environmental anomaly for the shipping container, wherein the layered alert notification identifies a targeted mediation action and establishes a mediation response priority, and
        (d) initiate a mediation response by the fire suppression system related to the targeted mediation action and the mediation response priority.

2. The system of claim 1, wherein the fire suppressant material reservoir comprises a pressurized container that temporarily maintains the fire suppressant material at a storage pressure prior to when the fire suppressant material is released.

3. The system of claim 1, wherein each of the wireless ID nodes comprises a sensor-based ID node operative that broadcasts sensor data as part of the signals broadcast over the first wireless communication path; and
    wherein the master node of the fire suppression system is programmatically configured to be further operative to
        (d) initiate the mediation response as a stepped mediation response comprising at least:
            (1) initiate a first stage response that further assesses the identified environmental anomaly using the sensor data from at least one or more of the wireless ID nodes, and
            (2) initiate a second stage response that causes deployment of the fire suppressant material to the shipping container based upon and in response to the further assessment of the identified environmental anomaly in (1).

4. The system of claim 3, wherein the master node of the fire suppression system is programmatically configured to initiate the first stage response by being configured and operative to:

detect sensor data from the monitored signals being broadcasted from the wireless sensor-based ID nodes;

refine the identity of the environmental anomaly for the shipping container when the detected sensor data does not include the sensor data from at least a threshold number of the wireless sensor-based ID nodes, and further refine the identity of the environmental anomaly for the shipping container when the detected sensor data indicates an environmental condition that exceeds an environmental threshold.

5. The system of claim 1, wherein the fire suppression system further comprises a plurality of shipping container sensors coupled to the master node, wherein each of the shipping container sensors providing sensor data to the master node about the shipping container; and wherein the master node of the fire suppression system is programmatically configured to be further operative to (d) initiate the mediation response as a stepped mediation response comprising at least:

(1) initiate a first stage response that further assesses the identified environmental anomaly using at least one or more of the shipping container sensors, and (2) initiate a second stage response that causes deployment of the fire suppressant material to the shipping container based upon and in response to the further assessment of the identified environmental anomaly in (1).

6. The system of claim 5, wherein the master node of the fire suppression system is programmatically configured to initiate the first stage response by being configured and operative to:

detect sensor data from the shipping container sensors, the shipping container sensors being disposed outside the shipping container and focusing on the exterior of the shipping container; and refine the identity of the environmental anomaly for the shipping container when the detected sensor data indicates an environmental condition that exceeds an environmental threshold.

7. The system of claim 5, wherein the at least one or more of the shipping container sensors is disposed on the articulating delivery nozzle such that when then the articulating delivery nozzle is disposed within the shipping container, the at least one or more of the shipping container sensors is exposed to an interior of the shipping container; and wherein the master node of the fire suppression system is programmatically configured to initiate the first stage response by being configured and operative to:

detect sensor data from the at least one or more of the shipping container sensors, and refine the identity of the environmental anomaly for the shipping container when the detected sensor data indicates an environmental condition that exceeds an environmental threshold.

8. The system of claim 7, wherein the detected sensor data from the at least one or more of the shipping container sensors comprises a detected temperature.

9. The system of claim 7, wherein the detected sensor data from the at least one or more of the shipping container sensors comprises a detected radiation level.

10. The system of claim 7, wherein the detected sensor data from the at least one or more of the shipping container sensors comprises a detected chemical.

11. The system of claim 10, wherein the detected chemical is indicative of an explosive within the shipping container.

12. The system of claim 10, wherein the detected chemical is indicative of a fire within the shipping container.

13. The system of claim 10, wherein the detected chemical comprises one of either CO or $CO_2$ disposed within the shipping container.

14. The system of claim 7, wherein the at least one or more of the shipping container sensors is disposed on a delivery end of the articulating delivery nozzle, wherein when then the articulating delivery nozzle is deployed with the delivery end puncturing and disposed within the shipping container, the at least one or more of the shipping container sensors is exposed to an interior of the shipping container.

15. The system of claim 7, wherein the at least one or more of the shipping container sensors comprises a wireless RF environmental sensor operative to capture the sensor data.

16. The system of claim 5, wherein a first portion of the shipping container sensors is disposed on the articulating delivery nozzle such that when then the articulating delivery nozzle is deployed within the shipping container, the first portion of the shipping container sensors being exposed to an interior of the shipping container;

wherein a second portion of the shipping container sensors is disposed outside the shipping container and focusing on the exterior of the shipping container; and wherein the master node of the fire suppression system is programmatically configured to initiate the first stage response by being configured and operative to:

detect sensor data from the first portion of the shipping container sensors and the second portion of the shipping container sensors, and refine the identity of the environmental anomaly for the shipping container when the detected sensor data indicates an environmental condition that exceeds an environmental threshold.

17. The system of claim 5, wherein each of the wireless ID nodes comprises a sensor-based ID node operative to broadcast sensor data as part of the signals broadcast over the first wireless communication path; and wherein a first portion of the shipping container sensors is disposed on a delivery end of the articulating delivery nozzle such that when then the articulating delivery nozzle is deployed with the delivery end puncturing and disposed within the shipping container, the first portion of the shipping container sensors being exposed to an interior of the shipping container;

wherein a second portion of the shipping container sensors is disposed outside the shipping container and focusing on the exterior of the shipping container; and wherein the master node of the fire suppression system is programmatically configured to initiate the first stage response by being configured and operative to:

detect first sensor data from the first portion of the shipping container sensors, detect second sensor data from the second portion of the shipping container sensors, detect third sensor data from the monitored signals being broadcasted from the wireless sensor-based ID nodes, and refine the identity of the environmental anomaly for the shipping container when a collective assessment of the first sensor data, the second sensor data, and the third sensor data indicates an environmental condition that exceeds an environmental threshold.

18. The system of claim 1, wherein the master node is further operative to responsively identify the environmental anomaly based upon the monitored signals broadcast from the ID nodes by being operative to identity of the environmental anomaly for the shipping container when the signals being broadcast from the ID nodes as wirelessly monitored by the master node indicate at least a threshold number of the wireless ID nodes are in a state of ceased broadcasting.

19. The system of claim 1, wherein each of the wireless ID nodes comprises:
  an ID node processor;
  an ID node memory coupled to the ID node processor, the memory maintaining at least an ID node monitoring program code;
  at least one environmental sensor configured to generate sensor data related to an environmental condition proximate the respective wireless ID node;
  a wireless radio transceiver coupled to the ID node processing unit, the wireless radio transceiver being configured to access the sensor data generated by the at least one environmental sensor and broadcast the sensor data in response to a report command from the ID node processor when the ID node processing unit executes the ID node monitoring program code.

20. The system of claim 1, wherein the master node of the fire suppression system is further configured to operate as the primary monitor for the environmental anomaly by being further operative to (e) transmit the layered alert notification to a targeted mediation recipient according to the mediation response priority.

21. The system of claim 20, wherein the targeted mediation recipient comprises the external transceiver, wherein the external transceiver having a display used by an operator of the transit vehicle that can alter movement of the transit vehicle.

22. The system of claim 20, wherein the targeted mediation recipient comprises the external transceiver, wherein the external transceiver having a display used a logistics crew member of the transit vehicle that can inspect the shipping container.

23. The system of claim 1, wherein the master node is further programmatically configured to identify the targeted mediation action based at least upon how many of the wireless ID nodes were not detected above a threshold number of the wireless ID nodes.

24. The system of claim 23, wherein the targeted mediation action depends upon what is loaded within the shipping container as indicated by shipping information maintained on the master node of the fire suppression system.

25. The system of claim 4, wherein the master node is further programmatically configured to identify the targeted mediation action based upon at least one of (a) how many of the wireless ID nodes were not detected above the threshold number of the wireless sensor-based ID nodes and (b) how much the environmental condition exceeds the environmental threshold.

26. The system of claim 25, wherein the targeted mediation action depends upon what is loaded within the shipping container as indicated by shipping information maintained on the master node of the fire suppression system.

27. The system of claim 4, wherein the master node is further programmatically configured to automatically establish the mediation response priority based upon at least one of (a) how many of the wireless ID nodes were not detected above the threshold number of the wireless ID nodes and (b) how much the environmental condition exceeds the environmental threshold.

28. The system of claim 27, wherein the mediation response priority comprises a high priority level indicating further travel by the transit vehicle is to be at least minimized as part of the mediation response.

29. The system of claim 27, wherein the mediation response priority comprises an intermediate priority level indicating further travel by the transit vehicle is permissible as part of the mediation response.

30. The system of claim 1, wherein the transit vehicle comprises an airplane.

31. The system of claim 1, wherein the transit vehicle comprises one from the group consisting of a railway conveyance, a maritime vessel, and a roadway conveyance.

32. The system of claim 1, wherein the master node is further operative to wirelessly monitor the signals being broadcast from the ID nodes by being operative to:
  detect the signals broadcasted by the wireless ID nodes according to a broadcast profile maintained by each of the wireless ID nodes, the broadcast profile defining a first messaging rate used to regulate how often the signals are broadcast to the master node, the first messaging rate being higher than a default messaging rate; and
  instruct each of the wireless ID nodes to broadcast future signals at a second messaging rate that exceeds the first messaging rate after initiating the mediation response.

33. The system of claim 32, wherein the master node is further operative to instruct each of the wireless ID nodes to change from the default messaging rate to the first messaging rate.

34. The system of claim 32, wherein the first messaging rate for the wireless ID nodes comprises an initial value correlated to an environmental risk associated with material maintained within the shipping container.

35. The system of claim 4, wherein the master node is further operative to detect the sensor data from the monitored signals being broadcast from the wireless sensor-based ID nodes by being operative to:
  detect the sensor data broadcasted by the wireless sensor-based ID nodes according to a broadcast profile maintained by each of the wireless sensor-based ID nodes, the broadcast profile defining a first messaging rate used to regulate how often the generated sensor data is transmitted to the master node, the first messaging rate being higher than a default messaging rate; and
  instruct each of the wireless sensor-based ID nodes to broadcast future generated sensor data at a second messaging rate that exceeds the first messaging rate after initiating the mediation response.

36. The system of claim 35, wherein the master node is further operative to instruct each of the wireless sensor-based ID nodes to change from the default messaging rate to the first messaging rate.

37. The system of claim 35, wherein the first messaging rate for the wireless sensor-based ID nodes comprises an initial value correlated to an environmental risk associated with material maintained within the shipping container.

38. The system of claim 1, wherein the master node is further programmatically configured to operate as a primary monitor for the environmental anomaly by being further operative to:
  receive an altered trigger limit related to the targeted mediation action; and
  initiate the mediation response using the altered trigger limit related to the targeted mediation action.

39. The system of claim 38, wherein the master node receives the altered trigger limit from the external transceiver on the transit vehicle.

40. The system of claim 39, wherein the altered trigger limit is defined by an operator of the transit vehicle using the external transceiver.

41. The system of claim 39, wherein the altered trigger limit is defined by a logistics crew member of the transit vehicle using the external transceiver.

42. The system of claim 39, wherein the altered trigger limit related to the targeted mediation action is provided to the external transceiver of the transit vehicle from a remote control center in communication with the external transceiver.

43. The system of claim 20, wherein the master node is further configured to receive a request to initiate a secondary mediation response by the fire suppression system related to the targeted mediation action and the mediation response priority, the request being provided to the master node from the external transceiver in response to the layered alert notification.

44. An improved system on a transit vehicle for coordinated mediation action in response to an identified environmental anomaly on a shipping container being transported by the transit vehicle, the transit vehicle including an external transceiver, the system comprising:
 a plurality of wireless ID nodes disposed at different locations within the shipping container, wherein each of the ID nodes being at a low level of a hierarchical wireless node network and each of the ID nodes being respectively configured and operative to broadcast signals over a first wireless communication path;
 a fire suppression system disposed on the transit vehicle transporting the shipping container, the fire suppression system comprising at least
  a pressurized fire suppressant material container that temporarily maintains a fire suppressant material,
  a release nozzle coupled to the pressurized fire suppressant material container that receives the pressurized fire suppressant material and selectively opens to allow the fire suppressant material to flow from the pressurized fire suppressant material container, in response to an activation input signal, to deliver the fire suppressant material to the shipping container, and
  a wireless transceiver-based controller operating as a master node at a middle level of the hierarchical wireless node network, the master node being operative to generate the activation input signal and cause the release nozzle to open and deliver the fire suppressant material to the shipping container;
 wherein the master node of the fire suppression system is further configured to operate as a primary monitor for the environmental anomaly by being operative to:
  (a) wirelessly monitor the signals being broadcast from the ID nodes,
  (b) responsively identify the environmental anomaly based upon the monitored signals broadcast from the ID nodes,
  (c) generate a layered alert notification related to the environmental anomaly for the shipping container in response to identifying the environmental anomaly for the shipping container, wherein the layered alert notification identifies a targeted mediation action and establishes a mediation response priority, and
  (d) initiate a mediation response by the fire suppression system related to the targeted mediation action and the mediation response priority.

45. The system of claim 44, wherein each of the wireless ID nodes comprises a sensor-based ID node operative to broadcast sensor data as part of the signals broadcast over the first wireless communication path; and
 wherein the master node of the fire suppression system is programmatically configured to be further operative to
  (d) initiate the mediation response as a stepped mediation response comprising at least:
  (1) initiate a first stage response that further assesses the identified environmental anomaly using the sensor data from at least one or more of the wireless ID nodes, and
  (2) initiate a second stage response that causes deployment of the fire suppressant material to the shipping container based upon and in response to the further assessment of the identified environmental anomaly in (1).

46. The system of claim 45, wherein each of the wireless ID nodes comprises a sensor-based ID node that broadcasts sensor data as part of the signals broadcast over the first wireless communication path; and
 wherein the master node of the fire suppression system is programmatically configured to initiate the first stage response by being configured and operative to:
  detect sensor data from the monitored signals being broadcasted from the wireless sensor-based ID nodes;
  refine the identity of the environmental anomaly for the shipping container when the detected sensor data does not include the sensor data from at least a threshold number of the wireless sensor-based ID nodes, and
  further refine the identity of the environmental anomaly for the shipping container when the detected sensor data indicates an environmental condition that exceeds an environmental threshold.

47. The system of claim 44, wherein the fire suppression system further comprises a plurality of shipping container sensors coupled to the master node, wherein each of the shipping container sensors providing sensor data to the master node about the shipping container; and
 wherein the master node of the fire suppression system is programmatically configured to be further operative to
  (d) initiate the mediation response as a stepped mediation response comprising at least:
  (1) initiate a first stage response that further assesses the identified environmental anomaly using at least one or more of the shipping container sensors, and
  (2) initiate a second stage response that causes deployment of the fire suppressant material to the shipping container based upon and in response to the further assessment of the identified environmental anomaly in (1).

48. The system of claim 47, wherein the master node of the fire suppression system is programmatically configured to initiate the first stage response by being configured and operative to:
 detect sensor data from the shipping container sensors, the shipping container sensors being disposed outside the shipping container and focusing on the exterior of the shipping container; and
 refine the identity of the environmental anomaly for the shipping container when the detected sensor data indicates an environmental condition that exceeds an environmental threshold.

49. The system of claim 44, wherein the master node is further operative to responsively identify the environmental anomaly based upon the monitored signals broadcast from the ID nodes by being operative to identity of the environmental anomaly for the shipping container when the signals being broadcast from the ID nodes as wirelessly monitored by the master node indicate at least a threshold number of the wireless ID nodes are in a state of ceased broadcasting.

50. The system of claim 44, wherein each of the wireless ID nodes comprises:
an ID node processor;
an ID node memory coupled to the ID node processor, the memory maintaining at least an ID node monitoring program code;
at least one environmental sensor configured to generate sensor data related to an environmental condition proximate the respective wireless ID node;
a wireless radio transceiver coupled to the ID node processing unit, the wireless radio transceiver being configured to access the sensor data generated by the at least one environmental sensor and broadcast the sensor data in response to a report command from the ID node processor when the ID node processing unit executes the ID node monitoring program code.

51. The system of claim 44, wherein the master node of the fire suppression system is further configured to operate as the primary monitor for the environmental anomaly by being further operative to (e) transmit the layered alert notification to a targeted mediation recipient according to the mediation response priority.

52. The system of claim 51, wherein the targeted mediation recipient comprises the external transceiver, wherein the external transceiver having a display used by an operator of the transit vehicle that can alter movement of the transit vehicle.

53. The system of claim 51, wherein the targeted mediation recipient comprises the external transceiver, wherein the external transceiver having a display used a logistics crew member of the transit vehicle that can inspect the shipping container.

54. The system of claim 44, wherein the master node is further programmatically configured to identify the targeted mediation action based at least upon how many of the wireless ID nodes were not detected above a threshold number of the wireless ID nodes.

55. The system of claim 54, wherein the targeted mediation action depends upon what is loaded within the shipping container as indicated by shipping information maintained on the master node of the fire suppression system.

56. The system of claim 46, wherein the master node is further programmatically configured to identify the targeted mediation action based upon at least one of (a) how many of the wireless ID nodes were not detected above the threshold number of the wireless sensor-based ID nodes and (b) how much the environmental condition exceeds the environmental threshold.

57. The system of claim 56, wherein the targeted mediation action depends upon what is loaded within the shipping container as indicated by shipping information maintained on the master node of the fire suppression system.

58. The system of claim 46, wherein the master node is further programmatically configured to automatically establish the mediation response priority based upon at least one of (a) how many of the wireless ID nodes were not detected above the threshold number of the wireless ID nodes and (b) how much the environmental condition exceeds the environmental threshold.

59. The system of claim 58, wherein the mediation response priority comprises a high priority level indicating further travel by the transit vehicle is to be at least minimized as part of the mediation response.

60. The system of claim 58, wherein the mediation response priority comprises an intermediate priority level indicating further travel by the transit vehicle is permissible as part of the mediation response.

61. The system of claim 44, wherein the transit vehicle comprises an airplane.

62. The system of claim 44, wherein the transit vehicle comprises one from the group consisting of a railway conveyance, a maritime vessel, and a roadway conveyance.

63. The system of claim 44, wherein the master node is further operative to wirelessly monitor the signals being broadcast from the ID nodes by being operative to:
detect the signals broadcasted by the wireless ID nodes according to a broadcast profile maintained by each of the wireless ID nodes, the broadcast profile defining a first messaging rate used to regulate how often the signals are broadcast to the master node, the first messaging rate being higher than a default messaging rate; and
instruct each of the wireless sensor-based ID nodes to broadcast future generated sensor data at a second messaging rate that exceeds the first messaging rate after transmitting the layered alert notification to the transceiver.

64. The system of claim 63, wherein the master node is further operative to instruct each of the wireless sensor-based ID nodes to change from the default messaging rate to the first messaging rate.

65. The system of claim 63, wherein the first messaging rate for the wireless sensor-based ID nodes comprises an initial value correlated to an environmental risk associated with material maintained within the shipping container.

66. The system of claim 46, wherein the master node is further operative to detect the sensor data from the monitored signals being broadcast from the wireless sensor-based ID nodes by being operative to:
detect the sensor data broadcasted by the wireless sensor-based ID nodes according to a broadcast profile maintained by each of the wireless sensor-based ID nodes, the broadcast profile defining a first messaging rate used to regulate how often the generated sensor data is transmitted to the master node, the first messaging rate being higher than a default messaging rate; and
instruct each of the wireless sensor-based ID nodes to broadcast future generated sensor data at a second messaging rate that exceeds the first messaging rate after transmitting the layered alert notification to the transceiver.

67. The system of claim 66, wherein the master node is further operative to instruct each of the wireless sensor-based ID nodes to change from the default messaging rate to the first messaging rate.

68. The system of claim 66, wherein the first messaging rate for the wireless sensor-based ID nodes comprises an initial value correlated to an environmental risk associated with material maintained within the shipping container.

69. The system of claim 44, wherein the master node is further programmatically configured to operate as a primary monitor for the environmental anomaly by being further operative to:
receive an altered trigger limit related to the targeted mediation action; and
initiate the mediation response using the altered trigger limit related to the targeted mediation action.

70. The system of claim 69, wherein the master node receives the altered trigger limit from the external transceiver on the transit vehicle.

71. The system of claim 70, wherein the altered trigger limit is defined by an operator of the transit vehicle using the external transceiver.

72. The system of claim 70, wherein the altered trigger limit is defined by a logistics crew member of the transit vehicle using the external transceiver.

73. The system of claim 70, wherein the altered trigger limit related to the targeted mediation action is provided to the external transceiver of the transit vehicle from a remote control center in communication with the external transceiver.

74. The system of claim 51, wherein the master node is further configured to receive a request to initiate a secondary mediation response by the fire suppression system related to the targeted mediation action and the mediation response priority, the request being provided to the master node from the external transceiver in response to the layered alert notification.

\* \* \* \* \*

UNITED STATES PATENT AND TRADEMARK OFFICE
CERTIFICATE OF CORRECTION

PATENT NO. : 10,755,552 B2
APPLICATION NO. : 16/546427
DATED : August 25, 2020
INVENTOR(S) : Ole Petter Skaaksrud Page 1 of 1

It is certified that error appears in the above-identified patent and that said Letters Patent is hereby corrected as shown below:

In the Specification

Beginning at Column 36, Line 28, cancel the text "(e.g., how many nodes are anticipated to occupy a corridor, such as structure 2200 shown in Figure 22A, or a storage facility through which a particular ID node is anticipated to transit on its shipping path)".

Beginning at Column 41, Line 56, cancel the text "Figures 22A-C also provide a more detailed application of such exemplary association and communication activities when an exemplary ID node moves along a transit path (e.g., through a corridor) and is tracked and managed by different master nodes and a server in an embodiment.".

Beginning at Column 46, Line 8, cancel the entire paragraph.

Beginning at Column 46, Line 20, cancel the entire paragraph.

Beginning at Column 46, Line 34, cancel the entire paragraph.

Beginning at Column 46, Line 50, cancel the entire paragraph.

Beginning at Column 46, Line 64, cancel the entire paragraph.

Beginning at Column 47, Line 10, cancel the entire paragraph.

Beginning at Column 47, Line 33, cancel the entire paragraph.

Beginning at Column 47, Line 53, cancel the entire paragraph.

Beginning at Column 47, Line 63, cancel the entire paragraph.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*